(12) United States Patent  (10) Patent No.: US 8,841,312 B2
Connors et al.  (45) Date of Patent: Sep. 23, 2014

(54) FUSED PYRIDINE, PYRIMIDINE AND TRIAZINE COMPOUNDS AS CELL CYCLE INHIBITORS

(75) Inventors: Richard V. Connors, Pacifica, CA (US); Dai Kang, Albany, CA (US); John Eksterowicz, San Francisco, CA (US); Pingchen Fan, Fremont, CA (US); Benjamin Fisher, San Mateo, CA (US); Jiasheng Fu, Foster City, CA (US); Kexue Li, Mountain View, CA (US); Zhihong Li, Millbrae, CA (US); Lawrence R. McGee, Pacifica, CA (US); Rajiv Sharma, Mumbai (IN); Xiaodong Wang, Millbrae, CA (US); Dustin L. McMinn, Pacifica, CA (US); Jeffrey T. Mihalic, San Francisco, CA (US); Jeffrey Deignan, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 1057 days.

(21) Appl. No.: 12/808,621

(22) PCT Filed: Dec. 18, 2008

(86) PCT No.: PCT/US2008/013849
§ 371 (c)(1),
(2), (4) Date: Nov. 2, 2010

(87) PCT Pub. No.: WO2009/085185
PCT Pub. Date: Jul. 9, 2009

(65) Prior Publication Data
US 2011/0142796 A1  Jun. 16, 2011

Related U.S. Application Data

(60) Provisional application No. 61/008,429, filed on Dec. 19, 2007.

(51) Int. Cl.
*A61K 31/519* (2006.01)
*A61K 31/5377* (2006.01)
*A61K 31/5386* (2006.01)
*C07D 403/14* (2006.01)
*C07D 413/14* (2006.01)

(52) U.S. Cl.
CPC ............ *C07D 403/14* (2013.01); *C07D 413/14* (2013.01); *A61K 31/519* (2013.01); *A61K 31/5377* (2013.01); *A61K 31/5386* (2013.01)
USPC .......................... 514/267; 544/250; 544/251

(58) Field of Classification Search
CPC ............ A61K 31/519; A61K 31/5377; A61K 31/5386; C07D 403/14; C07D 413/14
USPC .................. 514/267; 544/250, 251
See application file for complete search history.

(56) References Cited

U.S. PATENT DOCUMENTS

| 3,452,013 A * | 6/1969 | Gladych et al. ............ 544/184 |
| 6,498,163 B1 | 12/2002 | Boschelli et al. |
| 6,627,637 B2 | 9/2003 | Ritzeler et al. |
| 7,026,313 B2 | 4/2006 | Repine |
| 7,208,489 B2 | 4/2007 | Barvian et al. |
| 7,452,887 B2 | 11/2008 | Dickson et al. |
| 8,623,885 B2 * | 1/2014 | Chen et al. ................... 514/267 |
| 2003/0203907 A1 | 10/2003 | Hayama et al. |
| 2004/0236084 A1 | 11/2004 | Biwersi et al. |
| 2005/0059670 A1 | 3/2005 | Beylin et al. |
| 2005/0137214 A1 | 6/2005 | Barvian et al. |
| 2005/0182078 A1 | 8/2005 | Barvian et al. |
| 2005/0222163 A1 | 10/2005 | Eck et al. |
| 2005/0272755 A1 | 12/2005 | Denis et al. |
| 2006/0047118 A1 | 3/2006 | Stadtmueller et al. |
| 2006/0074102 A1 | 4/2006 | Cusack et al. |
| 2006/0142312 A1 | 6/2006 | Flamme et al. |
| 2006/0194805 A1 | 8/2006 | Bakthavatchalam et al. |
| 2007/0004684 A1 | 1/2007 | Sennhenn et al. |
| 2007/0060566 A1 | 3/2007 | Bailey et al. |
| 2007/0072863 A1 | 3/2007 | Bennett et al. |
| 2007/0072882 A1 | 3/2007 | Guzi et al. |
| 2007/0082900 A1 | 4/2007 | Guzi et al. |
| 2007/0185143 A1 | 8/2007 | Traquandi et al. |
| 2007/0270362 A1 | 11/2007 | Harlan et al. |
| 2007/0281943 A1 | 12/2007 | Andrews et al. |
| 2007/0293558 A1 | 12/2007 | Gao et al. |
| 2008/0070914 A1 | 3/2008 | Freyne et al. |
| 2008/0125588 A1 | 5/2008 | Erdman et al. |
| 2008/0182853 A1 | 7/2008 | Kruman et al. |
| 2009/0030005 A1 | 1/2009 | Kamb et al. |

(Continued)

FOREIGN PATENT DOCUMENTS

| WO | WO 83/01446 | 4/1983 |
| WO | WO 01/70741 A1 | 9/2001 |

(Continued)

OTHER PUBLICATIONS

West, Anthony R., Solid State Chemistry and Its Applications, Wiley, New York, 1988, 358.*
International Search Report for parent PCT Application No. PCT/US2008/013849, Apr. 23, 2009.
Written Opinion for parent PCT Application No. PCT/US2008/013849, May 13, 2009.
International Preliminary Report on Patentability for parent PCT Application No. PCT/US2008/013849, Jun. 22, 2010.
Original Spanish language Pre-Grant Opposition in corresponding Costa Rican patent application, Jan. 14, 2011.

(Continued)

*Primary Examiner* — Erich A Leeser
(74) *Attorney, Agent, or Firm* — Bernard P Friedrichsen

(57) ABSTRACT

Compounds, pharmaceutical compositions and methods are provided that are useful in the treatment of CDK4-mediated disorders, such as cancer. The subject compounds are fused pyridine, pyrimide and triazine derivatives.

35 Claims, No Drawings

(56) References Cited

U.S. PATENT DOCUMENTS

| | | |
|---|---|---|
| 2009/0062318 A1 | 3/2009 | Gangjee |
| 2009/0082374 A1 | 3/2009 | Gangjee |
| 2009/0142337 A1 | 6/2009 | Squires |

FOREIGN PATENT DOCUMENTS

| | | |
|---|---|---|
| WO | WO 01/72717 A1 | 10/2001 |
| WO | WO 02/02550 A1 | 1/2002 |
| WO | WO 03/062236 A1 | 7/2003 |
| WO | WO 03/080064 A1 | 10/2003 |
| WO | WO 2004/065378 A1 | 8/2004 |
| WO | WO 2005/077951 A2 | 8/2005 |
| WO | WO 2006/021547 A1 | 3/2006 |
| WO | WO 2006/042102 A2 | 4/2006 |
| WO | WO 2006/074985 A1 | 7/2006 |
| WO | WO 2006/077428 A1 | 7/2006 |
| WO | WO 2006/131552 A1 | 12/2006 |
| WO | WO 2007/024680 A1 | 3/2007 |
| WO | WO 2007/120752 A2 | 10/2007 |
| WO | WO 2007/125405 A2 | 11/2007 |
| WO | WO 2007/140222 A2 | 12/2007 |
| WO | WO 2008/001076 A1 | 1/2008 |
| WO | WO 2008/082490 A2 | 7/2008 |
| WO | WO 2008/115974 A2 | 9/2008 |
| WO | WO 2009/061345 A2 | 5/2009 |
| WO | WO 2009/061781 A1 | 5/2009 |
| WO | WO 2009/083780 A1 | 7/2009 |
| WO | WO 2009/087225 A2 | 7/2009 |

OTHER PUBLICATIONS

English Translation of Pre-Grant Opposition in corresponding Costa Rican patent application, Jan. 14, 2011.
Barbara, J-G et al., "Quantal release at a neuronal nicotinic synapse from rat adrenal gland," Proc. Natl. Acad. Science 93(18), 9905-9909, Sep. 1996.
Baughn, L. B. et al., "A Novel Orally Active Small Molecule Potently Induces $G_1$ Arrest in Primary Myeloma Cells and Prevents Tumor Growth by Specific Inhibition of Cyclin-Dependent Kinase," Cancer Research 66(15), 7661-7667 (2006).
Brooks, E.E. et al., "CVT-313, a specific and Potent Inhibitor of CDK2 That Prevents Neointimal Proliferation", The Journal of Biological Chemistry 272(46), 29207-29211 (1997).
Bukanov, N.O. et al., "Long-lasting arrest of murine polycystic kidney disease with CDK inhibitor roscovitine", Nature 444(7121), 949-952 (2006).
Chang, M.W. et al., "Adenovirus-mediated Over-expression of the Cyclin/Cyclin-dependent Kinase Inhibitor, p21 Inhibits Vascular Smooth Muscle Cell Proliferation and Neointima Formation in the Rat Carotid Artery Model of Balloon Angioplasty", Journal of Clinical Investigation 96(5), 2260-2268 (1995).
Chen, X. et al., "Protection of Normal Proliferating Cells Against Chemotherapy by Staurosporine-Mediated, Selective, and Reversible $G_1$ Arrest", Journal of the National Cancer Institute 92(24), 1999-2008 (2000).
de Carcer, G. et al., "Targeting Cell Cycle Kinases for Cancer Therapy", Current Medicinal Chemistry 14(9), 969-985 (2007).
Fry, D. W. et al., "Specific inhibition of cyclin-dependent kinase 4/6 by PD 0332991 and associated antitumor activity in human tumor xenografts," Molecular Cancer Therapeutics 3(11), 1427-1438 (2004).
Gladych, J.M. Z et al. "Antiviral agents. 5H-as-Triazino[5,6-b]Indoles", Journal Medicinal Chemistry vol. 15(3), pp. 277-281 (1972).
Hassan, A.A. et al., "Novel Heterocyclics from 3-Substituted-5H-1,2,4-Triazino[5,6-b]indoles and Pi-Acceptors", Tetrahedron, vol. 50(33), pp. 9997-10010 (1994).
Kamb, A., "Cyclin-Dependent Kinase Inhibitors and Human Cancer", Current Topics in Microbiology and Immunology 227, 139-148 (1998).

Leach, A.G. et al., "Matched Molecular Pairs as a Guide in the Optimization of Pharmaceutical Properties; a Study of Aqueous Solubility, Plasma Protein Binding and Oral Exposure," Journal of Medicinal Chemistry 49(23), 6672-6682 (2006).
Lu, H. et al., "Toward Understanding the Structural Basis of Cyclin-Dependent Kinase 6 Specific Inhibition," Journal of Medicinal Chemistry 49(13), 3826-3831 (2006).
Malumbres, M. et al, "To Cycle or Not to Cycle: A Critical Decision in Cancer", Nature Rev Cancer 1, 222-231 (2001).
Mascarenhas, N.M. et al., "Combined Ligand and Structure Based Approaches for Narrowing on the Essential Physicochemical Characteristics for CDK4 Inhibition," Journal of Chemical Information and Modeling 48(7), 1325-1336 (2008).
Menu, E. et al., "A Novel Therapeutic Combination Using PD 0332991 and Bortezomib: Study in the 5T33MM Myeloma Model," Cancer Research 68(14), 5519-5523 (2008).
Menu, E. et al., "Correction on Combination Therapy Using PD 0332991 and Bortezomib," Cancer Research 69(5), 2149 (2009).
Mohammed, M.I., "Synthesis and antibacterial activity of some novel heterocycles," Bulgarian Chemical Communications 36(4), 241-248 (2004).
Morgan D.O., "Cyclin-Dependent Kinases: Engines, Clocks and Microprocessors," Annu. Rev. Cell. Dev. Biol. 13, 261-291 (1997).
Novak, M. et al., "Kinetics of Hydrolysis of 8-(Arylamino)-2'-deoxyguanosines," Journal of Organic Chemistry 67(7), 2303-2308 (2002).
Perry, B. et al., "Optimization of a series of multi-isoform PI3 kinase inhibitors," Bioorganic & Medicinal Chemistry Letters 18(19), 5299-5302 (2008).
Saab, R. et al., "Pharmacologic inhibition of cyclin-dependent kinase 4/6 activity arrests proliferation in myoblasts and rhabdomyosarcoma-derived cells," Molecular Cancer Therapeutics 5(5), 1299-1308 (2006).
Saris, C.P. et al., "Chemical properties of the ultimate metabolites of 2-amino-5-phenylpyridine (PHE-P-1) and its ortho-methyl derivative," Chemico-Biological Interactions 95(1,2), 29-40 (1995).
Schang, L.M. et al., "Requirement for cellular cyclin-dependent kinases in herpes simplex virus replication and transcription", Journal of Virology 72(7), 5626-5637 (1998).
Schmidt, M. et al., "Protection against chemotherapy-induced cytotoxicity by cyclin-dependent kinase inhibitors (CKI) in CKI-responsive cells compared with CKI-unresponsive cells," Oncogene 20(43), 6164-6171 (2001).
Taniguchi, K. et al., "Induction of the p16INK4a senescence gene as a new therapeutic strategy for the treatment of rheumatoid arthritis", Nature Medicine 5(7) 760-767 (1999).
Toogood, P.L. et al., "Discovery of a Potent and Selective Inhibitor of Cyclin-Dependent Kinase 4/6," Journal of Medicinal Chemistry 48(7), 2388-2406 (2005).
Wang, L. et al., "Pharmacologic inhibition of CDK4/6: mechanistic evidence for selective activity or acquired resistance in acute myeloid leukemia," Blood 110(6), 2075-2083 (2007).
Wyatt, P. G. et al., "Identification of N-(4-Piperidinyl)-4-(2,6-dichlorobenzoylamino)-1H-pyrazole-3- carboxamide (AT7519), a Novel Cyclin Dependent Kinase Inhibitor Using Fragment-Based X-Ray Crystallography and Structure Based Drug Design," Journal of Medicinal Chemistry 51(16), 4986-4999 (2008).
Youssef, A. S. A. et al., "Synthesis of some heterocyclic systems of anticipated biological activities via 6-aryl-4-pyrazol-1-ylpyridazin-3-one," Canadian Journal of Chemistry 83(3), 251-259 (2005).
Youssef, A. S. A. et al., "Synthesis of some heterocyclic systems of anticipated biological activities via 6-aryl-4-pyrazol-1-ylpyridazin-3-one," Afinidad 61(514), 500-509 (2004).
Zhang, C. et al, "Advancing Bioluminescence Imaging Technology for the Evaluation of Anticancer Agents in the MDA-MB-435-HAL-Luc Mammary Fat Pad and Subrenal Capsule Tumor Models," Clinical Cancer Research 15(1), 238-246 (2009).

\* cited by examiner

FUSED PYRIDINE, PYRIMIDINE AND TRIAZINE COMPOUNDS AS CELL CYCLE INHIBITORS

FIELD OF THE INVENTION

This invention is in the field of pharmaceutical agents and specifically relates to compounds, compositions, uses and methods for treating cancer.

BACKGROUND OF THE INVENTION

Cyclin-dependent kinases (Cdks) are a family of serine/threonine protein kinases playing important cellular functions. The cyclins are the regulatory subunits that activate the catalytic Cdks. Cdk1/Cyclin B1, Cdk2/Cyclin A, Cdk2/Cyclin E, Cdk4/Cyclin D, Cdk6/Cyclin D are critical regulators of cell cycle progression. Cdks also regulate transcription, DNA repair, differentiation, senescence and apoptosis (Morgan D. O., *Annu. Rev. Cell. Dev. Biol.* 1997; 13:261-291).

Small molecule inhibitors of Cdks have been developed to treat cancer (de Carcer G et al., *Curr Med Chem.* 2007; 14:969-85). Large amount of genetic evidence support that Cdks play critical roles in the development of most human cancers (Malumbres M. et al, *Nature Rev Cancer,* 2001; 1:222-231). Genetic alterations in Cdks, their substrates or regulators have been shown to be associated with human cancer. Endogenous protein inhibitors of Cdks including p16, p21 and p27 inhibit Cdk activity and their overexpression result in cell cycle arrest and inhibition of tumor growth in preclinical models (Kamb A., *Curr. Top. Microbiolo. Immunol.,* 1998; 227:139-148).

Small molecule inhibitors of Cdks may also be used to treat variety of other diseases that result from aberrant cell proliferation, including cardiovascular disorders, renal diseases, certain infectious diseases and autoimmune diseases. Cell proliferation regulatory pathways including genes involved in the cell cycle G1 and S phase checkpoint (p53, pRb, p15, p16, and Cyclins A, D, E, Cdk 2 and Cdk4) have been associated with plaque progression, stenosis and restenosis after angioplasty. Over-expression of the Cdk inhibitor protein p21 has been shown to inhibit vascular smooth muscle proliferation and intimal hyperplasia following angioplasty (Chang M. W. et al., *J. Clin. Invest.,* 1995; 96:2260; Yang Z-Y. et al., *Proc. Natl. Acad. Sci.* (*USA*) 1996; 93:9905). A small molecule Cdk2 inhibitor CVT-313 (Ki=95 nM) was shown to cause in significant inhibition of neointima formation in animal models (Brooks E. E. et al., *J. Biol. Chem.* 1997; 272: 29207-29211). Disregulation of cell cycle has been associated with polycystic kidney diseases, which are characterized by the growth of fluid-filled cysts in renal tubules. Treatment with small molecule inhibitors of Cdks yielded effective arrest of cystic disease in mouse models (Bukanov N. O., et al., *Nature,* 2006; 4444:949-952). Infection by a variety of infectious agents, including fungi, protozoan parasites such as *Plasmodium falciparum*, and DNA and RNA viruses may be treated with Cdk inhibitors. Cdks have been shown to be required for replication of herpes simplex virus (HSV) (Schang L. M. et al., *J. Virol.* 1998; 72:5626). Cdks are essential proteins in yeast. Synovial tissue hyperplasia plays important roles in the development of rheumatoid arthritis; inhibition of synovial tissue proliferation may suppress inflammation and prevent joint destruction. It has been shown that over-expression of Cdk inhibitor protein p16 inhibited synovial fibroblast growth (Taniguchi K. et al., *Nat. Med.* 1999; 5:760-767) and joint swelling was substantially inhibited in animal arthritis models.

Selective inhibitors of some Cdks may also be used to protect normal untransformed cells by inhibiting specific phases of cell cycle progression (Chen et al. *J. Natl. Cancer Institute,* 2000; 92:1999-2008). Pre-treatment with a selective Cdk inhibitor prior to the use of a cytotoxic agent that inhibits a different phase of the cell cycle may reduce the side effects associated with the cytotoxic chemotherapy and possibly increase the therapeutic widow. It has been shown that induction of cellular protein inhibitors of Cdks (p16, p27 and p21) conferred strong resistance to paclitaxel- or cisplatin-mediated cytotoxicity on the inhibitor-responsive cells but not on the inhibitor-unresponsive cells (Schmidt, M, *Oncogene,* 2001 20:6164-71).

DESCRIPTION OF THE INVENTION

A class of compounds useful in treating cancer is defined by the following Formula I or II A compound of Formula I or II

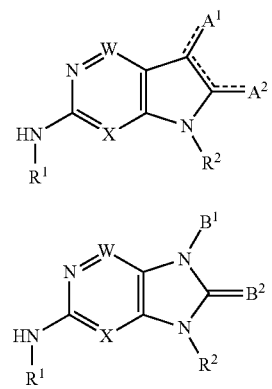

enantiomers, diastereomers, salts and solvates thereof wherein

W and X are independently CH or N;

$A^1$ and $A^2$ together with ring carbon atoms to which they are attached combine to form benzene, cyclopentadiene, pyridine, pyridone, pyrimidine, pyrazine, pyridazine, 2H-pyran, pyrrole, imidazole, pyrazole, triazole, furan, oxazole, isoxazole, oxadiazole, thiophene, thiazole, isothiazole or thiadiazole any of which may be optionally partially saturated, and any of which may be optionally independently substituted with one or more $R^x$ groups as allowed by valance;

$B^1$ and $B^2$ together with the ring atoms to which they are attached combine to form dihydropyridine, dihydropyridone, dihydropyrimidine, dihydropyrimidone, dihydropyrazine, dihyrdopyridazine, pyrrole, imidazole, pyrazole, triazole, or tetrazole any of which may be optionally partially saturated, and any of which may be optionally independently substituted with one or more $R^x$ groups as allowed by valance;

$R^1$ is —Y-(alkylene)$_m$-$R^a$;

Y is alkyl, alkenyl, alkynyl, cycloalkyl, cycloalkenyl, heterocyclo, aryl or heteroaryl any of which may be optionally independently substituted with one or more $R^x$ groups as allowed by valance;

$R^a$ is heterocyclo, heteroaryl, —NR$^3$R$^4$, —C(═O)NR$^3$R$^4$; —O—R$^5$, —S(O)$_n$-R$^5$, or —S(O)$_n$-NR$^3$R$^4$ any of which may be optionally independently substituted with one or more $R^x$ groups as allowed by valance, and wherein two $R^x$ groups bound to the same or adjacent atom may optionally combine to form a ring;

$R^2$ is alkyl, cycloalkyl, heterocyclo, aryl, —S(O)$_n$R$^5$, —C(=O)R$^5$, —C(=S)R$^5$, —C(=O)OR$^5$, —C(=S)OR$^5$, —C(=O)NR$^3$R$^4$, —C(=S)NR$^3$R$^4$, —SO$_2$NR$^3$R$^4$, any of which may be optionally independently substituted with one or more $R^x$ groups as allowed by valance;

$R^3$ and $R^4$ at each occurance are independently
  (i) hydrogen or
  (ii) alkyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance, and wherein two $R^x$ groups bound to the same or adjacent atom may optionally combine to form a ring;

or $R^3$ and $R^4$ together with the nitrogen atom to which they are attached may combine to form a heterocyclo ring optionally independently substituted with one or more $R^x$ groups as allowed by valance, and wherein two $R^x$ groups bound to the same or adjacent atom may optionally combine to form a ring;

$R^{3*}$ and $R^{4*}$ at each occurance are independently
  (i) hydrogen or
  (ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance;

or $R^{3*}$ and $R^{4*}$ together with the nitrogen atom to which they are attached may combine to form a heterocyclo ring optionally independently substituted with one or more $R^x$ groups as allowed by valance;

$R^5$ and $R^{5*}$ at each occurance is
  (i) hydrogen or
  (ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance;

$R^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-S(O)$_n$R$^5$, -(alkylene)$_m$-NR$^3$R$^4$, -(alkylene)$_m$-C(=O)R$^5$, -(alkylene)$_m$-C(=S)R$^5$, -(alkylene)$_m$-C(=O)OR$^5$, -(alkylene)$_m$-OC(=O)R$^5$, -(alkylene)$_m$-C(=S)OR$^5$, -(alkylene)$_m$-C(=O)NR$^3$R$^4$, -(alkylene)$_m$-C(=S)NR$^3$R$^4$, -(alkylene)$_m$-N(R$^3$)C(=O)NR$^3$R$^4$, -(alkylene)$_m$-N(R$^3$)C(=S)NR$^3$R$^4$, -(alkylene)$_m$-N(R$^3$)C(=O)R$^5$, -(alkylene)$_m$-N(R$^3$)C(=S)R$^5$, -(alkylene)$_m$-OC(=O)NR$^3$R$^4$, -(alkylene)$_m$-OC(=S)NR$^3$R$^4$, -(alkylene)$_m$-SO$_2$NR$^3$R$^4$, -(alkylene)$_m$-N(R$^3$)SO$_2$R$^5$, -(alkylene)$_m$-N(R$^3$)SO$_2$NR$^3$R$^4$, -(alkylene)$_m$-N(R$^3$)C(=O)OR$^5$, -(alkylene)$_m$-N(R$^3$)C(=S)OR$^5$, or -(alkylene)$_m$-N(R$^3$)SO$_2$R$^5$;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-CN, -(alkylene)$_m$-OR$^{5*}$, -(alkylene)$_m$-S(O)$_n$R$^{5*}$, -(alkylene)$_m$-NR$^{3*}$R$^{4*}$, -(alkylene)$_m$-C(=O)R$^{5*}$, -(alkylene)$_m$-C(=S)R$^{5*}$, -(alkylene)$_m$-C(=O)OR$^{5*}$, -(alkylene)$_m$-OC(=O)R$^{5*}$, -(alkylene)$_m$-C(=S)OR$^{5*}$, -(alkylene)$_m$-C(=O)NR$^{3*}$R$^{4*}$, -(alkylene)$_m$-C(=S)NR$^{3*}$R$^{4*}$, -(alkylene)$_m$-N(R$^{3*}$)C(=O)NR$^{3*}$R$^{4*}$, -(alkylene)$_m$-N(R$^{3*}$)C(=S)NR$^{3*}$R$^{4*}$, -(alkylene)$_m$-N(R$^{3*}$)C(=O)R$^{5*}$, -(alkylene)$_m$-N(R$^{3*}$)C(=S)R$^{5*}$, -(alkylene)$_m$-OC(=O)NR$^{3*}$R$^{4*}$, -(alkylene)$_m$-OC(=S)NR$^{3*}$R$^{4*}$, -(alkylene)$_m$-SO$_2$NR$^{3*}$R$^{4*}$, -(alkylene)$_m$-N(R$^{3*}$)SO$_2$R$^{5*}$, -(alkylene)$_m$-N(R$^{3*}$)SO$_2$NR$^{3*}$R$^{4*}$, -(alkylene)$_m$-N(R$^{3*}$)C(=O)OR$^{5*}$, -(alkylene)$_m$-N(R$^{3*}$)C(=S)OR$^{5*}$, or -(alkylene)$_m$-N(R$^{3*}$)SO$_2$R$^{5*}$;

n is independently 0, 1 or 2; and m is independently 0 or 1.

Compounds of this invention are selective inhibitors of cyclin dependent kinase Cdk4, which is to say that they inhibit Cdk4 with higher potency than they inhibit tyrosine kinases and other serine-threonine kinases including other cyclin-dependent kinases such as Cdk1. Cdk6 is structurally and functionally similar to Cdk4.

Compounds of the present invention also inhibit Cdk6 at similar concentrations to those to inhibit Cdk4. Preferred embodiments of the present invention are compounds of the formula I inhibit Cdk4 at least about 100-fold more potently than they inhibit Cdk1.

The compounds of the present invention are useful for treating cancer including leukemia and solid cancer of the lung, breast, prostate, and skin such as melanoma, and other diseases with abnormal cell proliferation including but not limited to psoriasis, HSV, HIV, restenosis, and atherosclerosis.

Preferred compounds within the scope of Formula I include compounds wherein $A^1$ and $A^2$ together with the ring atoms to which they are attached combine to form

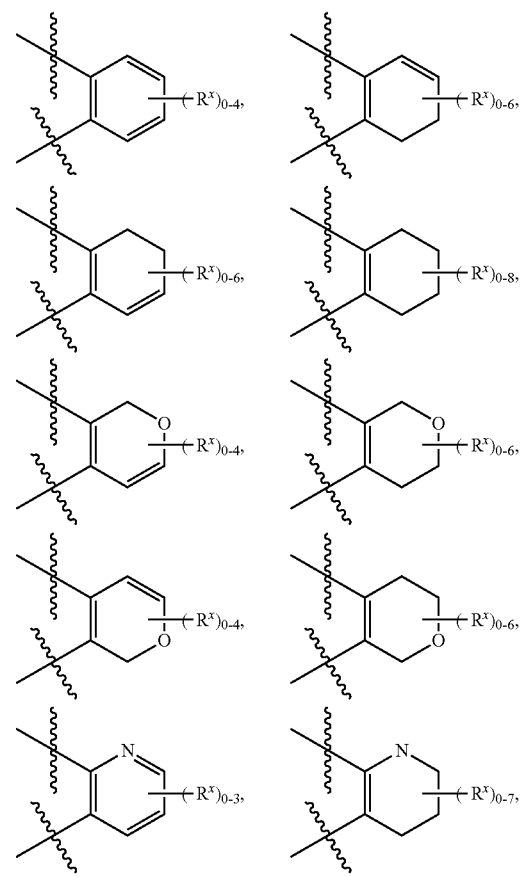

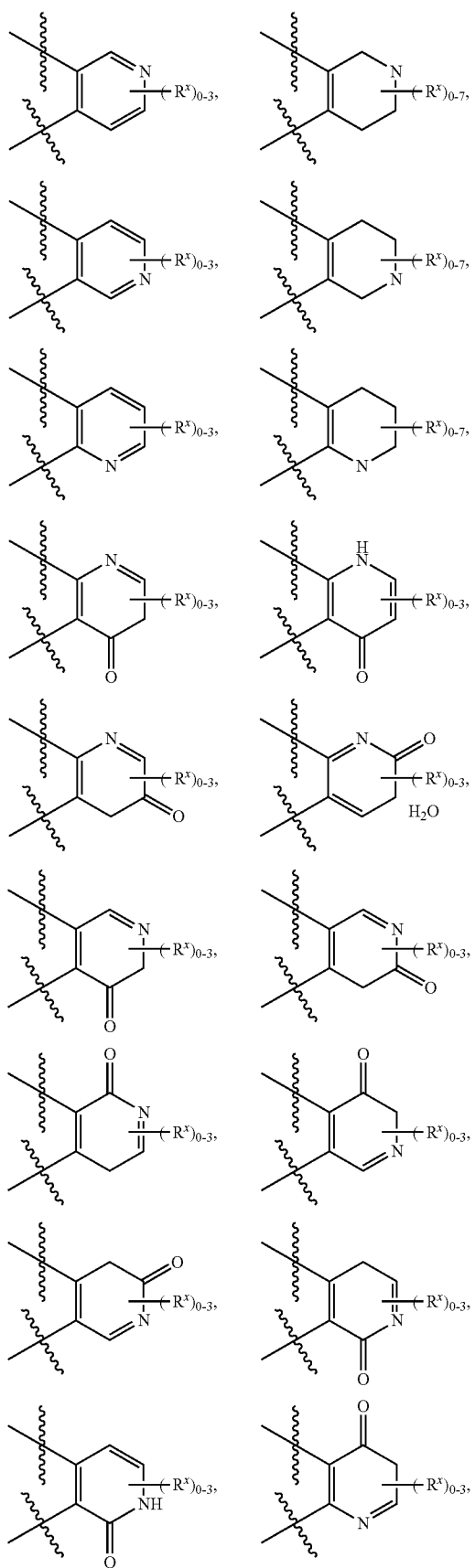
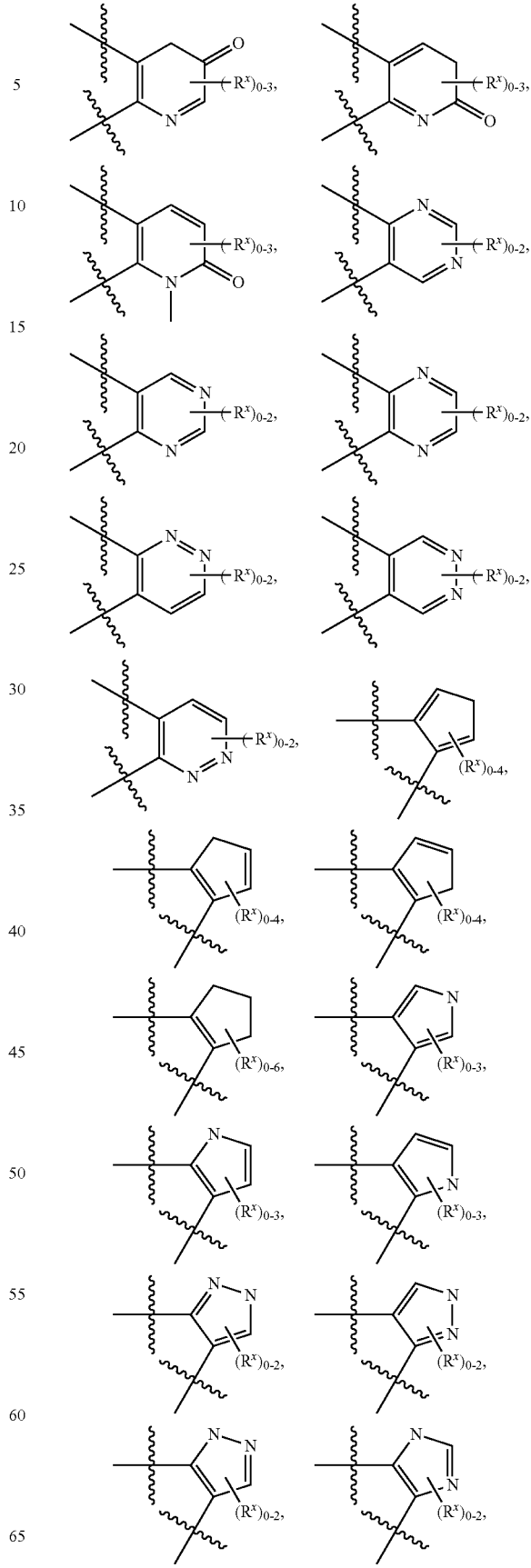

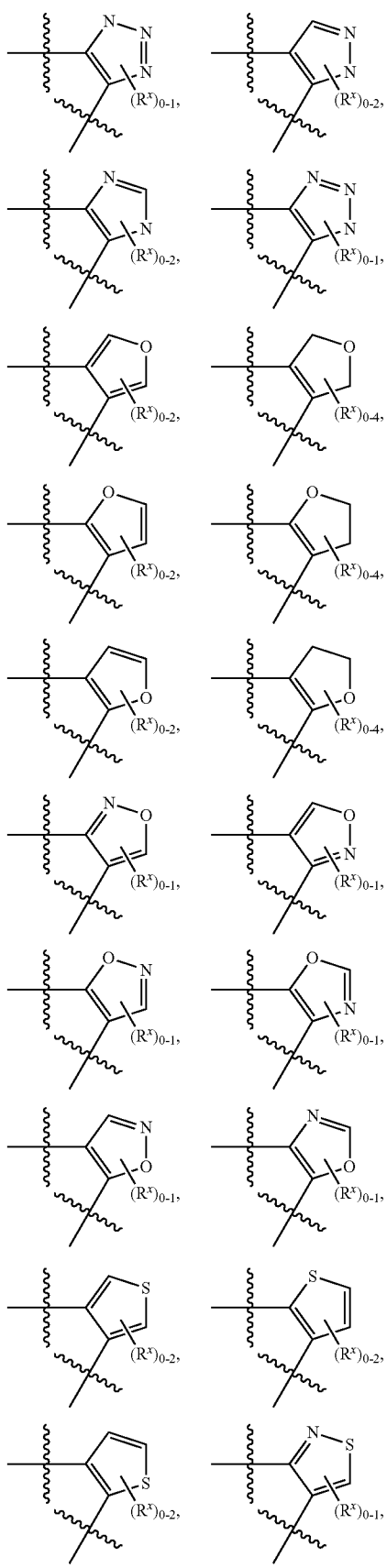
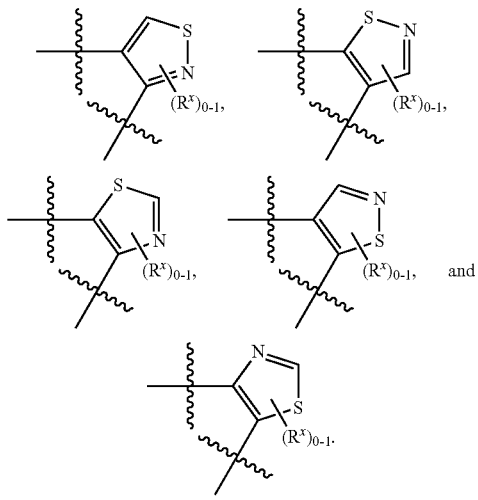
Preferred compounds within the scope of Formula II include compounds wherein $B^1$ and $B^2$ together with the ring atoms to which they are attached combine to form
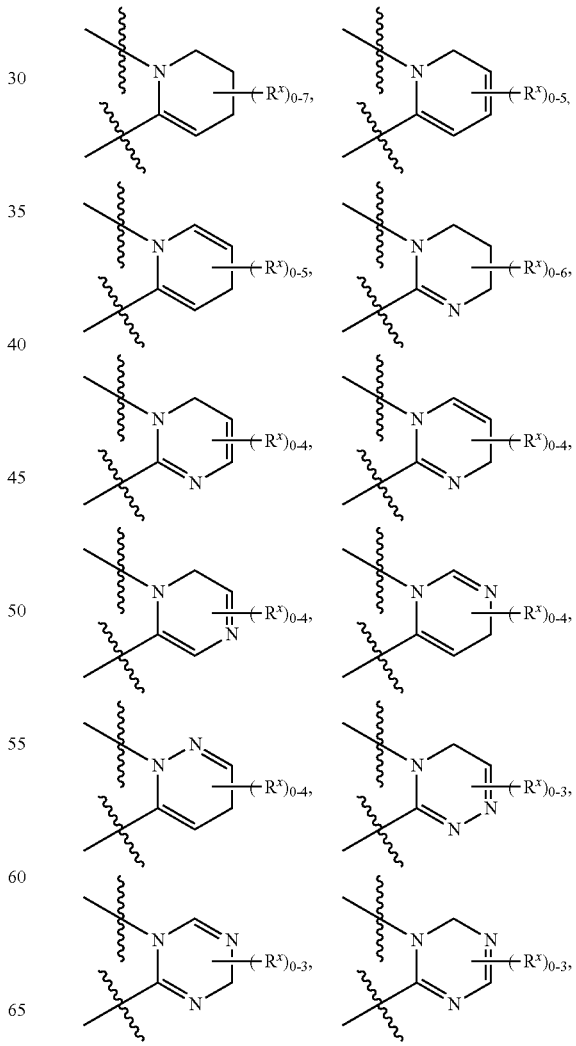

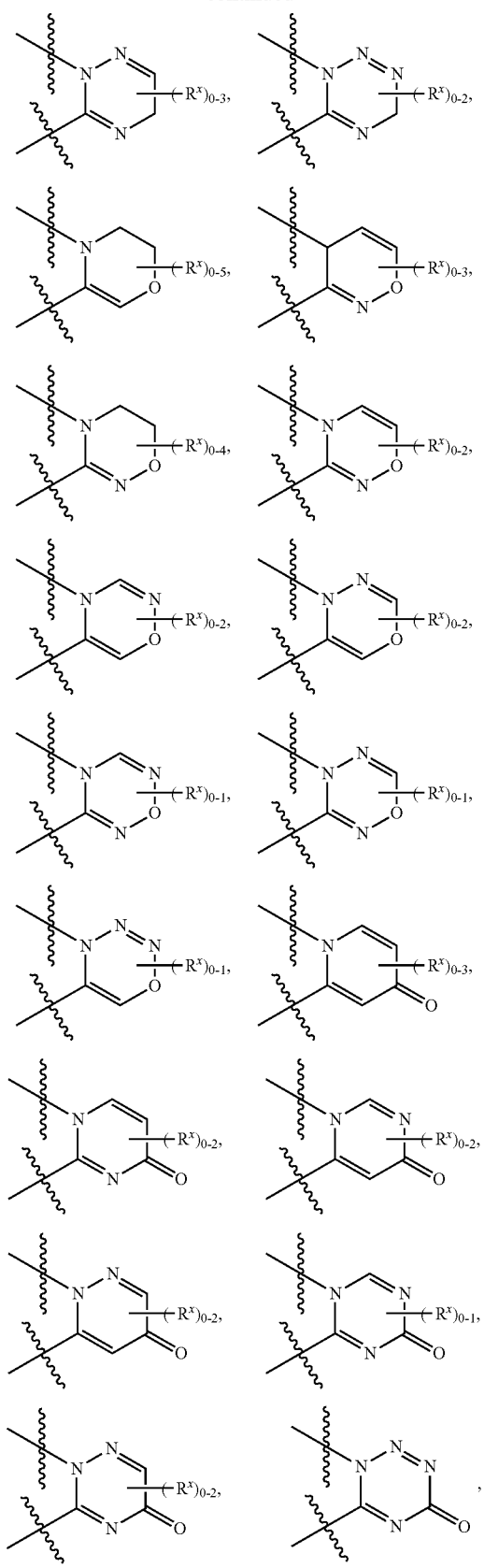
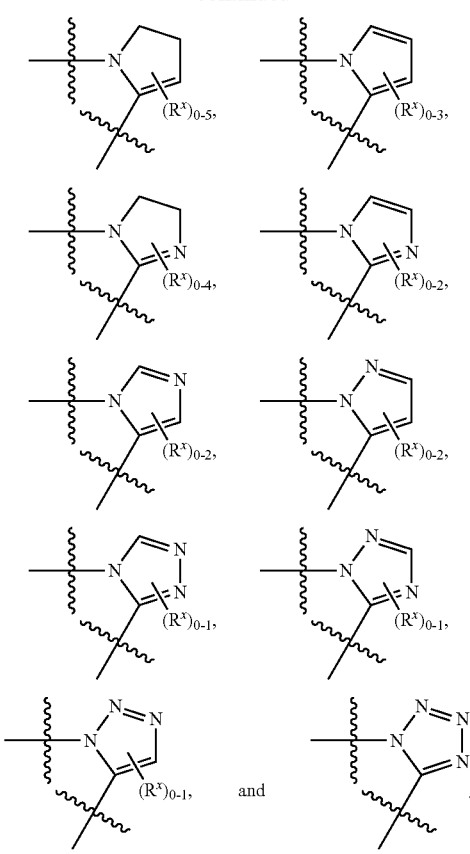
Preferred compounds within the scope of Formula I and II include compounds where Y is cyclopentyl, cyclohexyl, piperidinyl, piperazinyl, phenyl, pyridinyl, pyrimidinyl, cyclopentadienyl, pyrrolyl, imidazolyl, oxazolyl or thiazolyl.
Preferred compounds within the scope of Formula I and II further include compounds where $R^1$ is selected from
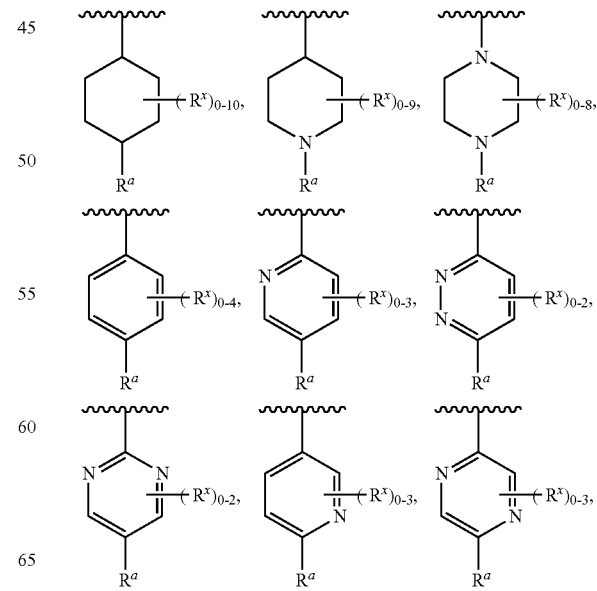

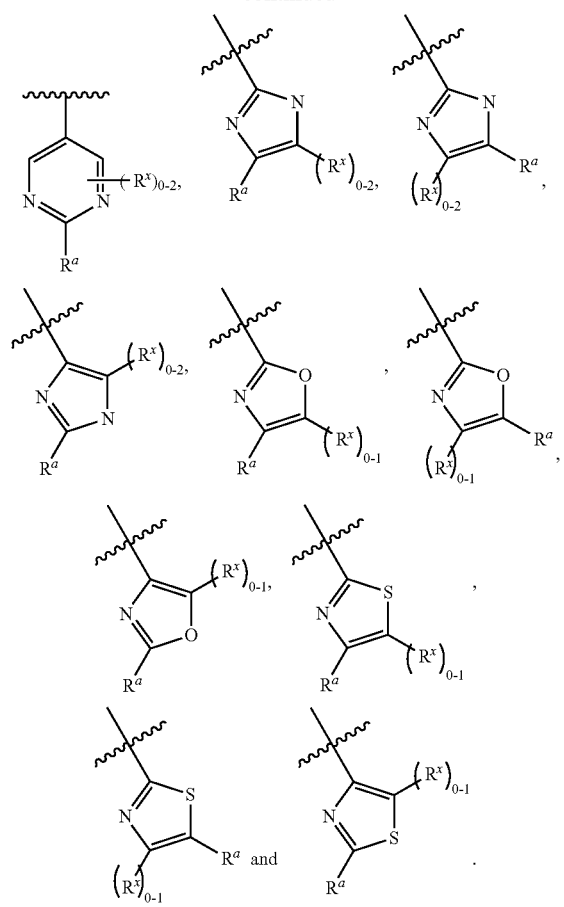

Preferred compounds within the scope of Formula I and II further include compounds where R³ is selected from (a) —OR⁵ or —S(O)ₙR⁵ where R⁵ is alkyl optionally independently substituted with one or more —OR⁵*, or —NR³*R⁴*;

(b) —C(=O)NR³R⁴ or —NR³R⁴ where R³ and R⁴ are independently alkyl optionally independently substituted with one or more —OR⁵*, or —NR³*R⁴*;

or R³ and R⁴ together with the nitrogen atom to which they are attached combine to form

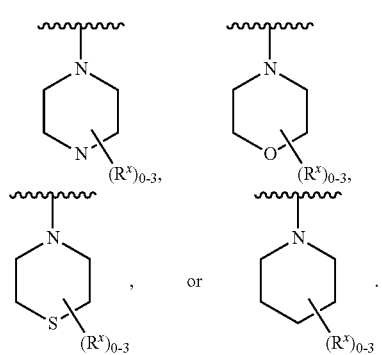

Preferred compounds within the scope of Formula I and II further include compounds where R² is

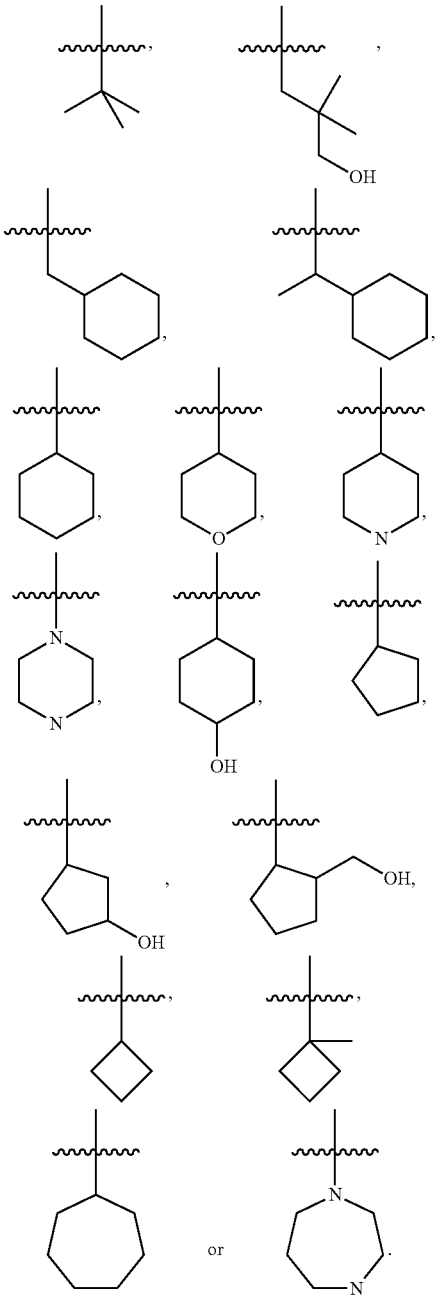

Preferred compounds within the scope of Formula I include compounds of the following formula IA

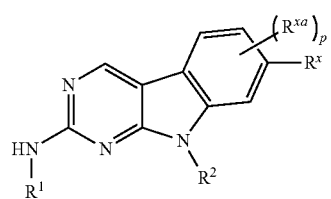

wherein $R^{xa}$ is at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-S(O)$_n$R$^5$, -(alkylene)$_m$-NR$^3$R$^4$, -(alkylene)$_m$-C(=O)R$^5$, -(alkylene)$_m$-C(=S)R$^5$, -(alkylene)$_m$-C(=O)OR$^5$, -(alkylene)$_m$-OC(=O)R$^5$, -(alkylene)$_m$-C(=S)OR$^5$, -(alkylene)$_m$-C(=O)NR$^3$R$^4$, -(alkylene)$_m$-C(=S)NR$^3$R$^4$, -(alkylene)$_m$-N(R$^3$)C(=O)NR$^3$R$^4$, -(alkylene)$_m$-N(R$^3$)C(=S)NR$^3$R$^4$, -(alkylene)$_m$-N(R$^3$)C(=O)R$^5$, -(alkylene)$_m$-N(R$^3$)C(=S)R$^5$, -(alkylene)$_m$-OC(=O)NR$^3$R$^4$, -(alkylene)$_m$-OC(=S)NR$^3$R$^4$, -(alkylene)$_m$-SO$_2$NR$^3$R$^4$, -(alkylene)$_m$-N(R$^3$)SO$_2$R$^5$, -(alkylene)$_m$-N(R$^3$)SO$_2$NR$^3$R$^4$, -(alkylene)$_m$-N(R$^3$)C(=O)OR$^5$, -(alkylene)$_m$-N(R$^3$)C(=S)OR$^5$, or -(alkylene)$_m$-N(R$^3$)SO$_2$R$^5$;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-OR$^{5*}$, -(alkylene)$_m$-S(O)$_n$R$^{5*}$, -(alkylene)$_m$-NR$^{3*}$R$^{4*}$, -(alkylene)$_m$-C(=O)R$^{5*}$, -(alkylene)$_m$-C(=S)R$^{5*}$, -(alkylene)$_m$-C(=O)O R$^{5*}$, -(alkylene)$_m$-OC(=O)R$^{5*}$, -(alkylene)$_m$-C(=S)R$^{5*}$, -(alkylene)$_m$-C(=O)NR$^{3*}$R$^{4*}$, -(alkylene)$_m$-C(=S)NR$^{3*}$R$^{4*}$, -(alkylene)$_m$-N(R$^{3*}$)C(=O)NR$^{3*}$R$^{4*}$, -(alkylene)$_m$-N(R$^{3*}$)C(=S)NR$^{3*}$R$^{4*}$, -(alkylene)$_m$-N(R$^{3*}$)C(=O)R$^{5*}$, -(alkylene)$_m$-N(R$^{3*}$)C(=S)R$^{5*}$, -(alkylene)$_m$-OC(=O)NR$^{3*}$R$^{4*}$, -(alkylene)$_m$-OC(=S)NR$^{3*}$R$^{4*}$, -(alkylene)$_m$-SO$_2$NR$^{3*}$R$^{4*}$, -(alkylene)$_m$-N(R$^{3*}$)SO$_2$R$^{5*}$, -(alkylene)$_m$-N(R$^{3*}$)SO$_2$NR$^{3*}$R$^{4*}$, -(alkylene)$_m$-N(R$^{3*}$)C(=O)OR$^{5*}$, -(alkylene)$_m$-N(R$^{3*}$)C(=S)OR$^{5*}$, or -(alkylene)$_m$-N(R$^{3*}$)SO$_2$R$^{5*}$;

m is 0 or 1; and
p is zero to three.

Preferred compounds within the scope of Formula IA include compounds having any of the preferred Y, R$^1$, R$^a$ and/or R$^2$ substituents previously listed above.

Preferred compounds within the scope of Formula I include compounds having the following Formula IB

IB wherein R$^{xa}$ is at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-S(O)$_n$R$^5$, -(alkylene)$_m$-NR$^3$R$^4$, -(alkylene)$_m$-C(=O)R$^5$, -(alkylene)$_m$-C(=S)R$^5$, -(alkylene)$_m$-C(=O)OR$^5$, -(alkylene)$_m$-OC(=O)R$^5$, -(alkylene)$_m$-C(=S)OR$^5$, -(alkylene)$_m$-C(=O)NR$^3$R$^4$, -(alkylene)$_m$-C(=S)NR$^3$R$^4$, -(alkylene)$_m$-N(R$^3$)C(=O)NR$^3$R$^4$, -(alkylene)$_m$-N(R$^3$)C(=S)NR$^3$R$^4$, -(alkylene)$_m$-N(R$^3$)C(=O)R$^5$, -(alkylene)$_m$-N(R$^3$)C(=S)R$^5$, -(alkylene)$_m$-OC(=O)NR$^3$R$^4$, -(alkylene)$_m$-OC(=S)NR$^3$R$^4$, -(alkylene)$_m$-SO$_2$NR$^3$R$^4$, -(alkylene)$_m$-N(R$^3$)SO$_2$R$^5$, -(alkylene)$_m$-N(R$^3$)SO$_2$NR$^3$R$^4$, -(alkylene)$_m$-N(R$^3$)C(=O)OR$^5$, -(alkylene)$_m$-N(R$^3$)C(=S)OR$^5$, or -(alkylene)$_m$-N(R$^3$)SO$_2$R$^5$;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-OR$^{5*}$, -(alkylene)$_m$-S(O)$_n$R$^{5*}$, -(alkylene)$_m$-NR$^{3*}$R$^{4*}$, -(alkylene)$_m$-C(=O)R$^{5*}$, -(alkylene)$_m$-C(=S)R$^{5*}$, -(alkylene)$_m$-C(=O)O R$^{5*}$, -(alkylene), -OC(=O)R$^{5*}$, -(alkylene)$_m$-C(=S)OR$^{5*}$, -(alkylene)$_m$-C(=O)NR$^{3*}$R$^{4*}$, -(alkylene)$_m$-C(=S)NR$^{3*}$R$^{4*}$, -(alkylene)$_m$-N(R$^{3*}$)C(=O)NR$^{3*}$R$^{4*}$, -(alkylene)$_m$-N(R$^{3*}$)C(=S)NR$^{3*}$R$^{4*}$, -(alkylene)$_m$-N(R$^{3*}$)C(=O)R$^{5*}$, -(alkylene)$_m$-N(R$^{3*}$)C(=S)R$^{5*}$, -(alkylene)$_m$-OC(=O)NR$^{3*}$R$^{4*}$, -(alkylene)$_m$-OC(=S)NR$^{3*}$R$^{4*}$, -(alkylene)$_m$-SO$_2$NR$^{3*}$R$^{4*}$, -(alkylene)$_m$-N(R$^{3*}$)SO$_2$R$^{5*}$, -(alkylene)$_m$-N(R$^{3*}$)SO$_2$NR$^{3*}$R$^{4*}$, -(alkylene)$_m$-N(R$^{3*}$)C(=O)OR$^{5*}$, -(alkylene)$_m$-N(R$^{3*}$)C(=S)OR$^{5*}$, or -(alkylene)$_m$-N(R$^{3*}$)SO$_2$R$^{5*}$;

m is 0 or 1; and
q is zero to two.

Preferred compounds within the scope of Formula IB include compounds having any of the preferred Y, R$^1$, R$^a$ and/or R$^2$ substituents previously listed above.

Preferred compounds within the scope of Formula I include compounds having the following Formula IC

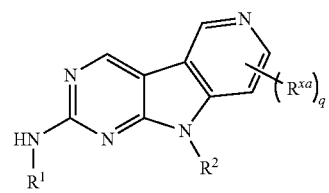

IC wherein R$^{xa}$ is at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-S(O)$_n$R$^5$, -(alkylene)$_m$-NR$^3$R$^4$, -(alkylene)$_m$-C(=O)R$^5$, -(alkylene)$_m$-C(=S)R$^5$, -(alkylene)$_m$-C(=O)OR$^5$, -(alkylene)$_m$-OC(=O)R$^5$, -(alkylene)$_m$-C(=S)OR$^5$, -(alkylene)$_m$-C(=O)NR$^3$R$^4$, -(alkylene)$_m$-C(=S)NR$^3$R$^4$, -(alkylene)$_m$-N(R$^3$)C(=O)NR$^3$R$^4$, -(alkylene)$_m$-N(R$^3$)C(=S)NR$^3$R$^4$, -(alkylene)$_m$-N(R$^3$)C(=O)R$^5$, -(alkylene)$_m$-N(R$^3$)C(=S)R$^5$, -(alkylene)$_m$-OC(=O)NR$^3$R$^4$, -(alkylene)$_m$-OC(=S)NR$^3$R$^4$, -(alkylene)$_m$-SO$_2$NR$^3$R$^4$, -(alkylene)$_m$-N(R$^3$)SO$_2$R$^5$, -(alkylene)$_m$-N(R$^3$)SO$_2$NR$^3$R$^4$, -(alkylene)$_m$-N(R$^3$)C(=O)OR$^5$, -(alkylene)$_m$-N(R$^3$)C(=S)OR$^5$, or -(alkylene)$_m$-N(R$^3$)SO$_2$R$^5$;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-OR$^{5*}$, -(alkylene), —S(O)$_n$R$^{5*}$, -(alkylene)$_m$-NR$^{3*}$R$^{4*}$, -(alkylene)$_m$-C(=O)R$^{5*}$, -(alkylene)$_m$-C(=S)R$^{5*}$, -(alkylene)$_m$-C(=O)O R$^{5*}$, -(alkylene)$_m$-OC(=O)R$^{5*}$, -(alkylene)$_m$-C(=S)OR$^{5*}$, -(alkylene)$_m$-C(=O)NR$^{3*}$R$^{4*}$, -(alkylene)$_m$-C(=S)NR$^{3*}$R$^{4*}$, -(alkylene)$_m$-N(R$^{3*}$)C(=O)NR$^{3*}$R$^{4*}$, -(alkylene)$_m$-N(R$^{3*}$)C(=S)NR$^{3*}$R$^{4*}$, -(alkylene)$_m$-N(R$^{3*}$)C(=O)R$^{5*}$, -(alkylene)$_m$-N(R$^{3*}$)C(=S)R$^{5*}$, -(alkylene)$_m$-OC(=O)NR$^{3*}$R$^{4*}$, -(alkylene)$_m$-OC(=S)NR$^{3*}$R$^{4*}$, -(alkylene)$_m$-SO$_2$NR$^{3*}$R$^{4*}$, -(alkylene)$_m$-N(R$^{3*}$)SO$_2$R$^{5*}$, -(alkylene)$_m$-

N(R³*)SO₂NR³*R⁴*, -(alkylene)ₘ-N(R³*)C(=O)OR⁵*, -(alkylene)ₘ-N(R³*)C(=S)OR⁵*, or -(alkylene)ₘ-N(R³*)SO₂R⁵*;

m is 0 or 1; and q is zero to two.

Preferred compounds within the scope of Formula IC include compounds having any of the preferred Y, R¹, Rᵃ and/or R² substituents previously listed above.

Preferred compounds within the scope of Formula I include compounds having the following Formula ID

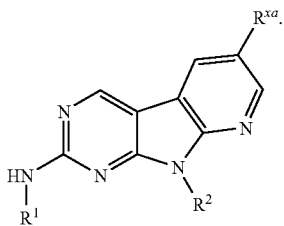

ID wherein R^xa is at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)ₘ-OR⁵, -(alkylene)ₘ-S(O)ₙR⁵, -(alkylene)ₘ-NR³R⁴, -(alkylene)ₘ-C(=O)R⁵, -(alkylene)ₘ-C(=S)R⁵, -(alkylene)ₘ-C(=O)OR⁵, -(alkylene)ₘ-OC(=O)R⁵, -(alkylene)ₘ-C(=S)OR⁵, -(alkylene)ₘ-C(=O)NR³R⁴, -(alkylene)ₘ-C(=S)NR³R⁴, -(alkylene)ₘ-N(R³)C(=O)NR³R⁴, -(alkylene)ₘ-N(R³)C(=S)NR³R⁴, -(alkylene)ₘ-N(R³)C(=O)R⁵, -(alkylene)ₘ-N(R³)C(=S)R⁵, -(alkylene)ₘ-OC(=O)NR³R⁴, -(alkylene)ₘ-OC(=S)NR³R⁴, -(alkylene)ₘ-SO₂NR³R⁴, -(alkylene)ₘ-N(R³)SO₂R⁵, -(alkylene)ₘ-N(R³)SO₂NR³R⁴, -(alkylene)ₘ-N(R³)C(=O)OR⁵, -(alkylene)ₘ-N(R³)C(=S)OR⁵, or -(alkylene)ₘ-N(R³)SO₂R⁵;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)ₘ-OR⁵*, -(alkylene),-S(O)ₙR⁵*, -(alkylene)ₘ-NR³*R⁴*, -(alkylene)ₘ-C(=O)R⁵*, -(alkylene)ₘ-C(=S)R⁵*, -(alkylene)ₘ-C(=O)O R⁵*, -(alkylene)ₘ-OC(=O)R⁵*, -(alkylene)ₘ-C(=S)OR⁵*, -(alkylene)ₘ-C(=O)NR³*R⁴*, -(alkylene)ₘ-C(=S)NR³*R⁴*, -(alkylene)ₘ-N(R³*)C(=O)NR³*R⁴*, -(alkylene)ₘ-N(R³*)C(=S)NR³*R⁴*, -(alkylene)ₘ-N(R³*)C(=O)R⁵*, -(alkylene)ₘ-N(R³*)C(=S)R⁵*, -(alkylene)ₘ-OC(=O)NR³*R⁴*, -(alkylene)ₘ-OC(=S)NR³*R⁴*, -(alkylene)ₘ-SO₂NR³*R⁴*, -(alkylene)ₘ-N(R³*)SO₂R⁵*, -(alkylene)ₘ-N(R³*)SO₂NR³*R⁴*, -(alkylene)ₘ-N(R³*)C(=O)OR⁵*, -(alkylene)ₘ-N(R³*)C(=S)OR⁵*, or -(alkylene)ₘ-N(R³*)SO₂R⁵*;

m is 0 or 1; and q is zero to two.

Preferred compounds within the scope of Formula ID include compounds having any of the preferred Y, R¹, Rᵃ and/or R² substituents previously listed above.

Preferred compounds within the scope of Formula I include compounds having the following Formula IE

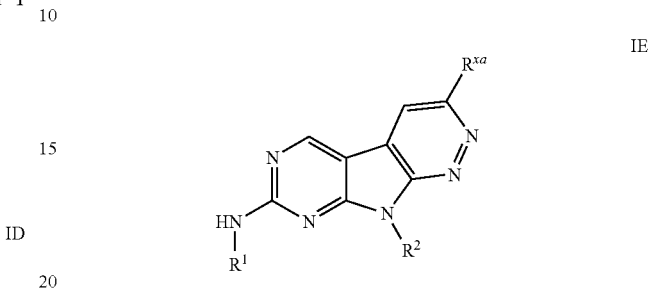

IE wherein R^xa is at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)ₘ-OR⁵, -(alkylene)ₘ-S(O)ₙR⁵, -(alkylene)ₘ-NR³R⁴, -(alkylene)ₘ-C(=O)R⁵, -(alkylene)ₘ-C(=S)R⁵, -(alkylene)ₘ-C(=O)OR⁵, -(alkylene)ₘ-OC(=O)R⁵, -(alkylene)ₘ-C(=S)OR⁵, -(alkylene)ₘ-C(=O)NR³R⁴, -(alkylene)ₘ-C(=S)NR³R⁴, -(alkylene)ₘ-N(R³)C(=O)NR³R⁴, -(alkylene)ₘ-N(R³)C(=S)NR³R⁴, -(alkylene)ₘ-N(R³)C(=O)R⁵, -(alkylene)ₘ-N(R³)C(=S)R⁵, -(alkylene)ₘ-OC(=O)NR³R⁴, -(alkylene)ₘ-OC(=S)NR³R⁴, -(alkylene)ₘ-SO₂NR³R⁴, -(alkylene)ₘ-N(R³)SO₂R⁵, -(alkylene)ₘ-N(R³)SO₂NR³R⁴, -(alkylene)ₘ-N(R³)C(=O)OR⁵, -(alkylene)ₘ-N(R³)C(=S)OR⁵, or -(alkylene)ₘ-N(R³)SO₂R⁵;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)ₘ-OR⁵*, -(alkylene)ₘ-S(O)ₙR⁵*, -(alkylene)ₘ-NR³*R⁴*, -(alkylene)ₘ-C(=O)R⁵*, -(alkylene)ₘ-C(=S)R⁵*, -(alkylene)ₘ-C(=O)O R⁵*, -(alkylene)ₘ-OC(=O)R⁵*, -(alkylene)ₘ-C(=S)OR⁵*, -(alkylene)ₘ-C(=O)NR³*R⁴*, -(alkylene)ₘ-C(=S)NR³*R⁴*, -(alkylene)ₘ-N(R³*)C(=O)NR³*R⁴*, -(alkylene)ₘ-N(R³*)C(=S)NR³*R⁴*, -(alkylene)ₘ-N(R³*)C(=O)R⁵*, -(alkylene)ₘ-N(R³*)C(=S)R⁵*, -(alkylene)ₘ-OC(=O)NR³*R⁴*, -(alkylene)ₘ-OC(=S)NR³*R⁴*, -(alkylene)ₘ-SO₂NR³*R⁴*, -(alkylene)ₘ-N(R³*)SO₂R⁵*, -(alkylene)ₘ-N(R³*)SO₂NR³*R⁴*, -(alkylene)ₘ-N(R³*)C(=O)OR⁵*, -(alkylene)ₘ-N(R³*)C(=S)OR⁵*, or -(alkylene)ₘ-N(R³*)SO₂R⁵*;

m is 0 or 1; and q is zero to two.

Preferred compounds within the scope of Formula IE include compounds having any of the preferred Y, R¹, Rᵃ and/or R² substituents previously listed above.

Certain compounds within the scope of the present invention exist as keto-enol tautomers. For example compounds such as the following:

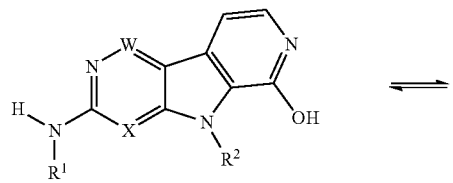  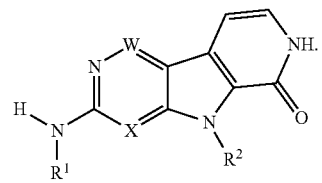

The current invention further provides a method of treating disorders or conditions consisting of abnormal cell proliferation, such as cancer, atherosclerosis, postsurgical vascular stenosis, restenosis, and endometriosis; infections, including viral infections such as DNA viruses like herpes and RNA viruses like HIV, and fungal infections; autoimmune diseases such as psoriasis, inflammation like rheumatoid arthritis, lupus, type 1 diabetes, diabetic nephropathy, multiple sclerosis, and glomerulonephritis, organ transplant rejection, including host versus graft disease, in a mammal, including human, comprising administering to said mammal an amount of a compound of formula I or II, or a pharmaceutically acceptable salt thereof, that is effective in treating such disorder or condition.

This invention further provides compounds of Formula I and II that are useful for treating abnormal cell proliferation such as cancer. The invention provides a method of treating a abnormal cell proliferation disorder such as myeloid disorders, lymphoid disorders, Hodgkin's hairy cells, leukemia, cancers of the breast, lung, colon, ovary, cervix, prostrate, testis, esophagus, stomach, skin, bone, pancreas, thyroid, biliary passages, buccal cavity and pharyns (oral), lip, tongue, mouth, pharynx, small intestine, colon-rectum, large intestine, rectum, brain and central nervous system, glioblastoma, neuroblastoma, keratocanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, and kidney carcinoma, comprising administering a therapeutically effective amount of a compound of formula I, or a pharmaceutically acceptable salt thereof, to a subject with one or more above disorders.

Embodiment of this invention is also a method of treating subjects with diseases caused by vascular smooth muscle cell proliferation. The method comprises administering to a subject with such a disorder an amount of a compound of formula I, or a pharmaceutically acceptable salt thereof.

This invention further provides a method of treating a subject suffering from gout comprising administering to said subject in need of treatment an amount of a compound of formula I, or a pharmaceutically acceptable salt thereof, sufficient to treat the condition.

The present invention further provides a method of treating a subject with kidney disease, such as polycystic kidney disease, comprising administering to said subject in need of treatment an amount of a compound of formula I and II, or a pharmaceutically acceptable salt thereof, sufficient to treat the condition.

Definitions

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

The term "treatment" includes therapeutic treatment as well as prophylactic treatment (either preventing the onset of disorders altogether or delaying the onset of a pre-clinically evident stage of disorders in individuals).

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylene" embraces bridging divalent alkyl radicals such as methylene, ethylene, propylene, isopropylene and the like. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

Alkyl, alkylenyl, alkenyl, and alkynyl radicals may be optionally substituted with one or more functional groups such as halo, hydroxy, nitro, amino, cyano, haloalkyl, aryl, heteroaryl, heterocyclo and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 or more substituents such as lower alkyl, hydroxyl, halo, haloalkyl, nitro, cyano, alkoxy, lower alkylamino, and the like. Phenyl substituted with —O—CH$_2$—O-forms the aryl benzodioxolyl substituent.

The term "heterocyclyl" (or "heterocyclo") embraces saturated, and partially saturated heteroatom-containing ring radicals, where the heteroatoms may be selected from nitrogen, sulfur and oxygen. Heterocyclic rings comprise monocyclic 6-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term heterocyclyl, (or heterocyclo) also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl].

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—$SO_2NH_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "aminocarbonyl" denotes an amide group of the formula —C(=O)$NH_2$.

The terms "N-alkylaminocarbonyl" and "N,N-dialkylaminocarbonyl" denote aminocarbonyl radicals independently substituted with one or two alkyl radicals, respectively. More preferred are "lower allylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "aralkylamino" denotes amino groups, which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups, which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament.

The present invention comprises a pharmaceutical composition comprising a therapeutically effective amount of a compound of the current invention in association with a least one pharmaceutically acceptable carrier, adjuvant or diluent.

The present invention also comprises a method of treating angiogenesis related disorders in a subject having or susceptible to such disorder, the method comprising treating the subject with a therapeutically effective amount of a compound of the current invention.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of the current invention may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycin, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Wamer-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminol evulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracilltegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including N-(4-chlorophenyl)-4-(4-pyridinylmethyl)-1-phthalazinamine;

4-[4-[[[[4-chloro-3-(trifluoromethyl)phenyl]amino]carbonyl]amino]phenoxy]-N-methyl-2-pyridinecarboxamide;

N-[2-(diethylamino)ethyl]-5-[(5-fluoro-1,2-dihydro-2-oxo-3H-indol-3-ylidene)methyl]-2,4-dimethyl-1H-pyrrole-3-carboxamide;

3-[(4-bromo-2,6-difluorophenyl)methoxy]-5-[[[[4-(1-pyrrolidinyl)butyl]amino]carbonyl]amino]-4-isothiazolecarboxamide;

N-(4-bromo-2-fluorophenyl)-6-methoxy-7-[(1-methyl-4-piperidinyl)methoxy]-4-quinazolinamine;

3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine;

N-[5-[[[5-(1 , 1-dimethyl ethyl)-2-o xazolyl]methyl]thio]-2-thiazolyl]-4-piperidinecarboxamide;

N-[3-chloro-4-[(3-fluorophenyl)methoxy]phenyl]-6-[5-[[[2-(methylsulfonyl)ethyl]amino]methyl]-2-furanyl]-4-quinazolinamine 4-[(4-Methyl-1-piperazinyl)methyl]-N-[4-methyl-3-[[4-(3-pyridinyl)-2-pyrimidinyl]amino]-phenyl]benzamide N-(3-chloro-4-fluorophenyl)-7-methoxy-6-[3-(4-morpholinyl)propoxy]-4-quinazolinamine N-(3-ethynylphenyl)-6,7-bis(2-methoxyethoxy)-4-quinazolinamine N-(3-((((2R)-1-methyl-2-pyrrolidinypmethyl)oxy)-5-(trifluoromethyl)phenyl)-2-((3-(1,3-oxazol-5-yl)phenyl)amino)-3-pyridinecarboxamide;

2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide;

N-[3-(Azetidin-3-ylmethoxy)-5-trifluoromethyl-phenyl]-2-(4-fluoro-benzylamino)-nicotinamide.

6-fluoro-N-(4-(1-methylethyl)phenyl)-2-((4-pyridinylmethyl)amino)-3-pyridinecarboxamide;

2-((4-pyridinylmethyl)amino)-N-(3-(((2S)-2-pyrrolidinylmethyl)oxy)-5-(trifluoromethyl)phenyl)-3-pyridinecarboxamide;

N-(3-(1 , 1-dimethylethyl)-1H-pyrazol-5-yl)-2-((4-pyridinylmethyl)amino)-3-pyridinecarboxamide;

N-(3,3-dimethyl-2,3-dihydro-1-benzofuran-6-yl)-2-((4-pyridinylmethyl)amino)-3-pyridinecarboxamide;

N-(3-((((2S)-1-methyl-2-pyrrolidinyl)methyl)oxy)-5-(trifluoromethyl)phenyl)-2-((4-pyridinylmethyl)amino)-3-pyridinecarboxamide;

2-((4-pyridinylmethyl)amino)-N-(3-((2-(1-pyrrolidinyl)ethyl)oxy)-4-(trifluoromethyl)phenyl)-3-pyridinecarboxamide;

N-(3,3-dimethyl-2,3-dihydro-1H-indol-6-yl)-2-((4-pyridinylmethyl)amino)-3-pyridinecarboxamide;

N-(4-(pentafluoroethyl)-3-(((2S)-2-pyrrolidinylmethypoxy)phenyl)-2-((4-pyridinylmethyl)amino)-3-pyridinecarboxamide;

N-(3-((3-azetidinylmethypoxy)-5-(trifluoromethyl)phenyl)-2-((4-pyridinylmethyl)amino)-3-pyridinecarboxamide;

N-(3-(4-piperidinyloxy)-5-(trifluoromethyl)phenyl)-2-((2-3-pyridinyl)ethyl)amino)-3-pyridinecarboxamide;

N-(4,4-dimethyl-1,2,3,4-tetrahydro-isoquinolin-7-yl)-2-(1H-indazol-6-ylamino)-nicotinamide;

2-(1H-indazol-6-ylamino)-N-[3-(1-methylpyrrolidin-2-ylmethoxy)-5-trifluoromethyl-phenyl]-nicotinamide;

N-[1-(2-dimethylamino-acetyl)-3,3-dimethyl-2,3-dihydro-1H-indol-6-yl]-2-(1H-indazol-6-ylamino)-nicotinamide;

2-(1H-indazol-6-ylamino)-N-[3-(pyrrolidin-2-ylmethoxy)-5-trifluoromethyl-phenyl]-nicotinamide;

N-(1-acetyl-3,3-dimethyl-2,3-dihydro-1H-indol-6-yl)-2-(1H-indazol-6-ylamino)-nicotinamide;
N-(4,4-dimethyl-1-oxo-1,2,3,4-tetrahydro-isoquinolin-7-yl)-2-(1H-indazol-6-ylamino)-nicotinamide;
N-[4-(tert-butyl)-3-(3-piperidylpropyl)phenyl][2-(1H-indazol-6-ylamino)(3-pyridyl)]carboxamide;
N-[5-(tert-butyl)isoxazol-3-yl][2-(1H-indazol-6-ylamino)(3-pyridyl)]carboxamide; and
N-[4-(tert-butyl)phenyl][2-(1H-indazol-6-ylamino)(3-pyridyl)]carboxamide.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ERBITIA™ (IMC-C225), and VECTIBIX™ (panitumumab) IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents. The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-Met" as well as small molecules inhibitors of the c-Met kinase activity.

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (WAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG , (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors (such as panitumumab), CDK inhibitors, TNF inhibitors, metallomatrix proteases inhibitors (MMP), COX-2 inhibitors including celecoxib, NSAID's, $\alpha_v\beta_3$ inhibitors, phosphatidylinitisol 3-kinase inhibitors, AKT/PCK inhibitors, proteasome inhibitors (such as Velcade™), Trail receptor agonists (such as AMG 655), Trail (such as AMG 951), XIAP inhibitors, BCl2 inhibitors, Aurora kinase inhibitors, Raf kinases inhibitors, ubiquitin ligase inhibitors, HGF inhibitors (such as AMG 102), and c-Met inhibitors (such as compounds described WO 06/116713 and U.S. Ser. No. 11/879,034).

Also included in the family of compounds of the current are the pharmaceutically acceptable salts and solvates thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the current invention may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, f3-hydroxybutyric, salicylic, galactaric and galacturonic acid. Suitable pharmaceutically-acceptable base addition salts of compounds of the current invention include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of the current invention. When a basic group and an acid group are present in the same molecule, a compound of the current invention may also form internal salts.

General Synthetic Procedures

The compounds of the invention can be synthesized according to the procedures illustrated in the following working examples, as well as by alternative methods known to those of ordinary skill in the art.

Additional analogs can be prepared by the following general schemes.

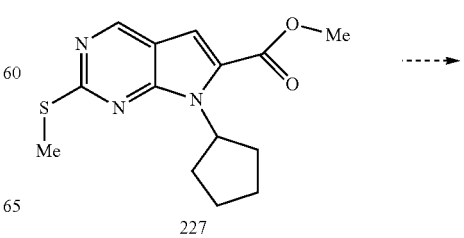

227

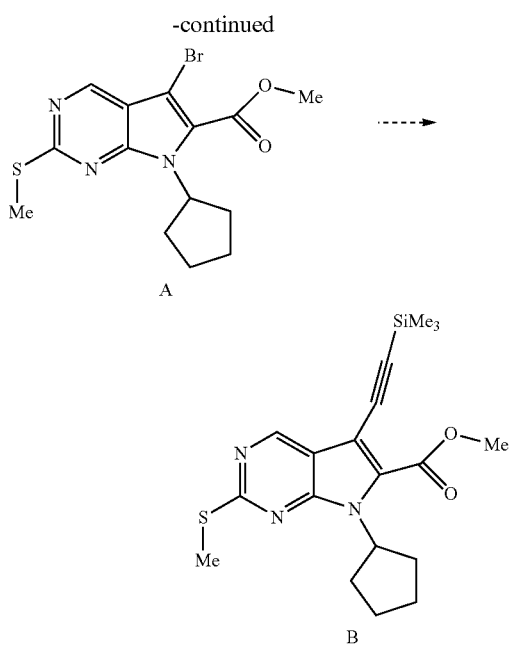

Bromination of compound 227 with NBS in analogy to the preparation of compound 230 of example 168 provides bromo ester A. Sonagshira coupling provides the alkyne B. Grignard addition provides the tertiary alcohol C. Mild acidic workup provides the fused pyran D.

The thiomethyl group of compounds D and E can be converted to typical substituted heteroaryl and aryl amines in analogy to example 168 providing inhibitors such as F and G.

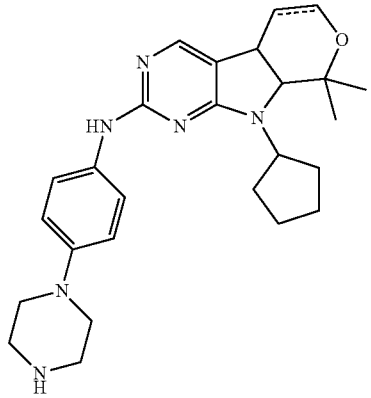

F/G

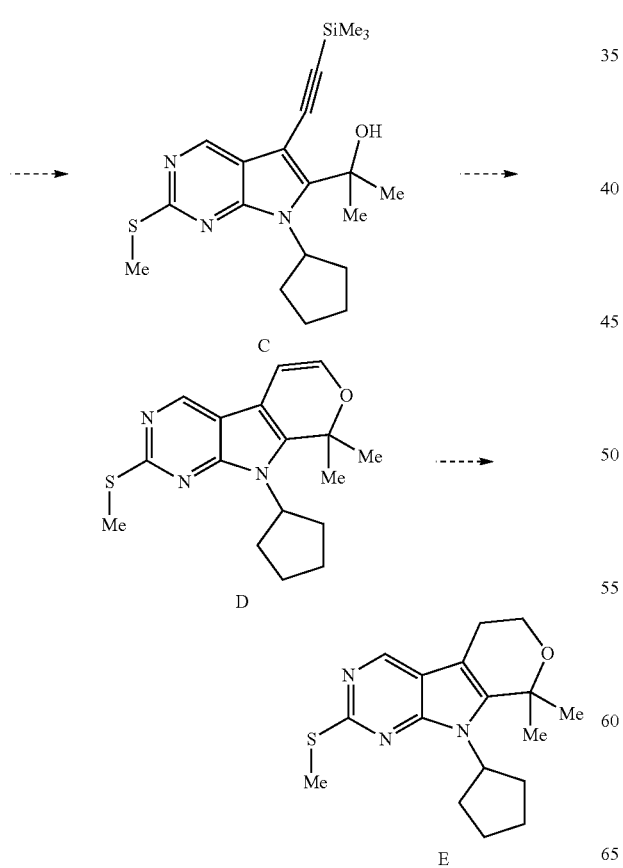

Condensation of amine 225 with pyrimidine 222 provides diester A2 which can undergo claisen condensation to the keto ester B2, which is a versatile intermediate for a number of transformations. Condensation with hydrazines can lead to fused pyrazoles such a C2 and D2, which can be further modified to examples of this invention.

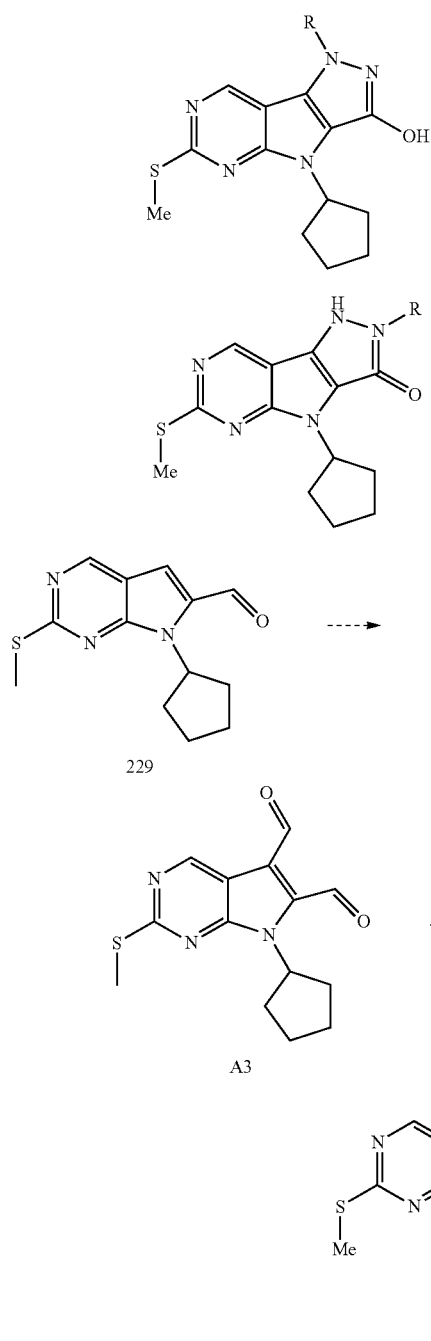

229

A3

B3

Aldehdye 229 can be formylated to an equivalent of the dialdehyde A3 which can be used to form the fused pyridazine B3, which can be further modified to examples of this invention.

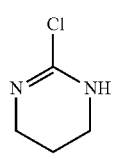

A4

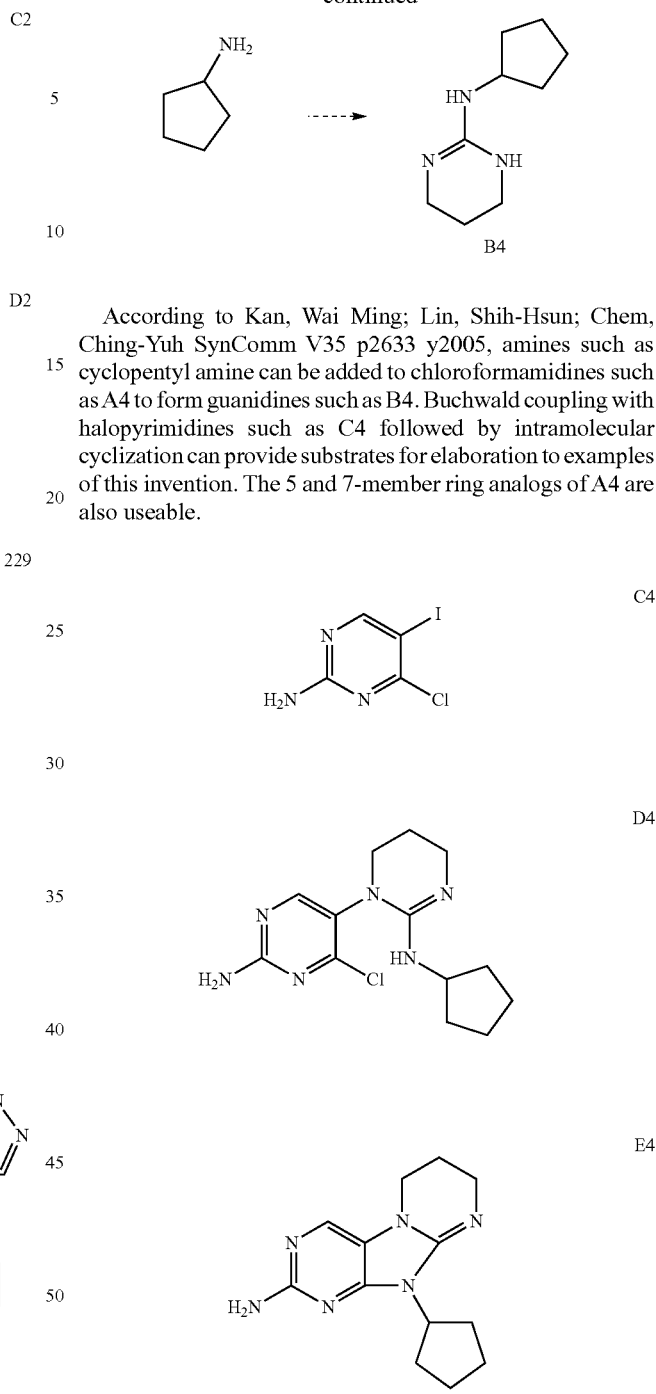

B4

According to Kan, Wai Ming; Lin, Shih-Hsun; Chem, Ching-Yuh SynComm V35 p2633 y2005, amines such as cyclopentyl amine can be added to chloroformamidines such as A4 to form guanidines such as B4. Buchwald coupling with halopyrimidines such as C4 followed by intramolecular cyclization can provide substrates for elaboration to examples of this invention. The 5 and 7-member ring analogs of A4 are also useable.

C4

D4

E4

The use of uracil A5 or dialkoxypyrimidine heterocycles can lead to more elaborate analogs.

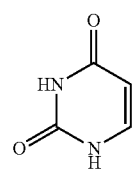

B5

37
-continued

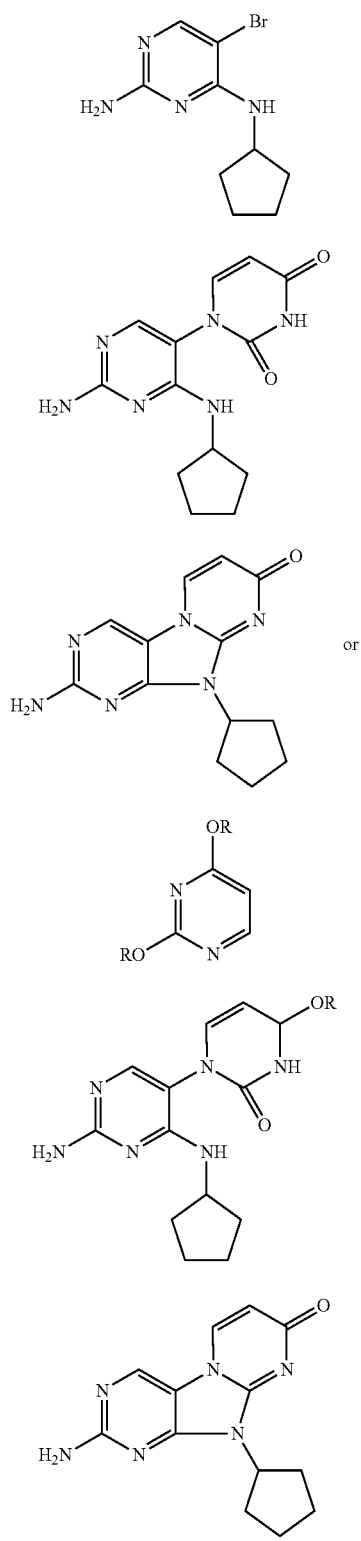

38 readily recognize a variety of noncritical parameters that could be changed or modified to yield essentially similar results.

Example 1

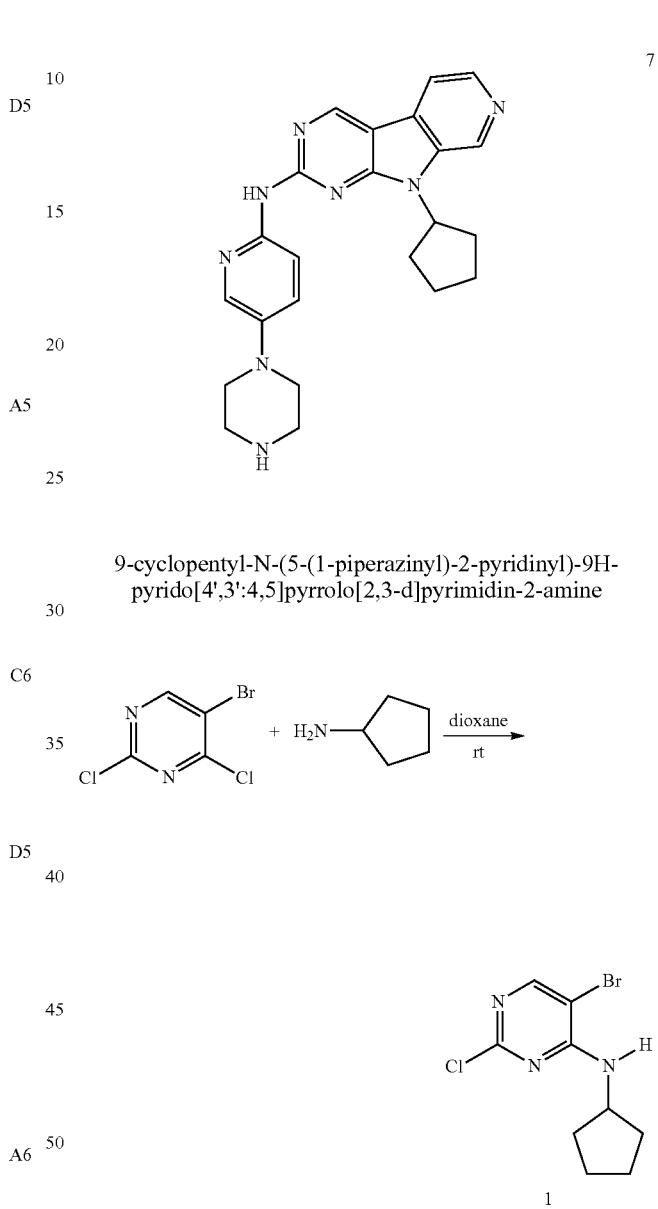

9-cyclopentyl-N-(5-(1-piperazinyl)-2-pyridinyl)-9H-pyrido[4',3':4,5]pyrrolo[2,3-d]pyrimidin-2-amine

EXAMPLES

The following examples are provided by way of illustration only and not by way of limitation. Those of skill in the art will 5-Bromo-2-chloro-N-cyclopentylpyrimidin-4-amine (1): To a solution of 5-bromo-2,4-dichloropyrimidine (45.6 g, 200 mmol) in dioxane (400 mL) was added N-cyclopentylamine (20.4 g, 240 mmol) at room temperature. The mixture thus obtained was stirred at room temperature for 6 h. The reaction mixture was then diluted with ethyl acetate and washed with brine and dried over MgSO$_4$. The solvent was evaporated to give the title compound as a light yellow solid (56 g, 100%) which was used in next step without further purification. $^1$H NMR (500 MHz, DMSO-d6) δ 8.23 (1H, s), 7.37 (1H, d, J=7.3 Hz), 4.31 (1H, m), 1.92 (2H, m), 1.71 (2H, m), 1.53-1.59 (4H, m) ppm; LCMS-ESI (POS), M/Z, M+1: Found 276.0, Calculated 275.9.

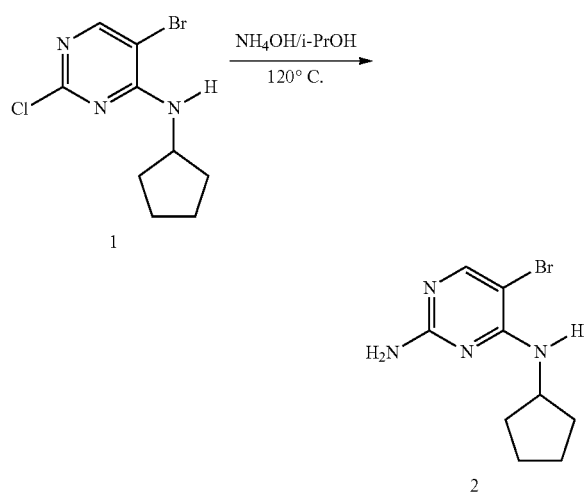

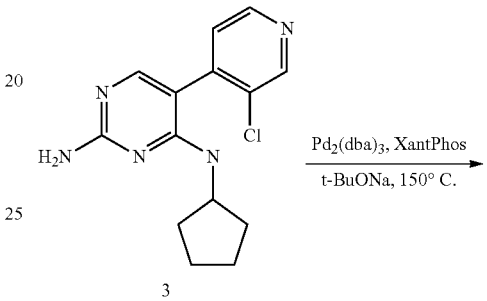

5-Bromo-N⁴-cyclopentylpyrimidine-2,4-diamine (2): A solution of 1 (45 g, 200 mmol) in 28% NH₄OH/iso-propanol (1/1, 400 mL) was heated at 120° C. in a sealed tube for 22 h. The product was extracted with dichloromethane and the organic layers were washed with brine and dried. The solvent was evaporated and the residue was purified by flash chromatography on silica gel eluting with 25% ethyl acetate in hexanes to give the titled compound (2) as a white solid (34 g, 66%). ¹H NMR (500 MHz, DMSO-d₆) δ 7.77 (1H, s), 6.19 (2H, br. s), 6.12 (1H, d, 1H, J=7.3 Hz), 4.33 (1H, m) 1.90 (2H, m), 1.69 (2H, m), 1.49-1.55 (4H, m) ppm; LCMS-ESI (POS), M/Z, M+1: Found 257.0, Calculated 257.0.

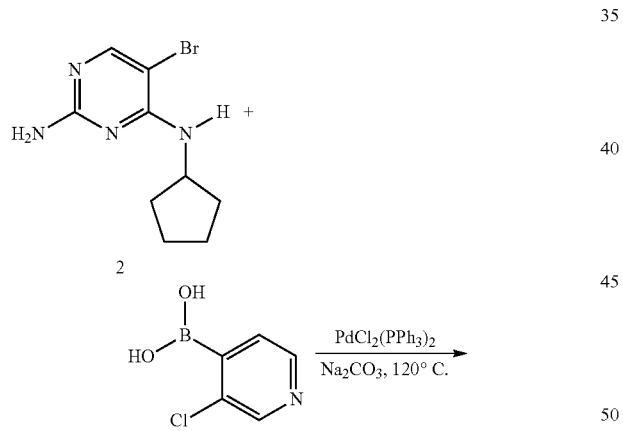

5-(3-Chloropyridin-4-yl)-N⁴-cyclopentylpyrimidine-2,4-diamine (3): To a solution of 2 (2.57 g, 10.0 mmol) in dioxane (75 mL) were added 3-chloropyridine-4-boronic acid (4.72 g, 10.0 mmol), trans-dichlorobis(triphenylphosphine)-palladium(II) (702 mg, 1.0 mmol), and sodium carbonate (3.82 g, 36 mmol, in 36 mL of water). The mixture thus obtained was purged with N₂ for 10 min and heated at 120° C. in a sealed tube for 22 h. The reaction mixture was diluted with water and the product was extracted with chloroform. The organic layers were dried (MgSO₄) and concentrated. The residue was purified by flash chromatography on silica gel eluting with 2.5% methanol in dichloromethane to give the title compound (3) as a white solid (2.31 g, 80%). ¹H NMR (500 MHz, DMSO-d₆) δ 8.64 (1H, s), 8.50 (1H, d, J=4.9 Hz), 7.51 (1H, s), 7.34 (1H, d, 1H, J=4.9 Hz), 6.21 (2H, d, 1H, br s), 5.97 (1H, d, J =7.6 Hz), 4.43 (1H, p, J=7.4 Hz), 1.84 (2H, m), 1.62 (2H, m), 1.40-1.49 (4H, m) ppm; LCMS-ESI (POS), M/Z, M+1: Found 290.0, Calculated 290.1.

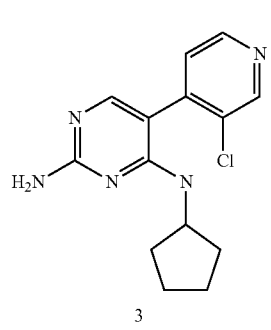

9-Cyclopentyl-9H-pyrido[4',3':4,5]pyrrolo[2,3-d]pyrimidin-2-amine (4): To a solution of 3 (2.3 g, 7.9 mmol) in dioxane (60 mL) were added tris(dibenzylideneacetone)dipalladium (0) (368 mg, 0.4 mmol), 4,5-bis(diphenylphosphino)-9,9-dimethylxanthene (696 mg, 1.2 mmol), and sodium t-butoxide (1.15 g, 12 mmol). The mixture thus obtained was heated at 150° C. under microwave irradiation for 3 h. The reaction mixture was passed through a short pack silica gel column and concentrated. The residue was purified by flash chromatography on silica gel eluting with 2% methanol in dichloromethane to give the title compound (4) as a white solid (1.71 g, 85%). ¹H NMR (500 MHz, DMSO-d₆) δ 9.05 (1H, s), 8.87 (1H, br. s), 8.37 (1H, d, J=4.9 Hz), 7.93 (1H, d, J=5.1 Hz), 6.97 (2H, br. s), 5.33 (1H, p, J=8.6 Hz), 2.27 (2H, m), 2.04 (4H, m), 1.76 (2H, m) ppm; LCMS-ESI (POS), M/Z, M+1: Found 254.1, Calculated 254.1.

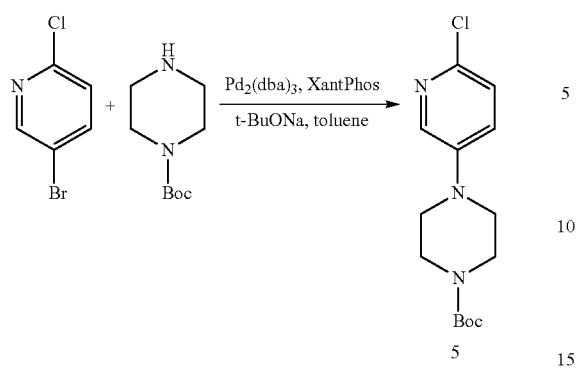

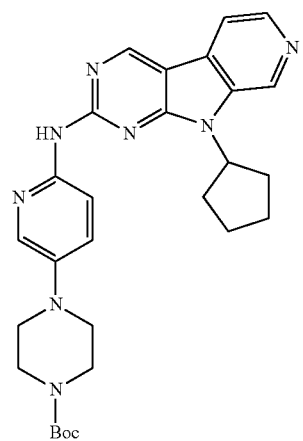

4-(4-Chloro-pyrid-2-yl)-piperidine-1-carboxylic acid t-butyl ester (5): As reported in Ji, J.; Li, T.; Bunnelle, W. H., *Org. Lett.* 2003, 5, (24), 4611-4614, t-butyl 1-piperazinecarboxylate (11.18 g, 60 mmol), sodium t-butoxide (8.64 g, 90 mmol), $Pd_2(dba)_3$ (1.10 g, 1.20 mmol), and XantPhos (2.08 g, 3.6 mmol) were added to a solution of 5-bromo-2-chloropyridine (11.54 g, 60 mmol) in toluene (300 mL). The mixture was evacuated and purged with argon (3 cycles), then heated at 100° C. for 5 h. The reaction mixture was then cooled to room temperature, diluted with ethyl acetate (1200 mL) and washed with water (300 mL). The organic solution was concentrated under pressure, and the residue was purified by flash chromatography on silica gel eluting with 17% ethyl acetate in hexane to give compound 5 as a light yellow solid (14.56 g, 82%). $^1$H NMR (400 MHz, $CDCl_3$) δ 8.02 (1H, s), 7.19-7.18 (2H, m), 3.59 (4H, dd, J=12 Hz, J=4 Hz), 3.14 (4H, dd, J=12 Hz, J=4 Hz), 1.49 (9H, s) ppm; LCMS-ESI (POS), M/Z, M+1: Found 298.1, Calculated 298.1.

t-Butyl 4-(6-((9-cyclopentyl-9H-pyrido[4',3':4,5]pyrrolo[2,3-d]pyrimidin-2-yl)amino)-3-pyridinyl)-1-piperazinecarboxylate (6): To a solution of compound 4 (1.6 g, 6.3 mmol) in dioxane (60 mL) were added compound 5 (2.3 g, 7.6 mmol), tris(dibenzylideneacetone) dipalladium (0) (293 mg, 0.32 mmol), 4,5-bis(diphenylphosphino)-9,9-dimethylxanthene (370 mg, 0.64 mmol), and sodium t-butoxide (908 mg, 9.45 mmol). The mixture thus obtained was heated at 150° C. under microwave irradiation for 1 h. The reaction mixture was passed through a short pack silica gel column and concentrated to give the title compound 6 as a yellow solid (3.28 g) which was used in next step without further purification. $^1$H NMR (500 MHz, DMSO-$d_6$) δ 9.11 (1H, s), 8.93 (1H, br. s), 8.53 (1H, d, J=5.1 Hz), 8.44 (1H, d, J=9.3 Hz), 8.28 (1H, br. s), 8.09 (1 H, d, J=2.9 Hz), 7.87 (1H, dd, J=5.1 Hz, 0.9 Hz), 7.41 (1H, dd, J=9.3 Hz, 2.9 Hz), 5.40 (1H, p, J=8.8 Hz), 3.65 (4H, t, J=5.2 Hz), 3.15 (4H, t, J=4.9 Hz), 2.46 (2H, m), 2.15-24 (4H, m), 1.91 (2H, m), 1.52 (9H, s) ppm; LCMS-ESI (POS), M/Z, M+1: Found 515.2, Calculated 515.3.

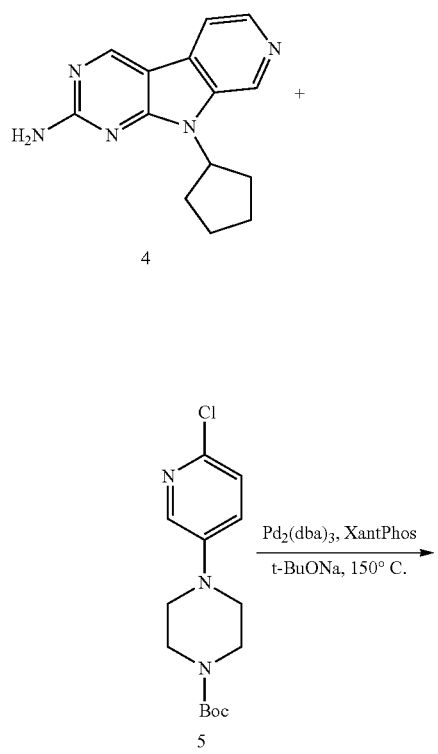

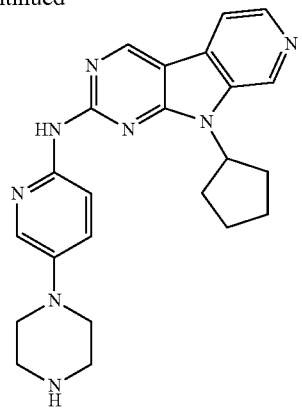

7

9-Cyclopentyl-N-(5-(1-piperazinyl)-2-pyridinyl)-9H-pyrido[4',3':4,5]pyrrolo[2,3-d]pyrimidin-2-amine (7): A solution of compound 6 (3.28 g, 6.37 mmol) in TFA/DCM (60, 1:1) was stirred at room temperature for 30 min. The reaction mixture was concentrated and the residue was purified by chromatography on silica gel eluting with $CH_2Cl_2$/methanol/ $NR_4OH$ (200:10:1) to give the title compound (7) as an off-white solid (2.60 g, 98%). $^1H$ NMR (400 MHz, DMSO-$d_6$) δ 9.86 (1H, s), 9.28 (1H, s), 9.01 (1H, s), 8.68 (1H, br s), 8.45 (1H, d, J=4 Hz), 8.23 (1 H, d, J=8 Hz), 8.10 (1H, d, J=4 Hz), 8.04 (1H, d, J=8 Hz), 7.54 (1H, dd, J=8 Hz, J=4 Hz), 5.43 (1H, p, J=8 Hz), 3.35 (4H, m), 3.26 (4H, m), 2.40 (2H, m), 2.03-2.10 (4H, m), 1.78 (2H, m) ppm; LCMS-ESI (POS), M/Z, M+1: Found 415.1, Calculated 415.2.

Example 2

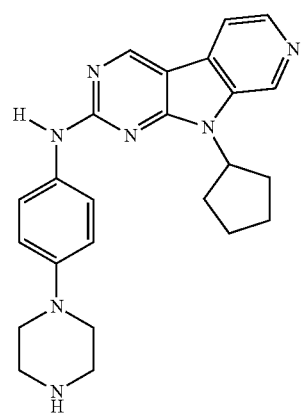

8

9-Cyclopentyl-N-(5-(1-($N^4$-methylpiperazinyl))-2-pyridinyl)-9H-pyrido-[4',3':4,5]pyrrolo[2,3-d]pyrimidin-2-amine Compound 8 was prepared using chemistry similar to that described in example 1. $^1H$ NMR (500 MHz, CDCl$_3$) δ 9.07 (1H, s), 8.90 (1H, s), 8.51 (1H, d, J=5 Hz), 8.39 (1H, d, J=8 Hz), 8.06 (1H, s), 8.05 (1 H, s), 7.84 (1H, d, J=5 Hz), 7.39 (1H, dd, J=8 Hz, J=2 Hz), 5.39 (1H, p, J=8 Hz), 3.22 (4H, t, J=5 Hz), 2.63 (4H, t, J=5 Hz), 2.44 (2H, m), 2.39 (3H, s), 2.14-2.21 (4H, m), 1.88 (2H, m) ppm; LCMS-ESI (POS), M/Z, M+1: Found 429.2, Calculated 429.2.

Example 3

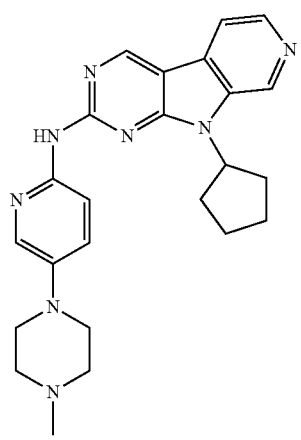

9

(9-Cyclopentyl-9H-pyrido[4',3':4,5]pyrrolo[2,3-d] pyrimidin-2-yl)-(4-piperazin-1-yl-phenyl)-amine Compound 9 was prepared using chemistry similar to that described in example 1. $^1H$ NMR (500 MHz, CD$_3$OD) δ 9.39 (1 H, s), 9.15 (1 H, s), 8.49 (2 H, s), 7.72 (2 H, d, J=5.0 Hz), 7.11 (2 H, d, J=5.0 Hz), 5.33 (1 H, m), 3.43 (8 H, m), 2.54 (2 H, m), 2.22 (2 H, m), 2.21 (2 H, m), 1.86 (2 H, m) ppm; LCMS-ESI (POS), M/Z, M+1: Found 414.2, Calculated 414.2.

Example 4

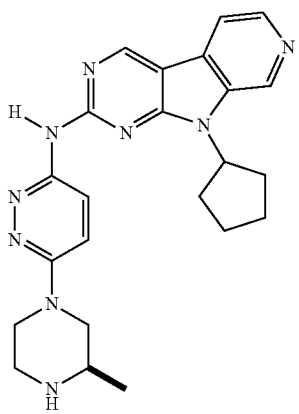

10

(R)-9-cyclopentyl-N-(6-(1-(3-methylpiperazinyl)-3-pyridazinyl)-9H-pyrido[4',3':4,5]-pyrrolo[2,3d]pyrimidin-2-amine

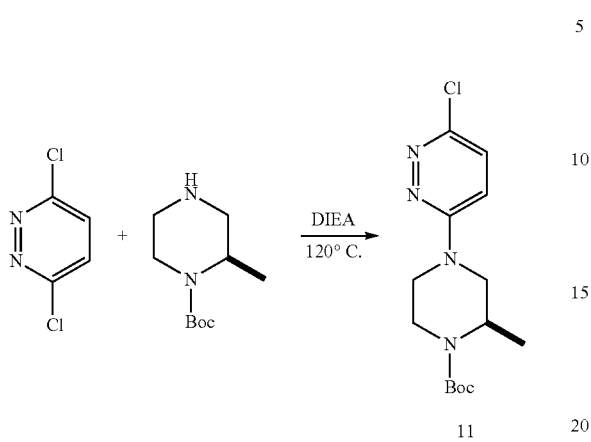

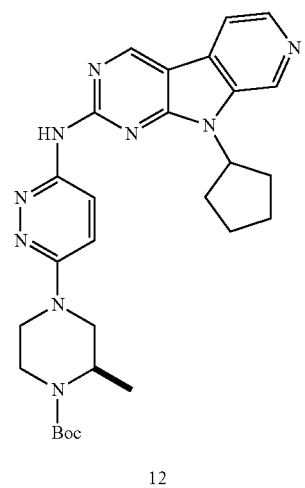

12

(R)-tert-butyl 4-(6-chloropyridazin-3-yl)-2-methylpiperazine-1-carboxylate (11): A mixture of 3,6-dichloropyridazine (298 mg, 2 mmol) and (R)-1-N-Boc-2-methyl piperazine (401 mg, 2.0 mmol) in N,N-diisopropylethylamine (0.7 mL, 4 mmol) was stirred at 120° C. for 5 h. The reaction mixture was diluted with ethyl acetate and washed with brine (2×), then dried over MgSO$_4$. The salts were removed by filtration and the filtrate was concentrated and the residue was purified by chromatography on silica gel eluting with 20% to 80% ethyl acetate in hexane to give compound 11 as a light yellow solid (511 mg, 82%). $^1$H NMR (500 MHz, CD$_3$OD) δ 7.24 (1H, d, J=10 Hz), 6.88 (1H, d, J=10 Hz), 4.38 (1H, br s), 4.17 (1H, d, J=10 Hz), 4.05-3.97 (2H, m), 3.39 (1H, dd, J=15 Hz, J=5 Hz), 3.29 (1H, ddd, J=15 Hz, J=10 Hz, J=5 Hz), 1.51 (9H, s), 1.21 (3H, d, J=10 Hz) ppm; LCMS-ESI (POS), M/Z, M+1: Found 313.1, Calculated 313.1.

t-Butyl 4-(6-((9-cyclopentyl-9H-pyrido[4',3':4,5]pyrrolo[2,3-d]pyrimidin-2-yl)amino)-3-pyridazinyl)-1-piperazinecarboxylate (12): To a solution of compound 4 (112 mg, 0.40 mmol) in dioxane (4 mL) were added compound 11 (150 mg, 0.48 mmol), tris(dibenzylideneacetone)dipalladium (0) (18.4 mg, 0.02 mmol), 4,5-bis(diphenylphosphino)-9,9-dimethylxanthene (35 mg, 0.06 mmol), and sodium t-butoxide (58 mg, 0.60 mmol). The mixture thus obtained was heated at 150° C. under microwave irradiation for 1 h. The reaction mixture was passed through short pack silica gel column and concentrated to give a crude 12 (purity=85%) as a yellow solid (240 mg) which was used in next step without further purification. LCMS-ESI (POS), M/Z, M+1: Found 530.3, Calculated 530.3.

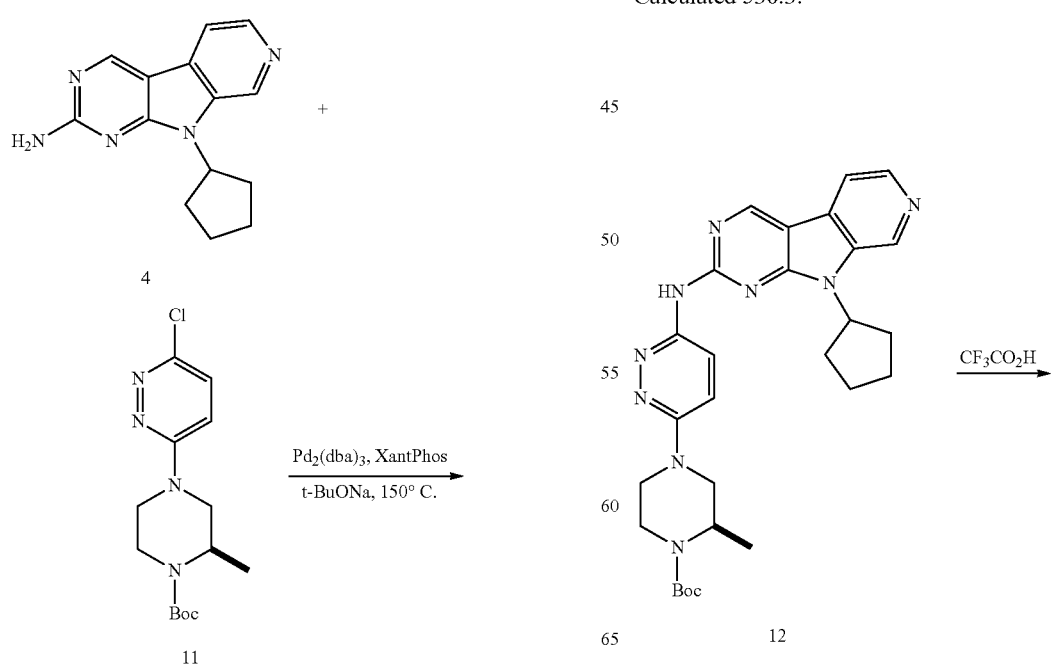

m), 2.32 (3H, s), 2.13 (2H, m), 2.00 (2H, m), 1.74 (2H, m) ppm; LCMS-ESI (POS), M/Z, M+1: Found 429.2, Calculated 429.2.

Example 6

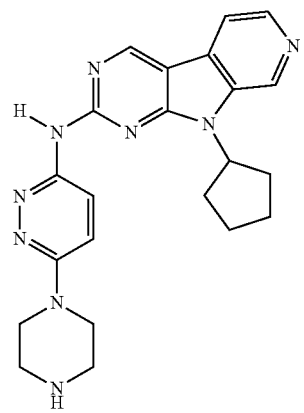

14

9-cyclopentyl-N-(6-(1-piperazinyl)-3-pyridazinyl)-9H-pyrido[4',3':4,5]-pyrrolo[2,3d]pyrimidin-2-amine Compound 14 was prepared using chemistry similar to that described in example 4. ¹H NMR (500 MHz, DMSO-d₆) δ 11.16 (1H, br s), 9.63 (1H, s), 9.41 (1H, s), 9.01 (2H, br s), 8.71 (1H, d, J=6.1 Hz), 8.64 (1H, d, J=6.1 Hz), 8.23 (1H, d, J=9.8 Hz), 7.69 (1H, d, J=9.8 Hz), 5.37 (1H, p, J=8.8 Hz), 3.82 (4H, t, J=5.4 Hz), 3.29 (4H, m), 2.39 (2H, m), 2.13 (2H, m), 2.04 (2H, m), 1.74 (2H, m) ppm; LCMS-ESI (POS), M/Z, M+1: Found 416.2, Calculated 416.2.

Example 7

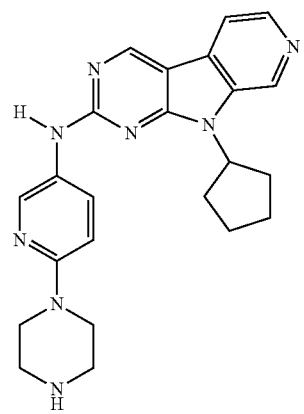

15

9-cyclopentyl-N-(6-(1-piperazinyl)-3-pyridinyl)-9H-pyrido[4',3':4,5]pyrrolo[2,3-d]pyrimidin-2-amine Compound 15 was prepared using chemistry similar to that described in example 4. ¹H NMR (500 MHz, CD₃OD) δ 9.43 (1H, s), 9.18 (1H, s), 8.65 (1H, d, J=2.6 Hz), 8.53 (2H, s), 8.10

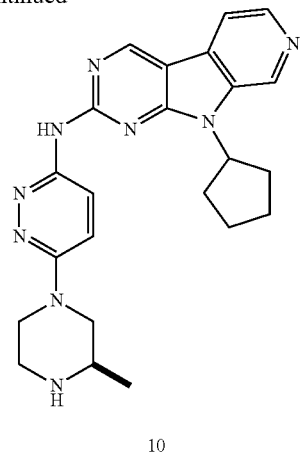

10

(R)-9-cyclopentyl-N-(6-(1-(3-methylpiperazinyl)-3-pyridazinyl)-9H-pyrido[4',3':4,5]-pyrrolo[2,3d]pyrimidin-2-amine (10): A solution of compound 12 (240 mg, purity=85%, 0.385 mmol) in TFA/DCM (4 mL, 1:1) was stirred at room temperature for 30 min. The reaction mixture was concentrated and the residue was purified by chromatography on silica gel eluting with CH₂Cl₂/methanol/NH₄OH (200:10:1) to give compound 10 as an off-white solid (120 mg, 73%). ¹H NMR (500 MHz, DMSO-d₆) δ 10.19 (1H, s), 9.27 (1H, s), 9.01 (1H, s), 8.46 (1H, d, J=5 Hz), 8.18 (1H, d, J=10 Hz), 8.05 (1H, d, J=5 Hz), 7.40 (1H, d, J=10 Hz), 5.34 (1H, p, J=10 Hz), 4.11 (2H, m), 2.97 (1H, m), 2.79-2.72 (3H, m), 2.44-2.34 (3H, m), 2.09-2.04 (4H, m), 1.74 (2H, m), 1.04 (3H, d, J=5 Hz) ppm; LCMS-ESI (POS), M/Z, M+1: Found 430.2, Calculated 430.2.

Example 5

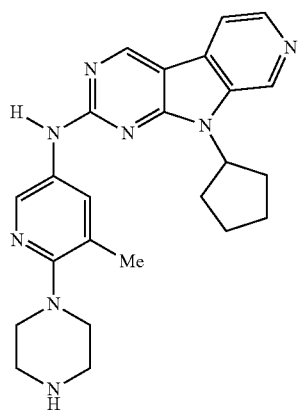

13

9-cyclopentyl-N-(5-methyl-6-(1-piperazinyl)-3-pyridinyl)-9H-pyrido-[4',3':4,5]pyrrolo[2,3-d]pyrimidin-2-amine Compound 13 was prepared using chemistry similar to that described in example 4. ¹H NMR (500 MHz, DMSO-d₆) δ 10.42 (1H, br s), 9.57 (1H, s), 9.38 (1H, s), 8.86 (2H, br s), 8.67 (1H, d,), 8.57 (1H, d, J=6.1 Hz), 8.52 (1H, d, J=2.7 Hz), 8.03 (1H, s), 5.33 (1H, p, J=8.8 Hz), 3.26 (8H, m), 2.43 (2H, (1H, dd, J=9.0 Hz, 2.4 Hz), 7.11 (1H, d, J=9.3 Hz), 5.37 (1H, p, J=8.6 Hz), 3.85 (4H, t, J=5.3 Hz), 3.40 (4H, t, J=5.1 Hz), 2.49 (2H, m), 2.23 (2H, m), 2.21 (2H, m), 1.86 (2H, m) ppm; LCMS-ESI (POS), M/Z, M+1: Found 415.1, Calculated 415.2.

Example 8

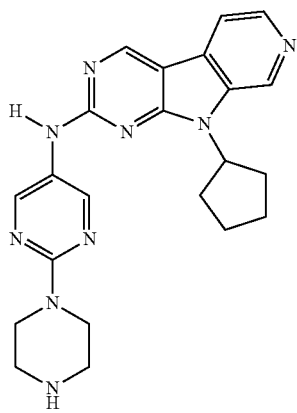

9-cyclopentyl-N-(2-(1-piperazinyl)-5-pyrimidinyl)-9H-pyrido[4',3':4,5]pyrrolo[2,3-d]pyrimidin-2-amine Compound 16 was prepared using chemistry similar to that described in example 4. $^1$H NMR (500 MHz, CD$_3$OD) δ 9.40 (1H, s), 9.16 (1H, s), 8.82 (2H, s), 8.51 (1H, d, J=6.1 Hz), 8.49 (1H, d, J=6.1 Hz), 5.35 (1H, p, J=8.5 Hz), 4.12 (4H, t, J=5.4 Hz), 3.35 (4H, t, J=5.4 Hz), 2.47 (2H, m), 2.23 (2H, m), 2.10 (2H, m), 1.85 (2H, m) ppm; LCMS-ESI (POS), M/Z, M+1: Found 416.2, Calculated 416.2.

Example 9

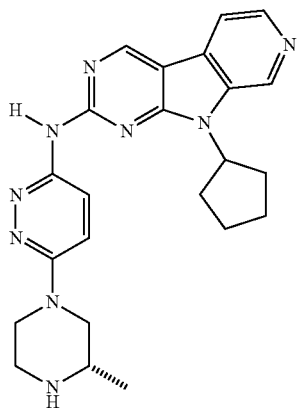

(S)-9-cyclopentyl-N-(6-(1-(3-methylpiperazinyl)-3-pyridazinyl)-9H-pyrido[4',3':4,5]-pyrrolo[2,3d]pyrimidin-2-amine Compound 17 was prepared using chemistry similar to that described in example 4. $^1$H NMR (500 MHz, DMSO-d$_6$-d6) δ 10.19 (1H, s), 9.27 (1H, s), 9.01 (1H, s), 8.46 (1H, d, J=5 Hz), 8.18 (1H, d, J=10 Hz), 8.05 (1H, d, J=5 Hz), 7.40 (1H, d, J=10 Hz), 5.34 (1H, p, J=10 Hz), 4.11 (2H, m), 2.97 (1H, m), 2.79-2.72 (3H, m), 2.44-2.34 (3H, m), 2.09-2.04 (4H, m), 1.74 (2H, m), 1.04 (3H, d, J=5 Hz) ppm; LCMS-ESI (POS), M/Z, M+1: Found 430.2, Calculated 430.2.

Example 10

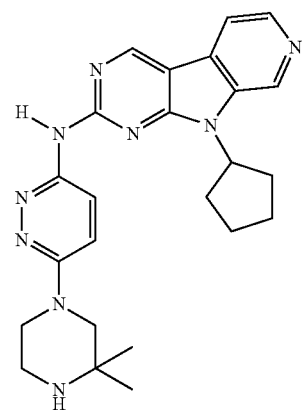

9-cyclopentyl-N-(6-(1-(3,3-dimethylpiperazinyl)-3-pyridazinyl)-9H-pyrido[4',3':4,5]-pyrrolo[2,3d]pyrimidin-2-amine Compound 18 was prepared using chemistry similar to that described in example 1. $^1$H NMR (500 MHz, CDCl$_3$) δ 9.37 (1H, br s), 9.19 (1H, s), 8.87 (1H, s), 8.50-8.46 (2H, m), 7.84 (1H, d, J=5 Hz), 7.04 (1H, d, J=5 Hz), 5.34 (1H, p, J=10 Hz), 3.54 (2H, t, J=5 Hz), 3.36 (2H, br s), 3.07 (2H, t, J=5 Hz), 2.36 (2H, m), 2.17 (2H, m), 2.09 (2H, m), 1.84 (2H, m), 1.21 (6H, s) ppm; LCMS-ESI (POS), M/Z, M+1: Found 444.2, Calculated 444.3.

Example 11

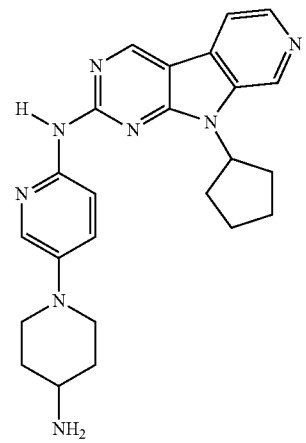

9-cyclopentyl-N-(5-(1-(4-aminopiperadinyl)-2-pyridinyl)-9H-pyrido[4',3':4,5]-pyrrolo[2,3d]pyrimidin-2-amine Compound 19 was prepared using chemistry similar to that described in example 1. $^1$H NMR (500 MHz, DMSO-d$_6$) δ 9.72 (1H, s), 9.26 (1H, s), 9.00 (1H, s), 8.44 (1H, d, J=5 Hz), 8.15 (1H, d, J=10 Hz), 8.03 (1H, d, J=5 Hz), 8.02 (1H, d, J=2 Hz), 7.46 (1H, dd, J=10 Hz, J=2 Hz), 5.36 (1H, p, J=5 Hz), 3.61 (2H, m), 2.77-2.71 (3H, m), 2.41-2.36 (3H, m), 2.09-2.05 (4H, m), 1.83-1.76 (4H, m), 1.39 (2H, m) ppm; LCMS-ESI (POS), M/Z, M+1: Found 429.2, Calculated 429.2.

Example 12

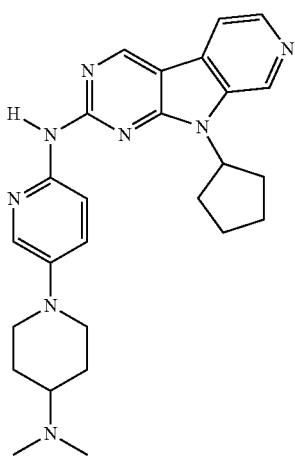

9-cyclopentyl-N-(5-(1-(N$^4$,N$^4$-dimethylaminopiperadinyl)-2-pyridinyl)-9H-pyrido[4',3':4,5]-pyrrolo[2,3d]pyrimidin-2-amine Compound 20 was prepared using chemistry similar to that described in example 1. $^1$H NMR (500 MHz, CDCl$_3$) δ 9.07 (1H, s), 8.90 (1H, s), 8.51 (1H, d, J=5 Hz), 8.38 (1H, d, J=10 Hz), 8.12 (1H, s), 8.07 (1H, d, J=2 Hz), 7.84 (1H, d, J=5 Hz), 7.41 (1H, dd, J=10 Hz, J=2 Hz), 5.38 (1H, p, J=10 Hz), 3.68 (2H, m), 2.77 (2H, td, J=15 Hz, J=5 Hz), 2.44 (2H, m), 2.34 (6H, s), 2.29 (1H, m), 2.22-2.14 (4H, m), 1.97 (2H, m), 1.88 (2H, m), 1.72 (2H, m) ppm; LCMS-ESI (POS), M/Z, M+1: Found 457.2, Calculated 457.3.

Example 13

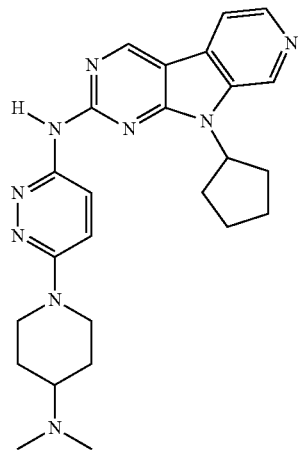

9-cyclopentyl-N-(6-(1-(N$^4$,N$^4$-dimethylaminopiperadinyl)-3-pyridazinyl)-9H-pyrido[4',3':4,5]-pyrrolo[2,3d]pyrimidin-2-amine Compound 21 was prepared using chemistry similar to that described in example 4. $^1$H NMR (500 MHz, DMSO-d$_6$) δ 10.17 (1H, s), 9.26 (1H, s), 9.00 (1H, s), 8.44 (1H, d, J=5 Hz), 8.16 (1H, d, J=10 Hz), 8.04 (1H, d, J=5 Hz), 7.42 (1H, d, J=10 Hz), 5.33 (1H, p, J=10 Hz), 4.30 (2H, m), 2.88 (2H, td, J=15 Hz, J=5 Hz), 2.36-2.32 (3H, m), 2.19 (6H, s), 2.10-2.02 (4H, m), 1.84 (2H, m), 1.74 (2H, m), 1.42 (2H, m) ppm; LCMS-ESI (POS), M/Z, M+1: Found 458.2, Calculated 458.3.

Example 14

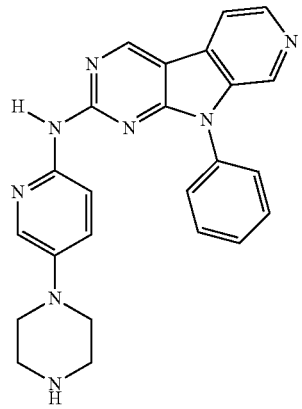

9-Phenyl-N-(5-(1-piperazinyl)-2-pyridinyl)-9H-pyrido[4',3':4,5]pyrrolo[2,3-d]pyrimidin-2-amine Compound 22 was prepared using chemistry similar to that described in example 1. $^1$H NMR (500 MHz, DMSO-d$_6$) δ

8.76 (1H, s), 8.52 (1H, d, J=5 Hz), 8.13 (1H, d, J=5 Hz), 8.08 (1H, d, J=10 Hz), 7.97 (1H, br s), 7.82-7.80 (2H, m), 7.32-7.30 (2H, m), 7.57 (1H, dd, J=10 Hz, J=5 Hz), 7.31 (1H, dd, J=10 Hz, J=5 Hz), 3.03 (4H, m), 2.85 (4H, m) ppm; LCMS-ESI (POS), M/Z, M+1: Found 423.2, Calculated 423.2.

Example 15

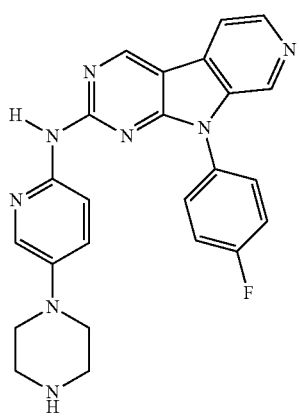

23

9-(4-fluorophenyl-N-(5-(1-piperazinyl)-2-pyridinyl)-9H-pyrido[4',3':4,5]pyrrolo[2,3-d]pyrimidin-2-amine Compound 23 was prepared using chemistry similar to that described in example 1. $^1$H NMR (500 MHz, DMSO-d$_6$) δ 9.86 (1H, s), 9.37 (1H, s), 8.73 (1H, s), 8.51 (1H, d, J=5 Hz), 8.13 (1H, d, J=5 Hz), 8.06 (1H, d, J=10 Hz), 7.97 (1H, s), 7.87 (2H, d, J=5 Hz), 7.55 (2H, dd, J=10 Hz, J=5 Hz), 7.34 (1H, dd, J=10 Hz, J=5 Hz), 3.03 (4H, m), 2.85 (4H, m) ppm; LCMS-ESI (POS), M/Z, M+1: Found 441.1, Calculated 441.2.

Example 16

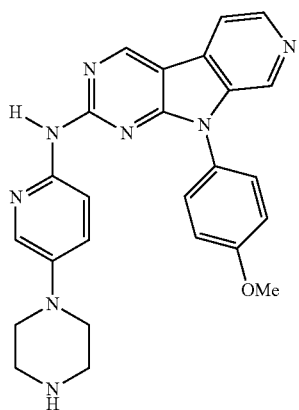

24

9-(4-methoxyphenyl-N-(5-(1-piperazinyl)-2-pyridinyl)-9H-pyrido-[4',3':4,5]pyrrolo[2,3-d]pyrimidin-2-amine Compound 24 was prepared using chemistry similar to that described in example 1. $^1$H NMR (500 MHz, DMSO-d$_6$) δ

9.82 (1H, s), 9.36 (1H, s), 8.68 (1H, s), 8.50 (1H, d, J=5 Hz), 8.11 (1H, d, J=5 Hz), 8.08 (1H, s), 7.98 (1H, d, J=5 Hz), 7.70 (2H, d, J=10 Hz), 7.34 (1H, d, J=10 Hz), 7.25 (1H, d, J=10 Hz), 3.89 (3H, s), 3.05 (4H, m), 2.88 (4H, m) ppm; LCMS-ESI (POS), M/Z, M+1: Found 453.2, Calculated 453.2.

Example 17

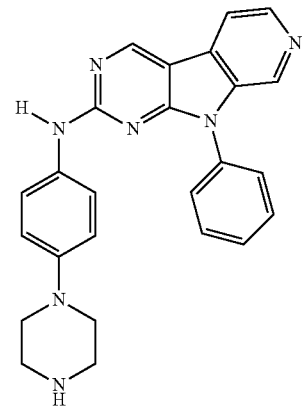

25

(9-Phenyl-9H-pyrido[4',3':4,5]pyrrolo[2,3-d]pyrimidin-2-yl)-(4-piperazin-1-yl-phenyl)amine Compound 25 was prepared using chemistry similar to that described in example 1. $^1$H NMR (500 MHz, CD$_3$OD) δ 9.10 (1H, s), 8.87 (1H, s), 8.58 (1H, d, J=5 Hz), 7.87 (1H, s), 7.74 (2H, d, J=5 Hz), 7.67 (2H, dd, J=10 Hz, J=5 Hz), 7.58-7.53 (3H, m), 6.92 (2H, d, J=5 Hz), 3.13 (4H, m), 3.07 (4H, m) ppm; LCMS-ESI (POS), M/Z, M+1: Found 422.2, Calculated 422.2.

Example 18

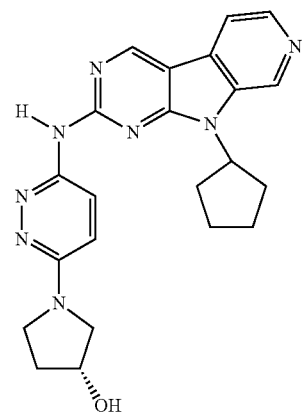

26

(R)-9-cyclopentyl-N-(6-(3-hydroxypyrrolidin-1-yl)-3-pyridazinyl)-9H-pyrido[4',3':4,5]-pyrrolo[2,3d]pyrimidin-2-amine

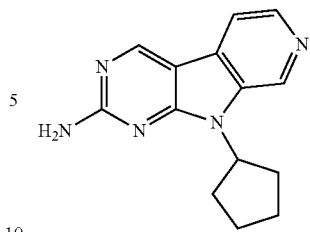

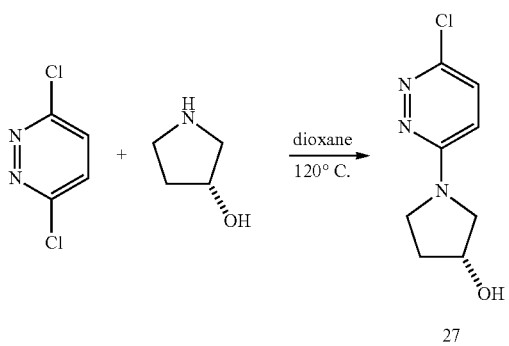 [SMILES: Clc1ccc(Cl)nn1 ; O[C@@H]1CCNC1 ; O[C@@H]1CCN(c2ccc(Cl)nn2)C1]

(R)-1-(6-Chloropyridazin-3-yl)pyrrolidin-3-ol (27): A solution of 3,6-dichloropydazine (1.49 g, 10 mmol) and (R)-3-hydroxypyrrolidine (871 mg, 10 mmol) in dioxane (20 mL) was heated at 120° C. for 10 h. The reaction mixture was diluted with ethyl acetate and washed with 5% NaHCO$_3$ and brine, dried. The solvent was evaporated and the residue was purified by chromatography on silica gel eluting with 2.5% methanol in dichloromethane to give the compound 27 as a yellow solid (815 mg, 41%). LCMS-ESI (POS), M/Z, M+1: Found 200.0, Calculated 200.0.

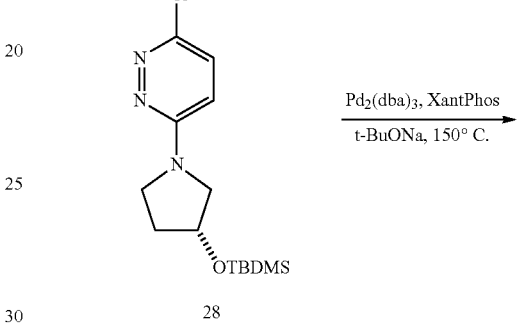

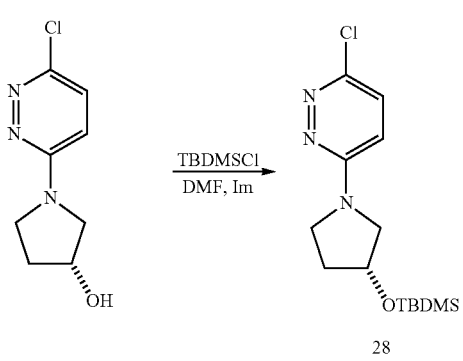 [SMILES: O[C@@H]1CCN(c2ccc(Cl)nn2)C1 ; "TBDMSCl" ; CC(C)(C)[Si](C)(C)O[C@@H]1CCN(c2ccc(Cl)nn2)C1]

(R)-3-(3-(tert-butyldimethylsilyloxy)pyrrolidin-1-yl)-6-chloropyridazine (28): To a solution of compound 27 (815 mg, 4.08 mmol) in DMF (15 mL) were added t-butyldimethylsilyl chloride (738 mg, 4.9 mmol) amd imidazole (556 mg, 8.16 mmol). The thus obtained solution was stirred at room temperature for 6 h. The reaction mixture was concentrated and the residue was purified by chromatography on silica gel eluting with 15% to 50% to give the compound 28 as a white solid (1.087 g, 85%). LCMS-ESI (POS), M/Z, M+1: Found 314.1, Calculated 314.1.

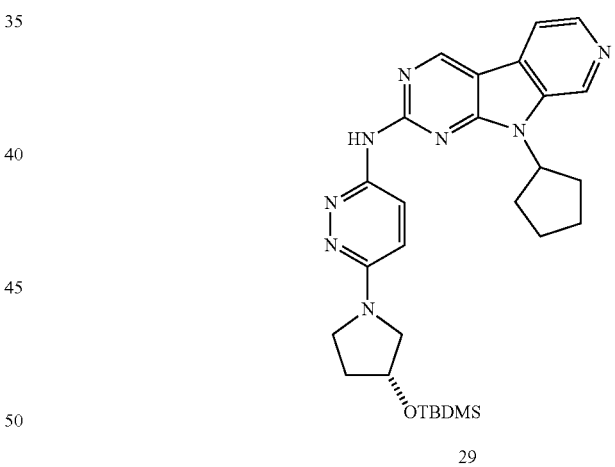

(R)-9-Cyclopentyl-N-(6-(3-(tert-butyldimethylsilyloxy)pyrrolidin-1-yl)-3-pyridazinyl)-9H-pyrido-[4',3':4,5]-pyrrolo[2,3d]pyrimidin-2-amine (29): To a solution of compound 4 (202 mg, 0.80 mmol) in dioxane (8 mL) were added compound 28 (313 mg, 1.0 mmol), tris(dibenzylideneacetone)dipalladium (0) (36.8 mg, 0.04 mmol), 4,5-bis(diphenylphosphino)-9,9-dimethylxanthene (69.4 mg, 0.12 mmol), and sodium t-butoxide (115 mg, 1.2 mmol). The mixture thus obtained was heated at 150° C. under microwave irradiation for 1 h. The reaction mixture was passed through a short pack silica gel column and concentrated to give compound 29 as a yellow solid (316 mg, 82% purity) which was used in next step without further purification. LCMS-ESI (POS), M/Z, M+1: Found 531.1, Calculated 531.2.

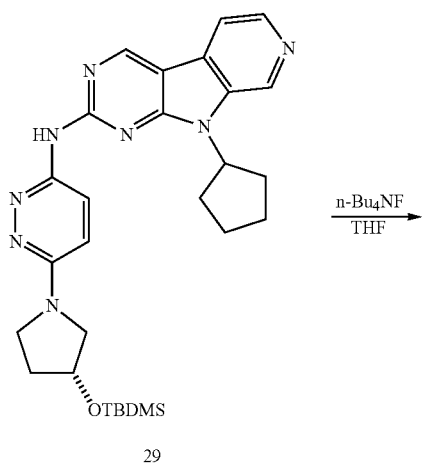

29

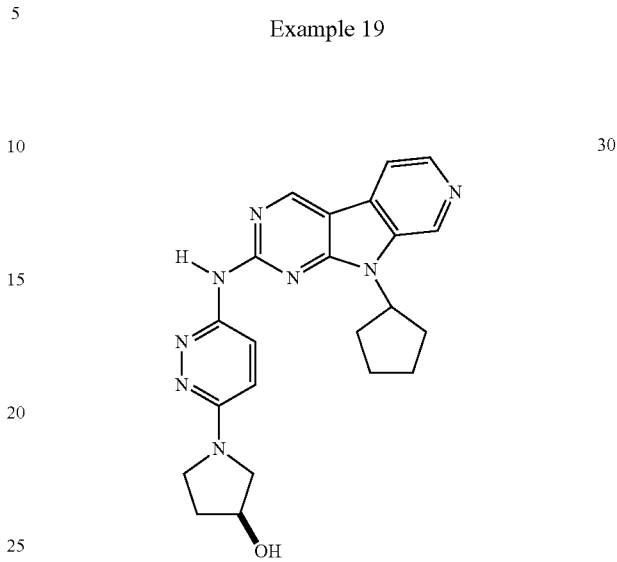

26

(R)-9-cyclopentyl-N-(6-(3-hydroxypyrrolidin-1-yl)-3-pyridazinyl)-9H-pyrido-[4',3':4,5]-pyrrolo[2,3d]pyrimidin-2-amine (26): A solution of compound 29 (316 mg, purity 82%, 0.49 mmol) in THF (4 mL) was treated with 1M tetrabutylammonium fluoride in THF (1 mL) at room temperature for 0.5 h. The reaction mixture was concentrated and the residue was purified by chromatography on silica gel eluting with 2.5% methanol in dichloromethane to give a yellow solid. The yellow solid was washed with dichloromethane to give compound 26 as a light yellow solid (182 mg, 90%). $^1$H NMR (500 MHz, DMSO-$d_6$) δ 10.05 (1H, s), 9.24 (1H, s), 8.99 (1H, s), 8.44 (1H, d, J=5 Hz), 8.10 (1H, d, J=10 Hz), 8.03 (1H, d, J=5 Hz), 6.99 (1H, d, J=10 Hz), 5.32 (1H, p, J=10 Hz), 5.00 (1H, d, J=5 Hz), 4.43 (1H, br s), 3.58-3.51 (3H, m), 3.40 (1H, m), 2.37-2.30 (2H, m), 2.09-2.02 (5H, m), 1.95 (1H, m), 1.74 (2H, m) ppm; LCMS-ESI (POS), M/Z, M+1: Found 417.3, Calculated 417.2.

Example 19

30

(S)-9-cyclopentyl-N-(6-(3-hydroxypyrrolidin-1-yl)-3-pyridazinyl)-9H-pyrido[4',3':4,5]-pyrrolo[2,3d]pyrimidin-2-amine Compound 30 was prepared using chemistry similar to that described in example 18. $^1$H NMR (500 MHz, DMSO-$d_6$) δ 10.05 (1H, s), 9.24 (1H, s), 8.99 (1H, s), 8.44 (1H, d, J=5 Hz), 8.10 (1H, d, J=10 Hz), 8.03 (1H, d, J=5 Hz), 6.99 (1H, d, J=10 Hz), 5.32 (1H, p, J=10 Hz), 5.00 (1H, d, J=5 Hz), 4.43 (1H, br s), 3.58-3.51 (3H, m), 3.40 (1H, m), 2.37-2.30 (2H, m), 2.09-2.02 (5H, m), 1.95 (1H, m), 1.74 (2H, m) ppm; LCMS-ESI (POS), M/Z, M+1: Found 417.3, Calculated 417.2.

Example 20

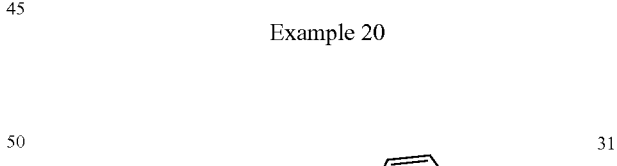

31

(5-piperazin-1-yl-pyridine-2-yl)-[9-(tetrahydro-pyran-4-yl)-9H-pyrido-[4',3',4,5]pyrrolo[2,3-d]pyrimidin-2-yl]-amine

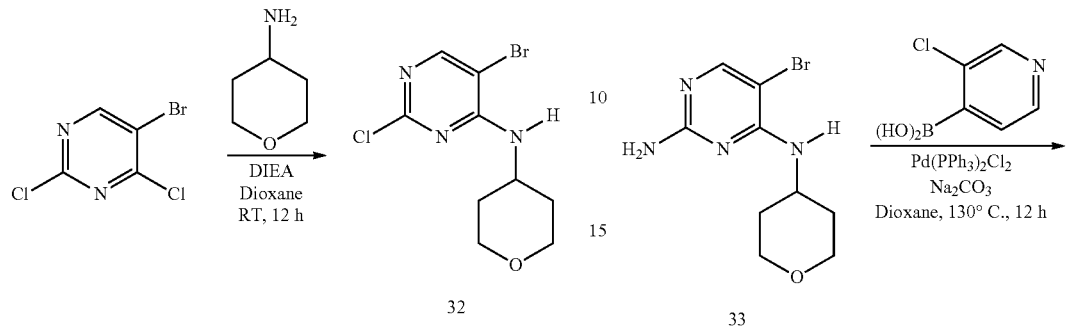

(5-bromo-2-chloro-pyrimidin-4-yl)-(tetrahydro-pyran-4-yl)-amine (32). 5-Bromo-2,4-dichloropyrimidine (5.0 g, 21.9 mmol), tetrahydro-2H-pyran-4-amine (2.22 g, 21.9 mmol), and N-ethyl-N-isopropylpropan-2-amine (4.25 g, 32.9 mmol) were dissolved in dioxane (50 ml) and the reaction was stirred at room temperature for 12 hours. Ethyl acetate was added to the reaction mixture and the organic layer was washed with water and brine. The organic layer was dried with sodium sulfate. Removal of solvent gave (5-bromo-2-chloro-pyrimidin-4-yl)-(tetrahydro-pyran-4-yl)-amine (32) as a light yellow solid (6.75 g, 99%). $^1$H NMR (500 MHz, CD$_3$OD) δ ppm 8.04 (1 H, s), 4.14-4.21 (1 H, m), 3.89 (2 H, dd, J=11.4, 4.3 Hz) 3.43 (2 H, td, J=11.9, 2.0 Hz), 1.80 (2 H, ddd, J=12.6, 4.2, 1.8 Hz), 1.63 (2 H, qd, J=12.2, 4.5, Hz); LCMS-ESI (POS), M/Z, M+1: Found 292.0, Calculated 292.

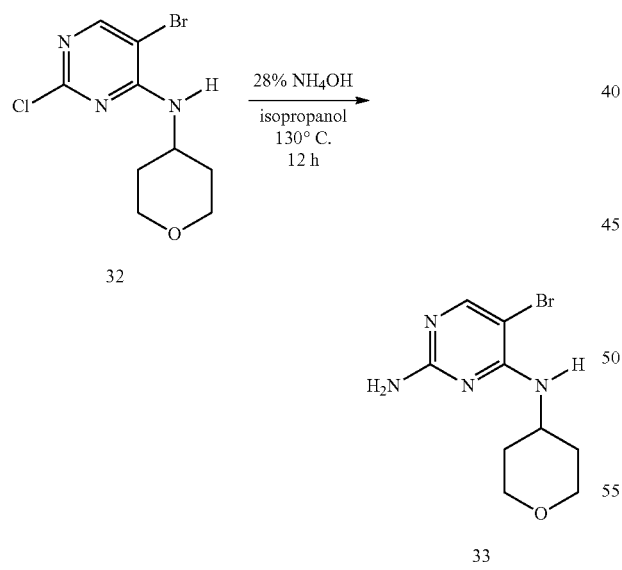

5-Bromo-N$^4$-(tetrahydro-pyran-4-yl)-pyrimidine-2,4-diamine (33): To a suspension of compound 32 (6.60 g, 23 mmol) in isopropyl alcohol (40 ml) was added ammonia (aq. 28%, 80 ml). This reaction mixture was heated to 130° C. for 14 hours in a pressure vessel. The reaction mixture was cooled down to room temperature and to this mixture was added ethyl acetate. The reaction mixture was washed with water and brine. The ethyl acetate layer was dried with sodium sulfate and concentrated to give compound 33 (4.75 g, 77%). $^1$H NMR (500 MHz, CD$_3$OD) δ ppm 7.79 (1 H, s), 4.24 (1 H, m), 3.99-4.02 (2 H, dd, J=11.0, 2.2 Hz), 3.52 (2 H, td, J=11.9, 2.0 Hz), 1.92-1.96 (2 H, m), 1.69 (2 H, m); LCMS-ESI (POS), M/Z, M+1: Found 273, Calculated 273.0

5-(3-Chloro-pyridin-4-yl)-N$^4$-(tetrahydro-pyran-4-yl)-pyrimidine-2,4-diamine (34): A mixture of compound 33 (2.03 g, 7.43 mmol), 3-chloropyridin-4-ylboronic acid (3.51 g, 22.3 mmol), and Pd(PPh$_3$)$_2$Cl$_2$ (0.522 g, 0.743 mmol) in dioxane (44 ml) in a pressure vessel was purged with N$_2$ for 20 minutes and to this mixture was added aq. Na$_2$CO$_3$ (1 M, 22 mL) by syringe. The reaction was further purged with N$_2$ for another 20 minutes and then heated to 130° C. for 12 hours. DCM was added to the reaction and the mixture was washed with water and brine. The organic layer was dried with sodium sulfate and concentrated to provide compound 34 (2.07 g, crude, 98%) which was used in the next reaction without further purification. LCMS-ESI (POS), M/Z, M+1: Found 306.1, Calculated 306.1.

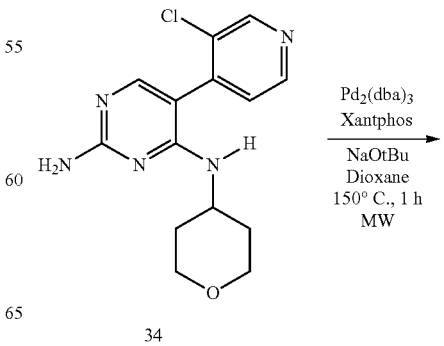

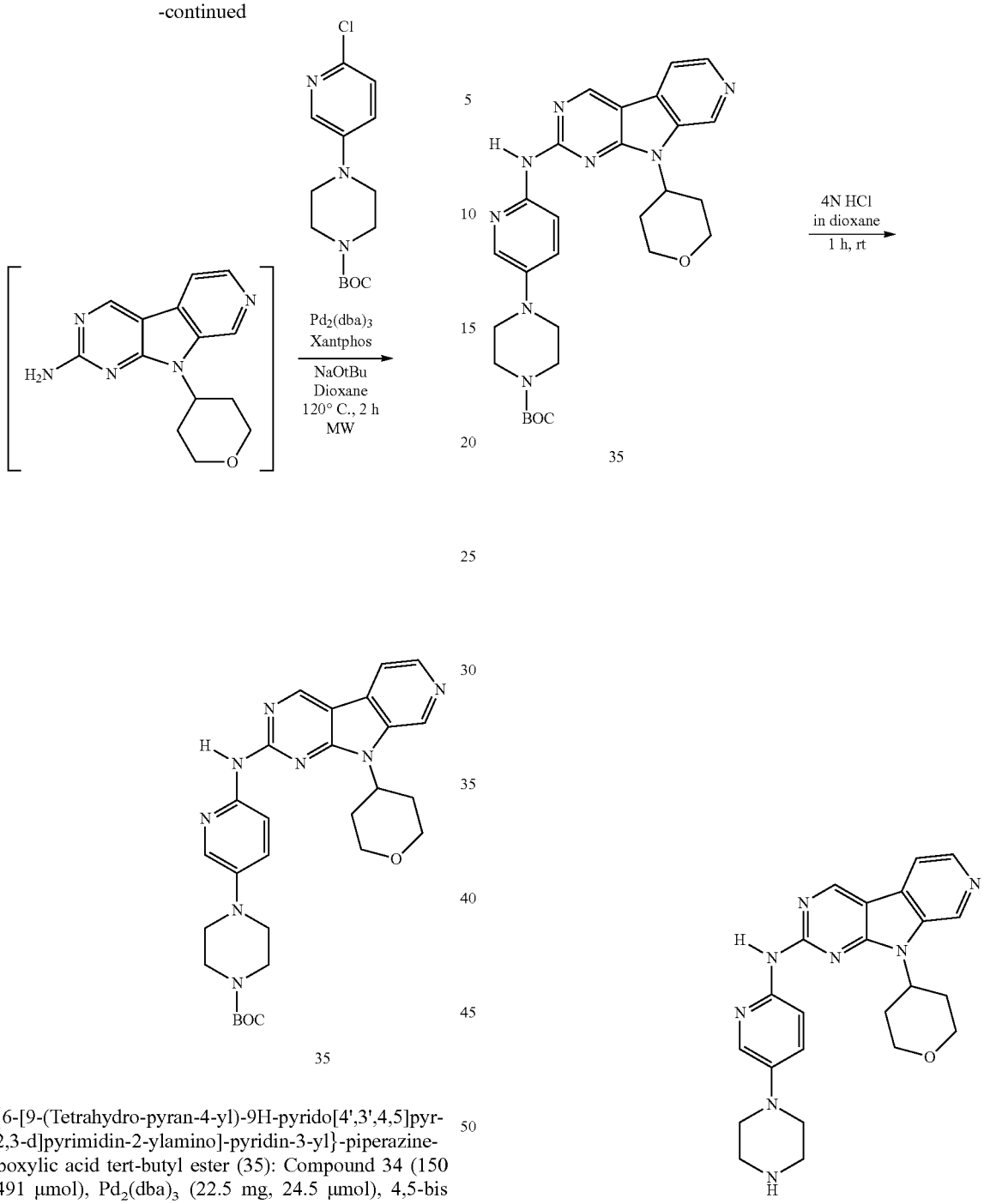

4-{6-[9-(Tetrahydro-pyran-4-yl)-9H-pyrido[4',3',4,5]pyrrolo[2,3-d]pyrimidin-2-ylamino]-pyridin-3-yl}-piperazine-1-carboxylic acid tert-butyl ester (35): Compound 34 (150 mg, 491 μmol), Pd$_2$(dba)$_3$ (22.5 mg, 24.5 μmol), 4,5-bis(diphenylphosphino)-9,9-dimethyl-9H-xanthene (28.4 mg, 49.1 μmol), sodium 2-methylpropan-2-olate (118 mg, 1226 μmol) in dioxane (4 ml) was purged with N2 for 20 minutes. The reaction was heated up to 150° C. in microwave for 1 hour. Then a solution of compound 5 (146 mg, 491 μmol) in dioxane (1 ml)) was added to the reaction mixture and the reaction was purged with N$_2$ for another 20 minutes. This reaction was heated to 120° C. under microwave irradiation for 2 hours. DCM was added to the reaction and the mixture was washed with water and brine. The organic layer was dried with sodium sulfate and concentrated. Purification by flash chromatography (DCM/methanol) gave compound 35 (102 mg). LCMS-ESI (POS), M/Z, M+1: Found 531.2, Calculated 531.3

(5-piperazin-1-yl-pyridine-2-yl)-[9-(tetrahydro-pyran-4-yl)-9H-pyrido[4',3',4,5]pyrrolo-[2,3-d]pyrimidin-2-yl]-amine (31): Compound 35 (100 mg) was treated with 5 mL of 4 N HCl in dioxane for 1 hour. The product, which was not soluble in dioxane, was collected and then washed with ethyl acetate and a small amount of methanol to obtain compound 31 as its HCl salt (20 mg, 25%). $^1$H NMR (500 MHz, DMSO-d$_6$) δ ppm 9.65 (1 H, s), 9.59 (1 H, s), 9.37 (1 H, s), 8.27 (2 H, s), 8.14 (1 H, s), 8.05 (1 H, s), 7.80 (1 H, s), 5.20 (2 H, m), 4.10 (2 H, d, J=3.2 Hz), 3.71 (br s), 3.6 (2 H, m), 3.46 (4 H, s), 3.27

(4 H, s), 2.83 (2 H, dd, J=11.9, 3.8 Hz), 1.90 (2 H, d, J=10.5 Hz); LCMS-ESI (POS), M/Z, M+1: Found 431.2, Calculated 431.2

Example 21

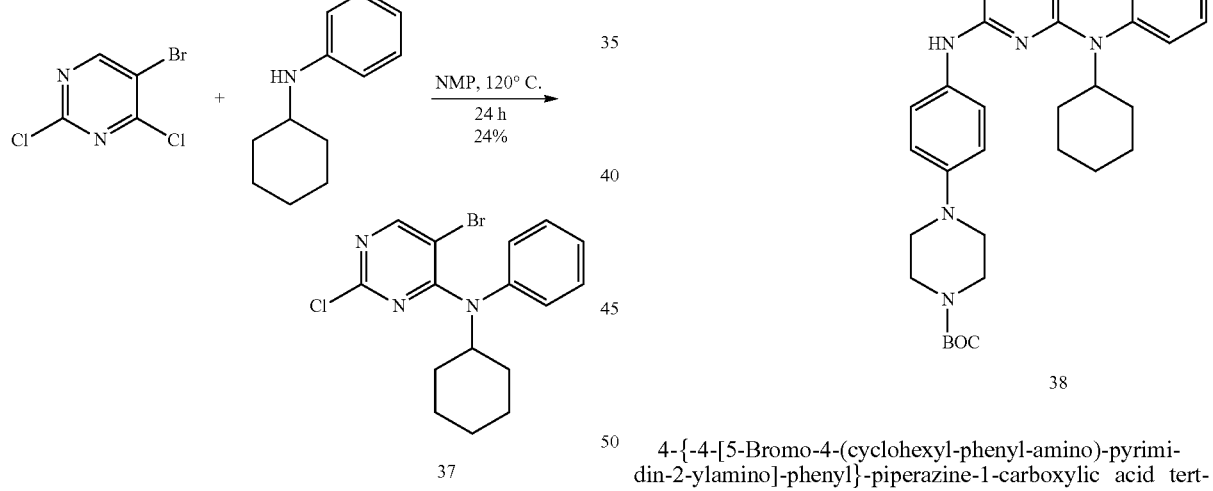

(9-Cyclohexyl-9H-pyrimido[4,5-b]indol-2-yl)-(4-piperazin-1-yl-phenyl)-amine (5-Bromo-2-chloro-pyrimidin-4-yl)-cyclohexyl-phenyl-amine (37): 5-Bromo-2,4-dichloro-pyrimidine (2.17 ml, 17.14 mmol) and cyclohexyl-phenyl-amine (2.0 g, 11.43 mmol) were dissolved in N-methylpyrrolidone (NMP) (25 ml), and this reaction was heated to 120° C. for 24 hours. The reaction was cooled to room temperature and diluted with ethyl acetate, washed with water and brine. The organic phase was dried using sodium sulfate and concentrated. Purification by flash chromatography (ethyl acetate/hexane) gave compound 37 as a yellow solid (855 mg, 24%). $^1$H NMR (500 MHz, DMSO-$d_6$) δ ppm 8.27 (1 H, s), 7.41 (3 H, m), 7.21 (2 H, m), 4.62 (1 H, m), 1.93 (2 H, d, J=10 Hz), 1.75 (2 H, d, J=10 Hz), 1.58 (1 H, d, J=10 Hz), 1.34 (2 H, m), 1.15 (2 H, m), 0.91 (1 H, m).

4-{-4-[5-Bromo-4-(cyclohexyl-phenyl-amino)-pyrimidin-2-ylamino]-phenyl}-piperazine-1-carboxylic acid tert-butyl ester (38): Compound 37 (0.42 g, 1.15 mmol) and 4-(4-amino-phenyl)-piperazine-1-carboxylic acid tert-butyl ester (0.64 g, 2.30 mmol) were dissolved in dioxane (2 mL), and this mixture was heated at 100° C. for 24 hours. The reaction was cooled to room temperature and diluted with ethyl acetate. This mixture was washed with water and brine. The organic layer was dried with sodium sulfate and purified by flash chromatography (ethyl acetate/hexane) to give compound 38 as a yellow solid (0.23 g, 33%). $^1$H NMR (500 MHz, DMSO-$d_6$) δ ppm 9.18 (1 H, s), 7.97 (1 H, s), 7.55 (2 H, d, J=10 Hz), 7.37 (2 H, m), 7.31 (1 H, m), 7.12 (2 H, m), 6.89 (2 H, d, J=10 Hz), 4.68 (1 H, m), 3.44 (4 H, m), 3.00 (4 H, m), 1.91 (2 H, d, J=10 Hz), 1.72 (2 H, d, J=10 Hz), 1.57 (1 H, d, J=10 Hz), 1.41 (9 H, s), 1.35 (2 H, m), 1.14 (2 H, m), 0.92 (1 H, m); LCMS-ESI (POS), M/Z, M+1: Found 609.2, Calculated 607.2/609.2.

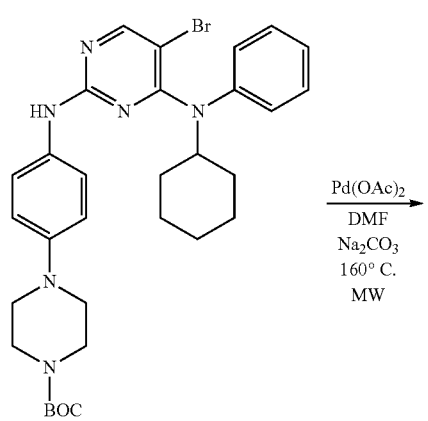

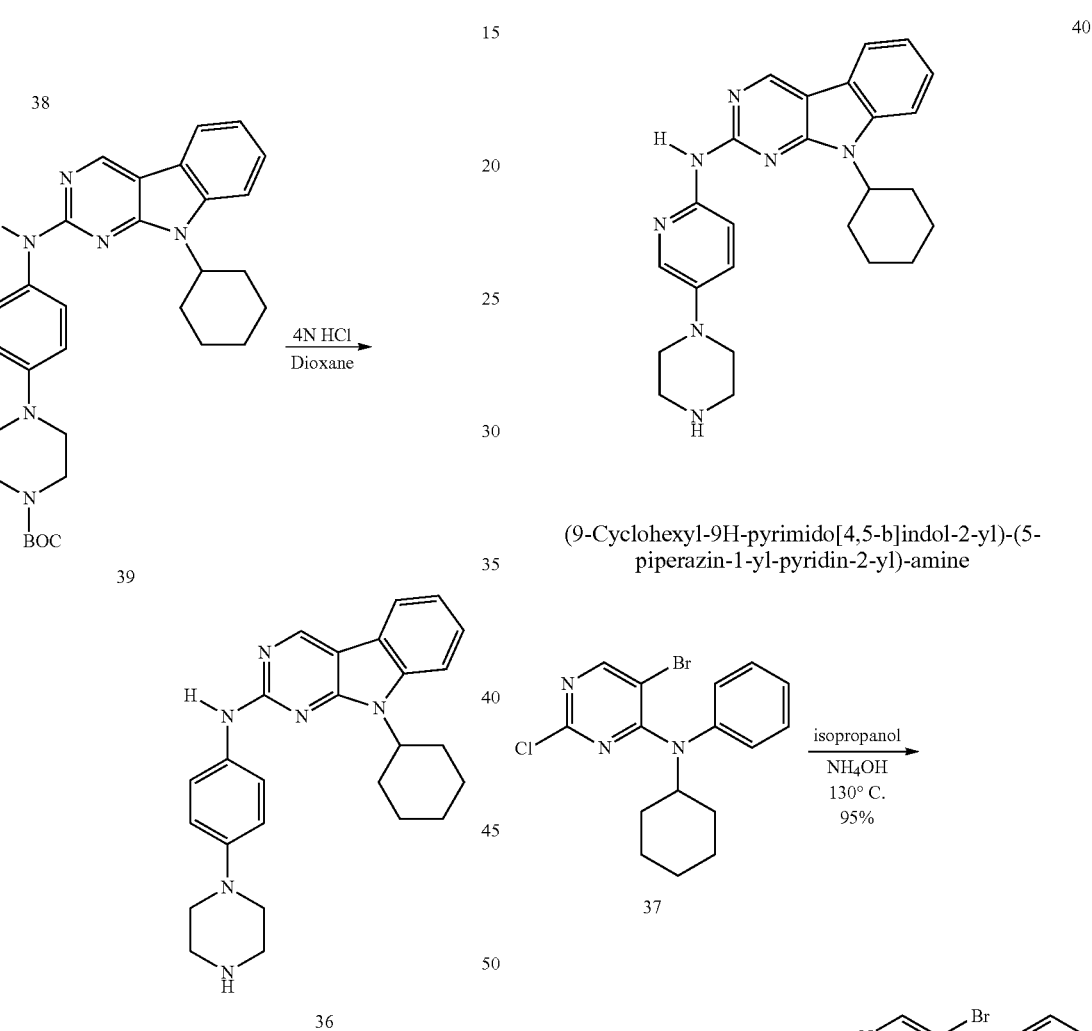

obtained as the HCl salt after removal of dioxane. $^{1}$H NMR (500 MHz, CD$_3$OD) δ ppm 8.81 (1 H, s), 8.00 (1 H, d, J=7.4 Hz), 7.66 (1 H, d, J=7.4 Hz), 7.51 (1 H, t, J=6.5 Hz), 7.43 (2 H, d, J=7.4 Hz), 7.32 (1 H, t, J=7.5 Hz), 7.09 (2 H, d, J=10 Hz), 4.60 (1 H, m), 3.40 (4 H, m), 3.33 (4 H, m), 2.39-2.48 (2 H, m), 1.80-1.89 (4 H, m), 1.70-1.73 (1 H, m), 1.41-1.51 (2 H, m), 1.19-1.27 (2 H, m); LCMS-ESI (POS), M/Z, M+1: Found 427.3, Calculated 427.3.

Example 22

(9-Cyclohexyl-9H-pyrimido[4,5-b]indol-2-yl)-(5-piperazin-1-yl-pyridin-2-yl)-amine (9-Cyclohexyl-9H-pyrimido[4,5-b]indol-2-yl)-(4-piperazin-1-yl-phenyl)-amine (36).

A mixture of compound 38 (0.12 g, 0.20 mmol), Pd(OAc)$_2$ (27 mg, 0.041 mmol), Na$_2$CO$_3$ (43 mg, 0.41 mmol) in DMF (2 mL) was purged with N$_2$ for 20 minutes and the reaction was heated at 160° C. in a sealed tube for 4 hours. The reaction was cooled to room temperature, diluted with ethyl acetate and washed with water and brine. The organic phase was dried over sodium sulfate and concentrated. Purification by reverse phase Prep-HPLC gave compound 39: LCMS-ESI (POS), M/Z, M+1: Found 527.3, Calculated 527.3. Compound 39 was treated with 2 N HCl in dioxane (2 mL) for 2 hours at room temperature. Compound 36 (7 mg) was 5-Bromo-N4-cyclohexyl-N4-phenyl-pyrimidine-2,4-diamine (41): Compound 41 was prepared using chemistry similar to that described in example 1. LCMS-ESI (POS), M/Z, M+1: Found 348.3, Calculated 348.3.

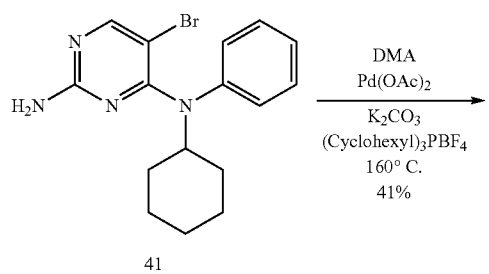

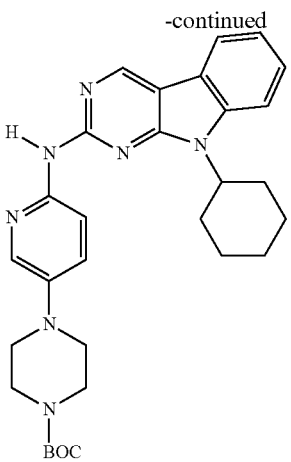

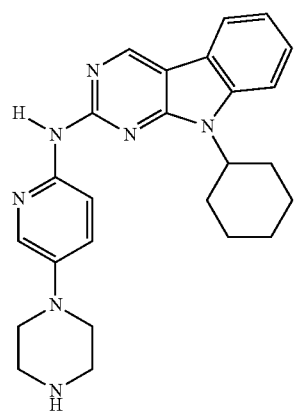

9-Cyclohexyl-9H-pyrimido[4,5-b]indol-2-ylamine (42). A mixture of compound 41 (0.35 g, 0.99 mmol), Pd(OAc)$_2$ (33 mg, 0.15 mmol), (cyclohexyl)$_3$PBF$_4$ (110 mg, 0.30 mmol), and K$_2$CO$_3$ (138 mg, 0.10 mmol) in DMA (3 mL) was purged with N$_2$ for 20 minutes and then heated at 160° C. for 3 hours. The reaction was cooled to room temperature and diluted with ethyl acetate. The organic layer was washed with water and brine, dried over sodium sulfate and concentrated. Purification by flash chromatography (ethyl acetate/hexane) gave compound 42 as a yellow solid (110 mg, 41%). LCMS-ESI (POS), M/Z, M+1: Found 267.1, Calculated 267.2.

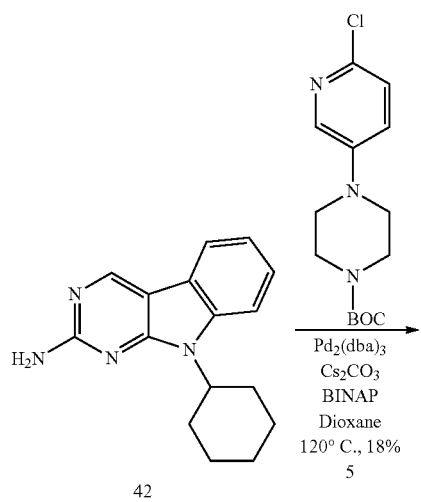

(9-Cyclohexyl-9H-pyrimido[4,5-b]indol-2-yl)-(5-piperazin-1-yl-pyridin-2-yl)-amine (40)

A mixture of compound 42 (98 mg, 0.37 mmol), compound 5 (121 mg, 0.41 mmol), Pd$_2$(dba)$_3$ (17 mg, 0.018 mmol), BINAP (23 mg, 0.037 mmol), and Cs$_2$CO$_3$ (168 mg, 0.52 mmol) in dioxane (3 mL) was purged with N$_2$ for 20 minutes. The reaction was heated at 120° C. for 14 hours. The reaction was then cooled down to room temperature and diluted with ethyl acetate. The reaction mixture was washed with water and brine. The organic layer was dried with sodium sulfate and concentrated. The residue was purified by flash chromatography (ethyl acetate/hexane) to give compound 43 (34 mg, 18%). LCMS-ESI (POS), M/Z, M+1: Found 528.3, Calculated 528.3.

Compound 43 was then treated with 4N HCl in dioxane (5 mL) for 3 hours. The reaction mixture was concentrated and the residue was purified by Prep-HPLC to give compound 40 as a yellow solid TFA salt (32 mg). $^1$H NMR (500 MHz, CD$_3$OD) δ 9.19 (1 H, s), 8.12-8.22 (2 H, m), 7.90 (1 H, d, J=7.3 Hz), 7.82 (1 H, d, J=7.9 Hz), 7.63 (1 H, t, J=7.6 Hz), 7.43 (1 H, t, J=7.0 Hz), 7.34 (1 H, d, J=7.9 Hz), 4.87 (1 H, s), 3.54 (4 H, s), 3.46 (4 H, s), 2.57-2.67 (2 H, m), 2.04 (2 H, d, J=14.0 Hz), 1.96 (2 H, d, J=11.0 Hz), 1.86 (1 H, d, J=12.2 Hz), 1.54-1.66 (2 H, m), 1.50 (1 H, d, J=12.2 Hz) ppm; LCMS-ESI (POS), M/Z, M+1: Found 428.2, Calculated 428.3.

Example 23

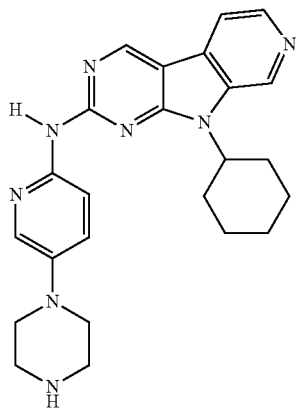

(9-Cyclohexyl-9H-pyrido[4',3',4,5]pyrrolo[2,3-d]pyrimidin-2-yl)-(5-piperazin-1-yl-pyridin-2-yl)-amine Compound 44 was prepared using chemistry similar to that described in example 1. $^1$H NMR (500 MHz, CD$_3$OD) δ ppm 9.84 (1 H, s), 9.59 (1 H, s), 8.88 (1 H, d, J=6.1 Hz), 8.74 (1 H, d, J=6.1 Hz), 8.32 (1 H, d, J=10.0 Hz), 8.12 (1 H, d, J=2.9 Hz), 7.67 (1 H, d, J=9.5 Hz), 5.03 (1 H, m), 3.76-3.78 (2 H, m), 3.64 (4 H, m), 3.48 (4 H, m), 2.63-2.70 (2 H, m), 2.06-2.09 (4 H, d, J=10.8 Hz), 2.03 (2 H, m), 1.64 (1 H, m); LCMS-ESI (POS), M/Z, M+1: Found 429.2, Calculated 429.2

Example 24

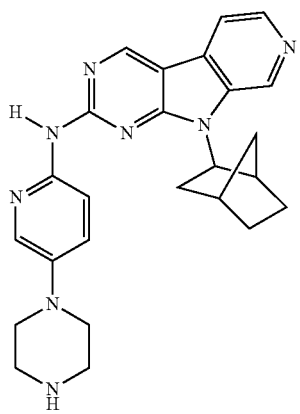

(9-Bicyclo[2.2.1]hept-2-yl-9H-pyrido[4',3':4,5]pyrrolo[2,3-d]pyrimidin-2-yl)-(5-piperazin-1-yl-pyridin-2-yl)-amine Compound 45 was prepared using chemistry similar to that described in example 1. $^1$H NMR (500 MHz, DMSO-d$_6$) δ 10.41 (1 H, s), 9.53 (1 H, s), 9.28 (1 H, s), 8.96 (2H, s), 8.63 (1 H, d, J=10 Hz), 8.14 (2 H, d, J=2.4 Hz), 7.65 (1 H, d, J=10 Hz), 4.78 (1 H, m), 3.42 (4 H, m), 3.28 (4 H, m), 2.90 (1 H, m), 2.83 (1 H, s), 2.58 (1 H, s), 2.25 (1 H, d, J=10 Hz), 2.02 (1 H, t, J=10 Hz), 1.60-1.65 (3 H, m), 1.35 (2 H, m) ppm; LCMS-ESI (POS), M/Z, M+1: Found 441.2, Calculated 441.2.

Example 25

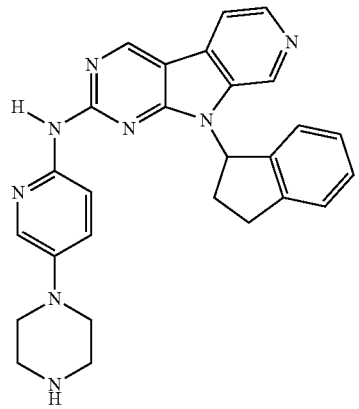

(9-Indan-1-yl-9H-pyrido[4',3':4,5]pyrrolo[2,3-d]pyrimidin-2-yl)-(5-piperazin-1-yl-pyridin-2-yl)-amine Compound 46 was prepared using chemistry similar to that described in example 1. $^1$H NMR (500 MHz, CD$_3$OD) δ 9.63 (1 H, s), 8.58-8.63 (2 H, dd, J=5.8, 21.1 Hz), 8.07 (1 H, d, J=2.7 Hz), 7.91 (1 H, s), 7.72 (1 H, s), 7.57 (1 H, d, J=5.0 Hz), 7.43 (1 H, t, J=5.0 Hz), 7.22 (1 H, t, J=5.0 Hz), 7.02 (1 H, d, J=5.0 Hz), 6.90 (1 H, t, J=5.0 Hz), 4.85 (1 H, m), 3.52 (4 H, m), 3.47 (4 H, m), 3.40 (1 H, m), 3.26 (1 H, m), 2.89 (1 H, m), 2.64 (1 H, m) ppm; LCMS-ESI (POS), M/Z, M+1: Found 463.1, Calculated 463.2.

Example 26

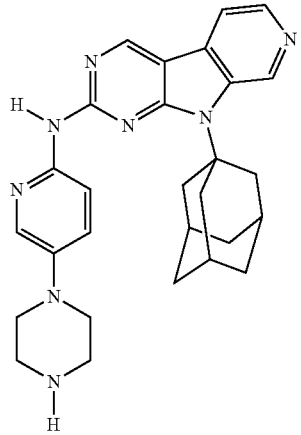

(9-Adamantan-1-yl-9H-pyrido[4',3':4,5]pyrrolo[2,3-d]pyrimidin-2-yl)-(5-piperazin-1-yl-pyridin-2-yl)-amine Compound 47 was prepared using chemistry similar to that described in example 1. $^1$H NMR (500 MHz, CD$_3$OD) δ 9.60 (1 H, s), 9.53 (1 H, s), 8.62 (1 H, d, J=5.0 Hz), 8.56 (1 H, d, J=5.0 Hz), 8.12 (1 H, t, J=2.5 Hz), 7.95 (1 H, m), 3.52 (4 H, m), 3.47 (4 H, m), 2.95 (6 H, d, J=2.5 Hz), 2.38 (3 H, s), 2.04 (1 H, s), 2.01 (2 H, s), 1.94 (2 H, s), 1.91 (1 H, s) ppm; LCMS-ESI (POS), M/Z, M+1: Found 481.3, Calculated 481.3.

Example 27

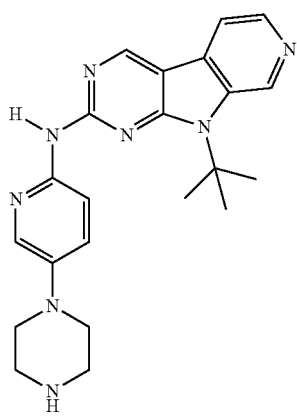

(9-tert-Butyl-9H-pyrido[4',3':4,5]pyrrolo[2,3-d]pyrimidin-2-yl)-(5-piperazin-1-yl-pyridin-2-yl)-amine Compound 48 was prepared using chemistry similar to that described in example 1. $^1$H NMR (500 MHz, CD$_3$OD) δ 9.85 (1 H, s), 9.60 (1 H, s), 8.88 (1 H, d, J=6.1 Hz), 8.71 (1 H, d, J=6.1 Hz), 8.33 (1 H, m), 8.11 (1 H, d, J=2.9 Hz), 7.69 (1 H, d, J=9.5 Hz), 3.61 (4 H, m), 3.48 (4 H, m), 2.17 (9 H, s) ppm; LCMS-ESI (POS), M/Z, M+1: Found 403.3, Calculated 403.2.

Example 28

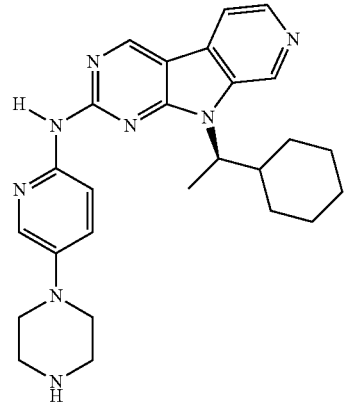

(R)-[9-(1-Cyclohexyl-ethyl)-9H-pyrido[4',3':4,5]pyrrolo[2,3-d]pyrimidin-2-yl]-(5-piperazin-1-yl-pyridin-2-yl)-amine Compound 49 was prepared using chemistry similar to that described in example 1. $^1$H NMR (500 MHz, CD$_3$OD) δ 9.68 (1 H, s), 9.43 (1 H, s), 8.69 (2 H, dd, J=7.3, 10.5 Hz), 8.12 (1 H, s), 8.10 (1 H, s), 7.80 (1 H, d, J=8.5 Hz), 4.93 (1 H, m), 3.57 (4 H, m), 3.47 (4 H, m), 2.18 (1 H, d, J=10.1 Hz), 1.92 (1 H, d, J=10.1 Hz), 1.82 (3 H, d, J=7.1 Hz), 1.69 (1 H, d, J=10.0 Hz), 1.59 (1 H, d, J=10.0 Hz), 1.40 (1 H, m), 1.23 (2 H, m), 1.10 (2 H, m), 0.96 (1 H, m) ppm; LCMS-ESI (POS), M/Z, M+1: Found 457.3, Calculated 457.3.

Example 29

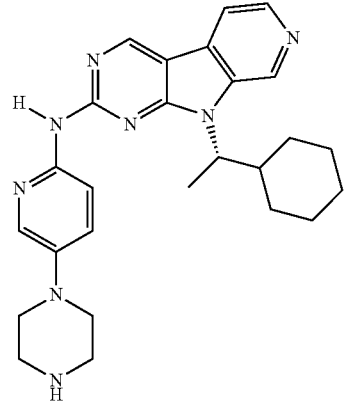

(S)-[[9-(1-Cyclohexyl-ethyl)-9H-pyrido[4',3':4,5]pyrrolo[2,3-d]pyrimidin-2-yl]-(5-piperazin-1-yl-pyridin-2-yl)-amine Compound 50 was prepared using chemistry similar to that described in example 1. $^1$H NMR (500 MHz, CD$_3$OD) δ 9.68

(1 H, s), 9.43 (1 H, s), 8.69 (2 H, dd, J=7.3, 10.5 Hz), 8.12 (1 H, s), 8.10 (1 H, s), 7.80 (1 H, d, J=8.5 Hz), 4.93 (1 H, m), 3.57 (4 H, m), 3.47 (4 H, m), 2.18 (1 H, d, J=10.1 Hz), 1.92 (1 H, d, J=10.1 Hz), 1.82 (3 H, d, J=7.1 Hz), 1.69 (1 H, d, J=10.0 Hz), 1.59 (1 H, d, J=10.0 Hz), 1.40 (1 H, m), 1.23 (2 H, m), 1.10 (2 H, m), 0.96 (1 H, m) ppm; LCMS-ESI (POS), M/Z, M+1: Found 457.3, Calculated 457.3.

Example 30

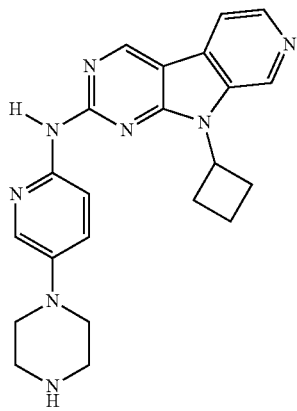

51

(9-Cyclobutyl-9H-pyrido[4',3':4,5]pyrrolo[2,3-d]pyrimidin-2-yl)-(5-piperazin-1-yl-pyridin-2-yl)-amine Compound 51 was prepared using chemistry similar to that described in example 1. $^1$H NMR (500 MHz, CD$_3$OD) δ 9.68 (1 H, s), 9.40 (1 H, s), 8.67-8.72 (2 H, dd, J=5.0, 15 Hz), 8.13 (1 H, dd, J=2.3, Hz), 8.10 (1 H, d, J=2.7 Hz), 7.83 (1 H, d, J=10.0 Hz), 5.52 (1 H, m), 3.58 (4 H, m), 3.48 (4 H, m), 3.29 (2 H, m), 2.69 (2 H, m), 2.13 (2 H, m) ppm; LCMS-ESI (POS), M/Z, M+1: Found 401.2, Calculated 401.2.

Example 31

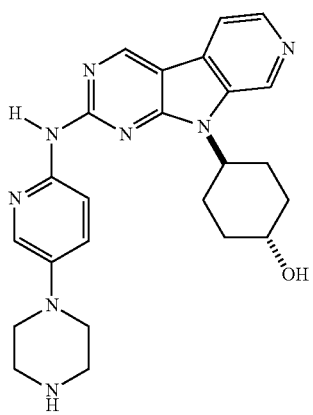

52

4-[2-(5-piperazin-1-yl-pyridin-2-ylamino)-pyrido[4',3':4,5]pyrrolo[2,3-d]pyrimidin-9-yl]-trans-cyclohexanol Compound 52 was prepared using chemistry similar to that described in example 1. $^1$H NMR (500 MHz, CD$_3$OD) δ 9.62 (1 H, s), 9.42 (1 H, s), 8.64 (2 H, s), 8.11 (1 H, d, J=2.5 Hz), 8.02 (1 H, d, J=10.0 Hz), 7.87 (1 H, d, J=10.0 Hz), 4.98 (1 H, m), 3.89 (1 H, m), 3.55 (4 H, m), 3.47 (4 H, m), 2.77 (2 H, m), 2.21 (1 H, d, J=15 Hz), 2.05 (2 H, m), 1.86 (1 H, m), 1.65 (2 H, m) ppm; LCMS-ESI (POS), M/Z, M+1: Found 445.1, Calculated 445.2.

Example 32

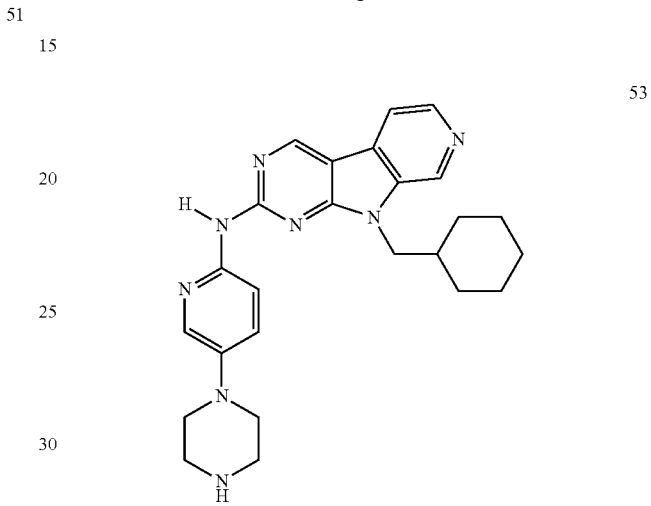

53

(9-Cyclohexylmethyl-9H-pyrido[4',3':4,5]pyrrolo[2,3-d]pyrimidin-2-yl)-(5-piperazin-1-yl-pyridin-2-yl)-amine Compound 53 was prepared using chemistry similar to that described in example 1. $^1$H NMR (500 MHz, DMSO-d$_6$) δ 9.73 (1 H, s), 9.60 (1 H, s), 9.56 (2 H, s), 8.75 (2 H, s), 8.14 (1 H, s), 8.08 (1 H, s), 7.96 (1 H, s), 4.41 (2 H, d, J=5.0 Hz), 3.48 (4 H, s), 3.26 (4 H, s), 2.08 (1 H, s), 1.57-1.67 (5 H, m), 1.13 (5 H, m) ppm; LCMS-ESI (POS), M/Z, M+1: Found 443.2, Calculated 443.3.

Example 33

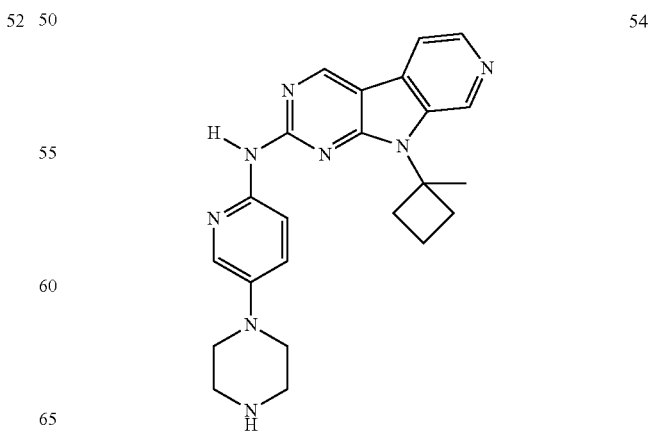

54

[9-(1-Methyl-cyclobutyl)-9H-pyrido[4',3':4,5]pyrrolo[2,3-d]pyrimidin-2-yl]-(5-piperazin-1-yl-pyridin-2-yl)-amine Compound 54 was prepared using chemistry similar to that described in example 1. $^1$H NMR (500 MHz, CD$_3$OD) δ 9.66 (1 H, s), 9.07 (1 H, s), 8.71 (1 H, d, J=5.0 Hz), 8.67 (1 H, d, J=5.0 Hz), 8.14 (1 H, dd, J=2.5, 10 Hz), 8.10 (1 H, d, J=2.5 Hz), 7.80 (1 H, d, J=10 Hz), 3.56 (4 H, m), 3.47 (4 H, m), 3.09 (2 H, q, J=5.0 Hz), 2.86 (2 H, t, J=2.5 Hz), 2.25 (1 H, m), 2.11 (1 H, m), 1.91 (3 H, s) ppm; LCMS-ESI (POS), M/Z, M+1: Found 415.1, Calculated 415.2.

Example 34

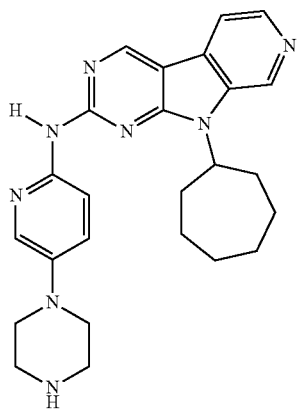

(9-Cycloheptyl-9H-pyrido[4',3':4,5]pyrrolo[2,3-d]pyrimidin-2-yl)-(5-piperazin-1-yl-pyridin-2-yl)-amine Compound 55 was prepared using chemistry similar to that described in example 1. $^1$H NMR (500 MHz, DMSO-d$_6$) δ 9.80 (1 H, s), 9.59 (1 H, s), 9.42 (2 H, s), 8.72 (2 H, s), 8.14 (1 H, s), 8.08 (1 H, s), 7.85 (1 H, s), 5.05 (1 H, m), 3.47 (4 H, s), 3.27 (4 H, s), 2.58 (4 H, s), 1.88 (1 H, m), 1.67-1.77 (10H, m) ppm; LCMS-ESI (POS), M/Z, M+1: Found 443.2, Calculated 443.3.

Example 35

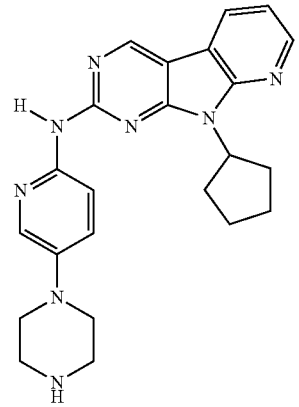

(9-Cyclopentyl-9H-pyrido[3',2':4,5]pyrrolo[2,3-d]pyrimidin-2-yl)-(5-piperazin-1-yl-pyridin-2-yl)-amine Compound 56 was prepared using chemistry similar to that described in example 1. $^1$H NMR (500 MHz, CD$_3$OD) δ 9.27 (1 H, s), 8.60 (1 H, dd, J=2.5, 5.0 Hz), 8.55 (1 H, dd, J=2.5, 5.0 Hz), 8.10 (1 H, d, J=5.0 Hz), 8.00 (1 H, dd, J=5.0, 10.0 Hz), 7.45 (2 H, m), 5.63 (1 H, q, J=10 Hz), 3.53 (4 H, m), 3.47 (4 H, m), 2.62 (2 H, m), 2.23 (2 H, m), 2.15 (2 H, m), 1.87 (2 H, m) ppm; LCMS-ESI (POS), M/Z, M+1: Found 415.1, Calculated 415.2.

Example 36

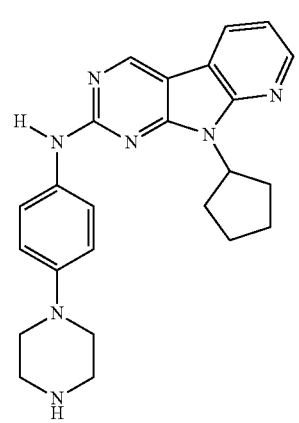

(9-Cyclopentyl-9H-pyrido[3',2':4,5]pyrrolo[2,3-d]pyrimidin-2-yl)-(4-piperazin-1-yl-phenyl)-amine Compound 57 was prepared using chemistry similar to that described in example 1. $^1$H NMR (500 MHz, CD$_3$OD) δ 8.99

(1 H, s), 8.49 (1 H, dd, J=2.5, 5.0 Hz), 8.40 (1 H, dd, J=2.5, 5.0 Hz), 7.59 (2 H, d, J=10 Hz), 7.38 (1 H, dd, J=5.0, 7.5 Hz), 7.14 (2 H, d, J=10.0 Hz), 5.53 (1 H, m), 3.44 (8 H, m), 2.52 (2 H, m), 2.06 (4 H, m), 1.77 (2 H, m) ppm; LCMS-ESI (POS), M/Z, M+1: Found 414.2, Calculated 414.2

Example 37

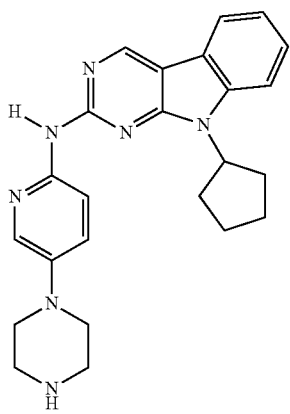

58

(9-Cyclopentyl-9H-pyrimido[4,5-b]indol-2-yl)-(5-piperazin-1-yl-pyridin-2-yl)-amine Compound 58 was prepared using chemistry similar to that described in example 22. $^1$H NMR (500 MHz, CD$_3$OD) δ 7.82 (1 H, s), 6.80 (2 H, d, J=6.1 Hz), 6.56 (1H, d, J=8.5 Hz), 6.34 (1 H, d, J=8.5 Hz), 6.24 (1H, t, J=7.3 Hz), 5.99-6.08 (2 H, m), 4.02-4.11 (1 H, m), 2.21 (4 H, m), 2.12 (4 H, m), 1.10 (2 H, s), 0.83 (4 H, s), 0.55 (2 H, s) ppm; LCMS-ESI (POS), M/Z, M+1: Found 414.2, Calculated 414.2

Example 38

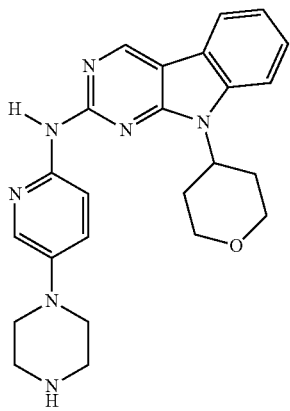

59

(5-piperazin-1-yl-pyridin-2-yl)-[9-(tetrahydro-pyran-4-yl)-9H-pyrimido[4,5-b]indol-2-yl]-amine Compound 59 was prepared using chemistry similar to that described in example 22. $^1$H NMR (500 MHz, CD$_3$OD) δ 7.93 (1 H, s), 6.91 (1 H, d, J=7.9 Hz), 6.86 (1 H, s), 6.65 (1 H, d, J=8.5 Hz), 6.56 (1 H, d, J=8.5 Hz), 6.36 (1 H, t, J=7.9 Hz), 6.16 (1 H, t, J=7.6 Hz), 6.07 (1 H, d, J=9.2 Hz), 3.79 (1H, m), 2.91 (2 H, dd, J=4.3, 11.6 Hz), 2.45 (2 H, m), 2.25 (4 H, m), 2.17 (4 H, s), 1.71 (2 H, dd, J=12.5, 4.6 Hz), 0.60 (2 H, d, J=9.8 Hz) ppm; LCMS-ESI (POS), M/Z, M+1: Found 430.1, Calculated 430.2.

Example 39

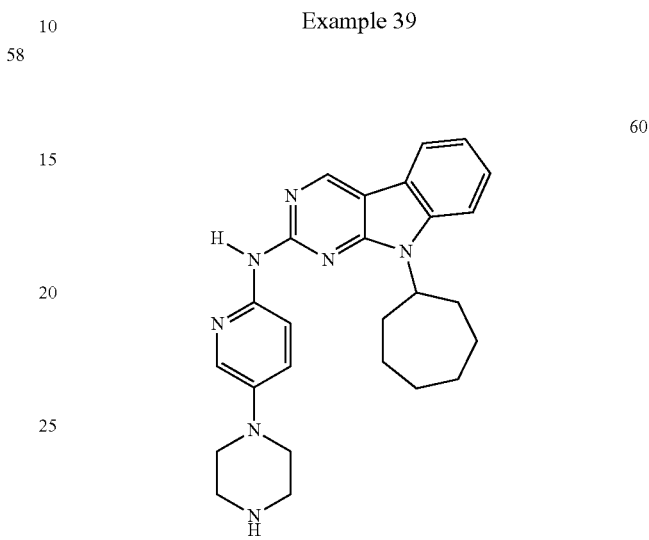

60

(9-Cycloheptyl-9H-pyrimido[4,5-b]indol-2-yl)-(5-piperazin-1-yl-pyridin-2-yl)-amine Compound 60 was prepared using chemistry similar to that described in example 22. $^1$H NMR (500 MHz, CD$_3$OD) δ 7.40 (1 H, s), 6.43 (1 H, d, J=7.3 Hz), 6.38 (1 H, d, J=3.1 Hz), 6.12 (1 H, dd, J=9.5, 2.7 Hz), 6.04 (1 H, d, J=7.9 Hz), 5.89 (1 H, t, J=10 Hz), 5.69 (1 H, t, J=10 Hz), 5.50 (1 H, d, J=10 Hz), 3.36 (1 H, m), 1.76 (4 H, m), 1.70 (4 H, m), 0.86 (2 H, m), 0.23-0.31 (4 H, m), 0.02-0.10 (6 H, m) ppm; LCMS-ESI (POS), M/Z, M+1: Found 442.3, Calculated 442.3.

Example 40

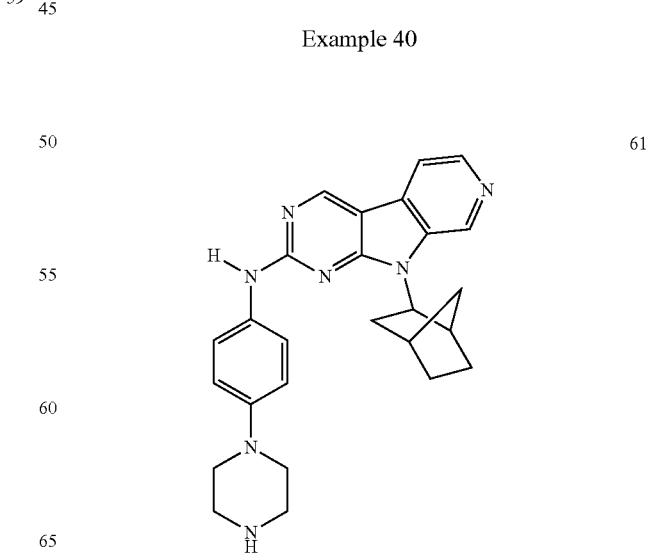

61

(9-Bicyclo[2.2.1]hept-2-yl-9H-pyrido[4',3':4,5]pyrrolo[2,3-d]pyrimidin-2-yl)-(4-piperazin-1-yl-phenyl)-amine Compound 61 was prepared using chemistry similar to that described in example 1. $^1$H NMR (500 MHz, CD$_3$OD) δ 9.37 (1 H, s), 9.10 (1 H, s), 8.50 (2 H, dd, J=5, 15 Hz), 7.72 (2 H, d, J=10 Hz), 7.11 (2 H, d, J=10 Hz), 4.72 (1 H, m), 3.44 (8 H, m), 2.96 (1 H, d, J=10 Hz), 2.92 (1 H, d, J=2.5 Hz), 2.58 (1 H, s), 2.33 (1 H, d, J=10 Hz), 2.08 (1 H, dd, J=5, 15 Hz), 1.75 (2 H, m), 1.59 (1 H, t, J=10 Hz), 1.44 (12H, t, J=10 Hz) ppm; LCMS-ESI (POS), M/Z, M+1: Found 440.2, Calculated 440.3.

Example 41

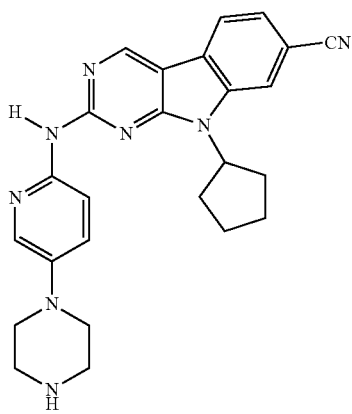

62

9-Cyclopentyl-2-(5-piperazin-1-yl-pyridin-2-ylamino)-9H-pyrimido[4,5-b]indole-7-carbonitrile Compound 62 was prepared using chemistry similar to that described in example 1. $^1$H NMR (500 MHz, CD$_3$OD) δ 9.33 (1 H, s), 8.34 (1 H, d, J=8.1 Hz), 8.13 (1 H, s), 8.07 (1 H, d, J=2.9 Hz), 8.01 (1 H, dd, J=9.4, 2.8 Hz), 7.71-7.73 (1 H, d, J=10 Hz), 7.63 (1 H, d, J=9.3 Hz), 5.39 (1 H, m), 3.54 (4 H, m), 3.47 (4 H, m), 2.52 (2 H, m), 2.20 (4 H, m), 1.91 (2 H, m) ppm; LCMS-ESI (POS), M/Z, M+1: Found 439.1, Calculated 439.2.

Example 42

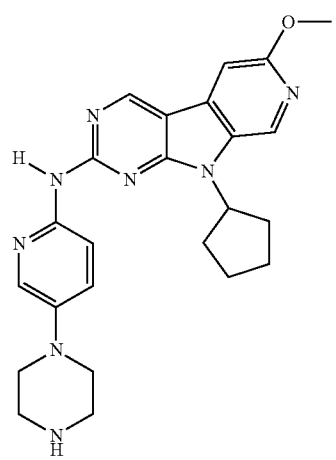

63

(9-Cyclopentyl-6-methoxy-9H-pyrido[4',3':4,5]pyrrolo[2,3-d]pyrimidin-2-yl)-(5-piperazin-1-yl-pyridin-2-yl)-amine Compound 63 was prepared via compound 65 using chemistry similar to that described in example 1. $^1$H NMR (500 MHz, CD$_3$OD) δ ppm 9.36 (1 H, s), 8.66 (1 H, s), 8.18 (1 H, d, J=2.7 Hz), 8.07 (1 H, dd, J=9.3, 2.7 Hz), 7.67 (1 H, s), 7.54 (1 H, d, J=9.3 Hz), 5.50 (1 H, m), 4.11 (3 H, s), 3.62 (4 H, m), 3.54 (4 H, m), 2.49-2.53 (2 H, m), 2.22-2.32 (4 H, m), 1.93-2.02 (2 H, m) ppm; LCMS-ESI (POS), M/Z, M+1: Found 445.2, Calculated 445.2.

Example 43

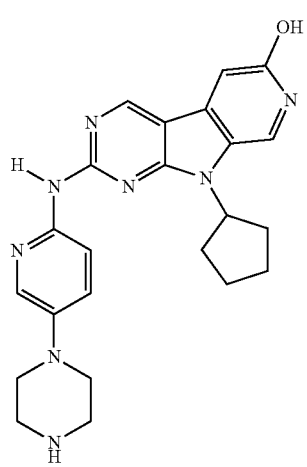

64

9-Cyclopentyl-2-(5-piperazin-1-yl-pyridin-2-ylamino)-9H-pyrido[4',3':4,5]pyrrolo[2,3-d]pyrimidin-6-ol

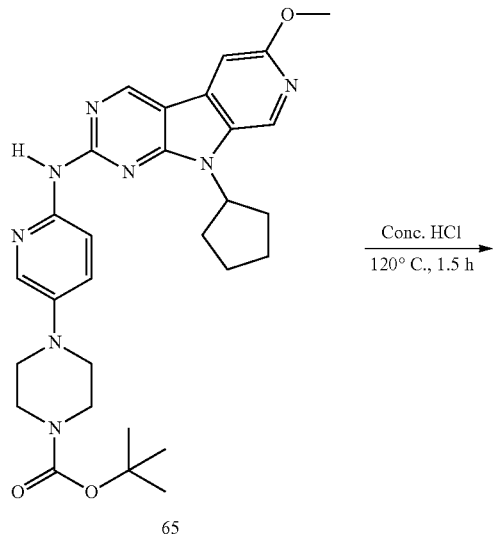

65

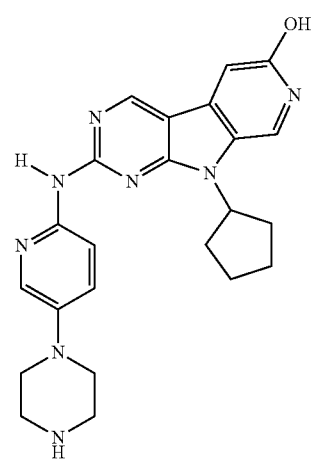

64

9-Cyclopentyl-2-(5-piperazin-1-yl-pyridin-2-ylamino)-9H-pyrido[4',3':4,5]pyrrolo[2,3-d]pyrimidin-6-ol (64) A mixture of compound 65 (366 mg) and conc. HCl (8 mL) was heated at 120° C. in a microwave reactor for 1.5 h. The reaction mixture was concentrated and purified by prep-HPLC to give compound 64 as a yellow solid (21%). $^1$H NMR (500 MHz, CD$_3$OD) δ 9.15 (1 H, s), 8.10 (1 H, d, J=2.7 Hz), 7.99 (1 H, dd, J=9.3, 2.9 Hz), 7.91 (1 H, s), 7.48 (1 H, d, J=9.3 Hz), 7.26 (1 H, s), 5.18 (1 H, s), 3.54 (4 H, m), 3.47 (4 H, m), 2.35-2.37 (2 H, m), 2.11-2.16 (4 H, m), 1.86 (2 H, m) ppm; LCMS-ESI (POS), ma, M+1: Found 431.2, Calculated 431.2.

Example 44

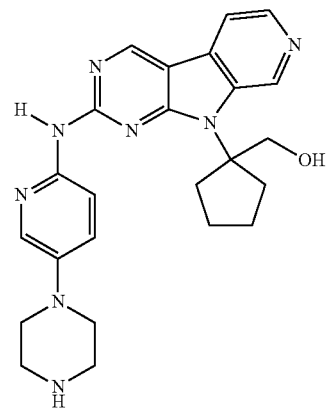

66

{1-[2-(5-piperazin-1-yl-pyridin-2-ylamino)-pyrido[4',3':4,5]pyrrolo[2,3-d]pyrimidin-9-yl]-cyclopentyl}-methanol Compound 66 was prepared using chemistry similar to that described in example 1. $^1$H NMR (500 MHz, CD$_3$OD) δ 9.67 (1 H, s), 9.36 (1 H, s), 8.70 (1 H, d, J=6.1 Hz), 8.62 (1 H, d, J=6.1 Hz), 8.10 (1 H, d, J=10 Hz), 8.08 (1 H, d, J=2.7 Hz), 7.80 (1 H, d, J=10 Hz), 3.99 (2 H, s), 3.55-3.57 (4 H, m), 3.46-3.48 (4 H, m), 3.07-3.11 (2 H, m), 2.60-2.66 (2 H, m), 1.97-2.01 (2 H, m), 1.89-1.92 (2 H, m) ppm; LCMS-ESI (POS), M/Z, M+1: Found 445.1, Calculated 445.2.

Example 45

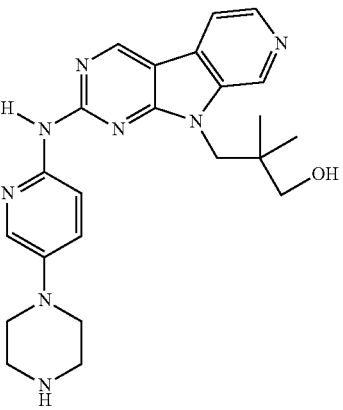

67

2,2-Dimethyl-3-[2-(5-piperazin-1-yl-pyridin-2-ylamino)-pyrido[4',3':4,5]pyrrolo[2,3-d]pyrimidin-9-yl]-propan-1-ol Compound 67 was prepared using chemistry similar to that described in example 1. $^1$H NMR (500 MHz, CD$_3$OD) δ 9.66

(1 H, s), 9.52 (1 H, s), 8.68 (2 H, s), 8.14-8.17 (1 H, dd, J=9.5, 2.9 Hz), 8.04 (1 H, d, J=2.9 Hz), 7.76 (1 H, d, J=9.5 Hz), 4.58 (2 H, s), 3.58 (4 H, m), 3.48 (4 H, m), 3.36 (2 H, s), 1.11 (6 H, s) ppm; LCMS-ESI (POS), M/Z, M+1: Found 433.1, Calculated 433.2.

Example 46

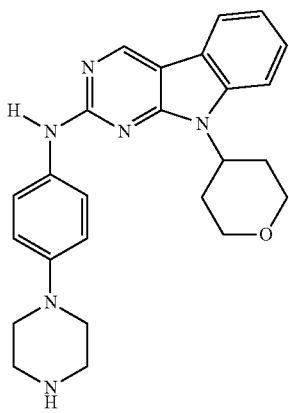

68

(4-piperazin-1-yl-phenyl)-[9-(tetrahydro-pyran-4-yl)-9H-pyrimido[4,5-b]indol-2-yl]-amine Compound 68 was prepared using chemistry similar to that described in example 22. $^1$H NMR (500 MHz, CD$_3$OD) δ 7.40 (1 H, s), 6.55 (1 H, d, J=9.2 Hz), 6.25 (1 H, d, J=9.2 Hz), 6.09 (3 H, m), 5.89 (1 H, t, J=9.2 Hz), 5.64 (2 H, d, J=9.2 Hz), 3.44 (1 H, m), 2.63 (2 H, dd, J=5, 10 Hz), 2.16 (2 H, t, J =10 Hz), 1.94 (4 H, m), 1.89 (4 H, m), 1.42 (2 H, td, J=5, 15 Hz), 0.35 (2 H, dd, J=10, 2.5 Hz) ppm; LCMS-ESI (POS), M/Z, M+1: Found 429.2, Calculated 429.2.

Example 47

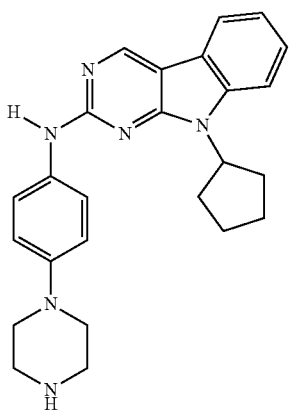

69

(9-Cyclopentyl-9H-pyrimido[4,5-b]indol-2-yl)-(4-piperazin-1-yl-phenyl)-amine

Compound 69 was prepared using chemistry similar to that described in example 22. $^1$H NMR (500 MHz, DMSO-d$_6$) δ 10.05 (1 H, s), 9.30 (1 H, s), 9.22 (1 H, s), 8.16 (1 H, d, J=7.8 Hz), 7.76 (1 H, d, J=8.3 Hz), 7.54-7.57 (3 H, m), 7.39 (1 H, t, J=7.5 Hz), 7.09 (2 H, d, J=9.0 Hz), 5.24 (1 H, m), 3.72 (4 H, m), 3.50 (4 H, m), 2.32 (2 H, m), 2.05 (2 H, m), 1.95 (2 H, m), 1.71 (2 H, m) ppm; LCMS-ESI (POS), M/Z, M+1: Found 413.2, Calculated 413.2.

Example 48

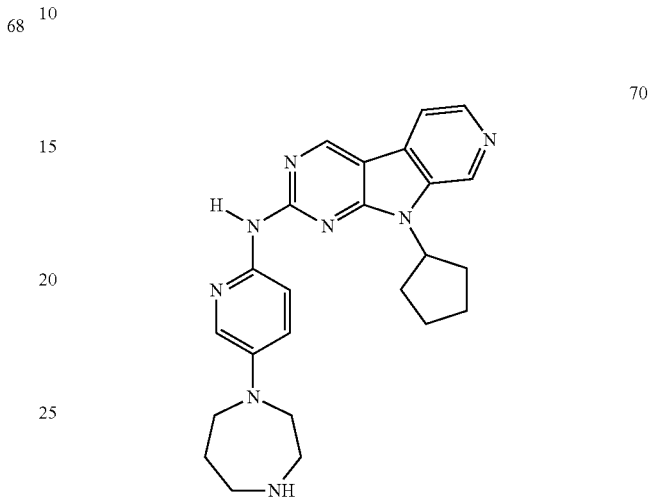

70

9-cyclopentyl-N-(5-(1,4-diazepan-1-yl)-2-pyridinyl)-9H-pyrido[4',3':4,5]pyrrolo[2,3-d]pyrimidin-2-amine Compound 70 was prepared using chemistry similar to that described in example 1. $^1$H NMR (500 MHz, DMSO-d$_6$) δ 10.75 (1H, br s), 9.56 (1H, s), 9.34 (1H, s), 8.83 (2H, br s), 8.67 (1H, d, J=6.3 Hz), 8.57 (1H, d, J=5.9 Hz), 7.96 (1H, d, J=2.7 Hz), 7.92 (1H, d, J=9.4 Hz), 7.55 (1H, br s), 5.36 (1H, p, J =8.7 Hz), 3.76 (2H, t, J=5.0 Hz), 3.56 (2H, t, J=6.3 Hz), 3.30 (2H, br s), 3.19 (2H, br s), 2.41 (2H, m), 2.09 (6H, m), 1.75 (2H, m) ppm; LCMS-ESI (POS), M/Z, M+1: Found 429.2

Example 49

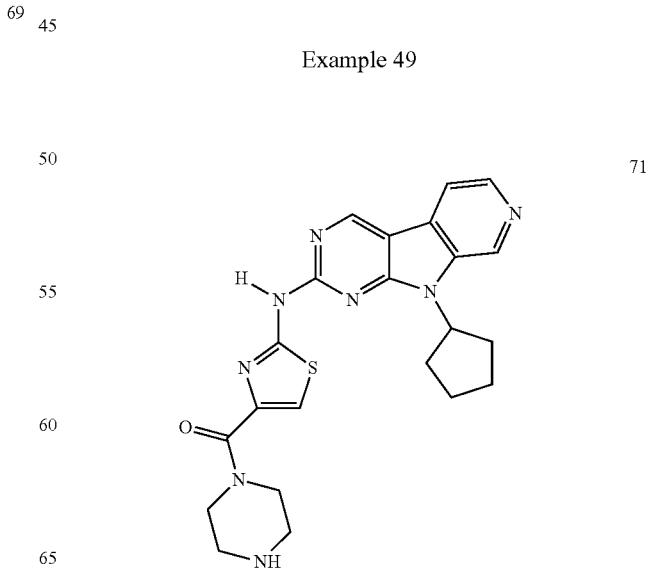

71

9-cyclopentyl-N-(4-(1-piperazinylcarbonyl)-1,3-thiazol-2-yl)-9H-pyrido-[4',3':4,5]pyrrolo[2,3-d]pyrimidin-2-amine

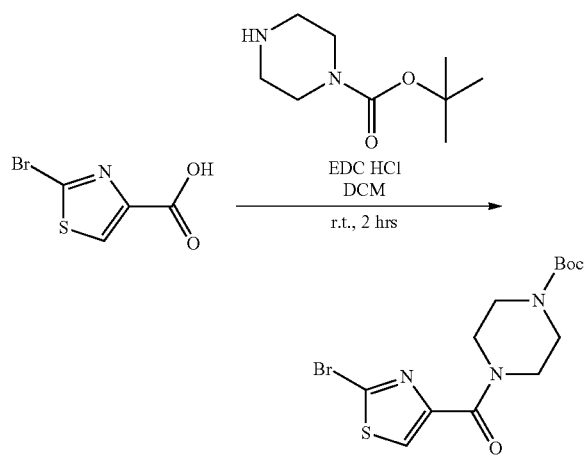

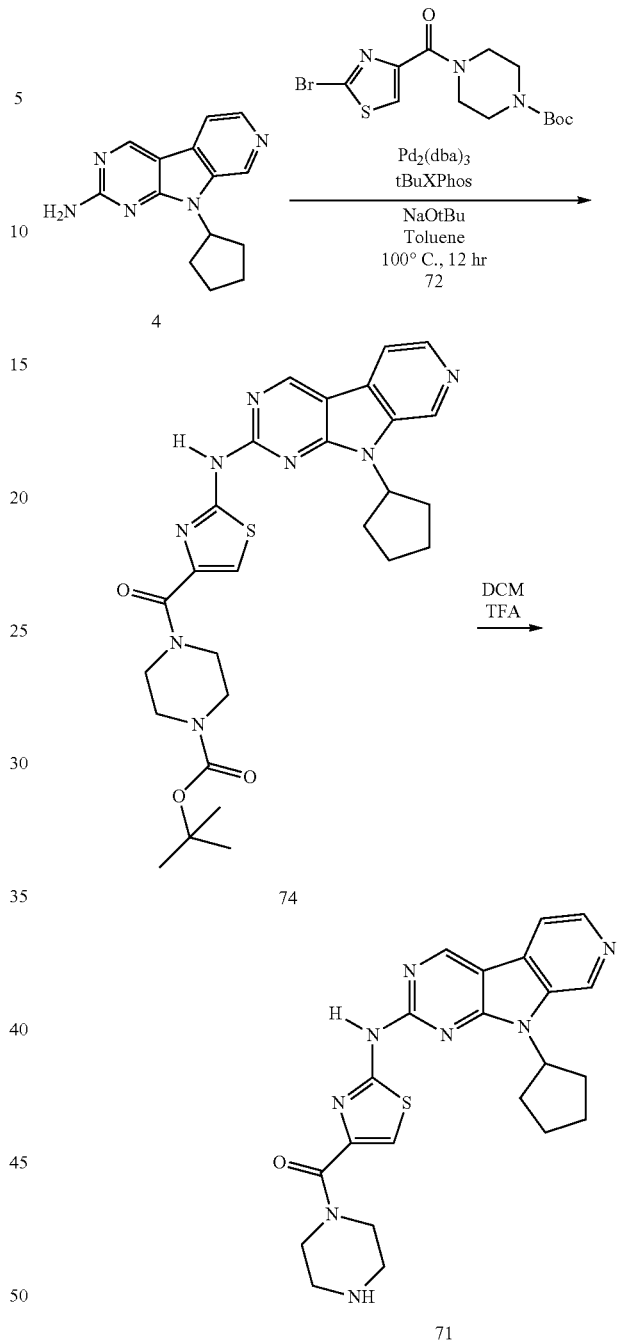

1,1-dimethylethyl 4-((2-bromo-1,3-thiazol-4-yl)carbonyl)-1-piperazinecarboxylate (72): 2-bromothiazole-4-carboxylic acid (1.31 g, 6.3 mmol) was combined with tert-butyl piperazine-1-carboxylate (1.2 g, 6.3 mmol) in DCM (15 mL), and then stirred at 20° C. until it formed a clear solution. N1-((ethylimino)methylene)-N3,N3-dimethylpropane-1,3-diamine hydrochloride (1.2 g, 6.3 mmol) was then added, and the reaction was stirred at 20° C. for 2 hours. The reaction was concentrated in vacuum, before transferring it to a separation funnel with ethyl acetate. The organic layer was washed with saturated NaHCO$_3$, water, NH$_4$Cl, and then with brine. After drying the organic layer with MgSO$_4$, it was concentrated in vacuum to yield compound 72 (2.2 g, 91%) as a light yellow solid. $^1$H NMR (500 MHz, DMSO-d$_6$) δ 8.16 (1H, s), 3.61 (4H, m), 3.38 (4H, m), 1.42 (9H, s) ppm; LCMS-ESI (POS), M/Z, M+1-C$_3$H$_9$: Found 320.0.

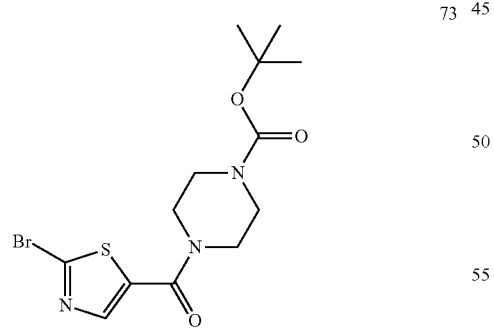

1,1-dimethylethyl 4-((2-bromo-1,3-thiazol-5-yl)carbonyl)-1-piperazinecarboxylate Compound 73 was prepared according to the methods described for compound 72 in example 49. $^1$H NMR (500 MHz, DMSO-d$_6$) δ 8.02 (1H, s), 3.62 (4H, m), 3.42 (4H, m), 1.43 (9H, s) ppm.

1,1-dimethylethyl 4-((2-((9-cyclopentyl-9H-pyrido[4',3': 4,5]pyrrolo[2,3-d]pyrimidin-2-yl)amino)-1,3-thiazol-4-yl) carbonyl)-1-piperazinecarboxylate (74): Compound 4 (0.075 g, 0.30 mmol) was combined with sodium 2-methylpropan-2-olate (0.085 g, 0.89 mmol) and compound 72 (0.14 g, 0.38 mmol) in toluene (2 mL). This mixture was degassed by bubbling nitrogen through this solution for ~2 min followed by the addition of Pd$_2$(dba)$_3$ (0.014 g, 0.015 mmol) and t-Butyl-XPhos (0.025 g, 0.059 mmol). The reaction was heated overnight at 60° C. Additional compound 72, 0.28 g, 0.76 mmol), Pd$_2$(dba)$_3$ (25 mg), t-Butyl-XPhos (54 mg), and the sodium 2-methylpropan-2-olate (0.085 g, 0.89 mmol) were added to the reaction which was heated overnight at 100° C. The reaction was cooled to 20° C. and poured into a separation funnel, with ethyl acetate and water. The layers were partitioned and the aqueous layer was washed with ethyl acetate. The combined organic fractions were dried over MgSO₄ and concentrated. The product was purified by flash column chromatography, eluting with a gradient of DCM-6% methanol/0.3% NH4OH/DCM to yield compound 74 (95 mg) as a brown film. LCMS-ESI (POS), M/Z, M+1: Found 549.3.

9-cyclopentyl-N-(4-(1-piperazinylcarbonyl)-1,3-thiazol-2-yl)-9H-pyrido[4',3':4,5]pyrrolo-[2,3-d]pyrimidin-2-amine (71): Compound 74 was dissolved in DCM (5 mL) and TFA (1.5 mL) and stirred at 20° C. for 2.5 hrs. The reaction was concentrated in vacuum and purified by preparative HPLC eluting with a gradient 10% MeCN/water/0.1% TFA -50% MeCN/water/0.1% TFA to provide compound 71 (23 mg) as a yellow solid. ¹H NMR (500 MHz, CD₃OD) δ 9.63 (1H, s), 9.32 (1H, s), 8.68 (1H, d, J=6.1 Hz), 8.63 (1H, d, J=6.4 Hz), 7.84 (1H, s), 5.56 (1H, p, J=8.1), 4.00-4.29 (4H, br s), 3.39 (4H, t, J=5.3 Hz), 2.63 (2H, m), 2.25 (4H, m), 1.98 (2H, m) ppm; LCMS-ESI (POS), M/Z, M+1: Found 449.2.

Example 50

75

9-cyclopentyl-N-(5-(1-piperazinylcarbonyl)-1,3-thiazol-2-yl)-9H-pyrido[4',3':4,5]pyrrolo[2,3-d]pyrimidin-2-amine Compound 75 was prepared according to the methods described in example 49. ¹H NMR (500 MHz, CD₃OD) δ 9.63 (1H, s), 9.34 (1H, s), 8.65 (1H, d, J=6.1 Hz), 8.62 (1H, d, J=6.1 Hz), 7.93 (1H, s), 5.52 (1H, p, J=9.3 Hz), 4.10 (4H, t, J=5.1 Hz), 3.39 (4H, t, J=5.1 Hz), 2.70 (2H, m), 2.28 (4H, m), 1.95 (2H, m) ppm; LCMS-ESI (POS), M/Z, M+1: Found 449.2.

Example 51

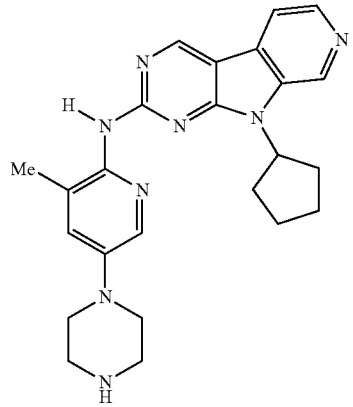

9-cyclopentyl-N-(3-methyl-5-(1-piperazinyl)-2-pyridinyl)-9H-pyrido[4',3':4,5]pyrrolo[2,3-d]pyrimidin-2-amine

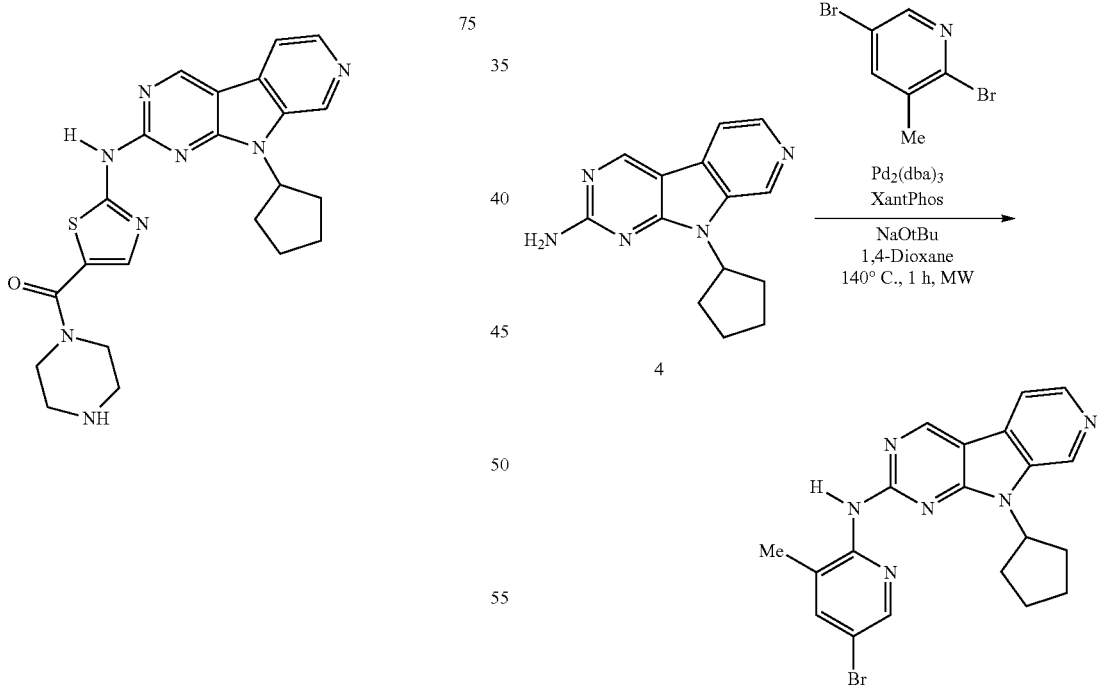

N-(5-bromo-3-methyl-2-pyridinyl)-9-cyclopentyl-9H-pyrido[4',3':4,5]pyrrolo[2,3-d]pyrimidin-2-amine (77): Sodium 2-methylpropan-2-olate (0.142 g, 1.48 mmol) was combined with compound 4 (0.125 g, 0.493 mmol) and 2,5-dibromo-3-methylpyridine (0.149 g, 0.592 mmol) in 1,4-dioxane (3 ml). The reaction mixture was degassed by bubbling nitrogen through the solution for ~1 mM, followed by the addition of XANTPHOS (0.0428 g, 0.0740 mmol) and Pd₂(dba)₃ (0.0339 g, 0.0370 mmol). The reaction was heated to 140° C. using microwave irradiation for 1 hour. The reaction mixture was poured into sat. NH₄Cl and extracted with 10% isopropanol/DCM. The organic layer was dried with MgSO₄ and concentrated in vacuum. Purification by flash column chromatography, eluting with a gradient of DCM-5% methanol/DCM provided compound 77 as a yellow solid (150 mg, 71%). LCMS-ESI (POS), M/Z, M+1: Found 423.1

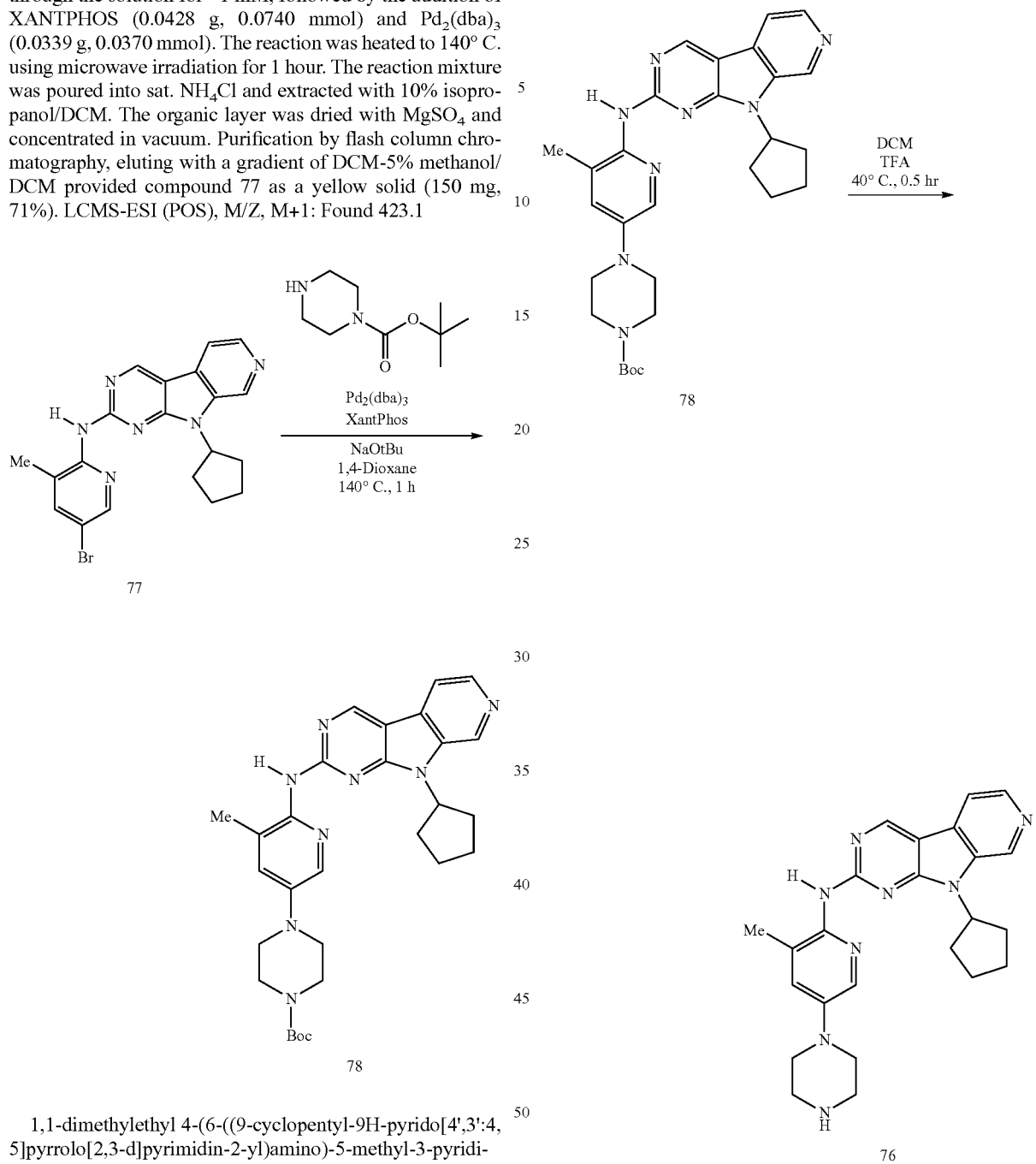

1,1-dimethylethyl 4-(6-((9-cyclopentyl-9H-pyrido[4',3':4,5]pyrrolo[2,3-d]pyrimidin-2-yl)amino)-5-methyl-3-pyridinyl)-1-piperazinecarboxylate (78): Sodium 2-methylpropan-2-olate (0.100 g, 1.06 mmol) was combined with compound 77 (0.150 g, 0.354 mmol) and tert-butyl 1-piperazinecarboxylate (0.099 g, 0.532 mmol) in 1,4-dioxane (3 ml). Nitrogen was bubbled through the solution for 1 min before adding XANTPHOS (0.031 g, 0.053 mmol) and Pd₂(dba)₃ (0.024 g, 0.026 mmol). The reaction mixture was heated to 140° C. using microwave irradiation for 1 hour. The reaction mixture was poured into sat. NH₄Cl, and extracted with 10% isopropanol/DCM. The organic layer was dried over MgSO₄ and concentrated in vacuum. The crude product was purified by flash column chromatography, eluting with a gradient of DCM-7% methanol/DCM to provide compound 78 as a brown oil (100 mg). LCMS-ESI (POS), M/Z, M+1: Found 529.3.

9-cyclopentyl-N-(3-methyl-5-(1-piperazinyl)-2-pyridinyl)-9H-pyrido[4',3':4,5]pyrrolo[2,3-d]pyrimidin-2amine (76): Compound 78 (0.100 g, 0.189 mmol) was dissolved in DCM (3 mL) followed by TFA (1 mL) and stirred at 40° C. in a water bath for 30 min. Concentration under vacuum provided a yellowish oil which was partially dissolved in water and then filtered. The filtrate was purified by preparative RP-HPLC eluting with a gradient of 5% MeCN/water/0.1% TFA-30% MeCN/water/0.1% TFA to yield compound 76 as a yellow solid (33 mg). ¹H NMR (500 MHz, DMSO-d₆) δ 10.18 (1H, s), 9.51 (1H, s), 9.31 (1H, s), 8.95 (2H, br s), 8.65 (1H, d, J=6.2 Hz), 8.55 (1H, d, J=6.1 Hz), 8.12 (1H, d, J=3.0), 7.58 (1H, d, J=2.4 Hz), 5.25 (1H, p, J=8.3 Hz), 3.46 (4H, t, J=5.4 Hz), 3.30 (4H, m), 2.24 (3H, s), 2.18 (2H, m), 2.01 (2H, m), 1.70 (2H, m), 1.55 (2H, m) ppm; LCMS-ESI (POS), M/Z, M+1: Found 429.2.

Example 52

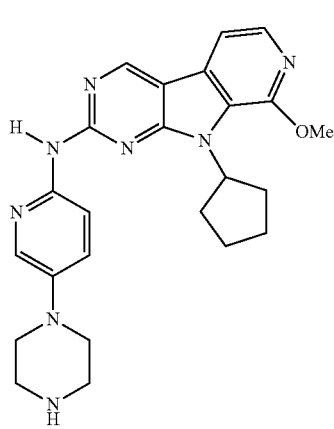

79

9-cyclopentyl-8-(methyloxy)-N-(5-(1-piperazinyl)-2-pyridinyl)-9H-pyrido[4',3':4,5]-pyrrolo[2,3-d]pyrimidin-2-amine Compound 79 was prepared using compound 82 and chemistry similar to that described in example 1. $^1$H NMR (500 MHz, CD$_3$OD) δ 9.12 (1 H, s), 8.24 (1 H, d), 8.02 (1 H, d), 7.98 (1 H, d), 7.63 (1 H, d), 7.56 (1 H, m), 5.90 (1 H, b), 4.15 (3 H, s), 3.20 (4 H, m), 3.06 (4 H, m), 2.50-2.60 (2 H, b), 2.09-2.11 (4H, b), 1.80 (2 H, b) ppm; LCMS-ESI (POS), M/Z, M+1: Found 445.1, calculated 445.2.

Example 53

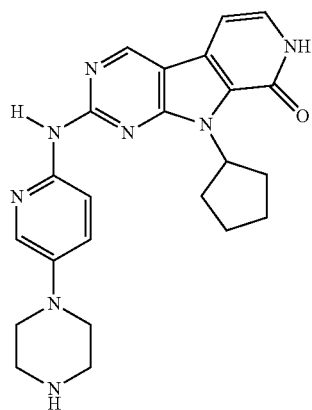

80

9-Cyclopentyl-2-((5-(1-piperazinyl)-2-pyridinyl) amino)-7,9-dihydro-8,1-pyrido[4',3':4,5]pyrrolo[2,3-d]pyrimidin-8-one

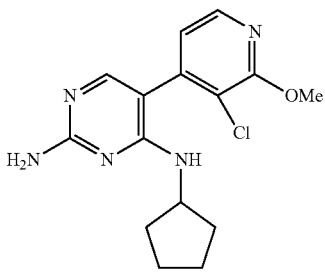

81

5-(3-chloro-2-(methyloxy)-4-pyridinyl)-N$^4$-cyclopentyl-2,4-pyrimidinediamine

Compound 81 was prepared using chemistry similar to that described in example 1. LCMS-ESI (POS), M/Z, M+1: Found 320.0, calculated 320.1.

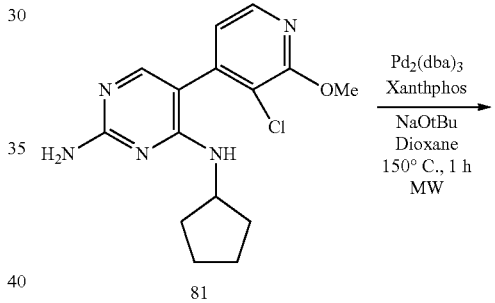

81

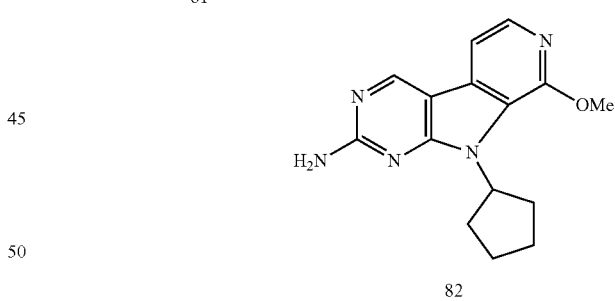

82

9-cyclopentyl-8-(methyloxy)-9H-pyrido[4',3':4,5]pyrrolo[2,3-d]pyrimidin-2-amine (82): A solution of Pd$_2$(dba)$_3$ (0.60 g, 0.65 mmol), sodium 2-methylpropan-2-olate (1.9 g, 20 mmol), 4,5-bis(diphenylphosphino)-9,9-dimethyl-9H-xanthene (0.75 g, 1.3 mmol) and compound 81 (2.08 g, 6.5 mmol) in dioxane (20 mL) was purged with N$_2$ for 20 min. The reaction mixture was heated at 150° C. for one hour under microwave irradiation. The reaction mixture was concentrated and residue was diluted with DCM. Resulting solution was washed with brine, dried and concentrated. Purification by flash chromatography (10% methanol/DCM/1% NH$_4$OH) gave compound 82 as a yellow solid (1.8 g, 98%). LCMS-ESI (POS), M/Z, M+1: Found 284.1, calculated 284.1.

93

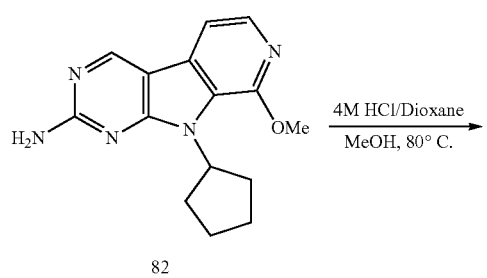

82

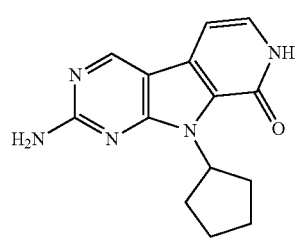

83

2-amino-9-cyclopentyl-7,9-dihydro-8H-pyrido[4',3':4,5]pyrrolo[2,3-d]pyrimidin-8-one (83): A solution of compound 82 (1.80 g, 6.35 mmol) in 4M HCl in dioxane (60 mL) and methanol (6 mL) was heated at 80° C. for one hour. Solid was collected by filtration to give a pale yellow solid as HCl salt which was then dissolved in water and basified by addition of solid sodium bicarbonate to pH 5~6. The precipitate was collected by filtration to provide compound 83 as a white solid. (0.715 g, 42%). LCMS-ESI (POS), M/Z, M+1: Found 270.1, calculated 270.1.

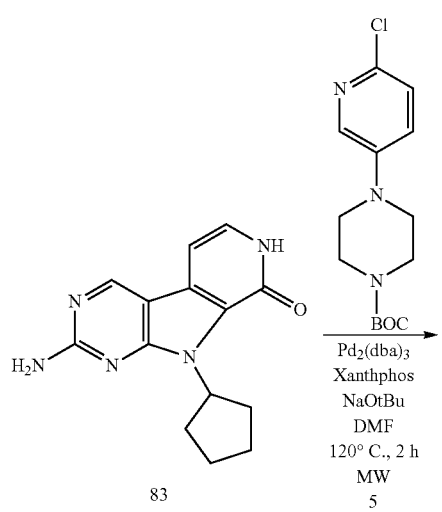

83

94

-continued

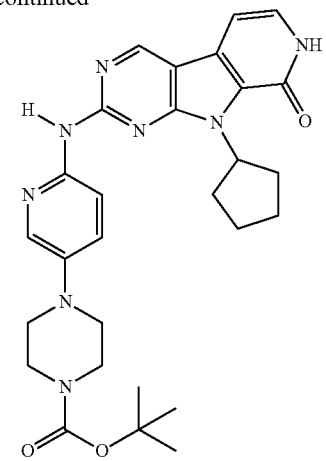

84

1,1-dimethylethyl 4-(6-((9-cyclopentyl-8-oxo-8,9-dihydro-7H-pyrido[4',3':4,5]pyrrolo[2,3-d]pyrimidin-2-yl)amino)-3-pyridinyl)-1-piperazinecarboxylate (84): Compound 84 was prepared by analogy to example 1. LCMS-ESI (POS), M/Z, M+1: Found 531.2, calculated 531.3.

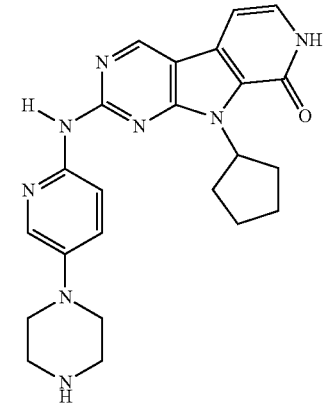

80

9-Cyclopentyl-2-((5-(1-piperazinyl)-2-pyridinyl)amino)-7,9-dihydro-8H-pyrido[4',3':4,5]-pyrrolo[2,3-d]pyrimidin- 8-one (80): Compound 80 was prepared according to the methods described in example 1. $^1$H NMR (500 MHz, CD$_3$OD) δ 9.31 (1 H, s), 8.03 (1 H, d), 8.01 (1 H, d), 7.75 (1 H, d), 7.35 (1 H, d), 7.16 (1 H, m), 6.25 (1 H, b), 3.52 (4 H, m), 3.47 (4 H, m), 2.50-2.60 (2 H, b), 2.09-2.25 (4 H, b), 1.75 (2 H, b) ppm; LCMS-ESI (POS), M/Z, M+1: Found 431.2, calculated 431.2

Example 54 was stirred at 0° C. for two hours. The reaction mixture was concentrated and dissolved in DCM. The resulting organic solution was washed with brine, dried and concentrated. Purification by flash chromatogaphy (10% methanol/DCM/1% NH$_4$OH) gave compound 86 (0.102 g, 67%) as a yellow solid. LCMS-ESI (POS), M/Z, M+1: Found 402.1, calculated 402.1.

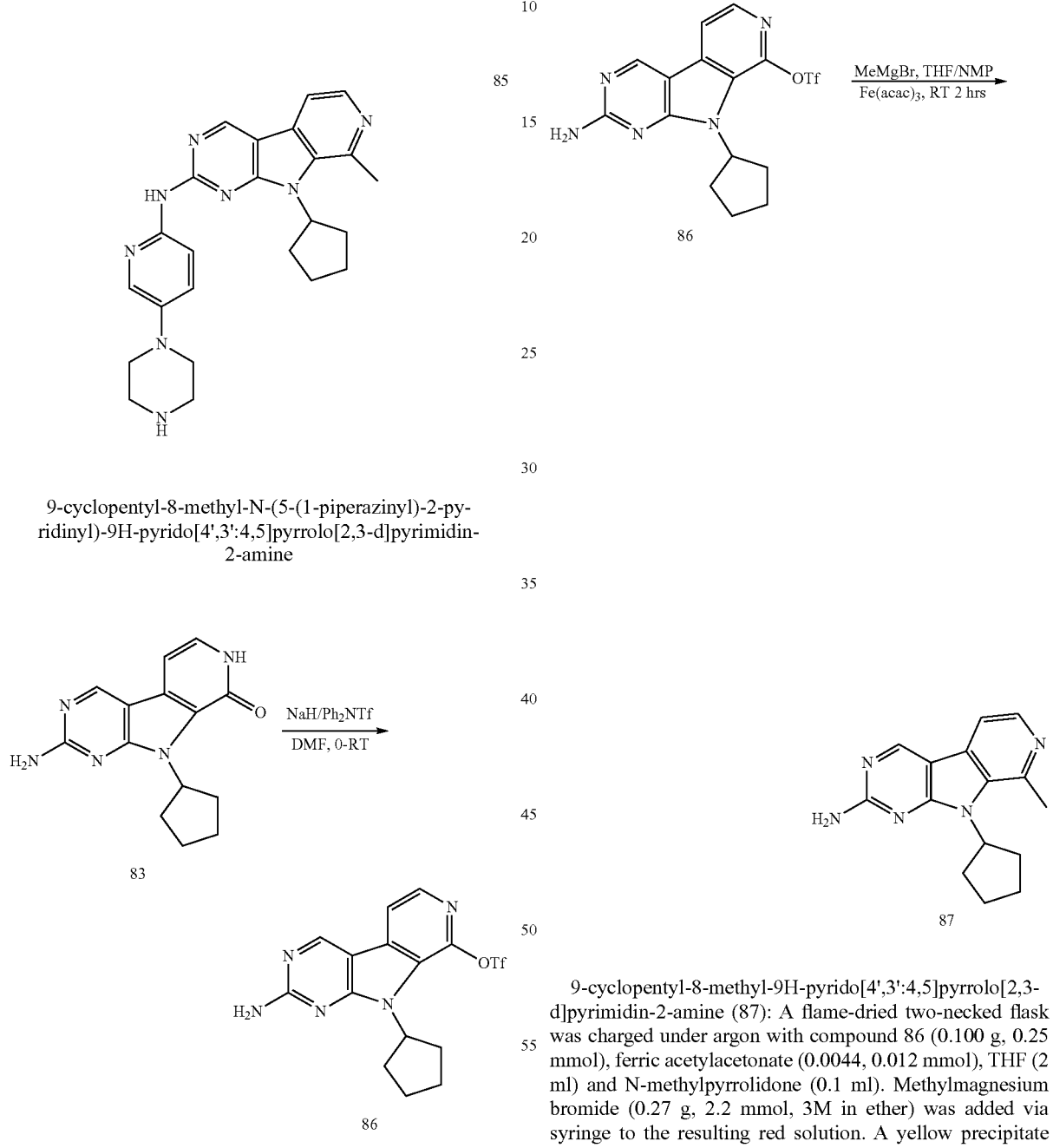

9-cyclopentyl-8-methyl-N-(5-(1-piperazinyl)-2-pyridinyl)-9H-pyrido[4',3':4,5]pyrrolo[2,3-d]pyrimidin-2-amine 2-Amino-9-cyclopentyl-9H-pyrido[4',3':4,5]pyrrolo[2,3-d]pyrimidin-8-yl trifluoromethanesulfonate (86): Sodium hydride (60% in oil, 16 mg) was added to a solution of compound 83 (0.100 g, 0.371 mmol) in DMF (2 mL) and stirred at CC for 30 min., then N-phenyl-bis(trifluoromethanesulfonimide)(0.146 g, 0.408 mmol) in DMF (1 mL) was added dropwise at 0° C. and the resulting mixture 9-cyclopentyl-8-methyl-9H-pyrido[4',3':4,5]pyrrolo[2,3-d]pyrimidin-2-amine (87): A flame-dried two-necked flask was charged under argon with compound 86 (0.100 g, 0.25 mmol), ferric acetylacetonate (0.0044, 0.012 mmol), THF (2 ml) and N-methylpyrrolidone (0.1 ml). Methylmagnesium bromide (0.27 g, 2.2 mmol, 3M in ether) was added via syringe to the resulting red solution. A yellow precipitate formed immediately. The reaction was stirred at room temperature for 30 min and quenched with 5% NaHCO$_3$, then extracted into DCM The resulting organic solution was washed with brine, dried and concentrated. Purification by flash chromatography (10% methanol/DCM/1% NH$_4$OH) gave compound 87 as a light yellow solid (0.036 g, 54%). LCMS-ESI (POS), M/Z, M+1: Found 268.1, calculated 268.2.

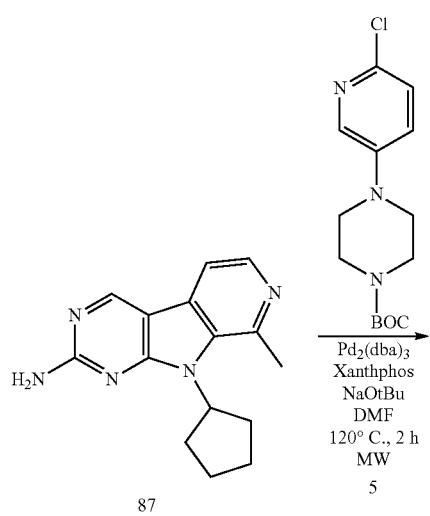

87

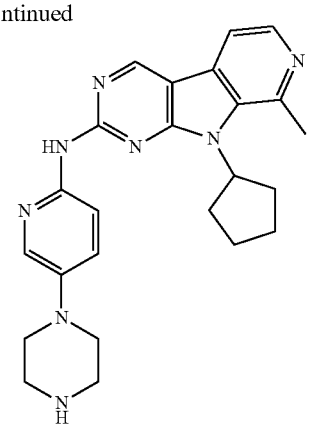

85

9-cyclopentyl-8-methyl-N-(5-(1-piperazinyl)-2-pyridinyl)-9H-pyrido[4',3':4,5]pyrrolo[2,3-d]pyrimidin-2amine 85): Compound 85 was prepared according to the methods described in example 1. $^1$H NMR (500 MHz, CD$_3$OD) δ 9.01 (1 H, s), 8.36 (1H, s), 8.29 (2 H, d), 8.01 (1 H, s), 7.62 (1H, d), 7.28 (1 H, d), 5.36 (1 H, m), 3.09 (4 H, m), 3.02 (4 H, m), 2.95 (3 H, s), 2.73-2.70 (2 H, m), 2.09-1.98 (4 H, m), 1.80 (2 H, m) ppm; LCMS-ESI (POS), M/Z, M+1: Found 429.2, calculated 429.2.

Example 55

88

1,1-dimethylethyl 4-(6-((9-cyclopentyl-8-methyl-9H-pyrido[4',3':4,5]pyrrolo[2,3-d]pyrimidin-2-yl)amino)-3-pyridinyl)-1-piperazinecarboxylate (88): Compound 88 was prepared according to the methods described in example 1. LCMS-ESI (POS), M/Z, M+1: Found 529.3, calculated 529.3.

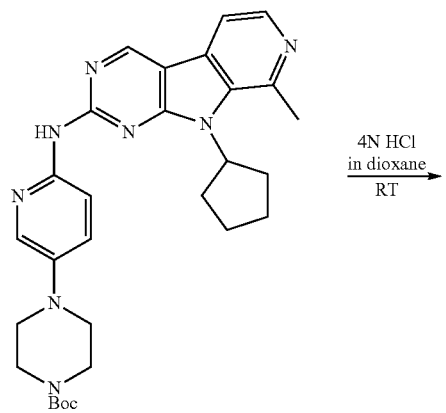

88

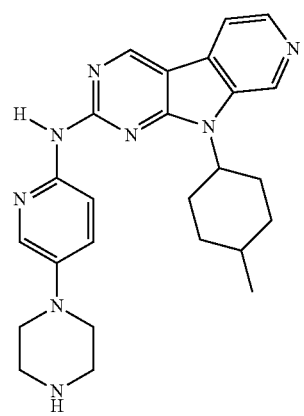

89

9-(4-methylcyclohexyl)-N-(5-(1-piperazinyl)-2-pyridinyl)-9H-pyrido[4',3':4,5]pyrrolo[2,3-d]pyrimidin-2-amine Compound 89 was prepared according to the methods described in example 1. $^1$H NMR (500 MHz, CD$_3$OD) δ 9.19 (1 H, s), 8.97 (1H, s), 8.39 (1 H, d), 8.29 (0.5H, d), 8.24 (0.5H, d), 8.05 (1H, m), 7.53 (1H, m), 3.20 (4H, m), 3.07 (4H, m), 2.80 (1H, m), 2.60 (1H, m), 2.10 (1H, b), 1.97 (3 H, b), 1.75

(3 H, m), 1.40 (1 H, m), 1.25 (1.5H, d), 1.08 (1.5H, d) ppm; LCMS-ESI (POS), M/Z, M+1: Found 443.2, calculated 443.2.

Hz), 6.58 (1 H, d, J=9.0 Hz), 4.30 (2 H, d, J=12.9 Hz), 2.79-2.91 (2 H, m), 2.49 (1 H, br. s.), 2.37 (6 H, s), 1.97 (2 H, d, J=12.5 Hz), 1.45-1.60 (2 H, m) ppm.

Example 56

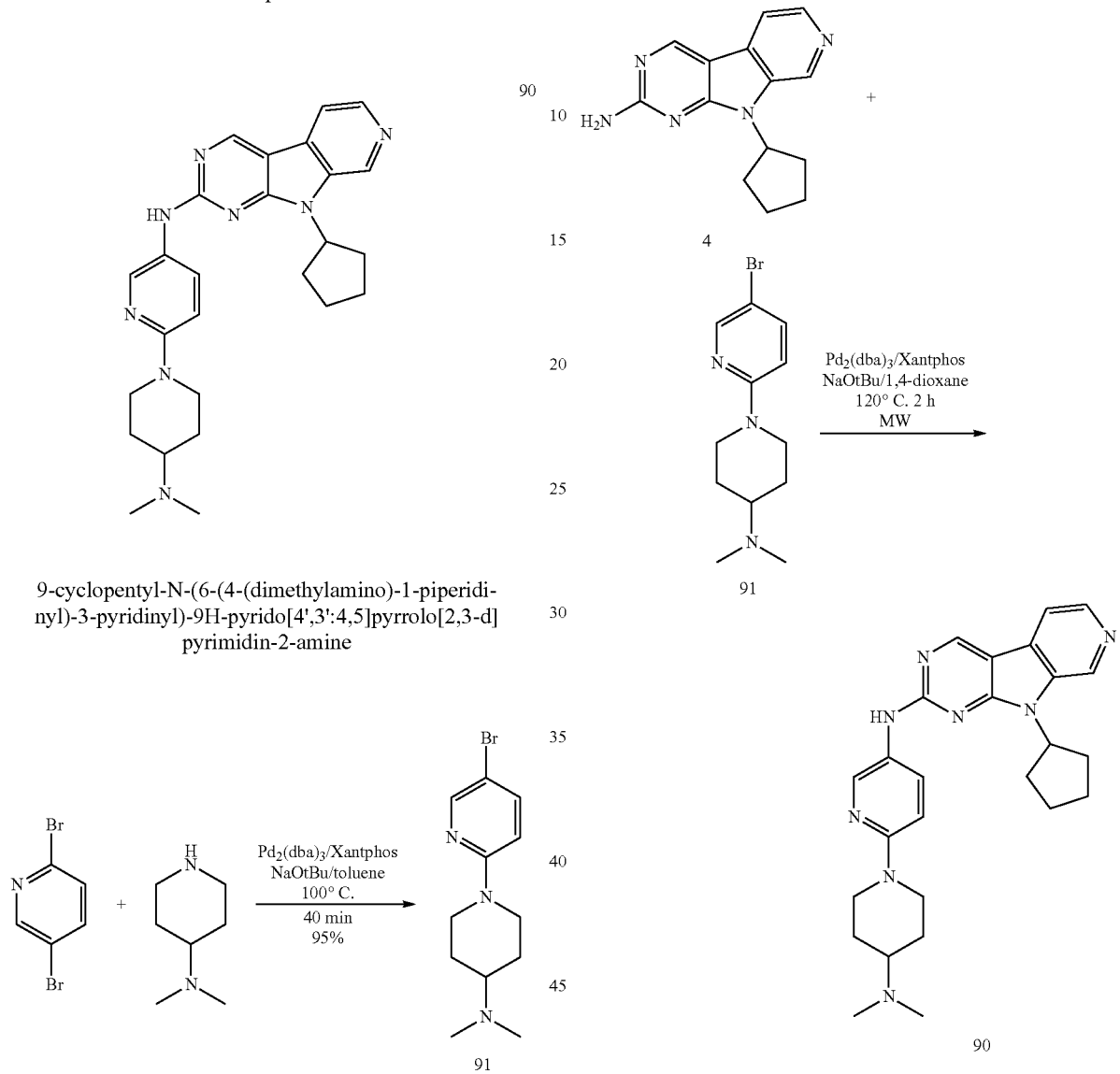

9-cyclopentyl-N-(6-(4-(dimethylamino)-1-piperidinyl)-3-pyridinyl)-9H-pyrido[4',3':4,5]pyrrolo[2,3-d]pyrimidin-2-amine 1-(5-bromopyridin-2-yl)-N,N-dimethylpiperidin-4-amine (91): To a 100 mL single-necked round-bottom flask were placed 2,5-dibromopyridine (2 g, 8 mmol), 4-(dimethylamino)piperidine (1 ml, 8 mmol), tris(dibenzylideneacetone)dipalladium (0) (0.07 g, 0.08 mmol), 9,9-dimethyl-4,5-bis(diphenylphosphino)xanthene (0.1 g, 0.2 mmol), and sodium t-butoxide (1 g, 12 mmol). The flask was subjected to 3 cycles of evacuation and back-filling with N₂ before toluene (40 mL) was introduced under N₂. The resulting mixture was stirred at a preheated oil bath at 100° C. for 40 min. The crude mixture was poured into ice and 4 N NaOH aqueous solution and extracted with ethyl acetate (2×). The combine organics were dried over sodium sulfate and concentrated in vacuo to give 2.7 g crude product. Trituration with ethyl acetate/hexanes gave highly pure 1-(5-bromopyridin-2-yl)-N,N-dimethylpiperidin-4amine (91) (1.9 g, 95%) ¹H NMR (400 MHz, CDCl₃) δ 8.18 (1 H, d, J=2.3 Hz), 7.52 (1 H, dd, J=9.0, 2.7

9-cyclopentyl-N-(6-(4-(dimethylamino)-1-piperidinyl)-3-pyridinyl)-9H-pyrido[4',3':4,5]-pyrrolo[2,3-d]pyrimidin-2amine (90): To a microwave reaction vessel were placed compound 4 (30 mg, 118 μmmol), compound 91 (50 mg, 178 μmol), tris(dibenzylideneacetone)dipalladium (0) (5.4 mg, 5.9 μmol), 9,9-dimethyl-4,5-bis(diphenylphosphino)xanthene (8.6 mg, 15 μmol), and sodium tert-butoxide (34 mg, 355 μmol). 1,4-dioxane (4 mL) was added and the vessel was purged with N₂ for 3 min, then capped and subjected to microwave irradiation for 2 h at 120° C. After removal of the volatiles, the residue was dissolved in methanol and filtered. The filtrate was subjected to reverse phase preparative HPLC (acetonitrile/water containing 0.1% TFA each, 40 min from 5 to 40%) to give ~15 mg of compound 90 as a TFA salt. ¹H NMR (400 MHz, CD₃OD) δ 9.43 (1 H, s), 9.16 (1 H, s), 8.65 (1 H, d, J=2.3 Hz), 8.48-8.57 (2 H, m), 8.12 (1 H, dd, J=9.4, 2.3 Hz), 7.21 (1 H, d, J=9.4 Hz), 5.29-5.47 (1 H, m), 4.45 (2 H, d, J=13.7 Hz), 3.49-3.58 (1 H, m), 3.03-3.18 (2 H, m), 2.92

(6 H, s), 2.37-2.54 (2 H, m), 2.04-2.29 (6 H, m), 1.76-1.93 (4 H, m) ppm; LCMS-ESI (POS), M/Z, M+1: Found 457.3, Calculated 457.2.

Example 57

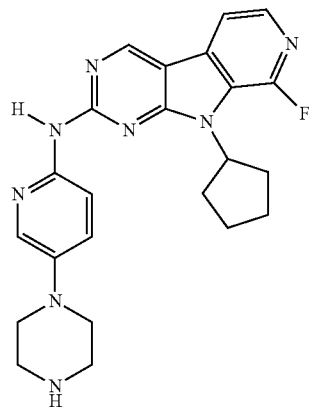

9-Cyclopentyl-8-fluoro-N-(5-(1-piperazinyl)-2-pyridinyl)-9H-pyrido[4',3':4,5]pyrrolo[2,3-d]pyrimidin-2-amine Compound 92 was prepared using chemistry similar to that described in example 22. $^1$H NMR (500 MHz, CD$_3$OD) δ 9.46 (1 H, s), 8.10-8.15 (3 H, m), 8.05 (1 H, d, J=2.9 Hz), 7.64 (1 H, d, J=9.5 Hz), 5.20 (1 H, m), 3.51-3.57 (4 H, m), 3.42-3.51 (4 H, m), 2.40-2.50 (2 H, m), 2.10-2.25 (4 H, m), 1.80-1.90 (2H, m) ppm, LCMS-ESI (POS), M/Z, M+1: Found 433.1, Calculated 433.2.

Example 58

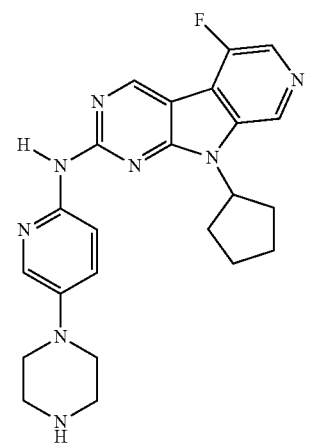

9-Cyclopentyl-5-fluoro-N-(5-(1-piperazinyl)-2-pyridinyl)-9H-pyrido[4',3':4,5]pyrrolo[2,3-d]pyrimidin-2-amine Compound 93 was prepared using chemistry similar to that described in example 22. $^1$H NMR (500 MHz, CD$_3$OD) δ 9.10 (1 H, s), 8.75 (1 H, s), 8.28 (1 H, s), 8.23 (1 H, d, J=9.0 Hz), 8.02 (1 H, d, J=2.9 Hz), 7.46-7.49 (1 H, dd, J=9.0, 2.6 Hz), 5.41 (1 H, m), 3.33 (4 H, m), 3.19 (1 H, m), 2.44-2.49 (2 H, m), 2.11-2.24 (4 H, m), 1.87-1.90 (2 H, m) ppm; LCMS-ESI (POS), M/Z, M+1: Found 433.1, Calculated 433.2.

Example 59

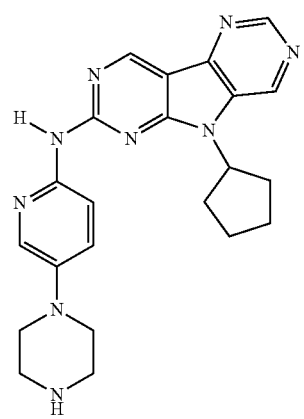

5-Cyclopentyl-N-(5-(1-piperazinyl)-2-pyridinyl)-5H-pyrimido[4',5':4,5]pyrrolo[2,3-d]pyrimidin-7-amine Compound 94 was prepared using chemistry similar to that described in example 22. $^1$H NMR (500 MHz, CD$_2$Cl$_2$) δ 9.21 (1 H, s), 8.96 (1 H, s), 8.83 (1 H, s), 8.32 (3 H, d, J=9.0 Hz), 7.98 (2 H, d, J=2.2 Hz), 7.31 (2 H, dd, J=9.0, 2.7 Hz), 5.23-5.31 (1 H, m), 3.05 (4 H, m), 2.95 (4 H, m), 2.47 (1 H, s), 2.28 (2 H, m), 2.10-2.20 (2 H, m), 1.98-2.08 (2 H, m), 1.70-1.84 (2 H, m) ppm, LCMS-ESI (POS), M/Z, M+1: Found 416.2, Calculated 416.2.

Example 60

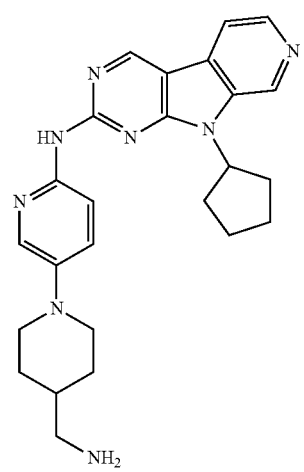

4-Aminomethyl-1-(6-((9-cyclopentyl-9H-pyrido[4',3':4,5]pyrrolo[2,3-d]pyrimidin-2-yl)amino)-3-pyridinyl)-piperidine

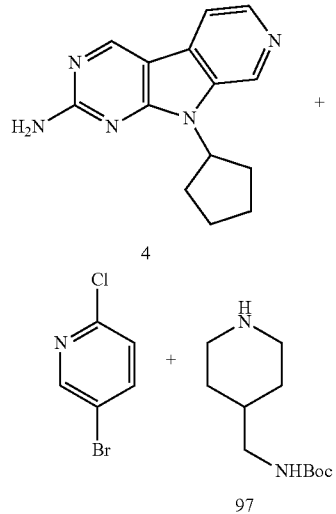

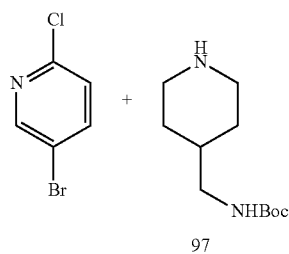

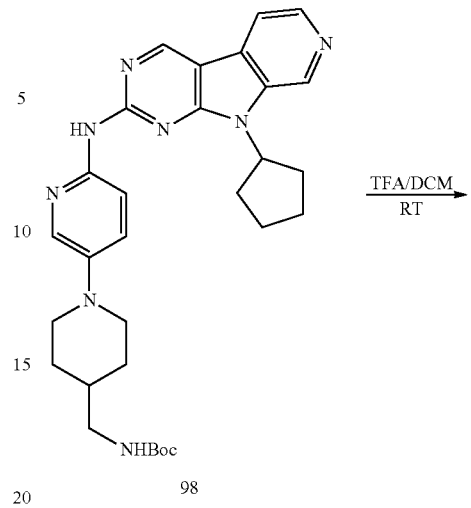

1,1-Dimethylethyl 1-(6-((9-cyclopentyl-9H-pyrido[4',3':4,5]pyrrolo[2,3-d]pyrimidin-2-yl)amino)-3-pyridinyl)-4-piperidinemethyl carboxylate (98): A mixture of 5-bromo-2-chloropyridine (0.019 g, 0.099 mmol), tert-butyl piperidin-4-ylmethylcarbamate (97) (0.024 g, 0.099 mmol), Xentphos (0.0086 g, 0.015 mmol), Pd$_2$(dba)$_3$ (0.0068 g, 0.0074 mmol), and sodium tert-butoxide (0.014 g, 0.15 mmol) in dioxane was purged with nitrogen gas for 1 min. The reaction was heated at 80° C. for 2 hours and then cooled to room temperature. Compound (4) (0.0250 g, 0.099 mmol), Xantphos (0.0086 g, 0.015 mmol), Pd$_2$(dba)$_3$ (0.0068 g, 0.0074 mmol) and sodium tert-butoxide (0.014 g, 0.15 mmol) were added. The mixture was purged again with nitrogen again for 1 min. And heated at 100° C. for 1.5-2 hours and then cooled to room temperature. The solvent was removed using Gene Vac. The residue was sonicated with 2 mL methanol. The solid was removed by filtration, washed with 2×1 mL methanol. The combined solution was purified on a C-18 reverse phase column (150×30 mm, 4 micro) using Mass directed preparative HPLC and gradient elution of acetonitrile in water containing 0.1% TFA to provide compound 98 as a TFA salt. LCMS-ESI (POS), M/Z, M+1: 543.2

4-Aminomethyl-1-(6-((9-cyclopentyl-9H-pyrido[4',3':4,5]pyrrolo[2,3-d]pyrimidin-2-yl)amino)-3-pyridinyl)-piperidine (95): Compound 98 was treated with 1:1 TFA/DCM (2 mL) at room temperature for an hour. The solvent was evaporated. The residue was re-dissolved in 4 ml methanol and purified on a C-18 reverse phase column (150×30 mm, 4 micro) using Mass directed preparative HPLC and gradient elution of acetonitrile in water containing 0.1% TFA to provide compound 95 as a TFA salt. LCMS retention time (minutes): 0.708. LCMS-ESI (POS), M/Z, M+1: 443.2

Examples 61-100 (listed in Table 1) were prepared using conditions as described for example 60 with deprotection when necessary, replacing 5-bromo-2-chloropyridine and 97 with proper chemical reagents. The reaction conditions such as temperature and reaction time were the same unless indicated in Table 1. All LCMS data was obtained using Agilent 1100 series LC/MSD, column: CAPCELL UG120 (3 um, 4.6 mm I.D.×50 mm), solvent system: water-acetonitrile 95:5 with 0.1% formic acid.

TABLE 1

| Example # | Structure | Reaction conditions | LSMS retention time (minutes) | LCMS-ESI (M + 1) |
|---|---|---|---|---|
| 61 | 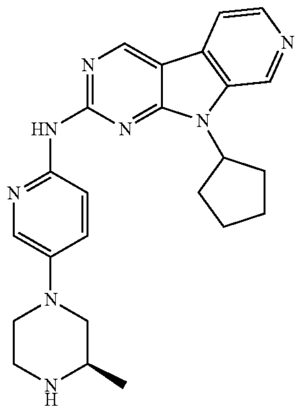 [SMILES: C[C@@H]1CN(c2ccc(Nc3ncc4c5ccncc5n(C5CCCC5)c4n3)nc2)CCN1] | | 0.701 | 429.2 |
| 62 | 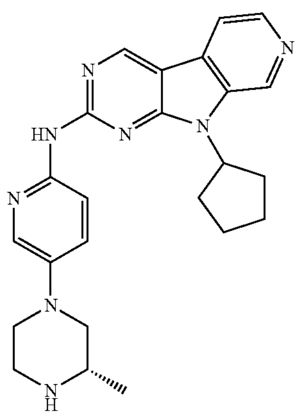 [SMILES: C[C@H]1CN(c2ccc(Nc3ncc4c5ccncc5n(C5CCCC5)c4n3)nc2)CCN1] | | 0.704 | 429.2 |
| 63 | 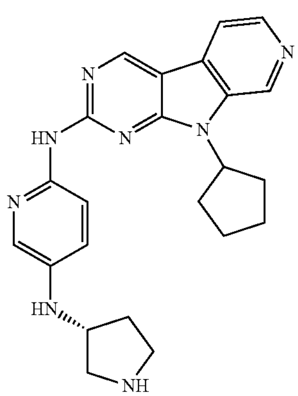 [SMILES: c1cc2c3cnc(Nc4ccc(N[C@@H]5CCNC5)cn4)nc3n(C3CCCC3)c2cn1] | | 0.660 | 415.1 |

TABLE 1-continued

| Example # | Structure | Reaction conditions | LSMS retention time (minutes) | LCMS-ESI (M + 1) |
|---|---|---|---|---|
| 64 | 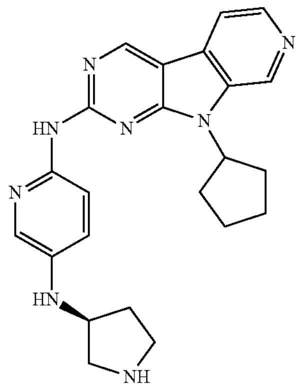 [SMILES: c1cc2c3cnc(Nc4ccc(N[C@H]5CCNC5)cn4)nc3n(C3CCCC3)c2cn1] | | 0.660 | 415.1 |
| 65 | 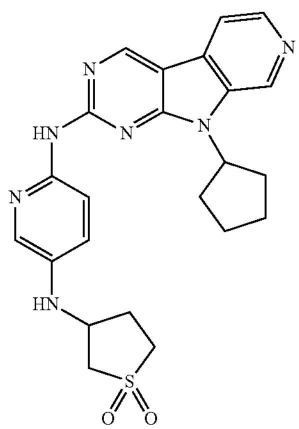 | | 0.842 | 464.2 |
| 66 | 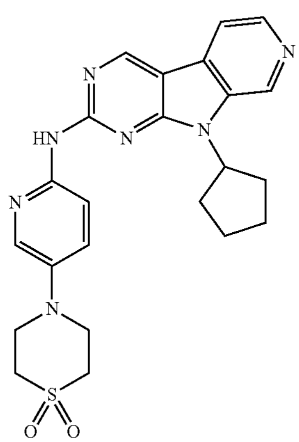 [SMILES: O=S1(=O)CCN(c2ccc(Nc3ncc4c5ccncc5n(C5CCCC5)c4n3)nc2)CC1] | | 0.878 | 464.2 |

TABLE 1-continued

| Example # | Structure | Reaction conditions | LSMS retention time (minutes) | LCMS-ESI (M + 1) |
|---|---|---|---|---|
| 67 | 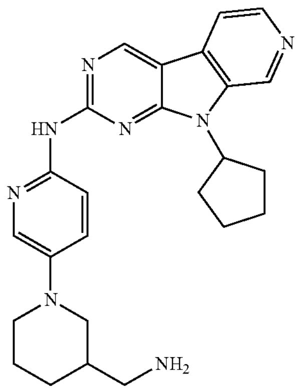 [SMILES: NCC1CCCN(c2ccc(Nc3ncc4c5ccncc5n(C5CCCC5)c4n3)nc2)C1] | | 0.753 | 443.2 |
| 68 | 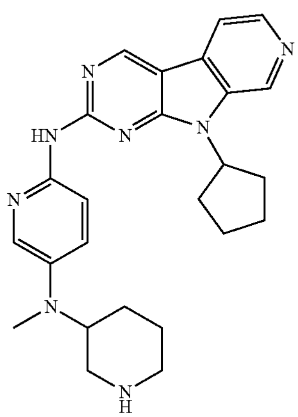 [SMILES: CN(c1ccc(Nc2ncc3c4ccncc4n(C4CCCC4)c3n2)nc1)C1CCCNC1] | | 0.742 | 443.2 |
| 69 | 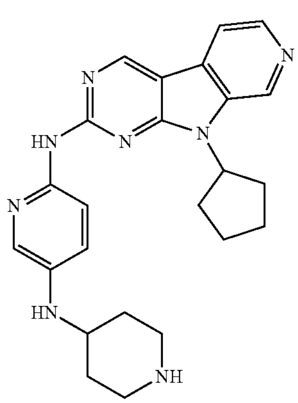 [SMILES: c1cc2c3cnc(Nc4ccc(NC5CCNCC5)cn4)nc3n(C3CCCC3)c2cn1] | | 0.672 | 429.2 |

TABLE 1-continued

| Example # | Structure | Reaction conditions | LSMS retention time (minutes) | LCMS-ESI (M + 1) |
|---|---|---|---|---|
| 70 | 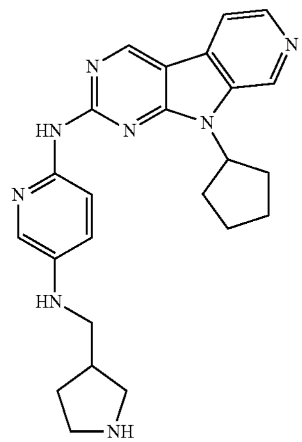 [SMILES: c1cc2c3cnc(Nc4ccc(NCC5CCNC5)cn4)nc3n(C3CCCC3)c2cn1] | | 0.718 | 429.2 |
| 71 | 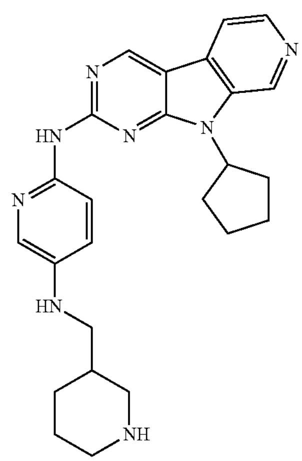 [SMILES: c1cc2c3cnc(Nc4ccc(NCC5CCCNC5)cn4)nc3n(C3CCCC3)c2cn1] | | 0.735 | 443.2 |
| 72 | 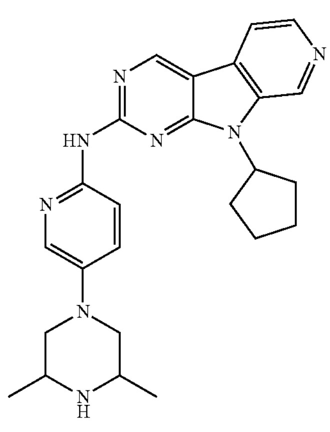 [SMILES: CC1CN(c2ccc(Nc3ncc4c5ccncc5n(C5CCCC5)c4n3)nc2)CC(C)N1] | Step 1. 70° C., 2 hour; Step 2. 90° C, 2 hour. | 0.696 | 443.2 |

TABLE 1-continued
| Example # | Structure | Reaction conditions | LSMS retention time (minutes) | LCMS-ESI (M + 1) |
|---|---|---|---|---|
| 73 | 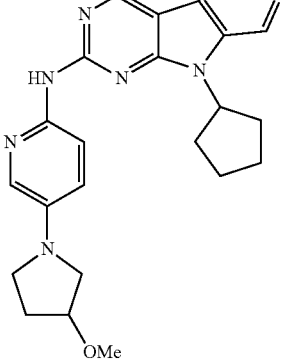 | | 0.942 | 430.1 |
| 74 | 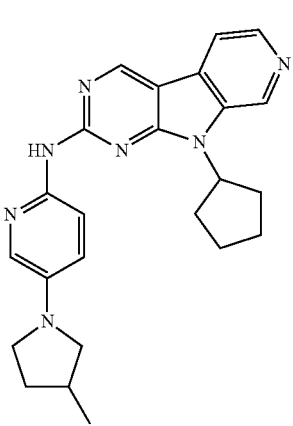 | | 1.20 | 414.2 |
| 75 | 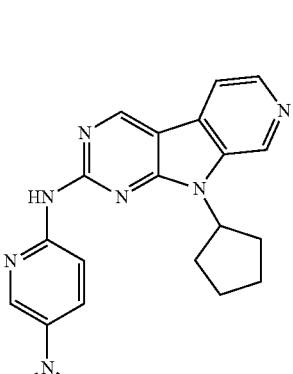 | | 0.742 | 443.2 |

TABLE 1-continued

| Example # | Structure | Reaction conditions | LSMS retention time (minutes) | LCMS-ESI (M + 1) |
|---|---|---|---|---|
| 76 | 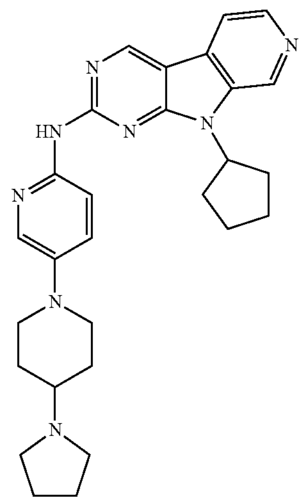 [SMILES: c1cc2c3cnc(Nc4ccc(N5CCC(N6CCCC6)CC5)cn4)nc3n(C3CCCC3)c2cn1] | | 0.765 | 483.3 |
| 77 | 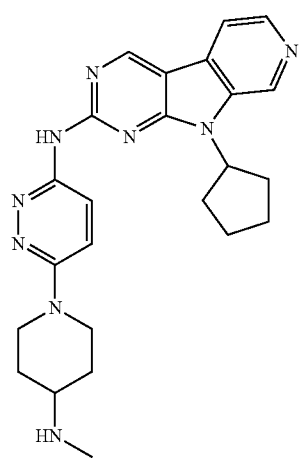 [SMILES: CNC1CCN(c2ccc(Nc3ncc4c5ccncc5n(C5CCCC5)c4n3)nn2)CC1] | Step 1. 80° C., 2 hour; 120° C., 2 hour. | 0.700 | 444.2 |
| 78 | 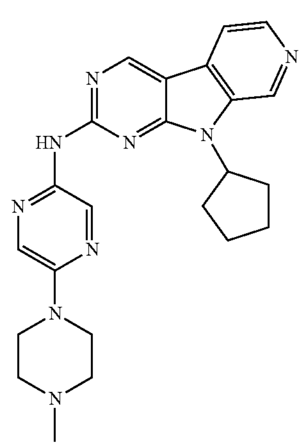 [SMILES: CN1CCN(c2cnc(Nc3ncc4c5ccncc5n(C5CCCC5)c4n3)cn2)CC1] | Step 1. 60° C., 2 hour; 80° C., 2 hour. | 0.736 | 430.2 |

TABLE 1-continued

| Example # | Structure | Reaction conditions | LSMS retention time (minutes) | LCMS-ESI (M + 1) |
|---|---|---|---|---|
| 79 | 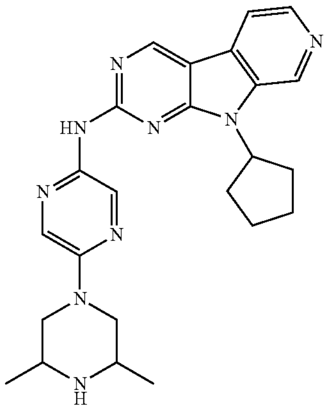 [SMILES: CC1CN(c2cnc(Nc3ncc4c5ccncc5n(C5CCCC5)c4n3)cn2)CC(C)N1] | Step 1. 60° C., 2 hour; 80° C., 2 hour. | 0.771 | 444.2 |
| 80 | 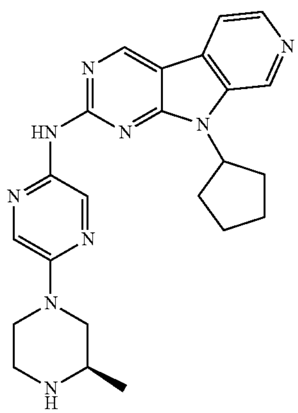 [SMILES: C[C@@H]1CN(c2cnc(Nc3ncc4c5ccncc5n(C5CCCC5)c4n3)cn2)CCN1] | Step 1. 60° C., 2 hour; 80° C., 2 hour. | 0.755 | 430.1 |
| 81 | 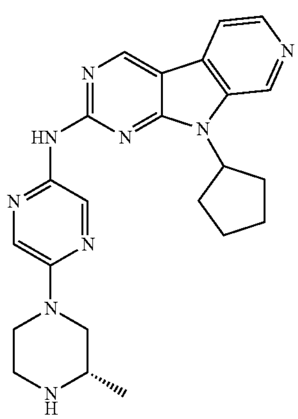 [SMILES: C[C@H]1CN(c2cnc(Nc3ncc4c5ccncc5n(C5CCCC5)c4n3)cn2)CCN1] | Step 1. 60° C., 2 hour; 80° C., 2 hour. | 0.757 | 430.2 |

TABLE 1-continued

| Example # | Structure | Reaction conditions | LSMS retention time (minutes) | LCMS-ESI (M + 1) |
|---|---|---|---|---|
| 82 | 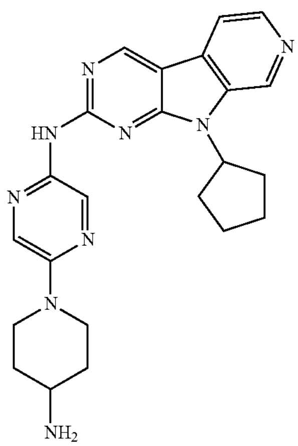 [SMILES: NC1CCN(c2cnc(Nc3ncc4c5ccncc5n(C5CCCC5)c4n3)cn2)CC1] | Step 1. 60° C., 2 hour; 80° C., 2 hour. | 0.771 | 430.2 |
| 83 | 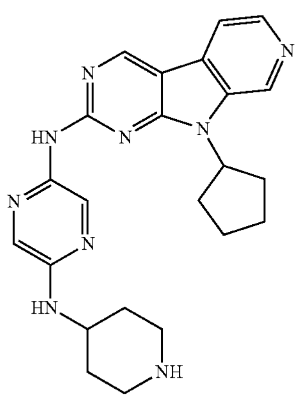 [SMILES: c1cc2c3cnc(Nc4cnc(NC5CCNCC5)cn4)nc3n(C3CCCC3)c2cn1] | Step 1. 60° C., 2 hour; 80° C., 2 hour. | 0.738 | 430.2 |
| 84 | 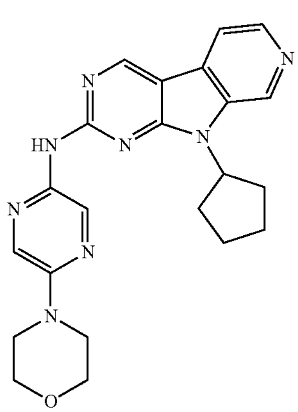 [SMILES: c1cc2c3cnc(Nc4cnc(N5CCOCC5)cn4)nc3n(C3CCCC3)c2cn1] | Step 1. 60° C., 2 hour; 80° C., 2 hour. | 1.07 | 417.3 |

TABLE 1-continued

| Example # | Structure | Reaction conditions | LSMS retention time (minutes) | LCMS-ESI (M + 1) |
| --- | --- | --- | --- | --- |
| 85 | 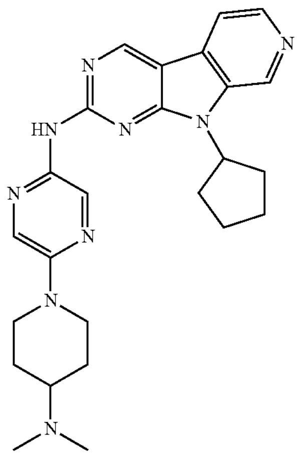 [SMILES: CN(C)C1CCN(c2cnc(Nc3ncc4c5ccncc5n(C5CCCC5)c4n3)cn2)CC1] | Step 1. 60° C., 2 hour; 80° C., 2 hour. | 0.817 | 458.2 |
| 86 | 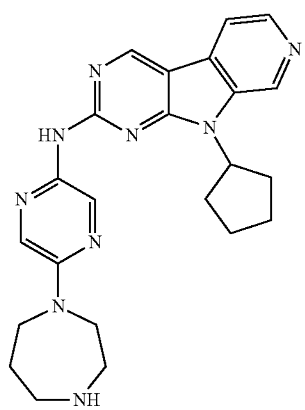 [SMILES: c1cc2c3cnc(Nc4cnc(N5CCCNCC5)cn4)nc3n(C3CCCC3)c2cn1] | Step 1. 60° C., 2 hour; 80° C., 2 hour. | 0.823 | 430.1 |
| 87 | 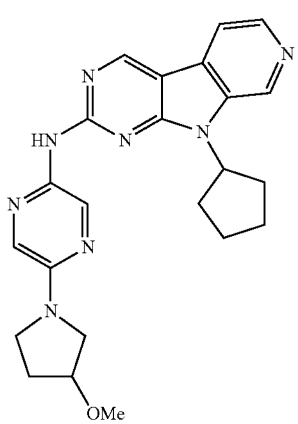 [SMILES: COC1CCN(c2cnc(Nc3ncc4c5ccncc5n(C5CCCC5)c4n3)cn2)C1] | Step 1. 60° C., 2 hour; 80° C., 2 hour. | 1.09 | 431.2 |

TABLE 1-continued

| Example # | Structure | Reaction conditions | LSMS retention time (minutes) | LCMS-ESI (M + 1) |
|---|---|---|---|---|
| 88 | 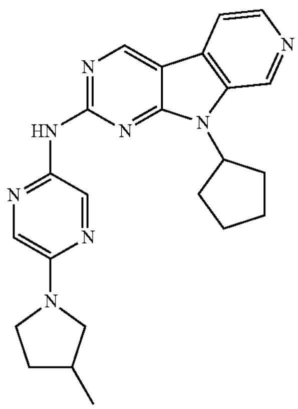 [SMILES: CC1CCN(c2cnc(Nc3ncc4c5ccncc5n(C5CCCC5)c4n3)cn2)C1] | Step 1. 60° C., 2 hour; 80° C., 2 hour. | 1.27 | 415.2 |
| 89 | 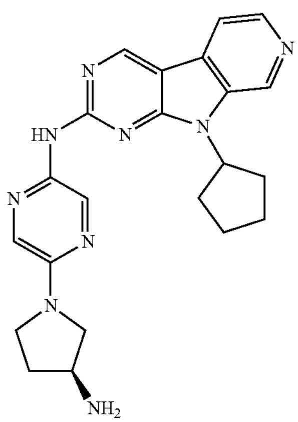 [SMILES: N[C@H]1CCN(c2cnc(Nc3ncc4c5ccncc5n(C5CCCC5)c4n3)cn2)C1] | Step 1. 60° C., 2 hour; 80° C., 2 hour. | 0.761 | 416.2 |
| 90 | 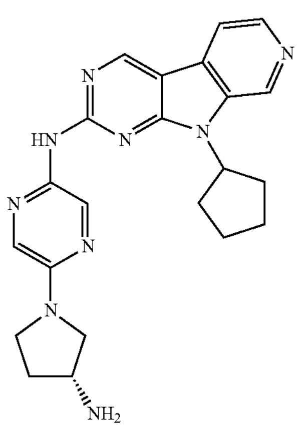 [SMILES: N[C@@H]1CCN(c2cnc(Nc3ncc4c5ccncc5n(C5CCCC5)c4n3)cn2)C1] | Step 1. 60° C., 2 hour; 80° C., 2 hour. | 0.740 | 416.2 |

TABLE 1-continued

| Example # | Structure | Reaction conditions | LSMS retention time (minutes) | LCMS-ESI (M + 1) |
|---|---|---|---|---|
| 91 | 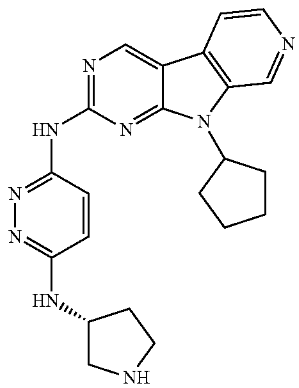 [SMILES: c1cc2c3cnc(Nc4ccc(N[C@@H]5CCNC5)nn4)nc3n(C3CCCC3)c2cn1] | Step 1. 70° C., 0.5 hour; 100° C., 0.5 hour. | 0.642 | 416.2 |
| 92 | 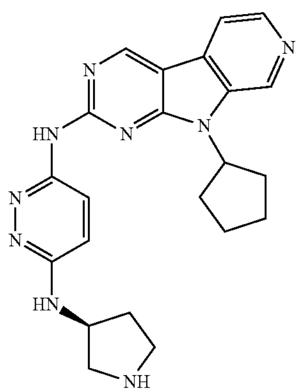 [SMILES: c1cc2c3cnc(Nc4ccc(N[C@H]5CCNC5)nn4)nc3n(C3CCCC3)c2cn1] | Step 1. 70° C., 0.5 hour; 100° C., 0.5 hour. | 0.649 | 416.2 |
| 93 | 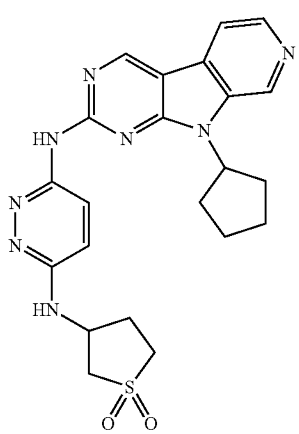 [SMILES: O=S1(=O)CCC(Nc2ccc(Nc3ncc4c5ccncc5n(C5CCCC5)c4n3)nn2)C1] | Step 1. 70° C., 0.5 hour; 100° C., 0.5 hour. | 0.792 | 465.1 |

TABLE 1-continued
| Example # | Structure | Reaction conditions | LSMS retention time (minutes) | LCMS-ESI (M + 1) |
|---|---|---|---|---|
| 94 | 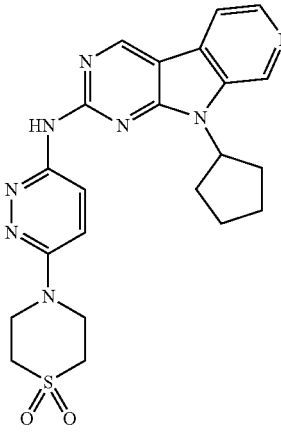 | Step 1. 70° C., 0.5 hour; 100° C., 0.5 hour. | 0.848 | 465.1 |
| 95 | 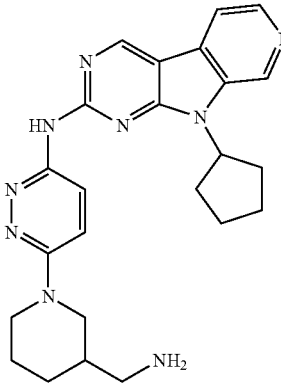 | Step 1. 70° C., 0.5 hour; 100° C., 0.5 hour. | 0.658 | 444.2 |
| 96 | 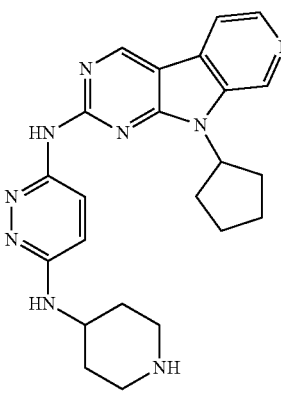 | Step 1. 60° C., 0.5 hour; 100° C., 0.5 hour. | 0.641 | 430.1 |

TABLE 1-continued

| Example # | Structure | Reaction conditions | LSMS retention time (minutes) | LCMS-ESI (M + 1) |
|---|---|---|---|---|
| 97 | 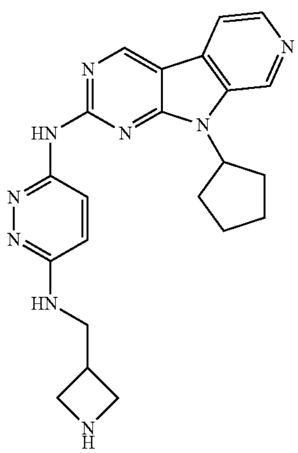 [SMILES: c1cc2c3cnc(Nc4ccc(NCC5CNC5)nn4)nc3n(C3CCCC3)c2cn1] | Step 1. 70° C., 0.5 hour; 100° C., 0.5 hour. | 0.624 | 416.2 |
| 98 | 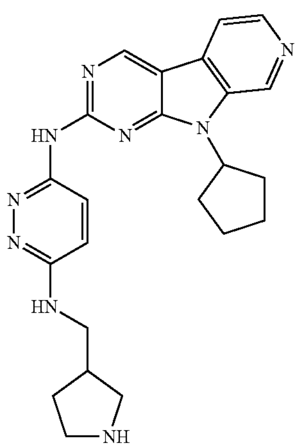 [SMILES: c1cc2c3cnc(Nc4ccc(NCC5CCNC5)nn4)nc3n(C3CCCC3)c2cn1] | Step 1. 80° C., 0.5 hour; 120° C., 0.5 hour. | 0.635 | 430.2 |
| 99 | 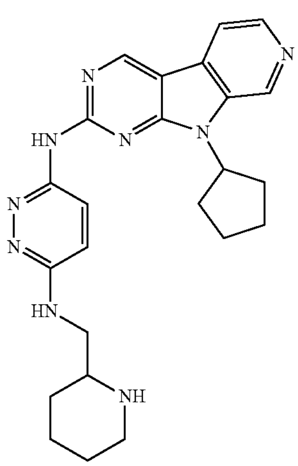 [SMILES: c1cc2c3cnc(Nc4ccc(NCC5CCCCN5)nn4)nc3n(C3CCCC3)c2cn1] | Step 1. 60° C., 0.5 hour; 100° C., 0.5 hour. | 0.675 | 444.2 |

TABLE 1-continued

| Example # | Structure | Reaction conditions | LSMS retention time (minutes) | LCMS-ESI (M + 1) |
|---|---|---|---|---|
| 100 | 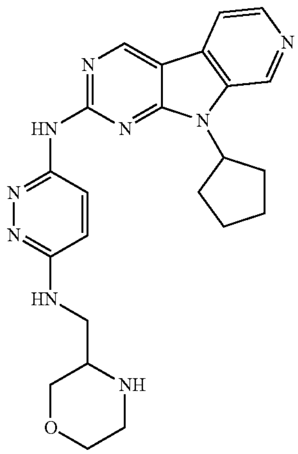 [SMILES: c1cc2c3cnc(Nc4ccc(NCC5COCCN5)nn4)nc3n(C3CCCC3)c2cn1] | Step 1. 70° C., 0.5 hour; 100° C., 0.7 hour. | 0.663 | 446.2 |

Example 101

138

4-Aminomethyl-1-(6-((9-cyclopentyl-9H-pyrido[4',3':4,5]pyrrolo[2,3-d]pyrimidin-2-yl)amino)-3-pyridazinyl)-piperidine

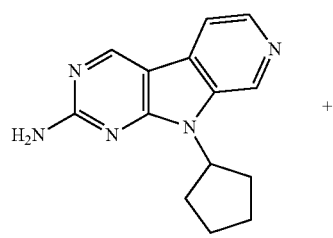

+

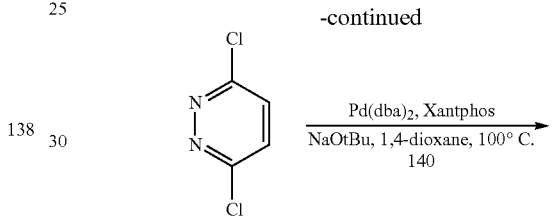

6-((9-cyclopentyl-9H-pyrido[4',3':4,5]pyrrolo[2,3-d]pyrimidin-2-yl)amino)-3-chloro-pyridazine (140): A mixture of compound 4 (1.50 g, 5.92 mmol), 3,6-dichloropyridazine (0.882 g, 5.92 mmol), bis(dibenzylideneacetone)palladium (0.170 g, 0.296 mmol), Xantphos (0.514 g, 0.888 mmol) and sodium tert-butoxide (0.854, 8.88 mmol) in toluene (80 mL) was purged with nitrogen. The reaction was then heated at 100° C. for one hour in a sealed vessel. After cooling to room temperature, the mixture was loaded onto a silica gel column and eluted with 2-10% methanol/DCM. Evaporation of combined fractions provided compound 140 (2.1 g) as a yellowish solid. LCMS-ESI, M+1: 366.1

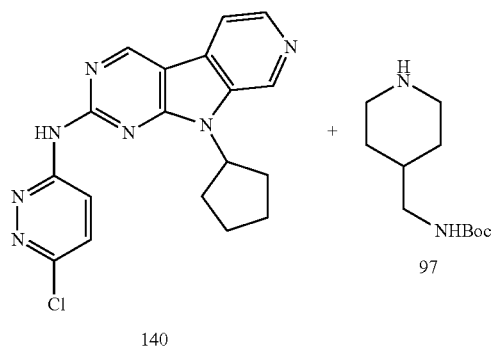

140

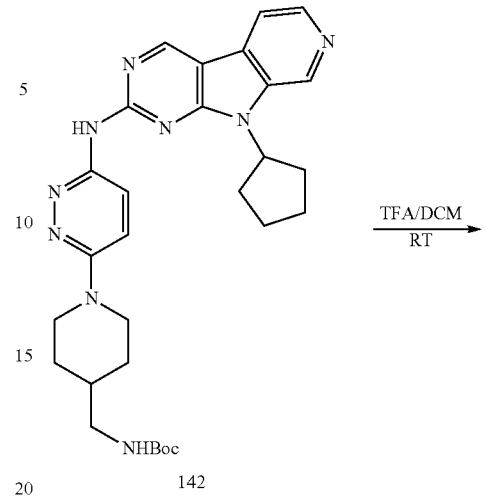

142

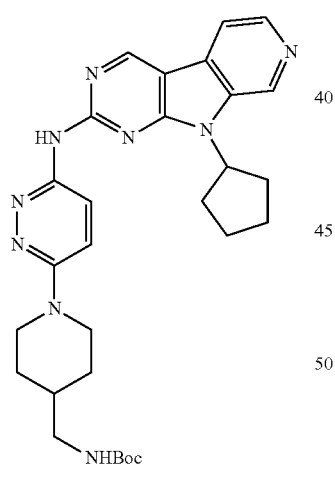

142

1,1-Dimethylethyl 1-(6-((9-cyclopentyl-9H-pyrido[4',3': 4,5]pyrrolo[2,3-d]pyrimidin-2-yl)amino)-3-pyridazinyl)-4piperidinemethyl carboxylate (142): The neat mixture of compound 140 (0.0300 g, 0.0820 mmol) and compound 97 (0.176 g, 0.820 mmol) was heated at 150° C. for 1.5 hours using microwave. The crude material was dissolved in 4 mL methanol, filtered and purified on a C-18 reverse phase column (150×30 mm, 4 micro) using Mass directed preparative HPLC and gradient elution of acetonitrile in water containing 0.1% TFA to provide the title compound 142 as a TFA salt. LCMS-ESI (POS), M/Z, M+1: 544.3

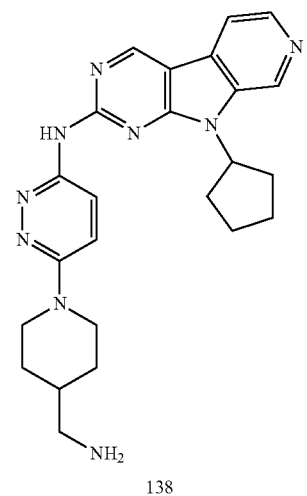

138

4-Aminomethyl-1-(6-((9-cyclopentyl-9H-pyrido[4',3':4, 5]pyrrolo[2,3-d]pyrimidin-2-yl)amino)-3-pyridazinyl)-piperidine (138): Compound 142 was treated with 15% TFA/DCM (2 mL) at room temperature for one hour. The solvent was evaporated. The residue was re-dissolved in 4 mL methanol and purified on a C-18 reverse phase column (150×30 mm, 4 micro) using Mass directed preparative HPLC and gradient elution of acetonitrile in water containing 0.1% TFA to provide the desired product as TFA salt. LCMS retention time (minutes): 0.666. LCMS-ESI (POS), M/Z, M+1: 444.3

Examples 102-121 (table 2) were prepared using conditions as described for example 101 with deprotection when necessary, replacing compound 97 with proper amine. The reaction conditions such as solvent, temperature, and reaction time for Step 2 were the same unless indicated in Table 2.

TABLE 2

| Example # | Structure | Reaction Conditions | LSMS retention time (min) | LCMS-ESI (M + 1) |
|---|---|---|---|---|
| 102 | 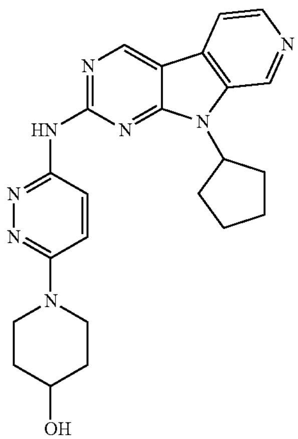 [SMILES: OC1CCN(c2ccc(Nc3ncc4c5ccncc5n(C5CCCC5)c4n3)nn2)CC1] | DMSO/155° C./1.5 hours | 0.835 | 431.2 |
| 103 | 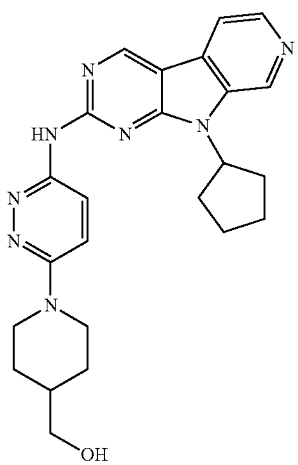 [SMILES: OCC1CCN(c2ccc(Nc3ncc4c5ccncc5n(C5CCCC5)c4n3)nn2)CC1] | DMSO/155° C./1.5 hours | 0.854 | 445.1 |
| 104 | 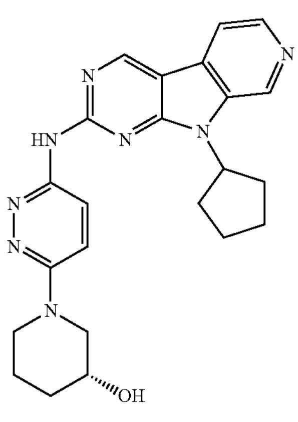 [SMILES: O[C@@H]1CCCN(c2ccc(Nc3ncc4c5ccncc5n(C5CCCC5)c4n3)nn2)C1] | NMP/180° C./2 hours | 0.790 | 431.2 |

TABLE 2-continued

| Example # | Structure | Reaction Conditions | LSMS retention time (min) | LCMS-ESI (M + 1) |
|---|---|---|---|---|
| 105 | 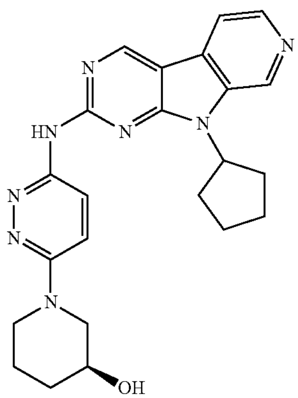 [SMILES: O[C@H]1CCCN(c2ccc(Nc3ncc4c5ccncc5n(C5CCCC5)c4n3)nn2)C1] | NMP/180° C./2 hours | 0.800 | 431.2 |
| 106 | 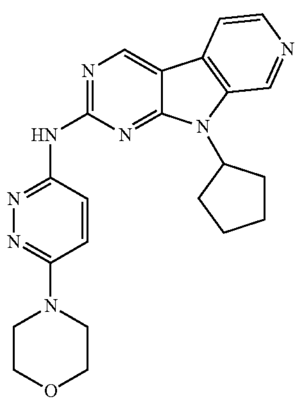 [SMILES: c1cc2c3cnc(Nc4ccc(N5CCOCC5)nn4)nc3n(C3CCCC3)c2cn1] | DMSO/155° C./1.5 hours | 0.909 | 417.3 |
| 107 | 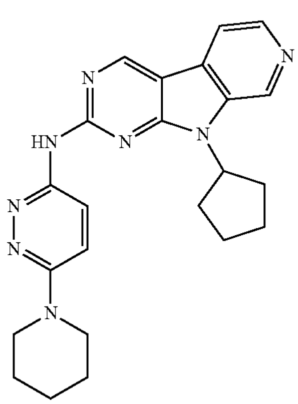 [SMILES: c1cc2c3cnc(Nc4ccc(N5CCCCC5)nn4)nc3n(C3CCCC3)c2cn1] | DMSO/150° C./1.5 hours | 0.997 | 415.1 |

TABLE 2-continued

| Example # | Structure | Reaction Conditions | LSMS retention time (min) | LCMS-ESI (M + 1) |
|---|---|---|---|---|
| 108 | 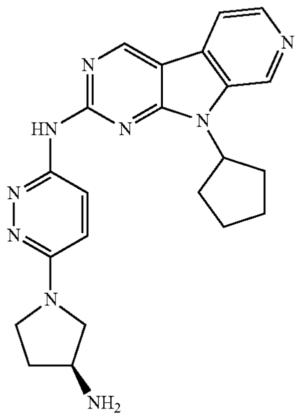 [SMILES: N[C@H]1CCN(c2ccc(Nc3ncc4c5ccncc5n(C5CCCC5)c4n3)nn2)C1] | DMSO/155° C./1.5 hours | 0.659 | 416.2 |
| 109 | 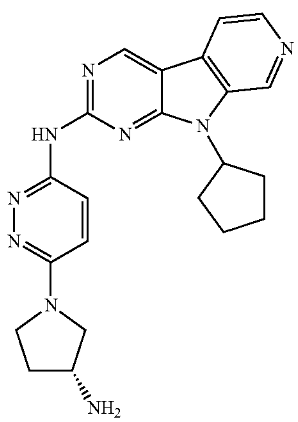 [SMILES: N[C@@H]1CCN(c2ccc(Nc3ncc4c5ccncc5n(C5CCCC5)c4n3)nn2)C1] | DMSO/145° C./0.5 hour | 0.620 | 416.1 |
| 110 | 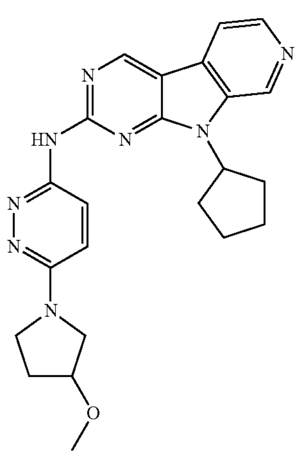 [SMILES: COC1CCN(c2ccc(Nc3ncc4c5ccncc5n(C5CCCC5)c4n3)nn2)C1] | NMP/165° C./0.7 hour | 0.808 | 431.2 |

TABLE 2-continued

| Example # | Structure | Reaction Conditions | LSMS retention time (min) | LCMS-ESI (M + 1) |
|---|---|---|---|---|
| 111 | 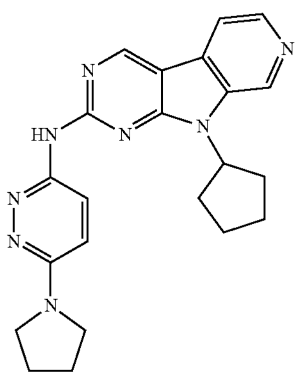 [SMILES: c1cc2c3cnc(Nc4ccc(N5CCCC5)nn4)nc3n(C3CCCC3)c2cn1] | DMSO/140° C./1 hour | 0.850 | 401.2 |
| 112 | 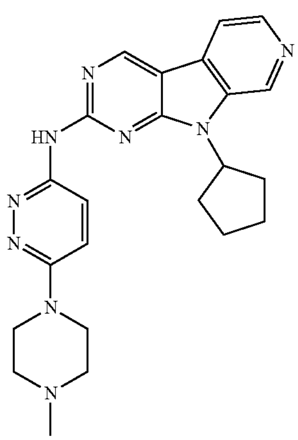 [SMILES: CN1CCN(c2ccc(Nc3ncc4c5ccncc5n(C5CCCC5)c4n3)nn2)CC1] | NMP/180° C./2 hours | 0.652 | 430.1 |
| 113 | 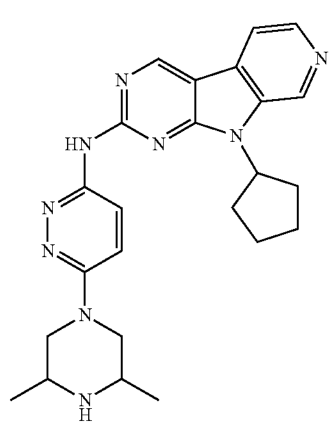 [SMILES: CC1CN(c2ccc(Nc3ncc4c5ccncc5n(C5CCCC5)c4n3)nn2)CC(C)N1] | NMP/180° C./1 hour | 0.747 | 444.2 |

TABLE 2-continued

| Example # | Structure | Reaction Conditions | LSMS retention time (min) | LCMS-ESI (M + 1) |
|---|---|---|---|---|
| 114 | 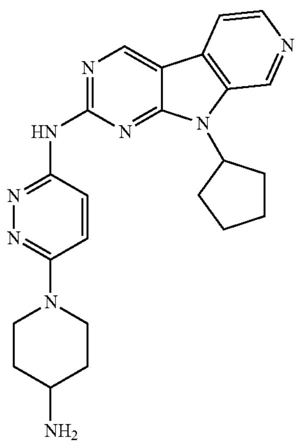 [SMILES: NC1CCN(c2ccc(Nc3ncc4c5ccncc5n(C5CCCC5)c4n3)nn2)CC1] | NMP/150° C./2 hours | 0.661 | 430.1 |
| 115 | 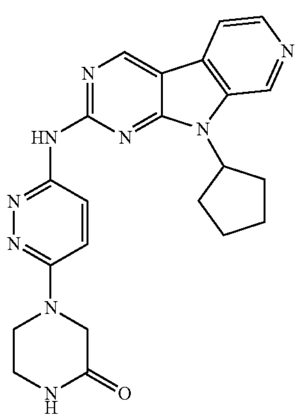 [SMILES: O=C1CN(c2ccc(Nc3ncc4c5ccncc5n(C5CCCC5)c4n3)nn2)CCN1] | NMP/185° C./2 hours | 0.769 | 430.1 |
| 116 | 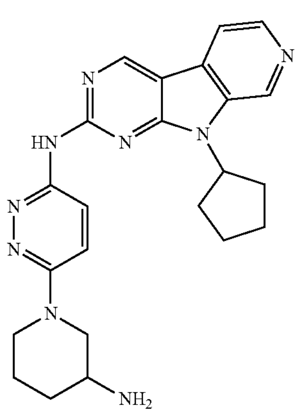 [SMILES: NC1CCCN(c2ccc(Nc3ncc4c5ccncc5n(C5CCCC5)c4n3)nn2)C1] | NMP/180° C./1 hour | 0.680 | 430.1 |

TABLE 2-continued
| Example # | Structure | Reaction Conditions | LSMS retention time (min) | LCMS-ESI (M + 1) |
|---|---|---|---|---|
| 117 | 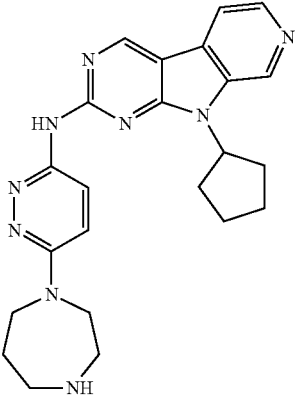 [SMILES: c1cc2c3cnc(Nc4ccc(N5CCCNCC5)nn4)nc3n(C3CCCC3)c2cn1] | DMSO/155° C./1.5 hours | 0.730 | 430.1 |
| 118 | 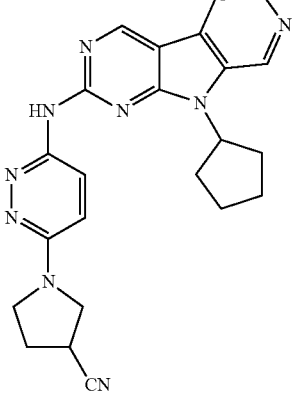 | NMP/175° C./1 hour | 0.836 | 426.2 |
| 119 | 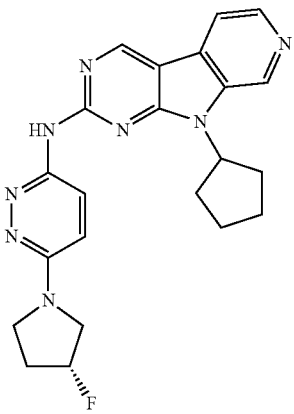 [SMILES: F[C@@H]1CCN(c2ccc(Nc3ncc4c5ccncc5n(C5CCCC5)c4n3)nn2)C1] | NMP/175° C./1 hour | 0.828 | 419.2 |

TABLE 2-continued
| Example # | Structure | Reaction Conditions | LSMS retention time (min) | LCMS-ESI (M + 1) |
|---|---|---|---|---|
| 120 | 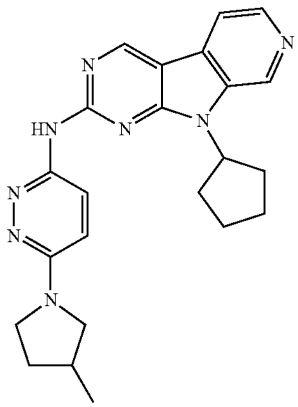 [SMILES: CC1CCN(c2ccc(Nc3ncc4c5ccncc5n(C5CCCC5)c4n3)nn2)C1] | NMP/175° C./1 hour | 0.885 | 415.1 |
| 121 | 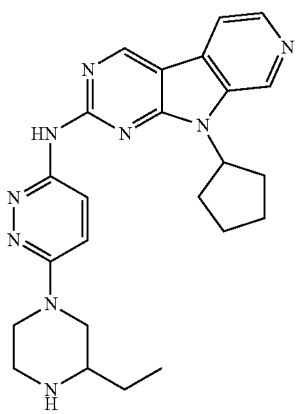 [SMILES: CCC1CN(c2ccc(Nc3ncc4c5ccncc5n(C5CCCC5)c4n3)nn2)CCN1] | NMP/175° C./1 hour | 0.743 | 444.2 |
Example 122
9-Cyclopentyl-2-(((6-(1-piperazinyl)-3-pyridazinyl)amino)-7,9-dihydro-8H-pyrido[4',3':4,5]pyrrolo[2,3-d]pyrimidin-8-one
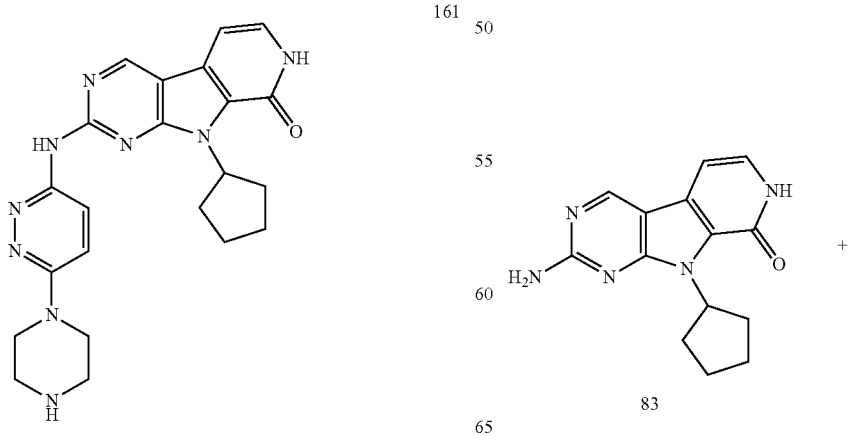

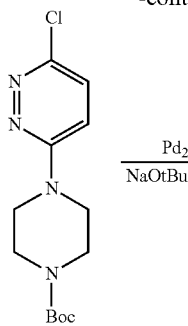

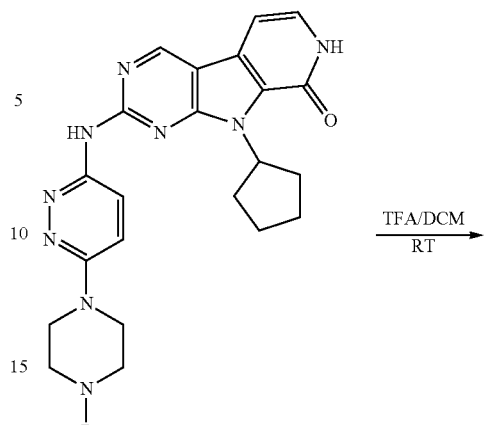

162

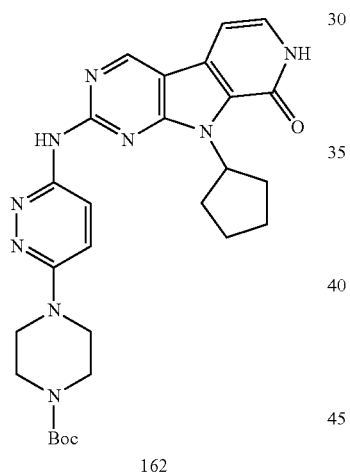

162

1,1-Dimethylethyl 4-(6-((9-cyclopentyl-8-oxo-8,9-dihydro-7H-pyrido[4',3':4,5]pyrrolo[2,3-d]pyrimidin-2-yl)amino)-3-pyridazinyl)-1-piperazinecarboxylate (162): A mixture of tert-butyl 4-(6-chloropyridazin-3-yl)piperazine-1-carboxylate (0.060 g, 0.20 mmol), compound 83 (0.054 g, 0.20 mmol), Xantphos (0.017 g, 0.030 mmol), Pd$_2$(dba)$_3$ (0.014 g, 0.015 mmol), and sodium tert-butoxide (0.029 g, 0.30 mmol) in dioxane was purged with nitrogen gas for 1 minute. The reaction was heated at 120° C. for 6 hours and then cooled to room temperature. The solvent was removed by filtration. The residue was washed with 2×1 ml dioxane. The product was then dissolved in 10 mL methanol/DCM (1:1) and concentrated. The crude material was re-dissolved in 4 mL methanol and purified on a C-18 reversephase column (150×30 mm, 4 micro) using Mass directed preperative HPLC and gradient elution of acetonitrile in water containing 0.1% TFA to give the title compound 162. LCMS-ESI (POS), M/Z, M+1: 532.3

9-Cyclopentyl-2-((6-(1-piperazinyl)-3-pyridazinyl)amino)-7,9-dihydro-8H-pyrido[4',3': 4,5]-pyrrolo[2,3-d]pyrimidin-8-one (161): Compound 162 was treated with 1:1 TFA/DCM (2 mL) at room temperature for an hour. The solvent was evaporated. The residue was re-dissolved in 4 mL1 methanol and purified on a C-18 reverse phase column (150×30 mm, 4 micro) using Mass directed preparative HPLC and gradient elution of acetonitrile in water containing 0.1% TFA to provide the title compound 161 as a TFA salt. LCMS retention time (minutes): 0.793. LCMS-ESI (POS), M/Z, M+1: 432.2

Examples 123-130 (table 3) were prepared using conditions as described for example 122 with deprotection when necessary, replacing tert-butyl 4-(6-chloropyridazin-3-yl)piperazine-1-carboxylate with proper reagent.

TABLE 3

| Example # | Structure | LCMS retention time (min) | LCMS-ESI (M + 1) |
|---|---|---|---|
| 123 | 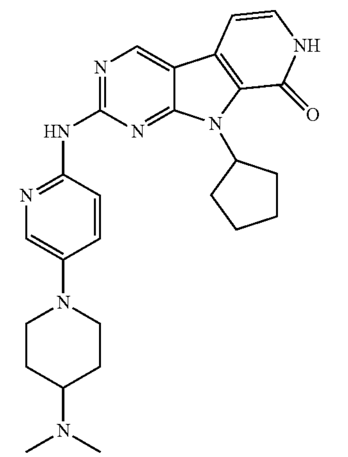 [SMILES: CN(C)C1CCN(c2ccc(Nc3ncc4c5cc[nH]c(=O)c5n(C5CCCC5)c4n3)nc2)CC1] | 0.884 | 473.4 |
| 124 | 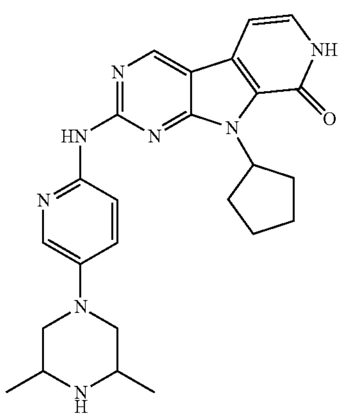 [SMILES: CC1CN(c2ccc(Nc3ncc4c5cc[nH]c(=O)c5n(C5CCCC5)c4n3)nc2)CC(C)N1] | 0.873 | 459.2 |
| 125 | 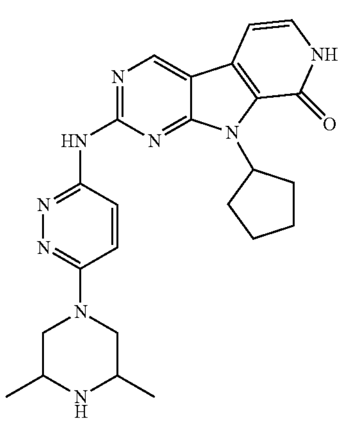 [SMILES: CC1CN(c2ccc(Nc3ncc4c5cc[nH]c(=O)c5n(C5CCCC5)c4n3)nn2)CC(C)N1] | 0.830 | 460.2 |
| 126 | | 0.821 | 446.2 |
| 127 | | 0.832 | 474.2 |
| 128 | | 0.809 | 446.2 |

TABLE 3-continued

| Example # | Structure | LCMS retention time (min) | LCMS-ESI (M + 1) |
|---|---|---|---|
| 129 | 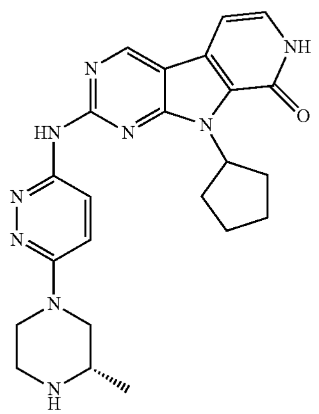 [SMILES: C[C@H]1CN(c2ccc(Nc3ncc4c5cc[nH]c(=O)c5n(C5CCCC5)c4n3)nn2)CCN1] | 0.819 | 446.2 |
| 130 | 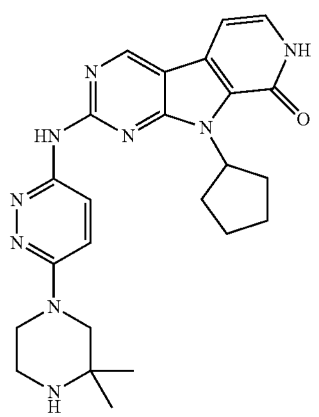 [SMILES: CC1(C)CN(c2ccc(Nc3ncc4c5cc[nH]c(=O)c5n(C5CCCC5)c4n3)nn2)CCN1] | 0.838 | 460.3 |

Example 131

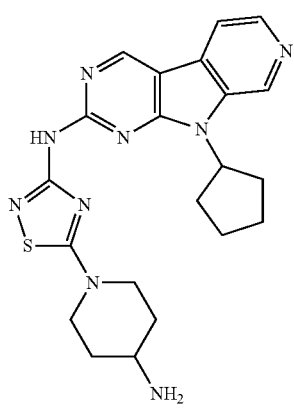

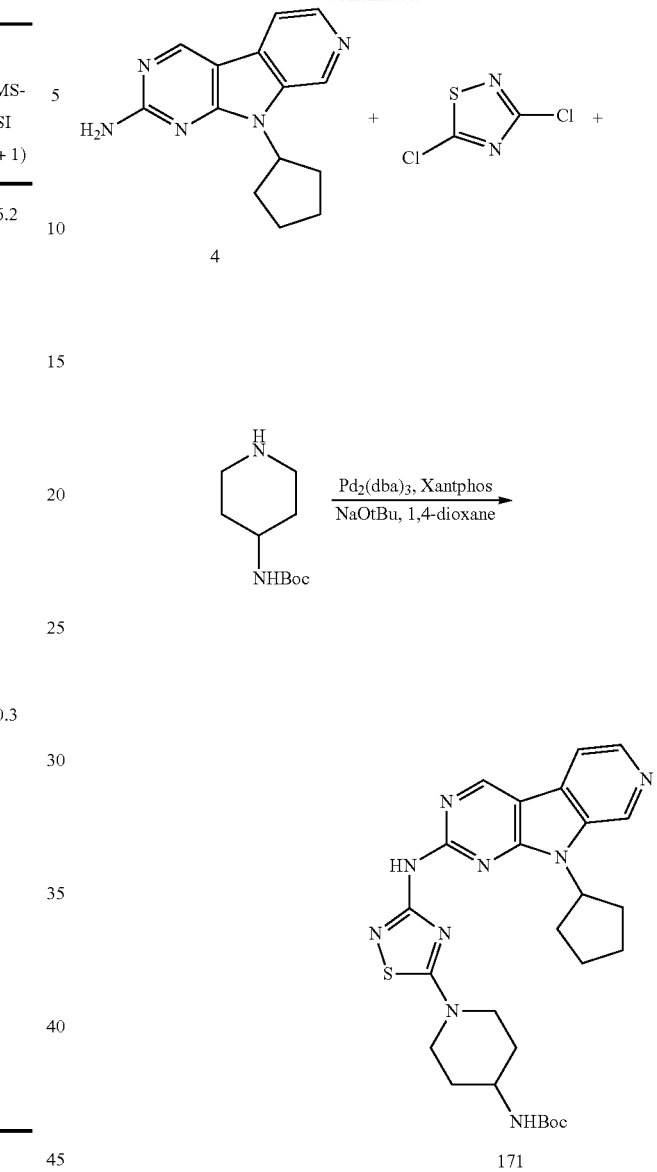

1,1-Dimethylethyl 1-(3-((9-cyclopentyl-9H-pyrido[4',3': 4,5]pyrrolo[2,3-d]pyrimidin-2-yl)amino)-5-1,2,4-thiadiazolyl)-4-piperidine carboxylate (171): A mixture of 3,5-dichloro-1,2,4-thiadiazole (0.015 g, 0.099 mmol) and tert-butyl piperidin-4-ylcarbamate (0.020 g, 0.099 mol) in 1 mL dioxane was purged with nitrogen gas for 1 minute. The reaction was stirred at room temperature for 30 minutes. To it was added compound 4 (0.0250 g, 0.099 mmol), Xantphos (0.0086 g, 0.015 mmol), $Pd_2(dba)_3$ (0.0068 g, 0.0074 mmol) and sodium tert-butoxide (0.024 g, 0.25 mmol). The mixture was purged again with nitrogen for 1 min and heated at 115° C. for 3 h. After cooling to room temperature, the solvent was removed using Gene Vac. The residue was sonicated with 2 mL methanol. The solid was removed by filtration, washed with 2×1 mL methanol. The combined solution was purified on a C-18 reverse phase column (150×30 mm, 4 micro) using Mass directed preparative HPLC and gradient elution of $CH_3CN$ in water containing 0.1% TFA to provide compound 171 as a TFA salt. LCMS-ESI (POS), M/Z, M+1: 536.2

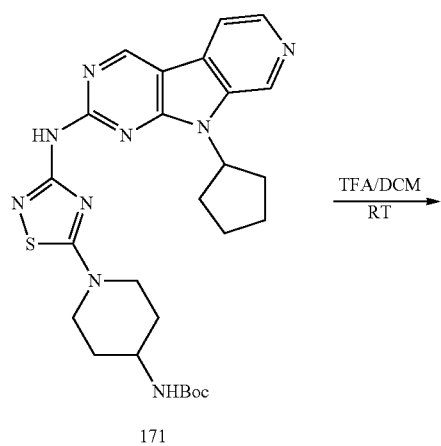

4-Amino-1-(3-((9-cyclopentyl-9H-pyrido[4',3':4,5]pyrrolo[2,3-d]pyrimidin-2-yl)amino)-5-1,2,4-thiadiazolyl)-piperidine (170): Compound 171 was treated with 15% TFA/DCM (2 mL) at room temperature for an hour. The solvent was evaporated. The residue was re-dissolved in 4 mL methanol and purified on a C-18 reverse phase column (150×30 mm, 4 micro) using Mass directed preparative HPLC and gradient elution of CH$_3$CN in water containing 0.1% TFA to provide compound 170 as a TFA salt. LCMS retention time (time): 0.752. LCMS-ESI (POS), M/Z, M+1: 436.1

Examples 132-135 (table 4) were prepared using conditions as described for example 131 with deprotection when necessary, replacing tert-butyl piperidin-4-ylcarbamate with proper amine.

TABLE 4

| Example # | Structure | LCMS retention time (min) | LCMS-ESI (M + 1) |
|---|---|---|---|
| 132 | 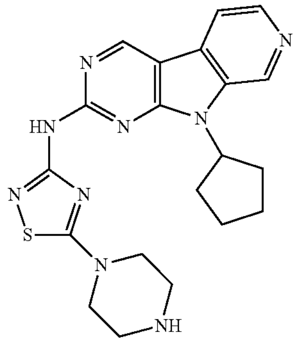 [SMILES: c1cc2c3cnc(Nc4nsc(N5CCNCC5)n4)nc3n(C3CCCC3)c2cn1] | 0.729 | 422.2 |
| 133 | 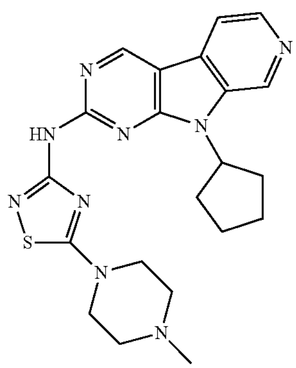 [SMILES: CN1CCN(c2nc(Nc3ncc4c5ccncc5n(C5CCCC5)c4n3)ns2)CC1] | 0.746 | 436.1 |
| 134 | 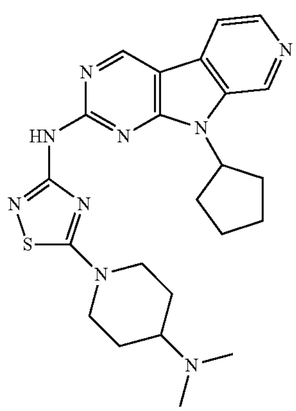 [SMILES: CN(C)C1CCN(c2nc(Nc3ncc4c5ccncc5n(C5CCCC5)c4n3)ns2)CC1] | 0.738 | 464.2 |
| 135 | 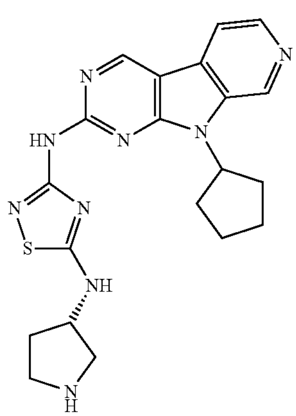 | 0.747 | 422.2 |

Example 136

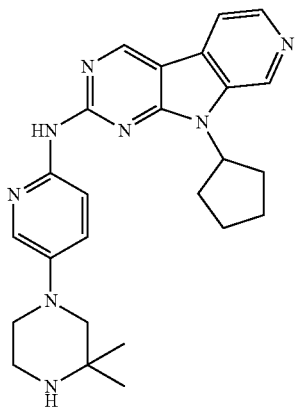

172

9-Cyclopentyl-N-(5-(3,3-dimethyl-1-piperazinyl)-2-pyridinyl)-9H-pyrido[4',3':4,5]pyrrolo[2,3-d]pyrimidin-2-amine Compound 172 was prepared using chemistry similar to that described in example 1. $^1$H NMR (500 MHz, DMSO-d6) δ 9.76 (1H, s), 9.26 (1H, s), 9.00 (1H, s), 8.44 (1H, d, J=5 Hz), 8.16 (1H, d, J=10 Hz), 8.02 (1 H, d, J=5 Hz), 8.00 (1H, d, J=2 Hz), 7.43 (1H, dd, J=10 Hz, J=2 Hz), 5.36 (1H, p, J=10 Hz), 2.99 (2H, t, m), 2.89 (2H, m), 2.83 (2H, s), 2.39 (2H, m), 2.20-2.05 (4H, m), 1.77 (2H, m), 1.13 (6H, s) ppm; LCMS-ESI (POS), M/Z, M+1: Found 442.2, Calculated 442.3.

Example 137

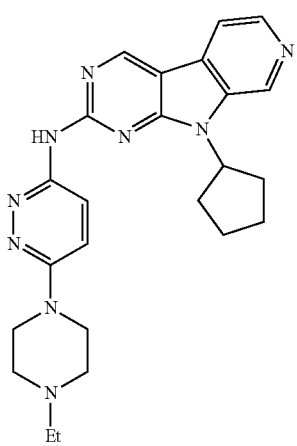

138

9-Cyclopentyl-N-(6-(4-ethyl-1-piperazinyl)-3-pyridazinyl)-9H-pyrido[4',3':4,5]pyrrolo[2,3-d]pyrimidin-2-amine Compound 173 was prepared using chemistry similar to that described in example 1. $^1$H NMR (500 MHz, CDCl$_3$) δ 9.08 (1H, s), 8.91 (1H, s), 8.55 (1H, d, J=10 Hz), 8.52 (1H, d, J=5 Hz), 8.33 (1H, s), 7.86 (1H, d, J=5 Hz), 7.09 (1H, d, J=10 Hz), 5.36 (1H, p, J=10 Hz), 3.66 (4H, t, J=5 Hz), 2.63 (4H, t, J=5 Hz), 2.51 (2H, q, J=5 Hz), 2.39 (2H, m), 2.20 (2H, m), 2.13 (2H, m), 1.89 (2H, m), 1.16 (3H, t, J=5 Hz) ppm; LCMS-ESI (POS), M/Z, M+1: Found 443.2, Calculated 443.3.

Example 138

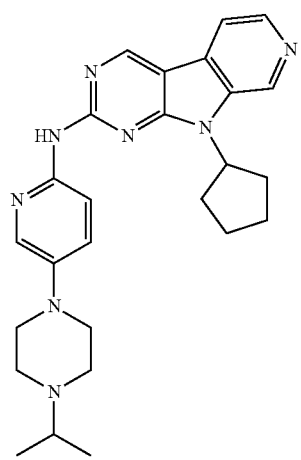

174

9-Cyclopentyl-N-(5-(4-(1-methylethyl)-1-piperazinyl)-2-pyridinyl)-9H-pyrido[4',3':4,5]pyrrolo[2,3-d]pyrimidin-2-amine Compound 174 was prepared using chemistry similar to that described in example 1. $^1$H NMR (500 MHz, CDCl$_3$) δ 9.09 (1H, s), 8.90 (1H, s), 8.51 (1H, d, J=5 Hz), 8.39 (1H, d, J=10 Hz), 8.33 (1 H, bs), 8.09 (1H, d, J=5 Hz), 7.83 (1H, dd, J=5 Hz, J=2 Hz), 7.39 (1H, dd, J=5 Hz, J=2 Hz), 5.36 (1H, p, J=10 Hz), 3.22 (4H, t, J=5 Hz), 2.76 (1H, m, J=10 Hz), 2.74 (4H, t, J=5 Hz), 2.44 (2H, m), 2.20 (2H, m), 2.14 (2H, m), 1.88 (2H, m), 1.12 (6H, d, J=10 Hz) ppm; LCMS-ESI (POS), M/Z, M+1: Found 456.1, Calculated 456.3.

Example 139

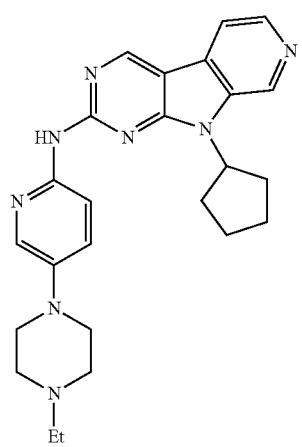

175

9-Cyclopentyl-N-(5-(4-ethyl-1-piperazinyl)-2-pyridinyl)-9H-pyrido[4',3':4,5]pyrrolo[2,3-d]pyrimidin-2-amine Compound 175 was prepared using chemistry similar to that described in example 1. $^1$H NMR (500 MHz, CDCl$_3$) δ 9.08 (1H, s), 8.91 (1H, s), 8.52 (1H, d, J=5 Hz), 8.41 (1H, d, J=10 Hz), 8.22 (1H, bs), 8.08 (1H, d, J=2 Hz), 7.83 (1H, d, J=5 Hz), 7.40 (1H, dd, J=10 Hz, J=2 Hz), 5.36 (1H, p, J=10 Hz), 3.27 (4H, m), 2.71 (2H, m), 2.56 (2H, m), 2.44 (2H, m), 2.20 (2H, m), 2.14 (2H, m), 1.89 (2H, m), 1.19 (3H, t, J=10 Hz) ppm; LCMS-ESI (POS), M/Z, M+1: Found 442.2, Calculated 442.3.

Example 140

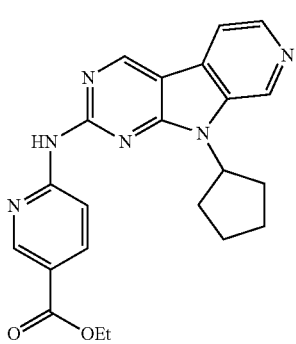

176

Ethyl 6-((9-cyclopentyl-9H-pyrido[4',3':4,5]pyrrolo[2,3-d]pyrimidin-2-yl)amino)-3-pyridinecarboxylate Compound 176 was prepared using chemistry similar to that described in example 1. NMR (500 MHz, DMSO-d6) δ 10.80 (1H, s), 9.48 (1H, s), 9.17 (1H, s), 8.87 (1H, d, J=2 Hz), 8.56 (1H, d, J=5 Hz), 8.53 (1H, d, J=10 Hz), 8.31 (1H, dd, J=10 Hz, J=2 Hz), 8.25 (1H, d, J=5 Hz), 5.36 (1H, p, J=10 Hz), 4.34 (2H, q, J=10 Hz), 2.42 (2H, m), 2.16-2.08 (4H, m), 1.81 (2H, m), 1.35 (3H, t, J=10 Hz) ppm; LCMS-ESI (POS), M/Z, M+1: Found 402.1, Calculated 402.2.

Example 141

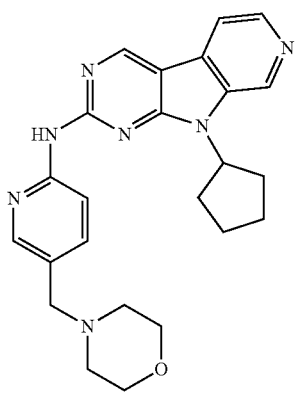

177

9-Cyclopentyl-N-(5-(4-morpholinylmethyl)-2-pyridinyl)-9H-pyrido[4',3':4,5]pyrrolo[2,3-d]pyrimidin-2-amine Compound 177 was prepared using chemistry similar to that described in example 1. $^1$H NMR (500 MHz, DMSO-d6) δ 10.04 (1H, s), 9.33 (1H, s), 9.04 (1H, s), 8.45 (1H, d, J=5 Hz), 8.35 (1H, d, J=10 Hz), 8.23 (1H, d, J=2 Hz), 8.07 (1 H, d, J=10 Hz), 7.75 (1H, dd, J=10 Hz, J=2 Hz), 5.39 (1H, p, J=10 Hz), 3.58 (4H, t, J=5 Hz), 2.05 (2H, s), 2.45-2.40 (6H, m), 2.20-2.06 (4H, m), 1.79 (2H, m) ppm; LCMS-ESI (POS), M/Z, M+1: Found 429.1, Calculated 429.2.

Example 142

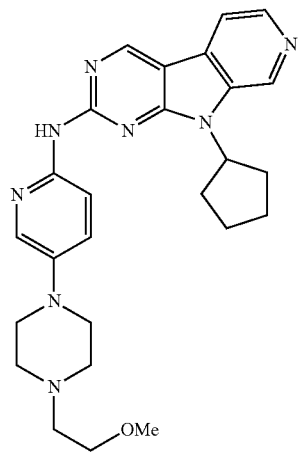

179

9-Cyclopentyl-N-(5-(4-(2-(methyloxy)ethyl)-1-piperazinyl)-2-pyridinyl)-9H-pyrido[4',3':4,5]pyrrolo[2,3-d]pyrimidin-2-amine Compound 179 was prepared using chemistry similar to that described in example 1. $^1$H NMR (500 MHz, DMSO-d6) δ 9.74 (1H, s), 9.25 (1H, s), 8.99 (1H, s), 8.43 (1H, d, J=5 Hz), 8.16 (1H, d, J=10 Hz), 8.03-8.02 (2 H, m), 7.46 (1H, dd, J=10 Hz, J=2 Hz), 5.35 (1H, p, J=10 Hz), 3.47 (2H, t, J=5 Hz), 3.25 (3H, s), 3.13 (4H, t, J=5 Hz), 2.58 (4H, t, J=5 Hz), 2.53 (2H, t, J=5 Hz), 2.38 (2H, m), 2.15-2.05 (4H, m), 1.76 (2H, m) ppm; LCMS-ESI (POS), M/Z, M+1: Found 472.2, Calculated 472.2.

Example 143

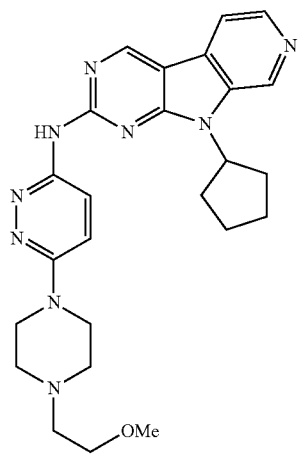

180

9-Cyclopentyl-N-(6-(4-(2-(methyloxy)ethyl)-1-piperazinyl)-3-pyridazinyl)-9H-pyrido[4',3':4,5]pyrrolo[2,3-d]pyrimidin-2-amine Compound 180 was prepared using chemistry similar to that described in example 1. $^1$H NMR (500 MHz, CDCl$_3$) δ 9.09 (1H, s), 8.92 (1H, s), 8.55 (1H, d, J=10 Hz), 8.53 (1H, d, J=5 Hz), 8.40 (1H, bs), 7.86 (1 H, d, J=5 Hz), 7.09 (1H, d, J=10 Hz), 5.39 (1H, p, J=10 Hz), 3.69 (4H, m), 3.60 (2H, t, J=5 Hz), 2.80-2.69 (6H, m), 2.37 (2H, m), 2.20 (2H, m), 2.13 (2H, m), 1.90 (2H, m) ppm; LCMS-ESI (POS), M/Z, M+1: Found 473.2, Calculated 473.3.

Example 144

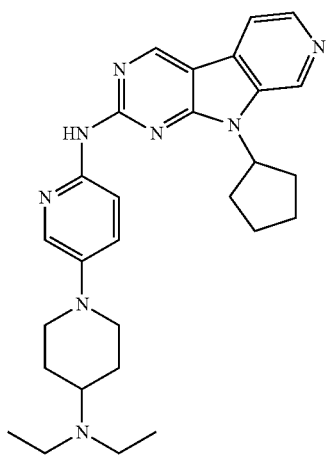

181

9-Cyclopentyl-N-(5-(4-(diethylamino)-1-piperidinyl)-2-pyridinyl)-9H-pyrido[4',3':4,5]pyrrolo[2,3-d]pyrimidin-2-amine Compound 181 was prepared using chemistry similar to that described in example 1. $^1$H NMR (500 MHz, DMSO-d6) δ 9.74 (1H, s), 9.26 (1H, s), 9.00 (1H, s), 8.44 (1H, d, J=5 Hz), 8.15 (1H, d, J=10 Hz), 8.03 (1 H, s), 8.02 (1H, d, J=2 Hz), 7.46 (1H, dd, J=10 Hz, J=5 Hz), 5.36 (1H, p, J=10 Hz), 3.72 (2H, d, J=15 Hz), 2.68 (2H, t, J=10 Hz), 2.52 (4H, m), 2.39 (2H, m), 2.07 (4H, m), 1.77 (4H, m), 1.57 (2H, m), 0.98 (6H, m) ppm; LCMS-ESI (POS), M/Z, M+1: Found 484.2, Calculated 484.3.

Example 145

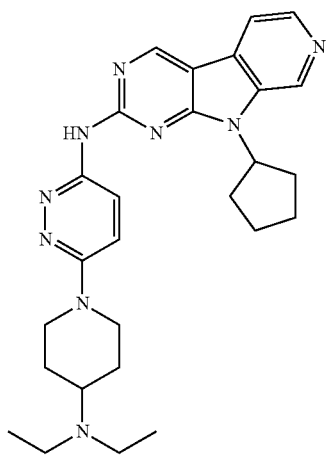

182

9-Cyclopentyl-N-(6-(4-(diethylamino)-1-piperidinyl)-3-pyridazinyl)-9H-pyrido[4',3':4,5]pyrrolo[2,3-d]pyrimidin-2-amine Compound 182 was prepared using chemistry similar to that described in example 1. $^1$H NMR (500 MHz, DMSO-d6) δ 10.16 (1H, s), 9.26 (1H, s), 9.00 (1H, s), 8.44 (1H, d, J=5 Hz), 8.15 (1H, d, J=10 Hz), 8.03 (1 H, s), 7.41 (1H, dd, J=10 Hz), 5.32 (1H, p, J=10 Hz), 4.32 (2H, d, J=15 Hz), 2.68 (2H, t, J=10 Hz), 2.52 (4H, m), 2.39 (2H, m), 2.07 (4H, m), 1.77

(4H, m), 1.57 (2H, m), 0.98 (6H, m) ppm; LCMS-ESI (POS), M/Z, M+1: Found 485.2, Calculated 485.3.

Example 146

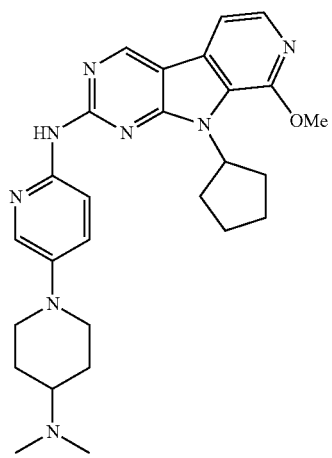

183

9-Cyclopentyl-N-(5-(4-(dimethylamino)-1-piperidinyl)-2-pyridinyl)-8-(methyloxy)-9H-pyrido[4',3':4,5]pyrrolo[2,3-d]pyrimidin-2-amine Compound 183 was prepared using chemistry similar to that described in example 53. $^1$H NMR (500 MHz, CDCl$_3$) δ 9.09 (1H, s), 8.38 (1H, d, J=10 Hz), 8.12 (1H, bs), 7.99 (1H, d, J=5 Hz), 7.44 (1H, d, J=5 Hz), 7.37 (1H, dd, J=10 Hz, J=5 Hz), 5.81 (1H, p, J=10 Hz), 4.14 (3H, s), 3.66 (2H, d, J=15 Hz), 2.75 (2H, t, J=10 Hz), 2.33 (6H, s), 2.31 (2H, m), 2.08 (4H, m), 1.80 (2H, m), 1.74 (2H, m), 1.69 (2H, m) ppm; LCMS-ESI (POS), M/Z, M+1: Found 486.2, Calculated 486.3.

Example 147

184

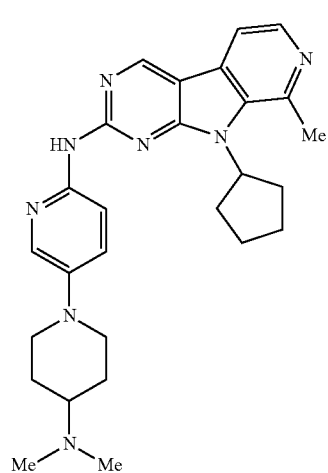

Example 148

9-cyclopentyl-N-(5-(4-(dimethylamino)-1-piperidinyl)-2-pyridinyl)-8-methyl-9H-pyrido[4',3':4,5]pyrrolo[2,3-d]pyrimidin-2-amine Compound 184 was prepared using chemistry similar to that described in example 54. $^1$H NMR (500 MHz, CDCl$_3$) δ 9.12 (1H, s), 8.82 (1H, s), 8.35 (1H, d, J=5 Hz), 8.33 (1 H, d, J=10 Hz), 8.12 (1H, d, J=2 Hz), 7.68 (1H, d, J=5 Hz), 7.35 (1H, dd, J=10 Hz, J=2 Hz), 5.42 (1H, p, J=10 Hz), 3.67 (2H, d, J=15 Hz), 3.02 (3H, s), 2.82-2.73 (4H, m), 2.33 (6H, s), 2.31 (1H, m), 2.14 (2H, m), 2.08 (2H, m), 1.99 (2H, m), 1.80 (2H, m), 1.69 (2H, m) ppm; LCMS-ESI (POS), M/Z, M+1: Found 470.3, Calculated 470.3.

Example 148

185

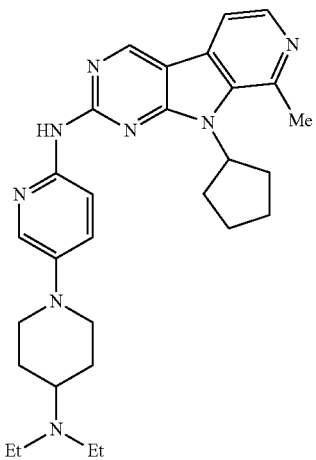

9-Cyclopentyl-N-(5-(4-(diethylamino)-1-piperidinyl)-2-pyridinyl)-8-methyl-9H-pyrido[4',3':4,5]pyrrolo[2,3-d]pyrimidin-2-amine Compound 185 was prepared using chemistry similar to that described in example 54. $^1$H NMR (500 MHz, CDCl$_3$) δ 9.05 (1H, s), 8.37 (1H, d, J=5 Hz), 8.32 (1 H, d, J=10 Hz), 8.05 (1H, d, J=2 Hz), 7.99 (1H, s), 7.68 (1H, d, J=5 Hz), 7.35 (1H, dd, J=10 Hz, J=2 Hz), 5.44 (1H, p, J=10 Hz), 3.68 (2H, d, J=15 Hz), 3.03 (3H, s), 2.80-2.73 (4H, m), 2.63-2.61 (5H, s), 2.16 (1H, m), 2.08 (2H, m), 1.93 (2H, m), 1.80 (2H, m), 1.75

(2H, m), 1.08 (6H, t, J=10 Hz) ppm; LCMS-ESI (POS), M/Z, M+1: Found 498.3, Calculated 498.3.

Example 149

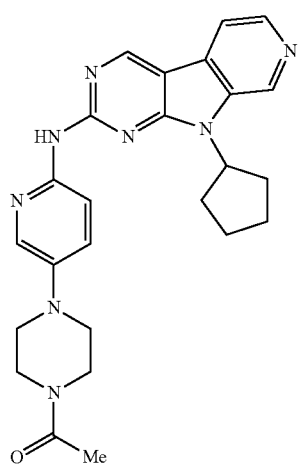

N-(5-(4-Acetyl-1-piperazinyl)-2-pyridinyl)-9-cyclopentyl-9H-pyrido[4',3':4,5]pyrrolo[2,3-d]pyrimidin-2-amine

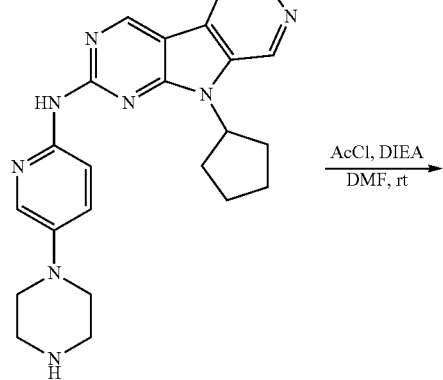

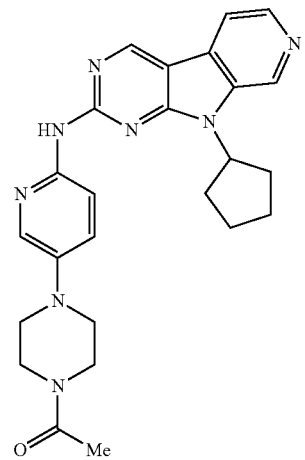

N-(5-(4-Acetyl-1-piperazinyl)-2-pyridinyl)-9-cyclopentyl-9H-pyrido[4',3':4,5]-pyrrolo[2,3-d]pyrimidin-2-amine (186): To a solution of compound 7 (207 mg, 0.50 mmol) in DMF (5 mL) were added N,N-diisopropylethylamine (174 uL, 1.0 mmol) and acetyl chloride (43 uL, 0.60 mmol) in DMF (2 mL) at 0° C. and the resulted mixture was stirred at 0° C. for 1 hr. The reaction mixture was concentrated and the residue was washed with water (sonicated) and the solid was collected by filtration, dried under high vacuumn to give compound 186 (170 mg, 74% yield) as a light yellow solid. $^1$H NMR (500 MHz, DMSO-d6) δ 9.82 (1H, s), 9.27 (1H, s), 9.01 (1H, s), 8.44 (1 H, d, J=5 Hz), 8.21 (1H, d, J=10 Hz), 8.07 (1H, d, J=2 Hz), 8.04 (1H, d, J=5 Hz), 7.52 (1H, dd, J=10 Hz, J=2 Hz), 5.37 (1H, p, J=10 Hz), 3.61 (4H, q, J=5 Hz), 3.17 (2H, t, J=5 Hz), 3.10 (2H, t, J=5 Hz), (3H, s), 2.40 (2H, m), 2.08 (4H, m), 2.06 (3H, s), 1.78 (2H, m) ppm; LCMS-ESI (POS), M/Z, M+1: Found 456.1, Calculated 456.2.

Example 150

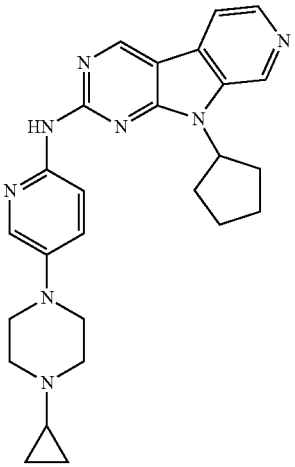

9-Cyclopentyl-N-(5-(4-cyclopropyl-1-piperazinyl)-2-pyridinyl)-9H-pyrido[4',3':4,5]pyrrolo[2,3-d]pyrimidin-2-amine

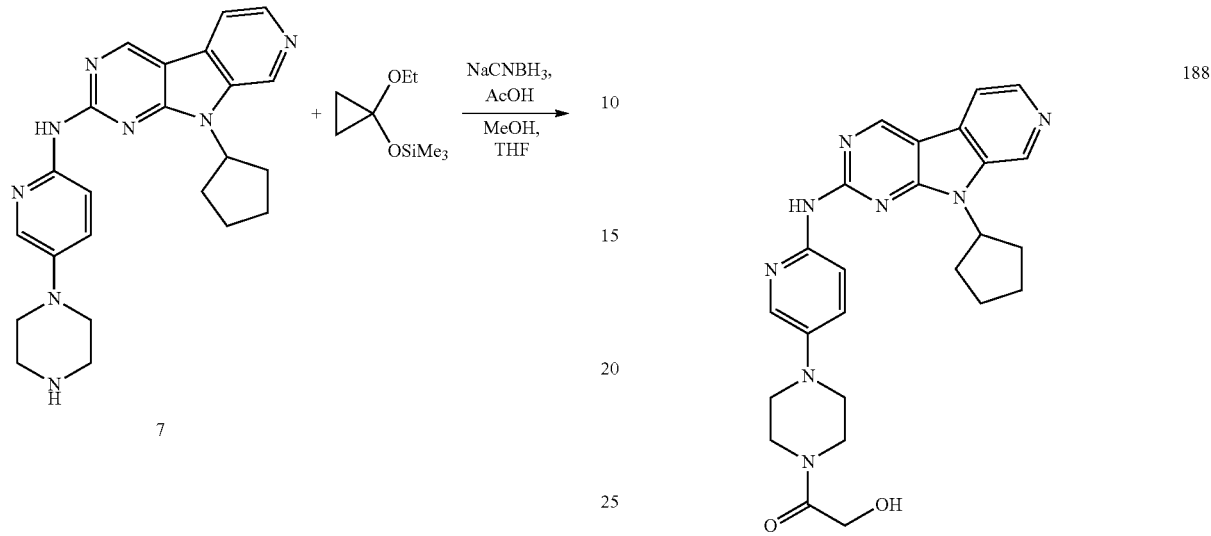

9-Cyclopentyl-N-(5-(4-cyclopropyl-1-piperazinyl)-2-pyridinyl)-9H-pyrido[4',3':4,5]-pyrrolo[2,3-d]pyrimidin-2-amine (187): To a solution of compound 7 (207 mg, 0.50 mmol) in THF (5 mL) were added water (0.05 mL), (1-ethoxy-1-cyclopropyloxy)-trimethylsilane (1174 mg, 1.0 mmol), acetic acid (0.55 mL) and sodium cyanoborohydride (1 mL, 1 M in THF, 1.0 mmol). The mixture was stirred at 60° C. overnight. The reaction mixture was concentrated and the residue was disolved in ethyl acetate and washed with saturated NaHCO$_3$ and brine then dried. The solvent was evaporated and the residue was purified by chromatography on silica gel eluting with CH$_2$Cl$_2$:methanol:NH$_4$OH (400:10:1) to give compound 187 as a yellow solid (60 mg, 26% yield). $^1$H NMR (500 MHz, CDCl$_3$) δ 9.08 (1H, s), 8.90 (1H, s), 8.51 (1H, d, J=5 Hz), 8.39 (1H, d, J=10 Hz), 8.18 (1H, bs), 8.07 (1H, d, J=2 Hz), 7.84 (1H, d, J=5 Hz), 7.39 (1H, dd, J=10 Hz, J=2 Hz), 5.38 (1H, p, J=10 Hz), 3.17 (4H, q, J=5 Hz), 2.83 (2H, t, J=5 Hz), 2.42 (2H, m), 2.21-2.14 (4H, m), 1.88 (2H, m), 1.71 (1H, m), 0.53-0.46 (4H, m) ppm; LCMS-ESI (POS), M/Z, M+1: Found 454.2, Calculated 454.3.

Example 151

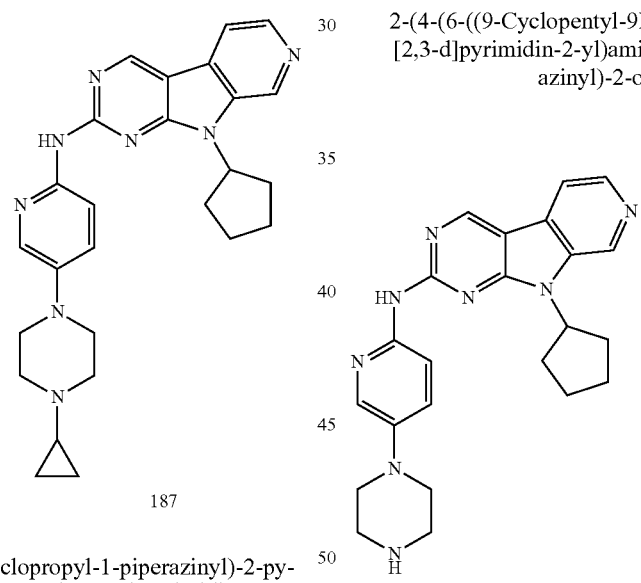

2-(4-(6-((9-Cyclopentyl-9H-pyrido[4',3':4,5]pyrrolo[2,3-d]pyrimidin-2-yl)amino)-3-pyridinyl)-1-piperazinyl)-2-oxoethanol

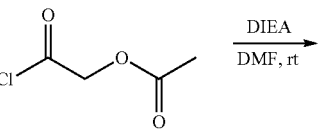

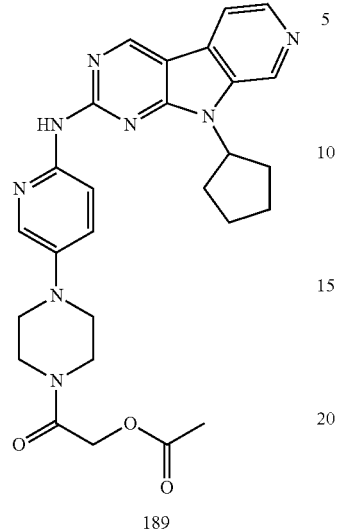

189

2-(4-(6-((9-Cyclopentyl-9H-pyrido[4',3':4,5]pyrrolo[2,3-d]pyrimidin-2-yl)amino)-3-pyridinyl)-1-piperazinyl)-2-oxo-ethyl acetate (189): To a solution of compound 7 (207 mg, 0.50 mmol) in DMF (5 mL) were added N,N-diisopropyl-ethylamine (174 uL, 1.0 mmol) and acetoxyacetyl chloride (65 uL, 0.60 mmol) and the resulted mixture was stirred at room temperature for 1 hr. The reaction mixture was concentrated to give compound 189 as a yellow solid which was used in next step without further purification. LCMS-ESI (POS), M/Z, M+1: Found 514.2, Calculated 514.2.

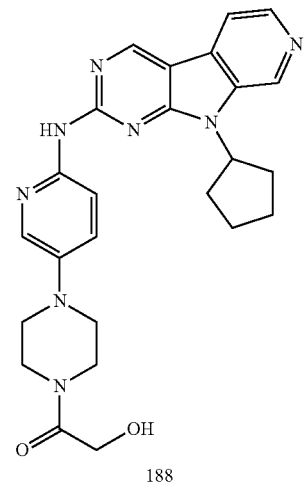

188

2-(4-(6-((9-Cyclopentyl-9H-pyrido[4',3':4,5]pyrrolo[2,3-d]pyrimidin-2-yl)amino)-3-pyridinyl)-1-piperazinyl)-2-oxo-ethanol (188): To a solution of compound 189 (~0.5 mmol) in THF/methanol/H2O (3:1:1, 10 mL) was added 12 mg of LiOH and the mixture was stirred at 60° C. overnight. The reaction mixture was concentrated and the residue was dissolved in dichloromethane then washed with water and brine then dried. The solvent was evaporated and the residue was purified by chromatography on silica gel eluting with $CH_2Cl_2$:methanol:$NH_4OH$ (400:10:1) to give compound 188 as a yellow solid (150 mg, 63% in two steps). $^1$H NMR (500 MHz, DMSO-d6) δ 9.82 (1H, s), 9.27 (1H, s), 9.01 (1H, s), 8.44 (1H, d, J=5 Hz), 8.21 (1H, d, J=10 Hz), 8.07 (1H, d, J=2 Hz), 8.04 (1H, d, J=5 Hz), 7.52 (1H, dd, J=10 Hz, J=2 Hz), 5.37 (1H, p, J=10 Hz), 4.65 (1H, t, J=5 Hz), 4.15 (2H, d, J=5 Hz), 3.65 (2H, m), 3.53 (2H, m), 3.15 (4H, m), 2.40 (2H, m), 2.08 (4H, m), 1.78 (2H, m) ppm; LCMS-ESI (POS), M/Z, M+1: Found 472.2, Calculated 472.3.

Example 152

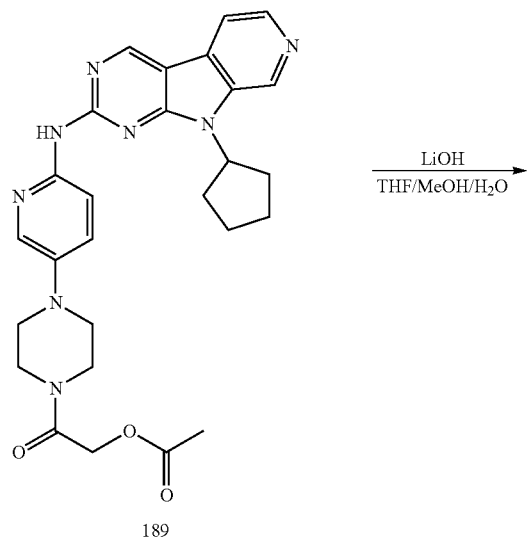

189

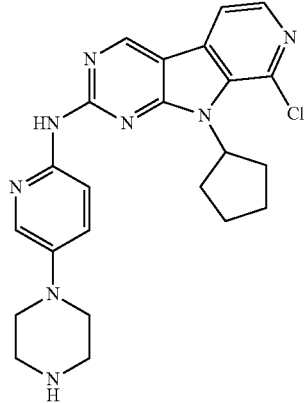

190

8-Chloro-9-cyclopentyl-N-(5-(1-piperazinyl)-2-pyridinyl)-9H-pyrido[4',3':4,5]pyrrolo[2,3-d]pyrimidin-2-amine

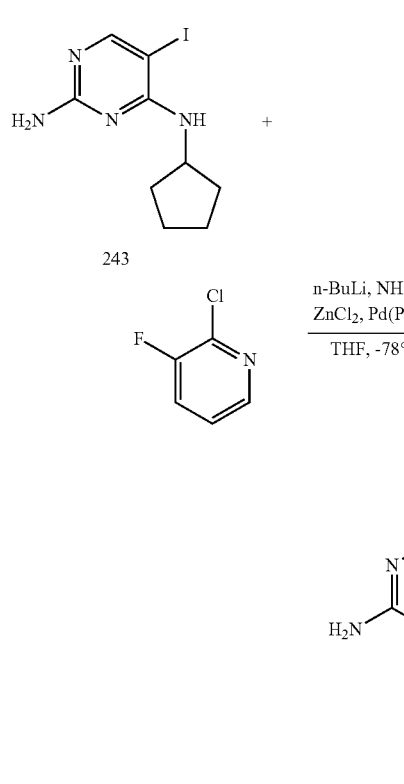

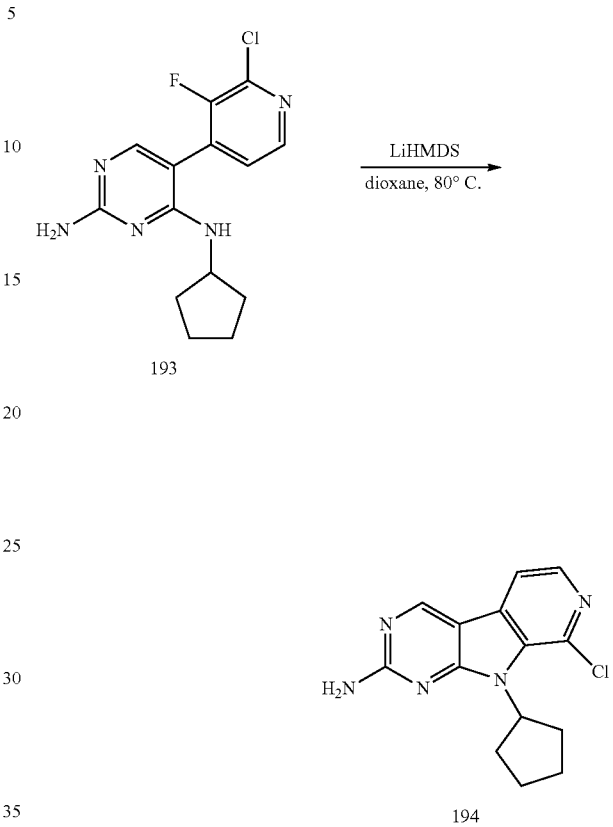

5-(2-Chloro-3-fluoropyridin-4-yl)-N4-cyclopentylpyrimidine-2,4-diamine (193): To a 500 mL three-necked round-bottomed flask equipped with a thermometer and a stir bar was added diisopropylamine (14.7 mL, 104 mmol). The flask was cooled in a Et$_2$O-dry ice bath and butyllithium 2.5M in hexane (43.0 mL, 107 mmol) was added cautiously. The solution was allowed to warm to room temperature. After stirring at room temperature for 5 minutes, a white solid formed and it was cooled in an Et$_2$O-dry ice bath then diluted with 170 mL of anhydrous THF. The solution was then cooled to −75° C. 2-chloro-3-fluoropyridine (10.3 mL, 104 mmol) was dissolved in 100 mL of anhydrous THF. This solution was then slowly cannulated into the LDA solution over a period of 20 minutes while the temperature was held below −69° C. The solution was stirred for 30 minutes before a solution of zinc (II) chloride 0.5M in THF (111 mL, 55.4 mmol) was slowly added with the temperature maintained below -68° C. The yellow solution was then allowed to warm to room temperature. After 30 minutes of stirring at room temperature, compound 243 (see example 200) (10.538 g, 34.6 mmol) and Pd(PPh$_3$)$_4$ (2.00 g, 1.73 mmol) were added and the solution was heated at 60° C. overnight. The solution was concentrated under vacuum, and then cooled in an ice bath. Saturated NH$_4$Cl aqueous solution was added with ice and the solution was stirred for 10 minutes and then extracted with DCM. The aqueous layer was washed with 10% i-PrOH/DCM. The combined organics were dried over MgSO$_4$ and concentrated under vacuum. The residue obtained was purified by flash chromatography (methanol/DCM/Aq NH$_4$OH) to give compound 193 (4.13 g, 38.7%) as a white solid. $^1$H NMR (500 MHz, DMSO-d$_6$) δ 8.22 (1 H, d, J=4.9 Hz), 7.63 (1 H, s), 7.40 (1 H, t, J=5.1 Hz), 6.28-6.41 (3 H, m), 4.37-4.49 (1 H, m), 1.78-1.93 (2 H, m), 1.57-1.69 (2 H, m), 1.36-1.54 (4 H, m) ppm; LCMS-ESI (POS), M/Z, M+1: Found 308.0.

8-Chloro-9-cyclopentyl-9H-pyrido[4',3':4,5]pyrrolo[2,3-d]pyrimidin-2-amine (194): Compound 193 (3.10 g, 10.1 mmol) was combined with 30 mL of anhydrous 1,4-dioxane. To this was added LiHMDS 1M in THF (30.2 mL, 30.2 mmol) and the solution was heated to 85° C. for 5 hours. The solution was cooled to room temperature and then diluted with ice/sat. NaHCO$_3$. The product was extracted with 15% 2-propanol/DCM and the organics were dried over MgSO$_4$ before being concentrated under vacuum. The residue obtained was purified on CombiFlash column (dry loaded), eluting with a gradient of 2% methanol/DCM to 6% methanol/DCM. Trituration with acetone and ethyl acetate left a light brown solid. Repurification of the supernatants provided additional material. The solids were combined to give compound 194 (1.60 g, 55.2%) as a light brown solid. $^1$H NMR (500 MHz, DMSO-d$_6$) δ 9.11 (1 H, s), 8.14 (1 H, d, J=4.9 Hz), 7.98 (1 H, d, J=4.9 Hz), 7.07 (2 H, br. s.), 5.90 (1 H, quin, J=8.7 Hz), 2.44-2.49 (2 H, m), 2.04-2.13 (2 H, m), 1.95-2.03 (2 H, m), 1.63-1.73 (2 H, m) ppm; LCMS-ESI (POS), M/Z, M+1: Found 288.1.

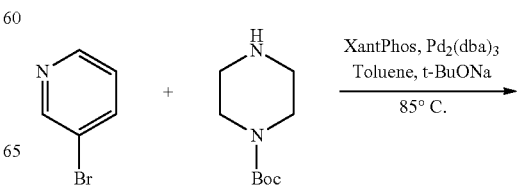

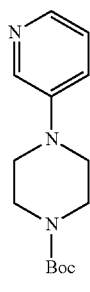

195

MHz, DMSO-d6) δ 8.07 (1 H, d, J=3.2 Hz), 7.42 (1 H, d, J=8.8 Hz), 7.34 (1 H, dd, J=8.9, 3.3 Hz), 3.42-3.48 (4 H, m), 3.12-3.21 (4 H, m), 1.42 (9 H, s) ppm; LCMS-ESI (POS), M/Z, M+1: Found 342.1.

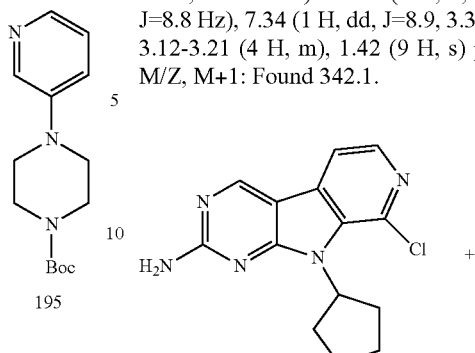

194 tert-Butyl 4-(pyridin-3-yl)piperazine-1-carboxylate (195): Sodium 2-methylpropan-2-olate (1.83 g, 19.1 mmol), 3-bromopyridine (2.010 g, 12.7 mmol), and tert-butyl piperazine-1-carboxylate (3.55 g, 19.1 mmol) were combined in 10 mL of anhydrous toluene. $N_2$ was bubbled through the solution briefly before adding 4,5-bis(diphenylphosphino)-9,9-dimethyl-9H-xanthene (0.368 g, 0.636 mmol) and $Pd_2(dba)_3$ (0.183 g, 0.318 mmol). The solution was then heated to 85° C. overnight.

The solution was cooled to room temperature and diluted with sat's $NH_4Cl$ and then extracted with DCM. The organics were dried over $MgSO_4$ and then concentrated under vacuum. The residue obtained was purified on CombiFlash column eluting with a gradient of DCM to 4% methanol/DCM. The fractions containing the product were combined and concentrated under vacuum to give compound 195 (2.06 g, 61.5% yield) as a reddish yellow solid. $^1$H NMR (500 MHz, DMSO-$d_6$) δ 8.31 (1 H, d, J=2.9 Hz), 8.02 (1 H, dd, J=4.5, 1.3 Hz), 7.33 (1 H, ddd, J=8.5, 3.0, 1.5 Hz), 7.20-7.24 (1 H, m), 3.43-3.49 (4 H, m), 3.11-3.20 (4 H, m), 1.42 (9 H, s) ppm; LCMS-ESI (POS), M/Z, M+1: Found 264.1.

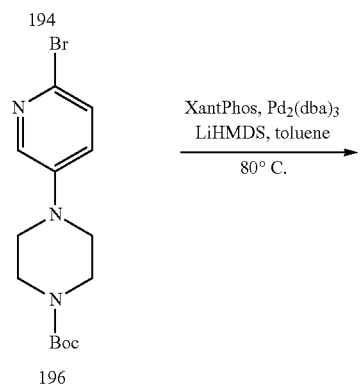

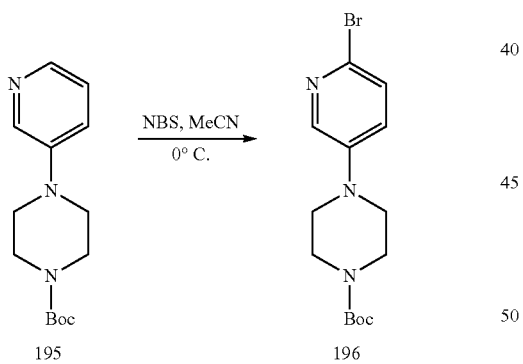

tert-Butyl 4-(6-bromopyridin-3-yl)piperazine-1-carboxylate (196): By the method of Audouze et al. J. Med. Chem. 49 (2006) 3159-3171, compound 195 (2.06 g, 7.82 mmol) was dissolved in 40 mL of acetonitrile under an atmosphere of $N_2$.

The solution was cooled in a ice bath before a solution of N-bromosuccinimide (1.46 g, 8.21 mmol) in 15 mL of acetonitrile was added over a period of 10 minutes. The solution was then stirred in the ice bath for 2 hours. Added silica gel and DCM, and the slurry was then concentrated under vacuum. Purified on CombiFlash column (dry loaded), eluting with a gradient of 5% ethyl acetate/hexane to 40% ethyl acetate/hexane. The fractions containing the product were combined and concentrated under vacuum to give compound 196 (1.9847 g, 74% yield) as an off white solid. $^1$H NMR (500

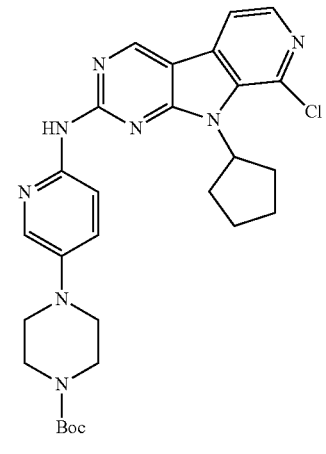

197 tert-Butyl 4-(6-((8-chloro-9-cyclopentyl-9H-pyrido[4',3': 4,5]pyrrolo[2,3-d]-pyrimidin-2-yl)amino)-3-pyridinyl)-1-piperazinecarboxylate (197): Compound 196 (0.178 g, 0.521 mmol), compound 194 (0.125 g, 0.434 mmol), and LiHMDS 1M in THF (1.30 mL, 1.30 mmol) were combined in 5 mL of anhydrous toluene. $N_2$ was bubbled through the solution briefly before adding $Pd_2(dba)_3$ (0.0298 g, 0.0326 mmol) and 4,5-bis(diphenylphosphino)-9,9-dimethyl-9H-xanthene (0.0377 g, 0.0652 mmol). The solution was then heated to 80° C. for 2 hours with microwave irradiation. The solution was diluted with DCM before it was poured into sat's $NH_4Cl$. Partitioned the layers and washed the aqueous layer with 10% i-PrOH/DCM. The combined organics were dried over MgSO4 and then concentrated under vacuum. The residue obtained was purified on CombiFlash column (dry loaded), eluting with a gradient of 60% ethyl acetate/hexane to 100% ethyl acetate. The fractions containing the product were combined and concentrated under vacuum. The residue obtained was repurified on CombiFlash column (dry loaded), eluting with a gradient of 2% methanol/0.1% NH₄OH (~28% in water)/DCM to 4% methanol/0.2% NH₄OH (~28% in water)/DCM. The fractions containing the product were combined and concentrated under vacuum. The residue obtained was sonicated in methanol. Filtration provided an off-white solid as compound 197 (0.173 g, 72%). LCMS-ESI (POS), M/Z, M+1: Found 549.1.

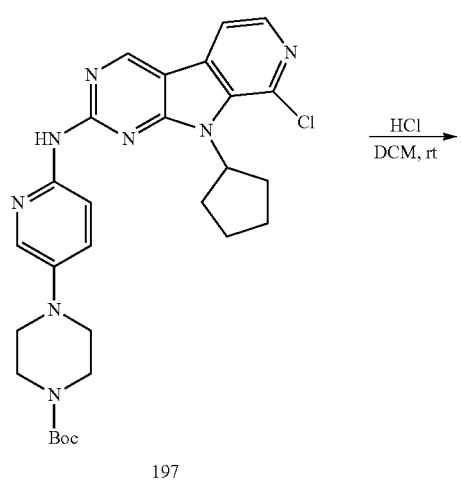

8-Chloro-9-cyclopentyl-N-(5-(1-piperazinyl)-2-pyridinyl)-9H-pyrido[4',3':4,5]-pyrrolo[2,3-d]pyrimidin-2-amine (190): Compound 197 (0.173 g, 0.315 mmol) was dissolved in 10 mL of DCM and to this was added 4N HCl in dioxane (1.97 mL, 7.88 mmol). The solution was stirred at room temperature overnight and then concentrated under vacuum to give a yellow solid. The solid obtained was sonicated in Et₂O and a yellowish solid was collected on filter paper to give compound 190 as an HCl salt (0.164 g, 100%). ¹H NMR (500 MHz, DMSO-d₆) δ 10.56 (1 H, br. s.), 9.42 (1 H, s), 8.87 (2 H, br. s.), 8.28 (1 H, d, J=4.9 Hz), 8.19 (1 H, d, J=5.1 Hz), 8.09 (1 H, d, J=2.9 Hz), 7.97 (1 H, d, J=9.0 Hz), 7.75 (1 H, dd, J=9.3, 2.0 Hz), 5.96-6.07 (2 H, m, J=9.2, 8.9, 8.8, 8.8 Hz), 3.37-3.43 (4 H, m), 3.26-3.33 (4 H, m), 2.54-2.65 (2 H, m), 2.01-2.12 (4 H, m), 1.66-1.77 (2 H, m) ppm; LCMS-ESI (POS), M/Z, M+1: Found 449.2.

Example 153

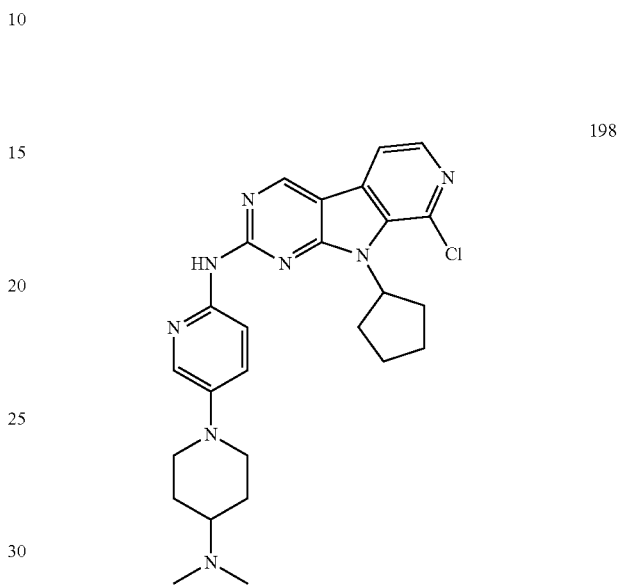

8-Chloro-9-cyclopentyl-N-(5-(4-(dimethylamino)-1-piperidinyl)-2-pyridinyl)-9H-pyrido[4',3':4,5]pyrrolo[2,3-d]pyrimidin-2-amine

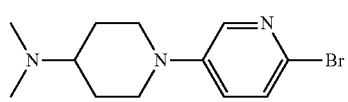

1-(6-Bromopyridin-3-yl)-N,N-dimethylpiperidin-4-amine (199): Compound 199 was prepared by analogy to compound 196. ¹H NMR (500 MHz, DMSO-d6) δ 8.05 (1H, d, J=2.7 Hz), 7.35-7.38 (1H, m), 7.30-7.33 (1H, m), 3.69-3.79 (2H, m), 2.73 (2H, td, J=12.2, 2.7 Hz), 2.19-2.27 (1H, m), 2.17 (6H, s), 1.75-1.86 (2H, m), 1.36-1.50 (2H, m) ppm; LCMS-ESI (POS), M/Z, M+1: Found 284.0.

8-Chloro-9-cyclopentyl-N-(5-(4-(dimethylamino)-1-piperidinyl)-2-pyridinyl)-9H-pyrido[4',3':4,5]pyrrolo[2,3-d]pyrimidin-2-amine (198) Compound 198 was prepared from compound 199 using methods described in example 152. ¹H NMR (500 MHz, D₂O) δ 8.79 (1 H, s), 7.97 (1 H, d, J=4.9 Hz), 7.78 (1 H, br. s.), 7.53 (1 H, br. s.), 7.20 (1 H, br. s.), 6.94 (1 H, d, J=9.0 Hz), 5.71 (1 H, br. s.), 3.65 (2 H, br. s.), 3.42 (1 H, br.

s.), 2.92 (6 H, s), 2.68-2.82 (2 H, m), 2.16-2.33 (4 H, m), 2.04 (4 H, br. s.), 1.74 (4 H, br. s.) ppm; LCMS-ESI (POS), M/Z, M+1: Found 491.2.

Example 154

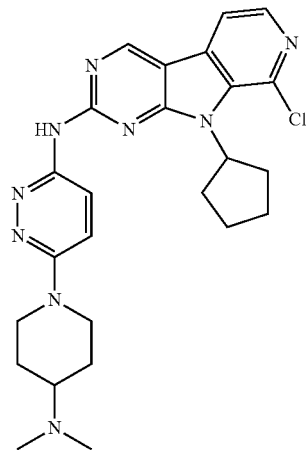

8-Chloro-9-cyclopentyl-N-(6-(4-(dimethylamino)-1-piperidinyl)-3-pyridazinyl)-9H-pyrido[4',3':4,5]pyrrolo[2,3-d]pyrimidin-2-amine

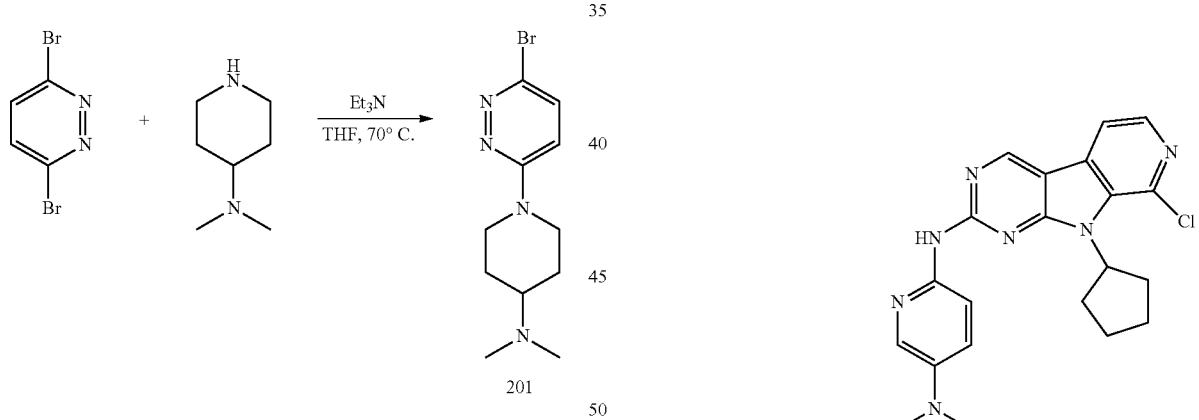

1-(6-Bromo-3-pyridazinyl)-N,N-dimethyl-4-piperidinamine (201): N,N-dimethylpiperidin-4-amine (0.505 g, 3.94 mmol), 3,6-dibromopyridazine (0.511 g, 2.15 mmol), and triethylamine (0.599 mL, 4.30 mmol) were combined in 5 mL of THF. The solution was heated at 70° C. for 17 hours. The solution was cooled to room temperature and then purified on CombiFlash column (dry loaded), eluting with 10% methanol/0.5% NH$_4$OH (~28% in water)/DCM isocratic. The fractions containing the product were combined and concentrated under vacuum to give compound 201 (0.550 g, 89.8% yield) as an off white solid. $^1$H NMR (500 MHz, MeOD-d3) δ 7.51 (1 H, d, J=9.8 Hz), 7.24 (1 H, d, J=9.8 Hz), 4.45 (2 H, d, J=13.7 Hz), 2.98 (2 H, td, J=13.0, 2.2 Hz), 2.61 (1 H, tt, J=11.5, 3.8 Hz), 2.38 (6 H, s), 1.99-2.07 (2 H, m), 1.45-1.58 (2 H, m, J=12.5, 12.2, 12.2, 4.2 Hz) ppm; LCMS-ESI (POS), M/Z, M+1: Found 285.0.

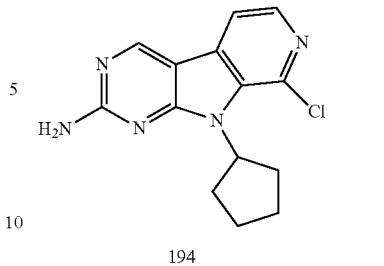

194

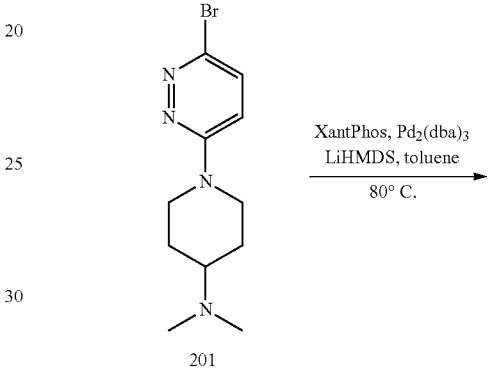

8-chloro-9-cyclopentyl-N-(6-(4-(dimethylamino)-1-piperidinyl)-3-pyridazinyl)-9H-pyrido[4',3':4,5]pyrrolo[2,3-d]pyrimidin-2-amine (200): Compound 200 was prepared using methods described in Example 152 using 201. $^1$H NMR (500 MHz, CD$_3$OD) δ 9.48 (1 H, s), 8.31 (1 H, d, J=5.1 Hz), 8.18 (1 H, d, J=5.1 Hz), 8.08 (1 H, d, J=10.3 Hz), 7.89 (1 H, d, J=10.0 Hz), 6.19 (1 H, quin, J=8.7 Hz), 4.54 (2 H, d, J=13.9 Hz), 3.53-3.62 (1 H, m), 3.11-3.19 (2 H, m), 2.92 (6 H, s), 2.63-2.73 (2 H, m), 2.13-2.29 (6 H, m), 1.79-1.91 (4 H, m)) ppm; LCMS-ESI (POS), M/Z, M+1: Found 492.2.

Example 155

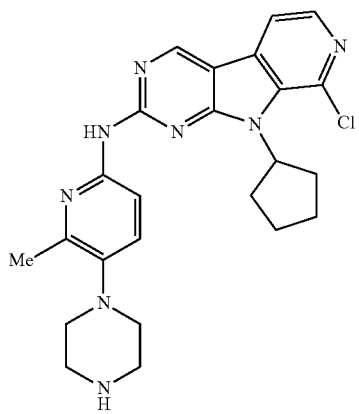

202

8-Chloro-9-cyclopentyl-N-(6-methyl-5-(1-piperazinyl)-2-pyridinyl)-9H-pyrido[4',3':4,5]pyrrolo[2,3-d]pyrimidin-2-amine Compound 202 was prepared using methods described in Example 152. $^1$H NMR (500 MHz, D$_2$O) δ 8.86 (1 H, s), 7.97 (1 H, d, J=4.9 Hz), 7.80-7.93 (2 H, m), 7.10 (1 H, d, J=9.0 Hz), 5.69-5.81 (1 H, m), 3.46-3.51 (4 H, m), 3.22 (4 H, br. s.), 2.52 (3 H, br. s.), 2.23-2.36 (2 H, m), 1.98-2.16 (4 H, m), 1.70-1.81 (2 H, m) ppm; LCMS-ESI (POS), M/Z, M+1: Found 463.1.

Example 156

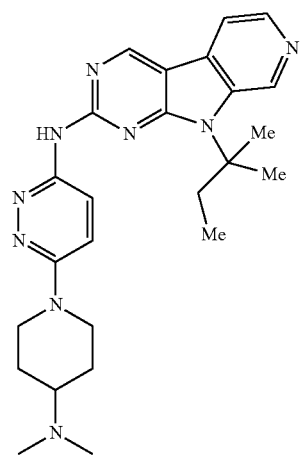

203

N-(6-(4-(dimethylamino)-1-piperidinyl)-3-pyridazinyl)-9-(1,1-dimethylpropyl)-9H-pyrido[4',3':4,5]pyrrolo[2,3-d]pyrimidin-2-amine Compound 203 was prepared using chemistry similar to that described in example 1. $^1$H NMR (400 MHz, DMSO-d$_6$) δ 11.69 (1 H, br. s.), 11.30-11.46 (1 H, m), 9.77 (1 H, s), 9.47 (1 H, s), 8.82 (1 H, d, J=6.3 Hz), 8.72 (1 H, d, J=6.3 Hz), 8.32 (1 H, d, J=10.2 Hz), 8.1.5 (1 H, d, J=10.2 Hz), 4.51 (2 H, d, J=13.3 Hz), 3.44-3.55 (1 H, m), 3.16 (2 H, t, J=12.3 Hz), 2.71 (6 H, d, J=5.1 Hz), 2.36 (2 H, q, J=7.4 Hz), 2.23 (2 H, d, J=11.7 Hz), 2.03 (6 H, s), 1.71-1.88 (2 H, m), 0.65 (3 H, t, J=7.2 Hz) ppm; LCMS-ESI (POS), M/Z, M+1: Found 460.3.

Example 157

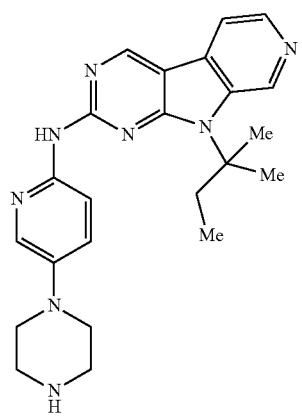

204

9-(1,1-dimethylpropyl)-N-(5-(1-piperazinyl)-2-pyridinyl)-9H-pyrido-[4',3':4,5]pyrrolo[2,3-d]pyrimidin-2-amine Compound 204 was prepared using chemistry similar to that described in example 1. $^1$H NMR (400 MHz, DMSO-d$_6$) δ 11.27 (1 H, br. s.), 9.74 (1 H, s), 9.56 (2 H, br. s.), 9.43 (1 H, s), 8.79 (1 H, d, J=5.9 Hz), 8.70 (1 H, d, J=5.9 Hz), 8.13 (1 H, d, J=2.3 Hz), 7.94-7.98 (1 H, m), 7.88-7.93 (1 H, m), 3.43-3.53 (4 H, m), 3.20-3.30 (4 H, m), 2.39 (2 H, q, J=7.2 Hz), 2.04 (6 H, s), 0.66 (3 H, t, J=7.4 Hz) ppm; LCMS-ESI (POS), M/Z, M+1: Found 417.3.

Example 158

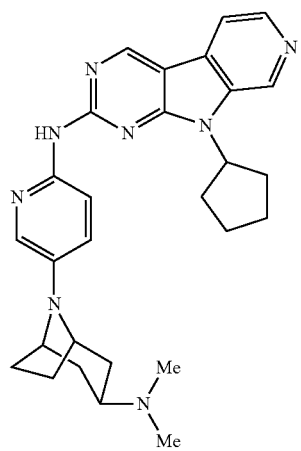

205

9-cyclopentyl-N-(5-(3-(dimethylamino)-8-azabicyclo[321]oct-8-yl)-2-pyridinyl)-9H-pyrido[4',3':4,5]pyrrolo[2,3-d]pyrimidin-2-amine Compound 205 was prepared using chemistry similar to that described in example 1. $^1$H NMR (500 MHz, DMSO-d$_6$) δ 11.41 (1 H, br. s.), 10.65 (1 H, br. s.), 9.71 (1 H, s), 9.47 (1 H, s), 8.75-8.79 (1 H, m), 8.71-8.74 (1 H, m), 8.04 (1 H, d, J=2.4 Hz), 7.92-7.98 (1 H, m), 7.88 (1 H, d, J=10.3 Hz), 5.43 (1 H, quin, J=8.7 Hz), 4.46-4.51 (2 H, m), 3.62-3.72 (1 H, m), 2.62 (6H, d, J=4.9 Hz), 2.37-2.47 (2 H, m), 2.06-2.18 (4 H, m), 1.99-2.05 (2 H, m), 1.90-1.97 (2 H, m), 1.80-1.90 (4 H, m), 1.71-1.80 (2 H, m) ppm; LCMS-ESI (POS), M/Z, M+1: Found 483.3.

Example 159

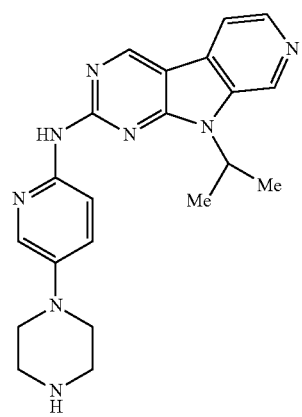

206

9-(1-methylethyl)-N-(5-(1-piperazinyl)-2-pyridinyl)-9H-pyrido[4',3':4,5]pyrrolo[2,3-d]pyrimidin-2-amine Compound 206 was prepared using chemistry similar to that described in example 1. $^1$H NMR (500 MHz, DMSO-d$_6$) δ 9.71 (1 H, s), 9.54 (3 H, br. s.), 8.76 (1 H, d, J=6.1 Hz), 8.72 (1 H, d, J=6.1 Hz), 8.14 (1 H, d, J=2.7 Hz), 8.03 (1 H, d, J=9.3 Hz), 7.93 (1 H, d, J=9.3 Hz), 5.35 (1 H, dt, J=13.9, 6.9 Hz), 3.45-3.51 (4 H, m), 3.22-3.28 (4 H, m), 1.72 (6 H, d, J=7.1 Hz) ppm; LCMS-ESI (POS), M/Z, M+1: Found 389.2.

Example 160

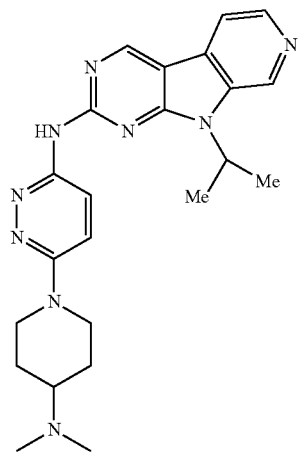

207

N-(6-(4-(Dimethylamino)-1-piperidinyl)-3-pyridazinyl)-9-(1-methylethyl)-9H-pyrido[4',3':4,5]pyrrolo[2,3-d]pyrimidin-2-amine Compound 207 was prepared using chemistry similar to that described in example 1. NMR (500 MHz, DMSO-d$_6$) δ 10.18 (1 H, s), 9.26 (1 H, s), 9.09 (1 H, s), 8.44 (1 H, d, J=5.1 Hz), 8.22 (1 H, d, J=9.5 Hz), 8.04 (1 H, d, J=5.1 Hz), 7.44 (1 H, d, J=9.8 Hz), 5.24 (1 H, dt, J=13.7, 6.8 Hz), 4.30 (2 H, d, J=12.5 Hz), 2.88 (2 H, t, J=11.9 Hz), 2.33-2.44 (1 H, m), 1.86 (2 H, d, J=10.0 Hz), 1.66 (6 H, d, J=6.8 Hz), 1.36-1.49 (2 H, m) ppm; LCMS-ESI (POS), M/Z, M+1: Found 432.2.

Example 161

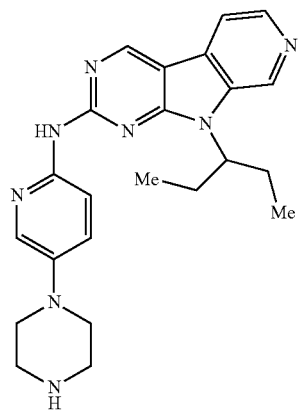

208

9-(1-Ethylpropyl)-N-(5-(1-piperazinyl)-2-pyridinyl)-9H-pyrido[4',3':4,5]pyrrolo[2,3-d]pyrimidin-2-amine Compound 208 was prepared using chemistry similar to that described in example 1. $^1$H NMR (500 MHz, DMSO-d$_6$)

δ 11.28 (1 H, br. s.), 9.73 (1 H, s), 9.58 (1 H, s), 9.52 (2 H, br. s.), 8.78 (1 H, d, J=5.9 Hz), 8.73 (1 H, d, J=6.1 Hz), 8.14 (1 H, d, J=2.7 Hz), 8.02 (1 H, br. s.), 7.92 (1 H, br. s.), 4.83-4.95 (1 H, m), 3.45-3.52 (4 H, m), 3.18-3.30 (4 H, m), 2.28-2.42 (2 H, m), 2.00-2.13 (2 H, m), 0.72 (6 H, t, J=7.3 Hz) ppm; LCMS-ESI (POS), M/Z, M+1: Found 417.3.

Example 162

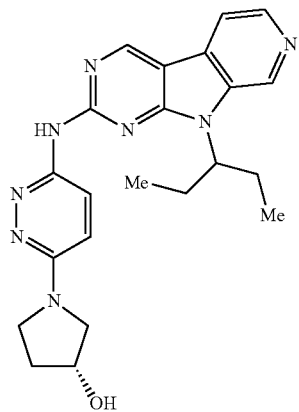

209

(3R)-1-(6-((9-(1-Ethylpropyl)-9H-pyrido[4',3':4,5]pyrrolo[2,3-d]pyrimidin-2-yl)-amino)-3-pyridazinyl)-3-pyrrolidinol Compound 209 was prepared using chemistry similar to that described in example 18. ¹H NMR (500 MHz, DMSO-d₆) δ 11.44 (1 H, br. s.), 9.75 (1 H, s), 9.62 (1 H, s), 8.78 (1 H, d, J=6.2 Hz), 8.73 (1 H, d, J=6.1 Hz), 8.48 (1 H, d, J=10.0 Hz), 7.92 (1 H, d, J=10.0 Hz), 4.82-4.91 (1 H, m), 4.47-4.56 (1 H, m), 3.65-3.84 (3 H, m), 3.57-3.64 (1 H, m), 2.25-2.41 (2 H, m), 1.92-2.17 (4 H, m), 0.70 (6 H, t, J=14.6 Hz) ppm; LCMS-ESI (POS), M/Z, M+1: Found 419.2.

Example 163

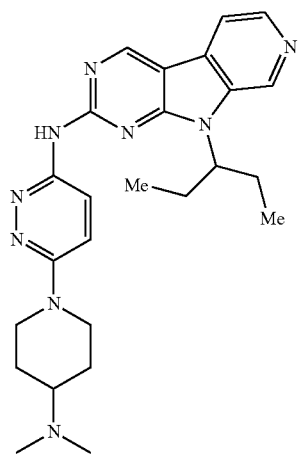

210

N-(6-(4-(Dimethylamino)-1-piperidinyl)-3-pyridazinyl)-9-(1-ethylpropyl)-9H-pyrido[4',3':4,5]pyrrolo[2,3-d]pyrimidin-2-amine Compound 210 was prepared using chemistry similar to that described in example 1. ¹H NMR (500 MHz, DMSO-d₆) δ 10.18 (1 H, br. s.), 9.28 (1 H, s), 9.06 (1 H, s), 8.44 (1 H, d, J=5.1 Hz), 8.20 (1 H, d, J=9.8 Hz), 8.05 (1 H, d, J=5.1 Hz), 7.45 (1 H, d, J=9.8 Hz), 4.75 (1 H, br. s.), 4.29 (2 H, d, J=13.0 Hz), 2.88 (2 H, t, J=11.6 Hz), 2.25-2.37 (3 H, m), 2.19 (6 H, s), 1.93-2.03 (2 H, m), 1.81-1.88 (2 H, m), 1.36-1.47 (2 H, m), 0.67 (6 H, t, J=7.3 Hz) ppm; LCMS-ESI (POS), M/Z, M+1: Found 460.3.

Example 164

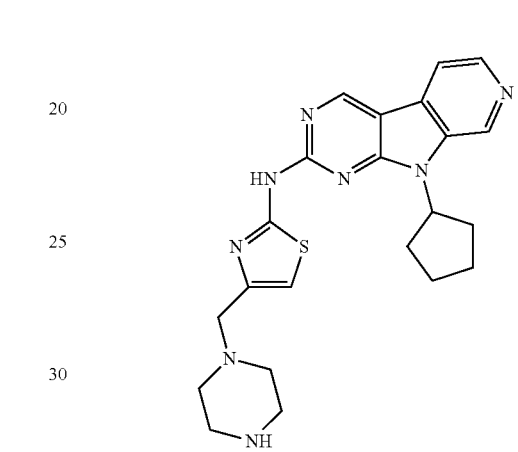

211

9-Cyclopentyl-N-(4-(1-piperazinylmethyl)-1,3-thiazol-2-yl)-9H-pyrido-[4',3':4,5]pyrrolo[2,3-d]pyrimidin-2-amine Compound 211 was prepared using chemistry similar to that described in example 1. ¹H NMR (500 MHz, DMSO-d₆) δ 12.47 (1 H, br. s.), 9.71 (1 H, s), 9.44 (1 H, s), 9.02 (2 H, br. s.), 8.73 (1 H, d, J=6.1 Hz), 8.65 (1 H, d, J=6.1 Hz), 7.41 (1 H, s), 5.39-5.53 (1 H, m), 4.15 (2 H, s), 3.30 (4 H, br. s.), 3.17 (4 H, br. s., J=7.6 Hz), 2.53-2.62 (2 H, m), 2.08-2.20 (4 H, m), 1.77-1.89 (2 H, m) ppm; LCMS-ESI (POS), M/Z, M+1: Found 435.2.

Example 165

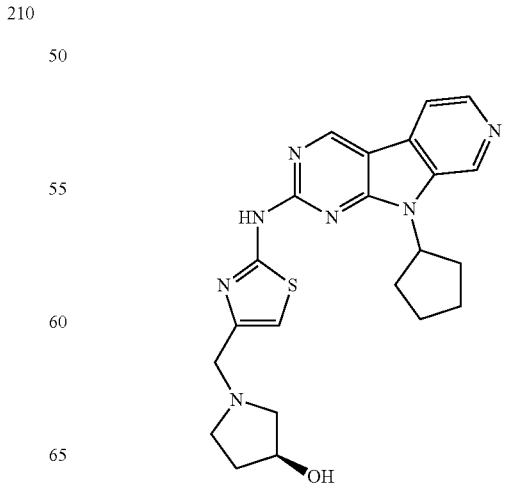

212

(3S)-1-((2-((9-Cyclopentyl-9H-pyrido[4',3':4,5]pyr-rolo[2,3-d]pyrimidin-2-yl)amino)-1,3-thiazol-4-yl)methyl)-3-pyrrolidinol Compound 212 was prepared using chemistry similar to that described in example 18. $^1$H NMR (500 MHz, MeOD-$d_3$) δ 9.28 (1 H, br. s.), 8.94 (1 H, br. s.), 8.43 (1 H, br. s.), 8.09 (1 H, br. s.), 6.94 (1 H, br. s.), 5.49-5.62 (1 H, m), 4.34-4.44 (1 H, m), 3.67-3.83 (2 H, m), 2.93-3.01 (1 H, m), 2.83-2.91 (1 H, m), 2.68-2.77 (1 H, m), 2.60-2.66 (1 H, m), 2.48-2.57 (2 H, m), 2.08-2.27 (5 H, m), 1.88-2.00 (2 H, m), 1.76 (1 H, br. s.) ppm; LCMS-ESI (POS), M/Z, M+1: Found 436.1.

Example 166

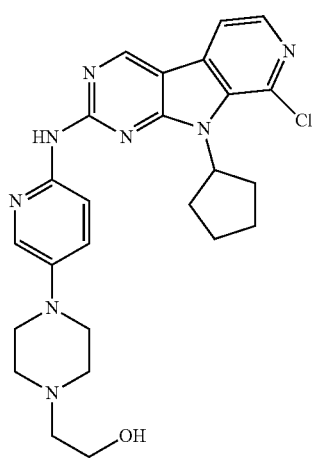

213

2-(4-(6-((8-Chloro-9-cyclopentyl-9H-pyrido[4',3':4,5]pyrrolo[2,3-d]pyrimidin-2-yl)amino)-3-pyridinyl)-1-piperazinyl)ethanol

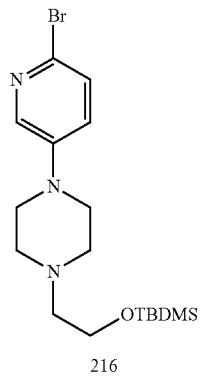

216

1-(6-Bromo-3-pyridinyl)-4-(2-((tert-butyl(dimethyl)silyl)oxy)ethyl)piperazine (216); 2-Bromo-5-iodopyridine (0.383 g, 1.35 mmol), compound 246 (see example 170) (0.330 g, 1.35 mmol), and sodium 2-methylpropan-2-olate (0.195 g, 2.02 mmol) were combined in 10 mL of anhydrous toluene. $N_2$ was bubbled briefly through the solution before adding Pd$_2$(dba)3 (0.0309 g, 0.0337 mmol) and 4,5-bis(diphenylphosphino)-9,9-dimethyl-9H-xanthene (0.0391 g, 0.0675 mmol). The solution was then stirred at room temperature overnight. After 17 hours, more 2-bromo-5-iodopyridine (0.383 g, 1.35 mmol), Pd$_2$(dab)$_3$ (0.0309 g, 0.0337 mmol), 4,5-bis(diphenylphosphino)-9,9-dimethyl-9H-xanthene (0.0391 g, 0.0675 mmol) and sodium 2-methylpropan-2-olate (0.195 g, 2.02 mmol) were added. The solution was stirred at room temperature for 48 hours. NH$_4$Cl (300 mg) was added and the solution was stirred at room temperature for 10 min. The product was purified on CombiFlash column (dry loaded), eluting with a gradient of 20% ethyl acetate/hexane to ethyl acetate. The fractions containing the product were combined and concentrated under vacuum to give compound 216 (100 mg, 19%) as a tan colored solid. $^1$H NMR (500 MHz, CDCl$_3$) δ ppm 8.01 (1 H, d, J=3.2 Hz), 7.29 (1 H, d, J=8.8 Hz), 7.07 (1 H, dd, J=8.8, 3.2 Hz), 3.79 (2 H, t, J=6.1 Hz), 3.15-3.24 (4 H, m), 2.67-2.75 (4 H, m), 2.60 (2 H, t, J=6.1 Hz), 0.90 (9 H, s), 0.07 (6 H, s) ppm; LCMS-ESI (POS), M/Z, M+1: Found 400.1.

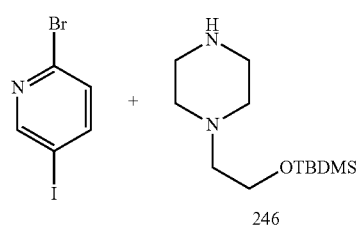

246

XantPhos, Pd$_2$(dba)$_3$
t-BuONa, toluene

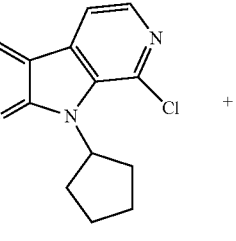

194

187
-continued

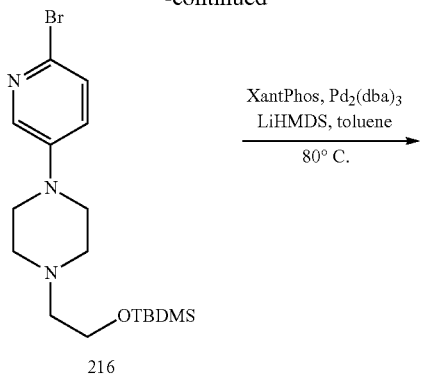

216

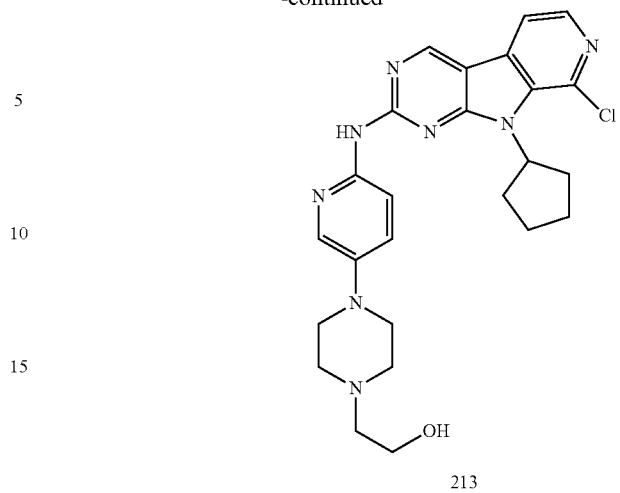

213

2-(4-(6-((8-Chloro-9-cyclopentyl-9H-pyrido[4',3':4,5] pyrrolo[2,3-d]pyrimidin-2-yl)amino)-3-pyridinyl)-1-piperazinyl)ethanol (213): Compound 217 (0.094 g, 0.15 mmol) was combined with 10 mL of methanol and 4 mL of 1N HCl. The solution was stirred at room temperature overnight. The solution was concentrated under vacuum and the residue obtained was purified on CombiFlash column (dry loaded), eluting with a gradient of 2% methanol/0.1% NH$_4$OH (~28% in water)/DCM to 10% methanol/0.5% NH$_4$OH (~28% in water)/DCM. The fractions containing the product were combined and concentrated under vacuum to give a yellow solid. The solid was partially dissolved in methanol and then collected on filter paper. Washed the solid off of the filter paper with DCM/methanol through a fritted funnel and then concentrated under vacuum to give compound 213 (0.065 g, 85% yield) as a yellow solid. $^1$H-NMR (500 MHz, DMSO-d$_6$) δ 9.92 (1 H, s), 9.33 (1 H, s), 8.22 (1 H, d, J=5.1 Hz), 8.10 (1 H, d, J=4.9 Hz), 8.04 (1 H, d, J=2.9 Hz), 8.02 (1 H, d, J=9.0 Hz), 7.46 (1 H, dd, J=9.0, 2.9 Hz), 5.95-6.05 (1 H, m), 4.43 (1 H, t, J=5.4 Hz), 3.54 (2 H, q, J=6.1 Hz), 3.12-3.19 (4 H, m), 2.55-2.65 (6 H, m), 2.45 (2 H, t, J=6.4 Hz), 1.98-2.08 (4 H, m), 1.65-1.75 (2 H, m) ppm; LCMS-ESI (POS), M/Z, M+1: Found 493.1.

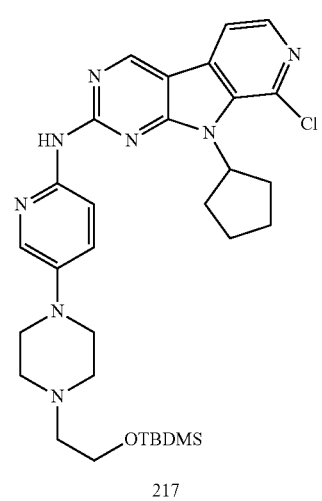

217

N-(5-(4-(2-((tert-Butyl(dimethyl)silyl)oxy)ethyl)-1-piperazinyl)-2-pyridinyl)-8-chloro-9-cyclopentyl-9H-pyrido[4',3':4,5]pyrrolo[2,3-d]pyrimidin-2-amine (217): Compound 217 was prepared from compounds 194 and 216 using methods described in example 152. LCMS-ESI (POS), M/Z, M+1: Found 607.4.

Example 167

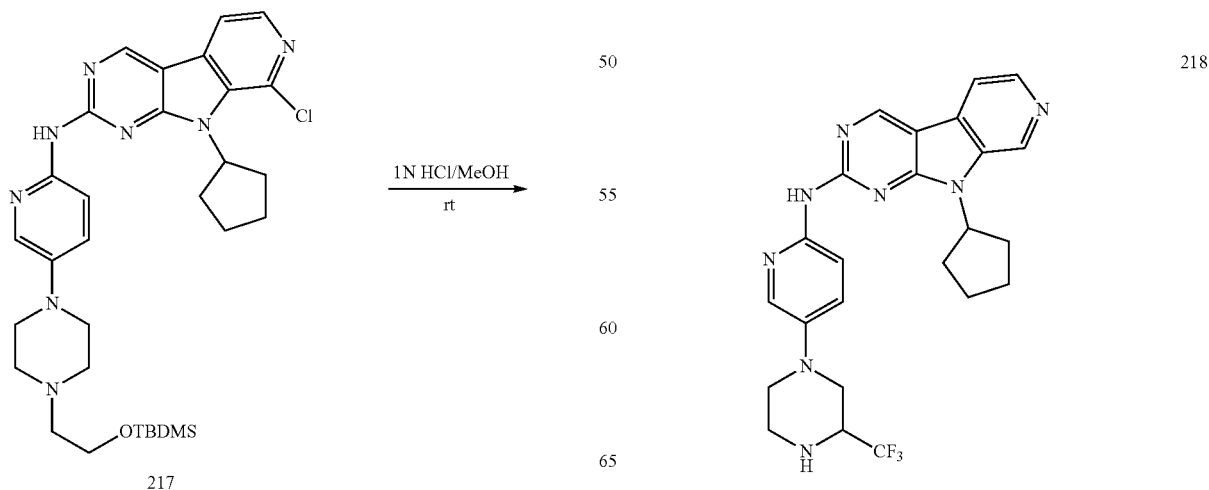

189

4-(6-((9-Cyclopentyl-9H-pyrido[4',3':4,5]pyrrolo[2,3-d]pyrimidin-2-yl)amino)-3-pyridinyl)-3-(trifluoromethyl)piperazine

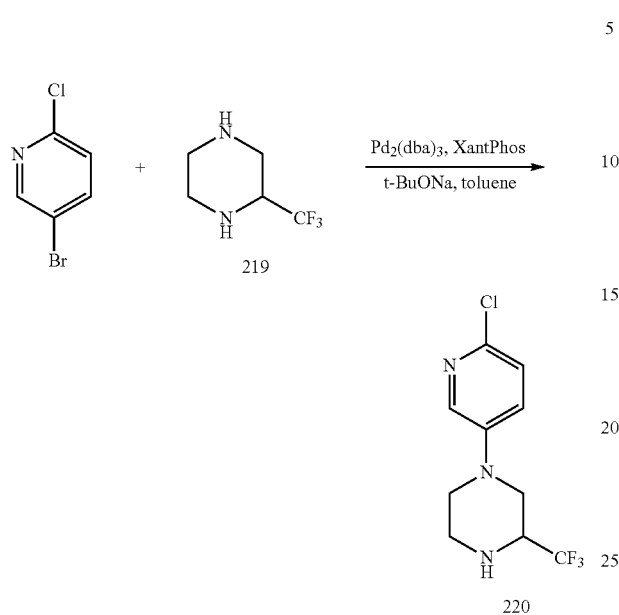

219

1-(6-Chloropyridin-3-yl)-3-(trifluoromethyl)piperazine (220): Compound 220 was prepared using methods described in example 1 using compound 219. $^1$H NMR (500 MHz, CDCl$_3$) δ 7.97 (s, 1 H) 7.09-7.18 (m, 2 H) 3.52-3.60 (m, 1 H) 3.34-3.48 (m, 2 H) 3.09-3.22 (m, J=11.98 Hz, 1 H) 2.91-3.01 (m, 1 H) 2.75-2.88 (m, 2 H) 1.84 (s, 1 H) ppm.

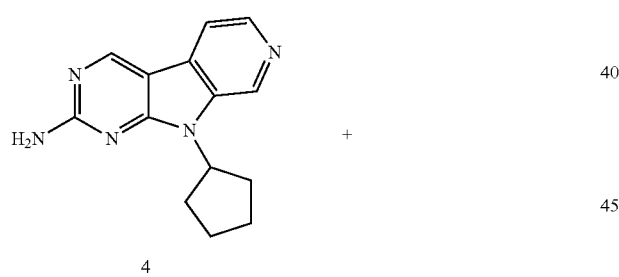

4

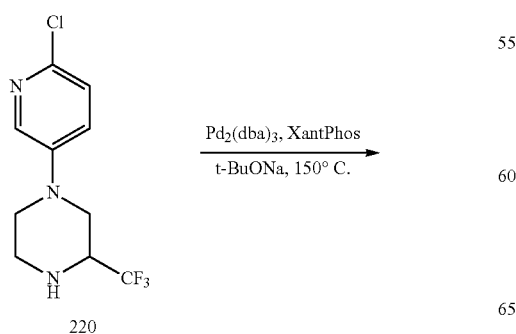

220

190

-continued

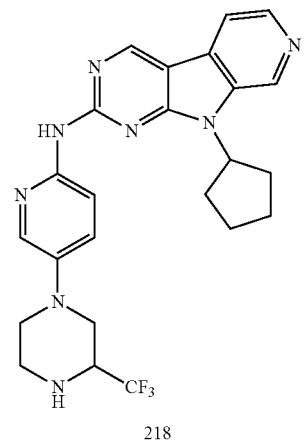

218

4-(6-((9-Cyclopentyl-9H-pyrido[4',3':4,5]pyrrolo[2,3-d]pyrimidin-2-yl)amino)-3-pyridinyl)-3-(trifluromethyl)piperazine (218): Compound 218 was prepared from compounds 4 and 220 using methods described in example 1. $^1$H NMR (500 MHz, DMSO-d$_6$) δ 9.84 (s, 1 H) 9.28 (s, 1 H) 9.00 (s, 1 H) 8.44 (d, J=4.89 Hz, 1 H) 8.21 (d, J=9.05 Hz, 1 H) 8.08 (d, J=2.93 Hz, 1 H) 8.04 (d, J=5.14 Hz, 1 H) 7.54 (dd, J=9.05, 2.93 Hz, 1 H) 5.29-5.47 (m, 1 H) 3.62 (d, J=11.25 Hz, 1 H) 3.49-3.59 (m, 1 H) 3.46 (d, J=11.49 Hz, 1 H) 2.98-3.10 (m, J=9.78 Hz, 1 H) 2.79-2.95 (m, 2 H) 2.65-2.79 (m, 2 H) 2.29-2.45 (m, 2 H) 1.95-2.18 (m, 4 H) 1.77 (d, J=5.38 Hz, 2 H) ppm.

Example 168

221

4-Cyclopentyl-N-(5-(1-piperazinyl)-2-pyridinyl)-4H-isothiazolo[5',4':4,5]pyrrolo[2,3-d]pyrimidin-6-amine

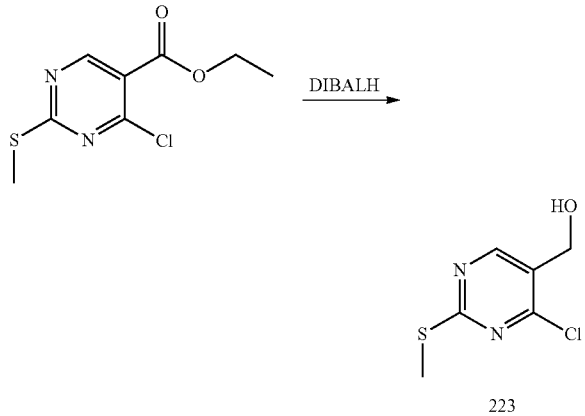

(4-Chloro-2-(methylthio)pyrimidin-5-yl)methanol (223): To ethyl 4-chloro-2-(methylthio)pyrimidine-5-carboxylate (20.0 g, 86 mmol) in dichloromethane (400 mL) at −78° C. was added diisobutylaluminum hydride, 1.0 M in toluene (172 mL, 172 mmol). The reaction was allowed to warm to 0° C. over 2 h. To the reaction was added a 20% Rochelle's (1600 mL) and diethyl ether (750 mL). The emulsion was stirred for 30 min. The organics were sequestered and the aqueous was extracted further with diethyl ether (2×500 mL). The combined organics were washed with water (500 mL), brine (500 mL), dried over MgSO$_4$, and concentrated in vacuo and filtered through a plug of silica eluting with 1:1; ethyl acetate: CH$_2$Cl$_2$ to obtain compound 223 (9.6 g, 59% yield). $^1$H NMR (500 MHz, CDCl$_3$) δ 8.55 (s, 1 H) 4.75 (d, J=5.87 Hz, 2 H) 2.58 (s, 3 H) 2.06-2.25 (m, J=5.14 Hz, 1H) ppm.

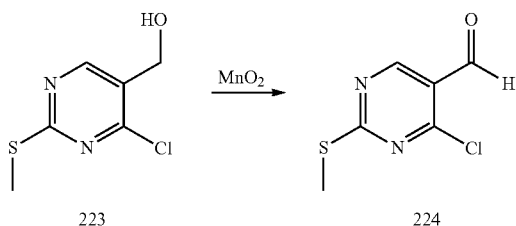

4-chloro-2-(methylthio)pyrimidine-5-carbaldehyde (224): Manganese(IV) oxide, <5 micron, activated (38.1 g, 439 mmol) was added to a solution of compound 223 (16.73 g, 87.8 mmol) in chloroform (800 mL). The reaction was stirred overnight, filtered through Celite, and the filtrate was concentrated in vacuo to yield compound 224 (13.7 g, 82.8% yield). $^1$H NMR (500 MHz, CDCl$_3$) δ 10.31 (s, 1 H) 8.88 (s, 1 H) 2.65 (s, 2 H) ppm.

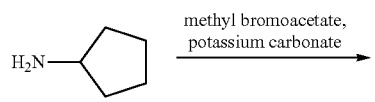

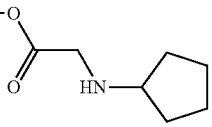

Methyl 2-(cyclopentylamino)acetate (225): A solution of methyl bromoacetate (17.4 mL, 188 mmol) in THF (40 mL) was dropwise added to a solution of cyclopentylamine (18.6 mL, 188 mmol) and triethylamine (26.1 mL, 188 mmol) in THF (150 mL) at 0° C. Following addition, the reaction was allowed to reach room temperature and was stirred overnight. The triethylammonium salts were filtered and rinsed with scant THF. The combined filtrates were concentrated in vacuo. The desired product was distilled from the residuals under reduced pressure to yield 20.2 g of compound 225 (68% yield). $^1$H NMR (500 MHz, CDCl$_3$) δ ppm 3.73 (s, 3 H) 3.41 (s, 2 H) 3.00-3.13 (m, J=12.90, 6.39, 6.39 Hz, 1 H) 1.77-1.87 (m, 2 H), 1.67-1.74 (m, 2 H) 1.48-1.59 (m, 2 H) 1.29-1.41 (m, 2 H) ppm.

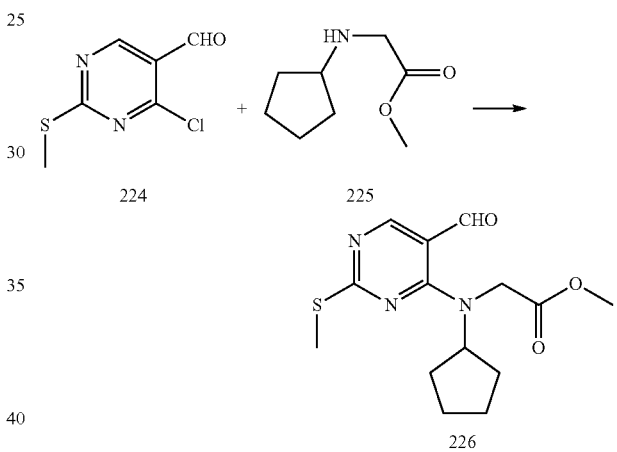

Methyl 2-(cyclopentyl(5-formyl-2-(methylthio)pyrimidin-4-yl)amino)acetate (226): Triethylamine (10.9 mL, 78.2 mmol) was added to a solution of compound 224 (12.3 g, 65.2 mmol) and compound 225 (12.8 g, 81.5 mmol) in THF (200 mL). The reaction was stirred at room temperature. After 6 h, the reaction contents were poured into saturated sodium bicarbonate and extracted with ethyl acetate. The combined organics were dried over MgSO$_4$ and concentrated in vacuo. The crude material was crystallized from ethyl acetate and hexanes to afford methyl 2-(cyclopentyl(5-formyl-2-(methylthio)pyrimidin-4-yl)amino)acetate (226) (17.55 g, 87.0% yield).

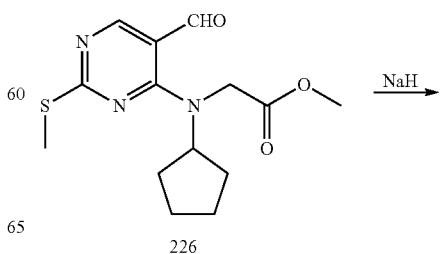

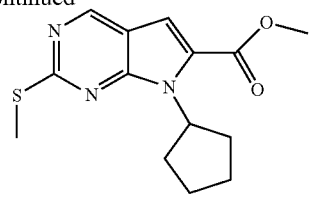
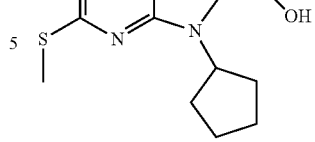

227

228

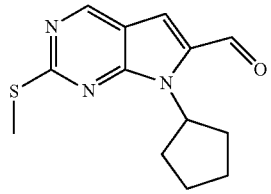

229

Methyl 7-cyclopentyl-2-(methylthio)-7H-pyrrolo[2,3-d]pyrimidine-6-carboxylate (227): Sodium hydride (3.85 g, 167 mmol) (freshly washed with hexane) was added to a solution of compound 226 (12.95 g, 41.9 mmol) in benzene (150 mL). The reaction was stirred at 70° C. After 1 h, the reaction contents were poured into water (300 mL) and extracted with ethyl acetate (2×100 mL). The combined organics were washed with brine, dried over MgSO$_4$, and concentrated in vacuo. Silica gel chromatography (gradient elution 0 to 50% ethyl acetate in hexanes) afforded compound 227 (4.24 g, 34.8% yield).

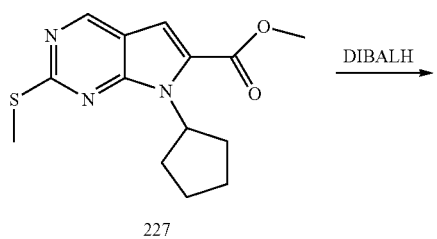

227

7-Cyclopentyl-2-(methylthio)-7H-pyrrolo[2,3-d]pyrimidine-6-carbaldehyde (229): Manganese dioxide (5.56 g, 64.0 mmol) was added to a solution of compound 228 (3.37 g, 12.8 mmol) in dichloromethane (250 mL). After 16 h, the reaction contents were filtered through Celite and organics were removed in vacuo to provide compound 229 (3.10 g, 92.7% yield).

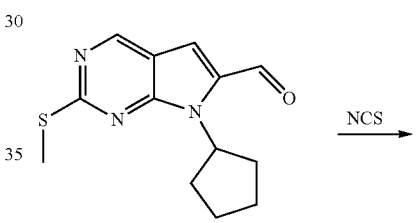

229

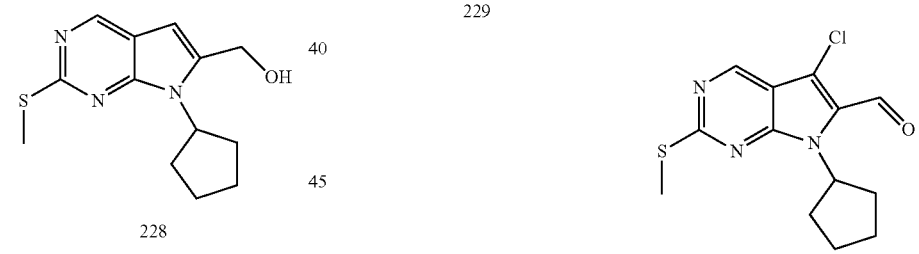

228

230

(7-Cyclopentyl-2-(methylthio)-7H-pyrrolo[2,3-d]pyrimidin-6-yl)methanol (228): DIBAL-H (1.0 M in toluene) (33.8 mL, 33.8 mmol) was added dropwise to a solution of compound 227 (4.93 g, 16.9 mmol) in dichloromethane (85 mL) at −78° C. The reaction was stirred for 20 minutes, then warmed to 0° C. and quenched with 400 mL of 0.5 M Rochelle's salt saturated with NaCl. The mixture was stirred for 3 h then extracted with ethyl acetate (4×250 mL). The combined organics were washed with brine, dried over MgSO$_4$, and concentrated in vacuo to provide 4.36 g of crude. The crude material was taken up in dichloromethane and methanol, plated onto silica gel, and flashed through a plug of silica using 30% ethyl acetate in hexanes, then switching to 10% methanol in DCM to provide compound 228 (3.37 g, 75.6% yield). $^1$H NMR (500 MHz, CDCl$_3$) δ 8.60 (s, 1H) 6.29 (s, 1H) 4.83-4.95 (m, J=17.30, 8.59, 8.59 Hz, 1 H) 4.79 (d, J=5.87 Hz, 2 H) 2.62 (s, 3 H) 2.47-2.58 (m, 2 H) 1.97-2.15 (m, 5 H) 1.67-1.81 (m, 2 H) ppm.

5-Chloro-7-cyclopentyl-2-(methylthio)-7H-pyrrolo[2,3-d]pyrimidine-6-carbaldehyde (230): Compound 229 (3.10 g, 11.9 mmol) and N-chlorosuccinimide (1.74 g, 13.0 mmol) were dissolved in DMF (30 mL) and stirred at 100° C. After 1 h, the temperature of the reaction was reduced to 65° C. and 0.35 eq of NCS were added. After 30 min, the reaction contents were poured into water (10×) and saturated bicarbonate was added (300 mL). The aqueous layer was extracted with dichloromethane (3×100 mL). The combined organics were dried with sodium sulfate and concentrated in vacuo. Silica gel chromatography (gradient elution 0 to 7% ethyl acetate in hexanes) afforded 5-chloro-7-cyclopentyl-2-(methylthio)-7H-pyrrolo[2,3-d]pyrimidine-6-carbaldehyde (230) (1.37 g, 39% yield). $^1$H NMR (500 MHz, CDCl$_3$) δ ppm 10.17 (s, 1 H) 8.91 (s, 1 H) 5.73-5.96 (m, 1 H) 2.63 (s, 3 H) 2.29-2.47 (m, 2 H) 1.97-2.16 (m, 4 H) 1.63-1.83 (m, 2 H) ppm.

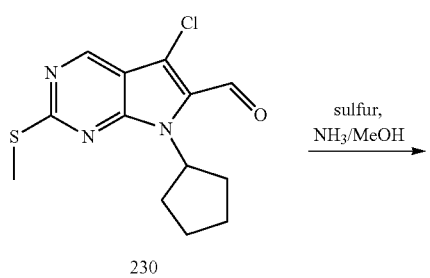

230

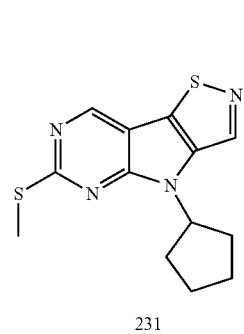

231

4-Cyclopentyl-6-(methylsulfanyl)-4H-isothiazolo[5',4':4,5]pyrrolo[2,3-d]pyrimidine (231): To sulfur (0.238 g, 0.926 mmol) and 5-chloro-7-cyclopentyl-2-(methylthio)-7H-pyrrolo[2,3-d]pyrimidine-6-carbaldehyde (1.37 g, 4.63 mmol) was added saturated methanolic ammonia (15 mL). The reaction was sealed and stirred at 80° C. overnight. The reaction was cooled to 0° C. and an aliquot was removed and partitioned between dichloromethane and saturated sodium bicarbonate. The organics were removed in vacuo and partitioned between dichloromethane (100 mL) and saturated sodium bicarbonate (200 mL). The aqueous was extracted further with dichloromethane (100 mL). The combined organics were dried with Na₂SO₄ and concentrated in vacuo. Silica gel chromatography (gradient elution 0 to 25% ethyl acetate in hexanes) afforded compound 231 (1.30 g, 96.6% yield). ¹H NMR (500 MHz, CDCl₃) δ 8.97 (s, 1 H) 8.62 (s, 1 H) 5.36-5.52 (m, 1 H) 2.69 (s, 3 H) 2.21-2.34 (m, 2 H) 1.97-2.18 (m, 4 H) 1.78-1.93 (m, 2 H) ppm.

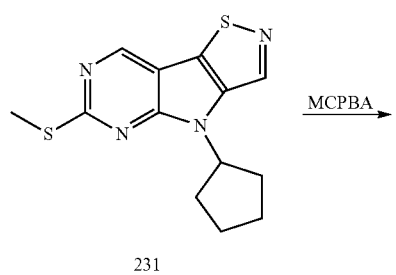

231

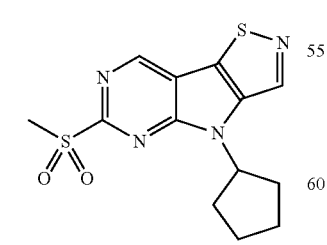

232

4-Cyclopentyl-6-(methylsulfonyl)-4H-isothiazolo[5',4':4,5]pyrrolo[2,3-d]pyrimidine (232): To reactant 231 (1.30 g, 4.48 mmol) in dichloromethane (25 mL) at 0° C. was added MCPBA (50%) (3.42 g, 9.85 mmol). The reaction was allowed to stir overnight while warming to room temperature. The reaction contents were poured into saturated sodium bicarbonate (150 mL) and extracted with dichloromethane (3×75 mL). Silica gel chromatography (gradient elution 20 to 60% ethyl acetate in hexanes) afforded compound 232 (1.30 g, 90.1% yield).

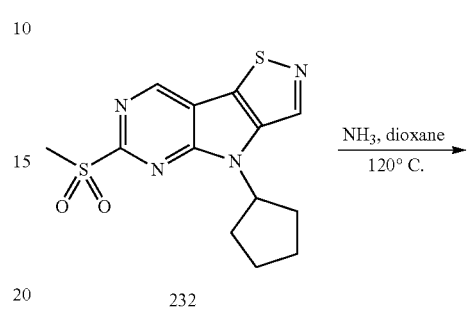

232

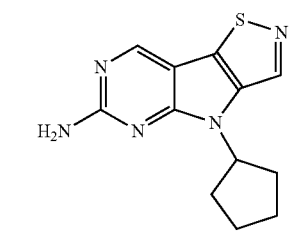

233

4-cyclopentyl-pyrimidino[4',5':2,3]4H-pyrrolo[2,3-d]isothiazole-6-amine (233): In a glass bomb, a solution of compound 232 (1.30 g, 4.06 mmol) in dioxane (35 mL) was saturated with ammonia gas. The bomb was sealed and the reaction was stirred at 120° C. After 16 h, LCMS indicated complete consumption of starting material. Solvent was removed in vacuo. Silica gel chromatography (gradient elution 20 to 50% THF in hexanes) afforded 430 mg of compound 233 (41% yield).

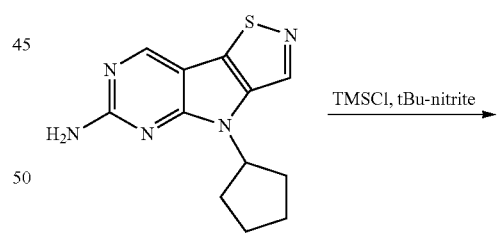

233

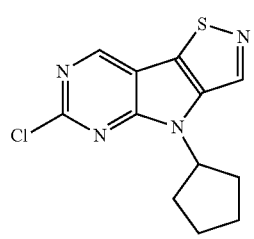

234

6-Chloro-4-cyclopentyl-pyrimidino[4',3':2,3]4H-pyrrolo[2,3-d]isothiazole (234): To a solution of compound 233

(0.100 g, 0.39 mmol) in dichloromethane (10 mL) at 0° C. was added dropwise trimethylsilyl chloride (0.15 mL, 1.2 mmol) followed by addition of tert-butyl nitrite (0.2 g, 1.9 mmol). The reaction was stirred at room temperature for 5 days. The reaction contents were poured into saturated sodium bicarbonate (20 mL). The aqueous layer was extracted with dichloromethane (1×20 mL). Silica gel chromatography (gradient elution 0 to 30% THF in hexanes) afforded compound 234 (0.025 g, 23% yield) which was carried on without further characterization.

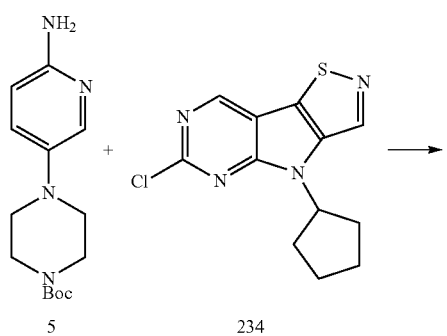

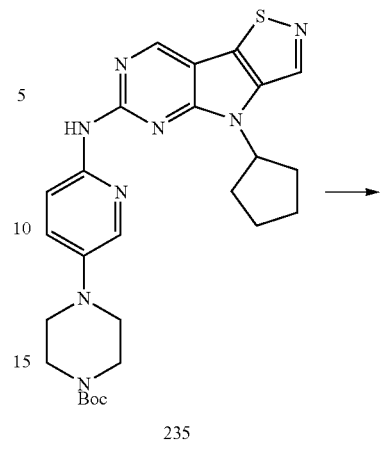

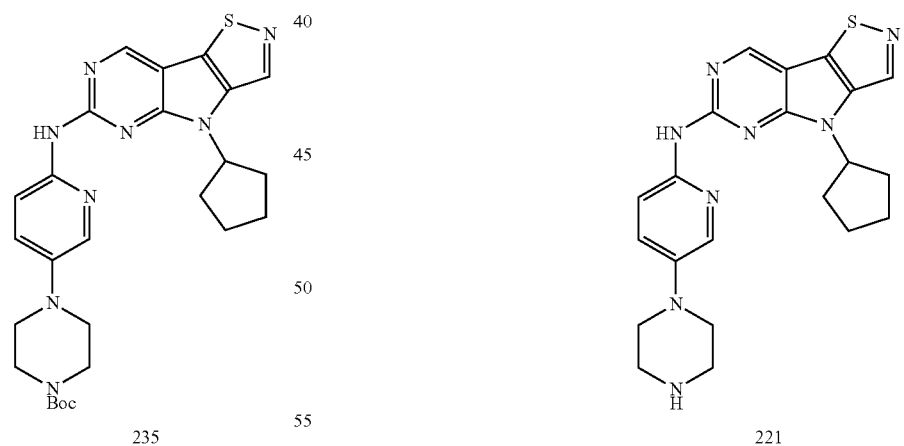

1,1-Dimethylethyl 4-(6-((4-cyclopentyl-4H-isothiazolo[5',4':4,5]pyrrolo[2,3-d]pyrimidin-6-yl)amino)-3-pyridinyl)-1-piperazinecarboxylate (235): In a screw cap vial were combined compound 5 (0.075 g, 0.27 mmol), compound 234 (0.025 g, 0.090 mmol) and DMSO (0.200 mL). The reaction was sealed and stirred at 100° C. over 4 d. DMSO was removed under high vacuum. Silica gel chromatography (gradient elution 0 to 10% methanol in DCM) afforded 15 mg of compound 235 (32% yield).

4-cyclopentyl-N-(5-(1-piperazinyl)-2-pyridinyl)-pyrimidino[4',3':2,3]4H-pyrrolo[2,3-d]isothiazole-6-amine (221): Compound 221 was prepared using methods described in Example 1. $^1$H NMR (500 MHz, CD$_3$OD) δ 9.57 (s, 1 H) 9.00 (s, 1 H) 8.13 (d, J=2.45 Hz, 1 H) 8.06 (dd, J=9.78, 2.69 Hz, 1 H) 7.24 (d, J=9.54 Hz, 1 H) 5.53 (quin, J=8.44 Hz, 1 H) 3.38-3.48 (m, 8 H) 2.21-2.40 (m, 4 H) 2.06-2.18 (m, 2 H) 1.83-1.95 (m, 2 H) ppm. LCMS-ESI (POS), M/Z, M+1: Found 421.0, Calculated 421.2.

Example 169

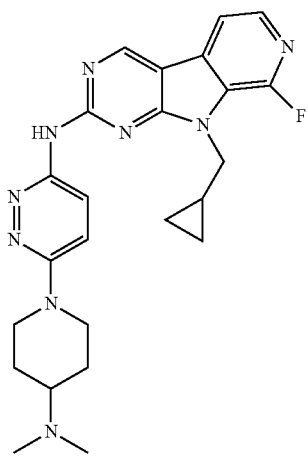

9-Cyclopentyl-8-fluoro-N-(6-(4-dimethylaminopiperidine-1-yl)-3-pyridazinyl)-9H-pyrido[4',3':4,5]-pyrrolo[2,3d]pyrimidin-2-amine

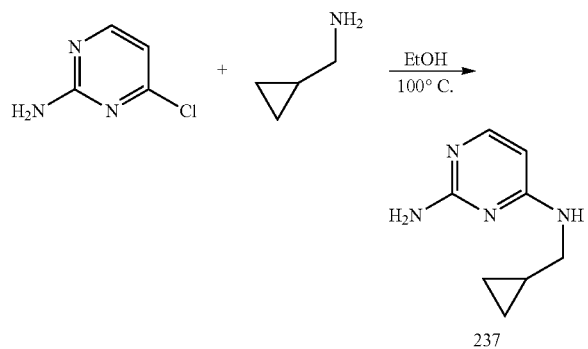

N4-(cyclopropylmethyl)pyrimidine-2,4-diamine (237): To cyclopropylmethanamine (3.62 g, 50.9 mmol) in ethanol (90 mL) was added solid 4-chloropyrimidin-2-amine (6.00 g, 46.3 mmol). The reaction was stirred at reflux (100° C. oil bath) for 16 h. The reaction was cooled to room temperature and solvent was removed in vacuo. The product 237 obtained in quantitative yield. LCMS-ESI (POS), M/Z, M+1: Found 165.0, Calculated 165.1.

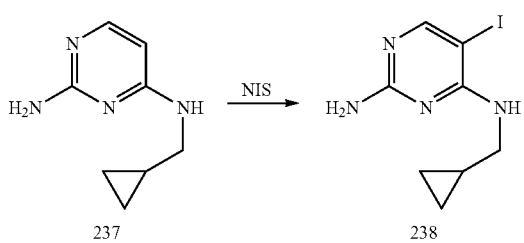

N4-(Cyclopropylmethyl)-5-iodopyrimidine-2,4-diamine (238): N-iodosuccinimide (11.5 g, 50.9 mmol) was added to a solution of compound 237 (7.60 g, 46.3 mmol) in AcOH (90 mL). The reaction was warmed to 80° C. and stirred for 1.5 h. Solvent was removed in vacuo. The residue was taken up in dichloromethane (200 mL) and water. The aqueous layer was brought to pH 12 with 5 N NaOH and organics were sequestered. The aqueous was extracted further with dichloromethane (2×100 mL). The combined organics were treated with solid sodium thiosulfate, dried with MgSO$_4$ and concentrated in vacuo. Silica gel chromatography (gradient elution 10 to 75% ethyl acetate in hexanes) afforded compound 238 (8.0 g, 60% yield).

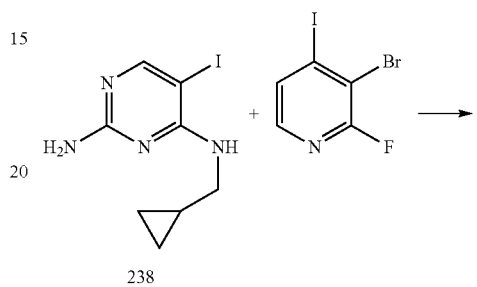

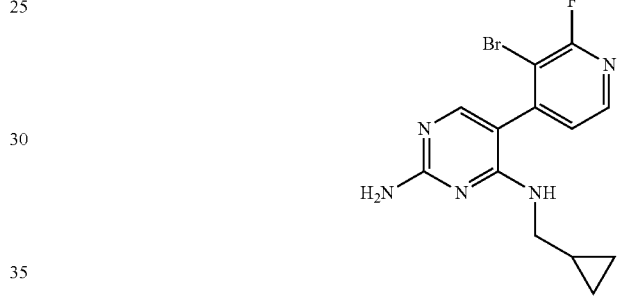

5-(3-Bromo-2-fluoropyridin-4-yl)-N4-(cyclopropylmethyl)pyrimidine-2,4-diamine (240): Isopropylmagnesium chloride, 2 M solution in THF (0.814 mL, 1.63 mmol) was added dropwise over 15 minutes to a degassed solution of 3-bromo-2-fluoro-4-iodopyridine (0.468 g, 1.55 mmol) in Et$_2$O (0.150 mL) and THF (0.850) cooled at −78° C. The solution was stirred for 0.5 h. Zinc chloride, 1.0 M solution in diethyl ether (0.776 mL, 0.776 mmol) was then added dropwise to the reaction over 10 minutes. The reaction was allowed to reach room temperature. The reaction warmed to room temperature within 15 min. A solution of compound 238 (0.150 g, 0.517 mmol) and tetrakis(triphenylphosphine) palladium (0.0418 g, 0.0362 mmol) in THF (0.50 mL) was added to the reaction. The reaction was equipped with a reflux condenser and stirred in a 60° C. oil bath. After 2 h the reaction was removed from heat and allowed to stand overnight. Saturated NH$_4$Cl (0.5 mL) and 12% 2-propanol in CH$_2$Cl$_2$ (2 mL) were added. The organics were sequestered and the aqueous was extracted with 12% 2-propanol in CH$_2$Cl$_2$ (4×4 mL). The combined organics were washed with brine, dried over MgSO$_4$, and concentrated in vacuo. Silica gel chromatography (elution 3% methanol in DCM with 0.175% NH$_4$OH additive) afforded compound 240 (0.140 g, 80.1% yield). $^1$H NMR (500 MHz, CDCl$_3$) δ ppm 0.22 (d, J=4.40 Hz, 2 H) 0.46-0.59 (m, 2H) 0.96-1.07 (m, 1H) 3.21-3.36 (m, 2 H) 4.51 (br. s., 1 H) 5.11 (br. s., 2 H) 7.16 (d, J=4.89 Hz, 1H) 7.69 (s, 1 H) 8.22 (d, J=4.89 Hz, 1 H) ppm.

201

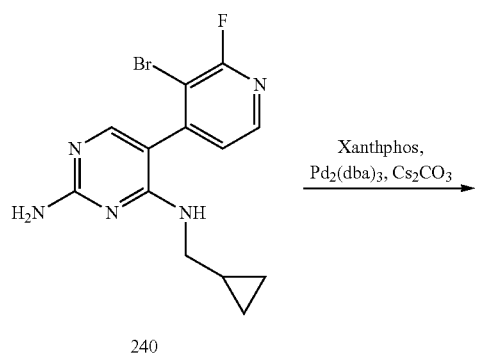

9-(Cyclopropylmethyl)-8-fluoro-9H-pyrido[4',3':4,5]pyrrolo[2,3-d]pyrimidin-2-amine (241): To a vacuum to argon purged vial containing 4,5-bis(diphenylphosphino)-9,9-dimethylxanthene (0.017 g, 0.030 mmol), tris(dibenzylideneacetone)dipalladium (0) (0.014 g, 0.015 mmol), cesium carbonate (0.19 g, 0.59 mmol) and compound 240 (0.100 g, 0.30 mmol) was added degassed dioxane (2.00 mL). The reaction was stirred at 100° C. After 4 h, the reaction was cooled and applied directly to silica. Silica gel chromatography (gradient elution 40 to 90% ethyl acetate in hexanes) afforded compound 241 (0.060 g, 79% yield). $^1$H NMR (500 MHz, CDCl$_3$) δ ppm 0.45-0.57 (m, 4 H) 1.34-1.47 (m, 1 H) 4.32 (d, J=7.09 Hz, 2 H) 5.46 (br. s., 2 H) 7.68 (dd, J=5.26, 2.81 Hz, 1 H) 8.02 (dd, J=5.13, 1.71 Hz, 1 H) 8.93 (s, 1 H).

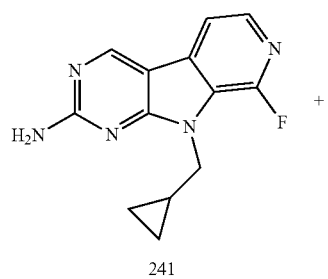

241

202

-continued

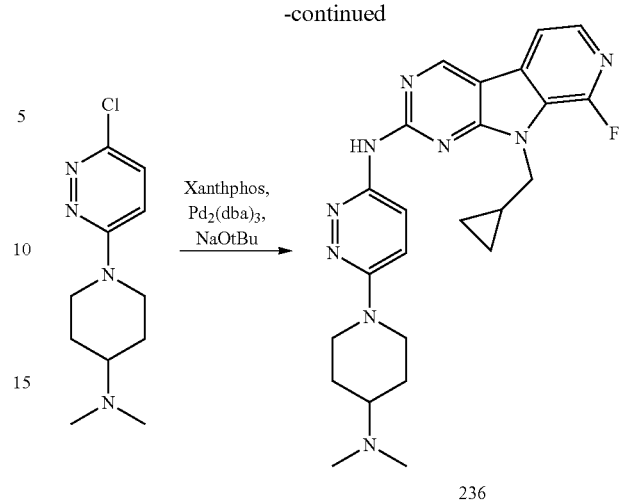

9-Cyclopentyl-8-fluoro-N-(6-(4-dimethylaminopiperidine-1-yl)-3-pyridazinyl)-9H-pyrido[4',3':4,5]-pyrrolo[2,3d]pyrimidin-2-amine (236): To tris(dibenzylideneacetone)dipalladium (0) (0.015 g, 0.016 mmol), Xantphos (0.019 g, 0.032 mmol), NaOtBu (0.025 g, 0.26 mmol), 1-(6-chloropyridazin-3-yl)-N,N-dimethylpiperidin-4-amine (0.051 g, 0.21 mmol), and compound 241 (0.0550 g, 0.21 mmol) was added degassed dioxane (1.0 mL). The reaction vessel was sealed and stirred at 105° C. After 13 h, the reaction contents were poured into saturated sodium bicarbonate (5 mL). The aqueous layer was extracted with 10% methanol in dichloromethane (3×10 mL). The combined organics were dried with sodium sulfate and concentrated in vacuo. Silica gel chromatography (0.175% NH$_4$OH 3% methanol in DCM to 100% 1% NH$_4$OH, 7% methanol, CH$_2$Cl$_2$) yielded compound 236 (0.038 g, 39% yield). $^1$H NMR (500 MHz, DMSO-d$_6$) δ 0.41-0.55 (m, 4 H) 1.29-1.50 (m, 3 H) 1.85 (d, J=11.98 Hz, 2 H) 2.20 (s, 6 H) 2.34 (tt, J=10.85, 3.58 Hz, 1 H) 2.90 (t, J=11.62 Hz, 2 H) 4.25-4.37 (m, 4 H) 7.44 (d, J=10.03 Hz, 1 H) 7.98-8.09 (m, 2 H) 8.24 (d, J=9.78 Hz, 1 H) 9.34 (s, 1 H) 10.35 (s, 1 H) ppm. LCMS-ESI (POS), M/Z, M+1: Found 462.0, Calculated 462.2.

Example 170

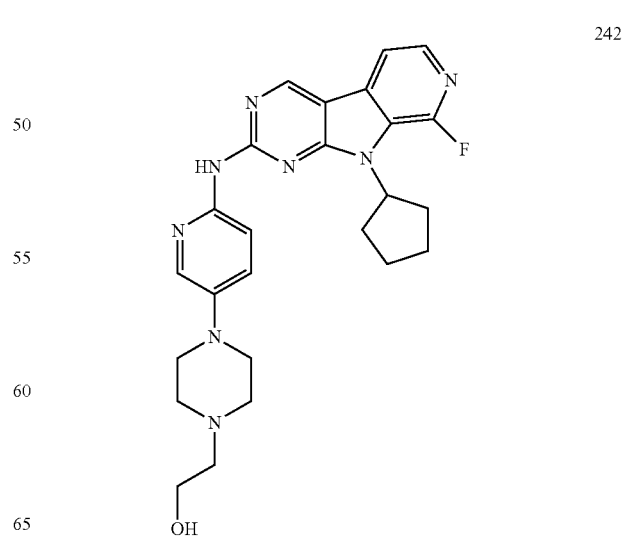

2-(4-(6-((9-Cyclopentyl-8-fluoro-9H-pyrido[4',3':4,5]pyrrolo[2,3-d]pyrimidin-2-yl)amino)-3-pyridinyl)-1-piperazinyl)ethanol

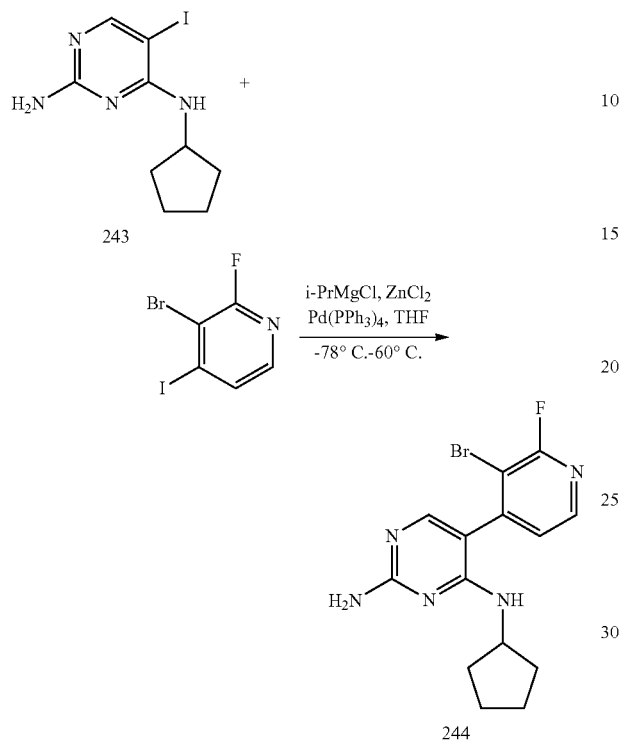

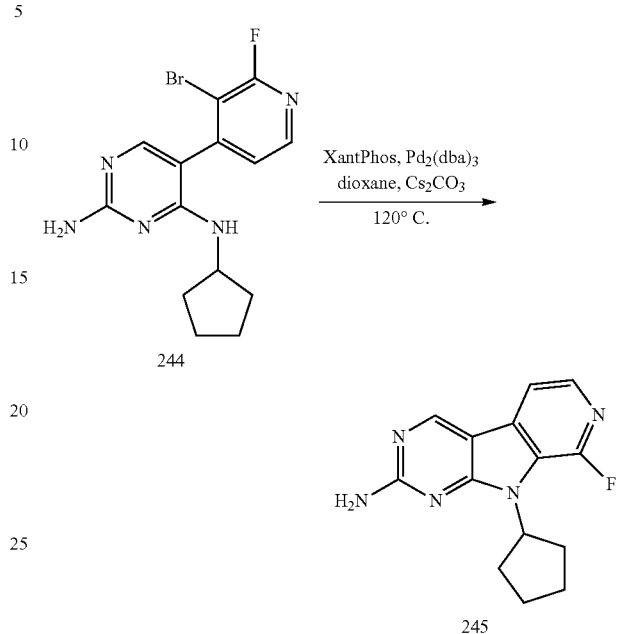

5-(3-Bromo-2-fluoro-4-pyridinyl)-N4-cyclopentyl-2,4-pyrimidinediamine (244): In a dry 3 neck 2 L flask equipped with a dry addition funnel, thermometer and stir bar was added 3-bromo-2-fluoro-4-iodopyridine (83.4 g, 276 mmol) followed by 300 mL of anhydrous THF under an atmosphere of nitrogen. The solution was cooled to −70° C. in 2-propanol/dry ice bath. A solution of isopropylmagnesium chloride 2.0 M in diethyl ether (145 mL, 290 mmol) was added drop wise over a period of 30 minutes. The solution was then stirred for 30 minutes before zinc (II) chloride 0.5 M in THF (276 mL, 138 mmol) was cannulated in. The solution was warmed to room temperature and stirred for 1 hour. The addition funnel was replaced with a reflux condenser and N4-cyclopentyl-5-iodopyrimidine-2,4-diamine (243, see example 200) (28.00 g, 92.1 mmol) was added, followed by Pd(PPh$_3$)$_4$ (5.32 g, 4.60 mmol). The solution was heated over night at a gentle reflux. After concentrating the solution to 1/10th of the volume under vacuum, it was cooled in an ice bath. To this was added 100 mL of cold saturated NH$_4$Cl, followed by 500 mL of water. 500 mL of 12% isopropanol/DCM was then added and the solution was stirred at room temperature for 1 hour before being filtered through filter paper. The filter cake was washed in succession with water, DCM and 12% 2-propanol/DCM. The filtrate was partitioned in a separation funnel and the aqueous layer was washed with 12% 2-propanol /DCM. The organics were dried over MgSO4 and then concentrated under vacuum. The residue obtained was partially dissolved in DCM with sonication and filtered off to give compound 244 (26.45 g, 81.6%) as a light yellow solid. $^1$H NMR (500 MHz, DMSO-d$_6$) δ ppm 8.18 (1 H, d, J=4.9 Hz), 7.52 (1 H, s), 7.26 (1 H, dd, J=4.9, 0.7 Hz), 6.34 (2 H, s), 6.12 (1 H, d, J=7.6 Hz), 4.42 (1 H, sxt, J=7.4 Hz), 1.76-1.96 (2 H, m), 1.55-1.68 (2 H, m), 1.31-1.53 (4 H, m)) ppm; LCMS-ESI (POS), M/Z, M+1: Found 352.0.

9-Cyclopentyl-8-fluoro-9H-pyrido[4',3':4,5]pyrrolo[2,3-d]pyrimidin-2-amine (245): Compound 244 (0.143 g, 0.41 mmol), and cesium carbonate (0.40 g, 1.2 mmol) were combined in 5 mL of anhydrous 1,4-dioxane. Nitrogen was bubbled through the solution briefly before adding Pd$_2$(dba)$_3$ (0.037 g, 0.041 mmol) and 4,5-bis(diphenylphosphino)-9,9-dimethyl-9H-xanthene (0.047 g, 0.081 mmol). The solution was heated at 120° C. with microwave irradiation for 1 hour. The solution was purified on CombiFlash column (dry loaded) eluting with a gradient of 2% methanol/0.1% NH$_4$OH (~28% in water)/DCM to 7% methanol/0.35% NH$_4$OH (~28% in water)/DCM. The fractions containing the pure product were combined and concentrated under vacuum to give compound 245 (94 mg, 85%) as a light brownish solid. $^1$H NMR (500 MHz, DMSO-d$_6$) δ 9.10 (1 H, s), 7.94 (1 H, dd, J=5.2, 1.5 Hz), 7.91 (1 H, dd, J=5.1, 2.9 Hz), 7.10 (2 H, br. s.), 5.38-5.49 (1 H, m), 2.10-2.23 (2 H, m), 1.93-2.08 (4 H, m), 1.64-1.79 (2 H, m) ppm; LCMS-ESI (POS), M/Z, M+1: Found 272.0.

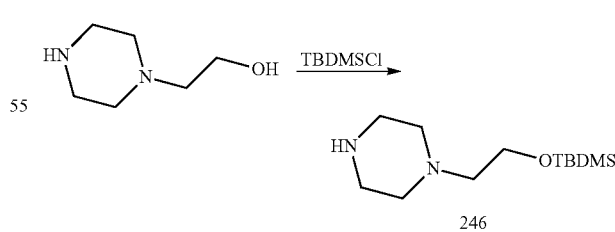

1-(2-(((1,1-Dimethylethyl) (dimethyl)silyl)oxy)ethyl)piperazine (246): To 1-(2-hydroxyethyl)-piperazine (3.36 g, 25.8 mmol) in dichloromethane (25 mL) was added tert-butyldimethylsilylchloride (3.89 g, 25.8 mmol). The reaction mixture was stirred at room temperature. The reaction mixture was stirred overnight, then diluted 1× with CH$_2$Cl$_2$ and extracted against 0.5 N NaOH (100 mL). The aqueous was extracted further with 10% methanol in $CH_2Cl_2$ (3×100 mL). The combined organics were dried with $Na_2SO_4$ and concentrated in vacuo. Silica gel chromatography (gradient elution 0 to 100% B (7% methanol in DCM+1% $NH_4OH$ additive) against A (3% methanol in DCM+0.175% $NH_4OH$ additive) afforded compound 246 (4.71 g, 74.7% yield). $^1$H NMR (500 MHz, $CDCl_3$) δ 0.06 (s, 6 H) 0.90 (s, 9 H) 2.36-2.59 (m, 6 H) 2.89 (t, J=4.77 Hz, 4 H) 3.76 (t, J=6.48 Hz, 2 H) ppm.

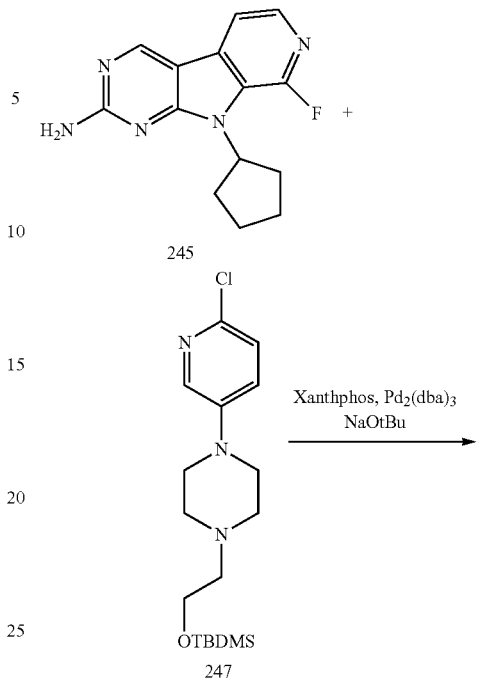

245

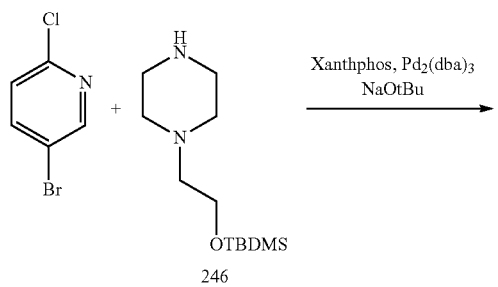

246

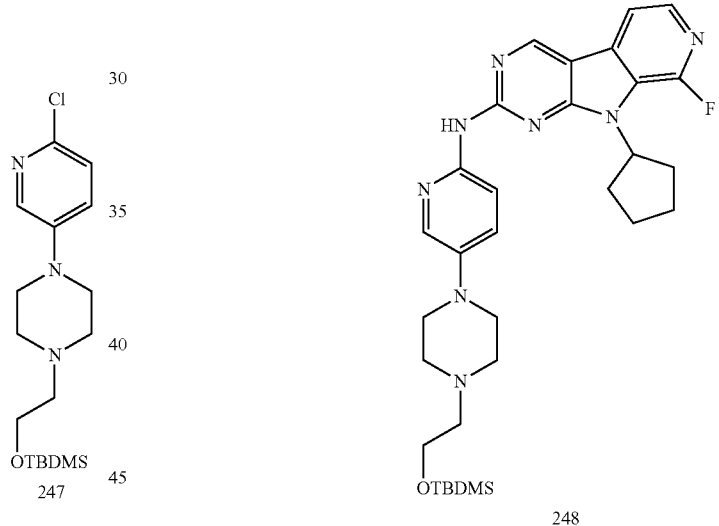

247

248

1-(6-chloro-3-pyridinyl)-4-(2-(((1,1-dimethylethyl)(dimethyl)silyl)oxy)ethyl)-piperazine (247): 5-Bromo-2-chloropyridine (3.15 g, 16.4 mmol), compound 246 (4.00 g, 16.4 mmol), $Pd_2(dba)_3$ (0.749 g, 0.818 mmol), 4,5-bis(diphenylphosphino)-9,9-dimethyl-9H-xanthene (0.947 g, 1.64 mmol) and sodium tert-butoxide (1.82 g, 19.0 mmol) were combined in a screw cap vial and solvated under argon atmosphere with degassed toluene (44 mL). The reaction was briefly sparged with argon, then sealed and stirred at 100° C. After 3 h, the reaction contents were poured into saturated sodium bicarbonate (100 mL) and extracted with 10% methanol in dichloromethane (3×200 mL). The combined organics were dried with sodium sulfate and concentrated in vacuo. Silica gel chromatography (gradient elution 0 to 100% ethyl acetate in hexanes switching to 3% methanol in DCM) afforded compound 247 (5.40 g, 92.7% yield). $^1$H NMR (500 MHz, $CDCl_3$) δ 0.08 (s, 6 H) 0.91 (s, 9 H) 2.60 (t, J=5.87 Hz, 2 H) 2.70 (br. s., 4 H) 3.20 (d, J=4.40 Hz, 4 H) 3.80 (t, J=6.11 Hz, 2 H) 7.17 (d, J=1.71 Hz, 2 H) 8.02 (s, 1 H) ppm.

9-Cyclopentyl-N-(5-(4-(2-(((1,1-dimethylethyl)(dimethyl)silyl)oxy)ethyl)-1-piperazinyl)-2-pyridinyl)-8-fluoro-9H-pyrido[4',3':4,5]pyrrolo[2,3-d]pyrimidin-2-amine (248): To tris(dibenzylideneacetone)dipalladium (0) (0.0289 g, 0.0316 mmol), xantphos (0.0366 g, 0.0632 mmol), NaOtBu (0.0486 g, 0.506 mmol), compound 247 (0.150 g, 0.421 mmol), and compound 245 (0.114 g, 0.421 mmol) was added degassed dioxane (2.0 mL). The reaction vessel was sealed and stirred at 105° C. overnight. The reaction was loaded directly to silica. Silica gel chromatography (gradient elution 1.5 to 5% 2 M methanolic $NH_3$ in DCM) afforded compound 248 (0.120 g, 48.2% yield). $^1$H NMR (400 MHz, $CDCl_3$) δ 0.09 (s, 6 H) 0.83-1.00 (m, 9 H) 1.75-1.90 (m, 2 H) 2.05-2.25 (m, 4 H) 2.36-2.53 (m, 2 H) 2.63 (br. s., 2 H) 2.75 (br. s., 4 H) 3.22 (br. s., 4 H) 3.82 (br. s., 2 H) 5.54 (quin, J=9.00 Hz, 1 H) 7.38 (dd, J=9.00, 2.74 Hz, 1 H) 7.72 (dd, J=5.09, 3.13 Hz, 1H) 8.00-8.04 (m, 1 H) 8.06 (d, J=2.74 Hz, 1 H) 8.10 (s, 1 H) 8.36 (d, J=9.00 Hz, 1 H) 9.08 (s, 1 H) ppm.

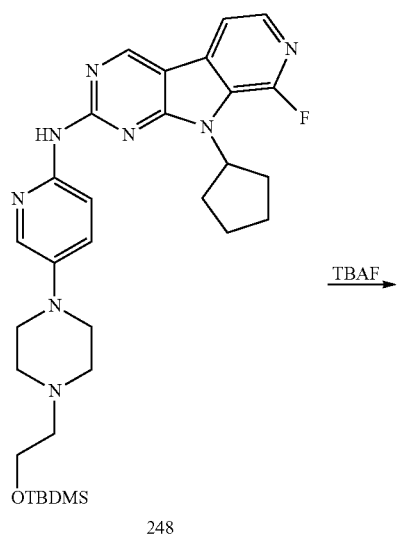

248

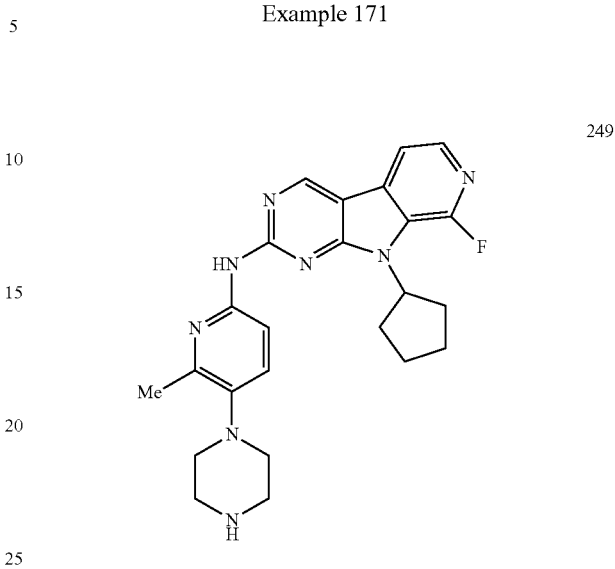

7.47 (dd, J=9.17, 2.81 Hz, 1H) 7.93-8.07 (m, 3 H) 8.11 (d, J=9.05 Hz, 1 H) 9.32 (s, 1 H) 9.89 (s, 1 H) ppm.

Example 171

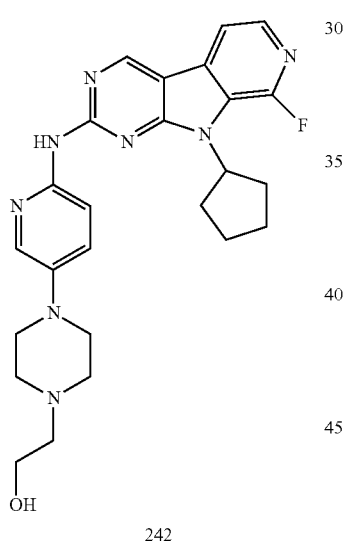

242

2-(4-(6-((9-Cyclopentyl-8-fluoro-9H-pyrido[4',3':4,5] pyrrolo[2,3-d]pyrimidin-2-yl)amino)-3-pyridinyl)-1-piperazinyl)ethanol (242): To compound 248 (0.115 g, 0.19 mmol) in THF (1.0 mL) was added tetrabutylammonium fluoride, 1.0 M in THF (0.49 mL, 0.49 mmol). The reaction was stirred at room temperature. After 1 h, the reaction contents were poured into water. The aqueous layer was brought to pH 12 with 5 N NaOH and extracted with 10% methanol in dichloromethane (3×25 mL). The combined organics were dried with Na$_2$SO$_4$ and concentrated in vacuo. Silica gel chromatography (gradient elution 3 to 7.5% 2M methanolic NH$_3$ in DCM) afforded compound 242 (0.070 g, 75% yield). $^1$H NMR (500 MHz, DMSO-d$_6$) δ 1.68-1.80 (m, 2 H) 1.92-2.05 (m, 2 H) 2.05-2.17 (m, 2 H) 2.25-2.40 (m, 2 H) 2.45 (t, J=6.11 Hz, 2H) 2.54-2.62 (m, 4 H) 3.00-3.27 (m, 4 H) 3.54 (q, J=5.95 Hz, 2 H) 4.43 (t, J=5.26 Hz, 1 H) 5.45 (quin, J=9.05 Hz, 1H)

9-Cyclopentyl-8-fluoro-N-(6-methyl-5-(1-piperazinyl)-2-pyridinyl)-9H-pyrido[4',3':4,5]pyrrolo[2,3-d] pyrimidin-2-amine Compound 249 was prepared using methods described in Example 170 and isolated as the HCl salt. $^1$H NMR (500 MHz, D$_2$O) δ ppm 8.97 (1 H, s), 8.03 (1 H, d, J=9.0 Hz), 7.87 (1 H, dd, J=5.1, 2.4 Hz), 7.79 (1 H, d, J=4.4 Hz), 7.12 (1 H, d, J=9.0 Hz), 5.35 (1 H, qd, J=8.7, 8.6 Hz), 3.47-3.55 (4 H, m), 3.23-3.32 (4 H, m), 2.65 (3 H, s), 2.17-2.28 (2 H, m), 1.97-2.17 (5 H, m), 1.73-1.87 (2 H, m) ppm; LCMS-ESI (POS), M/Z, M+1: Found 447.3.

Example 172

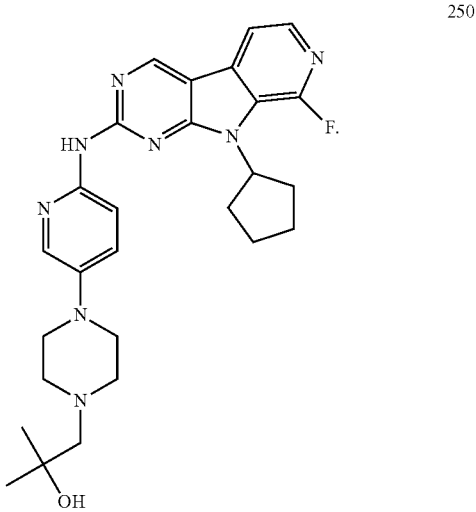 [SMILES: CC(C)(O)CN1CCN(c2ccc(Nc3ncc4c5ccnc(F)c5n(C5CCCC5)c4n3)nc2)CC1]

209

1-(4-(6-((9-Cyclopentyl-8-fluoro-9H-pyrido[4',3':4,5]pyrrolo[2,3-d]pyrimidin-2-yl)amino)-3-pyridinyl)-1-piperazinyl)-2-methyl-2-propanol

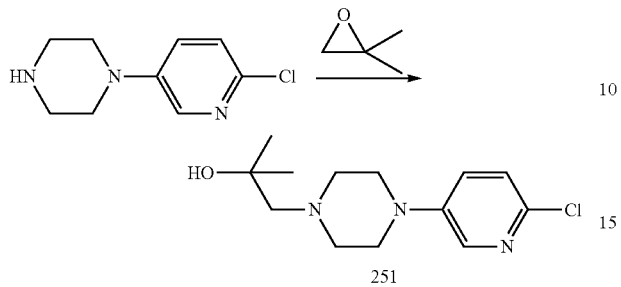

251

1-(4-(6-chloro-3-pyridinyl)-1-piperazinyl)-2-methyl-2-propanol (251): To 1-(6-chloropyridin-3-yl)piperazine (0.600 g, 3.04 mmol) in methanol (1.5 mL) was added dropwise isobutylene oxide (0.274 mL, 3.04 mmol). The reaction was left to stir at room temperature overnight. An additional 0.15 equivalents of isobutylene oxide were added and the reaction was placed in a 55° C. oil bath overnight. Solvent was removed in vacuo. Silica gel chromatography (gradient elution 2 to 10% methanol in DCM) afforded compound 251 (0.450 g, 55.0% yield). $^1$H NMR (400 MHz, CDCl$_3$) δ 0.95-1.50 (m, 7 H) 2.23-3.61 (m, 9 H) 7.12-7.24 (m, 2 H) 8.03 (br. s., 1 H) ppm.

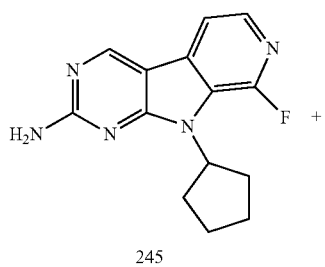

245

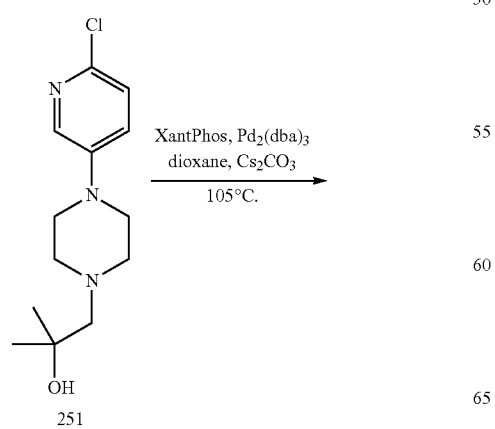

251

210

-continued

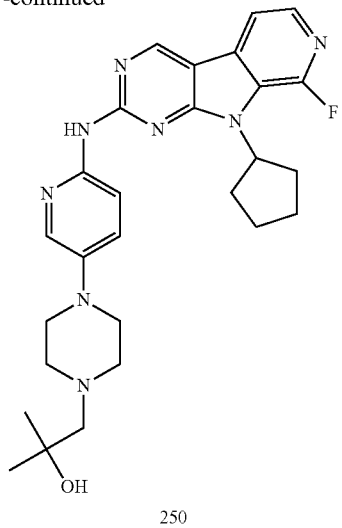

250

1-(4-(6-((9-Cyclopentyl-8-fluoro-9H-pyrido[4',3':4,5]pyrrolo[2,3-d]pyrimidin-2-yl)amino)-3-pyridinyl)-1-piperazinyl)-2-methyl-2-propanol (250): To tris(dibenzylideneacetone)dipalladium (0) (0.0190 g, 0.0207 mmol), Xantphos (0.0240 g, 0.0415 mmol), cesium carbonate (0.126 g, 0.387 mmol), 1-(4-(6-chloropyridin-3-yl)piperazin-1-yl)-2-methylpropan-2-ol (251) (0.0746 g, 0.276 mmol), and compound 245 (0.0750 g, 0.276 mmol) was added degassed dioxane (1.1 mL). The reaction was stirred at 105° C. overnight. After 16 h, the reaction was cooled to room temperature and partitioned between dichloromethane (30 mL) and water. The aqueous was brought to pH 12 w/5 N NaOH and extracted further with dichloromethane (15 mL) and 10% methanol in dichloromethane (10 mL). The combined organics were dried with sodium sulfate and concentrated in vacuo. Silica gel chromatography (1% to 5% 2M methanolic NH$_3$ in DCM) afforded compound 250 (0.135 g, 96.8% yield). $^1$H NMR (500 MHz, DMSO-d$_6$) δ 1.13 (s, 6 H) 1.67-1.81 (m, 2 H) 1.96-2.06 (m, 2 H) 2.07-2.16 (m, 2 H) 2.27 (s, 2 H) 2.33 (d, J=8.56 Hz, 2 H) 2.65-2.74 (m, 4 H) 3.10-3.17 (m, 4 H) 4.14 (s, 1 H) 5.46 (quin, J=9.05 Hz, 1 H) 7.47 (dd, J=9.17, 2.81 Hz, 0 H) 7.97-8.07 (m, 3 H) 8.12 (d, J=9.05 Hz, 0 H) 9.33 (s, 1 H) 9.90 (s, 1 H) ppm.

Example 173

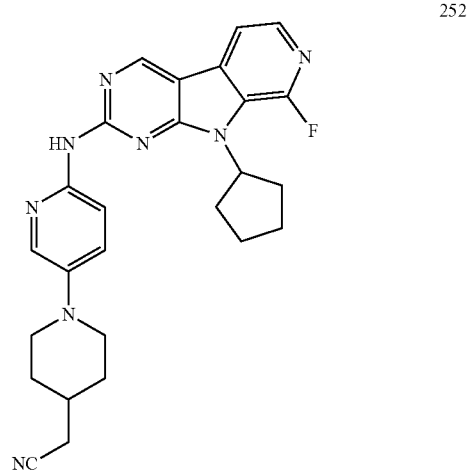 [SMILES: N#CCC1CCN(c2ccc(Nc3ncc4c5ccnc(F)c5n(C5CCCC5)c4n3)nc2)CC1]

252

211

(1-(6-((9-Cyclopentyl-8-fluoro-9H-pyrido[4',3':4,5]pyrrolo[2,3-d]pyrimidin-2-yl)amino)-3-pyridinyl)-4-piperidinyl)acetonitrile

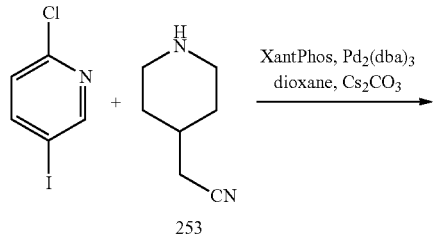

253

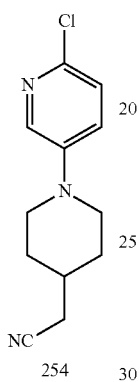

254

212

-continued

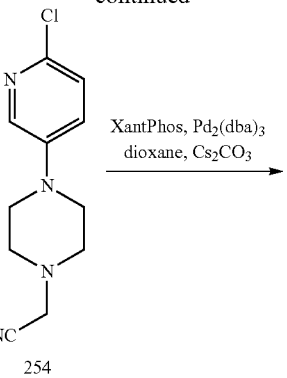

254

(1-(6-Chloro-3-pyridinyl)-4-piperidinyl)acetonitrile (254): 2-Chloro-5-iodopyridine (0.278 g, 1.16 mmol), 2-(piperidin-4-yl)acetonitrile hydrochloride (253) [Vidaluc, J.-L. et al., Novel *J. Med. Chem.* 1994, 37, (5), 689-695] (0.186 g, 1.16 mmol), $Pd_2(dba)_3$ (0.0531 g, 0.0580 mmol), 4,5-bis(diphenylphosphino)-9,9-dimethyl-9H-xanthene (0.0671 g, 0.116 mmol) and cesium carbonate (0.945 g, 2.90 mmol) were combined in a screw cap vial and solvated under argon atmosphere with degassed dioxane (4.5 mL). The reaction was briefly sparged with argon, then sealed and stirred at 105° C. After 3 h, the reaction was poured into water (30 mL) and extracted with 10% methanol in $CH_2Cl_2$ (3×20 mL). The combined organics were dried with sodium sulfate and concentrated in vacuo. Silica gel chromatography (gradient elution 10 to 50% ethyl acetate in hexanes) afforded compound 254 (0.110 g, 40.2% yield). $^1$H NMR (400 MHz, DMSO-$d_6$) δ 1.23-1.44 (m, J=11.98, 11.98, 11.84, 3.72 Hz, 2 H) 1.68-1.90 (m, 3 H) 2.54 (d, 2 H) 2.75 (td, J=12.42, 2.15 Hz, 2 H) 3.77 (d, J=12.52 Hz, 2 H) 7.26 (d, J=9.00 Hz, 1 H) 7.42 (dd, J=8.80, 3.33 Hz, 1 H) 8.06 (d, J=3.13 Hz, 1 H) ppm.

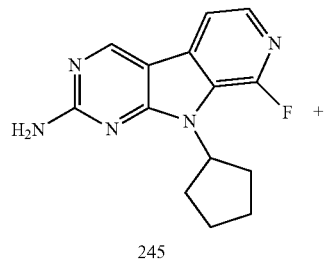

245

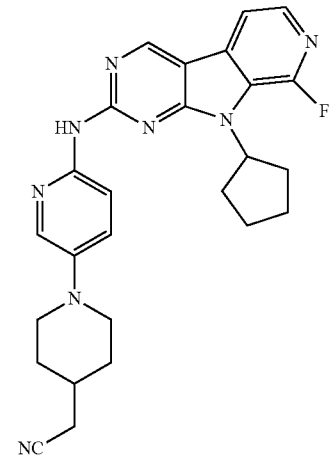

252

(1-(6-((9-Cyclopentyl-8-fluoro-9H-pyrido[4',3':4,5]pyrrolo[2,3-d]pyrimidin-2-yl)amino)-3-pyridinyl)-4-piperidinyl)acetonitrile (252): To tris(dibenzylideneacetone)dipalladium (0) (0.0147 g, 0.0160 mmol), xantphos (0.0186 g, 0.0321 mmol), $Cs_2CO_3$ (0.0975 g, 0.299 mmol), 2-(1-(6-chloropyridin-3-yl)piperidin-4-yl)acetonitrile (0.0504 g, 0.214 mmol), and compound 245 (0.0580 g, 0.214 mmol) was added degassed (Ar) dioxane (1.0 mL). The reaction was stirred at 105° C. overnight. After 16 h, the reaction was cooled to room temperature and loaded directly onto silica gel. Crystallization from THF and HCl salt formation provided compound 252 (55 mg). $^1$H NMR (400 MHz, DMSO-$d_6$) δ 1.43 (d, J=10.56 Hz, 2 H) 1.66-1.81 (m, 2 H) 1.86 (d, J=11.35 Hz, 3 H) 2.05 (d, J=6.26 Hz, 2 H) 2.15 (br. s., 2 H) 2.19-2.31 (m, 2 H) 2.59 (d, J=5.87 Hz, 2 H) 2.85 (t, J=11.74 Hz, 2 H) 3.75 (d, J=12.13 Hz, 2 H) 5.53 (quin, J=9.10 Hz, 1 H) 7.68 (d, J=9.39 Hz, 1 H) 8.00 (br. s., 1 H) 8.15 (d, J=5.09 Hz, 1 H) 8.20 (dd, J=9.39, 2.74 Hz, 1 H) 8.30 (dd, J=4.89, 2.93 Hz, 1 H) 9.55 (s, 1 H) 11.80 (br. s., 1 H) ppm.

Example 174

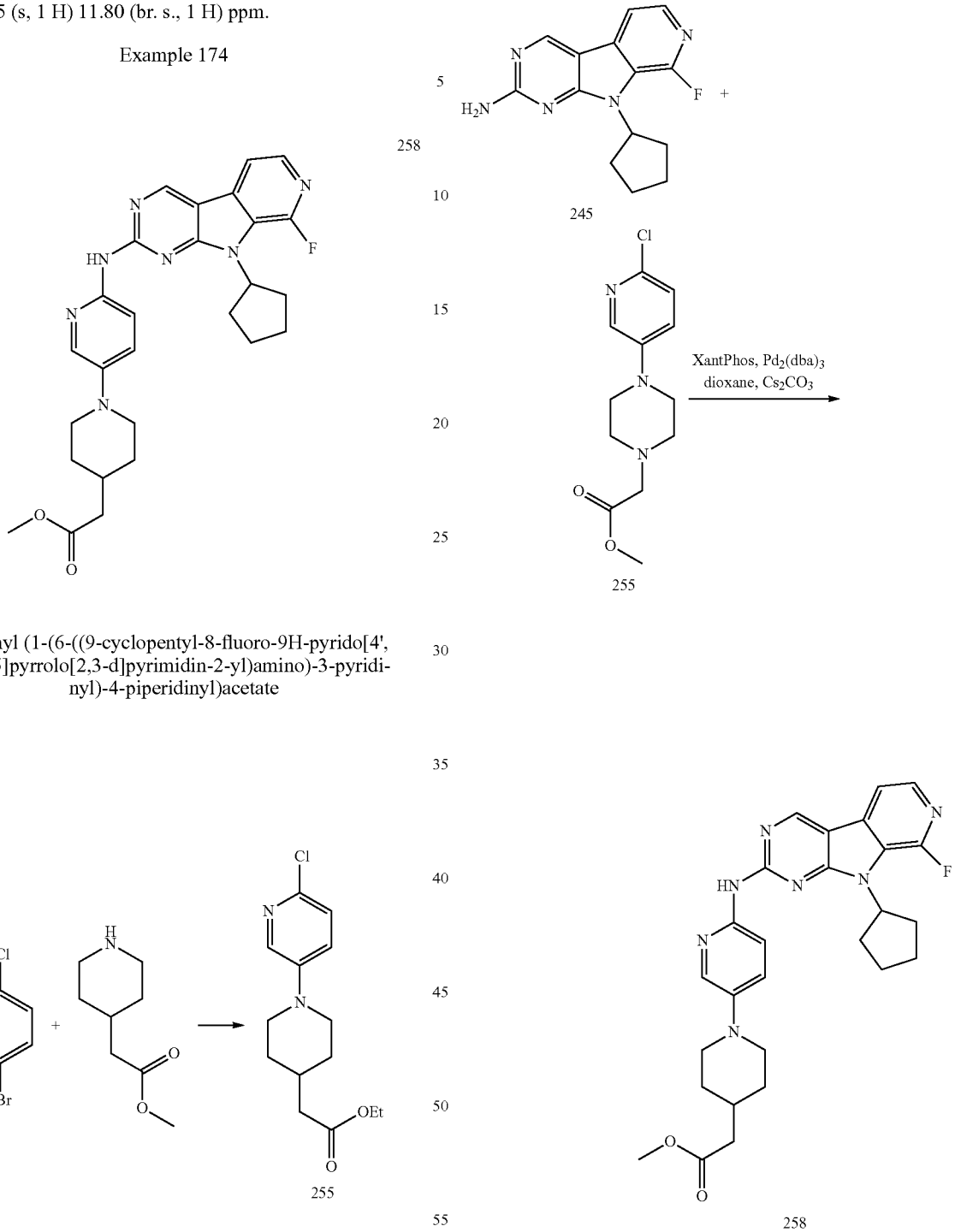

Methyl (1-(6-((9-cyclopentyl-8-fluoro-9H-pyrido[4',3':4,5]pyrrolo[2,3-d]pyrimidin-2-yl)amino)-3-pyridinyl)-4-piperidinyl)acetate Ethyl (1-(6-chloro-3-pyridinyl)-4-piperidinyl)acetate (255): Compound 255 was prepared using methods described in example 173. $^1$H NMR (400 MHz, DMSO-d$_6$) δ ppm 1.27 (qd, J=12.26, 3.91 Hz, 2 H) 1.72 (d, J=12.52 Hz, 2 H) 1.78-1.93 (m, J=11.05, 7.38, 7.38, 3.72, 3.72 Hz, 1 H) 2.29 (d, J=7.04 Hz, 2 H) 2.72 (td, J=12.32, 2.35 Hz, 2 H) 3.60 (s, 3 H) 3.72 (d, J=12.52 Hz, 2 H) 7.25 (d, J=9.00 Hz, 1 H) 7.40 (dd, J=9.00, 3.13 Hz, 1 H) 8.04 (d, J=3.13 Hz, 1 H) ppm.

Methyl (1-(6-((9-cyclopentyl-8-fluoro-9H-pyrido[4',3':4,5]pyrrolo[2,3-d]pyrimidin-2-yl)amino)-3-pyridinyl)-4-piperidinyl)acetate (258): Compound 258 was prepared using methods described for Example 173 and isolated as the HCl salt. $^1$H NMR (500 MHz, DMSO-d$_6$) δ 1.39 (br. s., 2 H) 1.71-1.86 (m, 4 H) 1.93 (d, J=8.80 Hz, 1 H) 2.05 (t, J=6.72 Hz, 2 H) 2.15 (d, J=7.58 Hz, 2 H) 2.20-2.31 (m, 2 H) 2.34 (d, J=6.85 Hz, 2 H) 2.86 (br. s., 2 H) 3.63 (s, 3 H) 3.71 (d, J=12.47 Hz, 2 H) 5.54 (quin, J=9.11 Hz, 1 H) 7.69 (br. s., 1 H), 8.01 (br. s., 1 H) 8.13-8.18 (m, 1 H) 8.20 (dd, J=9.54, 2.20 Hz, 1 H)

8.30 (dd, J=4.52, 2.81 Hz, 1 H) 9.56 (s, 1 H) ppm. LCMS-ESI (POS), M/Z, M+1: Found 504.2, Calculated 504.2.

Example 175

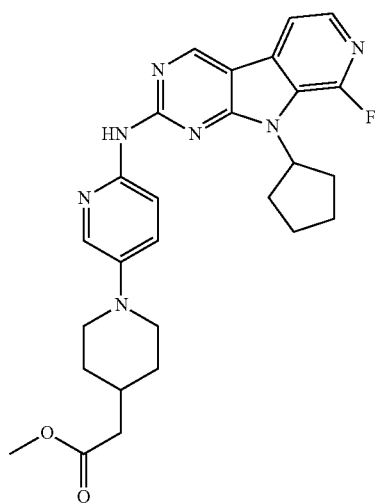

258

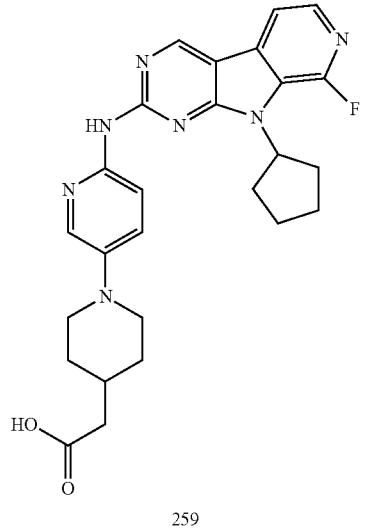

259

(1-(6-((9-Cyclopentyl-8-fluoro-9H-pyrido[4',3':4,5]pyrrolo[2,3-d]pyrimidin-2-yl)amino)-3-pyridinyl)-4-piperidinyl)acetic acid (259): Compound 258 (0.100 g, 0.20 mmol) was suspended in dioxane (4.8 mL) and methanol (4.8 mL). A solution of lithium hydroxide, monohydrate (0.0092 g, 0.22 mmol) in 2.0 mL of water was added to the suspension. The reaction was warmed to 70° C. After 1 hour, solvent was removed in vacuo. The residue was dissolved in water (3 mL). Dichloromethane was added (1 mL) and the pH was brought to ca. pH 10 with dilute NaOH. The organics were removed and the aqueous was brought to ca. pH 4 with dilute HCl. The resulting precipitate was filtered. Purification by RP-HPLC on C18 column (10-90% $CH_3CN$ in water with 0.1% TFA) provided compound 259 (5 mg) as a TFA salt. $^1$H NMR (500 MHz, DMSO-$d_6$) δ 1.28-1.41 (m, J=12.17, 12.01, 12.01, 3.18 Hz, 2 H) 1.68-1.94 (m, 5 H) 1.99-2.09 (m, 2 H) 2.09-2.19 (m, 2 H) 2.21-2.34 (m, 4 H) 2.81 (t, 11.49 Hz, 2 H) 3.71 (d, J=12.23 Hz, 2 H) 5.53 (quin, J=9.11 Hz, 1 H) 7.72 (d, J=9.05

Hz, 1 H) 7.98 (br. s., 1 H) 8.06 (d, J=8.56 Hz, 1 H) 8.11-8.18 (m, 1 H) 8.25 (dd, J=4.65, 2.93 Hz, 1 H) 9.51 (s, 1 H) 11.43 (br. s., 1 H) ppm. LCMS-ESI (POS), M/Z, M+1: Found 490.1, Calculated 490.2.

Example 176

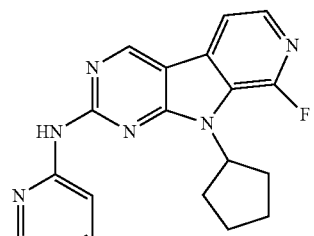

259

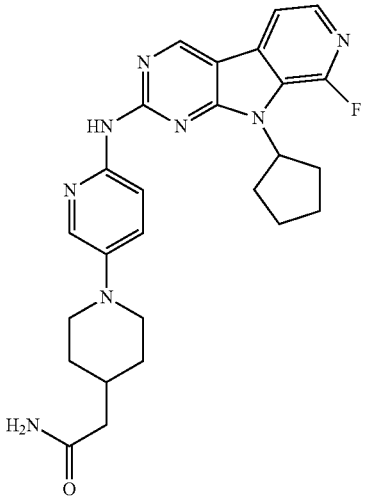

260

2-(1-(6-((9-Cyclopentyl-8-fluoro-9H-pyrido[4',3':4,5] pyrrolo[2,3-d]pyrimidin-2-yl)amino)-3-pyridinyl)-4-piperidinyl)acetamide (260): Compound 259 (0.077 g, 0.16 mmol) was suspended in DMF (1.5 mL) and 1,1'-carbonyldiimidazole (0.028 g, 0.17 mmol) was added. The reaction was stirred at 70° C. After 1 h, the suspension was cooled to 0° C. and ammonia gas was sparged therein. The tube was sealed and warmed to 70° C. After 1 h, the reaction was diluted in water (30 mL) and filtered. Purification by reversed phase HPLC (10-90% acetonitrile in water with 0.1% TFA) provided compound 260 (0.025 g, 26% yield) as a TFA salt. $^1$H NMR (500 MHz, DMSO-$d_6$) δ 1.25-1.39 (m, 2 H) 1.70-1.84 (m, 4 H) 1.89 (dt, J=7.27, 3.58 Hz, 1 H) 2.05 (d, J=7.09 Hz, 4 H) 2.14 (br. s., 2 H) 2.27 (d, J=8.31 Hz, 2 H) 2.80 (t, J=10.88 Hz, 2 H) 3.70 (d, J=12.23 Hz, 2 H) 5.52 (quin, J=9.05 Hz, 1 H) 6.80 (br. s., 1 H) 7.31 (br. s., 1 H) 7.74 (br. s., 1 H)

7.98 (br. s., 1 H) 8.05 (br. s., 1 H) 8.13 (d, J=3.91 Hz, 1 H) 8.21-8.28 (m, 1 H) 9.51 (s, 1 H) 11.36 (br. s., 1 H) ppm.

Example 177

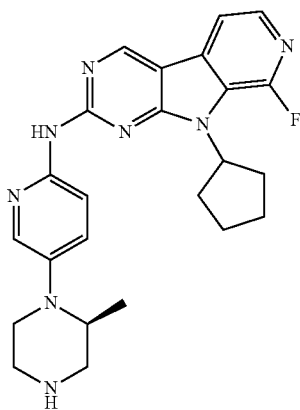

261

9-Cyclopentyl-8-fluoro-N-(5-((2S)-2-methyl-1-piperazinyl)-2-pyridinyl)-9H-pyrido[4',3':4,5]pyrrolo[2,3-d]pyrimidin-2-amine Tile compound 261 was prepared using methods described in Example 170 and isolated as the HCl salt. $^1$H NMR (500 MHz, DMSO-d$_6$) δ 0.91 (d, J=6.36 Hz, 3 H) 1.43 (s, 9 H) 1.67-1.81 (m, 2 H) 2.01 (br. s., 2 H) 2.05-2.16 (m, 2 H) 2.33 (br. s., 2 H) 2.91-3.02 (m, 1 H) 3.63 (d, J=11.74 Hz, 1 H) 3.75-3.96 (m, 2 H) 5.45 (quin, J=8.99 Hz, 1 H) 7.49 (dd, J=8.93, 2.57 Hz, 1 H) 7.95-8.07 (m, 3 H) 8.14 (d, J=9.05 Hz, 1 H) 9.33 (s, 1 H) 9.92 (s, 1 H) ppm.

Example 178

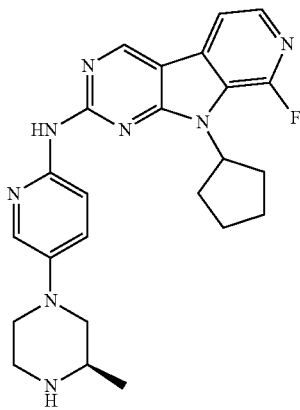

262

9-Cyclopentyl-8-fluoro-N-(5-((3R)-3-methyl-1-piperazinyl)-2-pyridinyl)-9H-pyrido[4',3':4,5]pyrrolo[2,3-d]pyrimidin-2-amine Compound 262 was prepared using methods described in example 170 and isolated as the HCl salt. $^1$H NMR (500 MHz, DMSO-d$_6$) δ 1.35 (d, J=6.60 Hz, 3 H) 1.62-1.86 (m, 2 H) 1.97-2.10 (m, 2 H) 2.10-2.20 (m, 2 H) 2.21-2.34 (m, 2 H) 2.93 (dd, J=12.47, 11.00 Hz, 1 H) 3.15 (d, J=6.85 Hz, 2 H) 3.37-3.46 (m, 2 H) 3.78 (d, J=8.31 Hz, 1 H) 3.84 (d, J=11.98 Hz, 1 H) 5.53 (quin, J=9.05 Hz, 1 H) 7.82 (d, J=9.78 Hz, 1 H) 8.09 (s, 2 H) 8.14 (d, J=3.91 Hz, 1 H) 8.22-8.33 (m, 1 H) 9.43 (br. s., 1 H) 9.54 (s, 1 H) 9.61 (br. s., 1 H) 11.54 (br. s., 1 H) ppm.

Example 179

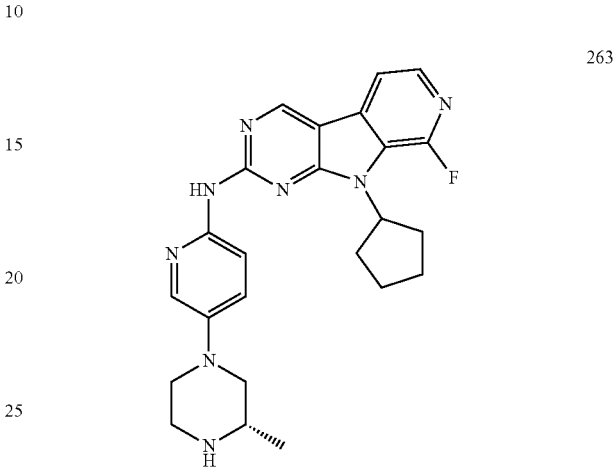

263

9-cyclopentyl-8-fluoro-N-(5-((3S)-3-methyl-1-piperazinyl)-2-pyridinyl)-9H-pyrido-[4',3':4,5]pyrrolo[2,3-d]pyrimidin-2-amine Compound 263 was prepared using methods described in example 170 and isolated as the HCl salt. $^1$H NMR (500 MHz, DMSO-d$_6$) δ 1.33 (d, J=6.60 Hz, 3 H) 1.69-1.82 (m, 2 H) 2.04 (t, J=6.72 Hz, 2 H) 2.14 (d, J=5.87 Hz, 2 H) 2.21-2.33 (m, 2 H) 2.91 (dd, J=12.47, 11.00 Hz, 1 H) 3.08-3.20 (m, 2 H) 3.77 (d, J=9.05 Hz, 1 H) 3.83 (d, J=11.98 Hz, 1 H) 5.52 (quin, J=9.05 Hz, 1 H) 7.81 (d, J=8.80 Hz, 1 H) 8.00-8.10 (m, 2 H) 8.13 (d, J=4.16 Hz, 1 H) 8.22-8.29 (m, 1 H) 9.42 (br. s., 1 H) 9.53 (s, 1 H) 9.57 (d, J=9.29 Hz, 1 H) 11.50 (br. s., 1 H) ppm.

Example 180

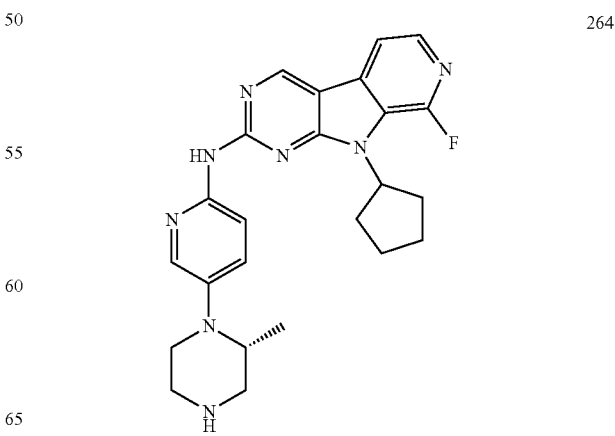

264

9-Cyclopentyl-8-fluoro-N-(5-((2R)-2-methyl-1-piperazinyl)-2-pyridinyl)-9H-pyrido[4',3':4,5]pyrrolo[2,3-d]pyrimidin-2-amine Compound 264 was prepared using methods described in example 170 and isolated as the HCl salt. ¹H NMR (500 MHz, DMSO-d₆) δ 1.15 (d, J=6.85 Hz, 3 H) 1.67-1.83 (m, 2 H) 1.95-2.08 (m, 2 H) 2.15 (br. s., 2 H) 2.25 (d, J=6.60 Hz, 2 H) 3.06-3.17 (m, 1 H) 3.18-3.36 (m, 3 H) 3.45-3.54 (m, 1 H) 4.06-4.20 (m, 1 H) 5.52 (quin, J=9.05 Hz, 1 H) 7.80 (d, J=9.29 Hz, 1 H) 8.01-8.12 (m, 2 H) 8.12-8.20 (m, 1 H) 8.28 (dd, J=4.77, 3.06 Hz, 1 H) 9.31 (br. s., 1 H) 9.55 (s, 1 H) 9.74 (br. s., 1 H) 11.69 (br. s., 1 H) ppm.

Example 181

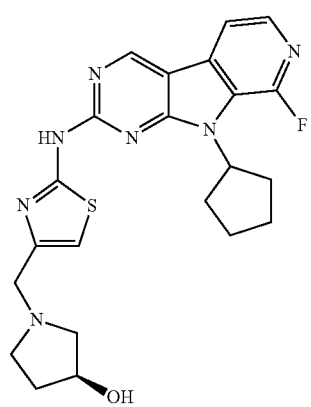

265

(3S)-1-((2-((9-Cyclopentyl-8-fluoro-9H-pyrido[4',3':4,5]pyrrolo[2,3-d]pyrimidin-2-yl)amino)-1,3-thiazol-4-yl)methyl)-3-pyrrolidinol Compound 265 was prepared using methods described in example 170. ¹H NMR (500 MHz, CDCl₃) δ 10.48 (2 H, br. s.), 9.30 (1 H, s), 8.08 (1 H, dd, J=5.3, 1.8 Hz), 7.79 (1 H, dd, J=5.1, 2.9 Hz), 6.83 (1 H, s), 5.64-5.74 (1 H, m), 4.35-4.43 (1 H, m), 3.84-3.98 (2 H, m), 3.03-3.11 (1 H, m), 2.88-2.96 (1 H, m), 2.69-2.77 (1 H, m), 2.41-2.59 (3 H, m), 2.11-2.29 (5 H, m), 1.76-1.94 (3 H, m) ppm; LCMS-ESI (POS), M/Z, M+1: Found 454.1.

Example 182

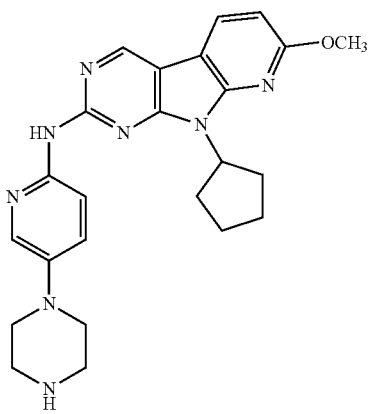

266

9-Cyclopentyl-7-methoxy-N-(5-(1-piperazinyl)-2-pyridinyl)-9H-pyrido[3',2':4,5]pyrrolo[2,3-d]pyrimidin-2-amine

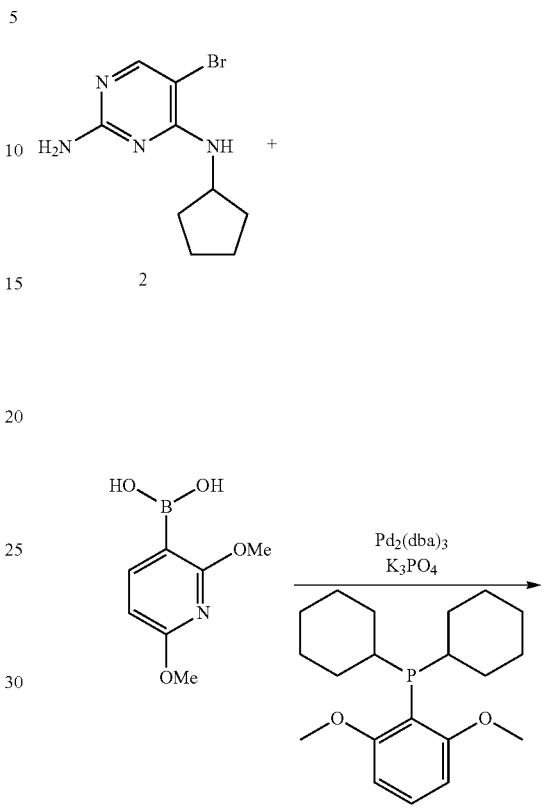

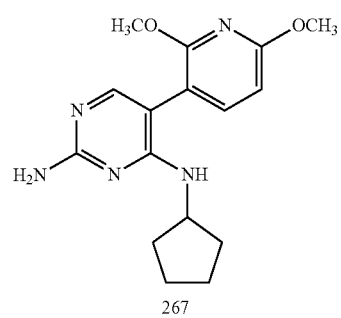

267

N4-Cyclopentyl-5-(2,6-dimethoxypyridin-3-yl)pyrimidine-2,4-diamine (267): Compound 2 (2.00 g, 7.78 mmol), 2,6-dimethoxypyridin-3-ylboronic acid (2.13 g, 11.7 mmol), tris(dibenzylideneacetone)dipalladium (0) (0.214 g, 0.233 mmol), and dicyclohexyl(2,6-dimethoxyphenyl)phosphine (0.156 g, 0.467 mmol), were dissolved in n-butanol (2.5 mL). The reaction was purged with argon and heated at 100° C. for 19 hours. The resulting solution was added to 80 mL water and extracted with ethyl acetate (2×150 mL). The combined organics were dried (MgSO₄) and evaporated to give an orange oil. Silica gel chromatography (gradient elution dichloromethane+2.5% TEA/0-5% methanol) afforded compound 267 as an off-white solid (1.29 g, 53%).

221

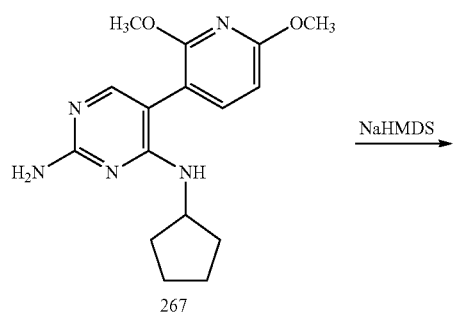

9-cyclopentyl-7-methoxy-9H-pyrido[3',2':4,5]pyrrolo[2,3-d]pyrimidin-2-amine (268): A 10 mL reaction vessel was charged with N4-cyclopentyl-5-(2,6-dimethoxypyridin-3-yl)pyrimidine-2,4-diamine (267) (50.0 mg, 159 μmol) dissolved in dry pyridine (1 mL) under argon. Sodium bis(trimethylsilyl)amide in THF (1.0M, 0.349 mL, 349 μmol) was added and the reaction heated with microwave energy (300 W) for 12 minutes at 150° C. The solvent was removed in vacuo. Silica gel chromatography of the residue (gradient elution dichloromethane/0-5% methanol) afforded compound 268 as an off-white solid (28 mg, 62%)

222

-continued

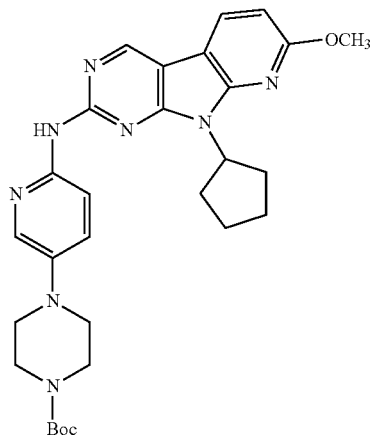

tert-Butyl 4-(6-((9-cyclopentyl-7-methoxy-9H-pyrido[3',2':4,5]pyrrolo[2,3-d]pyrimidin-2-yl)amino)-3-pyridinyl)-1-piperazinecarboxylate (269): A 10 mL reaction vessel was charged with compound 268 (100 mg, 353 μmol), compound 5 (126 mg, 424 μmol), and sodium t-butoxide (102 mg, 1059 μmol), followed by dioxane (3 mL). The reaction was purged with argon. 4,5-bis(diphenylphosphino)-9,9-dimethyl-9H-xanthene (40.8 mg, 70.6 μmol) and tris(dibenzylideneacetone)dipalladium (0) (32.3 mg, 35.3 μmol) were added and the reaction was again purged with argon. The reaction was heated with microwave energy (300 W) at 120° C. for 90 minutes. The resulting solution was diluted with ethyl acetate (75 mL) and added to water (75 mL). The layers were separated and the aqueous phase extracted with ethyl acetate (75 mL) and dichloromethane (75 mL). The combined organics were dried (MgSO₄) and evaporated to give a brown oil. Silica gel chromatography (gradient elution hexanes/50-100% ethyl acetate) afforded a tan solid, which was recrystallized from boiling ethyl acetate to give compound 269 as a white solid (120 mg, 62%)

223

-continued

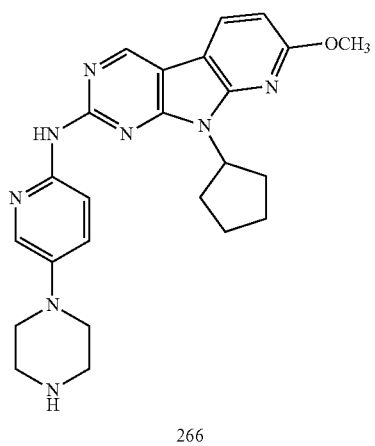

266

9-cyclopentyl-7-methoxy-N-(5-(1-piperazinyl)-2-pyridi-nyl)-9H-pyrido[3',2':4,5]-pyrrolo[2,3-d]pyrimidin-2-amine (266): Compound 269 (120 mg, 220 μmol) was dissolved in dichloromethane (4 mL). Trifluoroacetic acid (0.400 mL, 2203 μmol) was added and the reaction stirred at room temperature for 70 minutes. The reaction was added to aqueous $K_2CO_3$ (10%, 30 mL) and extracted thrice with dichloromethane. The combined organics were dried ($MgSO_4$) and evaporated to give a pale yellow solid, 82 mg. This residue was dissolved in dioxane (2 mL) and methanol (2 mL) and 1 mL of a saturated solution of HCl in dioxane was added. ethyl acetate (30 mL) followed by diethyl ether (30 mL) were added to precipitate the HCl salt, which was collected and dried in vacuo to give compound 266 as a yellow solid (77 mg, 84%). $^1$H NMR (500 MHz, DMSO-$d_6$) δ ppm 9.24-9.36 (m, 4 H) 9.19 (s, 1 H) 8.52 (s, 1 H) 7.97 (s, 1 H) 7.92-7.96 (m, 1 H) 7.44-7.54 (m, 1 H) 6.83 (d, J=8.56 Hz, 1 H) 5.31-5.43 (m, 1 H) 3.94 (s, 3 H) 3.33-3.41 (m, 4 H) 3.21 (br. s., 4 H) 1.95-2.11 (m, 4 H) 1.70 (none, 2 H) ppm.

Example 183

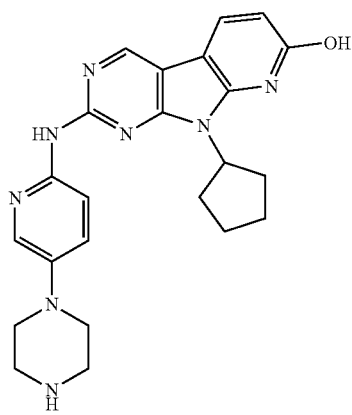

270

224

9-Cyclopentyl-2-((5-(1-piperazinyl)-2-pyridinyl) amino)-9H-pyrido[3',2':4,5]pyrrolo[2,3-d]pyrimidin-7-ol

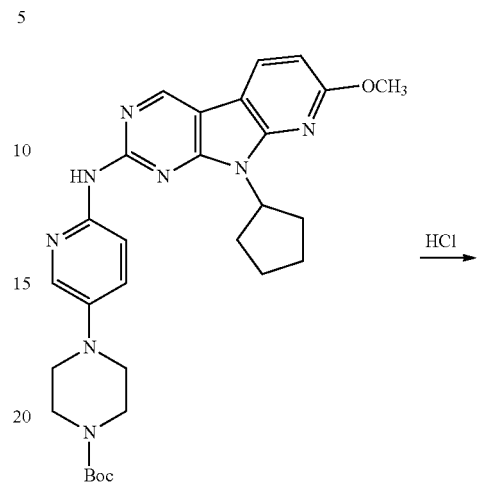

269

$\xrightarrow{\text{HCl}}$

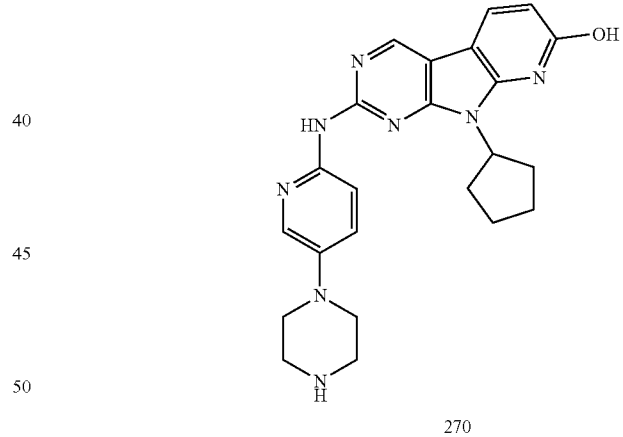

270

9-Cyclopentyl-2-((5-(1-piperazinyl)-2-pyridinyl)amino)-9H-pyrido[3',2':4,5]-pyrrolo[2,3-d]pyrimidin-7-ol (270): A 10 mL reaction tube vessel was charged with compound 269 (56.0 mg, 103 μmol) and concentrated hydrochloric acid (2.00 mL, 103 μmol). The reaction was heated with microwave energy (300 W) at 120° C. for 1 hour, then an additional 30 minutes at 140° C. The resulting solution was filtered through a 0.45 μM filter and washed with water. The solvent was removed in vacuo, and the residue coevaporated with water (10 mL) and then methanol (2×, 10 mL) to give compound 270 as a yellow solid (48 mg). $^1$H NMR (400 MHz, DMSO-$d_6$) δ ppm 11.63-11.91 (m, 2 H) 9.40 (br. s., 4 H) 9.19 (s, 1 H) 8.50 (d, J=8.61 Hz, 1 H) 8.04 (d, J=2.74 Hz, 1 H) 7.99 (dd, J=9.39, 2.74 Hz, 1 H) 7.51 (d, J=9.39 Hz, 1 H) 6.69-6.78

(m, 1 H) 5.35 (quin, J=8.71 Hz, 1 H) 3.37-3.51 (m, 4 H) 3.20-3.34 (m, 4 H) 2.06-2.18 (m, 2 H) 1.93-2.06 (m, 2 H) 1.66-1.82 (m, 2 H) ppm.

Example 184

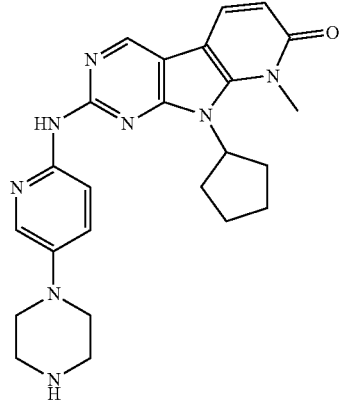

9-Cyclopentyl-8-methyl-2-((5-(1-piperazinyl)-2-pyridinyl)amino)-8,9-dihydro-7H-pyrido[3',2':4,5]pyrrolo[2,3-d]pyrimidin-7-one

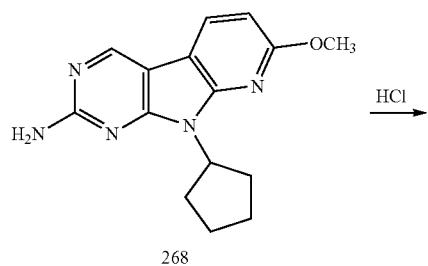

2-Amino-9-cyclopentyl-9H-pyrido[3',2':4,5]pyrrolo[2,3-d]pyrimidin-7-ol (272): Compound 268 (150 mg, 529 µmol) was dissolved in conc. hydrochloric acid (2 mL). The reaction was heated with microwave energy (300 W) for 40 min. at 140° C. The resulting solution was added to aqueous NaHCO$_3$ (20 mL, 50% sat.) and extracted with dichloromethane+10% methanol (3×30 mL). The combined organics were dried (MgSO$_4$) and evaporated to give an orange tar. Silica gel chromatography (gradient elution hexanes+2.5% TEA/0-100% ethyl acetate+2.5% TEA) afforded compound 272 as a tan solid, 120 mg (84%).

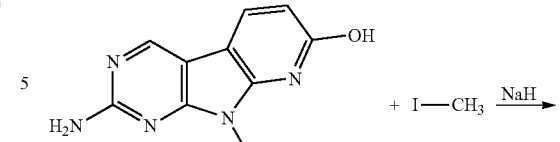

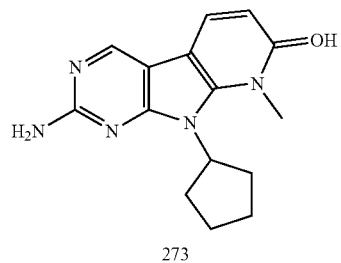

2-Amino-9-cyclopentyl-8-methyl-8,9-dihydro-7H-pyrido[3',2':4,5]pyrrolo[2,3-d]pyrimidin-7-one (273): Compound 272 (100 mg, 0.37 mmol) was dissolved in dry DMF (1 mL). Sodium hydride, 60% dispersion in oil (16.0 mg, 0.4 mmol) was added and the reaction stirred at 60° C. for 20 minutes. Iodomethane (26.5 µl, 423 µmol) was the added and the reaction stirred at 60° C. for 2 hr. The solution was allowed to cool and added to water (10 mLl) and aqueous K$_2$CO$_3$ (saturated, 2 mL), and extracted with ethyl acetate (2×30 mL), and dichloromethane+10% methanol (2×30 mLl). The combined organics were dried (MgSO$_4$) and evaporated to give an orange solid. Silica gel chromatography (gradient elution hexanes+2.5% TEA/0-70% ethyl acetate+2.5% TEA) afforded compound 273 as a white solid, 64 mg (61%).

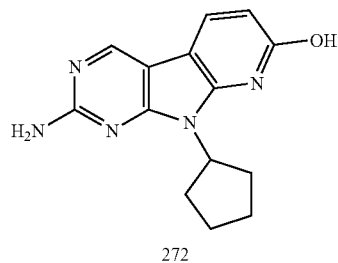

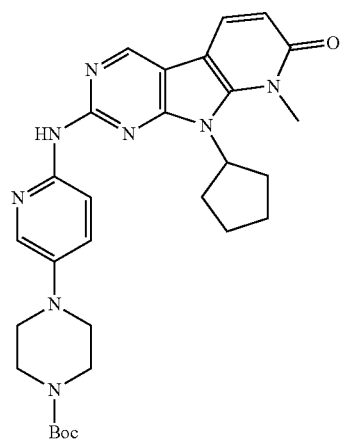

274 tert-Butyl 4-(6-((9-cyclopentyl-8-methyl-7-oxo-8,9-dihydro-7H-pyrido[3',2':4,5]-pyrrolo[2,3-d]pyrimidin-2-yl)amino)-3-pyridinyl)-1-piperazinecarboxylate (274): A 10 mL reaction vessel was charged with compound 273 (61.0 mg, 21.5 μmol), compound 5 (70.5 mg, 237 μmol), and sodium t-butoxide (62.1 mg, 646 μmol), followed by dioxane (3 mL). The reaction was purged thoroughly with argon. 4,5-bis(diphenylphosphino)-9,9-dimethyl-9H-xanthene (24.9 mg, 43.1 μmol) and tris(dibenzylideneacetone)dipalladium (0) (19.7 mg, 21.5 mop were added, and the reaction was again purged with argon. The reaction was heated with microwave energy (300 W) at 120° C. for 90 minutes. The resulting solution was diluted with ethyl acetate (75 mL) and added to water (75 mL). The layers were separated layers and the aqueous phase extracted with ethyl acetate (75 mL), followed by dichloromethane (75 mL). The combined organics were dried (MgSO₄) and evaporated to give the product as a tan solid. Recrystallization from boiling ethyl acetate gave compound 274 as a white solid (74 mg, 63%).

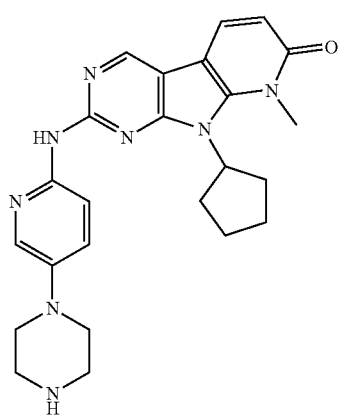

271

9-Cyclopentyl-8-methyl-2-((5-(1-piperazinyl)-2-pyridinyl)amino)-8,9-dihydro-7H-pyrido[3',2':4,5]pyrrolo[2,3-d]pyrimidin-7-one (271): Compound 274 (51 mg) was dissolved in 2 mL dioxane. Dioxane (1 mL) saturated at room temperature with HCl was added, followed by 1 mL methanol to aid solution. The reaction was stirred at room temperature for 80 min. The solution was then added dropwise to diethyl ether (8 mL) and the resulting precipitate was collected and dried in vacuo to give compound 271 as a yellow solid (26 mg, 62%). ¹H NMR (500 MHz, DMSO-d₆) δ 11.75 (br. s., 1 H) 9.36 (br. s., 2 H) 9.20 (s, 1 H) 8.53 (d, J=8.31 Hz, 1 H) 7.91-8.01 (m, 2 H) 7.49 (d, J=9.29 Hz, 1 H) 6.83 (d, J=8.56 Hz, 1 H) 5.37 (quin, J=8.56 Hz, 1 H) 3.35-3.43 (m, 5 H) 1.94-2.13 (m, 4 H) 1.64-1.79 (m, 2 H) ppm.

Example 185

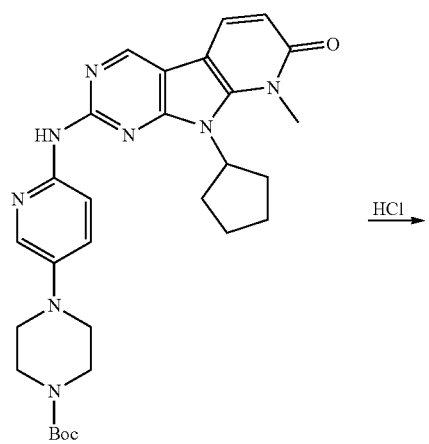

274

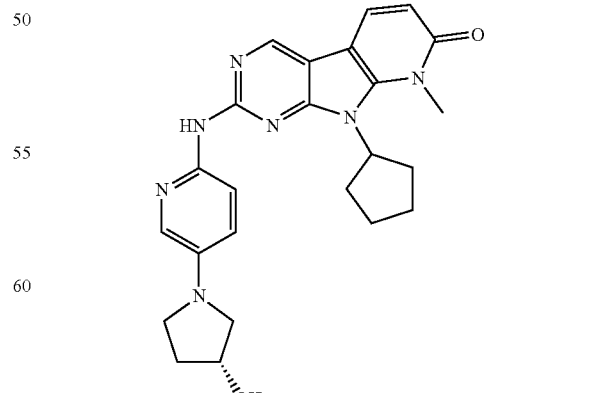

275

229

9-Cyclopentyl-2-((5-((3R)-3-hydroxy-1-pyrrolidinyl)-2-pyridinyl)amino)-8-methyl-8,9-dihydro-7H-pyrido[3',2':4,5]pyrrolo[2,3-d]pyrimidin-7-one

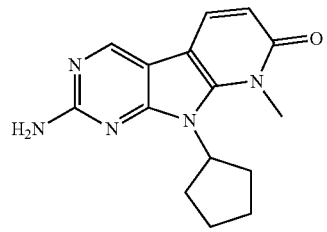

273

+

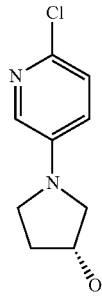

→ (Xantphos, Pd₂(dba)₃, t-BuONa)

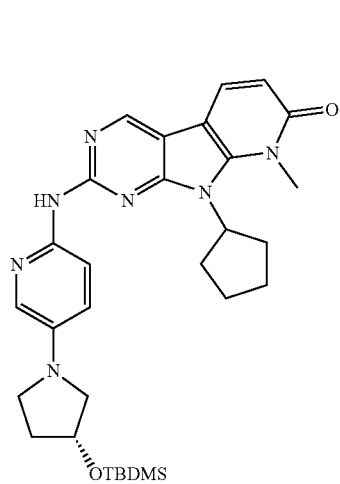

276

230

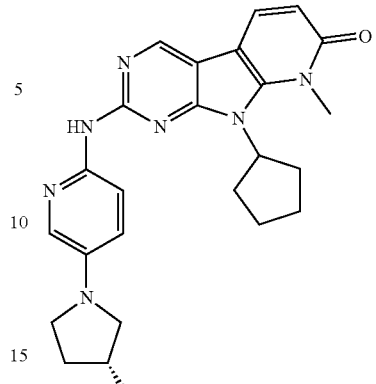

276

→ TBAF

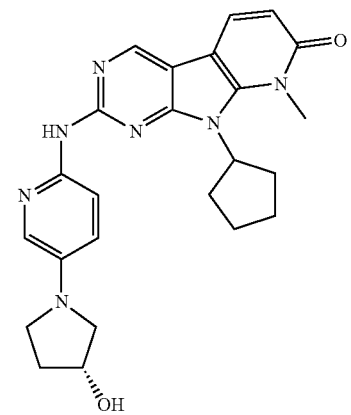

275

9-Cyclopentyl-2-((5-((3R)-3-(tert-butyldimethylsilyloxy)pyrrolidin-1-yl)-2-pyridinyl)amino)-8-methyl-8,9-dihydro-7H-pyrido[3',2':4,5]pyrrolo[2,3-d]-pyrimidin-7-one (276): A 10 mL reaction vessel was charged with compound 273 (55 mg, 193 μmol), (R)-5-(3-(t-butyldimethylsilyloxy)pyrrolidin-1-yl)-2-chloropyridine (60.3 mg, 193 μmol), tris(dibenzylideneacetone)dipalladium (0) (13 mg, 14 μmol), 4,5-bis(diphenylphosphino)-9,9-dimethyl-9H-xanthene (17 mg, 29 μmol), and sodium t-butoxide (22 mg, 231 μmol) in 2 mL dry dioxane. The reaction was purged with argon and heated with microwave energy (300 W) for 2 hours at 120° C. The resulting solution was taken up in ethyl acetate (40 mL) and washed with water (30 mL), and brine (30 mL). The organics were dried (MgSO₄) and evaporated to give a brown oil. Silica gel chromatography (gradient elution hexanes+2.5% TEA/0-50% ethyl acetate+2.5% TEA) afforded compound 276 as a yellow solid (53 mg, 49%).

9-Cyclopentyl-2-((5-((3R)-3-hydroxy-1-pyrrolidinyl)-2-pyridinyl)amino)-8-methyl-8,9-dihydro-7H-pyrido[3',2':4,5]pyrrolo[2,3-d]pyrimidin-7-one (275): Compound 276 (53.0 mg, 94.7 μmol) was dissolved in THF (2 mL).). Tetrabutylammonium fluoride, 1.0M in THF (0.500 mL, 500 μmol) was added and the reaction was stirred at room temperature for 4.5 hours. The solvent was evaporated to give an orange oil. Preparative reverse phase HPLC (gradient elution 0.1% TFA in water/10-70% acetonitrile) afforded a yellow solid. This residue was added to aqueous NaHCO₃ (saturated, 10 mL) and extracted with dichloromethane+10% methanol (3×30 mL). The combined organics were dried (MgSO₄) and evaporated to give a yellow solid. This product was taken up in methanol (2 mL) and 1 mL methanol (saturated at room temperature with HCl) was added. 20 mL diethyl ether was added to precipitate the product, which was washed with ether and dried in vacuo to give compound 275 as yellow solid (21 mg, 50%). ¹H NMR (500 MHz, DMSO-d₆) δ 9.21 (s, 2 H) 8.56 (d, J=8.56 Hz, 2 H) 7.63 (d, J=2.69 Hz, 4 H) 7.44-7.57 (m, 2 H) 6.87 (d, J=8.56 Hz, 2 H) 5.43 (quin, J=8.62 Hz, 1 H)

4.47 (br. s., 1 H) 4.00 (s, 3 H) 3.09-3.21 (m, 1H) 2.00-2.22 (m, 5 H) 1.90-2.04 (m, 1 H) 1.66-1.85 (m, 2 H) ppm.

Example 186a

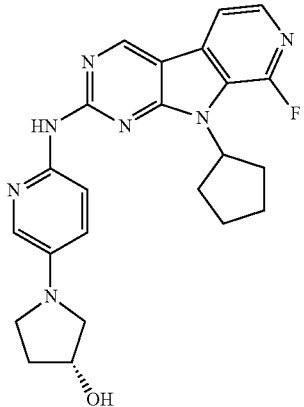

277

(3R)-1-(6-((9-cyclopentyl-8-fluoro-9H-pyrido[4',3': 4,5]pyrrolo[2,3-d]pyrimidin-2-yl)amino)-3-pyridinyl)-3-pyrrolidinol

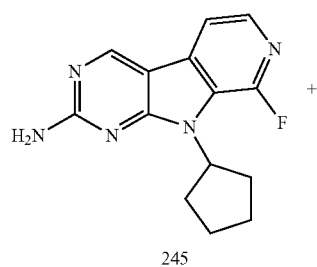

245

+

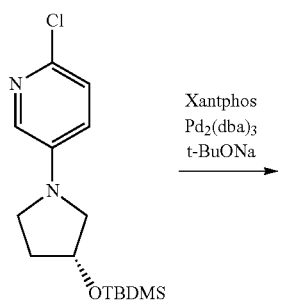

Xantphos
Pd₂(dba)₃
t-BuONa
→

-continued

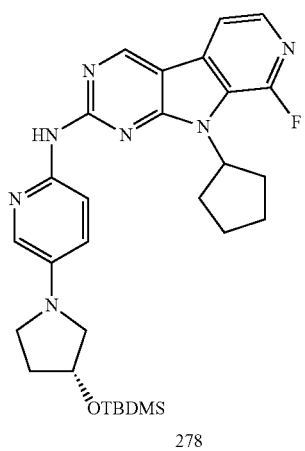

278

N-(5-((3R)-3-((tert-butyl(dimethyl)silyl)oxy)-1-pyrrolidinyl)-2-pyridinyl)-9-cyclopentyl-8-fluoro-9H-pyrido[4', 3':4,5]pyrrolo[2,3-d]pyrimidin-2-amine (278): A 10 mL reaction vessel was charged with compound 245 (75.0 mg, 276 μmol), (R)-5-(3-(t-butyldimethylsilyloxy)pyrrolidin-1-yl)-2-chloropyridine (86.5 mg, 276 μmol), tris(dibenzylideneacetone)dipalladium (0) (19.0 mg, 20.7 μmol), 4,5-bis (diphenylphosphino)-9,9-dimethyl-9H-xanthene (24.0 mg, 41.5 μmol), sodium t-butoxide (53.1 mg, 553 μmol), and dioxane (1.5 mL). The reaction was heated with microwave energy (300 W) for 2 hours at 120° C. in the resulting solution was added to ethyl acetate (40 mL) and washed with water (30 mL) followed by brine (30 mL). The organic phase was dried (MgSO₄) and evaporated to give an orange oil. Silica gel chrmatography (gradient elution 35% ethyl acetate in hexanes) afforded compound 278 as a yellow solid (59 mg, 39%)

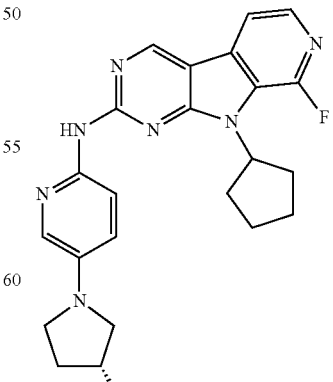

278

TBAF
→

233
-continued

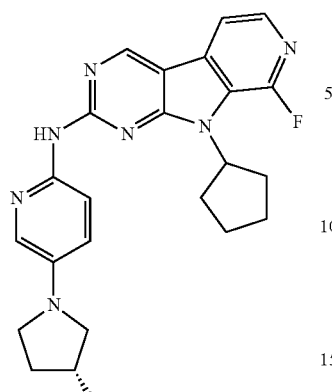
277

(3R)-1-(6-((9-cyclopentyl-8-fluoro-9H-pyrido[4',3':4,5]pyrrolo[2,3-d]pyrimidin-2-yl)amino)-3-pyridinyl)-3-pyrrolidinol (277): Compound 278 (58 mg, 106 µmol) was dissolved in THF (2 mL). Tetrabutylammonium fluoride, 1.0M in THF (0.5 mL, 0.500 mmol) was added and the reaction stirred at room temperature for 4 hours. The solvent was removed to give an orange oil. Silica gel chromatography (gradient elution ethyl acetate+2.5% TEA/0-5% methanol) afforded a yellow solid. This residue was taken up in methanol (2 mL) and HCl in ethanol (1.0M, 0.5 mL) was added. Diethyl ether (20 mL) was added to precipitate the product, which was filtered and dried in vacuo to give compound 277 as a yellow solid (23 mg, 50%). $^1$H NMR (500 MHz, DMSO-$d_6$) δ 9.72 (s, 1 H) 9.25-9.35 (m, 1 H) 7.94-8.11 (m, 4 H) 7.62-7.77 (m, 2 H) 7.05 (dd, J=8.93, 2.81 Hz, 1 H) 5.37-5.54 (m, 1 H) 4.99 (d, J=3.91 Hz, 1 H) 4.44 (br. s., 1 H) 3.46 (dd, J=10.03, 4.89 Hz, 2 H) 3.05-3.16 (m, 1 H) 2.26-2.42 (m, 3 H) 1.96-2.20 (m, 8 H) 1.85-1.96 (m, 2 H) 1.66-1.83 (m, 3 H) ppm.

Example 186b

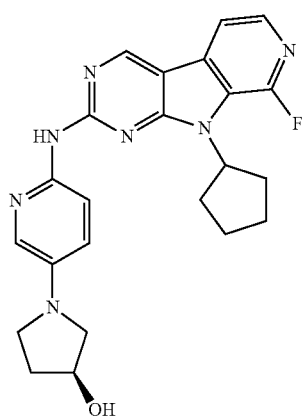 [SMILES: O[C@H]1CCN(c2ccc(Nc3ncc4c5ccnc(F)c5n(C5CCCC5)c4n3)nc2)C1]

234

(3S)-1-(6-((9-cyclopentyl-8-fluoro-9H-pyrido[4',3':4,5]pyrrolo[2,3-d]pyrimidin-2-yl)amino)-3-pyridinyl)-3-pyrrolidinol

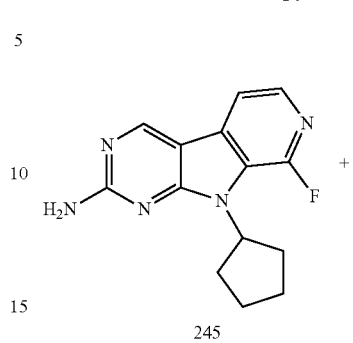
245

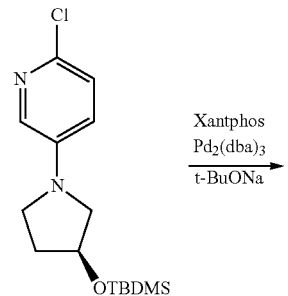

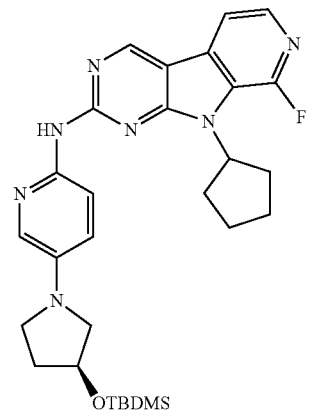
280

N-(5-((3S)-3-((tert-butyl(dimethyl)silyl)oxy)-1-pyrrolidinyl)-2-pyridinyl)-9-cyclopentyl-8-fluoro-9H-pyrido[4',3':4,5]pyrrolo[2,3-d]pyrimidin-2-amine (280): Compound 280 was prepared from compound 245 and (S)-5-(3-(tert-butyldimethylsilyloxy)-pyrrolidin-1-yl)-2-chloropyridine using methods described in Example 186a.

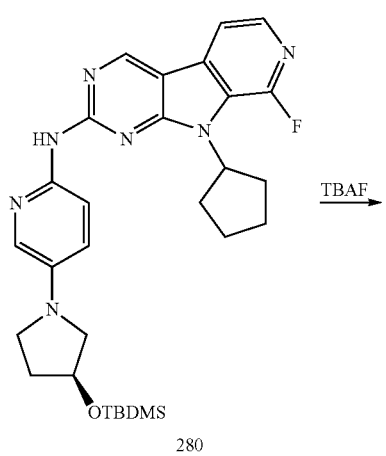

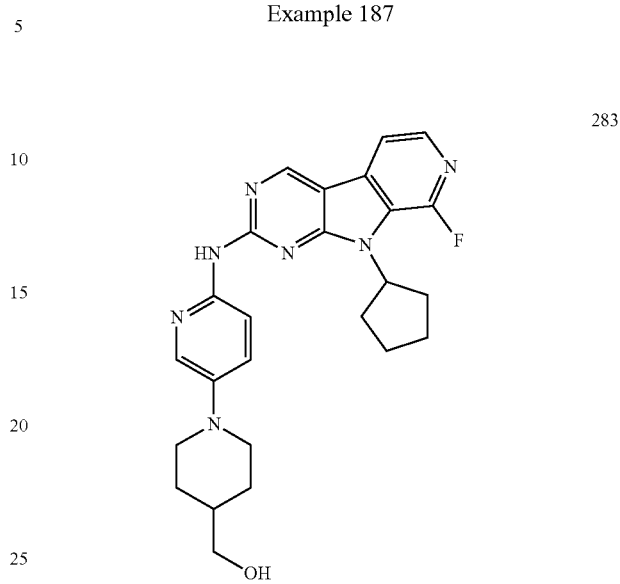

3.11-3.21 (m, 1 H) 3.11-3.22 (m, 1 H) 2.20-2.34 (m, 2 H) 1.88-2.20 (m, 6 H) 1.68-1.87 (m, 2 H) ppm Example 187

(1-(6-((9-Cyclopentyl-8-fluoro-9H-pyrido[4',3':4,5]pyrrolo[2,3-d]pyrimidin-2-yl)amino)-3-pyridinyl)-4-piperidinyl)methanol

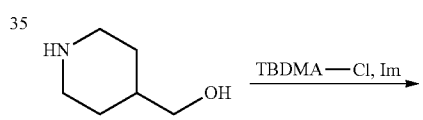

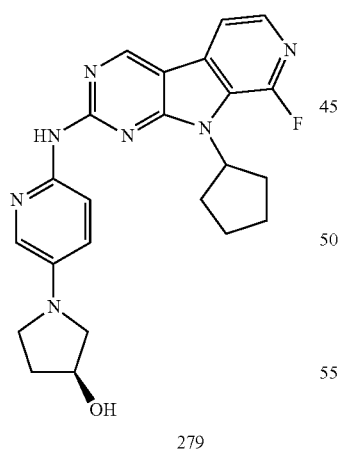

(3S)-1-(6-((9-cyclopentyl-8-fluoro-9H-pyrido[4',3':4,5]pyrrolo[2,3-d]pyrimidin-2-yl)amino)-3-pyridinyl)-3-pyrrolidinol (279): Compound 279 was prepared from compound 280 using methods described in Example 186a. ¹H NMR (500 MHz, DMSO-d₆) δ 9.44-9.57 (m, 1 H) 8.22-8.33 (m, 1 H) 8.09-8.19 (m, 1 H) 7.63-7.73 (m, 3 H) 5.45-5.59 (m, 1 H) 4.39-4.53 (m, 1 H) 3.45-3.53 (m, 2 H) 3.39 (none, 3 H)

4-((t-butyldimethylsilyloxy)methyl)piperidine (284): Piperidin-4-ylmethanol (2.50 g, 21.7 mmol), t-butylchlorodimethylsilane (4.13 g, 23.9 mmol), and imidazole (1.48 g, 21.7 mmol) were dissolved in dichloromethane (25 mL) and stirred at room temperature for 18 hours. The reaction was added to aqueous NaHCO₃ (200 mL, 50% saturated) and extracted with dichloromethane (3×150 mL). The combined organics were dried (MgSO₄) and evaporated to give a yellow oil. Silica gel chromatography (gradient elution dichloromethane+2.5% TEA/0-10% methanol) gave a soft white solid, which was then added to 0.5 M NaOH (100 mL) and extracted with dichloromethane+10% methanol (3×100 mL). The combined organics were dried (MgSO₄) and evaporated to give compound 284 as a pale yellow oil (4.75 g).

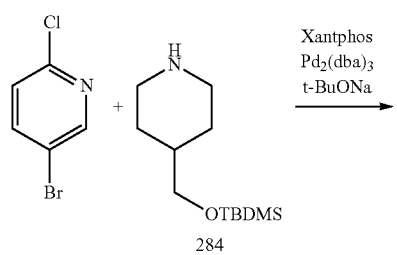

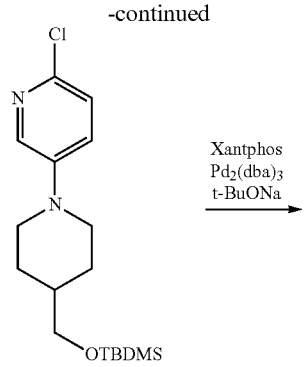

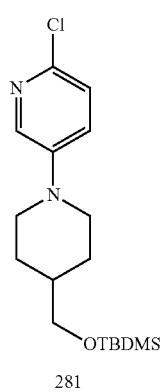

5-(4-((t-butyldimethylsilyloxy)methyl)piperidin-1-yl)-2-chloropyridine (281): 5-Bromo-2-chloropyridine (1.00 g, 5.20 mmol), 4-((t-butyldimethylsilyloxy)-methyl)piperidine (284), (1.19 g, 5.20 mmol), tris(dibenzylideneacetone)dipalladium (0) (0.0952 g, 0.104 mmol), 4,5-bis(diphenylphosphino)-9,9-dimethyl-9H-xanthene (0.180 g, 0.312 mmol), and sodium t-butoxide (0.749 g, 7.79 mmol) were dissolved in 40 mL dioxane under argon. The reaction was heated at 80° C. for 17 hours. The resulting solution was cooled an taken up in ethyl acetate (125 mL) and washed with aqueous $K_2CO_3$, (10%, 100 mL) water (100 mLl), and brine (100 mL). The organic phase was dried ($MgSO_4$) and evaporated to give an orange oil. Silica gel chromatography (gradient elution hexanes/0-10% ethyl acetate) afforded compound 281 as a white solid (158 mg, 9%).

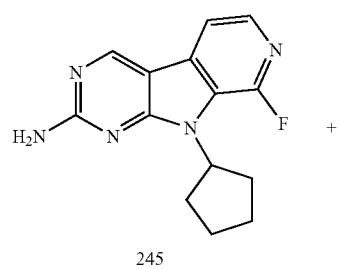

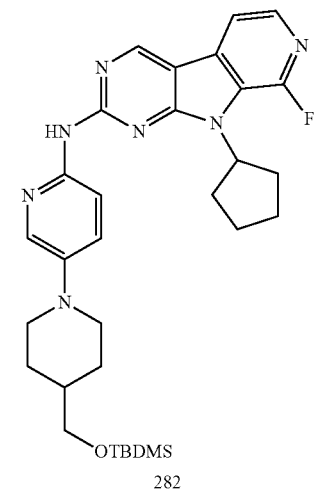

N-(5-(4-((((tert-Butyl(dimethyl)silyl)oxy)methyl)-1-piperidinyl)-2-pyridinyl)-9-cyclopentyl-8-fluoro-9H-pyrido[4',3':4,5]pyrrolo[2,3-d]pyrimidin-2-amine (282): A 10 mL reaction vessel was charged with compound 245 (100 mg, 369 µmol), compound 281 (126 mg, 369 µmol), tris(dibenzylideneacetone)dipalladium (0) (25.3 mg, 27.6 µmol), 4,5-bis(diphenylphosphino)-9,9-dimethyl-9H-xanthene (32.0 mg, 55.3 µmol), sodium t-butoxide (70.8 mg, 737 µmol), and dioxane (1.5 mL).). The reaction was purged with argon and heated with microwave energy (300 W) for 2 hours at 120° C. The resulting solution was added to ethyl acetate (40 mL) and washed with water (30 mL) and brine (30 mL). The organic phase was dried ($MgSO_4$) and evaporated to give an orange oil. Silica gel chromatography (gradient elution hexanes+2.5% TEA/0-35% ethyl acetate+2.5% TEA) afforded compound 282 as a yellow solid (121 mg, 57%).

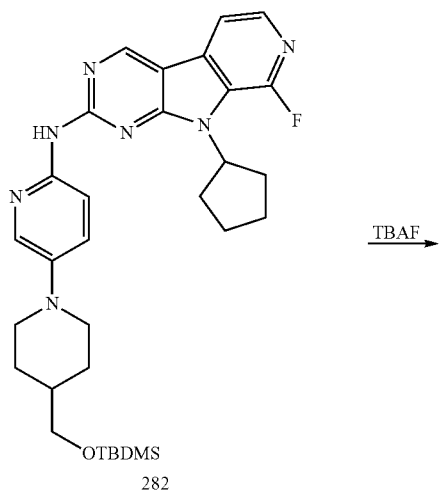

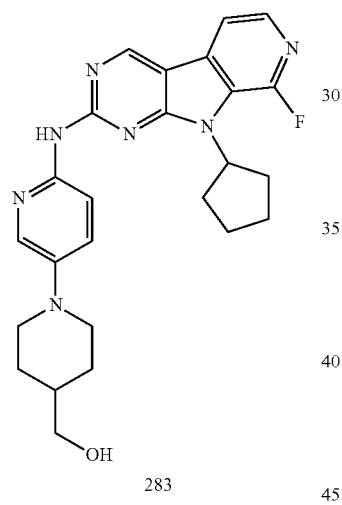

(1-(6-((9-cyclopentyl-8-fluoro-9H-pyrido[4',3':4,5]pyrrolo[2,3-d]pyrimidin-2-yl)-amino)-3-pyridinyl)-4-piperidinyl)methanol (283): Compound 282 (118 mg, 205 µmol) was dissolved in dry THF (3 mL). Tetrabutylammonium fluoride, 1.0M in THF (0.75 mL, 750 µmol) was added and the reaction was stirred at room temperature for 80 minutes. The resulting solution was added to aqueous $K_2CO_3$ (10%, 30 mL) and extracted with dichloromethane+10% methanol (2×30 mL). The combined organics were dried ($MgSO_4$) and evaporated to give an orange oil. Silica gel chromatography (gradient elution ethyl acetate+2.5% TEA/0-5% methanol) afforded a yellow solid. This residue was taken up in methanol (1.5 mL) and HCl in ethanol (1.0M, 0.5 mL) was added. Diethyl ether (20 mL) was added to precipitate the product as a yellow solid, which was filtered and dried in vacuo to give compound 283 as a yellow solid (26 mg, 27%). $^1$H NMR (500 MHz, DMSO-$d_6$) δ 9.87 (s, 1 H) 9.27-9.37 (m, 1 H) 8.11 (d, J=9.05 Hz, 1 H) 7.99-8.06 (m, 4 H) 7.48 (dd, J=9.17, 2.81 Hz, 1 H) 5.46 (quin, J=9.11 Hz, 1 H) 4.50 (t, J=5.26 Hz, 2 H) 3.70 (d, J=11.98 Hz, 2 H) 2.61-2.71 (m, 2 H) 2.35 (d, J=12.72 Hz, 2 H) 2.10 (br. s., 2 H) 1.95-2.06 (m, 2 H) 1.77 (t, 4 H) 1.45-1.59 (m, 1 H) 1.28 (qd, J=12.23, 3.67 Hz, 2 H) ppm.

Example 188

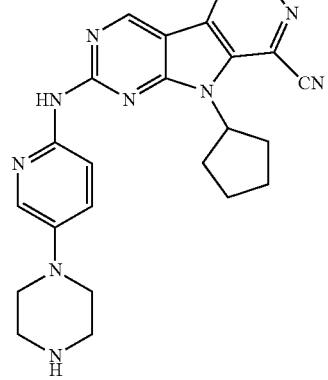

9-Cyclopentyl-2-((5-(1-piperazinyl)-2-pyridinyl)amino)-9H-pyrido[4',3':4,5]pyrrolo[2,3-d]pyrimidine-8-carbonitrile

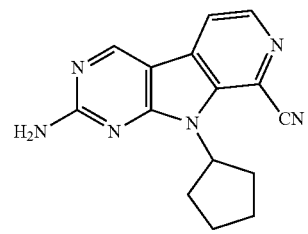

8-Cyano-9-cyclopentyl-9H-pyrido[4',3':4,5]pyrrolo[2,3-d]pyrimidin-2-amine (287): Compound 245 (150 mg, 553 µmol) and tetraethylammonium cyanide (130 mg, 829 µmol) were dissolved in DMSO (3 mL) and heated at 150° C. for 5.5 hours. The reaction was cooled and taken up in ethyl acetate (40 mL). This solution was washed with aqueous $K_2CO_3$ (30 mL), water (30 mL), and brine (30 mL). The organic phase was dried ($MgSO_4$) and evaporated to give an orange solid. Silica gel chromatography (gradient elution hexanes+2.5% TEA/0-70% ethyl acetate+2.5% TEA) afforded compound 287 as a tan solid (104 mg, 68%).

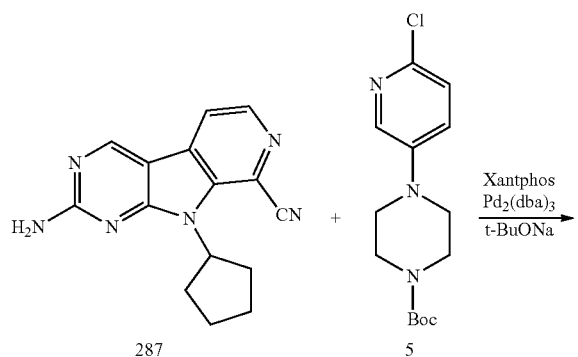
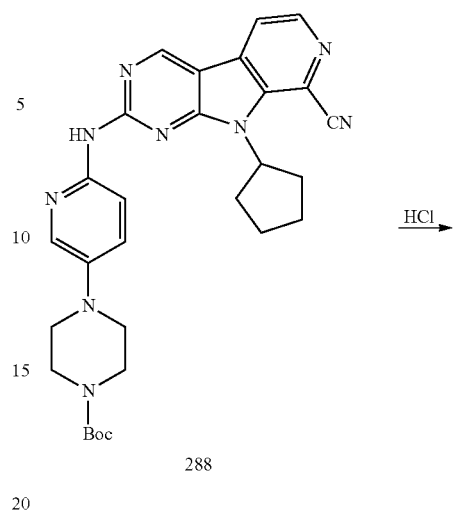

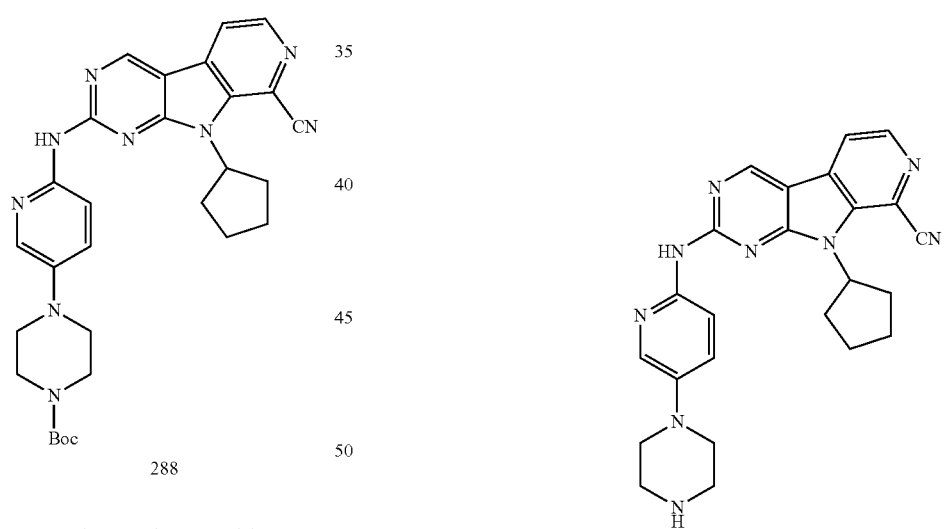

tert-Butyl 4-(6-((8-cyano-9-cyclopentyl-9H-pyrido[4',3':4,5]pyrrolo[2,3-d]pyrimidin-2-yl)amino)-3-pyridinyl)-1-piperazinecarboxylate (288): A 10 mL reaction vessel was charged with compound 287 (75.0 mg, 269 μmol, compound 5 (80.2 mg 269 μmol), tris(dibenzylideneacetone)dipalladium (0) (19.7 mg, 21.6 μmol), 4,5-bis(diphenylphosphino)-9,9-dimethyl-9H-xanthene (24.9 mg, 43.1 μmol), sodium t-butoxide (51.8 mg, 539 μmol), and dioxane (2.5 mL). The reaction was purged with argon and heated with microwave energy (300 W) for 2 hours at 120° C. The solvent was evaporated in vacuo. Silica gel chromatography (gradient elution hexanes+2.5% TEA/0-100% ethyl acetate+2.5% TEA, then ethyl acetate+2.5% TEA/0-5% methanol) afforded compound 288 as a yellow solid (44 mg, 30%).

9-Cyclopentyl-2-((5-(1-piperazinyl)-2-pyridinyl)amino)-9H-pyrido[4',3':4,5]-pyrrolo[2,3-d]pyrimidine-8-carbonitrile (286): Compound 288 (44.0 mg, 81.5 μmol) was suspended in 3 mL methanol. Mmethanol saturated at room temperature with HCl (1 mL) was added, and the reaction stirred at room temperature for 2.5 hours. The solvents were removed in vacuo. The residue was taken up in methanol (10 mL) and stripped again to give compound 286 as a yellow solid (37 mg, 91%). $^1$H NMR (500 MHz, DMSO-$d_6$) δ 1.68-1.80 (m, 2 H) 2.01-2.20 (m, 4 H) 2.64 (none, 2 H) 3.25-3.34 (m, 4 H) 3.34-3.44 (m, 5 H) 5.62-5.73 (m, 1 H) 7.60-7.73 (m, 1 H) 7.98-8.07 (m, 1 H) 8.09-8.16 (m, 1 H) 8.39-8.48 (m, 1 H) 8.58-8.65 (m, 1 H) 8.67-8.80 (m, 2 H) 9.40-9.49 (m, 1 H) 10.32-10.51 (m, 1 H) ppm.

Example 189

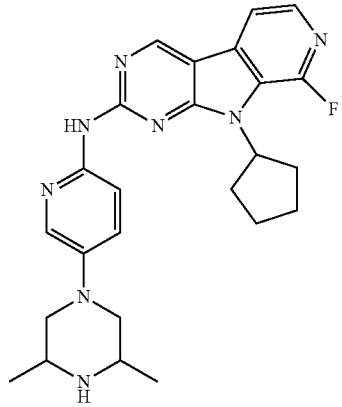

289

9-Cyclopentyl-N-(5-(3,5-dimethyl-1-piperazinyl)-2-pyridinyl)-8-fluoro-9H-pyrido[4',3':4,5]pyrrolo[2,3-d]pyrimidin-2-amine

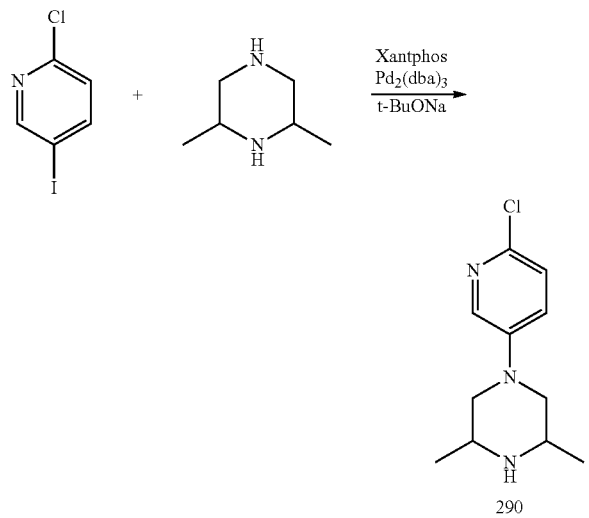

1-(6-chloropyridin-3-yl)-3,5-dimethylpiperazine (290): 2-chloro-5-iodopyridine (1.00 g, 4176 μmol), 2,6-dimethylpiperidine (477 mg, 4.18 mmol), tris(dibenzylideneacetone)-dipalladium (0) (191 mg, 209 μmol), 4,5-bis(diphenylphosphino)-9,9-dimethyl-9H-xanthene (242 mg, 418 μmol), and sodium t-butoxide (803 mg, 8.35 mmol) were dissolved in 20 mL dioxane. The reaction was purged with argon and heated at 80° C. for 4.5 hours. The solvent was removed in vacuo. Silica gel chromatography (gradient elution hexanes+2.5% TEA/0-100% ethyl acetate+2.5% TEA, then ethyl acetate+2.5% TEA/0-5% methanol) afforded compound 290 as an orange solid (545 mg, 58%).

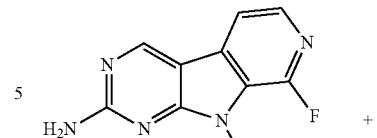

245

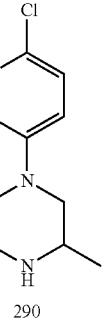

290

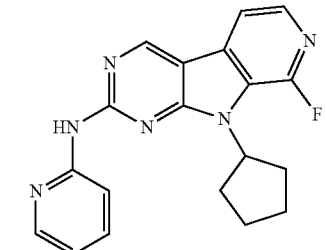

289

9-Cyclopentyl-N-(5-(3,5-dimethyl-1-piperazinyl)-2-pyridinyl)-8-fluoro-9H-pyrido-[4',3':4,5]pyrrolo[2,3-d]pyrimidin-2-amine (289): A 10 mL reaction vessel was charged with compound 245 (80.0 mg, 295 μmol), 1-(6-chloropyridin-3-yl)-3,5-dimethylpiperazine (66.6 mg, 295 μmol), tris(dibenzylideneacetone)dipalladium (0) (20.3 mg, 22.1 μmol), 4,5-bis(diphenylphosphino)-9,9-dimethyl-9H-xanthene (25.6 mg, 44.2 μmol), sodium t-butoxide (56.7 mg, 590 μmol), and dioxane (2.5 mL). The reaction was purged with argon and heated with microwave energy (300 W) for 3.5 hours at 120° C. The reaction was taken up in ethyl acetate (40 mL) and washed with water (30 mL) and brine (30 mL). The organic phase was dried (MgSO$_4$) and evaporated to give an orange oil. Silica gel chromatography (gradient elution hexanes+2.5% TEA/0-100% ethyl acetate+2.5% TEA, then ethyl acetate+2.5% TEA, 0-8% methanol) afforded a yellow solid. This residue was taken up in 2 mL methanol (2 mL) and 1M ethanolic HCl (1 mL) was added, followed by the addition of diethyl ether (20 mL). The resulting precipitate was collected and dried in vacuo to give compound 289 as a yellow solid (91 mg, 67%) $^1$H NMR (500 MHz, DMSO-d$_6$) δ 9.54-9.67 (m, 2 H) 9.47-9.54 (m, 1 H) 9.05-9.23 (m, 1 H) 8.19-8.30 (m, 1 H) 8.06-8.17 (m, 3 H) 7.94-8.04 (m, 1 H) 7.81-7.94 (m, 1 H) 5.45-5.58 (m, 1 H) 3.81-3.94 (m, 2 H) 3.34-3.48 (m, 2 H)

2.75-2.91 (m, 2 H) 2.23-2.35 (m, 2 H) 2.10-2.20 (m, 2 H) 2.05 (none, 2 H) 1.68-1.86 (m, 2 H) 1.34 (d, J=6.60 Hz, 7 H) ppm.

Example 190

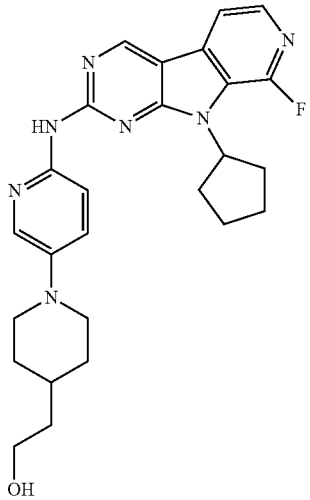

2-(1-(6-((9-Cyclopentyl-8-fluoro-9H-pyrido[4',3':4,5]pyrrolo[2,3-d]pyrimidin-2-yl)amino)-3-pyridinyl)-4-piperidinyl)ethanol

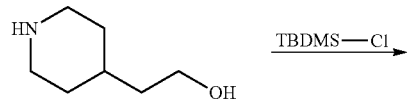

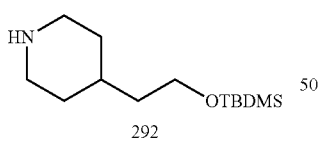

4-(2-(t-Butyldimethylsilyloxy)ethyl)piperidine (292): 2-(piperidin-4-yl)ethanol (2.00 g, 15.5 mmol), t-butylchlorodimethylsilane (2.57 g, 17.0 mmol), and imidazole (1.05 g, 15.5 mmol) were taken up in dichloromethane (15 mL) and stirred for 22 hours. This solution was added to aqueous K₂CO₃ (80 mL) and extracted with dichloromethane (3×30 mL). The combined organics were dried (MgSO₄) and evaporated to give a pale yellow oil. Silica gel chromatography (gradient elution dichloromethane+2.5% TEA/0-10% methanol) afforded a white solid. This solid was added to aqueous K₂CO₃ (60 mL) and extracted with dichloromethane+10% methanol (3×30 mL), the organics dried (MgSO₄) and evaporated to give compound 292 as a yellow oil (3.24 g, 86%).

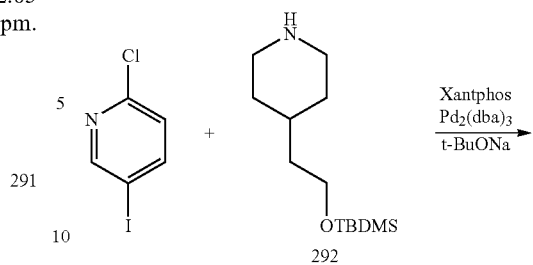

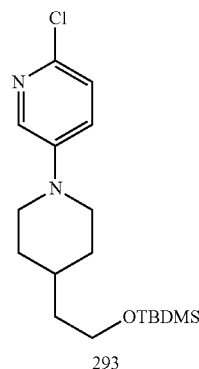

5-(4-(2-(t-Butyldimethylsilyloxy)ethyl)piperidin-1-yl)-2-chloropyridine (293): 2-chloro-5-iodopyridine (1.00 g, 4.18 mmol), compound 292 (1.02 g, 4.18 mmol), Tris(dibenzylideneacetone)dipalladium (0) (0.191 g, 0.209 mmol), 4,5-bis(diphenylphosphino)-9,9-dimethyl-9H-xanthene (0.242 g, 0.418 mmol), and sodium t-butoxide (0.803 g, 8.35 mmol) were dissolved in 20 mL dioxane. The reaction was purged with argon and heated at 80° C. for 16 hours. The solvent was removed in vacuo and silica gel chromatography (gradient elution hexanes/0-10% ethyl acetate) afforded compound 293 as a beige solid (597 mg, 40%).

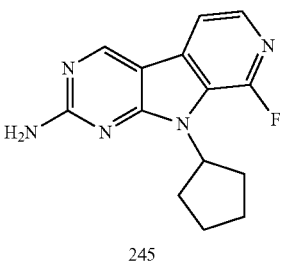 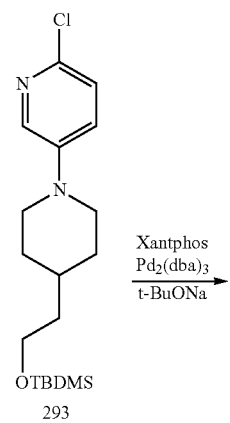

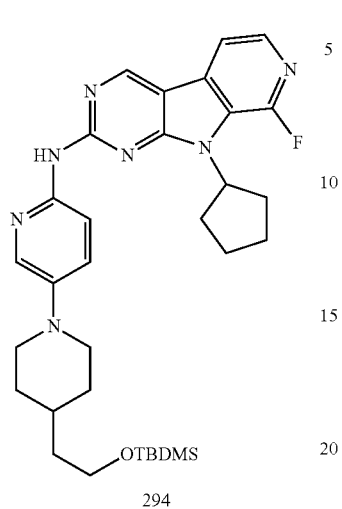

294

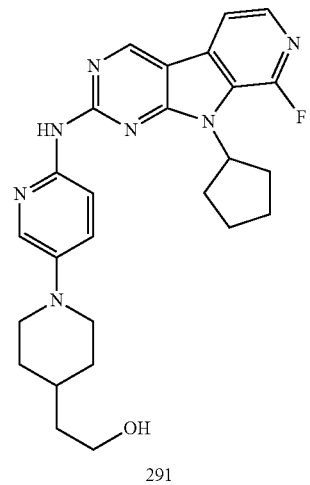

291

N-(5-(4-(2-((tert-butyl(dimethyl)silyl)oxy)ethyl)-1-piperidinyl)-2-pyridinyl)-9-cyclopentyl-8-fluoro-9H-pyrido[4',3':4,5]pyrrolo[2,3-d]pyrimidin-2-amine (294): A 10 mL microwave reaction tube was charged with compound 245 (80.0 mg, 295 μmol), 5-(4-(2-(t-butyldimethylsilyloxy)ethyl)piperidin-1-yl)-2-chloropyridine (293) (105 mg, 295 μmol), tris(dibenzylideneacetone)dipalladium (0) (20.3 mg, 22.1 μmol), 4,5-bis(diphenylphosphino)-9,9-dimethyl-9H-xanthene (25.6 mg, 44.2 μmol), sodium t-butoxide (56.7 mg, 590 μmol), and dioxane (3 mL). The reaction was purged with argon and heated with microwave energy (300 W) for 3.5 hours at 120° C. The reaction was taken up in ethyl acetate (40 mL) and washed with water (30 mL) and brine (30 mL). The organic phase was dried (MgSO$_4$) and evaporated to give an orange oil. Silica gel chromatography (gradient elution hexanes+2.5% TEA/0-100% ethyl acetate+2.5% TEA) afforded compound 294 as a yellow solid (113 mg, 65%).

2-(1-(6-((9-Cyclopentyl-8-fluoro-9H-pyrido[4',3':4,5]pyrrolo[2,3-d]pyrimidin-2-yl)amino)-3-pyridinyl)-4-piperidinyl)ethanol (291): Compound 294 (78 mg, 132 mop was dissolved in dry THF (3 mL). Tetrabutylammonium fluoride, 1.0M in THF (1.00 mL, 1.00 mmol) was added and the reaction stirred at room temperature for 4 hours. The solvent was removed in vacuo and silica gel chromatography (gradient elution hexanes+2.5%/0-100% ethyl acetate+2.5% TEA) afforded compound 291 as a beige solid (44 mg, 70%). $^1$H NMR (500 MHz, DMSO-d$_6$) δ 11.60-11.85 (m, 2 H) 9.49 (s, 2 H) 8.19-8.24 (m, 2 H) 8.13-8.19 (m, 2 H) 8.05-8.10 (m, 2 H) 7.96-8.04 (m, 2 H) 7.61-7.71 (m, 2 H) 5.48 (s, 1 H) 3.64 (d, J=11.98 Hz, 2 H) 3.44 (t, J=6.48 Hz, 2 H) 2.71-2.90 (m, 2 H) 2.20 (br. s., 2 H) 2.09 (br. s., 2 H) 2.00 (br. s., 2 H) 1.66-1.82 (m, 4 H) 1.52-1.66 (m, 1 H) 1.37 (d, J=6.60 Hz, 2 H) 1.28 (none, 2 H) ppm.

Example 191

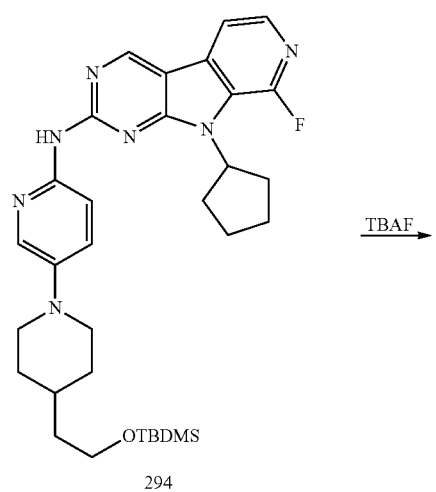

294

TBAF→

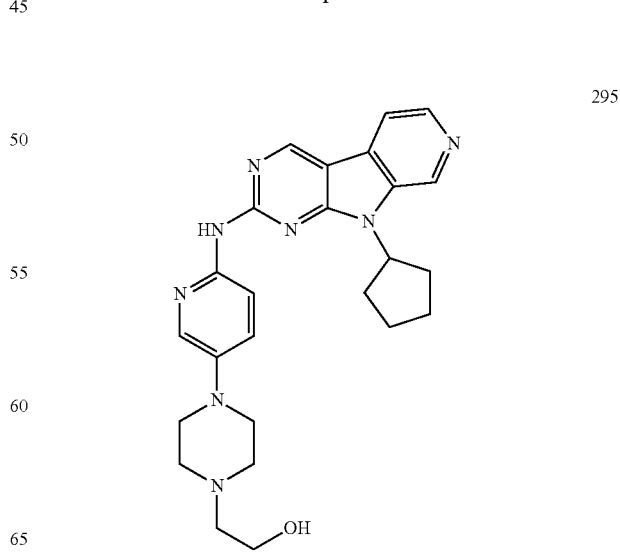

295

249

2-(4-(6-((9-Cyclopentyl-9H-pyrido[4',3':4,5]pyrrolo[2,3-d]pyrimidin-2-yl)amino)-3-pyridinyl)-1-piperazinyl)ethanol

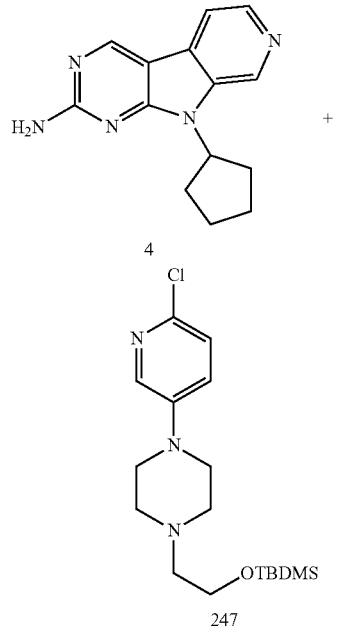

250

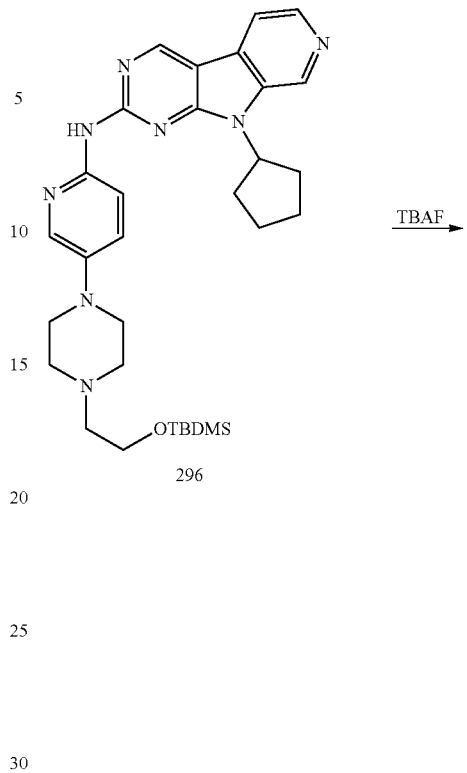

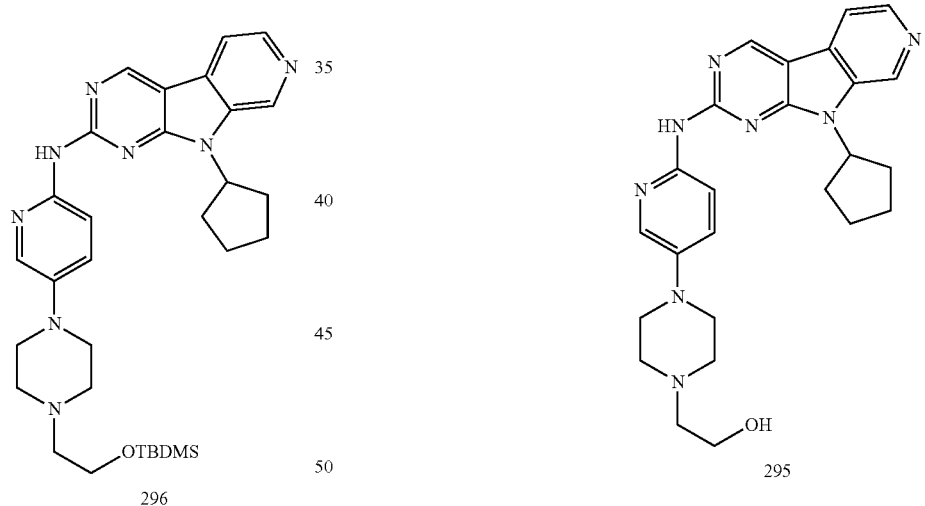

N-(5-(4-(2-((tert-butyl(dimethyl)silyl)oxy)ethyl)-1-piperazinyl)-2-pyridinyl)-9-cyclopentyl-9H-pyrido[4',3':4,5]pyrrolo[2,3-d]pyrimidin-2-amine (296): A 10 mL reaction vessel was charged with compound 4 (153 mg, 604 μmol), compound 247 (215 mg, 604 μmol), tris(dibenzylideneacetone)-dipalladium (0) (41.5 mg, 45.3 μmol), sodium t-butoxide (69.7 mg, 725 μmol), 4,5-bis(diphenylphosphino)-9,9-dimethyl-9H-xanthene (52.4 mg, 90.6 μmol), and dioxane (3 mL). The reaction was purged with argon and heated with microwave energy at 120° C. for 3.5 hours. The solvent was removed in vacuo and silica gel chromatography (gradient elution hexanes+2.5%/0-100% ethyl acetate+2.5% TEA, then ethyl acetate+2.5% TEA/0-5% methanol) afforded compound 296 as a yellow solid (85 mg, 25%).

2-(4-(6-((9-Cyclopentyl-9H-pyrido[4',3':4,5]pyrrolo[2,3-d]pyrimidin-2-yl)amino)-3-pyridinyl)-1-piperazinyl)ethanol (295): Compound 296 (85.0 mg, 148 μmol) was dissolved in dry THF (3 mL).). Tetrabutylammonium fluoride, 1.0M in THF (1.00 mL, 1.00 mmol) was added and the reaction stirred at room temperature for 2 hours. The solvent was removed in vacuo and silica gel chromatography (gradient elution hexanes+2.5%/0-100% ethyl acetate+2.5% TEA, then ethyl acetate+2.5% TEA/0-5% methanol) afforded a yellow solid. This residue was taken up in methanol (3 mL) and 1M ethanolic HCl (1 mL). Diethyl ether (20 mL) was added to precipitate the product, which was filtered and dried in vacuo to give compound 295 as a yellow solid (54 mg, 79%). $^1$H NMR (500 MHz, DMSO-$d_6$) δ 10.75-10.97 (m, 2 H) 9.70 (s, 2 H) 9.47 (s, 1 H) 8.74 (d, J=3.67 Hz, 2 H) 8.16 (d, J=2.45 Hz, 1 H) 7.99-8.10 (m, 1 H) 7.84-7.99 (m, 1 H) 5.30-5.52 (m, 1 H)

3.81-3.96 (m, 4 H) 3.62-3.72 (m, 2 H) 3.20-3.36 (m, 6 H) 2.39-2.49 (m, 2 H) 2.02-2.20 (m, 4 H) 0.88 (d, J=6.85 Hz, 2 H) ppm.

Example 192

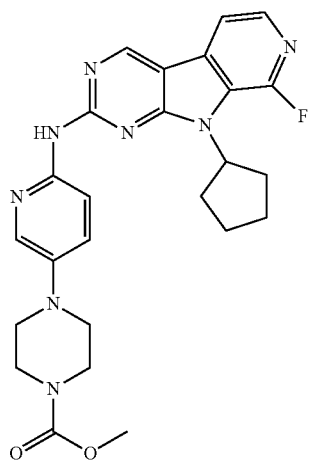

298

Methyl 4-(6-((9-cyclopentyl-8-fluoro-9H-pyrido[4', 3':4,5]pyrrolo[2,3-d]pyrimidin-2-yl)amino)-3-pyridinyl)-1-piperazinecarboxylate

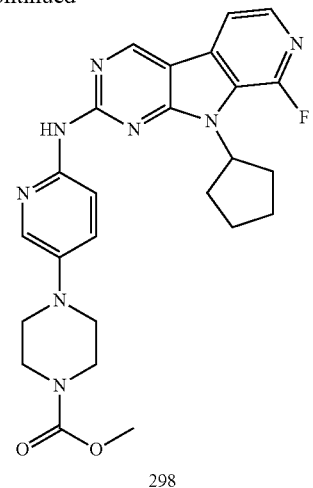

298

Methyl 4-(6-((9-cyclopentyl-8-fluoro-9H-pyrido[4',3':4, 5]pyrrolo[2,3-d]pyrimidin-2-yl)amino)-3-pyridinyl)-1-piperazinecarboxylate (298): Compound 92 (68.9 mg, 0.159 mmol) was partially dissolved in DMF (2 mL) and DIEA (0.200 mL, 1.15 mmol).). Methyl chloroformate (0.0122 mL, 0.159 mmol) was added and the reaction stirred at room temperature 16 for hours. The reaction mixture was diluted with dichloromethane+10% methanol (30 mL) and added to aqueous K$_2$CO$_3$ (10%, 30 mL). The layers were separated and the aqueous phase extracted with dichloromethane+10% methanol (2×30 mL) The combined organics were dried (MgSO$_4$) and evaporated to give a yellow oil. Preparative reverse phase HPLC (gradient elution 0.1% TFA in water/10-70% acetonitrile) afforded a yellow oil. This residue was taken up in aqueous K$_2$CO$_3$ and extracted with dichloromethane+10% methanol (3×30 mL). The combined organics were dried (MgSO$_4$) and evaporated to give a yellow solid. This was taken up in methanol (2 mL) and 1M HCl in ethanol (0.5 mL) was added. Diethyl ether (10 mL) was added to precipitate the product, which was filtered and dried in vacuo to give compound 298 as a yellow solid (24 mg, 31%). $^1$H NMR (500 MHz, DMSO-d$_6$) δ 9.54-9.66 (m, 1 H) 8.30-8.39 (m, 1 H) 8.12-8.25 (m, 2 H) 7.98-8.09 (m, 1 H) 7.68-7.84 (m, 1 H) 5.51-5.65 (m, 1 H) 3.71 (s, 4 H) 3.57-3.66 (m, 5 H) 3.20-3.34 (m, 5 H) 2.25-2.40 (m, 2 H) 2.14-2.25 (m, 2 H) 2.02-2.14 (m, 2 H) 1.83 (none, 2 H) ppm.

Example 193

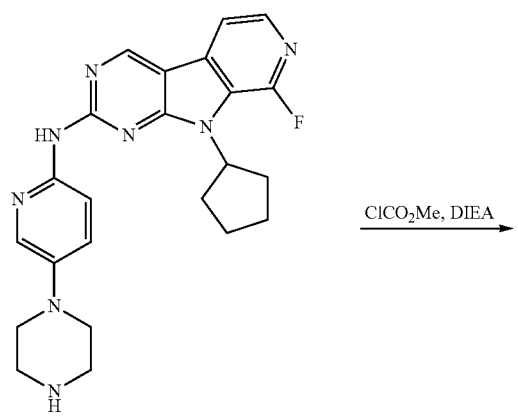

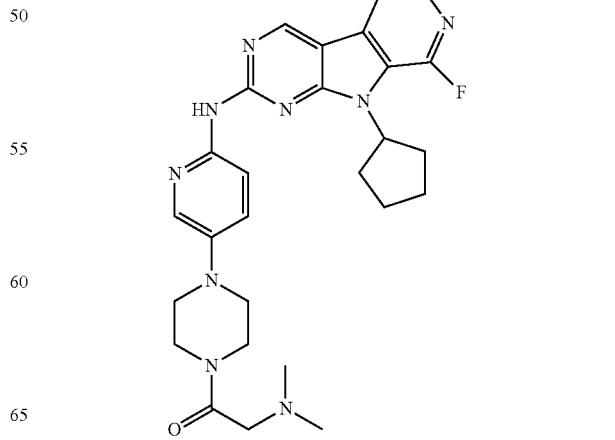

253

9-Cyclopentyl-N-(5-(4-((dimethylamino)acetyl)-1-piperazinyl)-2-pyridinyl)-8-fluoro-9H-pyrido[4',3':4,5]pyrrolo[2,3-d]pyrimidin-2-amine

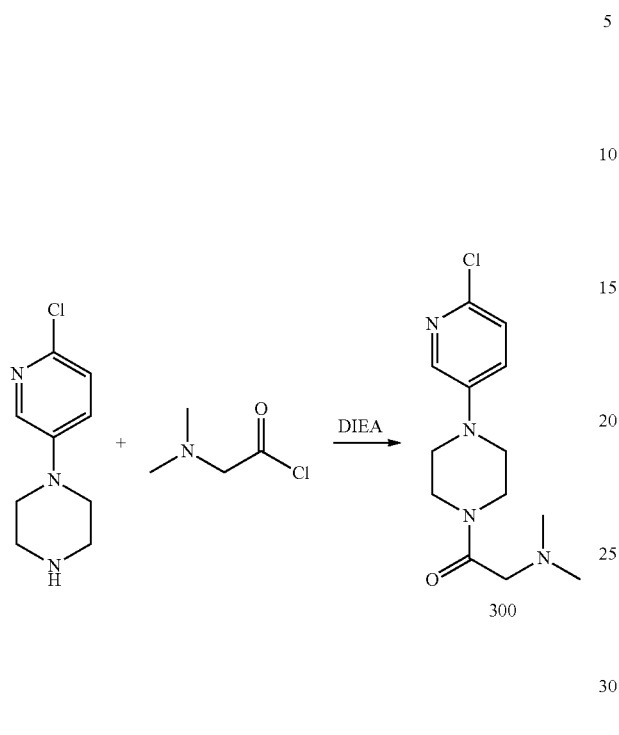

1-(4-(6-chloropyridin-3-yl)piperazin-1-yl)-2-(dimethylamino)ethanone (300): 1-(6-chloropyridin-3-yl)piperazine (250 mg, 1265 μmol) and dimethylaminoacetyl chloride hydrochloride, 85% (260 mg, 1644 μmol) were dissolved in DMF (6 mL) and DIEA (661 μl, 3794 μmol).). The reaction was stirred at room temperature for 4 hours and then 20 hours at 60° C. The resulting solution was taken up in ethyl acetate 80 mL) and washed with aqueous K$_2$CO$_3$ (10%, 70 mL), water (70 mL), and brine (70 mL). The organic phase was dried (MgSO$_4$) and evaporated to give a brown oil. Silica gel chromatography (gradient elution dichloromethane/0-10% 2M NH$_3$ in methanol) afforded compound 300 as an orange tar (174 mg, 49%).

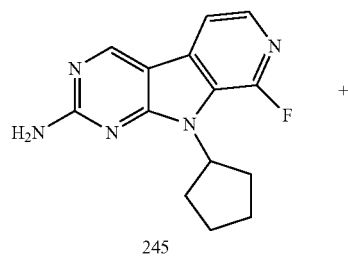

245

254

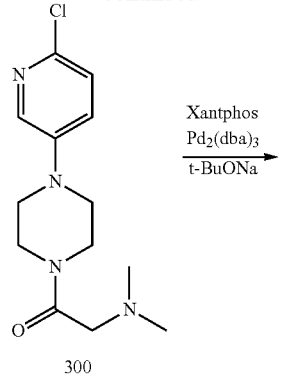

300

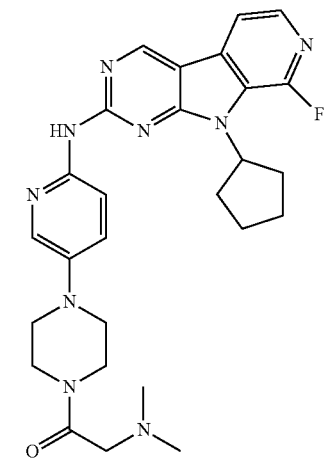

299

9-Cyclopentyl-N-(5-(4-(((dimethylamino)acetyl)-1-piperazinyl)-2-pyridinyl)-8-fluoro-9H-pyrido[4',3':4,5]pyrrolo[2,3-d]pyrimidin-2-amine (299): A 10 mL reaction vessel was charged with compound 245 (100 mg, 369 μmol), compound 300 (109 mg, 387 μmol), tris(dibenzylideneacetone)dipalladium (0) (25.3 mg, 27.6 μmol), 4,5-bis(diphenylphosphino)-9,9-dimethyl-9H-xanthene (32.0 mg, 55.3 μmol), sodium t-butoxide (70.8 mg, 737 μmol), and dioxane (2.5 mL). The reaction was purged with argon and heated with microwave energy (300 W) for 2.5 hours at 120° C. The reaction was added to aqueous K$_2$CO$_3$ (10%, 30 mL) and extracted with dichloromethane+10% methanol (3×30 mL). The combined organics were dried (MgSO$_4$) and evaporated to give an orange oil. Preparative reverse phase HPLC (gradient elution 0.1% TFA in water/10-70% acetonitrile) afforded. a yellow oil. This residue was taken up in aqueous K$_2$CO$_3$ (30 mL) and extracted with dichloromethane+10% methanol (3×30 mL). The combined organics were dried (MgSO$_4$) and evaporated to give a yellow solid. This was taken up in methanol (2 mL) and 1M HCl in ethanol (0.5 mL) was added. Diethyl ether (10 mL) was added to precipitate the product, which was filtered and dried in vacuo to give compound 299 as a yellow solid (32 mg, 17%). $^1$H NMR (500 MHz, DMSO-d$_6$) δ 9.43-9.61 (m, 1 H) 9.27-9.40 (m, 1 H) 8.01-8.12 (m, 1 H) 7.91-8.01 (m, 1 H) 7.75-7.91 (m, 3 H) 7.62-7.75 (m, 1 H) 5.27-5.42 (m, 1 H) 4.14-4.28 (m, 3 H) 3.10-3.18 (m, 3 H) 3.06 (none, 3 H) 2.68

(d, J=4.65 Hz, 8 H) 2.06-2.18 (m, 2 H) 1.93-2.06 (m, 2 H) 1.80-1.93 (m, 3 H) 1.48-1.69 (m, 3 H) ppm.

Example 194

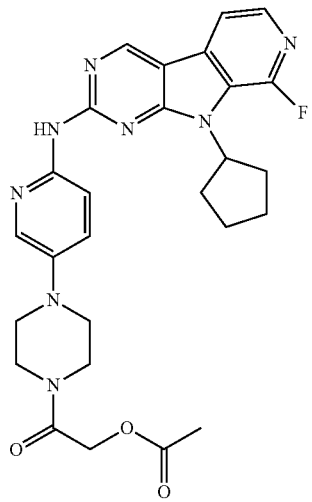

2-(4-(6-((9-cyclopentyl-8-fluoro-9H-pyrido[4',3':4,5]pyrrolo[2,3-d]pyrimidin-2-yl)amino)-3-pyridinyl)-1-piperazinyl)-2-oxoethyl acetate

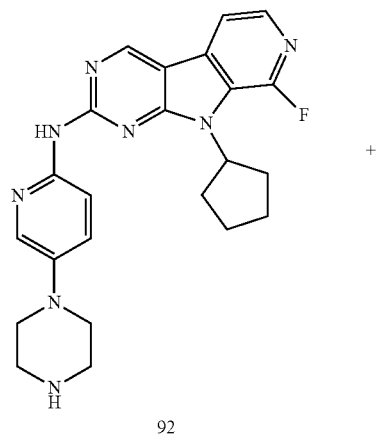

92

+

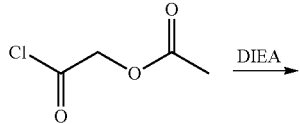

-continued

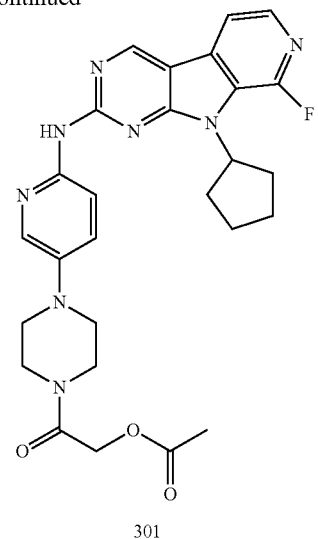

301

2-(4-(6-((9-Cyclopentyl-8-fluoro-9H-pyrido[4',3':4,5]pyrrolo[2,3-d]pyrimidin-2-yl)amino)-3-pyridinyl)-1-piperazinyl)-2-oxoethyl acetate (301): Compound 92 (75.0 mg, 173 μmol) was partially dissolved in DMF (2 mL) and DIEA (0.200 mL, 1148 μmol). Acetoxyacetyl chloride (0.0196 mL, 182 μmol) was added and the reaction was stirred at room temperature 16 for hours. The reaction was added to aqueous $K_2CO_3$ (10%, 30 mL) and extracted with dichloromethane+10% methanol (3×30 mL). The combined organics were dried ($MgSO_4$) and evaporated to give an orange oil. Preparative reverse phase HPLC (gradient elution 0.1% TFA in water/10-70% acetonitrile) afforded a yellow oil. This residue was taken up in aqueous $K_2CO_3$ (30 mL) and extracted with dichloromethane+10% methanol (3×30 mL). The combined organics were dried ($MgSO_4$) and evaporated to give a yellow solid. This was taken up in methanol (2 mL) and 1M HCl in ethanol (0.5 mL) was added. Diethyl ether (10 mL) was added to precipitate the product, which was filtered and dried in vacuo to give compound 301 as a yellow solid (24 mg, 26%). LCMS M+1 found 533.2 calculated 533.2

Example 195

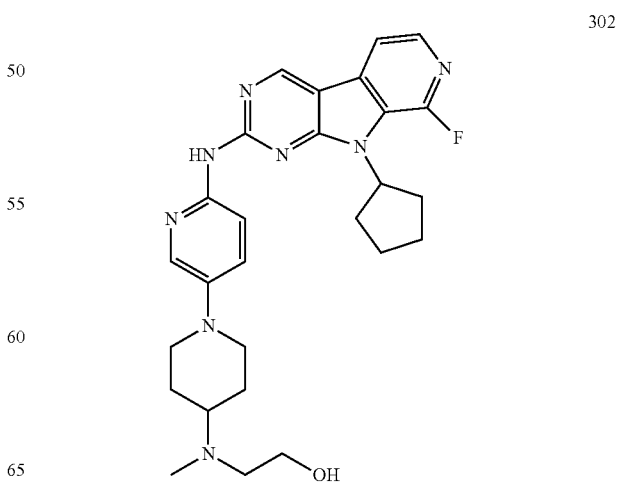

257

2-((1-(6-((9-Cyclopentyl-8-fluoro-9H-pyrido[4',3':4,5]pyrrolo[2,3-d]pyrimidin-2-yl)amino)-3-pyridinyl)-4-piperidinyl)(methyl)amino)ethanol

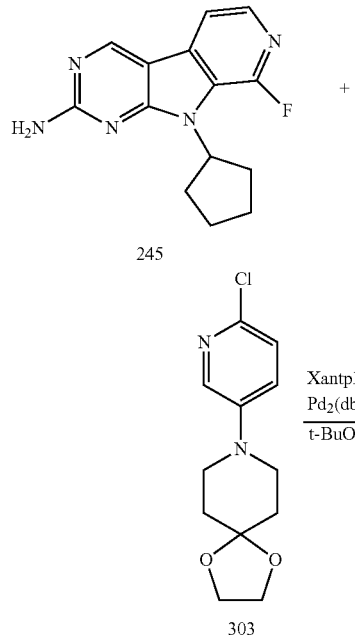

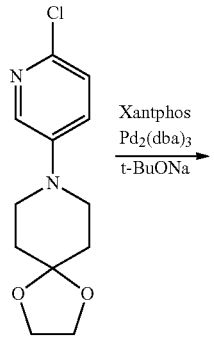

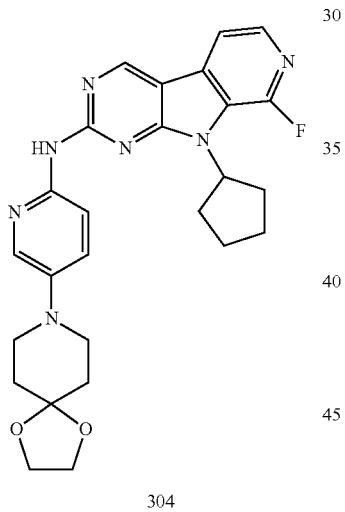

9-Cyclopentyl-N-(5-(1,4-dioxa-8-azaspiro[45]dec-8-yl)-2-pyridinyl)-8-fluoro-9H-pyrido[4',3':4,5]pyrrolo[2,3-d]pyrimidin-2-amine (304): A 35 mL reaction vessel was charged with compound 245 (300 mg, 1.10 mmol), compound 303 (see example 436) [Schön, U. et al. *Tetrahedron Lett.* 2007, 48, (14), 2519-2525] (310 mg, 1.22 mmol), tris(dibenzylideneacetone)dipalladium (0) (75.9 mg, 82.9 µmol), 4,5-bis(diphenylphosphino)-9,9-dimethyl-9H-xanthene (96.0 mg, 0.166 mmol), sodium t-butoxide (213 mg, 2.21 mmol), and dioxane (10 mL). The reaction was purged with argon and heated with microwave energy (300 W) for 3 hours at 120° C. The reaction was added to aqueous $K_2CO_3$ (10%, 30 mL) and extracted with dichloromethane+10% methanol (3×30 mL). The combined organics were dried ($MgSO_4$) and evaporated to give a yellow solid. Silica gel chromatography (gradient elution hexanes+2.5% TEA/50-100% ethyl acetate+2.5% TEA) afforded compound 304 as a yellow solid (228 mg, 42%).

258

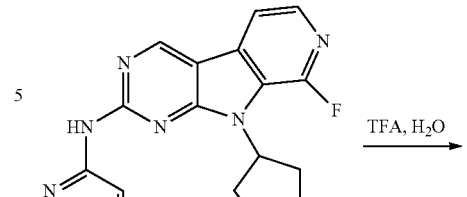

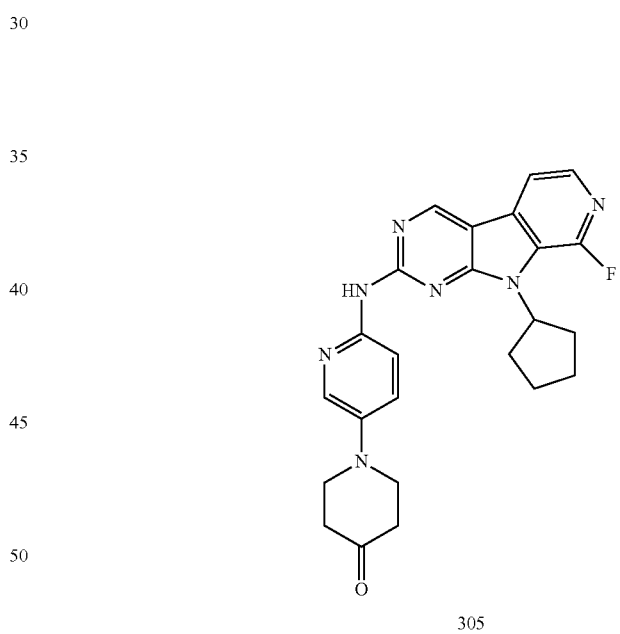

1-(6-((9-Cyclopentyl-8-fluoro-9H-pyrido[4',3':4,5]pyrrolo[2,3-d]pyrimidin-2-yl)amino)-3-pyridinyl)-4-piperidinone (305): Compound 245 (200 mg, 0.41 mmol) was dissolved in a solution of water (0.150 mL, 8.33 mmol) in trifluoroacetic acid (3.00 mL, 38.9 mmol). The solution was stirred at room temperature for 2 hours and then poured into aqueous $K_2CO_3$ (10%, 30 mL). This was extracted with dichloromethane+10% methanol (3×30 mL), and the combined organics were dried ($MgSO_4$) and evaporated to give a yellow solid. Silica gel chromatography (gradient elution hexanes+2.5% TEA/50-100% ethyl acetate+2.5% TEA) afforded compound 305 as a yellow solid (156 mg, 86%).

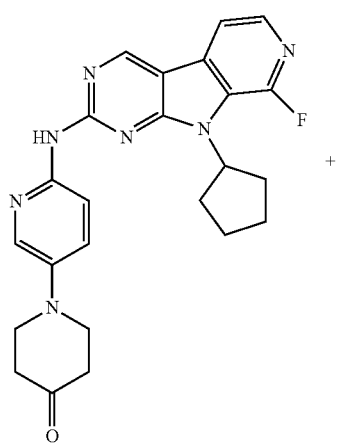

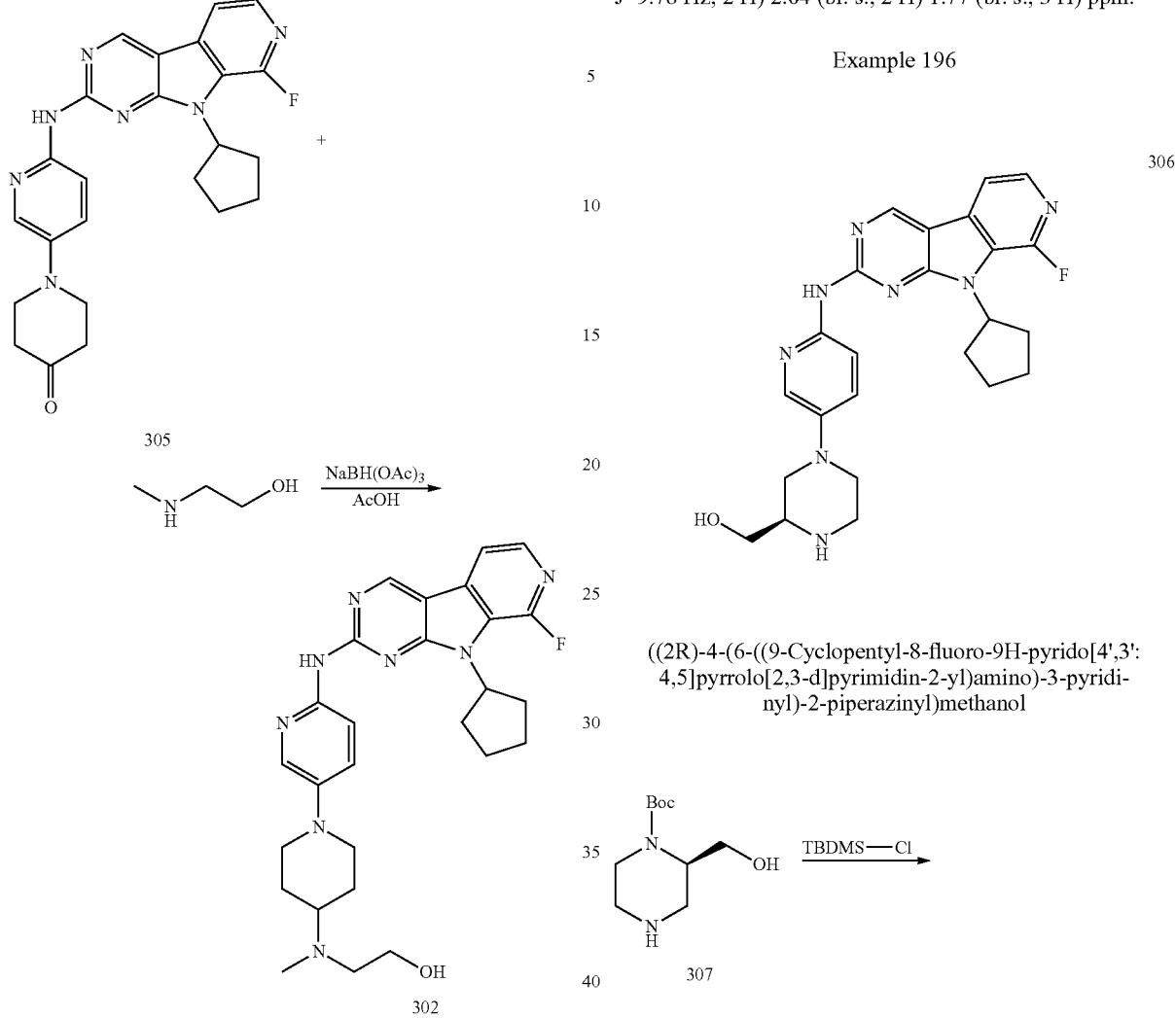

2-(((1-(6-((9-Cyclopentyl-8-fluoro-9H-pyrido[4',3':4,5]pyrrolo[2,3-d]pyrimidin-2-yl)amino)-3-pyridinyl)-4-piperidinyl)(methyl)amino)ethanol (302): Compound 305 (75.0 mg, 168 µmol), 2-(methylamino)ethanol (20.2 µl, 253 µmol), sodium triacetoxyborohydride (53.5 mg, 253 µmol), and acetic acid (9.64 µl, 168 µmol) in dichloroethane (2 mL) were stirred at room temperature for 45 hours. The reaction was diluted with dichloromethane+10% methanol (30 mL) and added to aqueous K₂CO₃ (10%, 30 mL). The layers were separated and the aqueous phase extracted with dichloromethane+10% methanol (2×30 mL). The combined organics were dried (MgSO₄) and evaporated to give a yellow oil. Silica gel chromatography (gradient elution ethyl acetate+ 2.5% TEA/6% 2M NH₃ in methanol) afforded a yellow solid. This residue was taken up in methanol (2 mL) and 1M ethanolic HCl (1 mL). Diethyl ether (20 mL) was added to precipitate the product, which was filtered and dried in vacuo to give compound 302 as a yellow solid (32 mg, 38%). $^1$H NMR (500 MHz, DMSO-d$_6$) δ 9.48 (s, 1 H) 8.16-8.25 (m, 1 H) 8.11 (br. s., 1 H) 8.06 (br. s., 1 H) 7.91-8.01 (m, 1 H) 7.83-7.92 (m, 1 H) 5.42-5.59 (m, 1 H) 3.88 (d, J=11.74 Hz, 2 H) 3.81 (br. s., 2 H) 3.58 (s, 3 H) 3.48 (d, J=2.93 Hz, 3 H) 3.27-3.37 (m, 2 H) 3.18 (s, 1 H) 3.06-3.15 (m, 1 H) 2.80-2.86 (m, 1 H) 2.78 (d, J=4.89 Hz, 3 H) 2.25-2.35 (m, 1 H) 2.18-2.25 (m, 1 H) 2.14 (d, J=9.78 Hz, 2 H) 2.04 (br. s., 2 H) 1.77 (br. s., 3 H) ppm.

Example 196

((2R)-4-(6-((9-Cyclopentyl-8-fluoro-9H-pyrido[4',3':4,5]pyrrolo[2,3-d]pyrimidin-2-yl)amino)-3-pyridinyl)-2-piperazinyl)methanol

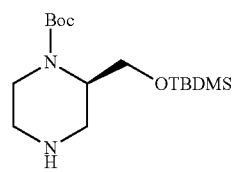

(R)-t-Butyl 2-((t-butyldimethylsilyloxy)methyl)piperazine-1-carboxylate (308): (R)-t-Butyl 2-(hydroxymethyl)piperazine-1-carboxylate (1.15 g, 5.32 mmol), t-butylchlorodimethylsilane (0.882 g, 5.85 mmol), and imidazole (0.796 g, 11.7 mmol) were stirred in dichloromethane (3 mL) for three days. The solution was added to aqueous K₂CO₃ (30 mL) and extracted with dichloromethane (3×30 mL). The combined organics were dried (MgSO₄) and evaporated to give a yellow oil. Silica gel chromatography (gradient elution hexanes/0-50% ethyl acetate) afforded compound 308 as a colorless oil (1.06 g, 60%).

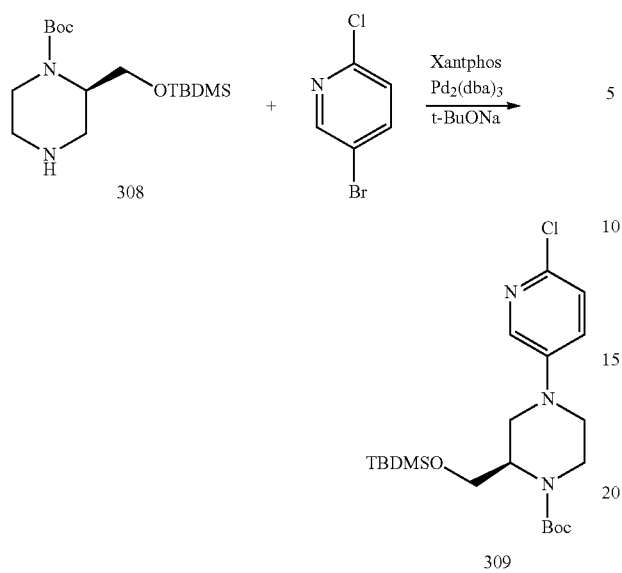
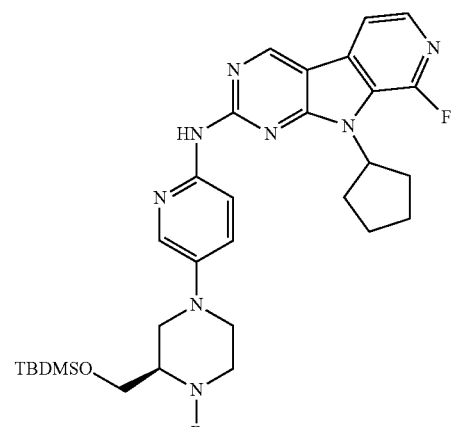

(R)-t-butyl 2-((t-butyldimethylsilyloxy)methyl)-4-(6-chloropyridin-3-yl)piperazine-1-carboxylate (309): Compound 308 (361 mg, 1091 μmol), 5-bromo-2-chloropyridine (200 mg, 1039 μmol), Tris(dibenzylideneacetone)dipalladium (0) (71.4 mg, 77.9 μmol), 4,5-bis(diphenylphosphino)-9,9-dimethyl-9H-xanthene (90.2 mg, 156 μmol), and sodium t-butoxide (200 mg, 2079 μmol) were taken up in toluene (5 mL). The reaction was purged with argon and heated at 80° C. for 5 hours. The resulting solution was added to aqueous K$_2$CO$_3$ (10%, 30 mL) and extracted with dichloromethane+ 10% methanol (3×30 mL). The combined organics were dried (MgSO$_4$) and evaporated to give an orange tar. Silica gel chromatography (gradient elution hexanes/0-20% ethyl acetate) afforded compound 309 as a pale yellow oil (219 mg, 48%).

tert-Butyl (2R)-2-(((tert-butyl(dimethyl)silyl)oxy)methyl)-4-(6-((9-cyclopentyl-8-fluoro-9H-pyrido[4',3':4,5]pyrrolo[2,3-d]pyrimidin-2-yl)amino)-3-pyridinyl)-1-piperazinecarboxylate (310): A 10 mL reaction vessel was charged with compound 245 (83.0 mg, 306 μmol), compound 309 (135 mg, 306 μmol), tris(dibenzylideneacetone)dipalladium (0) (21.0 mg, 22.9 μmol), 4,5-bis(diphenylphosphino)-9,9-dimethyl-9H-xanthene (26.6 mg, 45.9 μmol), sodium t-butoxide (58.8 mg, 612 μmol), and dioxane (2.5 mL). The reaction was purged with argon and heated with microwave energy (300 W) for 2 hours at 120° C. The resulting solution was added to aqueous K$_2$CO$_3$ (30 mL) and extracted with dichloromethane+10% methanol (3×30 mL). The combined organics were dried (MgSO$_4$) and evaporated to give a yellow oil. Silica gel chromatography (gradient elution hexanes/20-100% ethyl acetate) afforded compound 310 as a colorless oil (142 mg, 69%).

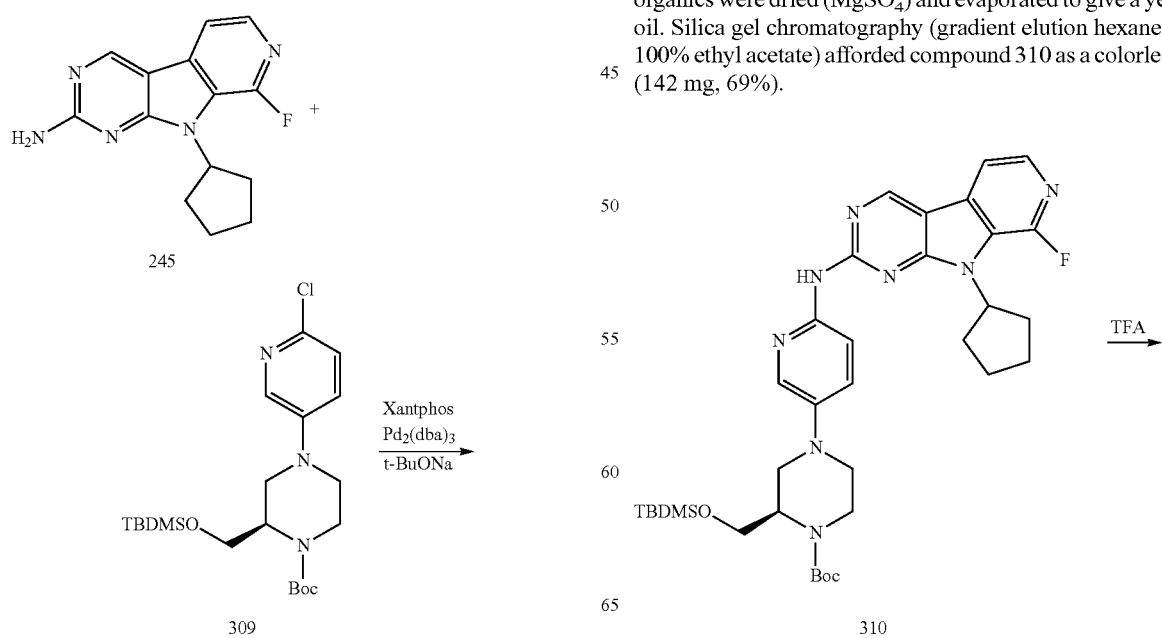

263
-continued

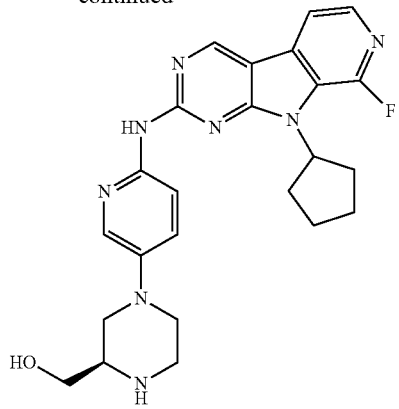

306

((2R)-4-(6-((9-Cyclopentyl-8-fluoro-9H-pyrido[4',3':4,5] pyrrolo[2,3-d]pyrimidin-2-yl)amino)-3-pyridinyl)-2-piperazinyl)methanol (306): Compound 310 (140 mg, 207 mop was dissolved in dichloromethane (6 mL).). Trifluoroacetic acid (2.00 mL, 2.60 mmol) and 3 drops water were added and the reaction was stirred at room temperature for 3 days. The resulting solution was added dropwise with stirring to aq. K₂CO₃ (10%, 30 mL), which was then extracted with dichloromethane+10% methanol (3×30 mL). The combined organics were dried (MgSO₄) and evaporated to give a yellow oil. Silica gel chromatography (gradient elution ethyl acetate+ 2.5% TEA/0-100% ethyl acetate+10% 2M NH₃ in methanol) afforded the product as a yellow solid. This residue was taken up in dichloromethane (3 mL) and trifluoroacetic acid (13.3 μl, 2.0 equiv.) was added. The solvent was removed in vacuo to give compound 306 as a yellow solid (54 mg). ¹H NMR (500 MHz, DMSO-d₆) δ 9.40 (s, 1 H) 9.03-9.22 (m, 1 H) 8.65-8.82 (m, 1 H) 8.10 (d, J=2.93 Hz, 4 H) 7.64-7.78 (m, 1 H) 5.38-5.58 (m, 1 H) 3.70-3.87 (m, 3 H) 3.61-3.69 (m, 1 H) 3.58 (s, 1 H) 3.41 (none, 2 H) 3.15-3.29 (m, 1 H) 3.07-3.15 (m, 0 H) 2.96-3.07 (m, 1 H) 2.83-2.94 (m, 1 H) 2.26-2.37 (m, 2 H) 2.08-2.18 (m, 2 H) 1.97-2.08 (m, 2 H) 1.69-1.84 (m, 2 H) 1.14-1.22 (m, 1 H) ppm.

Example 197

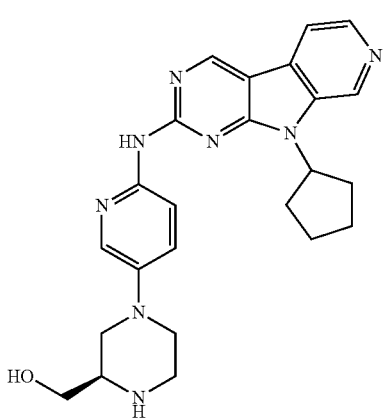

311

264

((2R)-4-(6-((9-Cyclopentyl-9H-pyrido[4',3':4,5]pyrrolo[2,3-d]pyrimidin-2-yl)amino)-3-pyridinyl)-2-piperazinyl)methanol Compound 311 was prepared using the methods described in Example 196 ¹H NMR (500 MHz, DMSO-d₆) δ 9.50-9.57 (m, 1H) 9.26-9.34 (m, 1H) 9.04-9.15 (m, 1H) 8.66-8.77 (m, 1H) 8.60-8.66 (m, 1H) 8.45-8.54 (m, 1H) 8.09-8.19 (m, 3H) 7.57-7.67 (m, 1H) 5.31-5.42 (m, 1H) 3.70-3.88 (m, 4H) 3.60-3.70 (m, 1H) 3.16-3.28 (m, 1H) 2.96-3.07 (m, 1H) 2.84-2.94 (m, 2H) 2.01-2.19 (m, 6H) 1.69-1.84 (m, 3H) 1.10 (none, 1H) ppm.

Example 198

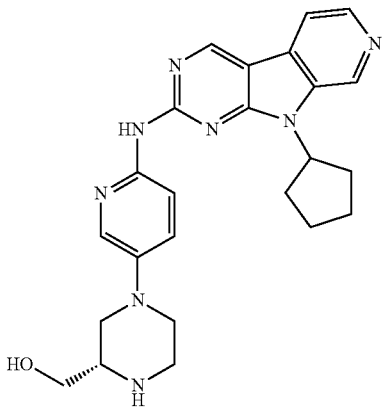

312

((2S)-4-(6-((9-cyclopentyl-9H-pyrido[4',3':4,5]pyrrolo[2,3-d]pyrimidin-2-yl)amino)-3-pyridinyl)-2-piperazinyl)methanol Compound 312 was prepared using the methods described in Example 196. ¹H NMR (500 MHz, DMSO-d₆) δ 9.54 (s, 1 H) 9.32 (s, 1 H) 9.10-9.20 (m, 1 H) 8.69-8.80 (m, 1 H) 8.65 (d, J=6.11 Hz, 1 H) 8.48-8.55 (m, 1 H) 8.15 (d, J=2.93 Hz, 2 H) 7.59-7.67 (m, 1 H) 5.32-5.43 (m, 1 H) 3.70-3.88 (m, 3 H) 3.60-3.69 (m, 1 H) 3.39 (d, 2 H) 3.16-3.29 (m, 1 H) 3.07-3.16

(m, 1 H) 2.97-3.07 (m, 1 H) 2.84-2.93 (m, 1 H) 2.38-2.48 (m, 2 H) 2.02-2.18 (m, 4 H) 1.70-1.83 (m, 2 H) 1.19 (s, 1 H) 1.10 (s, 1 H) ppm.

Example 199

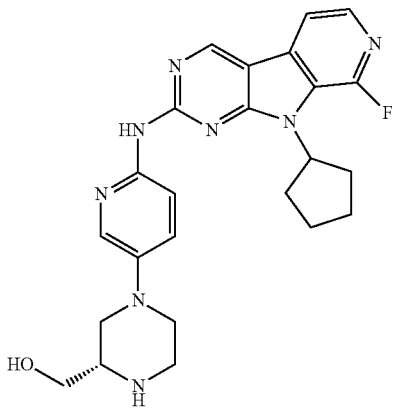

((2S)-4-(6-((9-cyclopentyl-8-fluoro-9H-pyrido[4',3': 4,5]pyrrolo[2,3-d]pyrimidin-2-yl)amino)-3-pyridinyl)-2-piperazinyl)methanol Compound 313 was prepared using the methods described in Example 196. $^1$H NMR (500 MHz, DMSO-$d_6$) δ 10.39 (none, 1 H) 9.40 (s, 1 H) 9.03-9.17 (m, 1 H) 8.60-8.80 (m, 1 H) 8.10 (d, J=2.45 Hz, 4 H) 7.62-7.77 (m, 1 H) 5.41-5.55 (m, 1 H) 3.68-3.86 (m, 3 H) 3.57-3.68 (m, 1 H) 3.35-3.42 (m, 2 H) 3.17-3.28 (m, 1 H) 2.97-3.06 (m, 1 H) 2.84-2.93 (m, 1 H) 2.26-2.40 (m, 2 H) 2.08-2.18 (m, 2 H) 1.97-2.08 (m, 2 H) 1.69-1.82 (m, 2 H) ppm.

Example 200

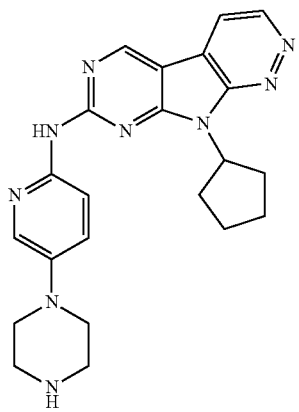

314

9-Cyclopentyl-N-(5-(1-piperazinyl)-2-pyridinyl)-9H-pyrimido[5',4':4,5]pyrrolo[2,3-c]pyridazin-7-amine

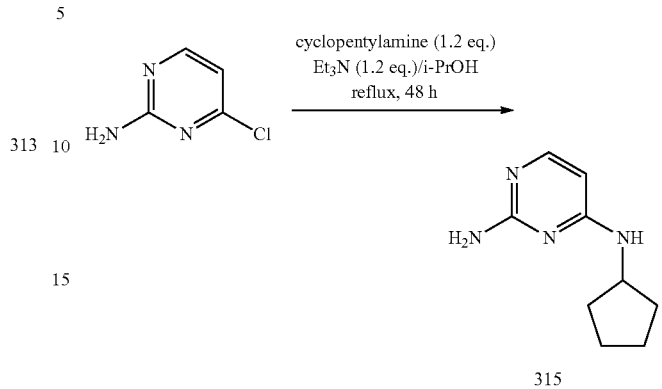

313

N4-Cyclopentyl-2,4-pyrimidinediamine (315): A mixture of 2-amino-4-chloropyrimidine (22.8 g, 176 mmol), cyclopentylamine (20.9 mL, 211 mmol) and triethylamine (29.4 mL, 211 mmol) in EtOH (200 mL) was heated at reflux (105° C., oil bath) for 48 h. Upon workup, the volatile was removed in vacuo. The residue was poured into ice and saturated Na$_2$CO$_3$ aqueous solution and extracted with ethyl acetate (3×). The combined organics were washed with saturated Na$_2$CO$_3$ aqueous solution (1×), dried over Na$_2$SO$_4$, and concentrated in vacuo to give N4-cyclopentylpyrimidine-2,4-diamine (315) (26.5 g) as a light yellow solid of 92% purity. This batch of material was taken onto the next step without further purification. LCMS-ESI (POS), M/Z, M+1: Found 179.1, Calculated 179.1.

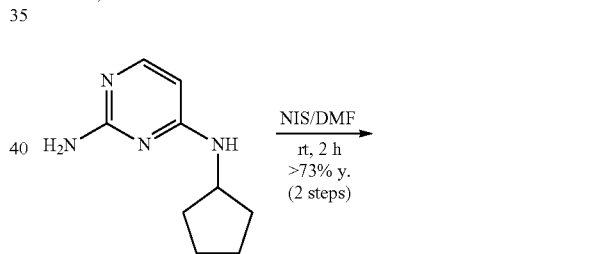

315

N4-Cyclopentyl-5-iodo-2,4-pyrimidinediamine (243): To a stirred solution of compound 315 (25.5 g, 143 mmol) in DMF (120 mL) was added N-iodosuccinimide (32 g, 143 mmol) in two portions at rt. The resulting mixture was stirred at rt for 2 h. Upon workup, the mixture was poured into ice and saturated Na$_2$CO$_3$ aqueous solution with some sodium sulfite and extracted with ethyl acetate (2×). The combined organics were washed with saturated Na$_2$CO$_3$ aqueous solution (3×), dried over Na$_2$SO$_4$, and concentrated in vacuo. The residue was subjected to combi-flash column chromatography (methanol/DCM) to give compound 243 (39 g, 73% yield in 2 steps). ¹H NMR (500 MHz, DMSO-d₆) δ ppm 7.89 (1 H, s), 6.18 (2 H, s), 5.63 (1 H, d, J=7.6 Hz), 4.30 (1 H, sxt, J=7.4 Hz), 1.84-1.96 (2 H, m), 1.61-1.74 (2 H, m), 1.42-1.58 (4 H, m). LCMS-ESI (POS), M/Z, M+1: Found 305.0.

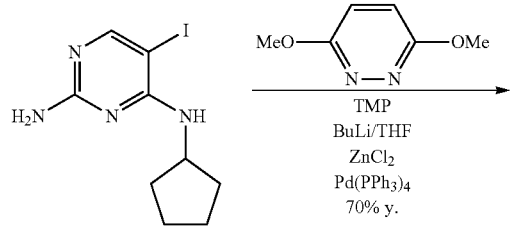

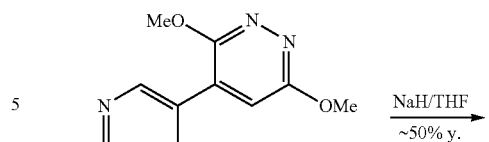

N4-Cyclopentyl-5-(3,6-dimethoxy-4-pyridazinyl)-2,4-pyrimidinediamine (316): A solution of butyllithium (2.5 m solution in hexanes) (7.5 mL, 19 mmol) was added to cold (acetonitrile-dry ice bath, -34° C. internal), stirred 2,2,6,6-tetramethylpiperidine (3.4 mL, 20 mmol). The resulting mixture was allowed to stand at 0° C. (ice-H₂O bath) for 30 min. The ice-H₂O was then replaced with dry ice-2-propanol bath and the mixture was cooled to –0° C. THF (24 mL) was added. A pre-cooled (ice-H₂O bath) solution of 3,6-dimethoxypyridazine (2.40 g, 17 mmol) in THF (40 mL) was added through a cannula over a period of 30 min. The internal temperature was observed fluctuating between –72° C. and -55° C. The resulting mixture was stirred at –70° C. for 1.5 h. A solution of zinc(II) chloride (0.5 M in THF) (34 mL, 17 mmol) was added through a syringe over a period of 15 min. The internal temperature fluctuated between –73° C. and –64° C. The cold bath was removed and the resulting mixture was allowed to warm up to rt (20.5° C.). A solution of compound 243 (1.7 g, 5.7 mmol) and tetrakis(triphenylphosphine)palladium (0.33 g, 0.29 mmol) in THF (20 mL) was added and the resulting mixture was heated at reflux for 18 h. Upon workup, the crude mixture was cooled in an ice-H₂O before poured into ice and saturated NH₄Cl aqueous solution and extracted with ethyl acetate (2×). The combined organics were combined, dried over Na₂SO₄, and concentrated in vacuo. The residue was subjected to combi-flash column chromatography (methanol/DCM with Et₃N) to give pure compound 316 (1.2 g, 66% yield) as an off-white solid. ¹H NMR (400 MHz, DMSO-d₆) δ ppm 7.53 (1 H, s), 7.01 (1 H, s), 6.18-6.38 (3 H, m), 4.35-4.51 (1 H, m, J=7.3, 7.3, 7.3, 7.3, 7.0 Hz), 3.95 (3 H, s), 3.91 (3 H, s), 1.77-1.90 (2 H, m), 1.55-1.69 (2 H, m), 1.35-1.55 (4 H, m). LCMS-ESI (POS), M/Z, M+1: Found 317.2.

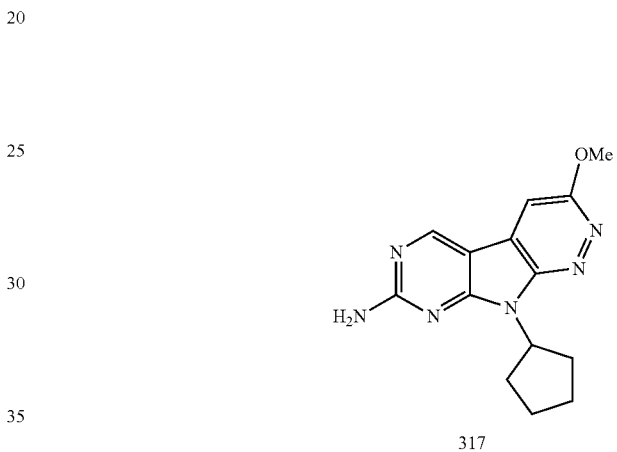

9-Cyclopentyl-3-methoxy-9H-pyrimido[5',4':4,5]pyrrolo [2,3-c]pyridazin-7-amine (317): To a 35 mL microwave reaction vessel were placed with compound 316 (200 mg, 0.63 mmol) followed by THF and sodium hydride, (60% in mineral oil, 0.063 g, 1.6 mmol). The resulting mixture was stirred at room temperature for 10 min to allow gas release. Then the vessel was subjected to microwave reaction condition (60 min at 150° C.). The crude mixture was subjected to combi-flash column chromatography (methanol/DCM) to give compound 317 (0.17 g) as a light yellow solid (contaminated with mineral oil). ¹H NMR (500 MHz, DMSO-d₆) δ ppm 8.97 (1 H, s), 7.57 (1 H, s), 7.28 (2 H, s), 5.28 (1 H, quin, J=8.7 Hz), 4.02 (3 H, s), 2.38-2.46 (2 H, m), 1.89-2.10 (4 H, m), 1.62-1.78 (2 H, m). LCMS-ESI (POS), M/Z, M+1: Found 285.1.

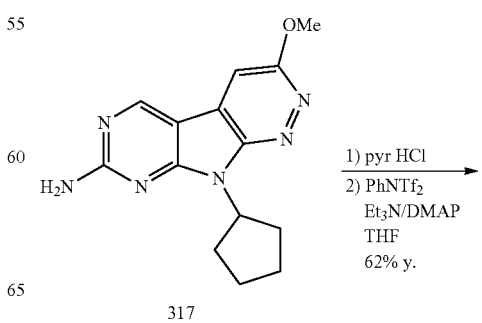

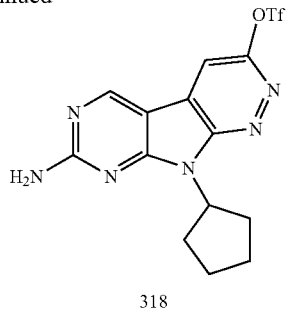

318

7-Amino-9-cyclopentyl-9H-pyrimido[5',4':4,5]pyrrolo[2,3-c]pyridazin-3-yl trifluoromethanesulfonate (318): A mixture of compound 317 (0.17 g, 0.60 mmol) and pyridine hydrochloride (0.69 g, 6.0 mmol) was heated at 200° C. (oil bath) overnight. After cooling to room temperature, the mixture was dissolved in THF (6 mL). Triethylamine (1.3 mL, 9.0 mmol) (2.0 mL), N,N-dimethylpyridin-4-amine (0.0073 g, 0.060 mmol) (catalytic amount), and N-phenyltrifluoromethanesulfonimide (0.54 g, 1.5 mmol) were added at room temperature. The resulting mixture was sonicated for 10 min and stirred for 2 h. Upon workup, the mixture was subjected to combi-flash column chromatography (ethyl acetate/Hexanes) to give compound 318 (0.15 g, 62% yield) as an off-white solid. LCMS-ESI (POS), M/Z, M+1: Found 403.0.

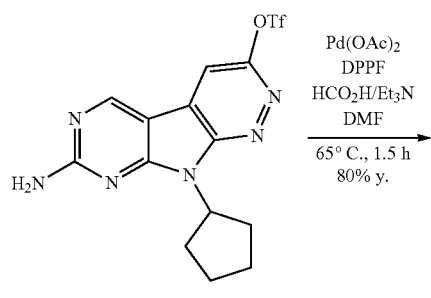

318

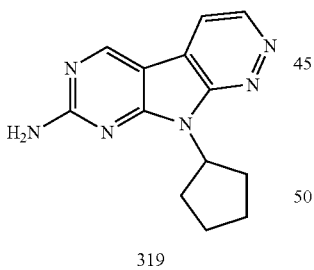

319

9-Cyclopentyl-9H-pyrimido[5',4':4,5]pyrrolo[2,3-c]pyridazin-7-amine (319): In a 25 mL single-necked round bottom flask were placed compound 318 (94 mg, 234 µmol, palladium diacetate (21 mg, 93 µmol), and 1,1'-bis(diphenylphosphino)ferrocene (130 mg, 234 µmol). The flask was subjected to 3 cycles of evacuation and back-filling with N₂. DMF (3 mL) was added under N₂ followed by triethylamine (715 µl, 5140 µmol) and formic acid, 98% (176 µl, 4.67 mmol). The resulting mixture was stirred in an oil bath at 65° C. for 1.5 h. The mixture was poured into ice and saturated NaHCO₃ aqueous solution and extracted with 10% i-PrOH/DCM (2×). The combined organics were dried over Na₂SO₄ and concentrated in vacuo. The residue was subjected to combi-flash column chromatography (methanol/DCM with Et₃N) to give compound 319 (48 mg, 80% yield) as an reddish solid. ¹H NMR (400 MHz, DMSO-d₆) δ ppm 9.08 (1 H, s), 9.01 (1 H, d, J=5.1 Hz), 8.07 (1 H, d, J=5.1 Hz), 7.28 (2 H, s), 5.42 (1 H, quin, J=8.6 Hz), 2.40-2.49 (2 H, m), 1.92-2.14 (4 H, m), 1.63-1.80 (2 H, m). LCMS-ESI (POS), M/Z, M+1: Found 255.1.

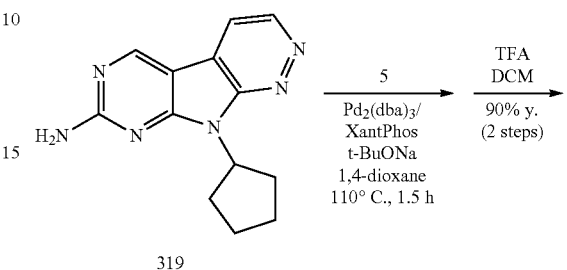

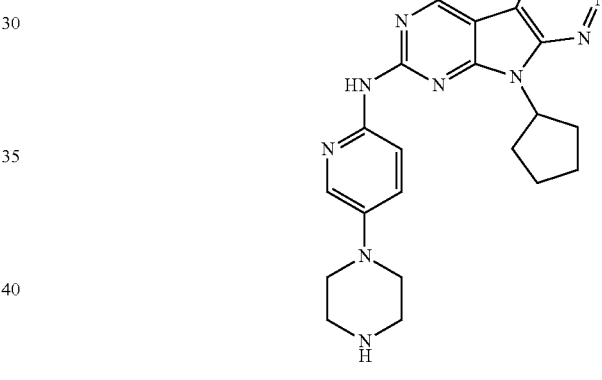

314

9-Cyclopentyl-N-(5-(1-piperazinyl)-2-pyridinyl)-9H-pyrimido[5',4':4,5]pyrrolo[2,3-c]pyridazin-7-amine (314): In a 10 mL microwave reaction vessel were placed compound 5 (42 mg, 142 µmol), tris(dibenzylideneacetone)dipalladium (0) (13 mg, 14 µmol), 9,9-dimethyl-4,5-bis(diphenylphosphino)xanthene (20 mg, 35 µmol), and sodium tert-butoxide (41 mg, 425 µmol) followed by a solution of compound 319 (36 mg, 142 µmol) in 1,4-dioxane (3 mL). The vessel was purged with N₂ for 3 min, then capped and sujected to microwave condition (1.5 h at 110° C.). After the volatiles were removed, the residue was subjected to combi-flash column chromatography (methanol/DCM. A solution of the intermediate in DCM (15 mL) was treated with trifluoroacetic acid (0.70 mL, 9.4 mmol) at room temperature for 1.5 h. After the volatiles were removed, the residue was subjected to preparative reverse phase HPLC (acetonitrile/H₂O containing 0.1% TFA each, 40 min from 10 to 40%). Lyophilization provided compound 314 (56 mg, bis-TFA salt) as a yellow solid. ¹H NMR (400 MHz, methanol) δ ppm 9.47 (1 H, s), 9.23 (1 H, d, J=5.5 Hz), 8.49 (1 H, d, J=5.5 Hz), 7.99-8.11 (2 H, m), 7.75 (1 H, d, J=9.4 Hz), 5.68 (1 H, quin, J=8.5 Hz), 3.49-3.58 (4 H, m), 3.41-3.49 (4 H, m), 2.50-2.71 (2 H, m), 2.12-2.29 (4 H, m), 1.76-1.94 (2 H, m). LCMS-ESI (POS), M/Z, M+1: Found 416.2.

Example 201

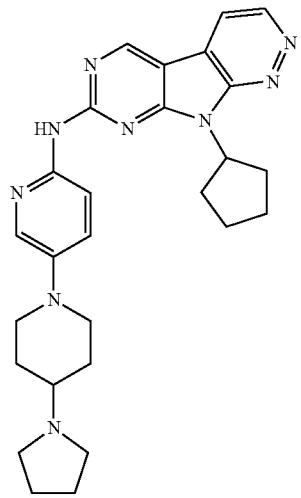

320

9-cyclopentyl-N-(5-(4-(1-pyrrolidinyl)-1-piperidinyl)-2-pyridinyl)-9H-pyrimido[5',4':4,5]pyrrolo[2,3-c]pyridazin-7-amine Compound 320 was prepared as a TFA salt using chemistry similar to that described in example 200. $^1$H NMR (400 MHz, CD$_3$OD) δ ppm 9.46 (1 H, s), 9.22 (1 H, d, J=5.1 Hz), 8.45 (1 H, d, J=5.5 Hz), 8.07 (1 H, dd, J=9.6, 2.9 Hz), 8.00 (1 H, d, J=2.7 Hz), 7.67 (1 H, d, J=9.8 Hz), 5.69 (1 H, qd, J=8.5, 8.2 Hz), 3.92 (2 H, d, J=12.9 Hz), 3.66-3.76 (2 H, m), 3.36-3.38 (1 H, m), 3.21 (2 H, d, J=11.0 Hz), 2.93 (2 H, td, J=12.5, 2.0 Hz), 2.54-2.68 (2 H, m), 2.33 (2 H, d, J=13.3 Hz), 2.13-2.27 (6 H, m), 1.96-2.10 (2 H, m), 1.79-1.95 (4 H, m). LCMS-ESI (POS), M/Z, M+1: Found 484.2.

Example 202

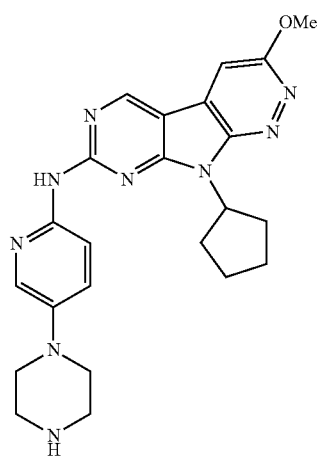

321

9-cyclopentyl-3-methoxy-N-(5-(1-piperazinyl)-2-pyridinyl)-9H-pyrimido[5',4':4,5]pyrrolo[2,3-c]pyridazin-7-amine Compound 321 was prepared as a TFA salt from 317 using chemistry similar to that described in example 1. $^1$H NMR (400 MHz, CD$_3$OD) δ ppm 9.22 (1H, s), 8.02 (1H, d, J=2.7 Hz), 7.95 (1 H, dd, J=9.6, 2.3 Hz), 7.71 (1 H, s), 7.61-7.68 (3 H, m), 5.50 (1 H, quin, J=8.6 Hz), 4.15 (3 H, s), 3.45-3.54 (4 H, m), 3.37-3.45 (4 H, m), 2.48-2.66 (2 H, m), 2.04-2.22 (4 H, m), 1.73-1.89 (2 H, m). LCMS-ESI (POS), M/Z, M+1: Found 446.0.

Example 203

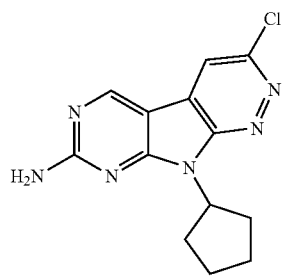

322

3-chloro-9-cyclopentyl-9H-pyrimido[5',4':4,5]pyrrolo[2,3-c]pyridazin-7-amine

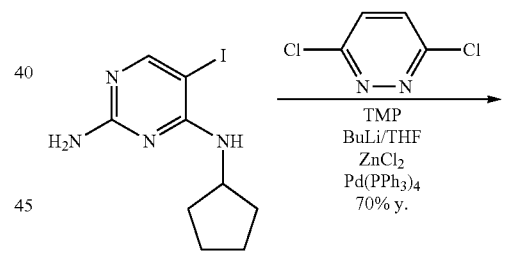

243

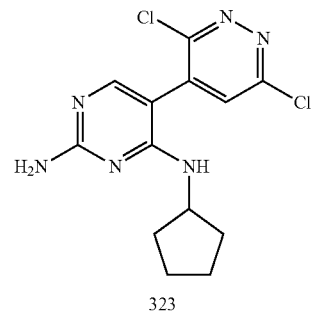

323

N4-Cyclopentyl-5-(3,6-dichloro-4-pyridazinyl)-2,4-pyrimidinediamine (323)

Compound 323 was prepared from compound 243 and 3,6-dichloropyridazine using chemistry similar to that described in example 200. LCMS-ESI (POS), M/Z, M+1: Found 325.0.

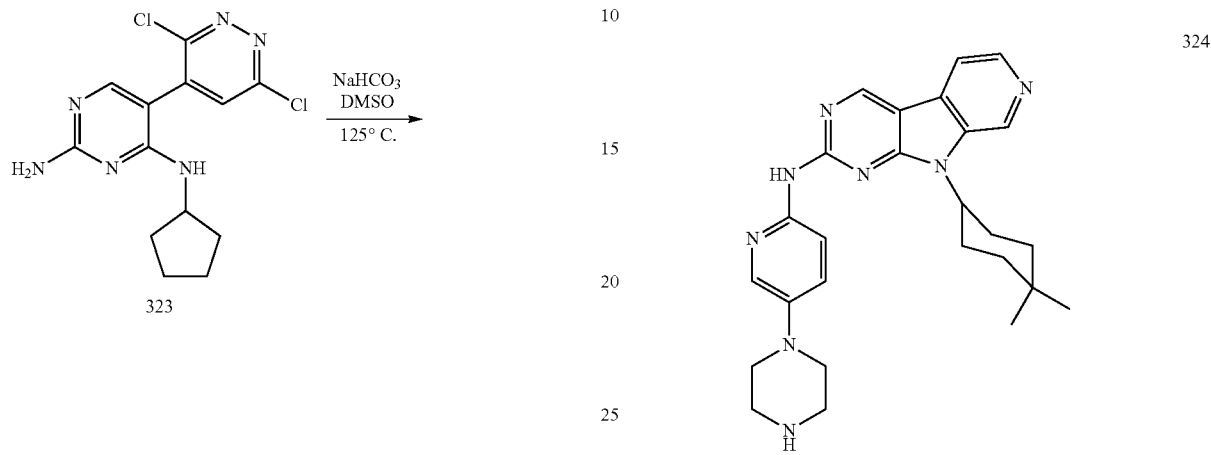

3-Chloro-9-cyclopentyl-9H-pyrimido[5',4':4,5]pyrrolo[2,3-c]pyridazin-7-amine (322): A mixture of crude N4-cyclopentyl-5-(3,6-dichloropyridazin-4-yl)pyrimidine-2,4-diamine (323) (0.27 g, 0.83 mmol) and sodium bicarbonate (0.065 mL, 1.7 mmol) in DMSO (10 mL) was heated in an oil bath at 110° C. for 11 h. Then the temperature was raised to 125° C. and stirred at this temperature for 200 min at which time LC-MS showed completion. Upon workup, the mixture was poured into ice and saturated NH$_4$Cl aqueous solution and extracted with ethyl acetate (3×). The combined organics were washed with saturated NH$_4$Cl aqueous solution (1×), dried over Na$_2$SO$_4$, and concentrated in vacuo. The residue was subjected to combi-flash column chromatography (methanol/DCM). The impure product thus obtained was subjected to subjected to preparative reverse phase HPLC (acetonitrile/H$_2$O containing 0.1% TFA each). After lyophilization, 15 mg of compound 322 was obtained as a TFA salt as an off-white solid.

$^1$H NMR (400 MHz, CD$_3$OD) δ ppm 9.06 (1 H, s), 8.21 (1 H, s), 5.50 (1 H, quin, J=8.6 Hz), 2.43-2.60 (2 H, m), 1.99-2.25 (4 H, m), 1.71-1.89 (2 H, m). LCMS-ESI (POS), M/Z, M+1: Found 289.1.

Example 204

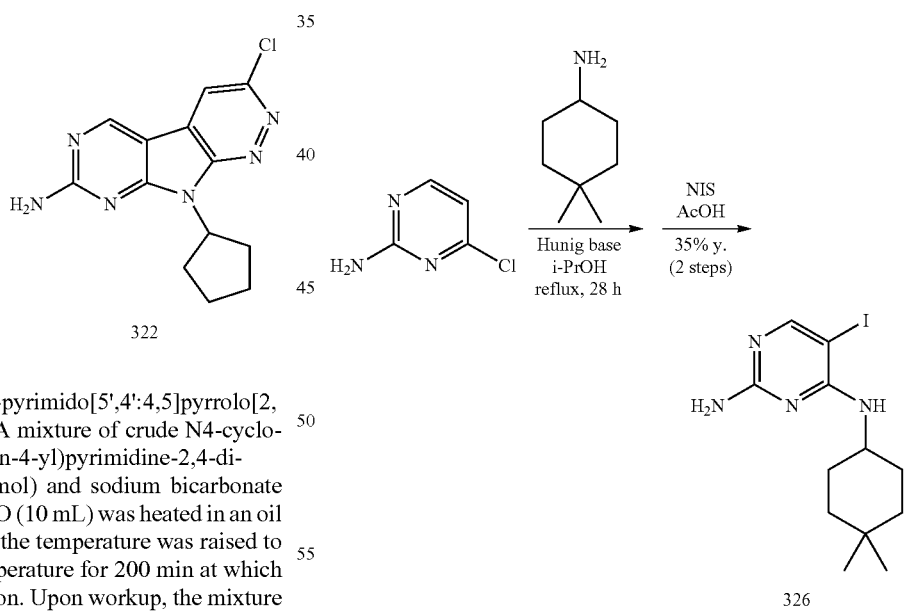

9-(4,4-dimethylcyclohexyl)-N-(5-(1-piperazinyl)-2-pyridinyl)-9H-pyrido[4',3':4,5]pyrrolo[2,3-d]pyrimidin-2-amine N4-(4,4-dimethylcyclohexyl)-5-iodo-2,4-pyrimidinediamine (326): Compound 326 was prepared as an off-white solid using chemistry similar to that described in example 200. $^1$H NMR (400 MHz, DMSO-d$_6$) δ ppm 7.88 (1 H, s), 6.13 (2 H, s), 5.66 (1 H, d, J=8.6 Hz), 3.78-3.95 (1 H, m), 1.49-1.66 (4 H, m), 1.30-1.41 (2 H, m), 1.15-1.28 (2 H, m), 0.94 (3 H, s), 0.91 (3 H, s). LCMS-ESI (POS), M/Z, M+1: Found 347.0.

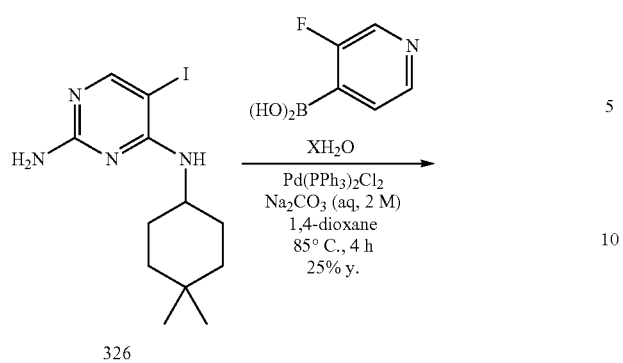
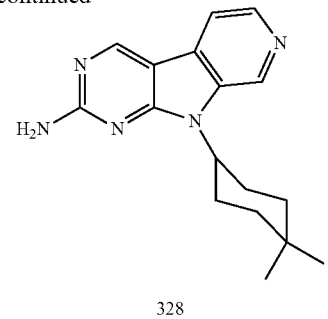

326

N4-(4,4-Dimethylcyclohexyl)-5-(3-fluoro-4-pyridinyl)-2,4-pyrimidinediamine (327): To a 50 mL single-necked round bottom flask were placed compound 236 (0.80 g, 2.3 mmol), 3-fluoropyridin-4-ylboronic acid (0.98 g, 6.9 mmol), trans-dichlorobis(triphenyl-phosphine)palladium (IIi) (0.16 g, 0.23 mmol), 1,4-dioxane (16 mL), and sodium carbonate, 2 N aqueous solution (3.5 mL, 6.9 mmol). The flask was purged with $N_2$ for 10 min. The resulting mixture was heated in an oil bath at 80° C. for 50 h. Upon workup, the mixture was poured into saturated $Na_2CO_3$ aqueous solution and extracted with ethyl acetate (2×). The combined organics were dried over $Na_2SO_4$ and concentrated in vacuo. The residue was subjected to combi-flash column chromatography (methanol/DCM) to give compound 327 (0.18 g, 25% yield) as a light yellow solid. $^1$H NMR (500 MHz, $CDCl_3$) δ ppm 8.56 (1 H, d, J=1.7 Hz), 8.48 (1 H, dd, J=4.9, 1.0 Hz), 7.78 (1 H, s), 7.27-7.30 (1 H, m), 4.89 (2 H, s), 4.43 (1 H, d, J=7.6 Hz), 3.88-4.01 (1 H, m), 1.79-1.88 (2 H, m), 1.26-1.43 (6 H, m), 0.94 (3 H, s), 0.91 (3 H, s). LCMS-ESI (POS), M/Z, M+1: Found 316.1.

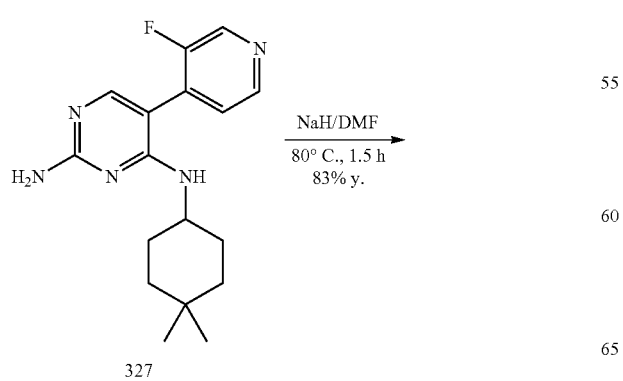

327

(4,4-Dimethylcyclohexyl)-9H-pyrido[4',3':4,5]pyrrolo[2,3-d]pyrimidin-2-amine (328): To a stirred solution of compound 327 (0.18 g, 0.57 mmol) in DMF (10 mL) was added sodium hydride, (60% in mineral oil, 0.11 g, 2.3 mmol). The resulting mixture was stirred at 80° C. for 1.5 h. Upon workup, the crude mixture was poured into ice and saturated $NaHCO_3$ aqueous solution and extracted with ethyl acetate (2×) followed by 10% i-PrOH/DCM (2×). The combined organics were dried over $Na_2SO_4$ and concentrated in vacuo. The residue was subjected to combi-flash column chromatography (methanol/DCM with $Et_3N$) to give compound 328 (0.14 g, 83% yield) as a light yellow solid. $^1$H NMR (500 MHz, DMSO-$d_6$) δ ppm 9.04 (1 H, s), 8.92 (1 H, s), 8.35 (1 H, d, J=4.9 Hz), 7.92 (1 H, dd, J=5.1, 1.0 Hz), 6.94 (2 H, s), 4.66-4.76 (1 H, m, J=12.6, 12.6, 4.1, 3.9 Hz), 2.52-2.63 (2 H, m), 1.52-1.66 (4 H, m), 1.39-1.50 (2 H, m), 1.16 (3 H, s), 1.01 (3 H, s). LCMS-ESI (POS), M/Z, M+1: Found 296.0.

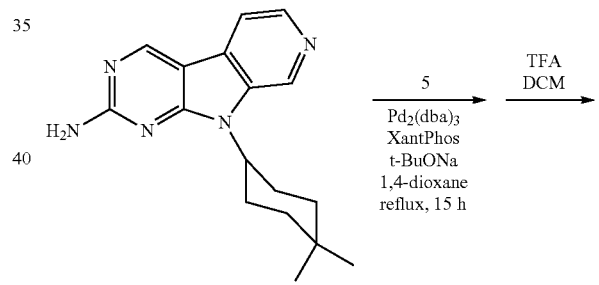

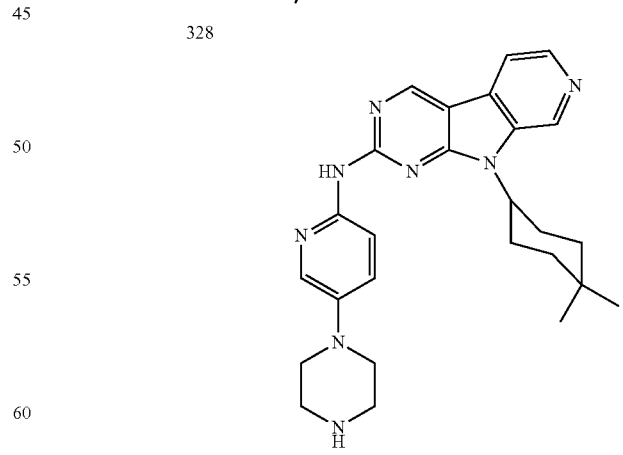

9-(4,4-dimethylcyclohexyl)-N-(5-(1-piperazinyl)-2-pyridinyl)-9H-pyrido[4',3':4,5]-pyrrolo[2,3-d]pyrimidin-2-amine (324): Compound 324 was prepared as a yellow solid (TFA salt) from compound 328 and compound 5 using chemistry similar to that described in example 200. ¹H NMR (400 MHz, DMSO-d₆) δ ppm 10.35 (1 H, s), 9.52 (1 H, s), 9.35 (1 H, s), 8.62 (1 H, d, J=5.9 Hz), 8.49 (1 H, d, J=5.9 Hz), 8.15 (1 H, d, J=2.9 Hz), 8.04 (1 H, d, J=9.0 Hz), 7.51 (1 H, dd, J=9.0, 2.9 Hz), 4.66-4.79 (1 H, m), 3.34-3.43 (4 H, m), 3.30 (4 H, br. s.), 2.62-2.77 (2 H, m), 1.73 (2 H, d, J=11.3 Hz), 1.46-1.63 (4 H, m), 1.11 (3 H, s), 1.02 (3 H, s). LCMS-ESI (POS), M/Z, M+1: Found 457.1.

J=10.5 Hz), 1.69 (2 H, d, J=10.5 Hz), 1.43-1.63 (6 H, m), 0.99 (6 H, s). LCMS-ESI (POS), M/Z, M+1: Found 499.3.

Example 206

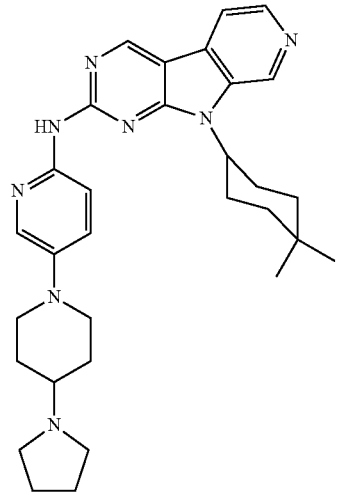

330

9-(4,4-dimethylcyclohexyl)-N-(5-(4-(1-pyrrolidinyl)-1-piperidinyl)-2-pyridinyl)-9H-pyrido[4',3':4,5]pyrrolo[2,3-d]pyrimidin-2-amine Compound 330 was prepared as yellow solid (TFA salt) from compound 328 using chemistry similar to that described in example 53. ¹H NMR (500 MHz, CD₃OD) δ ppm 9.58 (1 H, s), 9.31 (1 H, s), 8.54-8.65 (2 H, m), 8.03 (1 H, d, J=2.9 Hz), 7.99 (1 H, d, J=7.3 Hz), 7.77 (1 H, d, J=9.0 Hz), 4.89-5.01 (1 H, m), 3.91 (2 H, d, J=12.7 Hz), 3.71 (2 H, br. s.), 3.34-3.42 (1 H, m), 3.15-3.26 (2 H, m), 2.87-2.99 (2 H, m), 2.72-2.88 (2 H, m), 2.33 (2 H, d, J=12.0 Hz), 2.20 (2 H, br. s.), 2.05 (2 H, br. s.), 1.77-1.94 (4 H, m), 1.54-1.73 (4 H, m), 1.24 (3 H, s), 1.08 (3 H, s). LCMS-ESI (POS), M/Z, M+1: Found 525.3.

Example 205

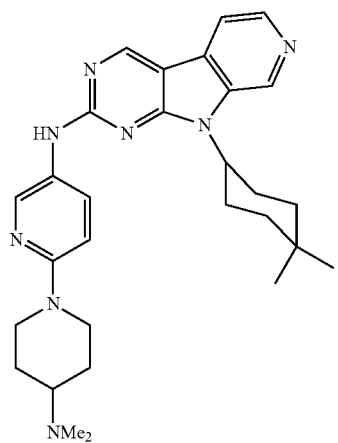

329

N-(6-(4-(dimethylamino)-1-piperidinyl)-3-pyridinyl)-9-(4,4-dimethylcyclohexyl)-9H-pyrido[4',3':4,5]pyrrolo[2,3-d]pyrimidin-2-amine Compound 329 was prepared as a yellow solid (TFA salt) from compound 328 and compound 91 using chemistry similar to that described in example 56. ¹H NMR (500 MHz, DMSO-d₆) δ ppm 9.46-9.58 (2 H, m), 9.36 (1 H, br. s.), 8.61 (1 H, d, J=6.1 Hz), 8.44-8.56 (2 H, m), 7.88 (1 H, dd, J=9.0, 2.7 Hz), 6.95 (1 H, d, J=9.3 Hz), 4.67 (1 H, br. s.), 4.42 (2 H, d, J=13.4 Hz), 3.35-3.45 (1 H, m, J=12.0, 12.0, 4.0, 4.0, 3.8 Hz), 2.72-2.85 (8 H, m), 2.58-2.70 (2 H, m), 2.07 (2 H, d, Example 207

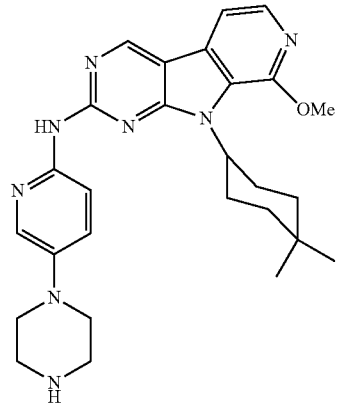

331

9-(4,4-dimethylcyclohexyl)-8-methoxy-N-(5-(1-piperazinyl)-2-pyridinyl)-9H-pyrido[4',3':4,5]pyrrolo[2,3-d]pyrimidin-2-amine

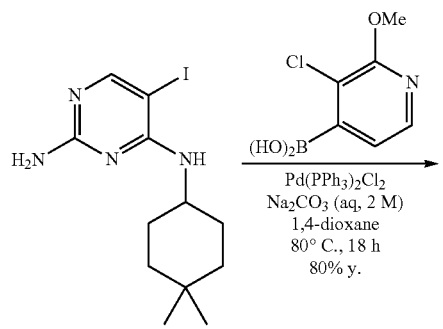

326

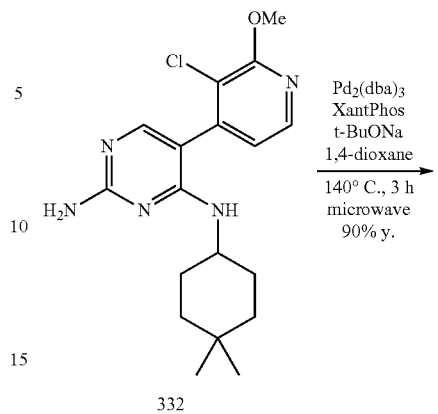

332

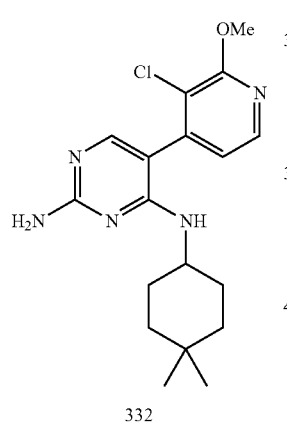

332

5-(3-Chloro-2-methoxy-4-pyridinyl)-N4-(4,4-dimethylcyclohexyl)-2,4-pyrimidinediamine (332): To a 50 mL single-necked round bottom flask were placed compound 326 (0.80 g, 2.3 mmol), 3-chloro-2-methoxypyridin-4-ylboronic acid (1.3 g, 6.9 mmol), and trans-dichlorobis(triphenyl-phosphine)palladium (ii) (0.16 g, 0.23 mmol). The flask was subjected to 3 cycles of evacuation and back-filling with $N_2$. 1,4-Dioxane (12 mL) was added followed with sodium carbonate (2 N aqueous solution) (5.8 mL, 12 mmol). The resulting mixture was heated in an oil bath at 80° C. for 18 h. Upon workup, the mixture was poured into ice and saturated $NaHCO_3$ aqueous solution and extracted with ethyl acetate (3×). The combined organics were dried over $Na_2SO_4$ and concentrated in vacuo. The residue was subjected to combi-flash column chromatography (methanol/DCM) to give compound 332 (0.68 g, 81% yield) as a light yellow solid. $^1$H NMR (500 MHz, DMSO-$d_6$) δ ppm 8.09 (1 H, d, J=5.1 Hz), 7.48 (1 H, s), 6.92 (1 H, d, J=5.1 Hz), 6.13 (2 H, s), 5.79 (1 H, d, J=8.3 Hz), 3.91-4.02 (4 H, m), 1.26-1.63 (6 H, m), 1.13-1.25 (2 H, m), 0.88 (6 H, d, J=9.8 Hz). LCMS-ESI (POS), M/Z, M+1: Found 362.0.

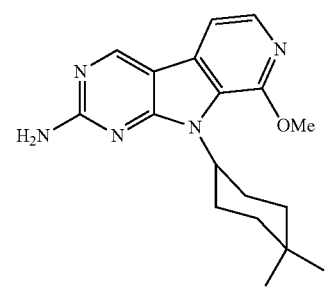

333

9-(4,4-Dimethylcyclohexyl)-8-methoxy-9H-pyrido[4',3':4,5]pyrrolo[2,3-d]pyrimidin-2-amine (333): To a 30 mL microwave reaction vessel were placed compound 332 (0.55 g, 1.5 mmol), tris(dibenzylideneacetone)dipalladium (0) (0.14 g, 0.15 mmol), 9,9-dimethyl-4,5-bis(diphenylphosphino)xanthene (0.22 g, 0.38 mmol), and sodium tert-butoxide (0.37 g, 3.8 mmol) followed by 1,4-dioxane (15 mL). The vessel was purged with $N_2$ for 5 min, then capped and subjected to microwave condition (3 h at 140° C.). After the volatiles were removed, the crude mixture was taken up in 4% methanol/DCM and subjected to combi-flash column chromatography (1% to 7% methanol in DCM) to give crude compound 333 as an off-white solid (0.65 g). $^1$H NMR (500 MHz, DMSO-$d_6$) δ ppm 9.01 (1 H, s), 7.92 (1 H, d, J=5.1 Hz), 7.59 (1 H, d, J=4.9 Hz), 6.86 (2 H, br. s.), 4.98-5.14 (1 H, m), 4.06 (3 H, s), 1.53 (4 H, br. s.), 1.31-1.44 (2 H, m), 1.16 (3 H, s), 1.00 (3 H, s). LCMS-ESI (POS), M/Z, M+1: Found 326.1.

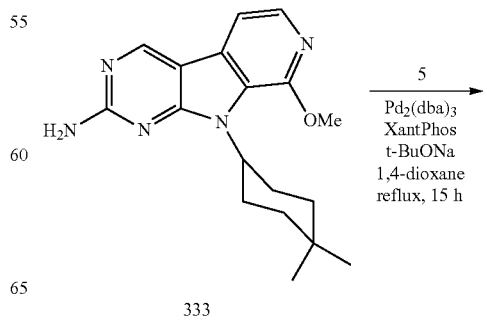

333

281

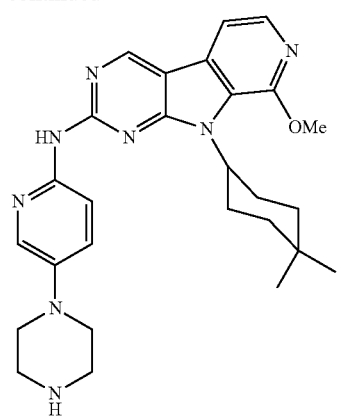

331

9-(4,4-Dimethylcyclohexyl)-8-methoxy-N-(5-(1-piperazinyl)-2-pyridinyl)-9H-pyrido[4',3':4,5]pyrrolo[2,3-d]pyrimidin-2-amine (331): In a 25 mL round bottom flask were placed compound 333 (130 mg, 399 μmol), compound 5 (119 mg, 399 μmol), tris(dibenzylideneacetone)dipalladium (0) (36.6 mg, 39.9 μmol), 9,9-dimethyl-4,5-bis(diphenylphosphino)xanthene (57.8 mg, 99.9 μmol), and sodium tert-butoxide (115 mg, 1198 mop. The flask was subjected to 3 cycles of evacuation and back-filling with $N_2$. 1,4-Dioxane (5 mL) was added and the resulting mixture was stirred at reflux for 14 h. After the volatiles were removed, the residue, which contained both Boc protected and deprotected product, was subjected to combi-flash column chromatography (methanol/DCM) followed by reverse phase preparative HPLC (acetonitrile/water containing 0.1% TFA each, 40 min from 10 to 60%). Fractions containing the desired product were lyophilized to provided compound 331 (16 mg) as a light yellow solid (TFA salt). $^1$H NMR (400 MHz, DMSO-$d_6$) δ ppm 9.30 (1 H, s), 8.70 (2 H, br. s.), 8.08 (1 H, d, J=2.7 Hz), 7.96-8.06 (2 H, m), 7.75 (1 H, br. s.), 5.10-5.31 (1 H, m), 4.09 (3 H, s), 3.24-3.37 (8 H, m), 1.33-1.77 (8 H, m), 1.13 (3 H, br. s.), 1.02 (3 H, s). LCMS-ESI (POS), M/Z, M+1: Found 487.1.

Example 208

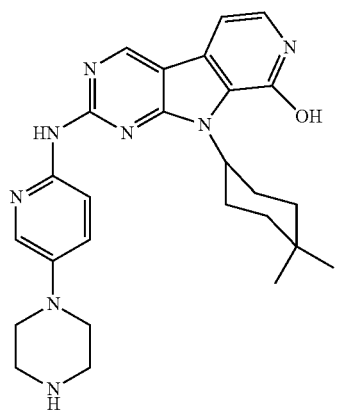

334

282

9-(4,4-dimethylcyclohexyl)-2-((5-(1-piperazinyl)-2-pyridinyl)amino)-9H-pyrido[4',3':4,5]pyrrolo[2,3-d]pyrimidin-8-ol

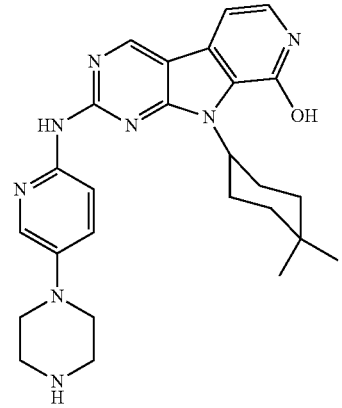

331

$\xrightarrow{\text{Pyr HCl}}$ 170° C., 4 h 9-(4,4-dimethylcyclohexyl)-2-((5-(1-piperazinyl)-2-pyridinyl)amino)-9H-pyrido[4',3':4,5]pyrrolo[2,3-d]pyrimidin-8-ol (334): A mixture of compound 331 (90 mg, 153 μmol) and pyridine hydrochloride (177 mg, 1.53 mmol) was heated at 170° C. (oil bath) for 4 h. After cooling to room temperature, the mixture was subjected to reverse phase preparative HPLC (acetonitrile/water containing 0.1% TFA each, 40 min from 10 to 50%). Lyophilization provided compound 334 (150 mg) as a yellow solid (TFA salt). $^1$H NMR (400 MHz, DMSO-$d_6$) δ ppm 11.66 (1 H, br. s.), 9.30 (1 H, s), 8.80 (2 H, br. s.), 8.05 (1 H, d, J=2.7 Hz), 7.92 (1 H, d, J=8.6 Hz), 7.75 (1 H, br. s.), 7.28 (1 H, t, J=5.7 Hz), 7.06 (1 H, d, J=6.3 Hz), 3.33-3.43 (4 H, m), 3.29 (5 H, d, J=1.6 Hz), 2.71-2.94 (2 H, m), 1.47-1.70 (4 H, m), 1.31-1.45 (2 H, m), 1.16 (3 H, s), 0.99 (3 H, s). LCMS-ESI (POS), M/Z, M+1: Found 473.2.

Example 209

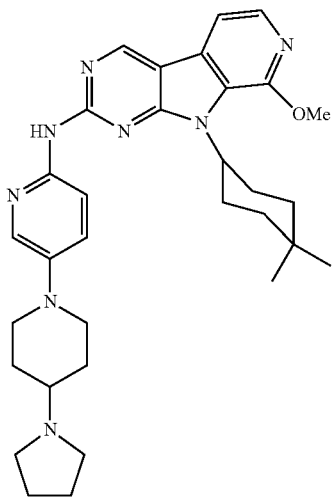

9-(4,4-dimethylcyclohexyl)-8-methoxy-N-(5-(4-(1-pyrrolidinyl)-1-piperidinyl)-2-pyridinyl)-9H-pyrido[4',3':4,5]pyrrolo[2,3-d]pyrimidin-2-amine Compound 335 was prepared from compound 333 using chemistry similar to that described in example 56. $^1$H NMR (400 MHz, CD$_3$OD) δ ppm 9.33 (1 H, s), 8.02-8.16 (2 H, m), 7.96 (1 H, d, J=2.7 Hz), 7.75 (1 H, d, J=5.1 Hz), 7.49 (0 H, br. s.), 5.27-5.41 (1 H, m), 4.19 (3 H, s), 3.89 (2 H, d, J=12.9 Hz), 3.71 (2 H, br. s.), 3.35-3.42 (1 H, m), 3.15-3.26 (2 H, m), 2.91 (2 H, td, J=12.5, 2.0 Hz), 2.33 (2 H, d, J=13.3 Hz), 2.13-2.25 (2 H, m), 1.97-2.09 (2 H, m), 1.81-1.94 (2 H, m), 1.60-1.70 (2 H, m), 1.44-1.57 (2 H, m), 1.26 (3 H, s), 1.05 (3 H, s). LCMS-ESI (POS), M/Z, M+1: Found 555.2.

Example 210

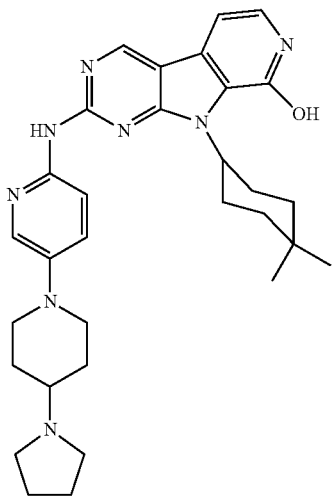

9-(4,4-dimethylcyclohexyl)-2-((5-(4-(1-pyrrolidinyl)-1-piperidinyl)-2-pyridinyl)amino)-9H-pyrido[4',3':4,5]pyrrolo[2,3-d]pyrimidin-8-ol Compound 336 was prepared as a yellow solid (TFA salt) from compound 333 using chemistry similar to that described in example 208. $^1$H NMR (400 MHz, CD$_3$OD) δ ppm 9.33 (1 H, s), 8.10 (1 H, dd, J=9.6, 2.9 Hz), 7.93 (1 H, d, J=2.7 Hz), 7.54 (1 H, d, J=9.8 Hz), 7.35 (1 H, d, J=7.0 Hz), 7.15 (1 H, d, J=6.7 Hz), 3.89 (2 H, d, J=12.9 Hz), 3.71 (2 H, br. s.), 3.35-3.41 (1 H, m), 3.15-3.27 (2 H, m), 2.86-3.03 (4 H, m), 2.33 (2 H, d, J=12.5 Hz), 2.20 (2 H, br. s.), 1.96-2.11 (2 H, m), 1.81-1.95 (2 H, m), 1.56-1.76 (4 H, m), 1.42-1.55 (2 H, m), 1.26 (3 H, s), 1.03 (3 H, s). LCMS-ESI (POS), M/Z, M+1: Found 541.3.

Example 211

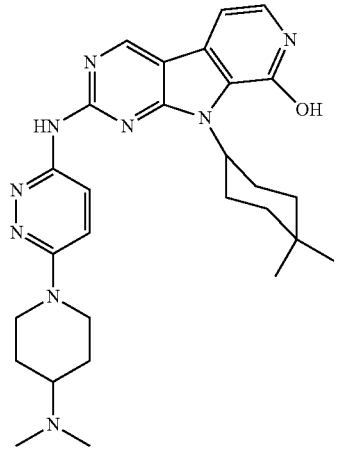

2-((6-(4-(dimethylamino)-1-piperidinyl)-3-pyridazinyl)amino)-9-(4,4-dimethylcyclohexyl)-9H-pyrido[4',3':4,5]pyrrolo[2,3-d]pyrimidin-8-ol Compound 337 was prepared as a yellow solid (TFA salt) from compound 333 using chemistry similar to that described in example 208. $^1$H NMR (500 MHz, DMSO-d$_6$) δ ppm 11.63 (1 H, br. s.), 9.49 (1 H, br. s.), 9.29 (1 H, s), 8.06 (1 H, d, J=9.8 Hz), 7.27 (1 H, t, J=5.9 Hz), 7.03 (1 H, d, J=6.1 Hz), 4.42 (2 H, d, J=13.2 Hz), 2.96 (2 H, t, J=12.6 Hz), 2.79 (9 H, d, J=5.1

Hz), 2.03-2.16 (2 H, m), 1.48-1.71 (6 H, m), 1.29-1.42 (2 H, m), 1.10 (3 H, br. s.), 0.98 (3 H, s). LCMS-ESI (POS), M/Z, M+1: Found 516.3.

Example 212

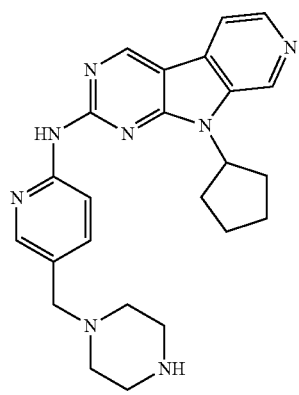

338

9-cyclopentyl-N-(5-(1-piperazinylmethyl)-2-pyridinyl)-9H-pyrido[4',3':4,5]pyrrolo[2,3-d]pyrimidin-2-amine

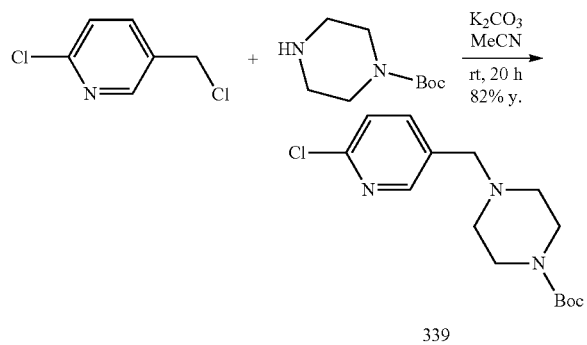

339 tert-Butyl 4-((6-chloro-3-pyridinyl)methyl)-1-piperazinecarboxylate (339): To a stirred suspension of 2-chloro-5-(chloromethyl)pyridine (2.0 g, 12 mmol) in acetonitrile (40 mL) was added potassium carbonate (1.5 mL, 25 mmol) followed by tert-butyl 1-piperazinecarboxylate (2.3 g, 12 mmol). The resulting mixture was stirred at room temperature for 20 h. Upon workup, the mixture was poured into ice and 2 N NaOH aqueous solution and extracted with ethyl acetate (2×). The combined organics were dried over $Na_2SO_4$ and concentrated in vacuo. The residue was subjected to combi-flash column chromatography (methanol/DCM) to give compound 339 (3.17 g, 82% yield) as a thick colorless liquid. $^1$H NMR $^1$H NMR (400 MHz, CHLOROFORM-d) δ ppm 8.32 (1 H, d, J=2.0 Hz), 7.66 (1 H, d, J=7.4 Hz), 7.30 (1 H, d, J=8.2 Hz), 3.50 (2 H, s), 3.37-3.47 (4 H, m), 2.38 (4 H, br. s.), 1.46 (9 H, s). LCMS-ESI (POS), M/Z, M+1: Found 312.1.

9-cyclopentyl-N-(5-(1-piperazinylmethyl)-2-pyridinyl)-9H-pyrido[4',3':4,5]-pyrrolo[2,3-d]pyrimidin-2-amine (338): Compound 338 was prepared as an off-white solid (TFA salt) from compound 4 and compound 339 using chemistry similar to that described in example 200. $^1$H NMR (500 MHz, $CD_3OD$) δ ppm 9.68 (1 H, s), 9.35 (1 H, s), 8.68 (2 H, q, J=6.3 Hz), 8.43 (1 H, d, J=1.5 Hz), 8.26 (1 H, dd, J=8.9, 2.1 Hz), 7.88 (1 H, d, J=8.8 Hz), 5.48 (1 H, quin, J=8.7 Hz), 3.78 (2 H, s), 3.27-3.30 (4 H, m), 2.83 (4 H, br. s.), 2.48-2.59 (2 H, m), 2.15-2.31 (4 H, m), 1.83-1.97 (2 H, m). LCMS-ESI (POS), M/Z, M+1: Found 429.2.

Example 213

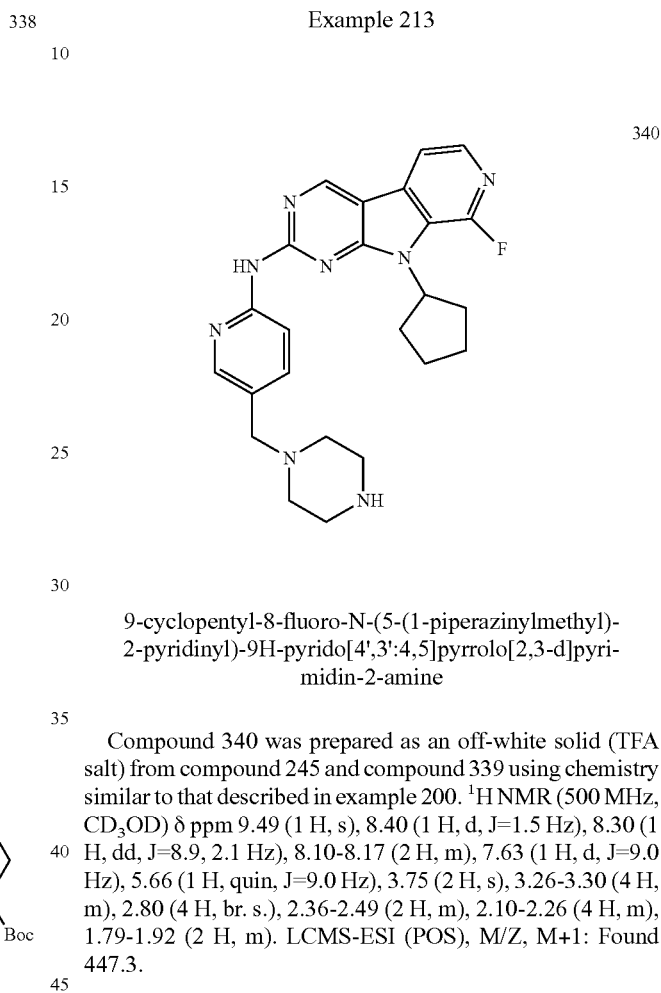

340

9-cyclopentyl-8-fluoro-N-(5-(1-piperazinylmethyl)-2-pyridinyl)-9H-pyrido[4',3':4,5]pyrrolo[2,3-d]pyrimidin-2-amine Compound 340 was prepared as an off-white solid (TFA salt) from compound 245 and compound 339 using chemistry similar to that described in example 200. $^1$H NMR (500 MHz, $CD_3OD$) δ ppm 9.49 (1 H, s), 8.40 (1 H, d, J=1.5 Hz), 8.30 (1 H, dd, J=8.9, 2.1 Hz), 8.10-8.17 (2 H, m), 7.63 (1 H, d, J=9.0 Hz), 5.66 (1 H, quin, J=9.0 Hz), 3.75 (2 H, s), 3.26-3.30 (4 H, m), 2.80 (4 H, br. s.), 2.36-2.49 (2 H, m), 2.10-2.26 (4 H, m), 1.79-1.92 (2 H, m). LCMS-ESI (POS), M/Z, M+1: Found 447.3.

Example 214

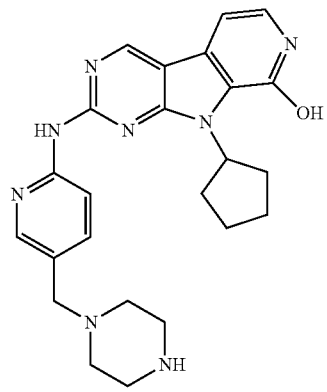

341

287

9-cyclopentyl-2-((5-(1-piperazinylmethyl)-2-pyridinyl)amino)-9H-pyrido[4',3':4,5]pyrrolo[2,3-d]pyrimidin-8-ol

288

1-((6-((9-cyclopentyl-9H-pyrido[4',3':4,5]pyrrolo[2,3-d]pyrimidin-2-yl)amino)-3-pyridinyl)methyl)-4-piperidinol

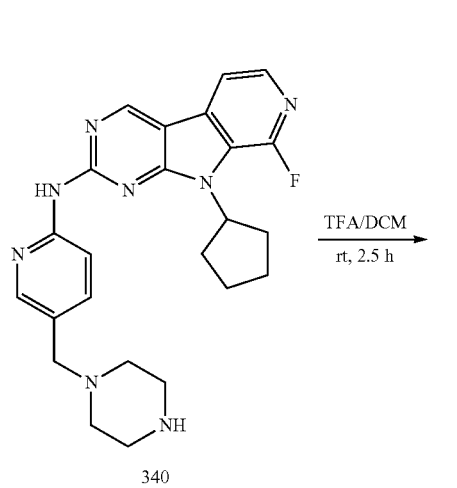

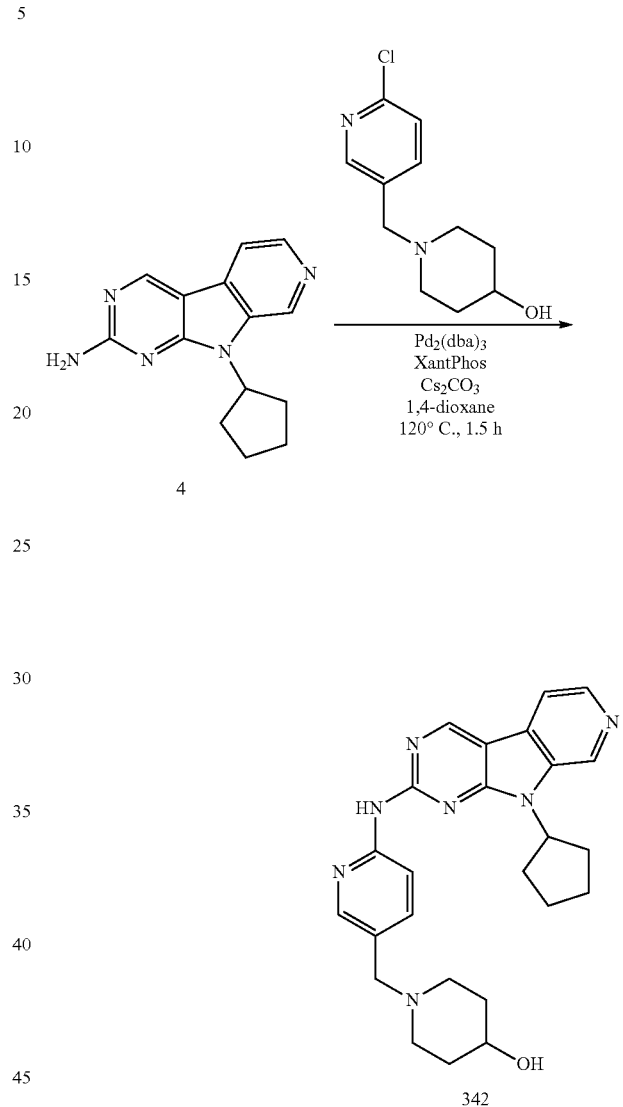

Compound 341 formed as a side product in example 213 and was isolated after reverse phase HPLC as a light yellow solid (TFA salt). LCMS-ESI (POS), M/Z, WI: Found 445.1.

Example 215

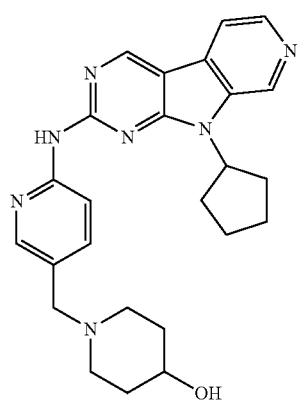

342

1-((6-((9-cyclopentyl-9H-pyrido[4',3':4,5]pyrrolo[2,3-d]pyrimidin-2-yl)amino)-3-pyridinyl)methyl)-4-piperidinol (342): In a 10 mL microwave reaction vessel were placed compound 4 (40 mg, 158 μmol), 1-(6-chloro-pyridin-3-ylmethyl)piperidin-4-ol (36 mg, 158 μmol), tris(dibenzylideneacetone)dipalladium (0) (7.2 mg, 7.9 μmol), 9,9-dimethyl-4,5-bis(diphenylphosphino)xanthene (11 mg, 20 μmol), and cesium carbonate (25 μl, 316 μmol) followed by 1,4-dioxane (3 mL). The vessel was purged with $N_2$ for 5 min, then capped and subjected to microwave condition (1.5 h at 120° C.). After the volatiles were removed, the residue was purified by combi-flash column chromatography followed by reverse phase preparative HPLC (acetonitrile/$H_2O$ containing 0.1% TFA each, 40 min from 10 to 40%). Lyophilization provided compound 342 (10 mg) as an off-white solid (TFA salt). $^1$H NMR (500 MHz, DMSO-$d_6$) δ ppm 10.00 (1 H, s), 9.32 (1 H, s), 9.03 (1 H, s), 8.46 (1 H, d, J=5.1 Hz), 8.32 (1 H, d, J=8.3 Hz), 8.19 (1 H, d, J=1.7 Hz), 8.04-8.10 (1 H, m), 7.72 (1 H, dd, J=8.6, 2.0 Hz), 5.39 (1 H, quin, J=8.8 Hz), 4.54 (1 H, d, J=3.9 Hz), 3.43 (3 H, s), 2.64-2.72 (2 H, m), 2.37-2.45 (2 H, m), 2.00-2.17 (6 H, m), 1.65-1.84 (4 H, m), 1.39 (2 H, t, J=9.9 Hz). LCMS-ESI (POS), M/Z, M+1: Found 444.2.

Example 216

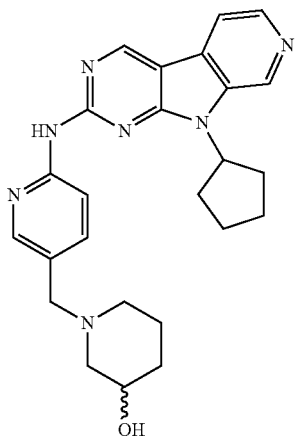

1-((6-((9-cyclopentyl-9H-pyrido[4',3':4,5]pyrrolo[2,3-d]pyrimidin-2-yl)amino)-3-pyridinyl)methyl)-3-piperidinol Compound 343 was prepared as a light yellow solid (TFA salt) from compound 4 using chemistry similar to that described in example 215. $^1$H NMR (500 MHz, CD$_3$OD) δ ppm 9.60 (1 H, s), 9.31 (1 H, s), 8.64-8.67 (1 H, m), 8.59-8.64 (1 H, m), 8.53 (1 H, d, J=2.0 Hz), 8.41 (1 H, d, J=8.6 Hz), 8.11 (1 H, dd, J=8.8, 2.2 Hz), 5.46 (1 H, quin, J=8.9 Hz), 4.05-4.53 (2 H, m), 3.53 (1 H, br. s.), 3.10 (1 H, br. s.), 2.50-2.64 (2 H, m), 2.14-2.36 (5 H, m), 1.75-2.00 (3 H, m). LCMS-ESI (POS), M/Z, M+1: Found 444.2.

Example 217 ethyl (4-(6-((9-cyclopentyl-9H-pyrido[4',3':4,5]pyrrolo[2,3-d]pyrimidin-2-yl)amino)-3-pyridazinyl)-1-piperazinyl)acetate

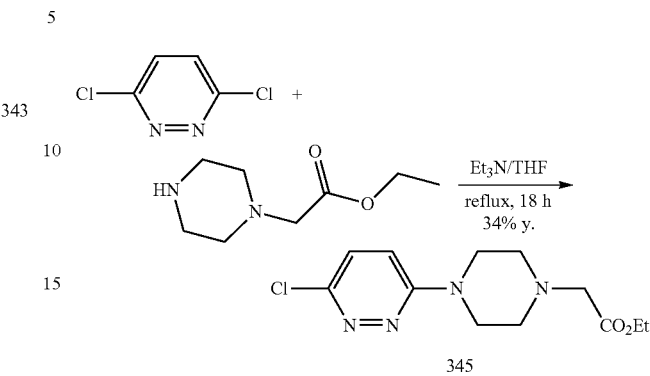

Ethyl 2-(4-(6-chloropyridazin-3-yl)piperazin-1-yl)acetate (345): Triethylamine (2.2 mL, 16 mmol) followed by 1-(ethoxycarbonylmethyl)piperazine (2.6 mL, 16 mmol) were added to a stirred suspension of 1-(ethoxycarbonylmethyl)piperazine (2.6 mL, 16 mmol) in THF (40 mL). The resulting mixture was stirred at reflux for 18 h. After cooling, the precipitate was removed by vacuum filtration through a layer of celite. The cake was washed with ethyl acetate. The filtrate was concentrated in vacuo and the residue was subjected to combi-flash column chromatography (methanol/DCM with Et$_3$N) to give compound 345 (1.5 g, 34% yield) as an off-white solid. $^1$H NMR (400 MHz, DMSO-d$_6$) δ ppm 7.53 (1 H, d), 7.38 (1 H, d, J=9.4 Hz), 4.09 (2 H, q, J=7.0 Hz), 3.54-3.63 (4 H, m), 3.29 (2 H, s), 2.57-2.65 (4 H, m), 1.19 (3 H, t, J=7.0 Hz). LCMS-ESI (POS), M/Z, M+1: Found 285.1.

ethyl (4-(6-((9-cyclopentyl-9H-pyrido[4',3':4,5]pyrrolo[2,3-d]pyrimidin-2-yl)amino)-3-pyridazinyl)-1-piperazinyl)acetate (344): Compound 344 was prepared as a light yellow solid (TFA salt) from compound 4 and compound 345 using chemistry similar to that described in example 200. $^1$H NMR (500 MHz, CD$_3$OD) δ ppm 9.65 (1 H, s), 9.33 (1 H, s), 8.63-8.68 (2 H, m), 8.15 (1 H, d, J=9.8 Hz), 7.94 (1 H, d, J=9.8 Hz), 5.46 (1 H, qt), 4.33 (2 H, q, J=7.1 Hz), 4.11 (2 H, s), 3.98 (4 H, br. s.), 3.46 (4 H, t, J=5.1 Hz), 2.45-2.59 (2 H, m), 2.13-2.31 (4 H, m), 1.84-1.96 (2 H, m), 1.34 (3 H, t, J=7.2 Hz). LCMS-ESI (POS), M/Z, M+1: Found 502.3.

Example 218

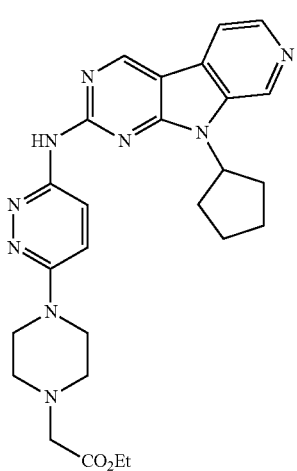

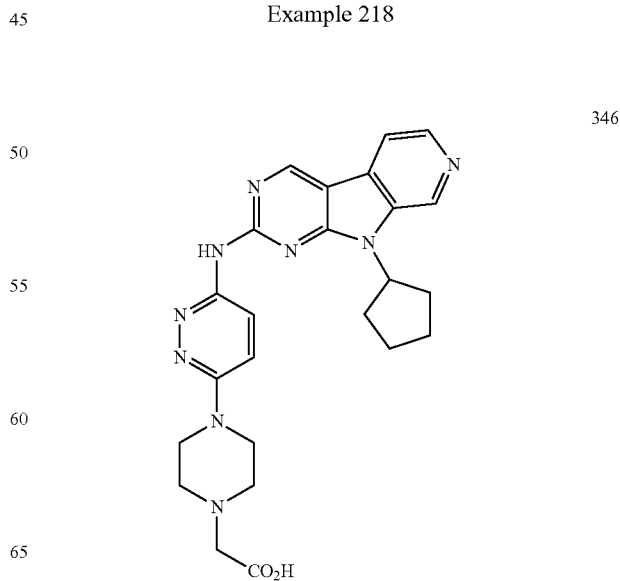

(4-(6-((9-cyclopentyl-9H-pyrido[4',3':4,5]pyrrolo[2,3-d]pyrimidin-2-yl)amino)-3-pyridazinyl)-1-piperazinyl)acetic acid

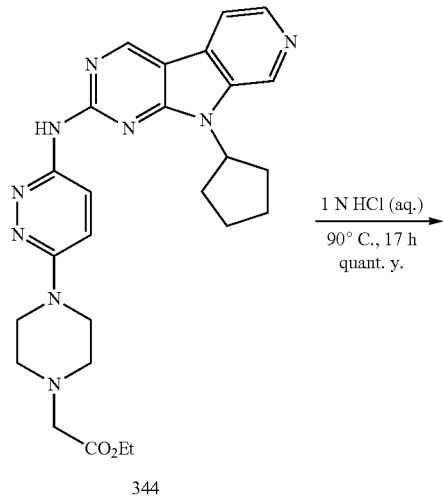

344

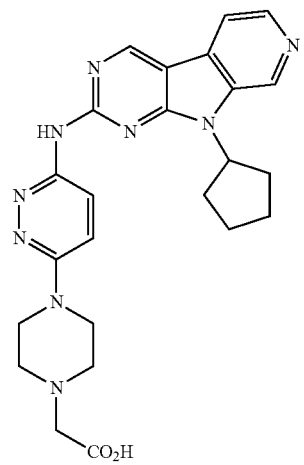

346

(4-(6-((9-cyclopentyl-9H-pyrido[4',3':4,5]pyrrolo[2,3-d]pyrimidin-2-yl)amino)-3-pyridazinyl)-1-piperazinyl)acetic acid (346): A mixture of compound 344 and hydrochloric acid (1 N aqueous solution) (7 mL) was stirred at 90° C. for 17 h. After concentration, the residue was subjected to reverse phase preparative HPLC (acetonitrile/H₂O containing 0.1% TFA each, 40 min from 10 to 30%). Lyophilization provided compound 346 (50 mg) as a yellow solid (TFA salt). ¹H NMR (500 MHz, DMSO-d₆) δ ppm 10.94 (1 H, br. s.), 9.55 (1 H, s), 9.33 (1 H, s), 8.65 (1 H, d, J=6.1 Hz), 8.53 (1 H, d, J=5.9 Hz), 8.23 (1 H, d, J=9.5 Hz), 7.60 (1 H, d, J=9.8 Hz), 5.34 (1 H, dq, J=8.9, 8.8 Hz), 4.16 (2 H, br. s.), 3.40 (8 H, br. s.), 2.33-2.44 (2 H, m), 1.92-2.18 (4 H, m), 1.62-1.81 (2 H, m). LCMS-ESI (POS), M/Z, M+1: Found 474.2.

Example 219

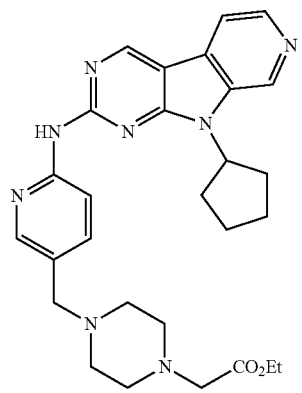

347

Ethyl (4-((6-((9-cyclopentyl-9H-pyrido[4',3':4,5]pyrrolo[2,3-d]pyrimidin-2-yl)amino)-3-pyridinyl)methyl)-1-piperazinyl)acetate

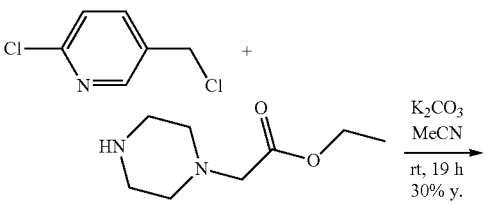

348

Ethyl 2-(4-((6-chloropyridin-3-yl)methyl)piperazin-1-yl)acetate (348): To a stirred suspension of 2-chloro-5-(chloromethyl)pyridine (2.0 g, 12 mmol) in acetonitrile (60 mL) was added potassium carbonate (1.5 mL, 25 mmol) followed by 1-(ethoxycarbonylmethyl)piperazine (2.0 mL, 12 mmol). The resulting mixture was stirred at room temperature for 19 h. The mixture was filtered through celite and the filter cake was washed with ethyl acetate. The filtrate was concentrated in vacuo and the residue was subjected to combi-flash column chromatography (methanol/DCM with Et₃N) to give compound 348 (1.1 g, 30% yield) as a colorless liquid. ¹H NMR (500 MHz, CHLOROFORM-d) δ ppm 8.31 (1 H, d, J=2.0 Hz), 7.66 (1 H, d, J=6.1 Hz), 7.28 (1 H, d, J=8.1 Hz), 4.18 (2 H, q, J=7.1 Hz), 3.50 (2 H, br. s.), 3.21 (2 H, s), 2.36-2.77 (8 H, m), 1.27 (3 H, t, J=7.2 Hz). LCMS-ESI (POS), M/Z, M+1: Found 298.1.

Ethyl (4-((6-((9-cyclopentyl-9H-pyrido[4',3':4,5]pyrrolo[2,3-d]pyrimidin-2-yl)amino)-3-pyridinyl)methyl)-1-piperazinyl)acetate (347): Compound 347 was prepared as an off-white solid (TFA salt) from compound 4 and compound 348 using chemistry similar to that described in example 200. $^1$H NMR (500 MHz, CD$_3$OD) δ ppm 9.57 (1 H, s), 9.27 (1 H, s), 8.60 (2 H, s), 8.47 (1 H, d, J=2.0 Hz), 8.32-8.43 (1 H, m), 8.07 (1 H, dd, J=8.8, 2.2 Hz), 5.46 (1 H, dq, J=9.0, 8.9 Hz), 4.12-4.28 (4 H, m), 3.65 (2 H, br. s.), 2.96-3.21 (8 H, m), 2.48-2.61 (2 H, m), 2.15-2.31 (4 H, m), 1.85-1.99 (2 H, m), 1.28 (3 H, t, J=7.2 Hz). LCMS-ESI (POS), M/Z, M+1: Found 515.2.

Example 220

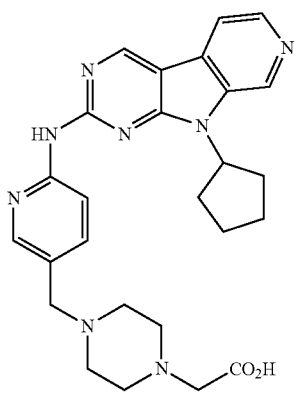

349

(4-((6-((9-cyclopentyl-9H-pyrido[4',3':4,5]pyrrolo[2,3-d]pyrimidin-2-yl)amino)-3-pyridinyl)methyl)-1-piperazinyl)acetic acid

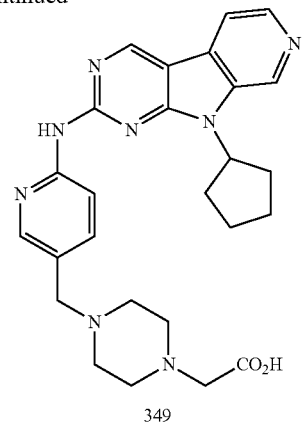

349

(4-((6-((9-cyclopentyl-9H-pyrido[4',3':4,5]pyrrolo[2,3-d]pyrimidin-2-yl)amino)-3-pyridinyl)methyl)-1-piperazinyl)acetic acid (349): A mixture of compound 347 (50 mg, 97 μmol) and lithium hydroxide, monohydrate (14 μl, 486 μmol) in methanol (9 mL) and water (3 mL) was heated at reflux for 2 h. After cooling, the crude mixture was subjected to reverse phase preparative HPLC (acetonitrile/H$_2$O containing 0.1% TFA each, 40 min from 10 to 40%). Lyophilization provided compound 349 (40 mg) as a light yellow solid (TFA salt). $^1$H NMR (400 MHz, DMSO-d$_6$) δ ppm 10.84 (1 H, s), 9.62 (1 H, s), 9.38 (1 H, s), 8.68 (1 H, d, J=5.9 Hz), 8.58 (1 H, d, J=6.3 Hz), 8.26-8.48 (2 H, m), 7.89-8.01 (1 H, m), 5.40 (1 H, quin, J=8.9 Hz), 2.75-4.63 (12 H, m), 2.39-2.47 (2 H, m), 2.01-2.23 (4 H, m), 1.70-1.87 (2 H, m). LCMS-ESI (POS), M/Z, M+1: Found 487.3.

Example 221

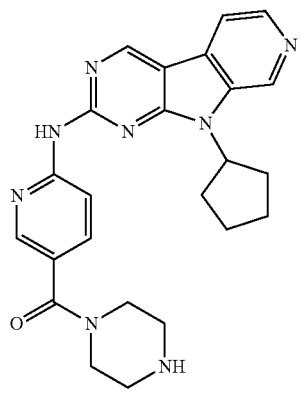

350

9-cyclopentyl-N-(5-(1-piperazinylcarbonyl)-2-pyridinyl)-9H-pyrido[4',3':4,5]pyrrolo[2,3-d]pyrimidin-2-amine

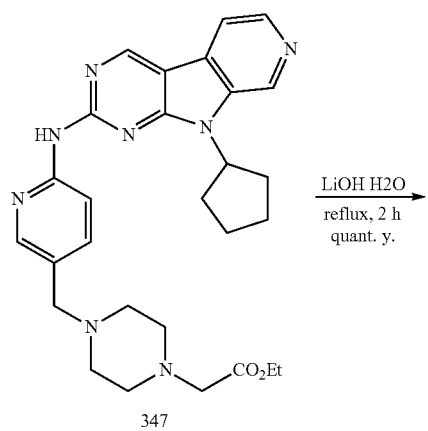

347

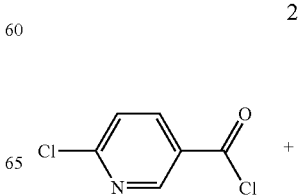

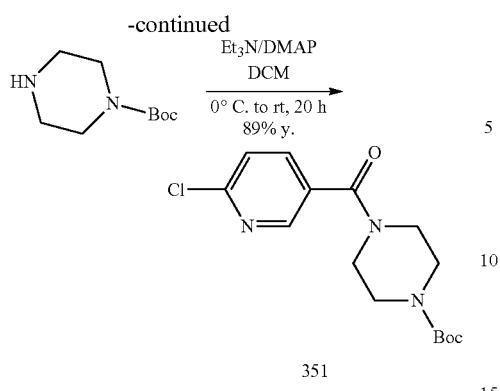

tert-Butyl 4-(2-chloronicotinoyl)piperazine-1-carboxylate (351): To a stirred ice-cooled solution of tert-butyl 1-piperazinecarboxylate (2.2 g, 12 mmol), triethylamine (3.2 mL, 23 mmol), and 4-dimethylaminopyridine (0.014 g, 0.11 mmol) in DCM (15 mL) was added 6-chloropyridine-3-carbonyl chloride (2.0 g, 11 mmol) in one portion. The resulting mixture was stirred at 0° C. and gradually warmed up to ambient temperature for 20 h. Upon workup, the mixture was subjected to combi-flash column chromatography (methanol/DCM) to give compound 351 (3.3 g, 89% yield) as a white solid. $^1$H NMR (400 MHz, CDCl$_3$) δ ppm 8.46 (1 H, d, J=2.0 Hz), 7.74 (1 H, dd, J=8.2, 2.3 Hz), 7.42 (1 H, dd, J=8.2, 0.8 Hz), 3.20-4.02 (8 H, m), 1.48 (9 H, s). LCMS-ESI (POS), M/Z, M+1: Found 326.0.

9-cyclopentyl-N-(5-(1-piperazinylcarbonyl)-2-pyridinyl)-9H-pyrido[4',3':4,5]pyrrolo[2,3-d]pyrimidin-2-amine (350): Compound 350 was prepared as a light yellow solid (HCl salt) from compound 4 and compound 351 using chemistry similar to that described in example 200. $^1$H NMR (500 MHz, DMSO-d$_6$) δ ppm 11.06 (1 H, br. s.), 9.70 (1 H, s), 9.47 (1 H, s), 9.39 (2 H, br. s.), 8.67-8.75 (2 H, m), 8.51 (1 H, d, J=1.7 Hz), 8.37 (1 H, d, J=8.6 Hz), 8.02 (1 H, dd, J=8.7, 2.3 Hz), 5.43 (1 H, dq, J=8.9, 8.8 Hz), 3.77 (4 H, br. s.), 3.18 (4 H, br. s.), 2.42-2.48 (2 H, m), 2.02-2.20 (4 H, m), 1.70-1.83 (2 H, m). LCMS-ESI (POS), M/Z, M+1: Found 443.2.

Example 222

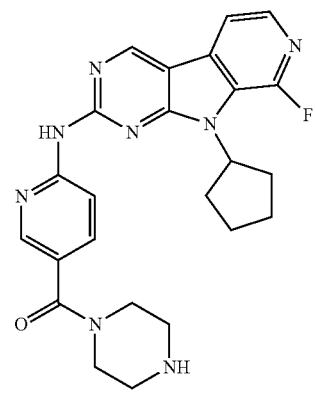

9-cyclopentyl-8-fluoro-N-(5-(1-piperazinylcarbonyl)-2-pyridinyl)-9H-pyrido[4',3':4,5]pyrrolo[2,3-d]pyrimidin-2-amine Compound 352 was prepared as an off-white solid (TFA salt) from compound 245 using chemistry similar to that described in example 200. $^1$H NMR (400 MHz, DMSO-d$_6$) δ ppm 10.60 (1 H, s), 9.45 (1 H, s), 8.83 (2 H, br. s.), 8.47 (1 H, d, J=1.6 Hz), 8.41 (1 H, d, J=8.6 Hz), 8.12 (1 H, dd, J=5.3, 2.9 Hz), 8.05-8.09 (1 H, m), 7.97 (1 H, dd, J=9.0, 2.3 Hz), 5.51 (1 H, quin, J=8.9 Hz), 3.74 (4 H, br. s.), 3.20 (4 H, br. s.), 2.33-2.41 (2 H, m), 1.98-2.22 (4 H, m), 1.69-1.85 (2 H, m). LCMS-ESI (POS), M/Z, M+1: Found 460.9.

Example 223

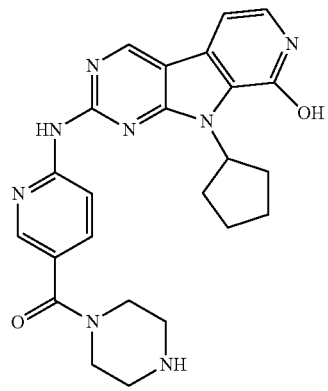

9-cyclopentyl-2-((5-(1-piperazinylcarbonyl)-2-pyridinyl)amino)-9H-pyrido[4',3':4,5]pyrrolo[2,3-d]pyrimidin-8-ol

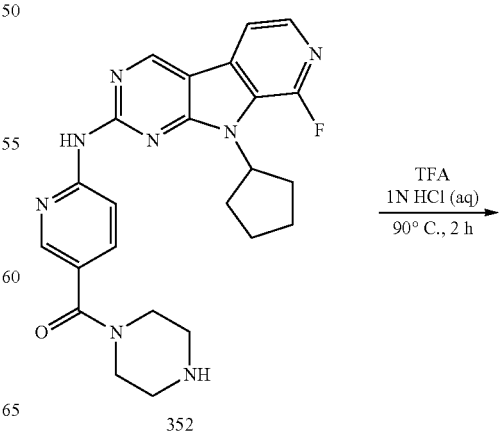

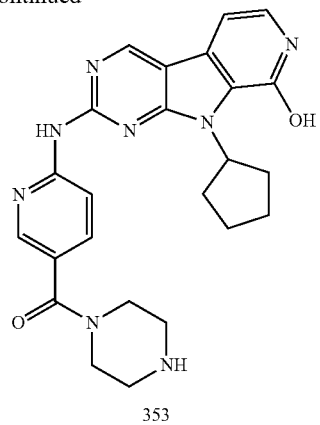

353

9-cyclopentyl-2-((5-(1-piperazinylcarbonyl)-2-pyridinyl)amino)-9H-pyrido-[4',3':4,5]pyrrolo[2,3-d]pyrimidin-8-ol (353): Compound 352 was treated with trifluoroacetic acid (4 mL, 54 mmol) in 1 N hydrochloric acid, aqueous solution (8 mL) for 2 h at 90° C. After the volatiles were partially removed, the residue was subjected to reverse phase preparative HPLC (acetonitrile/water containing 0.1% TFA each, 40 min from 10 to 40%). Lyophilization provided compound 353 (8 mg) as a light yellow solid (TFA salt). $^1$H NMR (400 MHz, CD$_3$OD) δ ppm 9.30 (1 H, s), 8.54 (1 H, s), 7.95-8.20 (2 H, m), 7.34 (1 H, d, J=6.7 Hz), 7.14 (1 H, d, J=6.7 Hz), 6.26 (1 H, dq, J=9.4, 9.1 Hz), 3.93 (4 H, br. s.), 3.33-3.38 (4 H, m), 2.53-2.70 (2 H, m), 2.04-2.28 (4 H, m), 1.68-1.91 (2 H, m). LCMS-ESI (POS), M/Z, M+1: Found 459.2.

Example 224

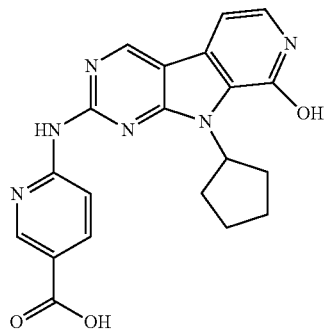

354

6-((9-cyclopentyl-8-hydroxy-9H-pyrido[4',3':4,5]pyrrolo[2,3-d]pyrimidin-2-yl)amino)-3-pyridinecarboxylic acid Compound 354 was obtained in the hydrolysis of compound 352 (example 223) as a light yellow solid (HCl salt). $^1$H NMR (500 MHz, CD$_3$OD) δ ppm 9.42 (1 H, s), 9.04 (1 H, d, J=1.5 Hz), 8.58 (1 H, dd, J=8.9, 2.1 Hz), 7.57 (1 H, d, J=9.0 Hz), 7.40 (1 H, d, J=6.8 Hz), 7.19 (1 H, d, J=6.6 Hz), 6.25 (1 H, dq, J=9.2, 9.0 Hz), 2.52-2.65 (2 H, m), 2.07-2.25 (4 H, m), 1.73-1.87 (2 H, m). LCMS-ESI (POS), M/Z, M+1: Found 391.1.

Example 225

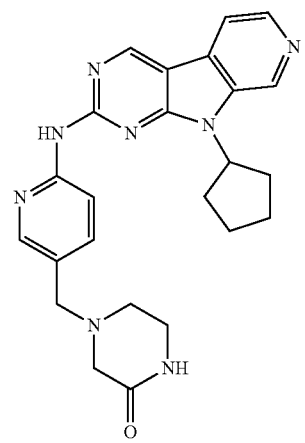

355

4-((6-((9-cyclopentyl-9H-pyrido[4',3':4,5]pyrrolo[2,3-d]pyrimidin-2-yl)amino)-3-pyridinyl)methyl)-2-piperazinone

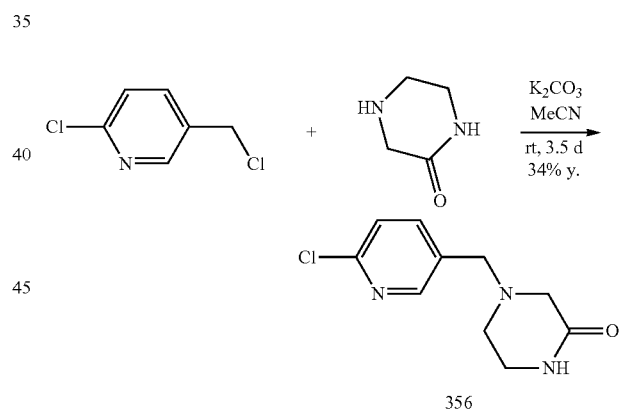

356

4-((6-Chloropyridin-3-yl)methyl)piperazin-2-one (356): A mixture of 2-chloro-5-(chloromethyl)pyridine (1.4 g, 8.4 mmol), piperazinone (0.84 g, 8.4 mmol), and potassium carbonate (1.0 mL, 17 mmol) in a mixed solvent consisting of acetonitrile (40 mL) and THF (20 mL) was stirred at room temperature for 3.5 days. Upon workup, the mixture was filtered through a layer of celite and the cake was washed with ethyl acetate. The filtrate was concentrated in vacuo and the residue was subjected to combi-flash column chromatography (methanol/DCM) to give compound 356 (0.65 g, 34% yield) as an off-white solid. $^1$H NMR (500 MHz, DMSO-d$_6$) δ ppm 8.35 (1 H, d, J=2.0 Hz), 7.81 (1 H, dd, J=8.1, 2.4 Hz), 7.76 (1 H, br. s.), 7.49 (1 H, d, J=8.3 Hz), 3.57 (2 H, s), 3.10-3.16 (2 H, m), 2.93 (2 H, s), 2.52-2.56 (2H, m). LCMS-ESI (POS), M/Z, M+1: Found 226.0.

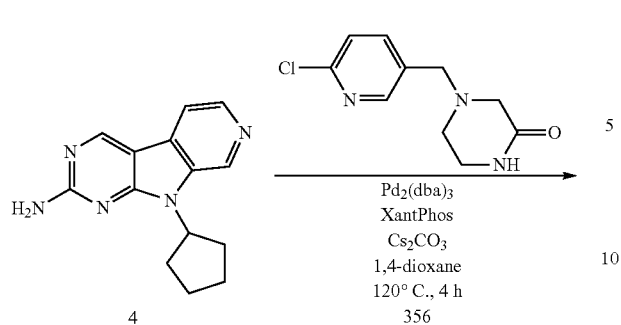

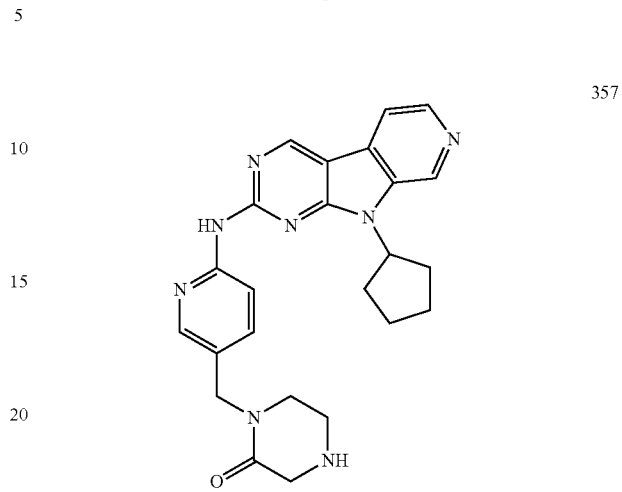

Hz), 2.48-2.60 (2 H, m), 2.14-2.32 (4 H, m), 1.85-1.98 (2 H, m). LCMS-ESI (POS), M/Z, M+1: Found 443.2.

Example 226

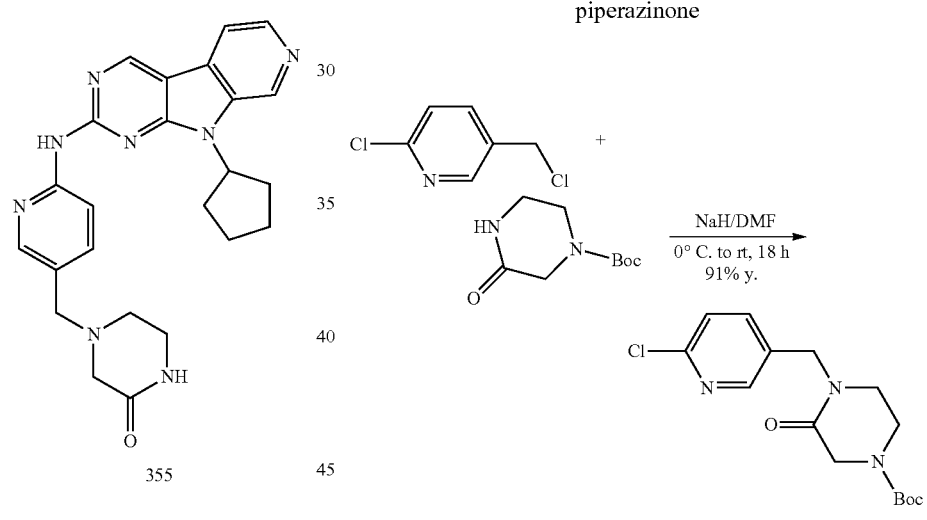

1-((6-((9-cyclopentyl-9H-pyrido[4',3':4,5]pyrrolo[2,3-d]pyrimidin-2-yl)amino)-3-pyridinyl)methyl)-2-piperazinone 4-((6-((9-Cyclopentyl-9H-pyrido[4',3':4,5]pyrrolo[2,3-d]pyrimidin-2-yl)amino)-3-pyridinyl)methyl)-2-piperazinone (355): In a 10 mL microwave reaction vessel were placed compound 4 (93 mg, 367 μmol), compound 356 (83 mg, 367 μmol), tris(dibenzylideneacetone)dipalladium (0) (17 mg, 18 μmol), 9,9-dimethyl-4,5-bis(diphenylphosphino)xanthene (27 mg, 46 μmol), and cesium carbonate (359 mg, 1101 μmol) followed by 1,4-dioxane (3 mL). The vessel was purged with $N_2$ for 5 min, then capped and subjected to microwave irradiation for 4 h at 120° C. The crude mixture was taken up in 4% methanol/DCM and subjected to combi-flash column chromatography (methanol/DCM) followed by preparative reverse phase HPLC (acetonitrile/water containing 0.1% TFA each, 40 min from 10 to 40%). Lyophilization provided compound 355 (100 mg) as an off-white solid (TFA salt). $^1$H NMR (500 MHz, $CD_3OD$) δ ppm 9.67 (1 H, s), 9.34 (1 H, s), 8.69 (1 H, d), 8.66 (1 H, d), 8.48 (1 H, d, J=1.7 Hz), 8.24 (1 H, dd, J=8.8, 2.2 Hz), 8.04 (1 H, d, J=8.6 Hz), 5.48 (1 H, quin, J=8.7 Hz), 4.03 (2 H, s), 3.40-3.49 (4 H, m), 3.09 (2 H, t, J=5.3 tert-Butyl 4-((6-chloropyridin-3-yl)methyl)-3-oxopiperazine-1-carboxylate (358): To a stirred ice-cooled suspension of sodium hydride, (60% dispersion in mineral oil, 0.83 g, 21 mmol) in DMF (15 mL) was added a suspension of tert-butyl 3-oxopiperazine-1-carboxylate (2.5 g, 12 mmol) in DMF (45 mL) through a syringe. The ice-$H_2O$ bath was removed and the resulting mixture, which was a suspension, was stirred at ambient temperature for 30 min. Complete dissolution was observed. 2-chloro-5-(chloromethyl)pyridine (2.0 g, 12 mmol) was added in one portion as a solid. The resulting mixture was stirred at ambient temperature for 18 h then poured into ice and saturated $NaHCO_3$ aqueous solution. It was extracted with ethyl acetate (2×). The combined organics were washed with saturated $NaHCO_3$ aqueous solution (3×), dried over $Na_2SO_4$, and concentrated in vacuo. The residue was subjected to combi-flash column chromatography (methanol/DCM) to give compound 358 (3.65 g, 91% yield) as a white solid. $^1$H NMR (500 MHz, $CDCl_3$) δ ppm 8.31 (1

H, d, J=2.2 Hz), 7.65 (1 H, dd, J=8.3, 2.4 Hz), 7.33 (1 H, d, J=8.1 Hz), 4.59 (2 H, s), 4.15 (2 H, s), 3.62 (2 H, t, J=5.4 Hz), 3.29 (2 H, t, J=5.1 Hz), 1.46 (9 H, s). LCMS-ESI (POS), M/Z, M+1: Found 326.0.

1-((6-((9-cyclopentyl-9H-pyrido[4',3':4,5]pyrrolo[2,3-d]pyrimidin-2-yl)amino)-3-pyridinyl)methyl)-2-piperazinone (357): Compound 357 was prepared as a off-white solid (TFA salt) from compound 4 and compound 358 using chemistry similar to that described in example 200. $^1$H NMR (500 MHz, CD$_3$OD) δ ppm 9.67 (1 H, s), 9.35 (1 H, s), 8.70 (1 H, d), 8.66 (1 H, d), 8.48 (1 H, d, J=1.7 Hz), 8.20 (1 H, dd, J=8.8, 2.2 Hz), 7.91 (1 H, d, J=8.8 Hz), 5.48 (1 H, quin, J=8.7 Hz), 4.76 (2 H, s), 3.96 (2 H, s), 3.71 (2 H, t, J=5.7 Hz), 3.53-3.62 (2 H, m), 2.46-2.61 (2 H, m), 2.14-2.33 (4 H, m), 1.82-1.98 (2 H, m). LCMS-ESI (POS), M/Z, M+1: Found 442.9.

Example 227

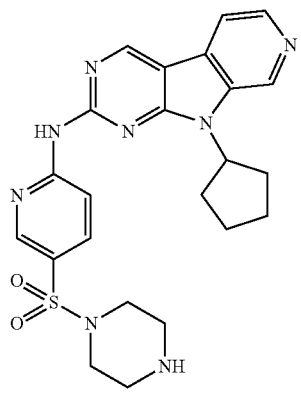

359

9-Cyclopentyl-N-(5-(1-piperazinylsulfonyl)-2-pyridinyl)-9H-pyrido[4',3':4,5]pyrrolo[2,3-d]pyrimidin-2-amine

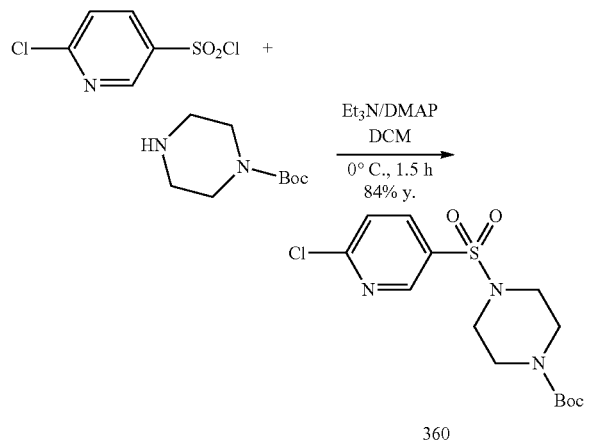

360 tert-Butyl 4-((6-chloro-3-pyridinyl)sulfonyl)-1-piperazinecarboxylate (360): To a stirred ice-cooled solution of tert-butyl 1-piperazinecarboxylate (0.88 g, 4.7 mmol), triethylamine (1.3 mL, 9.4 mmol), and 4-dimethylaminopyridine (0.0058 g, 0.047 mmol) in DCM (10 mL) was added 6-chloropyridine-3-sulfonyl chloride (1.0 g, 4.7 mmol) in one portion. The resulting mixture was stirred at 0° C. and gradually warmed up to ambient temperature for 1.5 h. Upon workup, the mixture was directly subjected to combi-flash column chromatography (methanol/DCM) to give compound 360 (1.44 g, 84% yield) as a white solid.

$^1$H NMR (500 MHz, DMSO-d$_6$) δ ppm 8.75 (1 H, d, J=2.0 Hz), 8.17 (1 H, dd, J=8.4, 2.6 Hz), 7.80 (1 H, d, J=9.0 Hz), 3.40 (4 H, t, J=4.8 Hz), 2.97 (4 H, t, J=5.0 Hz), 1.35 (9 H, s). LCMS-ESI (POS), M/Z, M+1: Found 306 (minus tBu) and 384 (plus Na$^+$).

9-Cyclopentyl-N-(5-(1-piperazinylsulfonyl)-2-pyridinyl)-9H-pyrido[4',3':4,5]-pyrrolo[2,3-d]pyrimidin-2-amine (359): Compound 359 was prepared as a white solid (TFA salt) from compound 4 and compound 360 using chemistry similar to that described in example 200. $^1$H NMR (500 MHz, CD$_3$OD) δ ppm 9.59 (1 H, s), 9.29 (1 H, s), 8.72-8.78 (2 H, m), 8.63-8.66 (1 H, m), 8.61 (1 H, d), 8.22 (1 H, dd, J=8.8, 2.4 Hz), 5.51 (1 H, quin, J=8.9 Hz), 3.37 (8 H, s), 2.46-2.60 (2 H, m), 2.13-2.34 (4 H, m), 1.87-2.01 (2 H, m). LCMS-ESI (POS), M/Z, M+1: Found 478.9.

Example 228

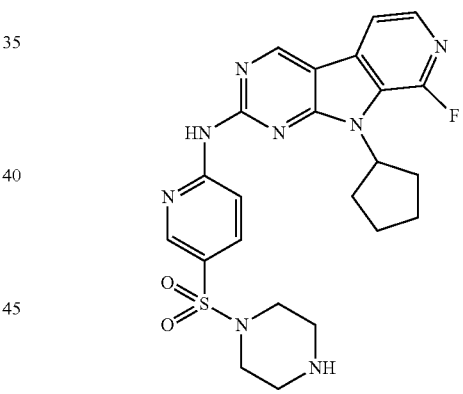

361

9-cyclopentyl-8-fluoro-N-(5-(1-piperazinylsulfonyl)-2-pyridinyl)-9H-pyrido[4',3':4,5]pyrrolo[2,3-d]pyrimidin-2-amine Compound 361 was prepared as a white solid (TFA salt) from compound 245 and compound 360 using chemistry similar to that described in example 200. $^1$H NMR (500 MHz, CD$_3$OD) δ ppm 9.37 (1 H, s), 8.73 (1 H, d, J=2.0 Hz), 8.68 (1 H, d, J=8.8 Hz), 8.21 (1 H, dd, J=9.0, 2.4 Hz), 8.01-8.08 (2 H, m), 5.67 (1 H, quin, J=9.2 Hz), 3.36 (8 H, s), 2.35-2.49 (2 H, m), 2.09-2.28 (4 H, m), 1.81-1.95 (2 H, m). LCMS-ESI (POS), M/Z, M+1: Found 497.2.

Example 229

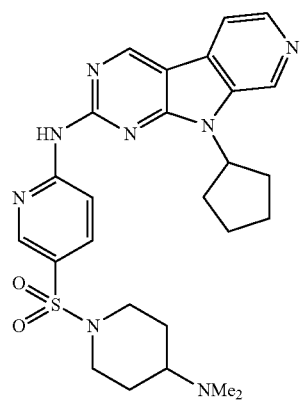

362

9-cyclopentyl-N-(5-((4-(dimethylamino)-1-piperidinyl)sulfonyl)-2-pyridinyl)-9H-pyrido[4',3':4,5]pyrrolo[2,3-d]pyrimidin-2-amine

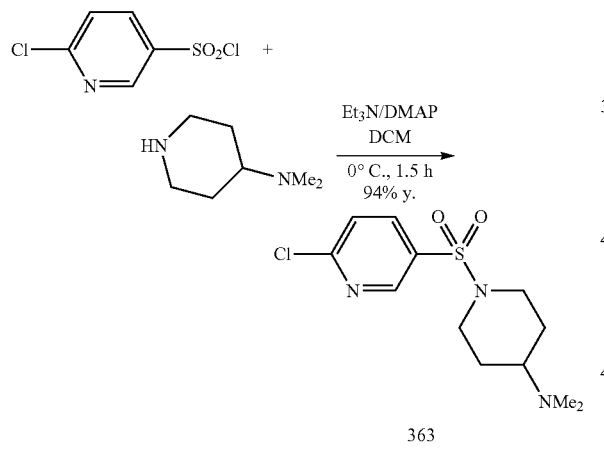

363

1-(6-Chloropyridin-3-ylsulfonyl)-N,N-dimethylpiperidin-4-amine (363): To a stirred ice-cooled solution of 4-(dimethylamino)piperidine (1.2 mL, 9.4 mmol), triethylamine (2.6 mL, 19 mmol), and 4-dimethylaminopyridine (0.012 g, 0.094 mmol) in DCM (18 mL) was added 6-chloropyridine-3-sulfonyl chloride (2.0 g, 9.4 mmol) in one portion. The resulting mixture was stirred at 0° C. for 1.5 h. Upon workup, the mixture was directly subjected to combi-flash column chromatography (methanol/DCM) to give compound 363 (2.7 g, 94% yield) as a white solid. LCMS-ESI (POS), M/Z, M+1: Found 304.0.

9-cyclopentyl-N-(5-((4-(dimethylamino)-1-piperidinyl)sulfonyl)-2-pyridinyl)-9H-pyrido[4',3':4,5]pyrrolo[2,3-d]pyrimidin-2-amine (362): Compound 362 was prepared as an off-white solid (TFA salt) from compound 4 and compound 363 using chemistry similar to that described in example 200. $^1$H NMR (400 MHz, CD$_3$OD) δ ppm 9.56 (1 H, s), 9.25 (1 H, s), 8.66-8.75 (2 H, m), 8.58 (2 H, s), 8.18 (1 H, dd, J=8.8, 2.5 Hz), 5.50 (1 H, quin, J=8.8 Hz), 4.01 (2 H, d, J=12.5 Hz), 3.22 (1 H, tt, J=12.1, 3.8 Hz), 2.86 (6 H, s), 2.44-2.60 (4 H, m), 2.12-2.35 (6 H, m), 1.74-2.01 (4 H, m). LCMS-ESI (POS), M/Z, M+1: Found 521.2.

Example 230

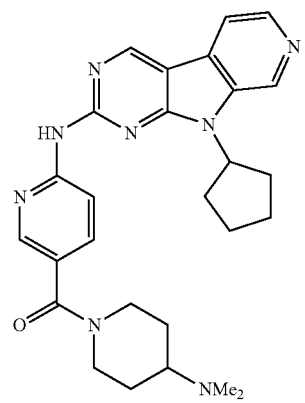

364

9-Cyclopentyl-N-(5-((4-(dimethylamino)-1-piperidinyl)carbonyl)-2-pyridinyl)-9H-pyrido[4',3':4,5]pyrrolo[2,3-d]pyrimidin-2-amine

365

(6-Chloropyridin-3-yl)(4-(dimethylamino)piperidin-1-yl)methanone (365): Compound 365 was prepared from 6-chloropyridine-3-carbonyl chloride using chemistry similar to that described in example 226. $^1$H NMR (400 MHz, DMSO-d$_6$) δ ppm 8.47 (1 H, d, J=2.3 Hz), 7.92 (1 H, dd, J=8.2, 2.3 Hz), 7.61 (1 H, d, J=8.2 Hz), 4.35-4.60 (1 H, m), 3.57 (1 H, br. s.), 3.09 (1 H, br. s.), 2.81 (2 H, br. s.), 2.39 (6 H, s), 1.67-1.98 (2 H, m), 1.48 (2 H, qd, J=12.0, 4.3 Hz). LCMS-ESI (POS), M/Z, M+1: Found 268.1.

9-Cyclopentyl-N-(5-((4-(dimethylamino)-1-piperidinyl)carbonyl)-2-pyridinyl)-9H-pyrido[4',3':4,5]pyrrolo[2,3-d]pyrimidin-2-amine (364): Compound 364 was prepared as a light yellow solid (TFA salt) from compound 4 and compound 365 using chemistry similar to that described in example 200. $^1$H NMR (500 MHz, CD$_3$OD) δ ppm 9.57 (1 H, s), 9.27 (1 H, s), 8.56-8.64 (2 H, m), 8.51 (1 H, d, J=1.7 Hz), 8.44 (1 H, d, J=8.8 Hz), 8.02 (1 H, dd, J=8.7, 2.3 Hz), 5.47 (1 H, quin, J=8.9 Hz), 3.49-3.60 (1 H, m, J=12.0, 12.0, 3.8, 3.7 Hz), 2.91 (6 H, s), 2.48-2.61 (2 H, m), 2.02-2.34 (6 H, m), 1.85-1.98 (2 H, m), 1.70-1.85 (2 H, m, J=12.3, 12.3, 12.2, 4.4 Hz). LCMS-ESI (POS), M/Z, M+1: Found 485.2.

Example 231

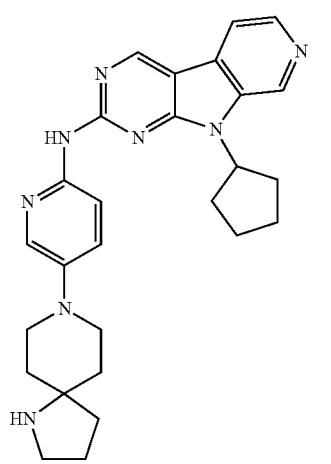

9-cyclopentyl-N-(5-(1,8-diazaspiro[45]dec-8-yl)-2-pyridinyl)-9H-pyrido[4',3':4,5]pyrrolo[2,3-d]pyrimidin-2-amine

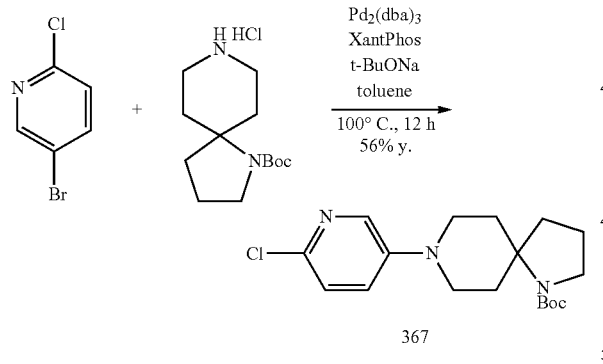

tert-Butyl 8-(6-chloro-3-pyridinyl)-1,8-diazaspiro[45]decane-1-carboxylate (367): Compound 367 was prepared as an off-white solid using chemistry similar to that described in Example 1. ¹H NMR (400 MHz, CDCl₃) δ ppm 7.99 (1 H, br. s.), 7.14 (2 H, br. s.), 3.55-3.83 (2 H, m), 3.47 (2 H, d, J=15.1 Hz), 2.49-3.08 (4 H, m), 1.86-2.07 (2 H, m), 1.72-1.84 (2 H, m), 1.29-1.55 (11 H, m). LCMS-ESI (POS), M/Z, M+1: Found 352.1.

9-cyclopentyl-N-(5-(1,8-diazaspiro[45]dec-8-yl)-2-pyridinyl)-9H-pyrido-[4',3':4,5]pyrrolo[2,3-d]pyrimidin-2-amine (366): Compound 366 was prepared as a yellow solid (TFA salt) from compound 4 and compound 367 using chemistry similar to that described in example 200. ¹H NMR (500 MHz, DMSO-d₆) δ ppm 9.55 (1 H, s), 9.32 (1 H, s), 8.70 (2 H, br. s.), 8.65 (1 H, d, J=6.1 Hz), 8.54 (1 H, d, J=5.9 Hz), 8.10 (1 H, d, J=2.9 Hz), 8.02 (1 H, d, J=8.3 Hz), 7.65 (1 H, d, J=8.3 Hz), 5.36 (1 H, quin, J=8.7 Hz), 3.57 (2 H, ddd, J=12.7, 4.6, 4.4 Hz), 3.28 (3 H, quin, J=6.4 Hz), 3.06 (2 H, ddd, J=12.8, 9.7, 3.2 Hz), 2.38-2.47 (2 H, m), 1.84-2.17 (12 H, m), 1.68-1.81 (2 H, m). LCMS-ESI (POS), M/Z, M+1: Found 469.3.

Example 232

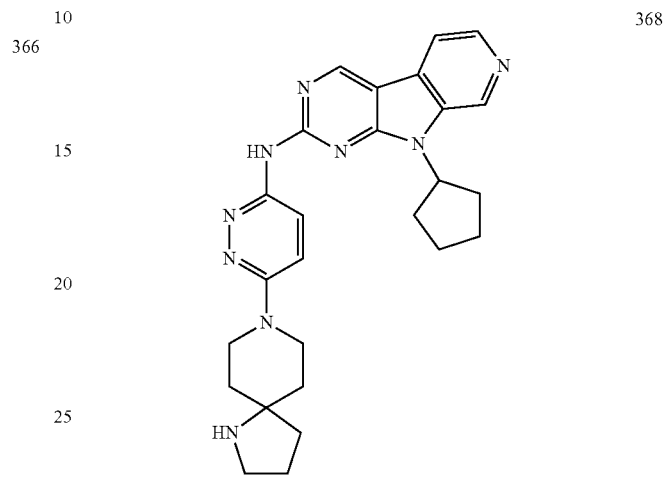

9-cyclopentyl-N-(6-(1,8-diazaspiro[45]dec-8-yl)-3-pyridazinyl)-9H-pyrido[4',3':4,5]pyrrolo[2,3-d]pyrimidin-2-amine

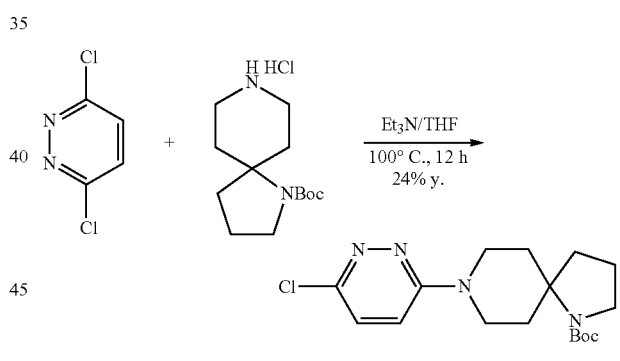

tert-Butyl 8-(6-chloro-3-pyridazinyl)-1,8-diazaspiro[45]decane-1-carboxylate (369): Compound 369 was prepared using chemistry similar to that described in example 4. ¹H NMR (500 MHz, CDCl₃) δ ppm 7.24 (1 H, d, J=10.0 Hz), 6.96 (1 H, d, J=9.8 Hz), 4.35 (2 H, d, J=12.7 Hz), 3.39-3.55 (2 H, m), 3.03 (2 H, t, J=12.8 Hz), 2.80-2.92 (1 H, m), 2.60 (1H, t, J=13.1 Hz), 1.94-2.11 (2 H, m), 1.81 (2 H, quin, J=6.8 Hz), 1.21-1.53 (11 H, m). LCMS-ESI (POS), M/Z, M+1: Found 353.0.

9-cyclopentyl-N-(6-(1,8-diazaspiro[45]dec-8-yl)-3-pyridazinyl)-9H-pyrido-[4',3':4,5]pyrrolo[2,3-d]pyrimidin-2-amine (368): Compound 368 was prepared as a yellow solid (TFA salt) from compound 4 and compound 369 using chemistry similar to that described in example 200. ¹H NMR (500 MHz, DMSO-d₆) δ ppm 10.98 (1 H, br. s.), 9.55 (1 H, s), 9.31 (1 H, s), 8.68-8.76 (1 H, m), 8.65 (1 H, d, J=5.9 Hz), 8.52 (1 H, d, J=5.6 Hz), 8.14 (1 H, d, J=9.8 Hz), 7.66 (1 H, d, J=9.3

Hz), 5.34 (1 H, quin, J=8.7 Hz), 4.04 (1 H, dt, J=13.9, 4.4 Hz), 3.34-3.40 (2 H, m), 3.29 (2 H, ddd, J=12.5, 6.6, 6.4 Hz), 2.32-2.42 (2 H, m), 1.94-2.17 (8 H, m), 1.83-1.94 (4 H, m), 1.65-1.79 (2 H, m). LCMS-ESI (POS), M/Z, M+1: Found 470.2.

Example 233

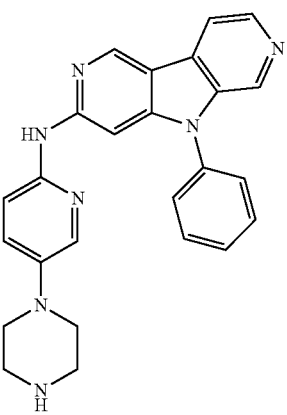

5-phenyl-N-(5-(1-piperazinyl)-2-pyridinyl)-5H-pyrido[3',2':4,5]pyrrolo[2,3-c]pyridin-3-amine

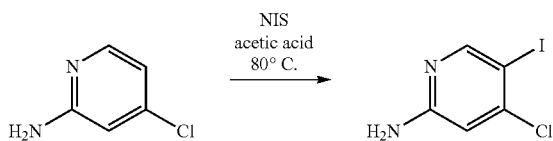 [SMILES: Nc1cc(Cl)ccn1 ; Nc1cc(Cl)c(I)cn1]

4-chloro-5-iodopyridin-2-amine. 4-Chloropyridin-2-amine (0.142 g, 1.10 mmol) and N-iodosuccinimide (0.273 g, 1.22 mmol) were combined in 1.5 mL of acetic acid. The solution was sonicated briefly and then heated to 80° C. After 1 hour the solution was cooled to room temperature and then concentrated under vacuum. After adjusting the pH to ~8/9 with aqueous ammonia, a light brown solid was collected by filtration. The solid was purified on a 12 g Combiflash column eluting with a gradient of DCM to 5% methanol/0.25% NH₄OH (~28% in water)/DCM. The fractions containing the product were combined and concentrated under vacuum to give 4-chloro-5-iodopyridin-2-amine (187 mg, 67%) as an off-white solid. 1H NMR (500 MHz, DMSO-d₆) δ ppm 8.20 (1 H, s), 6.69 (1 H, s), 6.40 (2 H, s); LCMS-ESI (POS), M/Z, M+1: Found 254.9.

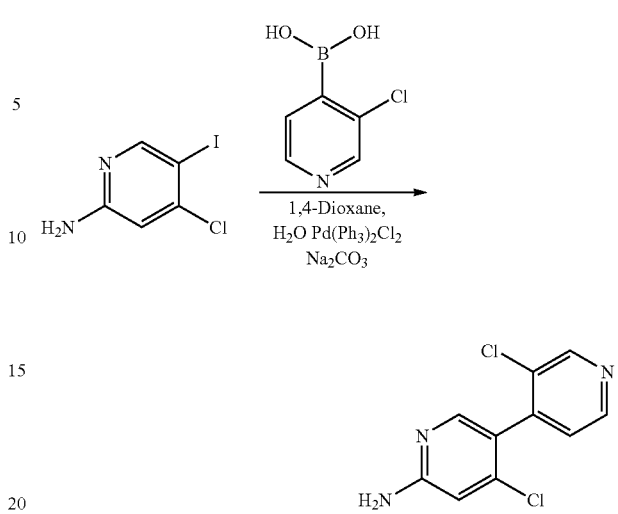

4-chloro-5-(3-chloropyridin-4-yl)pyridin-2-amine.
4-Chloro-5-iodopyridin-2-amine (8.100 g, 31.8 mmol), sodium carbonate (5.00 g, 47.7 mmol), and 3-chloropyridin-4-ylboronic acid hydrate (11.2 g, 63.7 mmol) were combined in 100 mL of 1,4-Dioxane and 25 mL of water. Nitrogen was bubbled through the solution for ~2 min before adding trans-dichlorobis(triphenyl-phosphine)palladium (II) (2.05 g, 2.92 mmol). The solution was heated to 60° C. overnight. Additional trans-dichlorobis(triphenyl-phosphine)palladium (II) (0.2 g, 0.285 mmol), 3-chloropyridin-4-ylboronic acid hydrate (4.00 g, 22.8 mmol), 15 mL of water (degassed) and sodium carbonate (1.75 g, 16.6 mmol) were added. The solution was heated to 100° C. for 5 hours. Additional 3-chloropyridin-4-ylboronic acid hydrate (4.00 g, 22.8 mmol) was added and the reaction continued for 2 h at 100° C. The solution was concentrated under vacuum to ⅕th the volume and extracted between DCM and water. The aqueous layer was extracted with 10% isopropanol/DCM. The combined organics were dried over MgSO₄ and then concentrated under vacuum to give an orange solid. The solid was slurried with DCM and then filtered through a fritted funnel. The solids were washed with additional DCM. The combined filtrate was purified on a 80 g Combiflash column (dry loaded), eluting with 2% methanol/0.1% NH4OH (~28% in water)/DCM to 8% methanol /0.4% NH4OH (~28% in water)/DCM. The fractions containing the product were concentrated under vacuum to give a yellowish solid. The solids were triturated with DCM to give 4-chloro-5-(3-chloropyridin-4-yl)pyridin-2-amine (3.93 g, 51%) as an off white solid. ¹H NMR (500 MHz, DMSO-d₆) δ ppm 8.73 (1 H, s), 8.58 (1 H, d, J=4.9 Hz), 7.87 (1 H, s), 7.44 (1 H, d, J=4.9 Hz), 6.64 (1 H, s), 6.55 (2 H, br. s.); LCMS-ESI (POS), M/Z, M+1: Found 239.9.

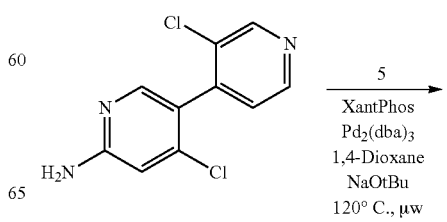

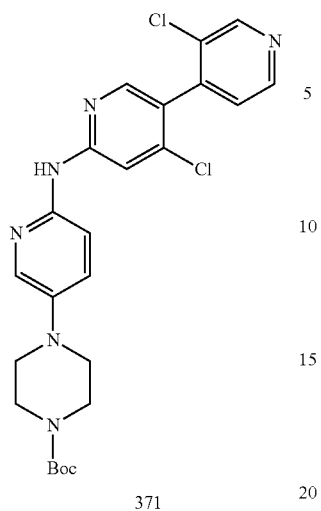

371

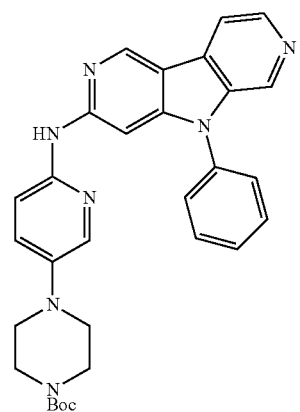

372 tert-Butyl 4-(6-(4-chloro-5-(3-chloropyridin-4-yl)pyridin-2-ylamino)pyridin-3-yl)piperazine-1-carboxylate (371). 4-Chloro-5-(3-chloropyridin-4-yl)pyridin-2-amine (0.263 g, 1.10 mmol), sodium 2-methylpropan-2-olate (0.316 g, 3.29 mmol), and compound 5 (0.424 g, 1.42 mmol) were combined in anhydrous 1,4-dioxane (5 mL). Nitrogen was bubbled through the solution for ~1 min before adding 4,5-bis(diphenylphosphino)-9,9-dimethyl-9H-xanthene (0.0634 g, 0.110 mmol) and Pd$_2$(dba)$_3$ (0.0502 g, 0.0548 mmol). The solution was then heated to 120° C. with microwave irradiation for 1 hour. The solution was purified on a 40 g CombiFlash column (dry loaded) eluting with a gradient of hexane to ethyl acetate. The fractions containing the product were combined and concentrated under vacuum to give compound 371 (0.492 g, 90%) as a yellow solid. $^1$H NMR (500 MHz, DMSO-d$_6$) δ ppm 9.95 (1 H, s), 8.78 (1 H, br. s.), 8.63 (1 H, d, J=4.9 Hz), 8.17 (1 H, s), 8.04 (1 H, s), 8.01 (1 H, d, J=2.9 Hz), 7.55 (1 H, d, J=9.0 Hz), 7.52 (1 H, d, J=4.9 Hz), 7.46 (1 H, dd, J=9.0, 2.9 Hz), 3.41-3.54 (4 H, m), 2.99-3.10 (4 H, m), 1.42 (9 H, s); LCMS-ESI (POS), M/Z, M+1: Found 501.1.

tert-Butyl 4-(6-((5-phenyl-5H-pyrido[3',4':4,5]pyrrolo[2,3-c]pyridin-3-yl)amino)-3-pyridinyl)-1-piperazinecarboxylate (372): In a 10 mL single-necked round bottom flask were placed tert-butyl 4-(6-(4-chloro-5-(3-chloropyridin-4-yl)pyridin-2-ylamino)pyridin-3-yl)piperazine-1-carboxylate (371) (50 mg, 100 μmol), palladium diacetate (11 mg, 50 μmol), Josiphos (28 mg, 50 μmol), and sodium tert-butoxide (29 mg, 299 μmol). The flask was subjected to 3 cycles of evacuation and back-filling with N$_2$. Aniline (36 μl, 399 μmol) was added under N$_2$ followed by 1,2-dimethoxyethane (3 mL). The resulting mixture was stirred at 100° C. for 20 h. After the volatiles were removed, the residue was subjected to combi-flash column chromatography (methanol/DCM). The product containing compound 372 after concentration was used without further purification. LCMS-ESI (POS), M/Z, M+1: Found 522.2.

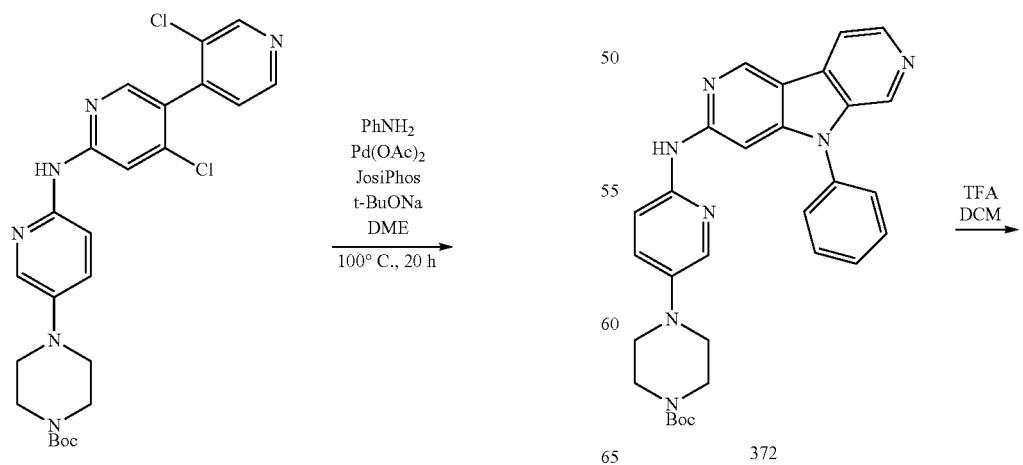

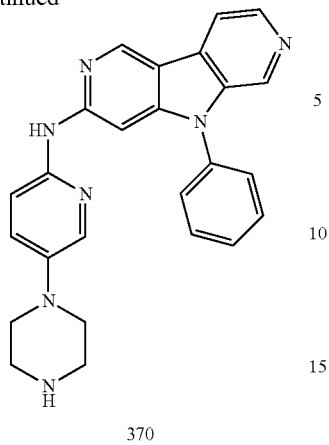

370

5-phenyl-N-(5-(1-piperazinyl)-2-pyridinyl)-5H-pyrido[3',2':4,5]pyrrolo[2,3-e]pyridin-3-amine (370): A solution of crude compound 372 in DCM (8 mL) was treated with trifluoroacetic acid (2.0 mL, 27 mmol) at room temperature for 2 h. After the volatiles were removed, the residue was subjected to reverse phase preparative HPLC (acetonitrile/H$_2$O containing 0.1% TFA each, 40 min from 10 to 40%). Lyophilization provided compound 370 (12 mg) as a yellow solid (TFA salt). $^1$H NMR (500 MHz, CD$_3$OD) δ ppm 9.46 (1 H, s), 8.80 (1 H, d, J=0.7 Hz), 8.65 (1 H, d, J=5.6 Hz), 8.53 (1 H, d, J=5.6 Hz), 8.05 (1 H, d, J=2.9 Hz), 7.90 (1 H, dd, J=9.3, 2.9 Hz), 7.77-7.83 (2 H, m), 7.68-7.76 (3 H, m), 7.24 (1 H, d, J=9.3 Hz), 7.14 (1 H, s), 3.46-3.53 (4 H, m), 3.40-3.46 (4 H, m). LCMS-ESI (POS), M/Z, M+1: Found 422.2.

Example 234

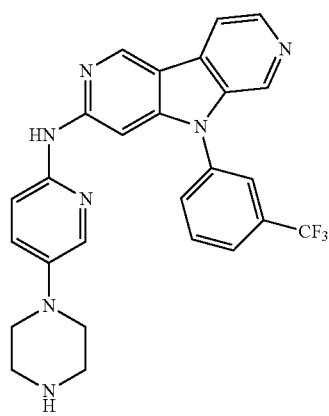

373

N-(5-(1-piperazinyl)-2-pyridinyl)-5-(3-(trifluoromethyl)phenyl)-5H-pyrido[3',2':4,5]pyrrolo[2,3-c]pyridin-3-amine Compound 373 was prepared as a yellow solid (TFA salt) using chemistry similar to that described in example 233. $^1$H NMR (500 MHz, CD$_3$OD) δ ppm 9.62 (1 H, d, J=1.0 Hz), 9.01 (1 H, s), 8.81 (1 H, d, J=5.4 Hz), 8.74 (1 H, d, J=5.9 Hz), 8.18 (1 H, s), 7.97-8.11 (5 H, m), 7.34 (1 H, d, J=9.5 Hz), 7.10 (1 H, s), 3.48-3.56 (4 H, m), 3.40-3.48 (4 H, m). LCMS-ESI (POS), M/Z, M+1: Found 490.1.

Example 235

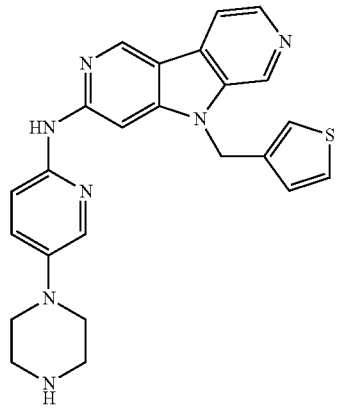

374

N-(5-(1-piperazinyl)-2-pyridinyl)-5-(3-thiophenylmethyl)-5H-pyrido[3',4':4,5]pyrrolo[2,3-c]pyridin-3-amine Compound 374 was prepared as a yellow solid (TFA salt) using chemistry similar to that described in example 233. $^1$H NMR (500 MHz, CD$_3$OD) δ ppm 9.44 (1 H, s), 9.21 (1 H, s), 8.63 (1 H, d, J=5.9 Hz), 8.56 (1 H, d, J=5.6 Hz), 8.05 (1 H, d, J=2.9 Hz), 7.95 (1 H, dd, J=9.5, 2.9 Hz), 7.45 (1 H, dd, J=5.1, 2.9 Hz), 7.40-7.43 (1 H, m), 7.37 (1 H, s), 7.30 (1 H, d, J=9.3 Hz), 7.05 (1 H, dd, J=5.1, 1.5 Hz), 5.77 (2 H, s), 3.47-3.52 (4 H, m), 3.41-3.47 (4 H, m). LCMS-ESI (POS), M/Z, M+1: Found 441.9.

Example 236

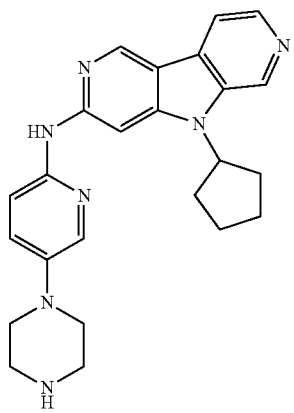

375

313

5-cyclopentyl-N-(5-(1-piperazinyl)-2-pyridinyl)-5H-pyrrolo[3',2':4,5]pyrrolo[2,3-c]pyridin-3-amine Compound 375 was prepared as a yellow solid (TFA salt) using chemistry similar to that described in example 233. LCMS-ESI (POS), M/Z, M+1: Found 414.1.

Example 237

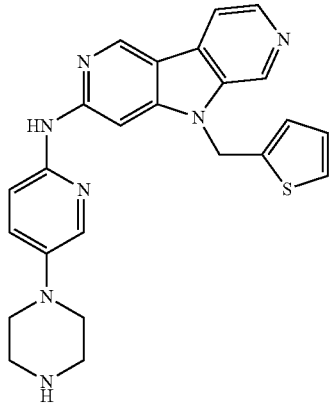

376

N-(5-(1-piperazinyl)-2-pyridinyl)-5-(2-thiophenylmethyl)-5H-pyrido[3',2':4,5]pyrrolo[2,3-c]pyridin-3-amine Compound 376 was prepared as a yellow solid (TFA salt) using chemistry similar to that described in example 233. $^1$H NMR (500 MHz, CD$_3$OD) δ ppm 9.40 (1 H, d, J=0.7 Hz), 9.25 (1 H, d, J=0.7 Hz), 8.62 (1 H, d, J=5.6 Hz), 8.50 (1 H, d, J=5.6 Hz), 8.06 (1 H, d, J=2.7 Hz), 7.93 (1 H, dd, J=9.3, 2.9 Hz), 7.44 (1 H, s), 7.37 (1 H, dd, J=5.1, 1.2 Hz), 7.31 (1 H, d, J=9.3 Hz), 7.27 (1 H, dd, J=3.7, 1.0 Hz), 7.01 (1 H, dd, 3.4 Hz), 5.96 (2 H, s), 3.47-3.53 (4 H, m), 3.42-3.47 (4 H, m). LCMS-ESI (POS), M/Z, M+1: Found 442.1.

Example 238

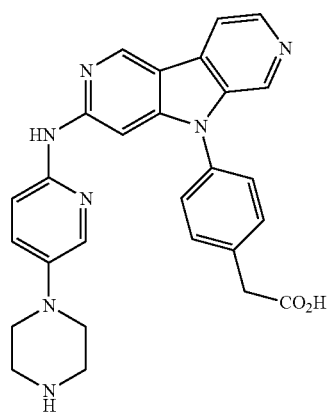

377

314

(4-(3-((5-(1-piperazinyl)-2-pyridinyl)amino)-5H-pyrido[3',2':4,5]pyrrolo[2,3-c]pyridin-5-yl)phenyl) acetic acid

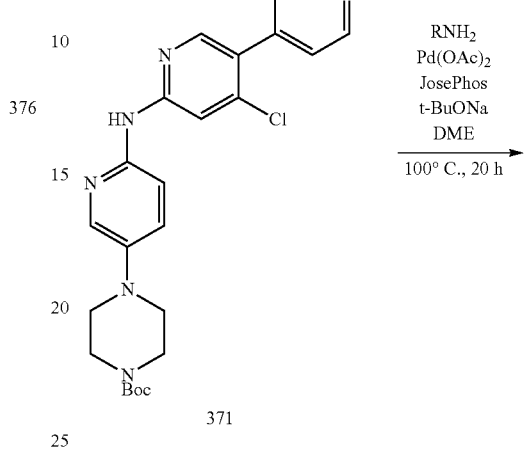

371

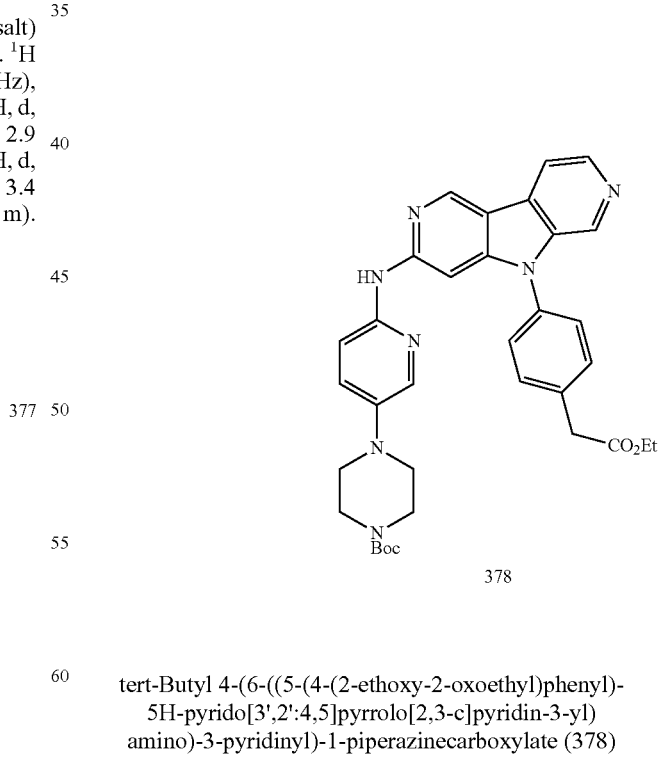

378 tert-Butyl 4-(6-((5-(4-(2-ethoxy-2-oxoethyl)phenyl)-5H-pyrido[3',2':4,5]pyrrolo[2,3-c]pyridin-3-yl)amino)-3-pyridinyl)-1-piperazinecarboxylate (378)

Compound 378 was prepared using chemistry similar to that described in example 233. LCMS-ESI (POS), M/Z, M+1: Found 608.3.

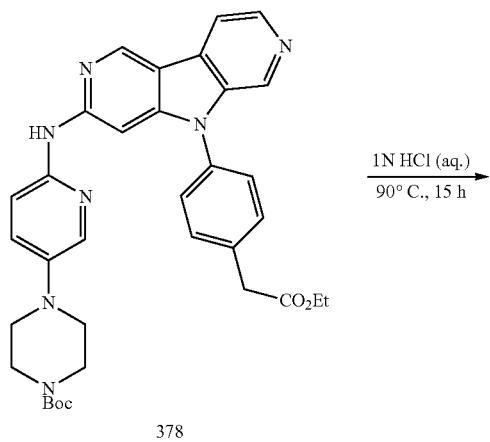

378

$\xrightarrow{\text{1N HCl (aq.)}}{90° C., 15 h}$

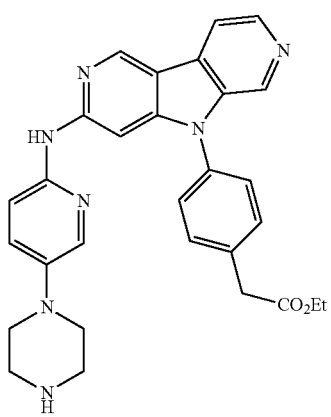

377

(4-(3-((5-(1-piperazinyl)-2-pyridinyl)amino)-5H-pyrido[3',4':4,5]pyrrolo[2,3-c]pyridin-5-yl)phenyl)acetic acid (377): A mixture of crude compound 378 and 1N hydrochloric acid (aqueous solution) (10 mL, 10.0 mmol) was stirred at 90° C. for 15 h. After concentration, the residue was taken up with 1 N HCl aqueous solution and subjected to reverse phase preparative HPLC (acetonitrile/water containing 0.1% TFA each, 40 min from 10 to 40%). Lyophilization provided compound 377 (6 mg) as a yellow solid (TFA salt). $^1$H NMR (500 MHz, CD$_3$OD) δ ppm 9.48 (1 H, s), 8.85 (1 H, s), 8.66 (1 H, d, J=5.6 Hz), 8.57 (1 H, d, J=5.6 Hz), 8.04 (1 H, d, J=2.7 Hz), 7.93 (1 H, dd, J=9.3, 2.9 Hz), 7.67-7.74 (4 H, m), 7.25 (1 H, d, J=9.3 Hz), 7.13 (1 H, s), 3.85 (2 H, s), 3.46-3.51 (4 H, m), 3.41-3.46 (4 H, m). LCMS-ESI (POS), M/Z, M+1: Found 480.2.

Example 239

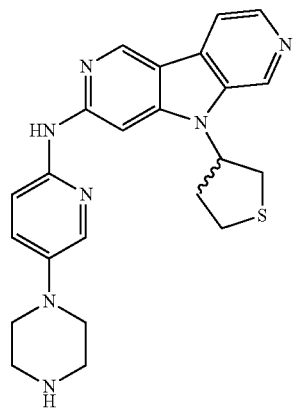

379

N-(5-(1-piperazinyl)-2-pyridinyl)-5-(tetrahydro-3-thiophenyl)-5H-pyrido[3',2':4,5]pyrrolo[2,3-c]pyridin-3-amine Compound 379 was prepared as a yellow solid (TFA salt) using chemistry similar to that described in example 233. $^1$H NMR (500 MHz, CD$_3$OD) δ ppm 9.54 (1 H, s), 9.44 (1 H, s), 8.72 (1 H, d), 8.67 (1 H, d, J=5.9 Hz), 8.08 (1 H, dd, J=9.5, 2.9 Hz), 8.01 (1 H, d, J=2.7 Hz), 7.61 (1 H, s), 7.41 (1 H, d, J=9.3 Hz), 5.64-5.74 (1 H, m), 3.48-3.56 (6 H, m), 3.42-3.47 (4 H, m), 3.12-3.20 (2 H, m), 2.59-2.81 (2 H, m). LCMS-ESI (POS), M/Z, M+1: Found 432.1.

Example 240

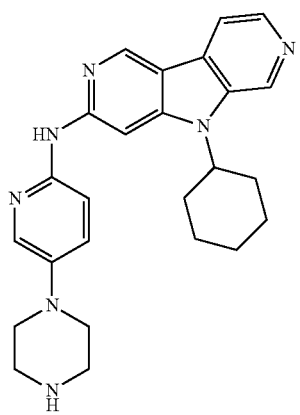

380

5-cyclohexyl-N-(5-(1-piperazinyl)-2-pyridinyl)-5H-pyrido[3',2':4,5]pyrrolo[2,3-c]pyridin-3-amine Compound 380 was prepared using chemistry similar to that described in example 233. $^1$H NMR (500 MHz, DMSO-d$_6$) δ ppm 9.56 (1 H, s), 9.47 (1 H, s), 8.77 (1 H, d, J=6.1 Hz), 8.65 (1 H, d, J=6.1 Hz), 8.10 (1 H, dd, J=9.5, 2.9 Hz), 8.00 (1 H, d, J=2.7 Hz), 7.54 (1 H, s), 7.42 (1 H, d, J=9.5 Hz), 4.77-4.84 (1 H, m), 3.50-3.54 (4 H, m), 3.43-3.48 (4 H, m), 2.31-2.44 (2 H, m), 2.04-2.16 (4 H, m), 1.86-1.95 (1 H, m), 1.65-1.77 (2 H, m), 1.46-1.59 (1 H, m); LCMS-ESI (POS), M/Z, M+1: Found 428.2.

Example 241

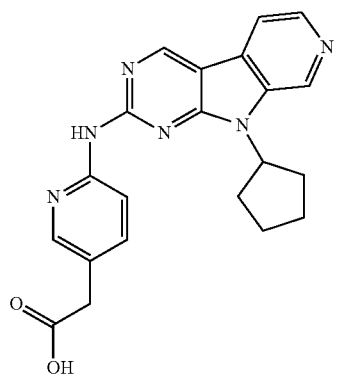

381

(6-((9-cyclopentyl-9H-pyrido[4',3':4,5]pyrrolo[2,3-d]pyrimidin-2-yl)amino)-3-pyridinyl)acetic acid Sodium 2-methylpropan-2-olate (97 mg, 1007 μmol) was added to a dioxane (3 mL) solution containing methyl 2-(6-chloropyridin-3-yl)acetate (69 mg, 369 μmol), tris(dibenzylideneacetone)dipalladium (23 mg, 25 μmol), 4,5-bis(diphenylphosphino)-9,9-dimethyl-9H-xanthene (29 mg, 50 μmol), and compound 4 (85 mg, 336 μmol). The resulting mixture was stirred in the microwave at 120° C. for 3 h. The mixture was then purified on silica eluting with a DCM/methanol gradient (0-10%). Desired fractions containing the ester were pooled and concentrated. The ester was then dissolved in a 3 N NaOH/methanol (1:1) solution and stirred for 3 h at 50° C. Next, the solution was acidified to pH 2 and concentrated to dryness. The resulting residue was then purified by prep HPLC. Desired fractions were pooled and lyophilized to give compound 381 (86 mg, 66% yield). $^1$H NMR (400 MHz, CD$_3$OD, TFA salt) δ ppm 1.82-2.05 (m, 2 H) 2.11-2.38 (m, 4 H) 2.45-2.64 (m, 2 H) 3.83 (s, 2 H) 5.50 (qn, J=8.61 Hz, 1 H) 7.84 (d, J=8.80 Hz, 1 H) 8.20 (dd, J=9.00, 2.15 Hz, 1 H) 8.41 (d, J=1.57 Hz, 1 H) 8.56-8.73 (m, 2 H) 9.23-9.40 (m, 1 H) 9.55-9.72 (m, 1 H); LCMS-ESI (POS), M/Z, M+1: Found 389, Calculated 389.

Example 242

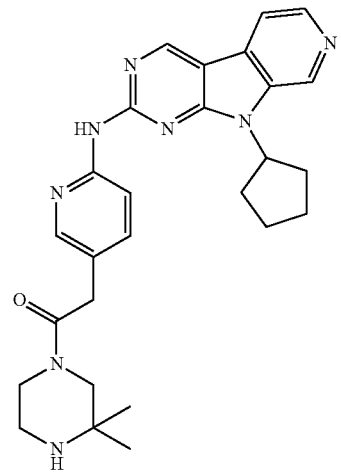

382

9-cyclopentyl-N-(5-(2-(3,3-dimethyl-1-piperazinyl)-2-oxoethyl)-2-pyridinyl)-9H-pyrido[4',3':4,5]pyrrolo[2,3-d]pyrimidin-2-amine Triethylamine (4 eq.) was added to a DMF solution containing 2,2-dimethylpiperazine (1.2 eq.), compound 381 (1 eq.), and PyBOP (1.1 eq.). The resulting solution was stirred for 3 h at room temperature. The product was purified via reverse phase HPLC (10-70% acetonitrile/water). Desired fractions were pooled and lyophilized to give compound 382. $^1$H NMR (400 MHz, CD$_3$OD, TFA salt) δ ppm 1.43 (s, 3 H) 1.50 (s, 3 H) 1.93 (d, J=6.06 Hz, 2 H) 2.15-2.34 (m, 4 H) 2.47-2.62 (m, 1 H) 3.43 (dd, J=3.33, 1.56 Hz, 1 H) 3.71 (s, 1 H) 3.77 (s, 1 H) 3.83-4.00 (m, 2 H) 4.06 (s, 1 H) 5.39-5.58 (m, 1 H) 7.94 (br. s., 1 H) 8.09 (dd, J=8.71, 2.05 Hz, 1 H) 8.35 (d, J=1.76 Hz, 1 H) 8.55-8.67 (m, 1 H) 9.29 (s, 1 H) 9.55-9.69 (m, 1 H); LCMS-ESI (POS), M/Z, M+1: Found 577.2, Calculated 577.

Example 243

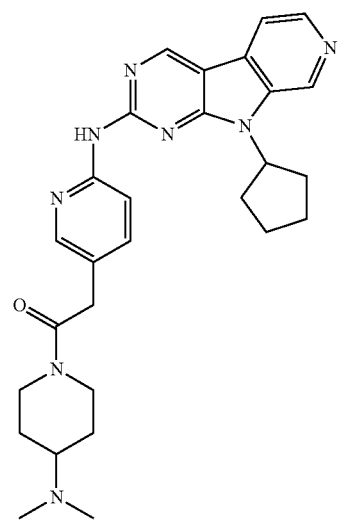

383

9-cyclopentyl-N-(5-(2-(4-(dimethylamino)-1-piperidinyl)-2-oxoethyl)-2-pyridinyl)-9H-pyrido[4',3':4,5]pyrrolo[2,3-d]pyrimidin-2-amine Compound 383 was prepared using chemistry similar to that described in example 242. ¹H NMR (500 MHz, CD₃OD, TFA salt) δ ppm 1.65 (dd, J=12.35, 4.52 Hz, 1 H) 1.81 (dd, J=12.35, 4.28 Hz, 1 H) 1.89-2.00 (m, 2 H) 2.11-2.35 (m, 6 H) 2.48-2.63 (m, 2 H) 2.70-2.84 (m, 1 H) 2.93 (s, 6 H) 3.23-3.29 (m, 1 H) 3.48-3.58 (m, 1 H) 4.01 (s, 2 H) 4.27-4.37 (m, 1 H) 4.72-4.82 (m, 1 H) 5.50 (qn, J=8.80 Hz, 1 H) 7.85 (d, J=8.80 Hz, 1 H) 8.14 (dd, J=8.80, 1.96 Hz, 1 H) 8.36 (d, J=1.71 Hz, 1 H) 8.63-8.70 (m, 2 H) 9.34 (s, 1 H) 9.64-9.71 (m, 1 H); LCMS-ESI (POS), M/Z, M+1: Found 499, Calculated 499.

Example 244

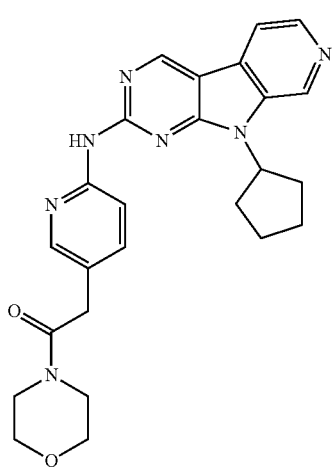

384

9-cyclopentyl-N-(5-(2-(4-morpholinyl)-2-oxoethyl)-2-pyridinyl)-9H-pyrido[4',3':4,5]pyrrolo[2,3-d]pyrimidin-2-amine Title compound 384 was prepared using chemistry similar to that described in example 242. ¹H NMR (500 MHz, CD₃OD, TFA salt) δ ppm 1.86-2.00 (m, 2 H) 2.16-2.35 (m, 4 H) 2.47-2.63 (m, 2 H) 3.63-3.67 (m, 2 H) 3.70 (ddd, J=14.37, 4.71, 4.40 Hz, 4 H) 3.74-3.78 (m, 2 H) 3.98 (s, 2 H) 5.50 (qn, J=8.80 Hz, 1 H) 7.81 (d, J=8.80 Hz, 1 H) 8.16 (dd, J=8.80, 2.20 Hz, 1H) 8.36 (d, J=1.96 Hz, 1 H) 8.62-8.71 (m, 2 H) 9.33 (s, 1 H) 9.62-9.71 (m, 1 H); LCMS-ESI (POS), M/Z, M+1: Found 458, Calculated 458

Example 245

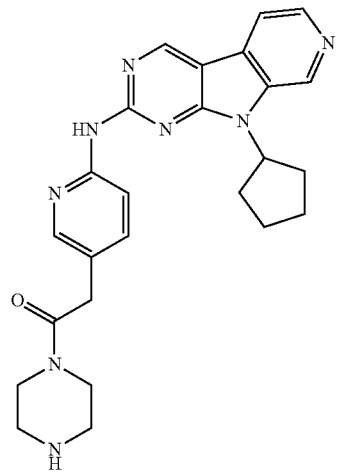

385

9-cyclopentyl-N-(5-(2-oxo-2-(1-piperazinyl)ethyl)-2-pyridinyl)-9H-pyrido[4',3':4,5]pyrrolo[2,3-d]pyrimidin-2-amine Compound 385 was prepared using chemistry similar to that described in example 242. ¹H NMR (500 MHz, CD₃OD, TFA salt) δ ppm 1.94 (ddd, J=11.49, 5.62, 5.38 Hz, 2 H) 2.17-2.35 (m, 4 H) 2.48-2.64 (m, 2 H) 3.30 (ddd, 2 H) 3.36-3.40 (m, 2 H) 3.83-3.99 (m, 4 H) 4.01 (s, 2 H) 5.50 (qn, J=8.80 Hz, 1 H) 7.89 (d, J=8.80 Hz, 1 H) 8.11 (dd, J=8.80, 1.96 Hz, 1 H) 8.35 (d, J=1.71 Hz, 1 H) 8.59-8.70 (m, 2 H) 9.30 (s, 1 H) 9.64 (s, 1 H); LCMS-ESI (POS), M/Z, M+1: Found 457, Calculated 457.

Example 246

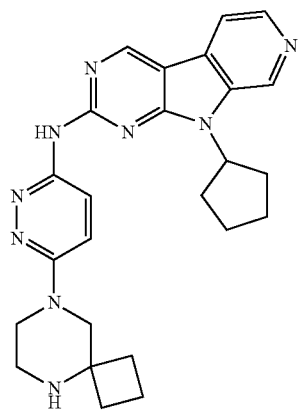

386

9-cyclopentyl-N-(6-(5,8-diazaspiro[3.5]non-8-yl)-3-pyridazinyl)-9H-pyrido[4',3':4,5]pyrrolo[2,3-d]pyrimidin-2-amine Compound 386 was prepared using chemistry similar to that described in example 1. $^1$H NMR (400 MHz, CD$_3$OD) δ ppm 1.80 (m, 2 H) 1.93-2.22 (m, 6 H) 2.22-2.44 (m, 4 H) 3.24-3.30 (m, 2 H) 3.69-3.82 (m, 2 H) 3.86 (s, 2 H) 5.35 (qn, J=8.71 Hz, 1 H) 7.65 (d, J=9.78 Hz, 1 H) 8.18-8.30 (m, 2 H) 8.41 (d, J=5.67 Hz, 1 H) 8.98 (s, 1 H) 9.30 (s, 1 H); LCMS-ESI (POS), M/Z, M+1: Found 456, Calculated 456.

Example 247

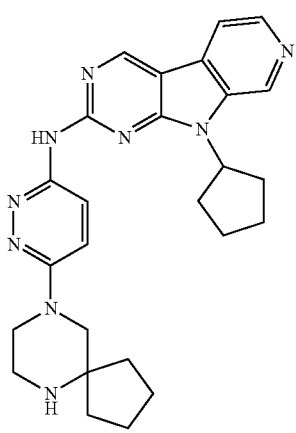

387

9-cyclopentyl-N-(6-(6,9-diazaspiro[4.5]dec-9-yl)-3-pyridazinyl)-9H-pyrido[4',3':4,5]pyrrolo[2,3-d]pyrimidin-2-amine Compound 387 was prepared using chemistry similar to that described in example 1. $^1$H NMR (500 MHz, CD$_3$OD, TFA salt) δ ppm 1.70-1.86 (m, 8 H) 1.88-1.99 (m, 2 H) 1.99-2.06 (m, 2 H) 2.06-2.15 (m, 2 H) 2.26-2.40 (m, 2 H) 3.29-3.38 (m, 2 H) 3.65 (s, 2 H) 3.73-3.84 (m, 2 H) 5.33 (qn, J=8.93 Hz, 1 H) 7.48 (d, J=10.03 Hz, 1 H) 8.04 (d, J=5.38 Hz, 1 H) 8.29-8.41 (m, 2 H) 8.85 (s, 1 H) 9.16 (s, 1 H); LCMS-ESI (POS), M/Z, M+1: Found 470, Calculated 470.

Example 248

388

[Structure of compound 388]

9-cyclopentyl-N-(6-(1,4-diazaspiro[5.5]undec-4-yl)-3-pyridazinyl)-9H-pyrido[4',3':4,5]pyrrolo[2,3-d]pyrimidin-2-amine Compound 388 was prepared using chemistry similar to that described in example 1. $^1$H NMR (400 MHz, CD$_3$OD, TFA salt) δ ppm 1.56-1.82 (m, 7 H) 1.82-1.97 (m, 2 H) 1.97-2.12 (m, 2 H) 2.12-2.34 (m, 4 H) 2.42-2.61 (m, 2 H) 3.40-3.56 (m, 2 H) 3.89-4.06 (m, 4 H) 5.47 (qn, J=8.80 Hz, 1 H) 7.96 (d, J=10.17 Hz, 1 H) 8.12 (d, J=9.78 Hz, 1 H) 8.66 (s, 2 H) 9.33 (s, 1 H) 9.66 (s, 1 H); LCMS-ESI (POS), M/Z, M+1: Found 470, Calculated 470.

Example 249

389

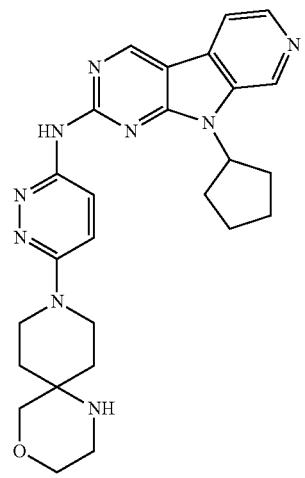

9-cyclopentyl-N-(6-(4-oxa-1,9-diazaspiro[5.5]undec-9-yl)-3-pyridazinyl)-9H-pyrido[4',3":4,5]pyrrolo[2,3-d]pyrimidin-2-amine

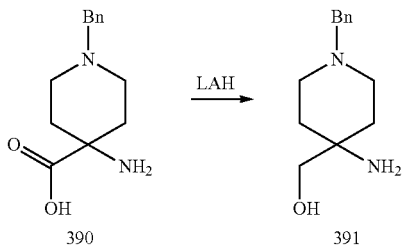 [SMILES: NC1(C(=O)O)CCN(Cc2ccccc2)CC1 ; NC1(CO)CCN(Cc2ccccc2)CC1]

390      391

(4-Amino-1-benzylpiperidin-4-yl)methanol (391): Lithium aluminum hydride (1.94 g, 51.2 mmol) was added to a THF (100 mL) solution of 4-amino-1-benzylpiperidine-4-carboxylic acid [Albert, J. S. et al. *J. Med. Chem.* 2002, 45, (18), 3972-3983] (390) (3.00 g, 12.8 mmol). The resulting mixture was stirred for 1.5 h at reflux. The reaction was cooled to room temperature and the following additions were made slowly: 2 mL of water followed by 2 mL of 1 N NaOH, and finally 4 mL of water. The mixture was then filtered and concentrated to give compound 391 as a thick clear oil (2.22 g, 79% yield). The material was used in the next step without further purification. LCMS-ESI (POS), M/Z, M+1: Found 221, Calculated 221.

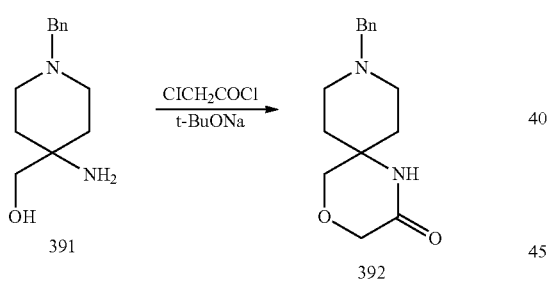

391      392

9-(phenylmethyl)-4-oxa-1,9-diazaspiro[5.5]undecan-2-one (392): Triethylamine (2 mL 14 mmol) was added to a DCM (50 mL) solution containing chloroacetyl chloride (1 mL, 14 mmol) and compound 391 (3 g, 14 mmol). The resulting mixture was stirred 2 h at 23° C. The solvent was stripped and THF was added followed by potassium tert-butoxide (5 g, 41 mmol). The resulting solution was stirred overnight at room temperature. The reaction was then concentrated to dryness and the resulting residue was washed with 200 mL of absolute ethanol. The ethanolic solution was then concentrated to give 3.16 g of 9-(phenylmethyl)-4-oxa-1,9-diazaspiro[5.5]undecan-2-one. The material was used in the next step without further purification. LCMS-ESI (POS), M/Z, M+1: Found 261, Calculated 261.

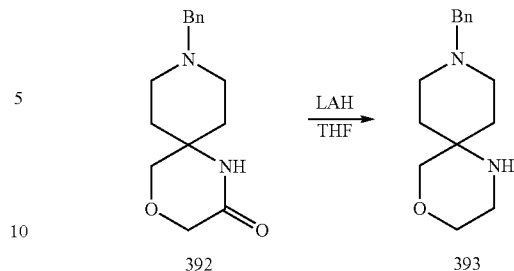

392      393

9-(phenylmethyl)-4-oxa-1,9-diazaspiro[5.5]undecane (393): LAH (2.00 g, 52.7 mmol) was added to a THF (100 mL) solution containing 9-(phenylmethyl)-4-oxa-1,9-diazaspiro[5.5]undecan-2-one (3.1893 g, 12.3 mmol). The resulting mixture was stirred 1 h at reflux. The reaction was then cooled to room temperature and the following additions were made slowly: 2 mL of water followed by 2 mL of 1 N NaOH, and finally 4 mL of water. The mixture was then filtered and concentrated to give a thick clear oil (2.66 g, 88% yield). The material was used in the next step without further purification. LCMS-ESI (POS), M/Z, M+1: Found 247, Calculated 247.

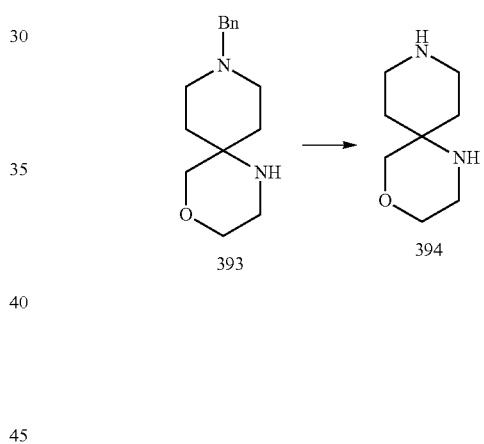

393      394

4-oxa-1,9-diazaspiro[5.5]undecane (395): Pearlman's Catalyst (28.5 mg, 203 µmol) was added to an ethanolic (40 mL) solution containing compound 393 (500 mg, 2030 µmol). The resulting mixture was placed under an atmosphere of hydrogen and stirred overnight at 100° C. (bath temperature). Next, the reaction was cooled to room temperature, filtered, and concentrated to give compound 394 (301 mg, 95% yield). The material was used without further purification. LCMS-ESI (POS), M/Z, M+1: Found 157, Calculated 157.

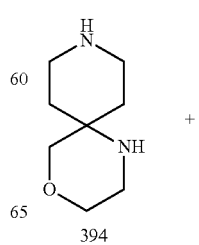

394                +

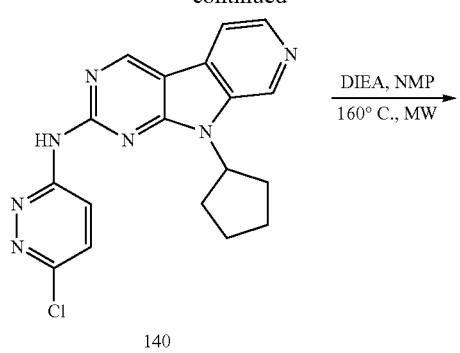

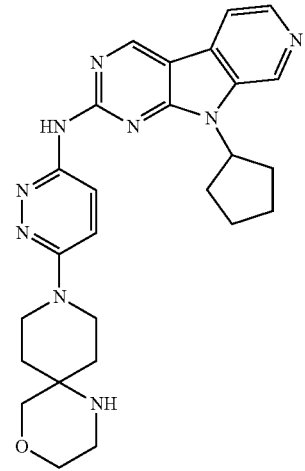

9-cyclopentyl-N-(6-(4-oxa-1,9-diazaspiro[5.5]undec-9-yl)-3-pyridazinyl)-9H-pyrido[4',3':4,5]pyrrolo[2,3-d]pyrimidin-2-amine (389): Compound 394 (30 mg, 191 µmol) was added to an NMP (4 mL) solution containing compound 140 (70 mg, 191 µmol) and N,N-diisopropyl-ethylamine (74 mg, 574 µmol). The resulting mixture was heated in a microwave for 12 h at 165° C. After cooling, the mixture was purified on the reverse phase HPLC (10-50% acetonitrile Method). Desired fractions were pooled and lyophilized to give compound 389 (10 mg, 11% yield). $^1$H NMR (400 MHz, CD$_3$OD, TFA salt) δ ppm 1.81-2.07 (m, 4 H) 2.10-2.38 (m, 6 H) 2.52 (m, 2 H) 3.37-3.42 (m, 3 H) 3.42-3.54 (m, 2 H) 3.91-4.03 (m, 3 H) 4.11-4.28 (m, 2 H) 5.49 (qn, J=8.80 Hz, 1 H) 7.97 (d, J=9.98 Hz, 1 H) 8.09 (d, J=9.98 Hz, 1 H) 8.58-8.63 (m, 1 H) 8.62-8.68 (m, 1 H) 9.30 (s, 1 H) 9.63 (s, 1 H); LCMS-ESI (POS), M/Z, M+1: Found 486, Calculated 486.

Example 250

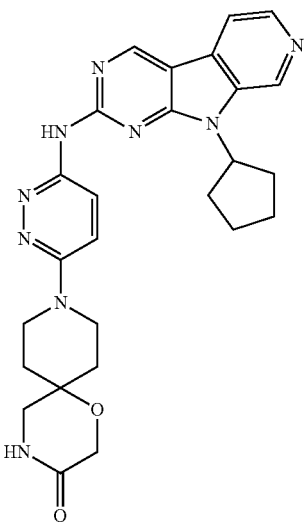

9-(6-((9-cyclopentyl-9H-pyrido[4',3':4,5]pyrrolo[2,3-d]pyrimidin-2-yl)amino)-3-pyridazinyl)-1-oxa-4,9-diazaspiro[5.5]undecan-3-one

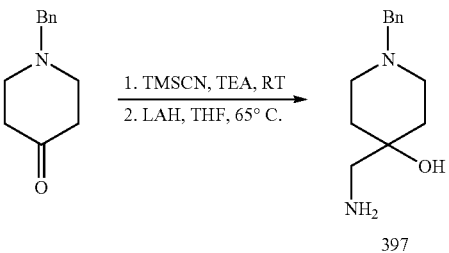 [SMILES: O=C1CCN(Cc2ccccc2)CC1 ; NCC1(O)CCN(Cc2ccccc2)CC1]

4-(aminomethyl)-1-benzylpiperidin-4-ol (397): To a pre-cooled solution (20° C.) of 1-benzyl-4-piperidone (35.0 mL, 196 mmol) and triethylamine (5.5 mL, 40 mmol) was added trimethylsilylcyanide (32.0 mL, 240 mmol), portionwise over 10 minutes. Once the addition was complete, the reaction mixture was stirred at room temperature for 3 hours. This reaction mixture was then cautiously added (10 mL portions over 12 minutes) to a stirring mixture of lithium aluminum hydride (8.5 g, 224 mmol) in tetrahydrofuran (420 mL). Once the addition was complete the reaction mixture was refluxed for 1.5 hours. After cooling to room temperature, the reaction was quenched with water (8.5 mL), followed by 1N NaOH (8.5 mL), and then water (2×8.5 mL). The resulting mixture was allowed to stir at room temperature overnight. The solids were filtered off and rinsed with DCM and ethanol. The filtrate was concentrated down to a solid and then purified by flash chromatography (0-20% methanol in DCM with 1% NH$_4$OH) to give compound 397 as a yellow solid (39.7 g, 92%). LCMS-ESI (POS), M/Z, M+1: Found 221.2, Calculated 221.2.

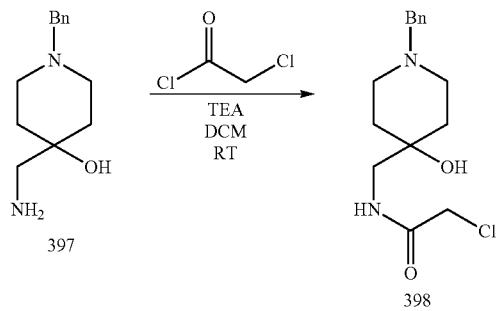 [SMILES: NCC1(O)CCN(Cc2ccccc2)CC1 ; O=C(Cl)CCl ; O=C(CCl)NCC1(O)CCN(Cc2ccccc2)CC1]

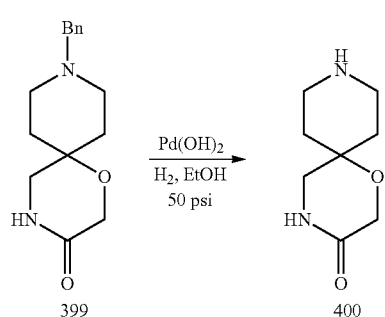

N-((1-benzyl-4-hydroxypiperidin-4-yl)methyl)-2-chloroacetamide (398): To a solution of compound 397 (39.7 g, 180 mmol) in dichloromethane (350 mL) was added triethylamine (50.0 mL, 359 mmol), followed by dropwise addition of chloroacetyl chloride (16.5 mL, 207 mmol) over 15 minutes. The resulting solution was stirred at room temperature for 1.25 hours. The crude mixture was diluted with DCM and water, and extracted with DCM twice. The combined organics were dried over $Na_2SO_4$ and concentrated in vacuo to give compound 398 (41.9 g, 78%). LCMS-ESI (POS), M/Z, M+1: Found 297.1, Calculated 297.1.

1-oxa-4,9-diazaspiro[5.5]undecan-3-one (400): To a solution of compound 399 (316.1 mg, 1214 µmol) in ethanol (15 mL) was added palladium hydroxide, 20 wt % pd (dry basis) on carbon, wet (300 mg, 427 µmol). After hydrogenating the reaction mixture at 50 psi for 6 days, the mixture was filtered thru a plug of celite and concentrated in vacuo to give compound 400 (287.0 mg). LCMS-ESI (POS), M/Z, M+1: Found 171.1, Calculated 171.1.

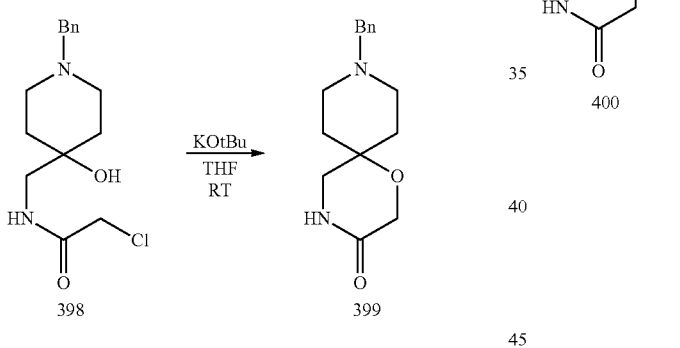

9-benzyl-1-oxa-4,9-diazaspiro[5.5]undecan-3-one (399): To a mixture of compound 398 (41.9 g, 141 mmol) in tetrahydrofuran (300 mL) was added potassium tert-butoxide (31.8 g, 283 mmol), portionwise over 40 minutes. After 3.5 hours of stirring at room temperature, the reaction was concentrated in vacuo. The residue was diluted with DCM and water, and then neutralized with 3N HCl. The remaining solids were filtered off and the filtrate was concentrated to an oil. The residue was taken up in hot ethanol (100 mL). After allowing the solution to cool to ~45° C., the salts were filtered off, and the filtrate was concentrated to a brown solid. The crude material was purified by flash chromatography (0-20% methanol in DCM with 1% $NH_4OH$) to give compound 399 as an orange solid (22.8 g, 62%). LCMS-ESI (POS), M/Z, M+1: Found 261.1, Calculated 261.1.

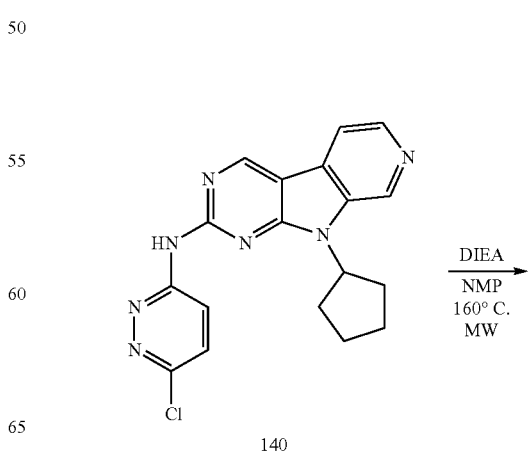

329

-continued

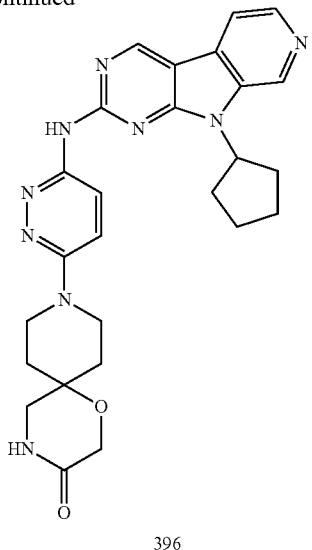

396

9-(6-((9-cyclopentyl-9H-pyrido[4',3':4,5]pyrrolo[2,3-d]pyrimidin-2-yl)amino)-3-pyridazinyl)-1-oxa-4,9-diazaspiro[5.5]undecan-3-one (396): To a mixture of compound 400 (110.0 mg, 646 μmol) and compound 140 (40.0 mg, 109 μmol) in N-methylpyrrolidinone (1.50 mL) was added N,N-diisopropylethylamine (DIEA) (0.100 mL, 575 μmol). The resulting mixture was heated at 160° C. under microwave irradiation for 6 h. The crude material was purified by reverse phase HPLC (acetonitrile/H$_2$O containing 0.1% TFA each, 25 min from 10 to 40%). The isolated material was further purified by prep-TLC (10% methanol in DCM with 1% NH$_4$OH) to give compound 396 as a yellow solid (2.5 mg, 5%). $^1$H NMR (500 MHz, CD$_3$OD) δ 9.21 (s, 1 H) 8.91 (s, 1 H) 8.37-8.46 (m, 2 H) 8.08 (d, J=5.38 Hz, 1 H) 7.46 (d, J=10.03 Hz, 1 H) 5.43 (quin, 1 H) 4.21 (s, 2 H) 4.06 (ddd, J=13.27, 3.48, 3.30 Hz, 2 H) 3.37-3.42 (m, 4 H) 2.44 (dd, J=12.96, 8.31 Hz, 2 H) 2.08-2.24 (m, 4 H) 2.03 (d, J=13.45 Hz, 2 H) 1.84-1.93 (m, 2 H) 1.74-1.83 (m, 2 H) ppm; LCMS-ESI (POS), M/Z, M+1: Found 500.2, Calculated 500.2.

Example 251

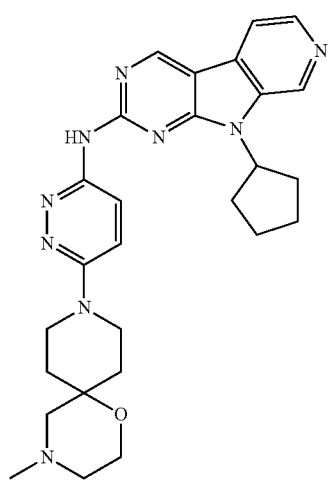

401

330

9-cyclopentyl-N-(6-(4-methyl-1-oxa-4,9-diazaspiro[5.5]undec-9-yl)-3-pyridazinyl)-9H-pyrido[4',3':4,5]pyrrolo[2,3-d]pyrimidin-2-amine

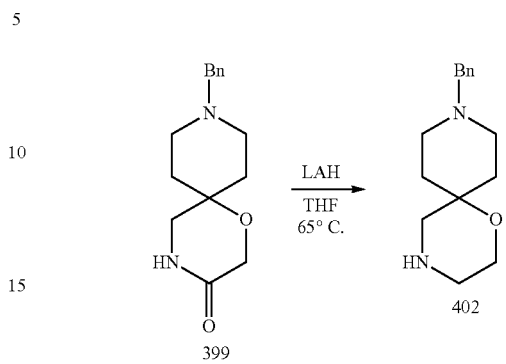

9-benzyl-1-oxa-4,9-diazaspiro[5.5]undecane (402): To a stirring mixture of lithium aluminum hydride (2.22 g, 58.5 mmol) in tetrahydrofuran (70 mL) was added compound 399 (3.60 g, 13.8 mmol), portionwise over three minutes. After 1.25 hours of reflux the reaction was cooled to room temperature and quenched with water (2.22 mL), then 1N NaOH (2.22 mL), then water (2×2.22 mL). The remaining solids were filtered off, and the filtrate was concentrated to give compound 402 (2.81 g, 82%). LCMS-ESI (POS), M/Z, M+1: Found 247.1, Calculated 247.2.

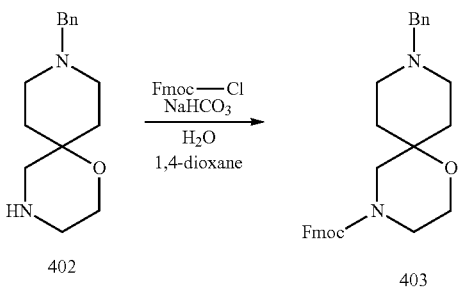

9H-fluoren-9-ylmethyl-9-(phenylmethyl)-1-oxa-4,9-diazaspiro[5,5]undecane-4-carboxylate (403): To a solution of compound 402 (2.81 g, 11.4 mmol) in 1,4-dioxane (53 mL) was added 10% sodium bicarbonate in water (21.5 mL) followed by 9-fluorenylmethyl chloroformate (2.96 g, 11.4 mmol). The resulting mixture was stirred at room temperature for four hours, and then neutralized with 3N HCl. The solution was concentrated to a solid and then purified by flash chromatography (0-10% methanol in DCM with 1% NH$_4$OH) to give compound 403 as a white solid (1.2 g, 22.5%). LCMS-ESI (POS), M/Z, M+1: Found 469.1, Calculated 469.2.

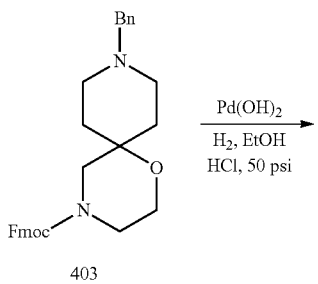

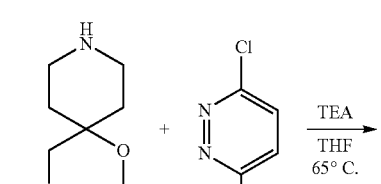

9H-fluoren-9-ylmethyl-1-oxa-4,9-diazaspiro[5.5]undecane-4-carboxylate (404): To a solution of compound 403 (1.43 g, 3.05 mmol) in ethanol (27 mL) was added palladium hydroxide, 20 wt % pd (dry basis) on carbon, wet (1.51 g, 2.15 mmol), followed by hydrochloric acid (0.10 mL). The sealed glass tube was then evacuated and purged with hydrogen three times. The sealed tube was then charged with hydrogen (50 psi), and allowed to stir at room temperature for three days. HPLC showed ~85% conversion to the desired product. After filtering the mixture through a plug of celite, the filtrate was concentrated to a solid and purified by flash chromatography (0-20% methanol in DCM with 1% NH₄OH) to give compound 404 (709 mg, 61%) as a white solid. LCMS-ESI (POS), M/Z, M+1: Found 379.1, Calculated 379.2.

9-(6-chloro-3-pyridazinyl)-4-methyl-1-oxa-4,9-diazaspiro[5.5]undecane (406): To a solution of compound 405 (406.0 mg, 2.39 mmol) in tetrahydrofuran (17 mL) was added 3,6-dichloropyridazine (361.7 mg, 2.43 mmol), followed by triethylamine (0.680 mL, 4.89 mmol). The resulting solution was stirred at reflux for 38 hours. The reaction mixture was then concentrated and the residue was purified by reverse phase HPLC (acetonitrile/H₂O containing 0.1% TFA each, 25 min from 10 to 40%) to give compound 406 as a sticky yellow solid (303 mg, 45%). LCMS-ESI (POS), M/Z, M+1: Found 283.1, Calculated 283.1.

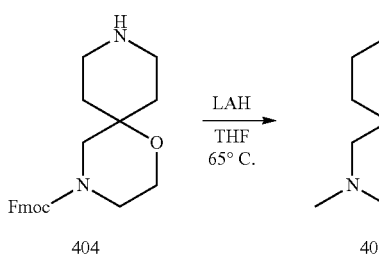

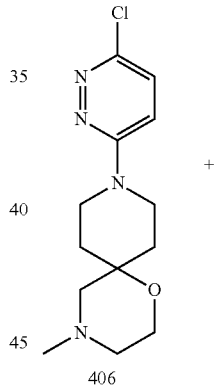

4-methyl-1-oxa-4,9-diazaspiro[5.5]undecane (405): To a mixture of compound 404 (586.4 mg, 1.545 mmol) in tetrahydrofuran (20 mL) was added lithium aluminum hydride (240.5 mg, 6.34 mmol). After 1.5 hours at reflux the reaction was cooled to room temperature and quenched with water (240.5 µl), followed by 1N NaOH (240.5 µL), and then water (2×240.5 µL). The remaining solids were filtered off, and the filtrate was concentrated to give compound 405 (406 mg), as a sticky white solid. LCMS-ESI (POS), M/Z, M+1: Found 171.1, Calculated 171.1.

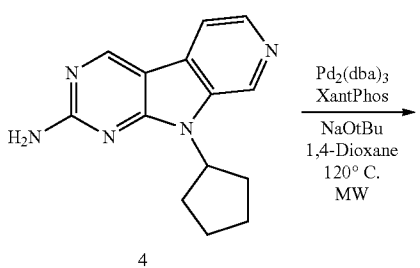

4

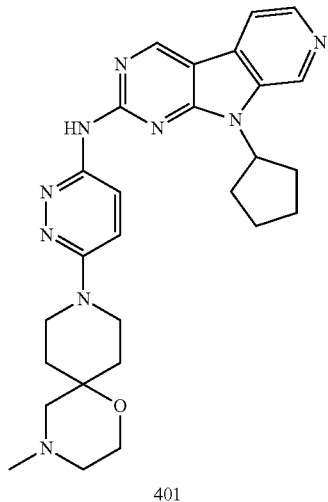

401

9-cyclopentyl-N-(6-(4-methyl-1-oxa-4,9-diazaspiro[5.5]undec-9-yl)-3-pyridazinyl)-9H-pyrido[4',3':4,5]pyrrolo[2,3-d]pyrimidin-2-amine (401): To a solution of compound 4 (53.2 mg, 0.210 mmol) in 1,4-dioxane (3 mL) were added compound 406 (61.3 mg, 0.22 mmol), 9,9-dimethyl-4,5-bis(diphenylphosphino)xanthene (32.0 mg, 55.3 µmol), tris(dibenzylideneacetone)dipalladium (0) (30.9 mg, 33.7 µmol), and sodium tert-butoxide (103.9 mg, 1.08 mmol). After purging with argon for 3 minutes, the reaction mixture was heated at 120° C. under microwave irradiation for 1.5 h. The reaction mixture was concentrated and the residue was purified by reverse phase HPLC (acetonitrile/H₂O containing 0.1% TFA each, 25 min from 10 to 30%) to give compound 401 as a TFA salt (26.7 mg, 15%). ¹H NMR (500 MHz, CD₃OD) δ 9.67 (s, 1 H) 9.35 (s, 1 H) 8.67 (br. s., 2 H) 7.99-8.14 (m, 2 H) 5.48 (quin, 1 H) 4.09-4.21 (m, 2 H) 3.94-4.07 (m, 2 H) 3.34-3.63 (m, 2 H) 2.93 (s, 3 H) 2.42-2.62 (m, 4 H) 2.11-2.33 (m, 6 H) 1.59-1.99 (m, 6 H) ppm; LCMS-ESI (POS), M/Z, M+1: Found 500.4, Calculated 500.3.

Example 252

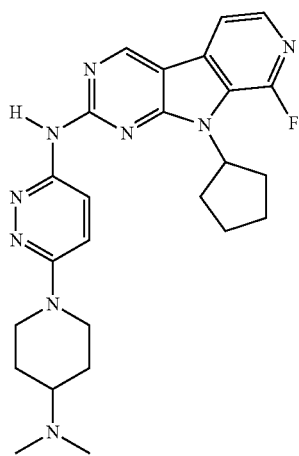

407

9-Cyclopentyl-N-(6-(4-(dimethylamino)-1-piperidinyl)-3-pyridazinyl)-8-fluoro-9H-pyrido[4',3':4,5]pyrrolo[2,3-d]pyrimidin-2-amine Compound 407 was prepared from compound 245 using chemistry similar to that described in example 4. The yield is 45%. ¹H NMR (500 MHz, CD₃OD) δ ppm 9.47 (1 H, s), 8.11 (2 H, s), 8.08 (1 H, d, J=10.0 Hz) 7.88 (1 H, d, J=10.0 Hz), 5.65 (1 H, t, J=9.0 Hz), 4.54-4.58 (2 H, m), 3.60 (1 H, m), 3.17 (2 H, ddd, J=14.5, 12.5, 1.8 Hz), 2.44 (2 H, m), 2.10-2.33 (6 H, m), 1.71-1.95 (4 H, m); LCMS-ESI (POS), M/Z, M+1: Found 476.2, Calculated 476.3

Example 253

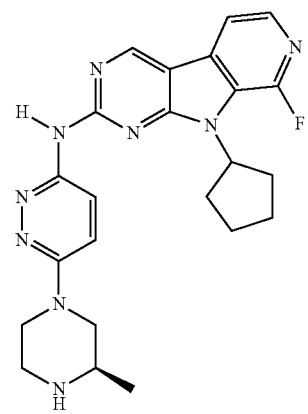

408

9-Cyclopentyl-8-fluoro-N-(6-((3R)-3-methyl-1-piperazinyl)-3-pyridazinyl)-9H-pyrido[4',3':4,5]pyrrolo[2,3-d]pyrimidin-2-amine

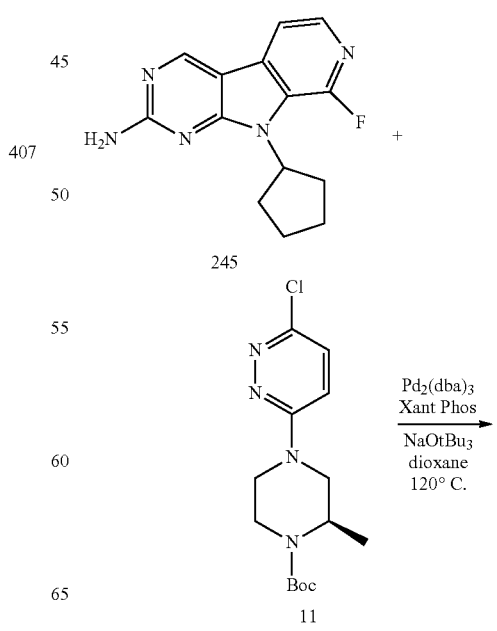

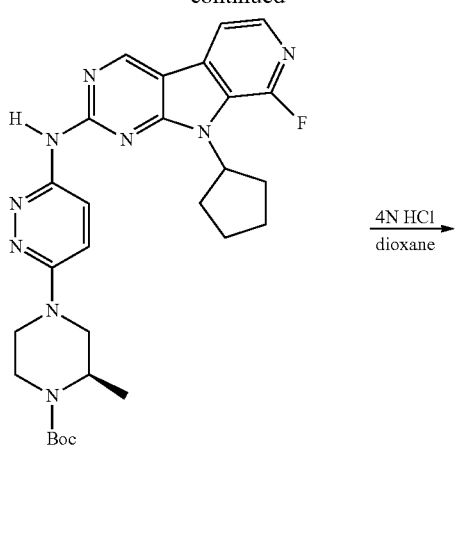

m), 1.46 (3 H, d, J=6.6 Hz); LCMS-ESI (POS), M/Z, M+1: Found 448.1, Calculated 448.2

Example 254

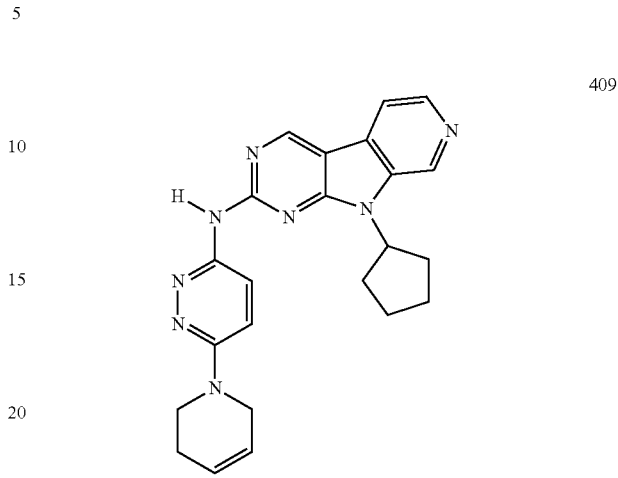

9-Cyclopentyl-N-(6-(3,6-dihydro-1(2 H)-pyridinyl)-3-pyridazinyl)-9H-pyrido[4',3':4,5]pyrrolo[2,3-d]pyrimidin-2-amine

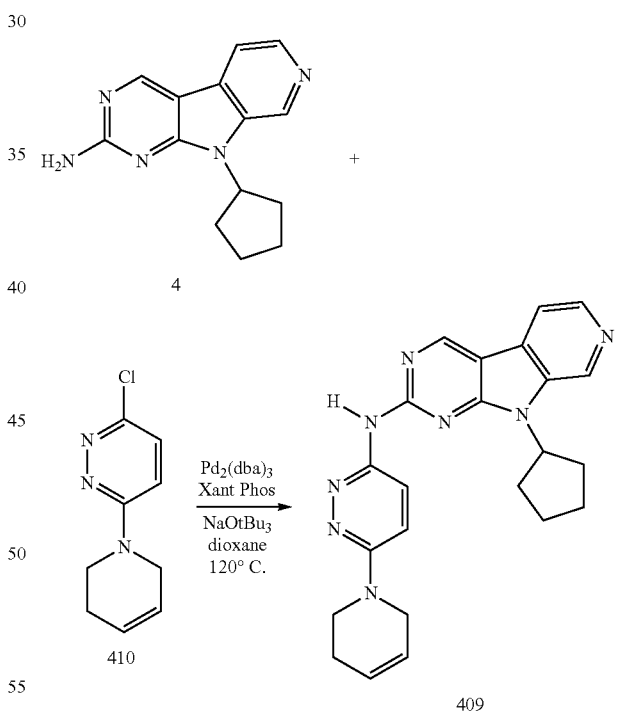

9-Cyclopentyl-8-fluoro-N-(6-((3R)-3-methyl-1-piperazinyl)-3-pyridazinyl)-9H-pyrido[4',3':4,5]pyrrolo[2,3-d]pyrimidin-2-amine (408): Compound 408 was prepared from compound 245 and compound 11 using chemistry similar to that described in example 4. The two step yield is 12%. ¹H NMR (500 MHz, CD₃OD) δ ppm 9.48 (1 H, s), 8.10-8.14 (2 H, m), 8.00 (1 H, d, J=10 Hz), 8.05 (1 H, d, J=10 Hz), 5.66 (1 H, t, J=9.0 Hz), 4.43-4.49 (2 H, m), 3.52-3.62 (2 H, m), 3.29-3.48 (2 H, m), 3.20 (1 H, dd, J=14.4, 10.8 Hz), 2.45 (2 H, ddd, J=9.2, 7.0, 4.5 Hz), 2.13-2.27 (4 H, m), 1.87-1.88 (2 H, 3-Chloro-6-(3,6-dihydro-1(2 H)-pyridinyl)pyridazine (410) was prepared using chemistry similar to that described for compound 11. The yield is 86%. ¹H NMR (500 MHz, CD₃OD) δ ppm 7.44 (1 H, d, J=9.5 Hz), 7.29 (1 H, d, J=9.5 Hz), 5.96 (1 H, m, J=10.1, 4.1, 4.1, 2.3, 2.1 Hz), 5.85 (1 H, m, J=10.1, 3.3, 3.3, 2.0, 1.7 Hz), 4.05 (2 H, dq, J=2.9, 2.8 Hz), 3.80 (2 H, t, J=5.6 Hz), 2.30 (2 H, d, J=2.7 Hz); LCMS-ESI (POS), M/Z, M+1: Found 196.0, Calculated 196.1.

9-Cyclopentyl-N-(6-(3,6-dihydro-1(2 H)-pyridinyl)-3-pyridazinyl)-9H-pyrido-[4',3':4,5]pyrrolo[2,3-d]pyrimidin-2- amine (409): Compound 409 was prepared from compound 4 and compound 410 using chemistry similar to that described in example 1. The yield is 20%. $^1$H NMR (500 MHz, CD$_3$OD) δ ppm 9.68 (1 H, d, J=1.5 Hz), 9.36 (1 H, s), 9.36 (1 H, d, J=0.5 Hz), 8.69 (3 H, t, J=2.2 Hz), 8.60-8.72 (1 H, m), 8.22 (1 H, d, J=10.5 Hz), 8.08 (1 H, dd, J=10.0, 1.0 Hz), 6.02-6.09 (1 H, m, J=8.1, 4.1, 4.1, 2.0 Hz), 5.89 (1 H, dddd, J=8.4, 3.4, 3.3, 1.5 Hz), 5.50 (2 H, t, J=8.8 Hz), 4.17 (3 H, qd, J=2.7, 2.6 Hz), 3.87 (3 H, t, J=5.7 Hz), 2.47-2.60 (3 H, m), 2.37-2.43 (2 H, m, J=6.1, 6.1, 3.5, 2.2 Hz), 2.15-2.35 (7 H, m), 1.87-1.99 (3 H, m); LCMS-ESI (POS), M/Z, M+1: Found 413.2, Calculated 413.2.

Example 255

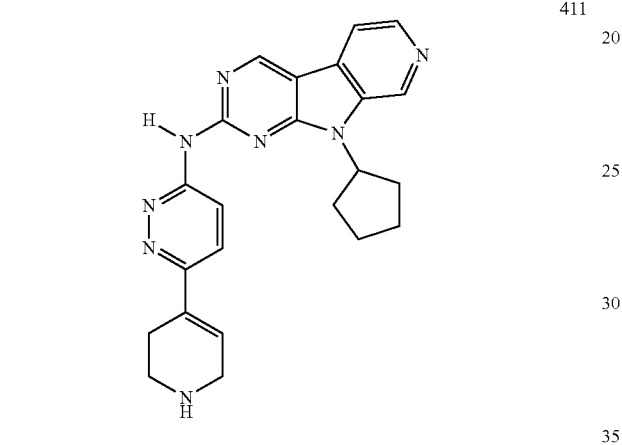

411

9-Cyclopentyl-N-(6-(1,2,3,6-tetrahydro-4-pyridinyl)-3-pyridazinyl)-9H-pyrido[4',3':4.5]pyrrolo[2,3-d]pyrimidin-2-amine

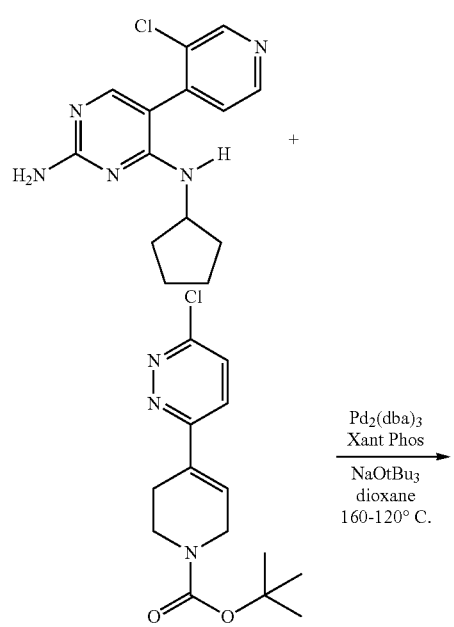

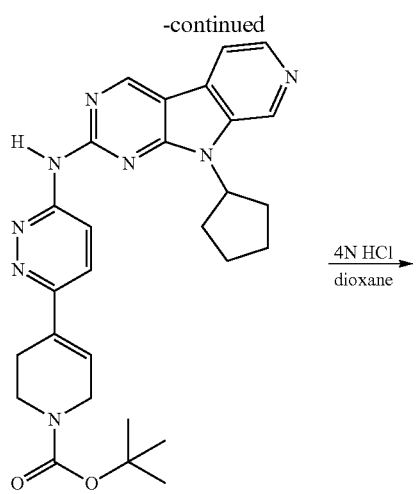

411

9-Cyclopentyl-N-(6-(1,2,3,6-tetrahydro-4-pyridinyl)-3-pyridazinyl)-9H-pyrido[4',3':4,5]pyrrolo[2,3-d]pyrimidin-2-amine (411): Compound 411 was prepared using chemistry similar to that described in example 20. The two step yield is 29%. $^1$H NMR (500 MHz, CD$_3$OD) δ ppm 9.62 (1 H, s), 9.30 (1 H, s), 8.61-8.73 (3 H, m), 8.15 (1 H, d, J=9.5 Hz), 6.77 (1 H, tt, J=3.5, 1.7 Hz), 5.50 (1 H, t, J=8.8 Hz), 4.01 (1 H, q, J=2.8 Hz), 3.07-3.12 (1 H, m, J=6.2, 4.1, 2.0, 2.0 Hz), 2.49-2.60 (2 H, m), 2.13-2.33 (4 H, m), 1.93 (1 H, dt, J=8.8, 2.3

Hz), 1.88-1.98 (1 H, m); LCMS-ESI (POS), M/Z, M+1: Found 413.2, Calculated 413.2.

Example 256

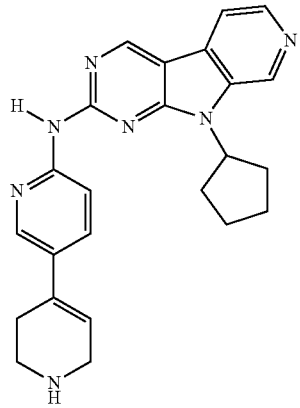

9-Cyclopentyl-N-(1',2',3',6'-tetrahydro-3,4'-bipyridin-6-yl)-9H-pyrido[4',3':4,5]pyrrolo[2,3-d]pyrimidin-2-amine

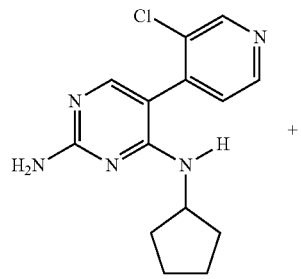

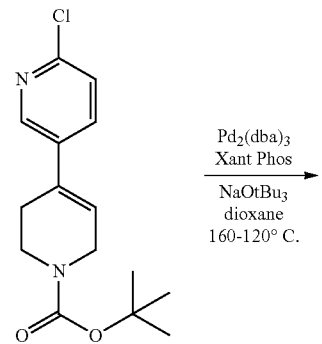

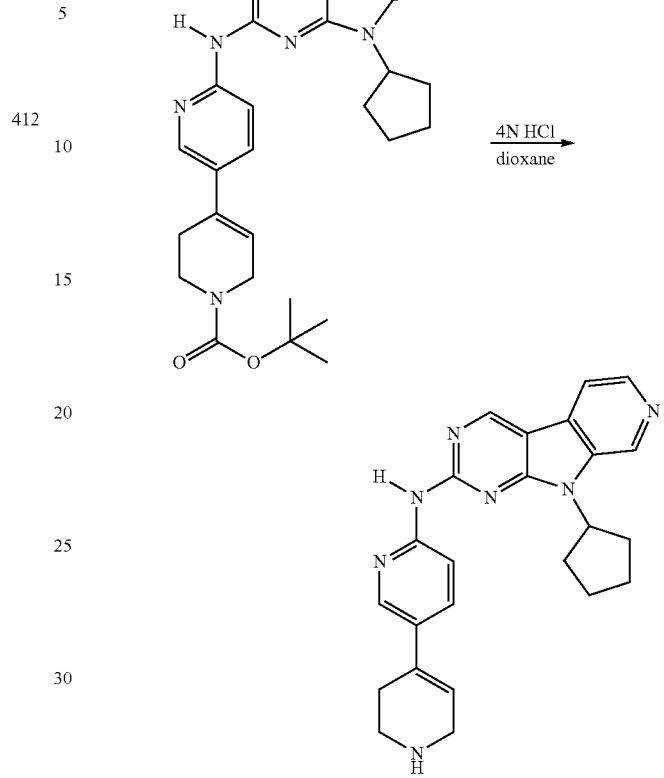

9-Cyclopentyl-N-(1',2',3',6'-tetrahydro-3,4'-bipyridin-6-yl)-9H-pyrido[4',3':4,5]-pyrrolo[2,3-d]pyrimidin-2-amine (412): Compound 412 was prepared using chemistry similar to that described in example 20. The two step yield is 70%. $^1$H NMR (500 MHz, CD$_3$OD) δ ppm 9.90 (1 H, s), 9.50 (1 H, s), 8.92 (1 H, d, J=6.1 Hz), 8.75-8.83 (1 H, m), 8.57-8.65 (2 H, m), 7.73-7.78 (1 H, m), 6.52 (1 H, tt, J=3.5, 1.7 Hz), 5.54 (1 H, quin, J=8.7 Hz), 3.96-4.01 (2 H, m), 3.68 (6 H, s), 3.58 (2 H, t, J=6.1 Hz), 2.88-2.95 (2 H, m, J=6.3, 6.3, 2.2, 2.1, 2.1 Hz), 2.57 (2 H, dq, J=12.8, 8.5 Hz), 2.21-2.37 (4 H, m), 1.89-2.00 (2 H, m); LCMS-ESI (POS), M/Z, M+1: Found 412.1, Calculated 412.2.

Example 257

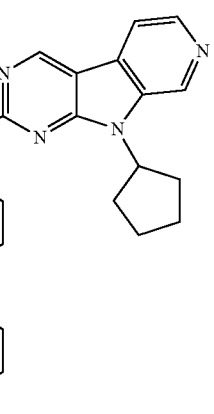

9-cyclopentyl-N-(5-(4-piperidinyl)-2-pyridinyl)-9H-pyrido[4',3':4,5]pyrrolo[2,3-d]pyrimidin-2-amine

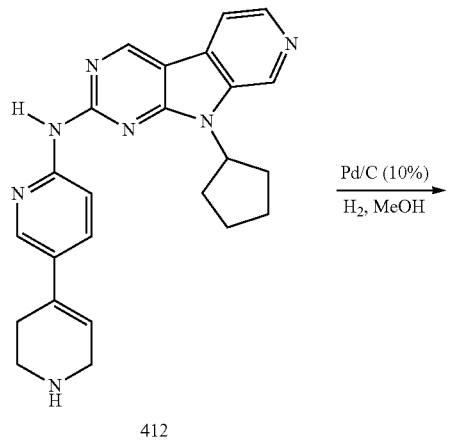

412

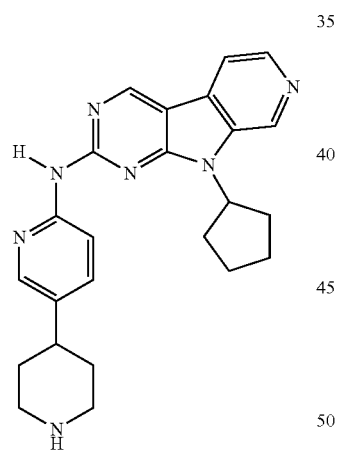

413

9-Cyclopentyl-N-(5-(4-piperidinyl)-2-pyridinyl)-9H-pyrido[4',3':4,5]pyrrolo[2,3-d]pyrimidin-2-amine (413): To a solution of compound 412 (90 mg, 0.22 mmol) in methanol (5 mL) was added Pd/C (10% wt, dry basis) (50 mg). The reaction was stirred at room temperature with $H_2$ ballon for 3 hours. Insolubles were removed by filtration. The filtrate was purified using prep-HPLC to give compound 413 as a yellow solid (30 mg, 33%). $^1$H NMR (500 MHz, DMSO-$d_6$) δ ppm 10.98 (1 H, br. s.), 9.64 (1 H, s), 9.42 (1 H, s), 8.83 (1 H, dd, J=3.5, 1.1 Hz), 8.71 (1 H, d, J=6.1 Hz), 8.55-8.68 (2 H, m), 8.30 (1 H, d, J=2.7 Hz), 8.17 (1 H, d, J=8.6 Hz), 7.85 (1 H, dd, J=8.8, 2.4 Hz), 5.41 (1 H, dq, J=8.9, 8.8 Hz), 3.43 (2 H, dd, J=10.4, 2.3 Hz), 2.96 (3 H, tt, J=12.1, 3.7 Hz), 2.42 (2 H, m), 2.00-2.08 (4 H, m), 1.68-1.92 (2H, m); LCMS-ESI (POS), M/Z, M+1: Found 414.2, Calculated 414.2.

Example 258

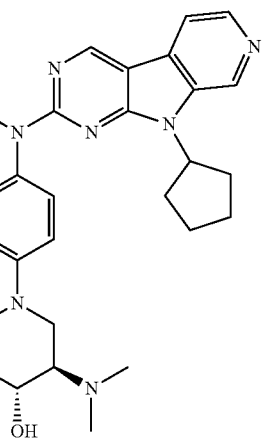

414A (chirality arbitrarily assigned)

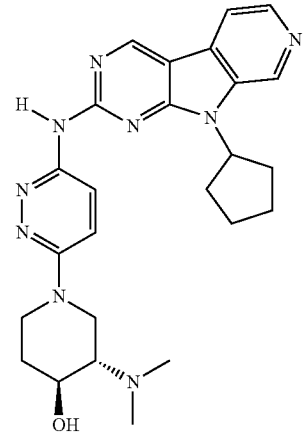

414B 1-(6-((9-Cyclopentyl-9H-pyrido[4',3':4,5]pyrrolo[2,3-d]pyrimidin-2-yl)amino)-3-pyridazinyl)-3-(dimethylamino)-4-piperidinol

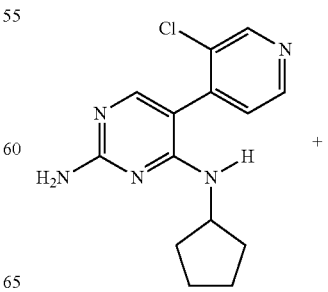

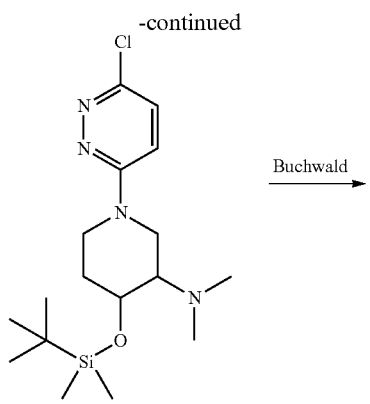

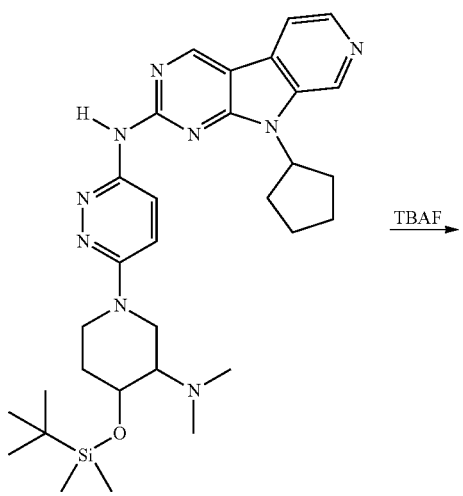

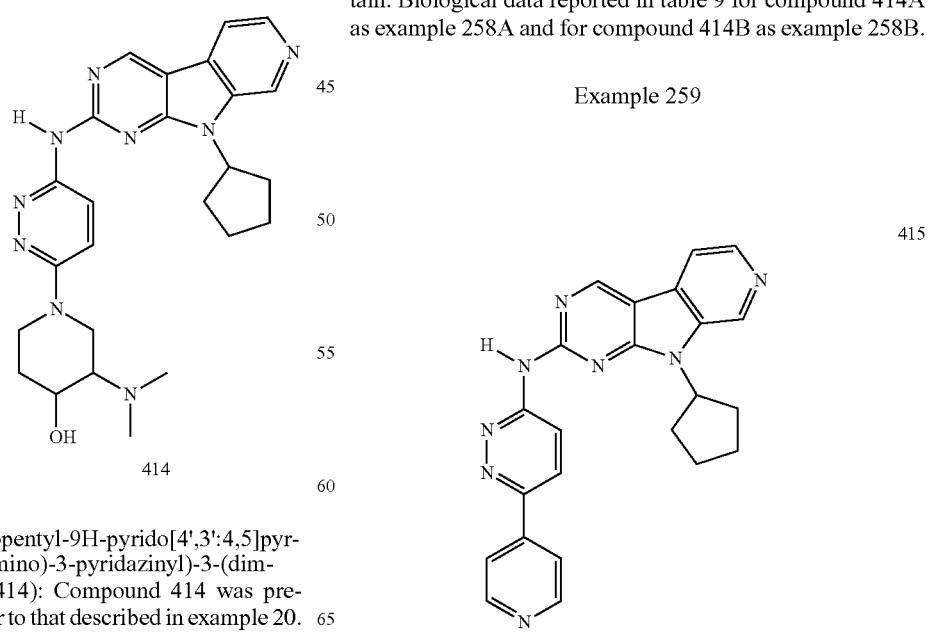

hours. After removal of solvent, the residue was dissolved in DMSO and purified by prep-HPLC to give the racemic alcohol 414 (33 mg, 82%). This compound was dissolved in 2 mL of MeOH and to this solution was added 4 drops of 4 N HCl in dioxane. The solution was concentrated to give a yellow solid as an HCl salt.

$^1$H NMR (500 MHz, CD$_3$OD) δ ppm 9.77 (1 H, s), 9.44 (1 H, s), 8.78 (1 H, d, J=6.1 Hz), 8.72 (1 H, d, J=6.1 Hz), 8.14 (1 H, m), 8.05 (1 H, m, J=10.0 Hz), 5.50 (1, quin, J=8.7 Hz), 4.80 (1 H, m), 4.33 (1 H, m), 4.15 (1 H, ddd, J=10.3, 8.0, 4.9 Hz), 3.26 (1 H, m), 2.66 (2 H, m), 2.15-2.34 (4 H, m), 1.85-1.98 (2 H, m), 1.61-1.80 (1 H, m); LCMS-ESI (POS), M/Z, M+1: Found 474.2, Calculated 474.3.

The two enantiomers were resolved by SFC (Resolution conditions: 250×30 mm AS-H SFC column with 50 g/min methanol (0.2% DEA)+75 g/min CO2 on. Thar 350 SFC. Outlet pressure=140 bar; Temp.=24 C; Wavelength=264 nm. Multiple 0.5 mL injections of 22 mg/8 mL sample in methanol solution (2.75 mg/mL). Cycle time=5.0 min; run time=6.0 min) to give yellow solids. Compound 414A has a retention time 4.13 minute and compound 414B has a retention time 4.43 minute. NMR as the free base (each enantiomer). $^1$H NMR (500 MHz, CD$_3$OD) δ ppm 9.09 (1 H, s), 8.77 (1 H, s), 8.23-8.33 (2 H, m), 7.94 (1 H, d, J=5.1 Hz), 7.28 (1 H, d, J=10.0 Hz), 5.29 (2 H, t, J=8.8 Hz), 4.27 (1 H, ddd, J=13.1, 4.2, 2.1 Hz), 4.07 (1 H, dd, J=11.2, 2.4 Hz), 3.77 (1 H, td, J=9.9, 4.6 Hz), 2.82-2.94 (2 H, m), 2.38 (6 H, s), 2.30 (2 M, m), 1.94-2.13 (6 H, m), 1.77 (2 H, dt, J=12.0, 6.8 Hz), 1.51 (1 H, ddd, J=10.4, 2.2, 2.1 Hz); LCMS-ESI (POS), M/Z, M+1: Found 474.2, Calculated 474.3; each ee 99%.

For convenience, they are arbitrarily assigned the structures as drawn, with absolute configuration remaining uncertain. Biological data reported in table 9 for compound 414A as example 258A and for compound 414B as example 258B.

Example 259

(3R*,4R*)-1-(6-((9-Cyclopentyl-9H-pyrido[4',3':4,5]pyrrolo[2,3-d]pyrimidin-2-yl)amino)-3-pyridazinyl)-3-(dimethylamino)-4-piperidinol (414): Compound 414 was prepared using chemistry similar to that described in example 20. The crude coupling product (50 mg, 0.085 mmol) was treated with 5 mL of 1M TBAF (in THF) at room temperature for 3

9-cyclopentyl-N-(6-(4-pyridinyl)-3-pyridazinyl)-9H-pyrido[4',3':4,5]pyrrolo[2,3-d]pyrimidin-2-amine

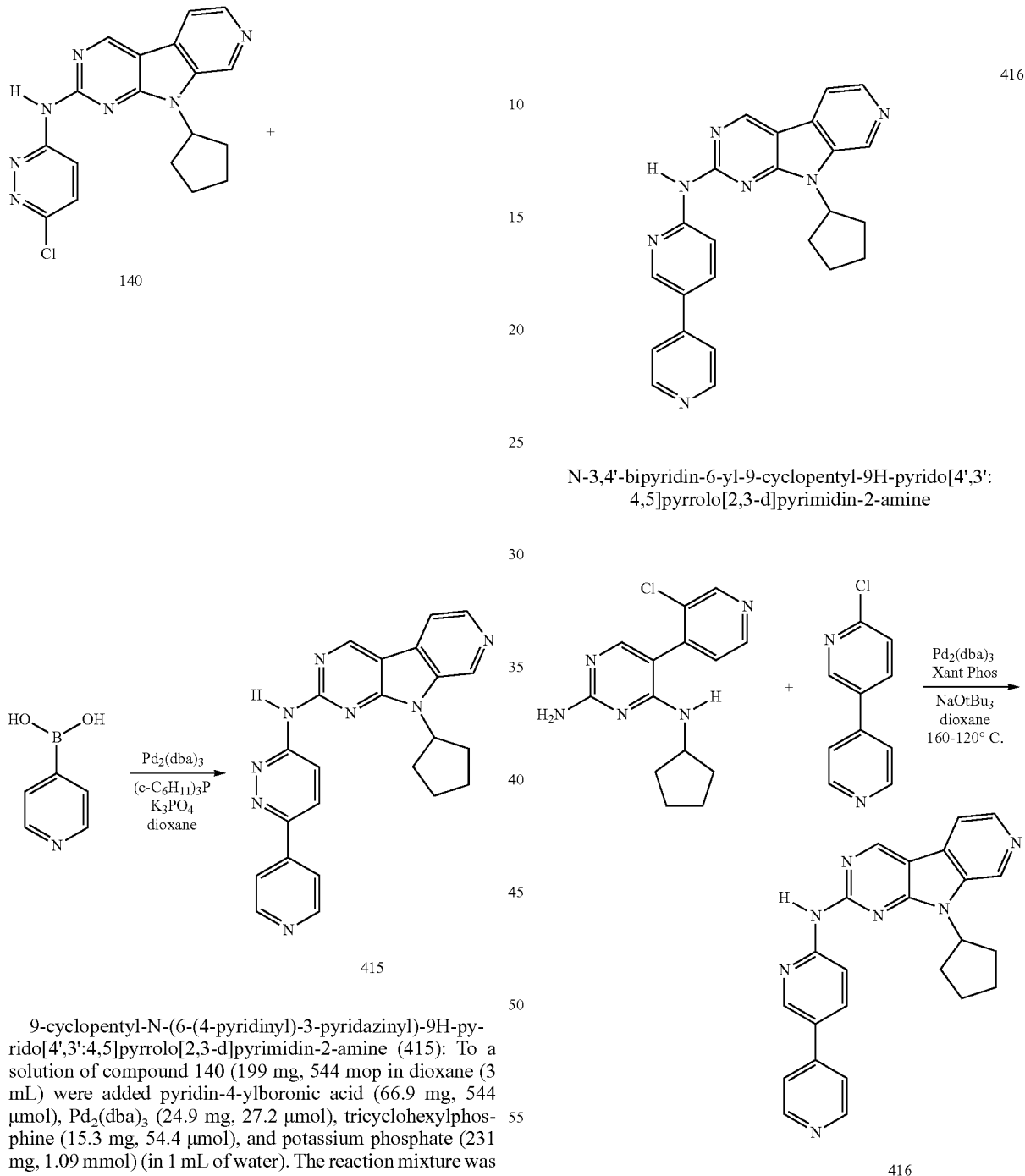

Example 260

N-3,4'-bipyridin-6-yl-9-cyclopentyl-9H-pyrido[4',3': 4,5]pyrrolo[2,3-d]pyrimidin-2-amine 9-cyclopentyl-N-(6-(4-pyridinyl)-3-pyridazinyl)-9H-pyrido[4',3':4,5]pyrrolo[2,3-d]pyrimidin-2-amine (415): To a solution of compound 140 (199 mg, 544 mop in dioxane (3 mL) were added pyridin-4-ylboronic acid (66.9 mg, 544 µmol), Pd$_2$(dba)$_3$ (24.9 mg, 27.2 µmol), tricyclohexylphosphine (15.3 mg, 54.4 µmol), and potassium phosphate (231 mg, 1.09 mmol) (in 1 mL of water). The reaction mixture was purged with N$_2$ for 20 minutes and the reaction was heated at 100° C. degree for 18 hours. DCM was added to the reaction and the mixture was washed with water and brine. The organic layer was dried with sodium sulfate. The product was purified using Combiflash (DCM/methanol) followed by trituration with ethyl acetate to give compound 415 as a yellow solid (63 mg, 28%). $^1$H NMR (500 MHz, CD$_2$Cl$_2$) δ ppm 9.25 (1 H, s), 8.97-9.05 (2 H, m), 8.92 (1 H, s), 8.79 (2 H, d, J=6.1 Hz), 8.57 (1 H, d, J=5.1 Hz), 8.00-8.08 (3 H, m), 7.96 (1 H, dd, J=5.1, 1.2 Hz), 5.48 (1 H, quin, J=8.9 Hz), 2.48 (2 H, m), 2.20-2.28 (4 H, m), 1.95 (2 H, dddd, J=8.2, 4.5, 4.3, 4.2 Hz), 1.63 (2 H, br. s.); LCMS-ESI (POS), M/Z, M+1: Found 409.1, Calculated 409.2.

N-3,4'-bipyridin-6-yl-9-cyclopentyl-9H-pyrido[4',3':4,5] pyrrolo[2,3-d]pyrimidin-2-amine (416): Compound 416 was prepared using chemistry similar to that described in example 20. The yield is 65%. $^1$H NMR (500 MHz, CD$_2$Cl$_2$) δ ppm 9.23 (1 H, s), 8.99 (1 H, d, J=1.2 Hz), 8.65-8.81 (4 H, m), 8.54 (1 H, d, J=5.1 Hz), 8.12 (1 H, dd, J=8.7, 2.6 Hz), 7.94 (1 H, dd, J=5.1, 1.2 Hz), 7.54-7.63 (2 H, m), 5.48 (1 H, quin, J=9.0 Hz), 2.46-2.57 (2 H, m), 2.13-2.31 (4 H, m), 1.89-2.00 (2 H, m, J=11.4, 7.8, 7.7, 7.7, 3.8 Hz), 1.63 (1 H, br. s.); LCMS-ESI (POS), M/Z, M+1: Found 408.2, Calculated 408.2.

Example 261

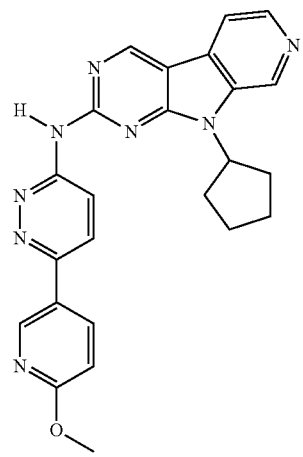

417

9-Cyclopentyl-N-(6-(6-methoxy-3-pyridinyl)-3-pyridazinyl)-9H-pyrido[4',3':4,5]pyrrolo[2,3-d]pyrimidin-2-amine

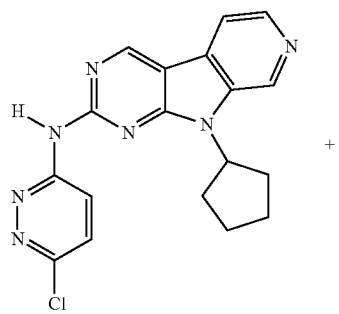

140

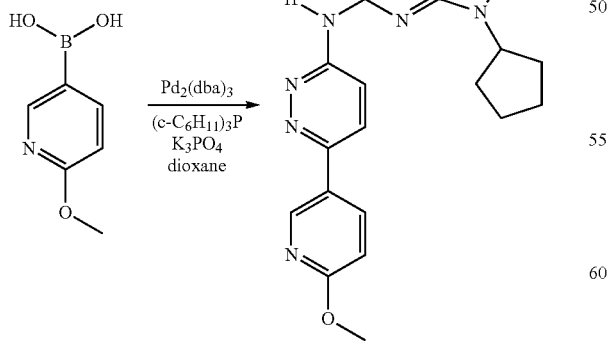

417

9-Cyclopentyl-N-(6-(6-methoxy-3-pyridinyl)-3-pyridazinyl)-9H-pyrido[4',3':4,5]-pyrrolo[2,3-d]pyrimidin-2-amine (417): Compound 417 was prepared using chemistry similar to that described in example 259. The yield is 26%. $^1$H NMR (500 MHz, CD$_2$Cl$_2$) δ ppm 9.31 (1 H, d, J=1.7 Hz), 8.99 (1 H, d, J=0.7 Hz), 8.92 (1 H, d, J=9.3 Hz), 8.85 (1 H, d, J=2.4 Hz), 8.56 (1 H, d, J=5.6 Hz), 8.40 (1 H, dd, J=8.7, 2.6 Hz), 8.10-8.15 (1 H, m), 7.97 (1 H, d, J=9.5 Hz), 6.94 (1 H, d, J=8.6 Hz), 5.45 (1 H, qd, J=9.0, 8.8 Hz), 4.05 (3 H, s), 2.43-2.52 (2 H, m), 2.16-2.33 (4 H, m), 1.91-2.00 (2 H, m); LCMS-ESI (POS), M/Z, M+1: Found 439.0, Calculated 439.2.

Example 262

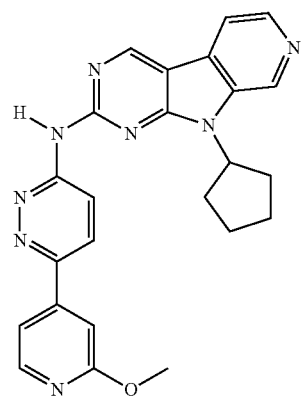

418

9-Cyclopentyl-N-(6-(2-methoxy-4-pyridinyl)-3-pyridazinyl)-9H-pyrido[4',3':4,5]pyrrolo[2,3-d]pyrimidin-2-amine Compound 418 was prepared using chemistry similar to that described in example 259. The yield is 52%. $^1$H NMR (500 MHz, CD$_2$Cl$_2$) δ ppm 9.23 (1 H, s), 8.97-9.02 (2 H, m), 8.75 (1 H, s), 8.56 (1 H, d, J=5.1 Hz), 8.34 (1 H, d, J=5.4 Hz), 7.96-8.03 (2 H, m), 7.65 (1 H, dd, J=5.4, 1.7 Hz), 7.44 (1 H, dd, J=1.5, 0.7 Hz), 5.47 (1 H, quin, J=9.0 Hz), 5.36 (25 H, d, J=1.2 Hz), 2.44-2.53 (2 H, m, J=13.0, 9.0, 8.7, 8.7 Hz), 2.16-2.31 (4 H, m), 1.90-1.99 (2 H, m, J=8.2, 4.5, 4.2, 4.2 Hz), 1.59 (1 H, d, J=8.1 Hz); LCMS-ESI (POS), M/Z, M+1: Found 439.1, Calculated 439.2.

Example 263

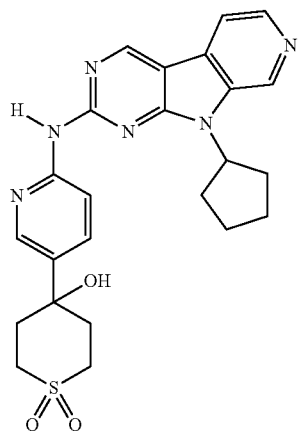

419

4-(6-((9-cyclopentyl-9H-pyrido[4',3':4,5]pyrrolo[2,3-d]pyrimidin-2-yl)amino)-3-pyridinyl)tetrahydro-2H-thiopyran-4-ol 1,1-dioxide

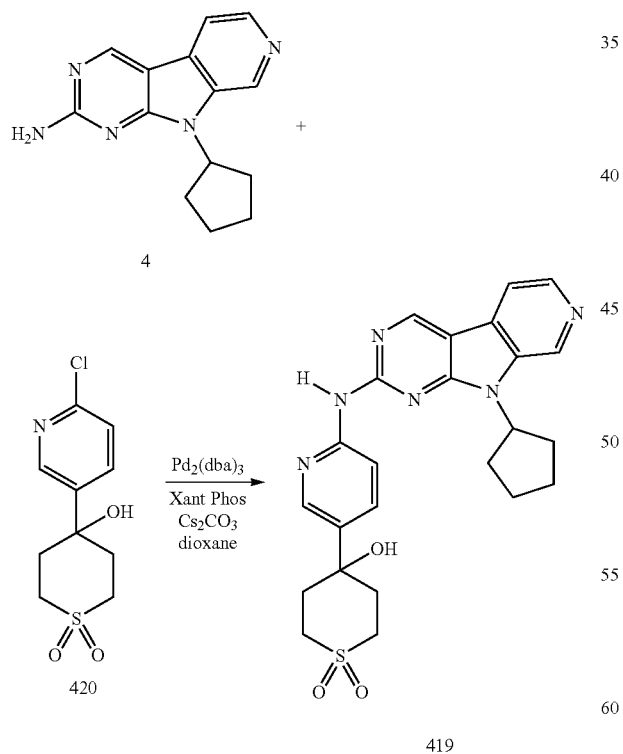

4-(6-((9-cyclopentyl-9H-pyrido[4',3':4,5]pyrrolo[2,3-d]pyrimidin-2-yl)amino)-3-pyridinyl)tetrahydro-2H-thiopyran-4-ol 1,1-dioxide (419): To a mixture of compound 4 (120 mg, 474 µmol), Pd$_2$(dba)$_3$ (21.7 mg, 23.7 µmol), 4,5-bis(diphenylphosphino)-9,9-dimethyl-9H-xanthene (27.4 mg, 47.4 µmol) and cesium carbonate (309 mg, 947 µmol) was added a solution of compound 420 (124 mg, 474 µmol) in dioxane (3 mL). The reaction was purged with N$_2$ for 20 minutes and then heated at 120 degree in microwave for 2 hours. DCM was added to the reaction and the mixture was washed with H2O and brine. The organic layer was dried with sodium sulfate. The crude product was purified using Combiflash (DCM/methanol) and suspended in methanol. A saturated solution of HCl in methanol (10 drops) was added. The solution was concentrated to give compound 419 as a light yellow solid (HCl salt) (18 mg, 8%). $^1$H NMR (500 MHz, CD$_3$OD) δ ppm 9.90 (1 H, s), 9.51 (1 H, s), 8.92 (1 H, d, J=6.1 Hz), 8.77 (1 H, d, J=5.9 Hz), 8.66-8.74 (1 H, m), 8.58 (1 H, dt, J=9.0, 1.0 Hz), 7.76 (1 H, d, J=9.3 Hz), 5.55 (1 H, qd, J=8.4, 8.2 Hz), 3.62 (2 H, tt, J=13.6, 1.7 Hz), 3.37 (2 H, s), 3.09 (2 H, dd, J=12.5, 1.0 Hz), 2.64-2.77 (2 H, m, J=13.7, 13.7, 1.8, 1.6 Hz), 2.57 (2 H, dd, J=12.6, 8.2 Hz), 2.19-2.41 (6 H, m), 1.87-2.01 (2 H, m); LCMS-ESI (POS), M/Z, M+1: Found 479.2, Calculated 479.2

Example 264

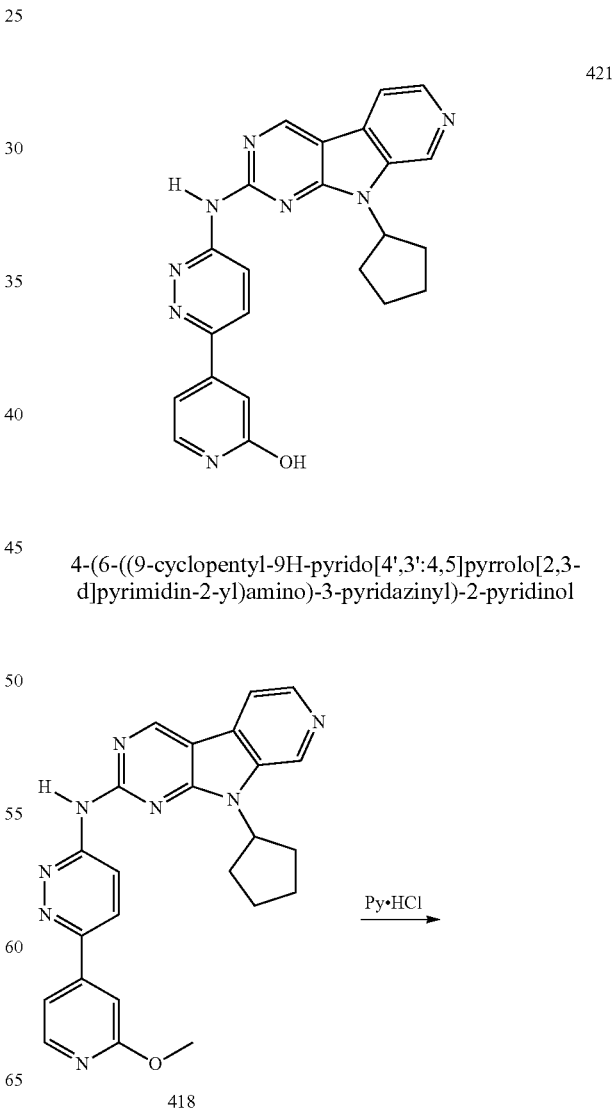

4-(6-((9-cyclopentyl-9H-pyrido[4',3':4,5]pyrrolo[2,3-d]pyrimidin-2-yl)amino)-3-pyridazinyl)-2-pyridinol

351

-continued

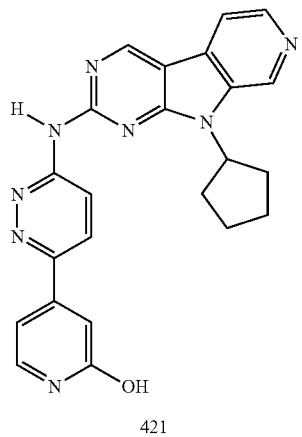

421

4-(6-((9-cyclopentyl-9H-pyrido[4',3':4,5]pyrrolo[2,3-d]pyrimidin-2-yl)amino)-3-pyridazinyl)-2-pyridinol (421): Compound 418 (25 mg, 57 µmol and pyridine hydrochloride (500 mg) in a small vial were heated at 150 degree (oil bath) for 1 hour. DCM was added to the reaction and sat. NaHCO$_3$ was added to wash. The crude product was collected by filtration and was further washed with DCM and a small amount of methanol. The pure product was then suspended in methanol and to this mixture was added 3 drops of saturated HCl methanol solution. Concentration of the solution gave compound 421 as a yellow solid (HCl salt). The yield is 96%. $^1$H NMR (500 MHz, CD$_3$OD) δ ppm 9.87 (1 H, s), 9.50 (1 H, s), 8.88 (1 H, d, J=6.1 Hz), 8.76 (1 H, d, J=6.1 Hz), 8.68 (1 H, d, J=9.5 Hz), 8.49 (1 H, d, J=9.5 Hz), 7.77 (1 H, d, J=6.8 Hz), 7.37 (1 H, d, J=0.7 Hz), 7.29 (1 H, dd, J=6.2, 1.1 Hz), 5.55 (1 H, quin, J=8.7 Hz), 2.54-2.63 (2 H, m), 2.22-2.38 (4 H, m), 1.91-2.01 (2 H, m); LCMS-ESI (POS), M/Z, M+1: Found 425.2, Calculated 425.2.

Example 265

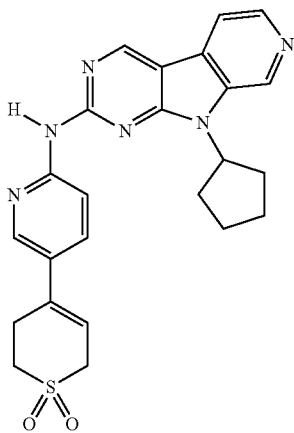

422

352

9-Cyclopentyl-N-(5-(1,1-dioxido-3,6-dihydro-2H-thiopyran-4-yl)-2-pyridinyl)-9H-pyrido[4',3':4,5]pyrrolo[2,3-d]pyrimidin-2-amine

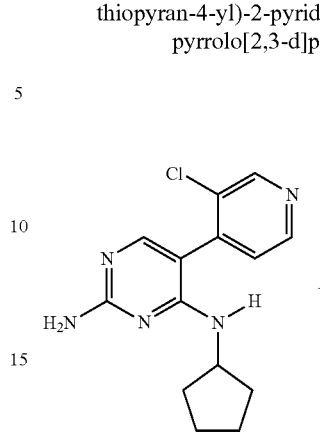

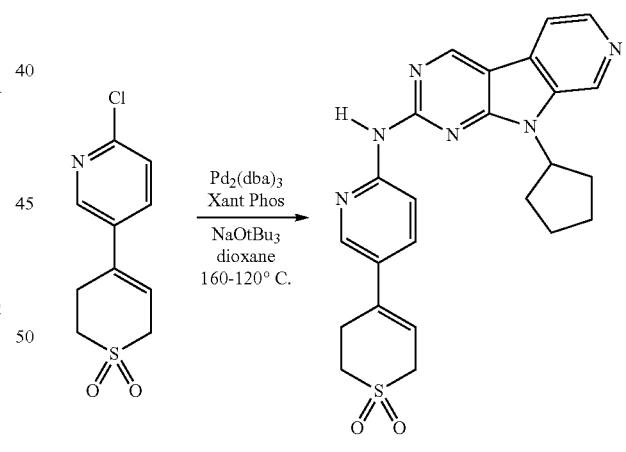

422

9-Cyclopentyl-N-(5-(1,1-dioxido-3,6-dihydro-2H-thiopyran-4-yl)-2-pyridinyl)-9H-pyrido[4',3':4,5]pyrrolo[2,3-d]pyrimidin-2-amine (422): Compound 422 was prepared using chemistry similar to that described in example 20. The two step yield is 75%. $^1$H NMR (500 MHz, CD$_3$OD) δ ppm 9.87 (1 H, s), 9.49 (1 H, s), 8.91 (1 H, d, J=6.1 Hz), 8.77 (1 H, d, J=6.1 Hz), 8.54-8.58 (2 H, m), 7.72 (1 H, d, J=9.8 Hz), 6.31 (1 H, t, J=1.5 Hz), 5.53 (1 H, dq, J=8.8, 8.6 Hz), 4.92 (1 H, br. s.), 3.98 (2 H, td, J=3.1, 1.5 Hz), 3.43-3.48 (2 H, m), 3.23 (2 H, td, J=6.4, 2.0 Hz), 2.57 (2 H, ddd, J=8.8, 6.5, 6.2 Hz), 2.21-2.35 (4 H, m), 1.90-1.99 (2 H, m); LCMS-ESI (POS), M/Z, M+1: Found 461.2, Calculated 461.2

Example 266

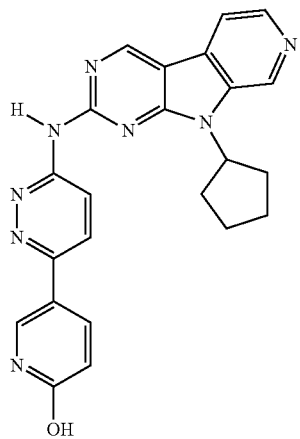

423

5-(6-((9-Cyclopentyl-9H-pyrido[4',3':4,5]pyrrolo[2,3-d]pyrimidin-2-yl)amino)-3-pyridazinyl)-2-pyridinol Compound 423 was prepared from compound 417 using chemistry similar to that described in example 264. The yield is 99%. ¹H NMR (500 MHz, CD₃OD) δ ppm 9.87 (1 H, s), 9.50 (1 H, s), 8.88 (1 H, d, J=5.0 Hz), 8.76 (1 H, d, J=5.0 Hz), 8.61 (1 H, d, J=10 Hz), 8.38-8.42 (1 H, m), 6.74 (1 H, d, J=10.0 Hz), 5.54 (1 H, t, J=8.7 Hz), 2.54-2.63 (2 H, m), 2.23-2.37 (4 H, m), 1.97 (2 H, dd, J=7.1, 1.2 Hz); LCMS-ESI (POS), M/Z, M+1: Found 425.2, Calculated 425.2

Example 267

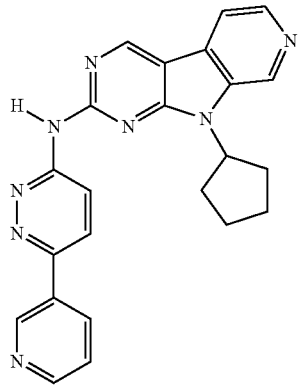

424

9-Cyclopentyl-N-(6-(3-pyridinyl)-3-pyridazinyl)-9H-pyrido[4',3':4,5]pyrrolo[2,3-d]pyrimidin-2-amine Compound 424 was prepared from compound 140 using chemistry similar to that described in example 259. The yield is 9%. ¹H NMR (500 MHz, CD₃OD) δ ppm 9.75 (1 H, s), 9.59 (1 H, d, J=1.0 Hz), 9.59 (1 H, s), 9.37 (1 H, s), 9.27 (1 H, dt, J=8.3, 1.7 Hz), 8.95 (1 H, d, J=0.7 Hz), 8.75 (1 H, d, J=6.1 Hz), 8.61-8.70 (1 H, m), 8.53 (1 H, d, J=9.5 Hz), 8.22 (1 H, dd, J=8.2, 5.7 Hz), 5.44 (1 H, quin, J=8.7 Hz), 2.42-2.52 (2 H, m), 2.08-2.26 (4 H, m), 1.79-1.90 (2 H, m); LCMS-ESI (POS), M/Z, M+1: Found 409.1, Calculated 409.2.

Example 268

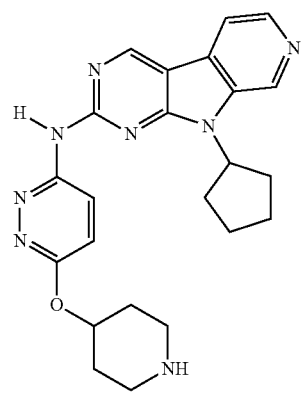

425

9-Cyclopentyl-N-(6-(4-piperidinyloxy)-3-pyridazinyl)-9H-pyrido[4',3':4,5]pyrrolo[2,3-d]pyrimidin-2-amine

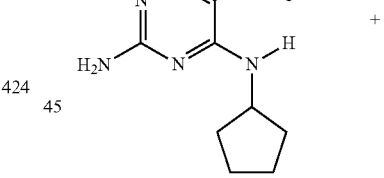

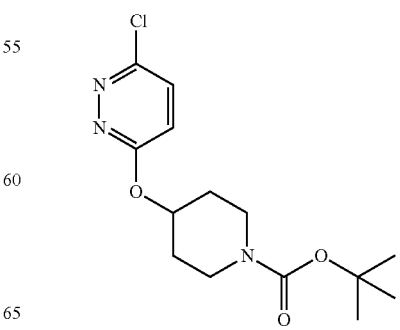

Pd₂(dba)₃
Xant Phos
⟶
NaOtBu₃
dioxane
160-120° C.

355

-continued

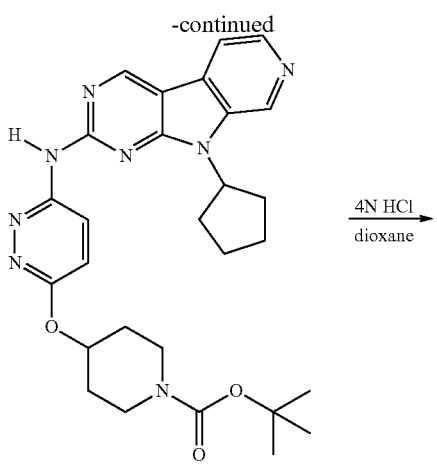

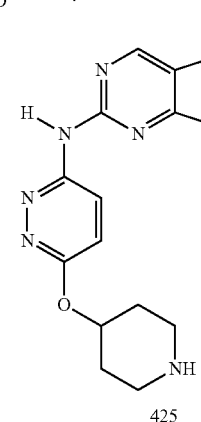

425

9-Cyclopentyl-N-(6-(4-piperidinyloxy)-3-pyridazinyl)-9H-pyrido[4',3':4,5]-pyrrolo[2,3-d]pyrimidin-2-amine (425): Compound 425 was prepared using chemistry similar to that described in example 20. The two step yield is 84%. ¹H NMR (500 MHz, CD₃OD) δ ppm 9.86 (1 H, s), 9.50 (1 H, s), 8.88 (1 H, d, J=6.1 Hz), 8.76 (1 H, d, J=6.1 Hz), 8.17 (1 H, d, J=9.5 Hz), 7.87 (1 H, d, J=9.5 Hz), 5.48 (1 H, tt, J=6.6, 3.3 Hz), 3.45-3.53 (3 H, m), 3.31-3.38 (6 H, m), 2.52-2.61 (2 H, m), 2.19-2.42 (4 H, m), 1.89-1.99 (2 H, m); LCMS-ESI (POS), M/Z, M+1: Found 431.2, Calculated 431.2

Example 269

426

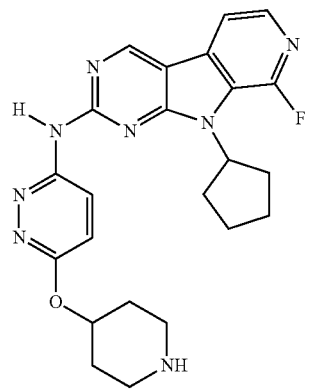

356

9-Cyclopentyl-8-fluoro-N-(6-(4-piperidinyloxy)-3-pyridazinyl)-9H-pyrido[4',3':4,5]pyrrolo[2,3-d]pyrimidin-2-amine

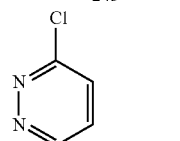

245

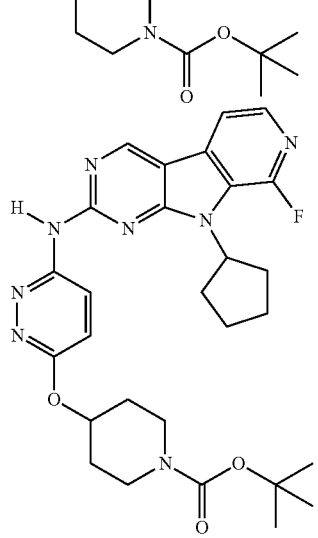

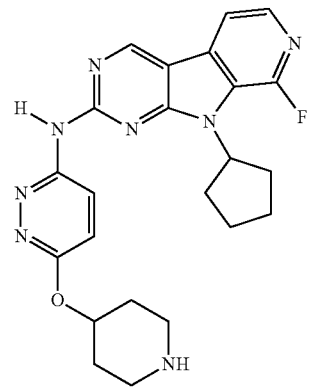

426

9-Cyclopentyl-8-fluoro-N-(6-(4-piperidinyloxy)-3-pyridazinyl)-9H-pyrido[4',3':4,5]-pyrrolo[2,3-d]pyrimidin-2-amine (426): Compound 426 was prepared from compound 245 using chemistry similar to that described in example 4. The two step yield is 11%. ¹H NMR (500 MHz, CD₃OD) δ ppm 9.59 (1 H, s), 8.18 (2 H, s), 8.02 (1 H, d, J=9.8 Hz), 7.84 (1 H, d, J=9.8 Hz), 5.69 (1 H, t, J=9.0 Hz), 5.46 (1 H, dt, J=6.5, 3.2 Hz), 3.45-3.53 (2 H, m), 2.47-2.51 (2 H, m), 2.46 (1 H, dd, J=5.4, 2.9 Hz), 2.31-2.42 (2 H, m), 2.11-2.31 (4 H, m), 1.81-1.93 (2 H, m); LCMS-ESI (POS), M/Z, M+1: Found 449.2, Calculated 449.2.

Example 270

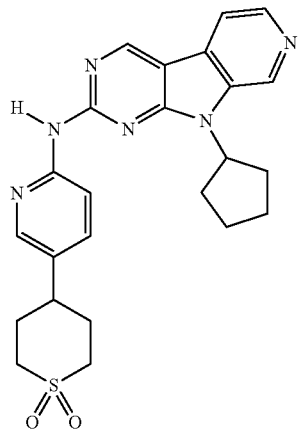

427

9-Cyclopentyl-N-(5-(1,1-dioxidotetrahydro-2H-thiopyran-4-yl)-2-pyridinyl)-9H-pyrido[4',3':4,5]pyrrolo[2,3-d]pyrimidin-2-amine Compound 427 was prepared from compound 422 using chemistry similar to that described in example 257. The yield is 20%. ¹H NMR (500 MHz, CD₃OD) δ ppm 9.88 (1 H, s), 9.50 (1 H, s), 8.92 (1 H, d, J=6.1 Hz), 8.77 (1 H, d, J=6.1 Hz), 8.41-8.52 (2 H, m), 7.73 (1 H, d, J=9.0 Hz), 5.54 (1 H, quin, J=8.7 Hz), 3.31-3.49 (2 H, m), 3.17-3.31 (3 H, m), 3.07 (2 H, q, J=7.3 Hz), 2.50-2.63 (2 H, m), 2.21-2.44 (8 H, m), 1.88-2.01 (2 H, m); LCMS-ESI (POS), M/Z, M+1: Found 463.1, Calculated 463.2

Example 271

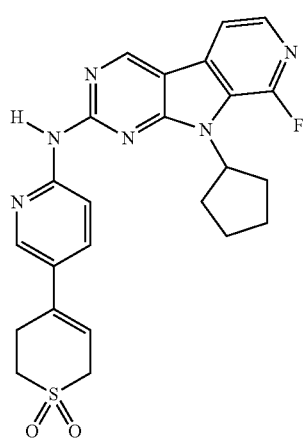

428

9-Cyclopentyl-N-(5-(1,1-dioxido-3,6-dihydro-2H-thiopyran-4-yl)-2-pyridinyl)-8-fluoro-9H-pyrido[4',3':4,5]pyrrolo[2,3-d]pyrimidin-2-amine

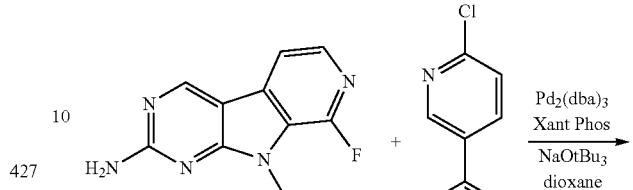

245

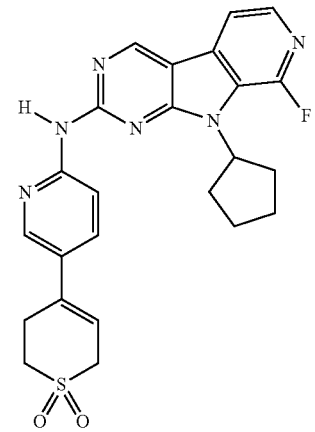

428

9-Cyclopentyl-N-(5-(1,1-dioxido-3,6-dihydro-2H-thiopyran-4-yl)-2-pyridinyl)-8-fluoro-9H-pyrido[4',3':4,5]pyrrolo[2,3-d]pyrimidin-2-amine (428): Compound 428 was prepared from compound 245 using chemistry similar to that described in example 1. The yield is 8%. ¹H NMR (500 MHz, CDCl₃) δ ppm 9.06 (1 H, s), 8.46 (1 H, d, J=8.8 Hz), 8.30 (1 H, d, J=2.2 Hz), 8.19 (1 H, s), 7.63-7.70 (2 H, m), 5.84-5.88 (1 H, m), 5.48 (1 H, qd, J=9.1, 8.9 Hz), 3.78 (2 H, dd, J=4.5, 1.3 Hz), 3.19-3.24 (2 H, m), 3.14 (2 H, dd, J=6.1, 1.5 Hz), 2.34-2.44 (2 H, m, J=7.3, 5.1, 2.7, 2.7 Hz), 2.34-2.44 (4 H, m), 1.97-2.15 (2 H, m); LCMS-ESI (POS), M/Z, M+1: Found 478.9, Calculated 479.2.

Example 272

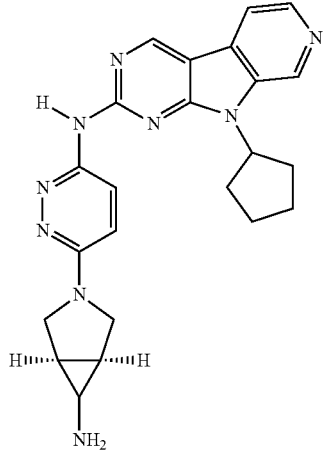

429

N-(6-(((1R,5S)-6-amino-3-azabicyclo[310]hex-3-yl)-3-pyridazinyl)-9-cyclopentyl-9H-pyrido[4',3':4,5]pyrrolo[2,3-d]pyrimidin-2-amine

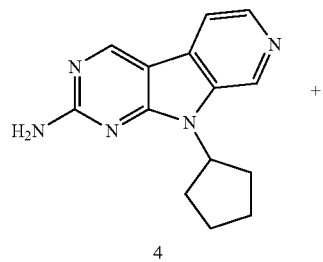

4

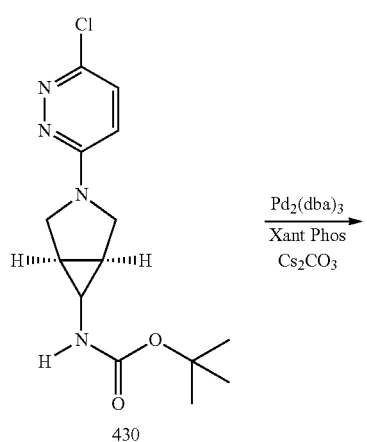

430

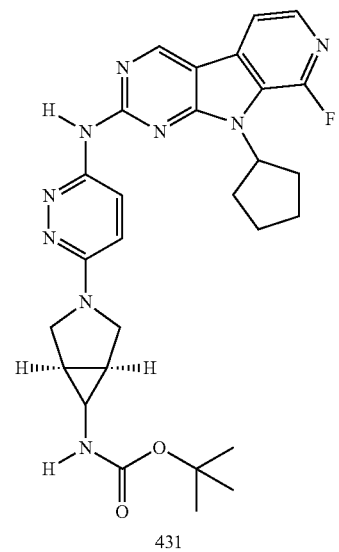

431

(1R,5S)-3-{6-[(9-cyclopentyl-9H-pyrido[4',3':4,5]pyrrolo[2,3-d]pyrimidin-2-yl)amino]-3-pyridazinyl-3-azabicyclo[310]hex-6-yl}carbamate (431)

In analogy to example 1, starting materials and reagents in dioxane (4 mL) were purged with $N_2$ for 20 minutes. (Compound 430 was prepared by the method used for compound 11 in example 4.) The reaction was then heated at 100° C. in a microwave reactor for 3.5 hours. DCM was added to the reaction and the mixture was washed with water and brine. The organic layer was dried with sodium sulfate. The product was purified using Combiflash (DCM/methanol) and further purified by HPLC to give compound 431 as a yellow solid (60 mg, 39%). $^1$H NMR (500 MHz, CD$_3$OD) δ ppm 9.62 (1 H, s), 9.33 (1 H, s), 8.64-8.70 (2 H, m), 8.38-8.49 (1 H, m), 7.72-7.78 (1 H, m), 5.48 (1 H, quin, J=8.8 Hz), 3.89-4.01 (2 H, m), 3.80 (2 H, dt, J=11.1, 2.4 Hz), 2.51 (2 H, dd, J=7.8, 1.2 Hz), 2.15-2.37 (4 H, m), 2.05 (2 H, t, J=3.4 Hz), 1.87-1.97 (2 H, m), 1.48 (9 H, s); LCMS-ESI (POS), M/Z, M+1: Found 528.3, Calculated 528.3.

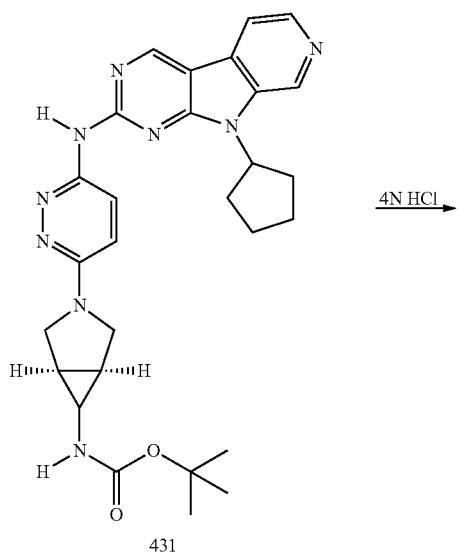

431

→ 4N HCl

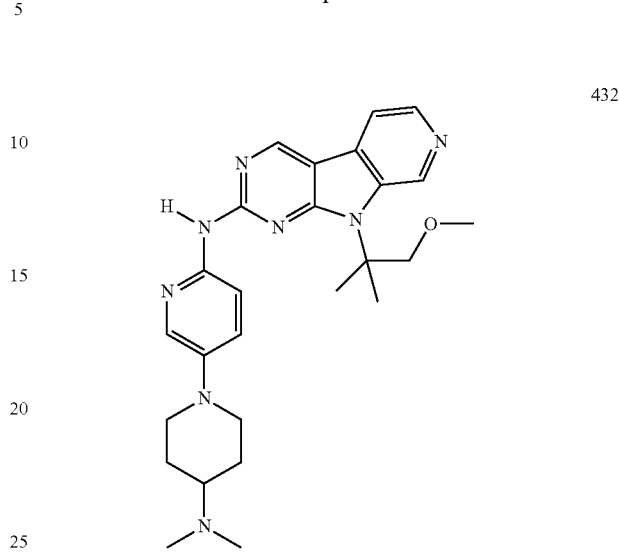

Hz), 1.87-1.97 (2 H, m); LCMS-ESI (POS), M/Z, M+1: Found 428.2, Calculated 428.2.

Example 273

432

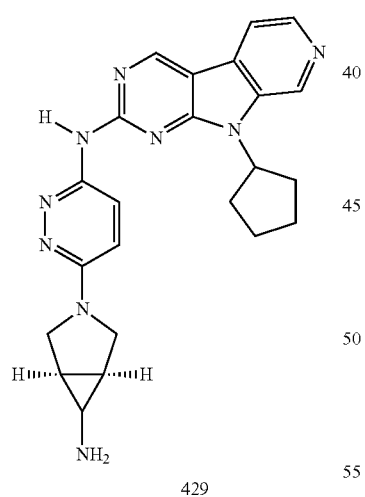

429

N-(6-((1R,5S)-6-amino-3-azabicyclo[310]hex-3-yl)-3-pyridazinyl)-9-cyclopentyl-9H-pyrido[4',3':4,5]pyrrolo[2,3-d]pyrimidin-2-amine (429): Compound 429 was prepared from compound 431 using chemistry similar to that described in example 20. The yield is 73%. $^1$H NMR (500 MHz, CD$_3$OD) δ ppm 9.62 (1 H, s), 9.33 (1 H, s), 8.64-8.70 (2 H, m), 8.38-8.49 (1 H, m), 7.72-7.78 (1 H, m), 5.48 (1 H, quin, J=8.8 Hz), 3.89-4.01 (2 H, m), 3.80 (2 H, dt, J=11.1, 2.4 Hz), 2.51 (2 H, dd, J=7.8, 1.2 Hz), 2.15-2.37 (4 H, m), 2.05 (2 H, t, J=3.4

N-(5-(4-(dimethylamino)-1-piperidinyl)-2-pyridinyl)-9-(2-methoxy-1,1-dimethylethyl)-9H-pyrido[4',3':4,5]pyrrolo[2,3-d]pyrimidin-2-amine Compound 432 was prepared using chemistry similar to that described in example 20. The yield is 39%. $^1$H NMR (500 MHz, CHLOROFORM-d) δ ppm 9.22 (1 H, d, J=1.0 Hz), 9.08 (1 H, s), 8.47 (1 H, d, J=5.1 Hz), 8.30 (1 H, d, J=9.0 Hz), 8.06 (1 H, d, J=2.9 Hz), 7.92 (1 H, s), 7.83 (1 H, dd, J=5.1, 1.2 Hz), 7.41 (1 H, dd, J=9.0, 2.9 Hz), 4.16 (2 H, s), 3.66-3.73 (2 H, m), 3.52 (1 H, s), 3.33 (6 H, s), 2.79 (2 H, td, J=12.0, 2.4 Hz), 2.08 (6 H, s), 1.95-2.15 (2 H, m), 1.66-1.79 (3 H, m, J=12.1, 12.0, 12.0, 4.3 Hz); LCMS-ESI (POS), M/Z, M+1: Found 475.3, Calculated 475.3.

Example 274

433

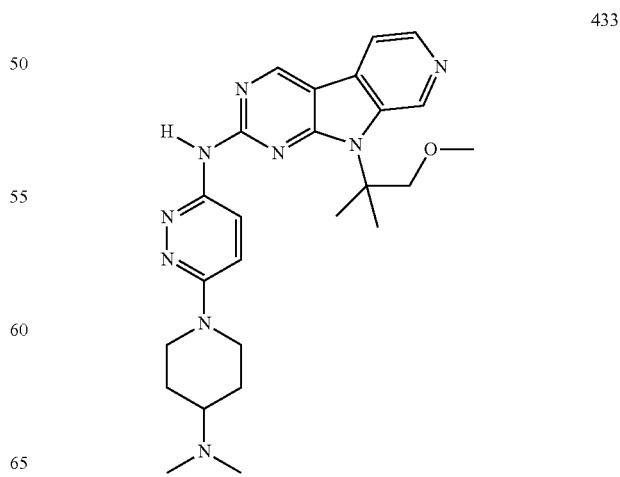

363

N-(6-(4-(dimethylamino)-1-piperidinyl)-3-pyridazinyl)-9-(2-methoxy-1,1-dimethylethyl)-9H-pyrido[4',3':4,5]pyrrolo[2,3-d]pyrimidin-2-amine

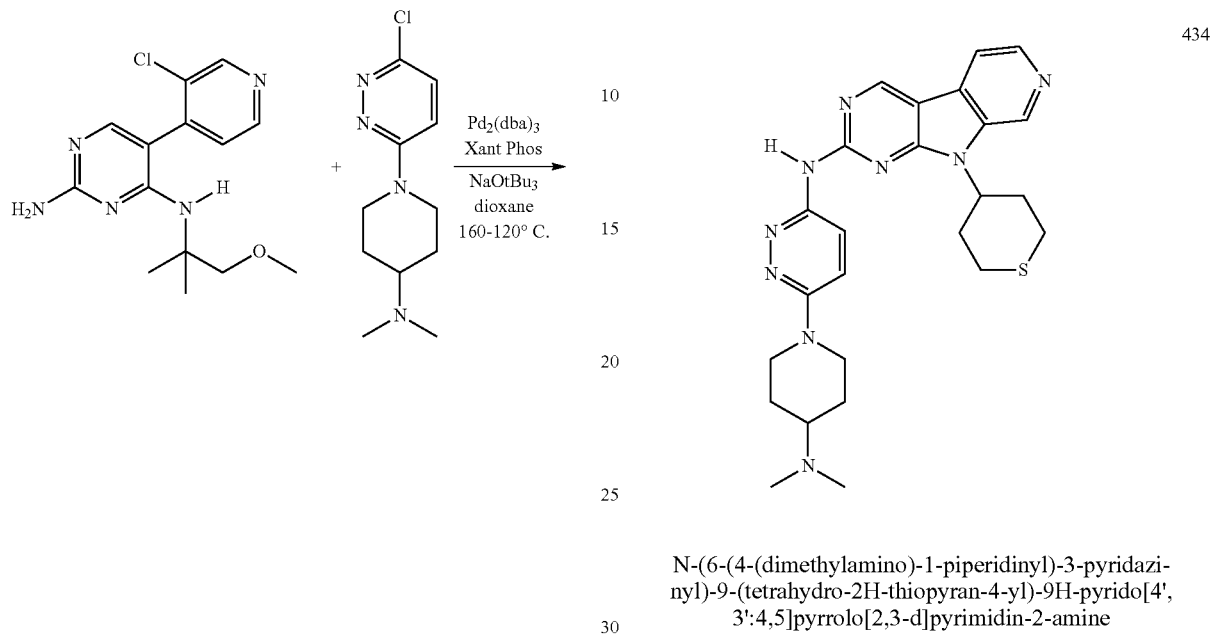

364

Hz), 2.15 (6 H, s), 1.87 (2 H, qd, J=12.4, 4.3 Hz); LCMS-ESI (POS), M/Z, M+1: Found 476.2, Calculated 476.3.

Example 275

N-(6-(4-(dimethylamino)-1-piperidinyl)-3-pyridazinyl)-9-(tetrahydro-2H-thiopyran-4-yl)-9H-pyrido[4',3':4,5]pyrrolo[2,3-d]pyrimidin-2-amine

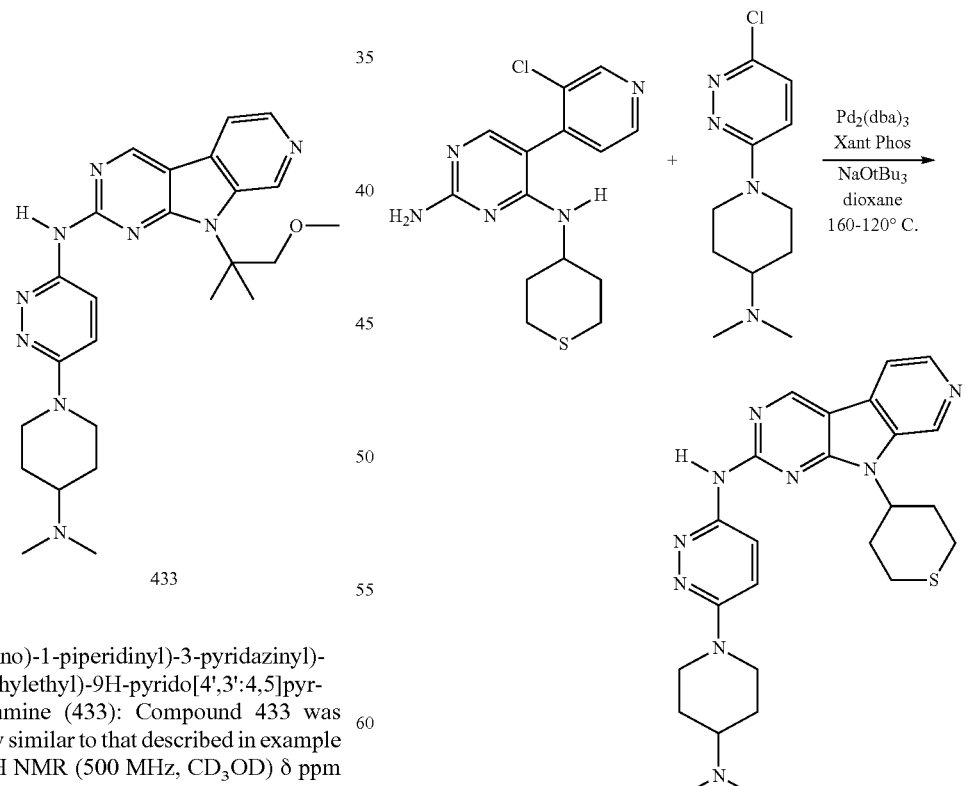

N-(6-(4-(dimethylamino)-1-piperidinyl)-3-pyridazinyl)-9-(2-methoxy-1,1-dimethylethyl)-9H-pyrido[4',3':4,5]pyrrolo[2,3-d]pyrimidin-2-amine (433): Compound 433 was prepared using chemistry similar to that described in example 20. The yield is 45%. $^1$H NMR (500 MHz, CD$_3$OD) δ ppm 9.78 (1 H, s), 9.49 (1 H, s), 8.79 (1 H, d, J=6.1 Hz), 8.69 (1 H, d, J=6.1 Hz), 8.14 (1 H, m), 8.04 (1 H, m), 4.58 (2 H, dddd, J=14.0, 4.7, 2.6, 2.4 Hz), 4.19 (2 H, s), 3.54-3.64 (1 H, m, J=12.0, 12.0, 3.8, 3.7 Hz), 3.37 (3 H, m), 3.20 (2 H, ddd, J=14.1, 11.7, 1.6 Hz), 2.94 (6 H, s), 2.29 (2 H, dd, J=4.2, 2.0

N-(6-(4-(dimethylamino)-1-piperidinyl)-3-pyridazinyl)-9-(tetrahydro-2H-thiopyran-4-yl)-9H-pyrido[4',3':4,5]pyrrolo[2,3-d]pyrimidin-2-amine (434): Compound 434 was prepared using chemistry similar to that described in example 20. The yield is 14%. $^1$H NMR (500 MHz, CD$_3$OD) δ ppm 9.71 (1 H, s), 9.50 (1 H, s), 8.74 (1 H, d, J=6.1 Hz), 8.63 (1 H, d, J=6.1 Hz), 8.05-8.12 (1 H, m), 8.01 (1 H, dd, J=11.4, 1.6 Hz), 4.90 (2 H, dt, J=11.9, 3.6 Hz), 4.74 (1 H, br. s.), 4.47-4.51 (1 H, m), 4.43-4.47 (1 H, m), 3.46-3.59 (2 H, m), 2.88-3.04 (4 H, m), 2.73-2.86 (8 H, m), 2.16-2.30 (4 H, m), 2.03-2.10 (1 H, m), 1.80 (2 H, qd, J=12.4, 4.4 Hz), 1.15-1.30 (1 H, m); LCMS-ESI (POS), M/Z, M+1: Found 490.1, Calculated 490.2.

Example 276

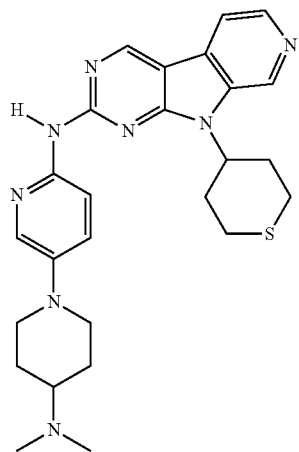

435

N-(5-(4-(dimethylamino)-1-piperidinyl)-2-pyridinyl)-9-(tetrahydro-2H-thiopyran-4-yl)-9H-pyrido[4',3':4,5]pyrrolo[2,3-d]pyrimidin-2-amine N-(5-(4-(dimethylamino)-1-piperidinyl)-2-pyridinyl)-9-(tetrahydro-2H-thiopyran-4-yl)-9H-pyrido[4',3':4,5]pyrrolo[2,3-d]pyrimidin-2-amine (435): Compound 435 was prepared using chemistry similar to that described in example 20. The yield is 60%. $^1$H NMR (500 MHz, CD$_3$OD) δ ppm 9.72 (1 H, s), 9.50 (1 H, s), 8.64-8.78 (2 H, m), 8.21 (1 H, dd, J=9.5, 2.9 Hz), 8.02-8.11 (1 H, m), 7.72 (1 H, d, J=9.5 Hz), 3.89-4.05 (2 H, m), 3.48 (1 H, tt, J=12.1, 3.9 Hz), 3.07 (6 H, m), 2.96 (6 H, s), 2.88 (4 H, m), 2.27-2.34 (4 H, m), 1.94 (2 H, qd, J=12.3, 4.4 Hz); LCMS-ESI (POS), M/Z, M+1: Found 489.2, Calculated 489.3.

Example 277

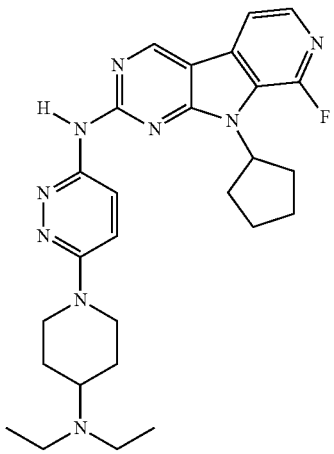

436

9-Cyclopentyl-N-(6-(4-(diethylamino)-1-piperidinyl)-3-pyridazinyl)-8-fluoro-9H-pyrido[4',3':4,5]pyrrolo[2,3-d]pyrimidin-2-amine Compound 436 was prepared from compound 245 using chemistry similar to that described in example 1. The yield is 86%. $^1$H NMR (500 MHz, CD$_3$OD) δ ppm 9.56 (1 H, s), 8.09-8.21 (3 H, m), 7.88-7.95 (1 H, m), 5.67 (1 H, quin, J=9.0 Hz), 4.57 (2 H, dt, J=13.9, 2.4 Hz), 3.81 (1 H, m, J=12.0, 12.0, 4.2, 3.9 Hz), 3.42 (4 H, m), 3.25 (6 H, m), 2.39-2.50 (2 H, m), 2.13-2.35 (6 H, m), 1.80-2.04 (4 H, m), 1.43 (6 H, t, J=7.2 Hz); LCMS-ESI (POS), M/Z, M+1: Found 504.2, Calculated 504.3.

Example 278

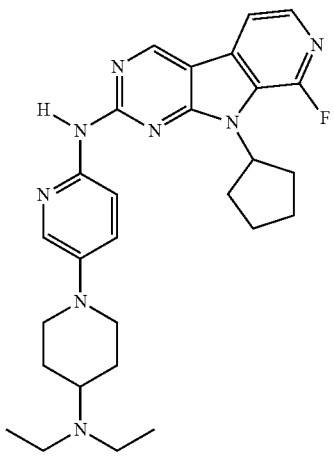

437

9-Cyclopentyl-N-(5-(4-(diethylamino)-1-piperidinyl)-2-pyridinyl)-8-fluoro-9H-pyrido[4',3':4,5]pyrrolo[2,3-d]pyrimidin-2-amine Compound 437 was prepared from compound 245 using chemistry similar to that described in example 1. The yield is 90%. $^1$H NMR (500 MHz, CD$_3$OD) δ ppm 9.50 (1 H, s), 8.21 (1 H, dd, J=9.5, 2.9 Hz), 8.15 (2 H, s), 8.02 (1 H, d, J=2.9 Hz), 7.54 (1 H, d, J=9.5 Hz), 4.57 (2 H, dt, J=13.9, 2.4 Hz), 3.81 (1 H, m, J=12.0, 12.0, 4.2, 3.9 Hz), 3.42 (4 H, m), 3.25 (6 H, m), 2.39-2.50 (2 H, m), 2.13-2.35 (6 H, m), 1.80-2.04 (4 H, m), 1.43 (6 H, t, J=7.2 Hz); LCMS-ESI (POS), M/Z, M+1: Found 503.4, Calculated 503.3.

Example 279

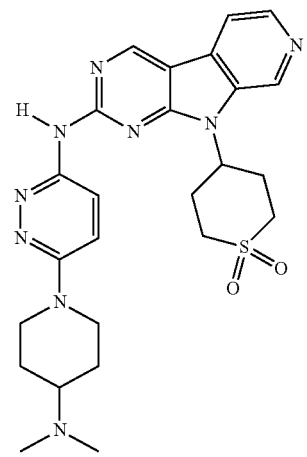

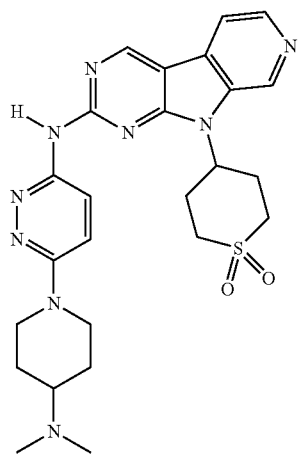

438

N-(6-(4-(dimethylamino)-1-piperidinyl)-3-pyridazinyl)-9-(1,1-dioxidotetrahydro-2H-thiopyran-4-yl)-9H-pyrido[4',3':4,5]pyrrolo[2,3-d]pyrimidin-2-amine N-(6-(4-(dimethylamino)-1-piperidinyl)-3-pyridazinyl)-9-(1,1-dioxidotetrahydro-2H-thiopyran-4-yl)-9H-pyrido[4',3':4,5]pyrrolo[2,3-d]pyrimidin-2-amine (438): Compound 438 was prepared using chemistry similar to that described in example 20. The yield is 8%. $^1$H NMR (500 MHz, CD$_3$OD) δ ppm 9.61 (1 H, s), 9.37 (1 H, s), 8.58-8.69 (2 H, m), 8.41 (1 H, dd, J=10.4, 0.6 Hz), 7.96 (1 H, d, J=10.0 Hz), 5.25 (1 H, t, J=11.9 Hz), 4.93 (1 H, br. s.), 4.56-4.61 (1 H, m), 4.51-4.56 (1 H, m), 3.46-3.65 (6 H, m), 3.27-3.39 (5 H, m), 3.15-3.27 (1 H, m), 3.22 (1 H, ddd, J=14.0, 11.9, 1.7 Hz), 2.94 (6 H, s), 2.35-2.45 (1 H, m), 2.29 (1 H, dd, J=4.0, 2.1 Hz), 2.26 (1 H, dd, J=2.4, 1.5 Hz), 1.90 (2 H, qd, J=12.4, 4.3 Hz); LCMS-ESI (POS), M/Z, M+1: Found 522.2, Calculated 522.2.

Example 280

439

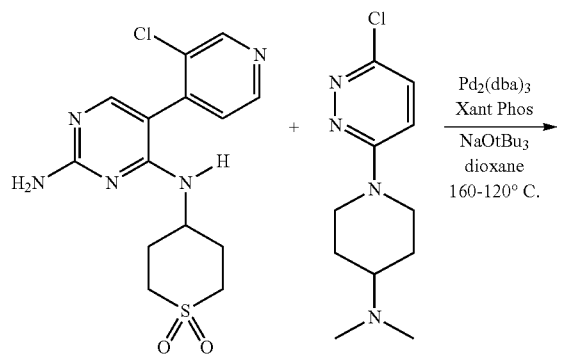

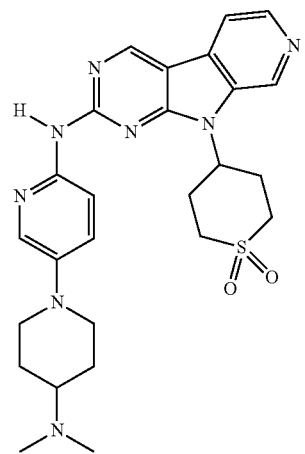

369

N-(5-(4-(dimethylamino)-1-piperidinyl)-2-pyridinyl)-9-(1,1-dioxidotetrahydro-2H-thiopyran-4-yl)-9H-pyrido[4',3':4,5]pyrrolo[2,3-d]pyrimidin-2-amine

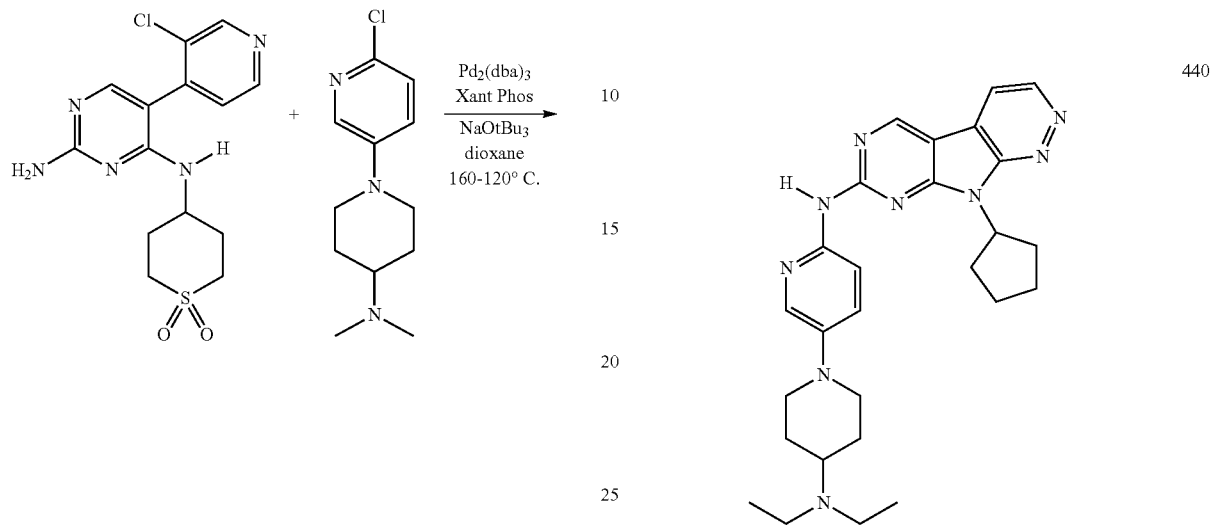

N-(5-(4-(dimethylamino)-1-piperidinyl)-2-pyridinyl)-9-(1,1-dioxidotetrahydro-2H-thiopyran-4-yl)-9H-pyrido[4',3':4,5]pyrrolo[2,3-d]pyrimidin-2-amine (439): Compound 439 was prepared using chemistry similar to that described in example 20. The yield is 30%. $^1$H NMR (500 MHz, CD$_3$OD) δ ppm 9.62 (1 H, s), 9.38 (1 H, s), 8.61-8.71 (2 H, m), 8.17 (1 H, br. s.), 8.12 (1 H, dd, J=9.7, 0.6 Hz), 7.94 (1 H, d, J=4.4 Hz), 5.27 (1 H, dd, J=7.8, 3.9 Hz), 3.95-4.04 (2 H, m, J=12.8, 4.8, 2.3, 2.3 Hz), 3.40-3.64 (4 H, m), 3.25-3.40 (1 H, m), 2.99 (2 H, m), 2.95 (6 H, s), 2.36-2.48 (2 H, m), 2.28 (2 H, dd, J=4.3, 2.1 Hz), 2.26 (2 H, dd, J=2.7, 1.2 Hz), 1.94 (2 H, qd, J=12.3, 4.3 Hz); LCMS-ESI (POS), M/Z, M+1: Found 521.3, Calculated 521.2.

Example 281

9-Cyclopentyl-N-(5-(4-(diethylamino)-1-piperidinyl)-2-pyridinyl)-9H-pyrimido[5',4':4,5]pyrrolo[2,3-c]pyridazin-7-amine

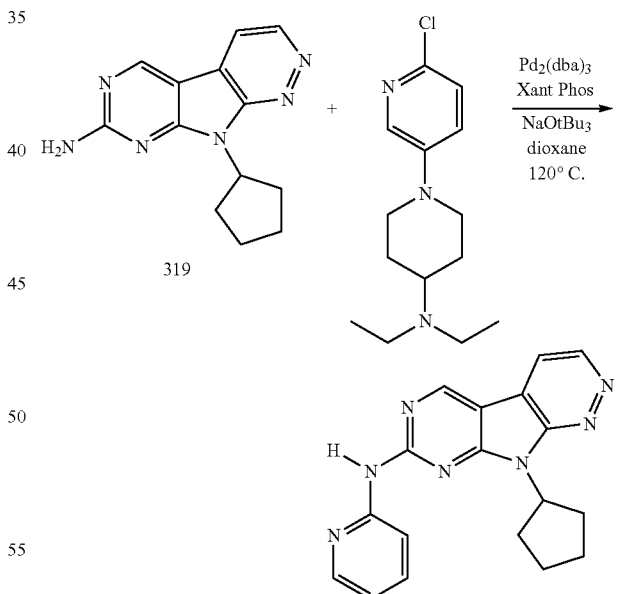

9-Cyclopentyl-N-(5-(4-(diethylamino)-1-piperidinyl)-2-pyridinyl)-9H-pyrimido-[5',4':4,5]pyrrolo[2,3-c]pyridazin-7-amine (440): Compound 440 was prepared from compound 319 using methods described in Example 1. The yield is 26%. ¹H NMR (500 MHz, CHLOROFORM-d) δ ppm 9.13 (1 H, s), 9.12 (1 H, s), 8.60 (1 H, d, J=0.5 Hz), 8.39 (1 H, d, J=9.0 Hz), 8.13 (1 H, d, J=0.5 Hz), 7.88 (1 H, d, J=5.1 Hz), 7.41 (1 H, dd, J=9.0, 2.9 Hz), 5.72 (1 H, quin, J=8.8 Hz), 3.70-3.78 (2 H, m, J=12.1, 4.8, 2.2, 2.2 Hz), 2.79 (2 H, m), 2.77 (2, H, m), 2.64 (4 H, m), 2.18 (4 H, m), 1.94 (2 H, ddd, J=12.7, 2.9, 2.7 Hz), 1.86 (2 H, m), 1.70 (4 H, m), 1.10 (6 H, t, J=7.1 Hz); LCMS-ESI (POS), M/Z, M+1: Found 486.4, Calculated 486.3.

Example 282

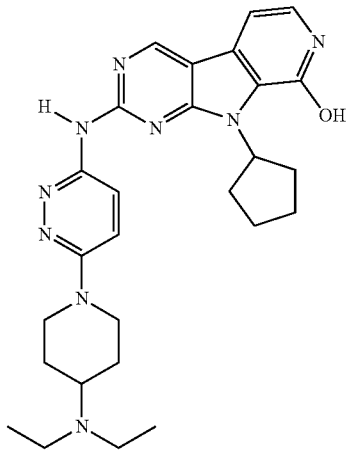

441

9-cyclopentyl-2-((6-(4-(diethylamino)-1-piperidinyl)-3-pyridazinyl)amino)-9H-pyrido[4',3':4,5]pyrrolo[2,3-d]pyrimidin-8-ol

Example 283

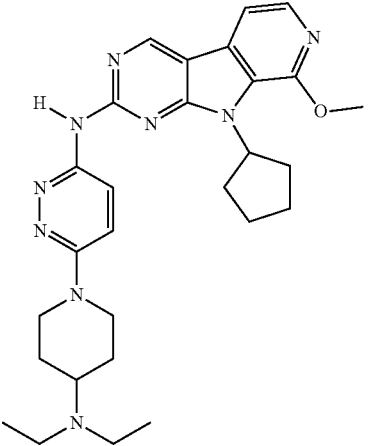

442

372

9-cyclopentyl-N-(6-(4-(diethylamino)-1-piperidinyl)-3-pyridazinyl)-8-methoxy-9H-pyrido[4',3':4,5]pyrrolo[2,3-d]pyrimidin-2-amine

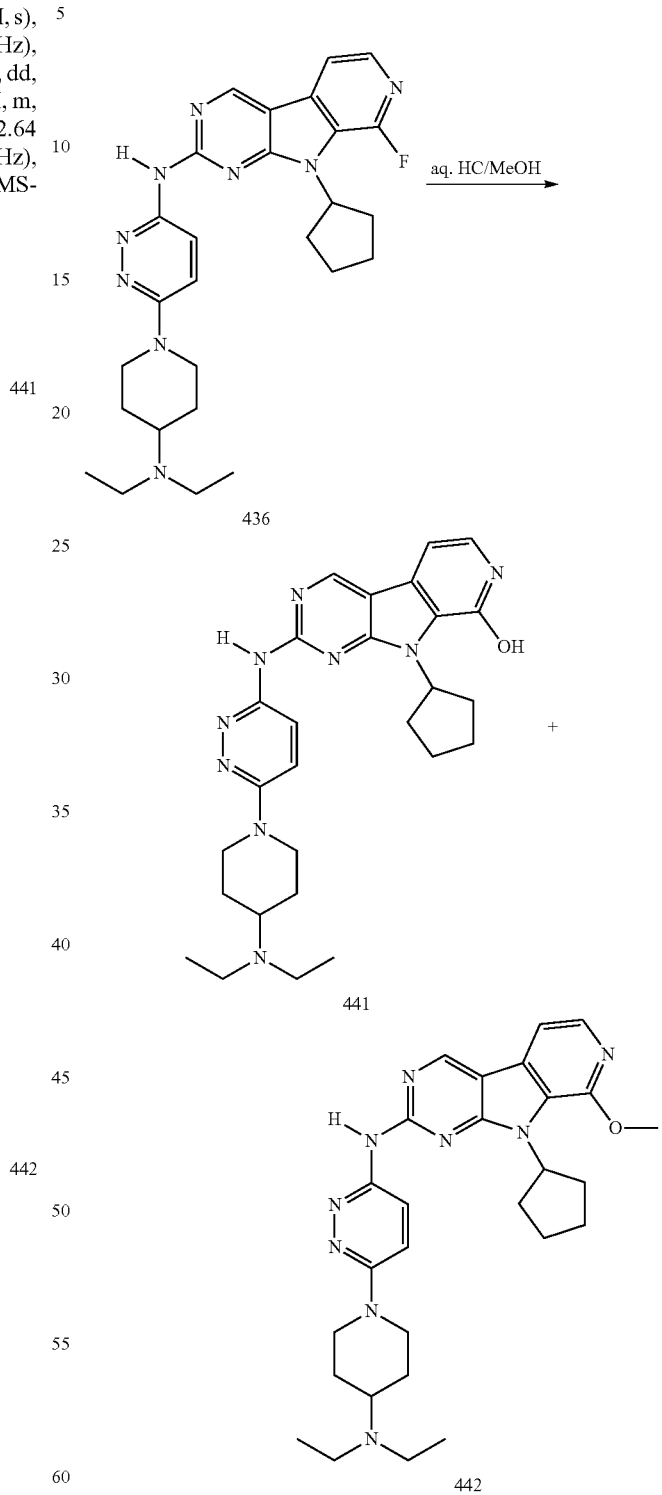

Compound 436 (33 mg, 66 μmol) in methanol (2 mL) was treated with 0.1 mL of 37% aq. HCl at 60° C. for 4 hours. The reaction mixture was diluted with methanol and then purified using HPLC to give compound 441 as a yellow solid (20 mg, 60%) and compound 442 as a yellow solid (4.7 mg, 14%).

9-cyclopentyl-2-((6-(4-(diethylamino)-1-piperidinyl)-3-pyridazinyl)amino)-9H-pyrido[4',3':4,5]pyrrolo[2,3-d]pyrimidin-8-ol (441): ¹H NMR (500 MHz, CD₃OD) δ ppm 9.35 (1 H, s), 8.04 (1 H, m, J=10.0 Hz), 7.80 (1 H, m, J=10.0 Hz), 7.34 (1 H, d, J=6.6 Hz), 7.15 (1 H, d, J=6.8 Hz), 6.28 (1 H, quin, J=8.9 Hz), 4.53-4.58 (2 H, m), 3.72-3.80 (1 H, m, J=12.0, 12.0, 3.8, 3.7 Hz), 3.41 (2 H, dt, J=14.1, 7.0 Hz), 3.27 (4 H, m), 3.19 (4 H, m), 2.54-2.65 (2 H, m), 2.12-2.30 (6 H, m), 1.95 (2 H, m), 1.82 (2 H, m), 1.40 (6 H, t, J=7.3 Hz); LCMS-ESI (POS), M/Z, M+1: Found 502.3, Calculated 502.3.

9-cyclopentyl-N-(6-(4-(diethylamino)-1-piperidinyl)-3-pyridazinyl)-8-methoxy-9H-pyrido[4',3':4,5]pyrrolo[2,3-d]pyrimidin-2-amine (442): ¹H NMR (500 MHz, CD₃OD) δ ppm 9.41 (1 H, s), 8.10 (1 H, d, J=5.4 Hz), 8.04-8.13 (1 H, m), 7.87 (1 H, d, J=9.8 Hz), 7.76 (1 H, d, J=5.4 Hz), 5.95 (1 H, quin, J=8.9 Hz), 4.55 (2 H, dt, J=13.9, 2.4 Hz), 4.19 (3 H, s), 3.71-3.79 (1 H, m, J=12.0, 12.0, 3.8, 3.7 Hz), 3.44 (2 H, m), 3.22 (2 H, m), 3.18 (2 H, m), 2.50-2.61 (2 H, m), 2.11-2.28 (6 H, m), 1.80-1.96 (4 H, m, J=12.2, 12.2, 11.9, 4.5 Hz), 1.41 (6 H, t, J=7.2 Hz); LCMS-ESI (POS), M/Z, M+1: Found 516.3, Calculated 516.3.

Example 284

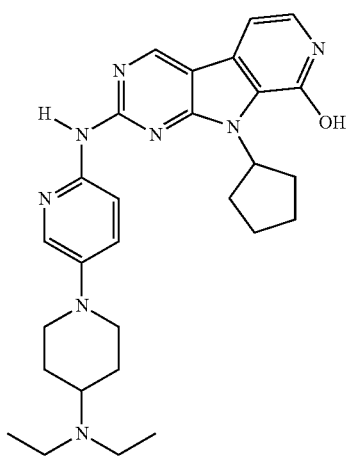

443

9-Cyclopentyl-2-((5-(4-(diethylamino)-1-piperidinyl)-2-pyridinyl)amino)-9H-pyrido[4',3':4,5]pyrrolo[2,3-d]pyrimidin-8-ol Compound 443 was prepared using methods described in examples 282 and 283 beginning with compound 437. ¹H NMR (500 MHz, CD₃OD) δ ppm 9.26 (1 H, s), 8.07 (1 H, dd, J=9.5, 2.9 Hz), 7.86 (1 H, d, J=2.9 Hz), 7.46 (1 H, d, J=9.5 Hz), 7.32 (1 H, d, J=6.8 Hz), 7.11 (1 H, d, J=6.6 Hz), 6.19 (1 H, quin, J=8.9 Hz), 3.91 (2 H, ddd, J=12.6, 2.4, 2.3 Hz), 3.61 (1 H, tt, J=12.1, 3.7 Hz), 3.37-3.48 (2 H, m), 3.23-3.36 (4 H, m), 2.97 (2 H, ddd, J=12.2, 11.0, 0.7 Hz), 2.90-3.02 (1 H, m), 2.56 (2 H, ddd, J=11.7, 5.9, 3.2 Hz), 2.26 (2 H, m), 2.18 (4 H, m), 1.99 (2 H, qd, J=12.3, 4.3 Hz), 1.72-1.87 (2 H, m), 1.42 (6 H, t, J=7.2 Hz); LCMS-ESI (POS), M/Z, M+1: Found 501.2, Calculated 501.3.

Example 285

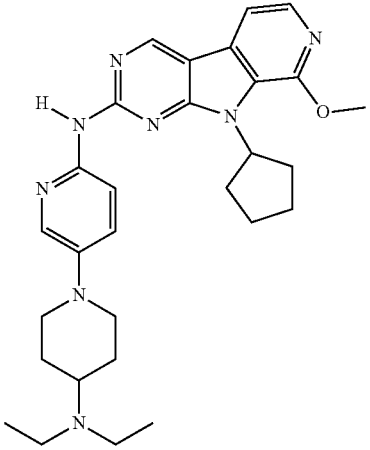

444

9-cyclopentyl-N-(5-(4-(diethylamino)-1-piperidinyl)-2-pyridinyl)-8-methoxy-9H-pyrido[4',3':4,5]pyrrolo[2,3-d]pyrimidin-2-amine Compound 444) was prepared using methods described in example 282 and 283 beginning with compound 437. ¹H NMR (500 MHz, CD₃OD) δ ppm 9.32 (1 H, s), 8.03-8.11 (2 H, m), 7.97 (1 H, d, J=2.9 Hz), 7.74 (1 H, d, J=5.4 Hz), 7.53 (1 H, d, J=9.3 Hz), 5.90 (1 H, quin, J=8.9 Hz), 4.17 (3 H, s), 3.93-3.98 (2 H, m), 3.60 (1 H, tt, J=12.1, 3.7 Hz), 3.40 (2 H, m), 3.27 (2 H, m), 2.97 (2 H, td, J=12.2, 1.2 Hz), 2.15-2.27 (6 H, m), 1.98 (2 H, qd, J=12.3, 4.3 Hz), 1.78-1.90 (2 H, m), 1.41 (6 H, t, J=7.2 Hz); LCMS-ESI (POS), M/Z, M+1: Found 515.3, Calculated 515.3

Example 286

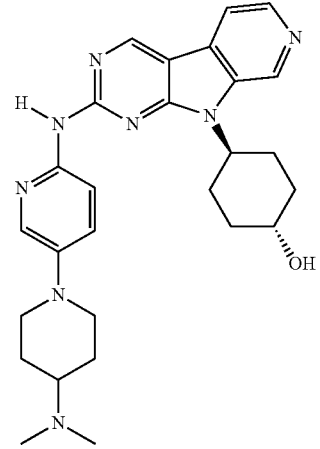

445

Trans-4-(2-((5-(4-(dimethylamino)-1-piperidinyl)-2-pyridinyl)amino)-9H-pyrido[4',3':4,5]pyrrolo[2,3-d]pyrimidin-9-yl)cyclohexanol Compound 445 was prepared using chemistry similar to that described in example 258. The two step yield is 58%. $^1$H NMR (500 MHz, CHLOROFORM-d) δ ppm 8.98 (1 H, s), 8.83 (H, d, J=1.0 Hz), 8.42 (1 H, d, J=5.1 Hz), 8.24 (1 H, d, J=9.0 Hz), 7.97-8.04 (2 H, m), 7.74 (1 H, dd, J=5.1, 1.2 Hz), 7.30 (1 H, m), 4.67 (1 H, tt, J=12.3, 4.0 Hz), 3.79-3.87 (1 H, m, J=11.1, 11.1, 4.4, 4.3 Hz), 3.54-3.67 (2 H, m), 3.27-3.34 (1 H, m), 2.54-2.76 (4 H, m), 2.27 (6 H, s), 2.16-2.20 (3 H, m, J=6.6, 6.6, 6.4, 2.6 Hz), 1.86-1.96 (6 H, m), 1.49-1.73 (6 H, m), 1.38 (1 H, d, J=7.3 Hz); LCMS-ESI (POS), M/Z, M+1: Found 487.3, Calculated 487.3.

Example 287

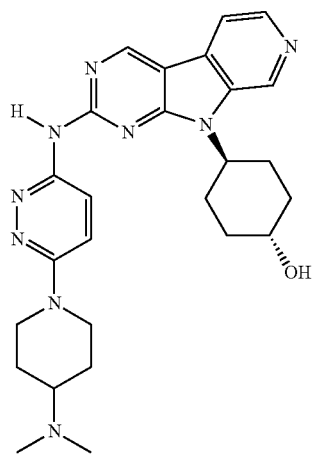

446

Trans-4-(2-((6-(4-(dimethylamino)-1-piperidinyl)-3-pyridazinyl)amino)-9H-pyrido[4',3':4,5]pyrrolo[2,3-d]pyrimidin-9-yl)cyclohexanol Compound 446 was prepared using chemistry similar to that described in example 258. The two step yield is 53%. $^1$H NMR (500 MHz, CD$_3$OD) δ ppm 9.73 (1 H, s), 9.53 (1 H, s), 8.65-8.77 (2 H, m), 8.08 (2 H, m), 5.02 (1 H, m, J=12.4, 12.4, 4.2, 4.0 Hz), 4.58-4.63 (2 H, m), 3.92 (1 H, tt, J=11.1, 4.2 Hz), 3.60 (1 H, tt, J=12.1, 3.9 Hz), 3.20 (2 H, ddd, J=14.2, 12.1, 2.6 Hz), 2.94 (6 H, s), 2.71-2.83 (2 H, m, J=13.1, 12.9, 12.9, 3.5 Hz), 2.17-2.32 (4 H, m), 2.08 (2 H, ddd, J=13.3, 2.4, 2.1 Hz), 1.87 (2 H, qd, J=12.5, 4.4 Hz), 1.60-1.73 (2 H, m); LCMS-ESI (POS), M/Z, M+1: Found 488.2, Calculated 488.3.

Table 5

Examples 288-289 (listed in Table 5) were prepared using conditions as described for example 60 with deprotection when necessary, replacing 5-bromo-2-chloropyridine and 97 with proper chemical reagents. The reaction conditions such as temperature and reaction time were the same unless indicated in the table. All LCMS data was obtained using Agilent 1100 series LC/MSD, column: CAPCELL UG120 (3 um, 4.6 mm I.D.×50 mm), solvent system: water-acetonitrile 95:5 with 0.1% formic acid.

TABLE 5

| Example # | Structure | Reaction conditions | LSMS retention time (minutes) | LCMS-ESI (M + 1) |
|---|---|---|---|---|
| 288 | 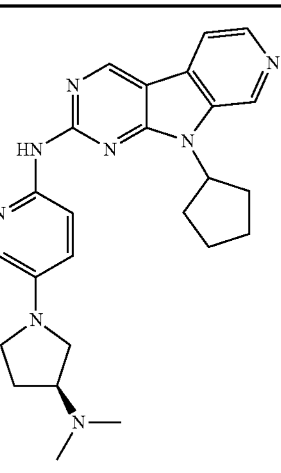 | | 0.874 | 443.2 |

TABLE 5-continued

| Example # | Structure | Reaction conditions | LSMS retention time (minutes) | LCMS-ESI (M + 1) |
|---|---|---|---|---|
| 289 | 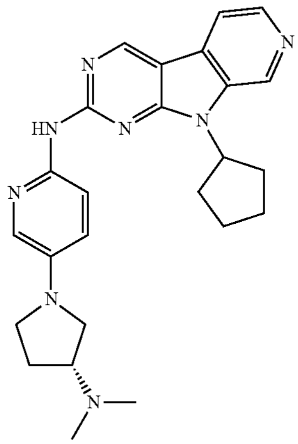 [SMILES: CN(C)[C@@H]1CCN(c2ccc(Nc3ncc4c5ccncc5n(C5CCCC5)c4n3)nc2)C1] | | 0.888 | 443.2 |

Examples 290-297 (table 6) were prepared using conditions as described for example 101 with deprotection when necessary, replacing compound 97 with proper amine. The reaction conditions such as solvent, temperature, and reaction time for Step 2 were the same unless indicated

TABLE 6

| Example # | Structure | Reaction Conditions | LSMS retention time (min) | LCMS-ESI (M + 1) |
|---|---|---|---|---|
| 290 | 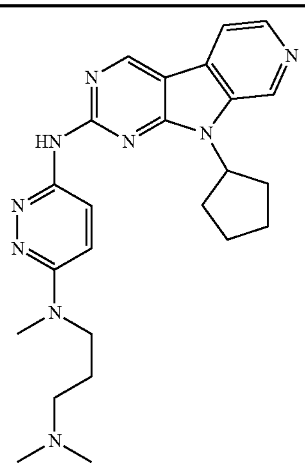 | | 0.766 | 446.2 |
| 291 | 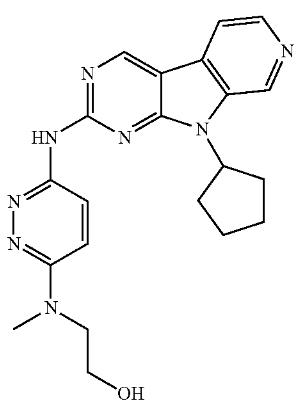 [SMILES: CN(CCO)c1ccc(Nc2ncc3c4ccncc4n(C4CCCC4)c3n2)nn1] | | 0.761 | 405.1 |

TABLE 6-continued

| Example # | Structure | Reaction Conditions | LSMS retention time (min) | LCMS-ESI (M + 1) |
|---|---|---|---|---|
| 292 | 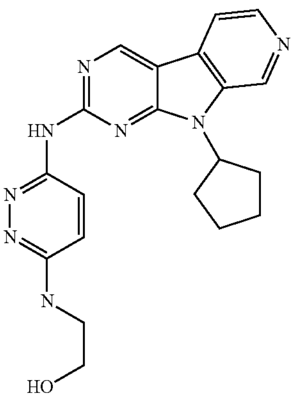 [SMILES: OCCNc1ccc(Nc2ncc3c4ccncc4n(C4CCCC4)c3n2)nn1] | | 0.742 | 391.1 |
| 293 | 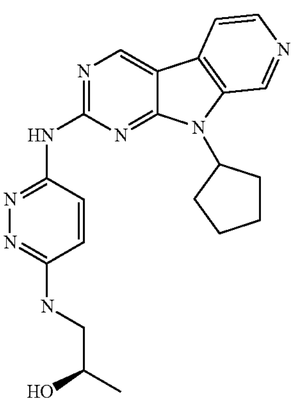 [SMILES: C[C@@H](O)CNc1ccc(Nc2ncc3c4ccncc4n(C4CCCC4)c3n2)nn1] | | 0.777 | 405.2 |
| 294 | 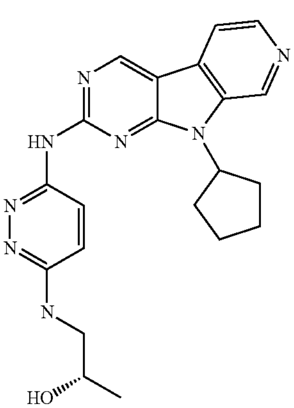 [SMILES: C[C@H](O)CNc1ccc(Nc2ncc3c4ccncc4n(C4CCCC4)c3n2)nn1] | | 0.781 | 405.2 |

TABLE 6-continued

| Example # | Structure | Reaction Conditions | LSMS retention time (min) | LCMS-ESI (M + 1) |
|---|---|---|---|---|
| 295 | 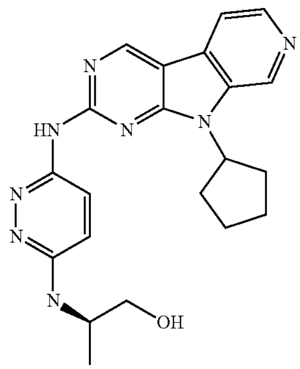 [SMILES: C[C@H](CO)Nc1ccc(Nc2ncc3c4ccncc4n(C4CCCC4)c3n2)nn1] | | 0.791 | 405.2 |
| 296 | 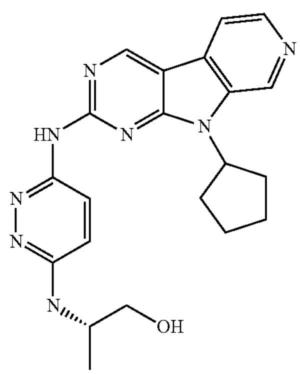 [SMILES: C[C@@H](CO)Nc1ccc(Nc2ncc3c4ccncc4n(C4CCCC4)c3n2)nn1] | | 0.785 | 405.2 |
| 297 | 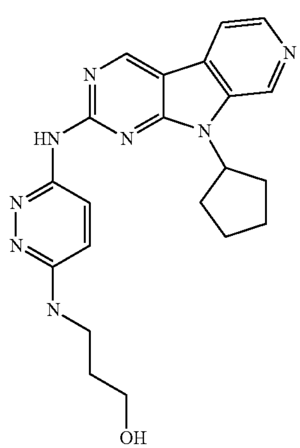 [SMILES: OCCCNc1ccc(Nc2ncc3c4ccncc4n(C4CCCC4)c3n2)nn1] | | 0.768 | 405.2 |

Table 7

Examples 298-432 (table 7) were prepared using conditions as described for example 122 with deprotection when necessary, replacing components with proper reagents prepared according to examples 1 or 4.

TABLE 7
| Example # | Structure | LCMS retention time (min) | LCMS-ESI (M + 1) |
|---|---|---|---|
| 298 | 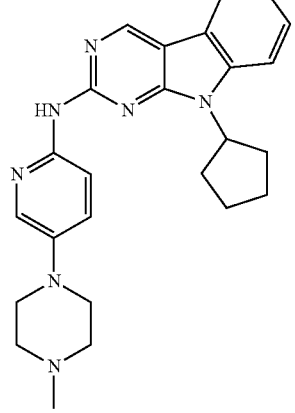 | 1.023 | 428.2 |
| 299 | 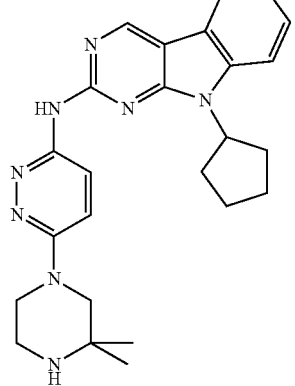 | 1.055 | 443.2 |
| 300 | 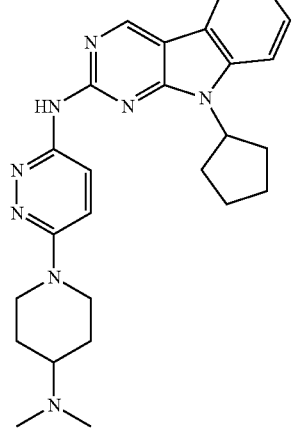 | 1.082 | 457.3 |
TABLE 7-continued
| Example # | Structure | LCMS retention time (min) | LCMS-ESI (M + 1) |
|---|---|---|---|
| 301 | 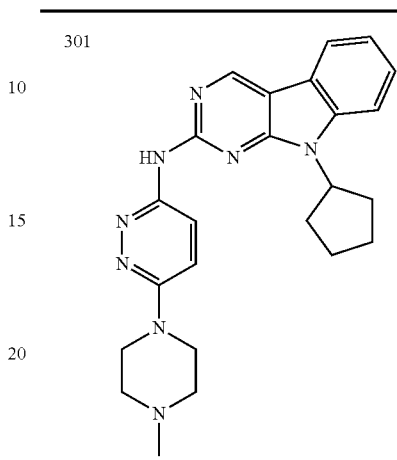 | 1.028 | 429.2 |
| 302 | 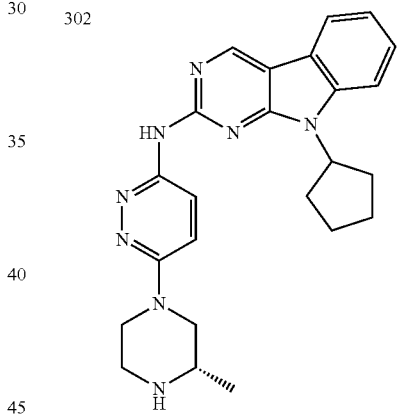 | 1.013 | 429.2 |
| 303 | 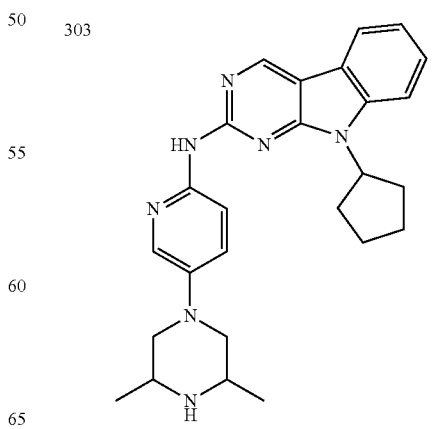 | 1.083 | 442.3 |

TABLE 7-continued
| Example # | Structure | LCMS retention time (min) | LCMS-ESI (M + 1) |
|---|---|---|---|
| 304 | 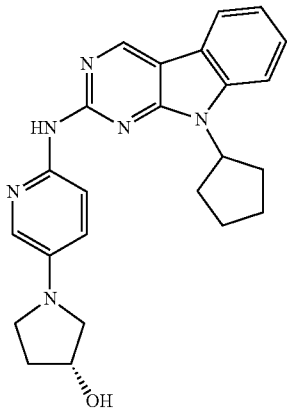 [SMILES: O[C@@H]1CCN(c2ccc(Nc3ncc4c5ccccc5n(C5CCCC5)c4n3)nc2)C1] | 1.360 | 415.1 |
| 305 | 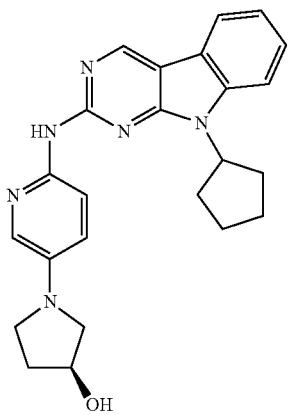 [SMILES: O[C@H]1CCN(c2ccc(Nc3ncc4c5ccccc5n(C5CCCC5)c4n3)nc2)C1] | 1.369 | 415.1 |
| 306 | 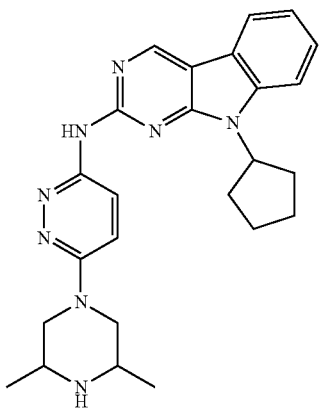 [SMILES: CC1CN(c2ccc(Nc3ncc4c5ccccc5n(C5CCCC5)c4n3)nn2)CC(C)N1] | 1.066 | 443.2 |
| 307 | 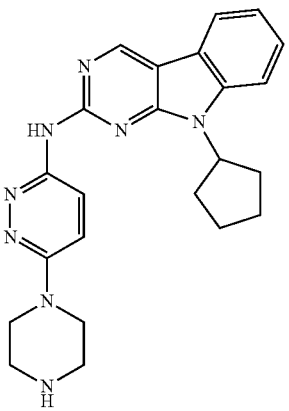 [SMILES: c1ccc2c(c1)c1cnc(Nc3ccc(N4CCNCC4)nn3)nc1n2C1CCCC1] | 1.048 | 415.1 |
| 308 | 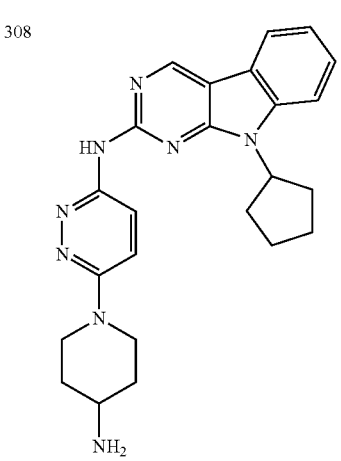 | 1.080 | 429.2 |
| 309 | 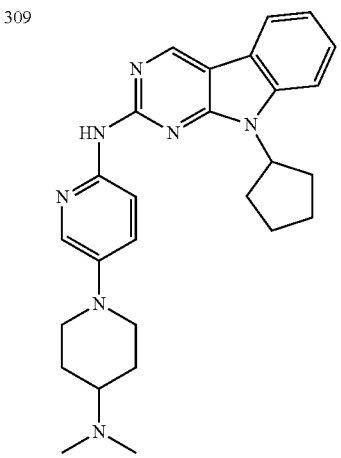 | 1.074 | 456.2 |

TABLE 7-continued
| Example # | Structure | LCMS retention time (min) | LCMS-ESI (M + 1) |
|---|---|---|---|
| 310 | 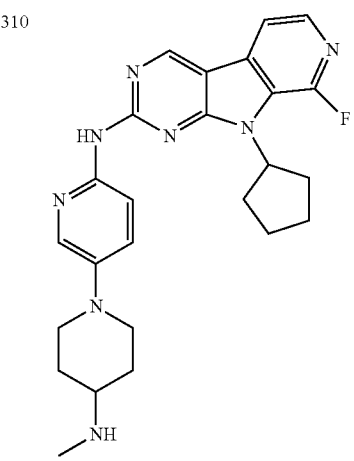 | 1.047 | 461.2 |
| 311 | 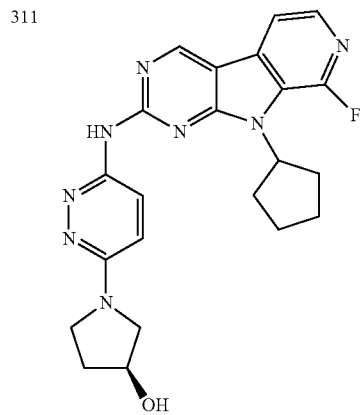 | 1.087 | 435.1 |
| 312 | 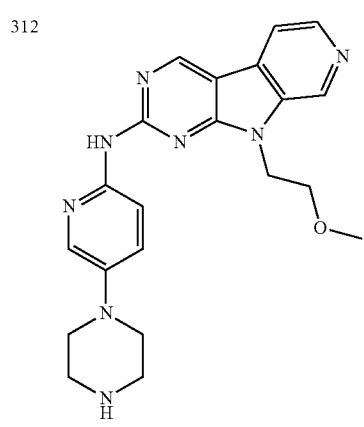 | 0.574 | 405.2 |
| 313 | 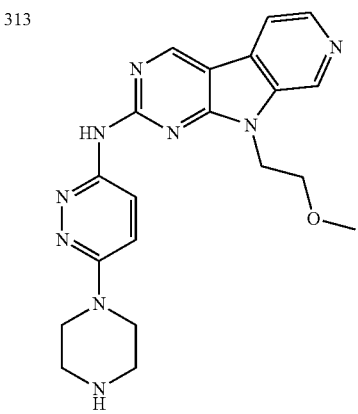 | 0.497 | 406.1 |
| 314 | 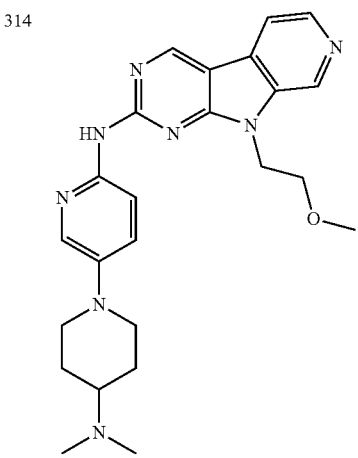 | 0.671 | 447.3 |
| 315 | | 0.613 | 448.1 |

TABLE 7-continued
| Example # | Structure | LCMS retention time (min) | LCMS-ESI (M + 1) |
|---|---|---|---|
| 316 | 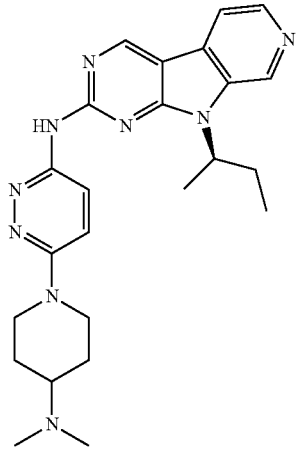 [SMILES: CC[C@@H](C)n1c2cnccc2c2cnc(Nc3ccc(N4CCC(N(C)C)CC4)nn3)nc21] | 0.701 | 446.2 |
| 317 | 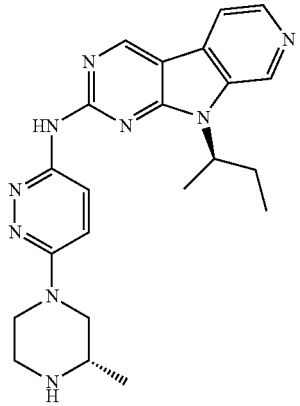 [SMILES: CC[C@@H](C)n1c2cnccc2c2cnc(Nc3ccc(N4CCN[C@@H](C)C4)nn3)nc21] | 0.693 | 418.1 |
| 318 | 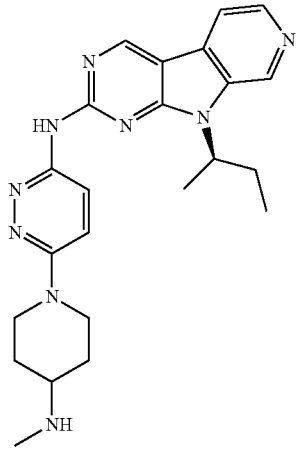 [SMILES: CC[C@@H](C)n1c2cnccc2c2cnc(Nc3ccc(N4CCC(NC)CC4)nn3)nc21] | 0.742 | 432.2 |
TABLE 7-continued
| Example # | Structure | LCMS retention time (min) | LCMS-ESI (M + 1) |
|---|---|---|---|
| 319 | 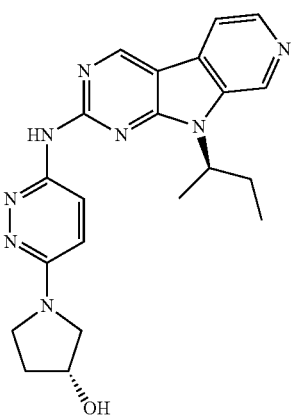 [SMILES: CC[C@@H](C)n1c2cnccc2c2cnc(Nc3ccc(N4CC[C@@H](O)C4)nn3)nc21] | 0.734 | 405.1 |
| 320 | 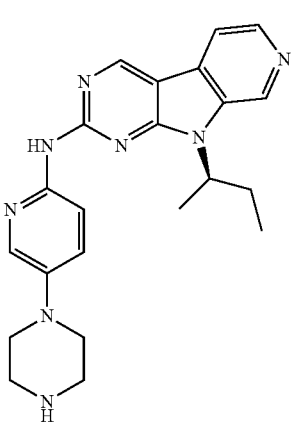 [SMILES: CC[C@@H](C)n1c2cnccc2c2cnc(Nc3ccc(N4CCNCC4)cn3)nc21] | 0.706 | 403.1 |
| 321 | 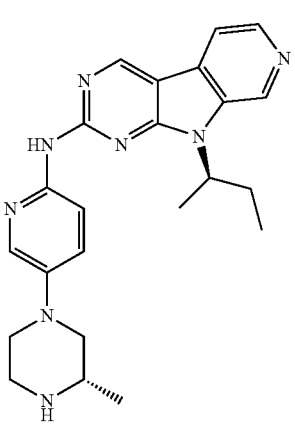 | 0.732 | 417.3 |

TABLE 7-continued
| Example # | Structure | LCMS retention time (min) | LCMS-ESI (M + 1) |
|---|---|---|---|
| 322 | 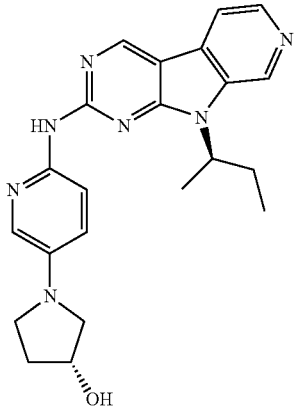 | 0.862 | 404.2 |
| 323 | 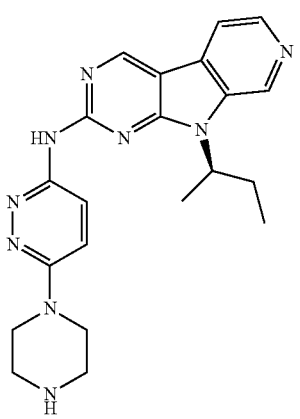 | 0.685 | 404.2 |
| 324 | 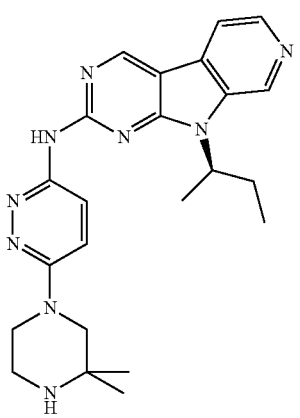 [SMILES: CC[C@@H](C)n1c2cnccc2c2cnc(Nc3ccc(N4CCNC(C)(C)C4)nn3)nc21] | 0.728 | 432.2 |
| 325 | | 0.731 | 431.2 |
| 326 | | 0.736 | 445.3 |
| 327 | | 0.732 | 446.2 |

| Example # | Structure | LCMS retention time (min) | LCMS-ESI (M + 1) |
|---|---|---|---|
| 328 | 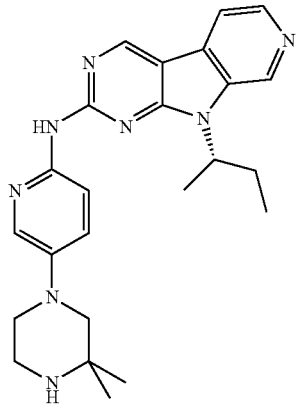 [SMILES: CC[C@H](C)n1c2cnccc2c2cnc(Nc3ccc(N4CCNC(C)(C)C4)cn3)nc21] | 0.783 | 431.2 |
| 329 | 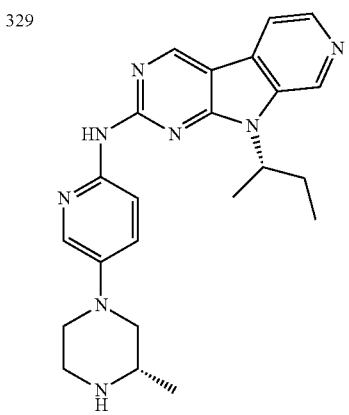 | 0.746 | 417.3 |
| 330 | 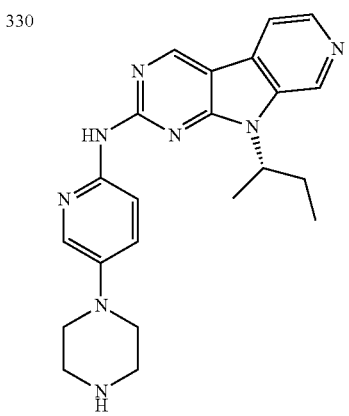 | 0.733 | 403.1 |
| 331 | 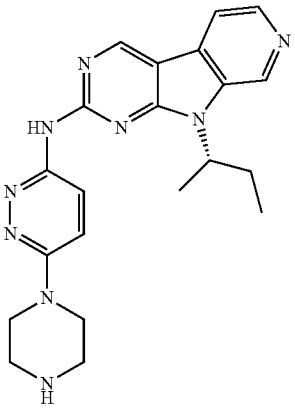 [SMILES: CC[C@H](C)n1c2cnccc2c2cnc(Nc3ccc(N4CCNCC4)nn3)nc21] | 0.720 | 404.2 |
| 332 | 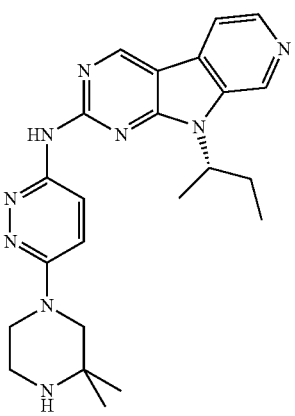 [SMILES: CC[C@H](C)n1c2cnccc2c2cnc(Nc3ccc(N4CCNC(C)(C)C4)nn3)nc21] | 0.753 | 432.2 |
| 333 | 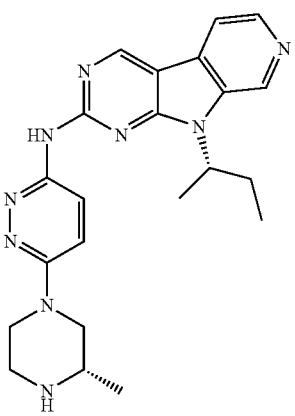 [SMILES: CC[C@H](C)n1c2cnccc2c2cnc(Nc3ccc(N4CCN[C@@H](C)C4)nn3)nc21] | 0.690 | 418.1 |

TABLE 7-continued
| Example # | Structure | LCMS retention time (min) | LCMS-ESI (M + 1) |
|---|---|---|---|
| 334 | 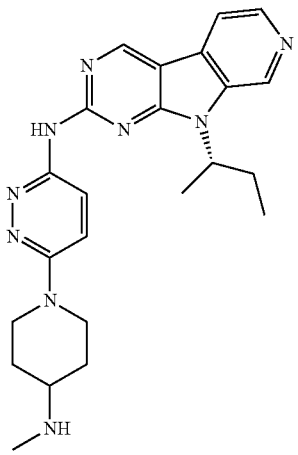 [SMILES: CC[C@H](C)n1c2cnccc2c2cnc(Nc3ccc(N4CCC(NC)CC4)nn3)nc21] | 0.753 | 432.2 |
| 335 | 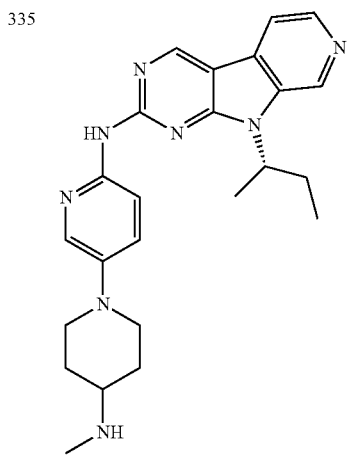 | 0.776 | 431.2 |
| 336 | 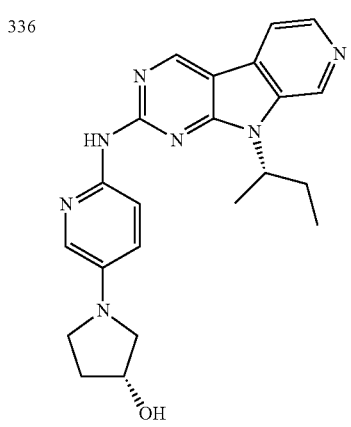 | 0.925 | 404.2 |
TABLE 7-continued
| Example # | Structure | LCMS retention time (min) | LCMS-ESI (M + 1) |
|---|---|---|---|
| 337 | 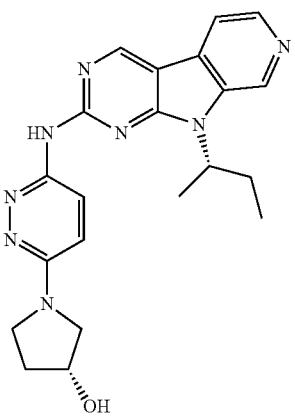 [SMILES: CC[C@H](C)n1c2cnccc2c2cnc(Nc3ccc(N4CC[C@@H](O)C4)nn3)nc21] | 0.736 | 405.1 |
| 338 | 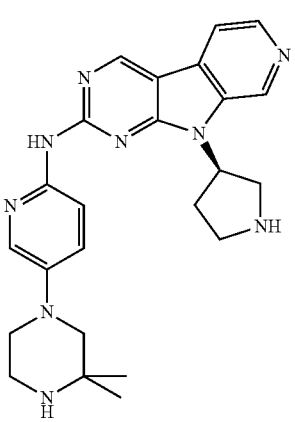 [SMILES: CC1(C)CN(c2ccc(Nc3ncc4c5ccncc5n([C@@H]5CCNC5)c4n3)nc2)CCN1] | 0.499 | 444.2 |
| 339 | 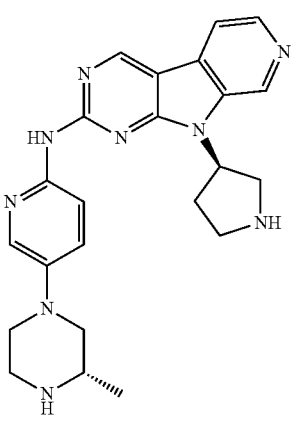 [SMILES: C[C@H]1CN(c2ccc(Nc3ncc4c5ccncc5n([C@@H]5CCNC5)c4n3)nc2)CCN1] | 0.382 | 430.1 |

TABLE 7-continued
| Example # | Structure | LCMS retention time (min) | LCMS-ESI (M + 1) |
|---|---|---|---|
| 340 | 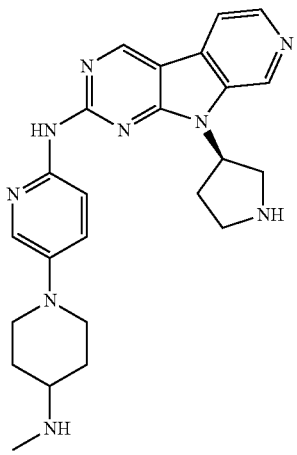 [SMILES: CNC1CCN(c2ccc(Nc3ncc4c5ccncc5n([C@@H]5CCNC5)c4n3)nc2)CC1] | 0.411 | 444.2 |
| 341 | 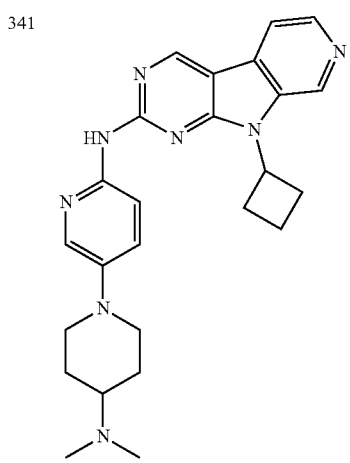 | 0.730 | 443.2 |
| 342 | 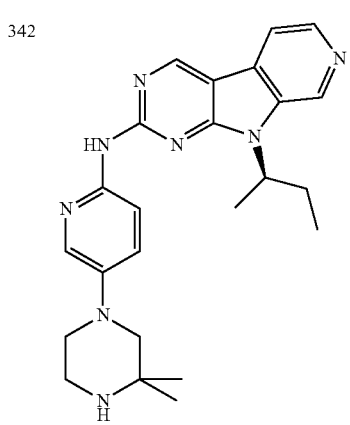 | 0.776 | 431.2 |
TABLE 7-continued
| Example # | Structure | LCMS retention time (min) | LCMS-ESI (M + 1) |
|---|---|---|---|
| 343 | 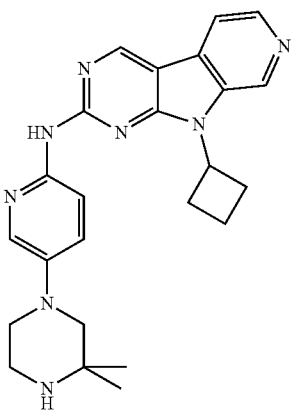 [SMILES: CC1(C)CN(c2ccc(Nc3ncc4c5ccncc5n(C5CCC5)c4n3)nc2)CCN1] | 0.728 | 429.2 |
| 344 | 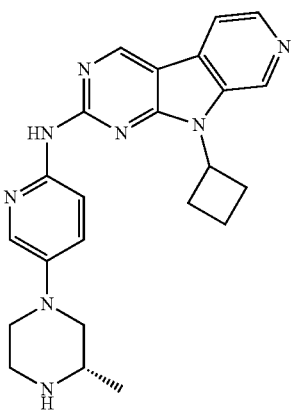 [SMILES: C[C@H]1CN(c2ccc(Nc3ncc4c5ccncc5n(C5CCC5)c4n3)nc2)CCN1] | 0.723 | 415.1 |
| 345 | 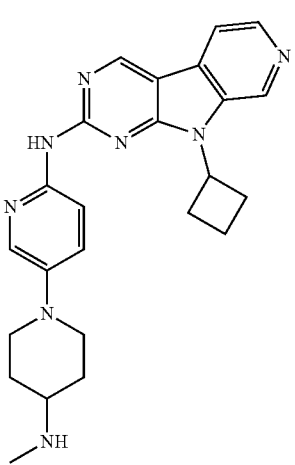 [SMILES: CNC1CCN(c2ccc(Nc3ncc4c5ccncc5n(C5CCC5)c4n3)nc2)CC1] | 0.719 | 429.2 |

TABLE 7-continued
| Example # | Structure | LCMS retention time (min) | LCMS-ESI (M + 1) |
|---|---|---|---|
| 346 | 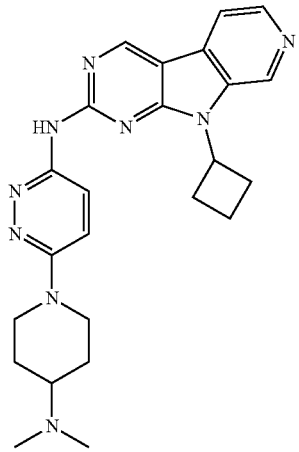 | 0.648 | 402.2 |
| 347 | 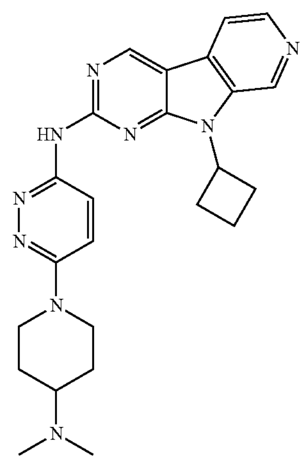 [SMILES: CN(C)C1CCN(c2ccc(Nc3ncc4c5ccncc5n(C5CCC5)c4n3)nn2)CC1] | 0.702 | 444.2 |
| 348 | 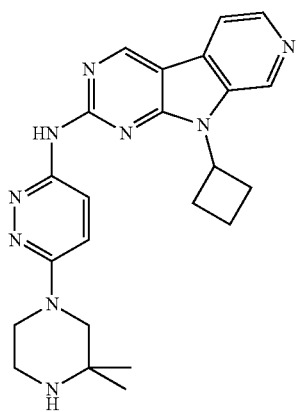 | 0.719 | 430.2 |
| 349 | 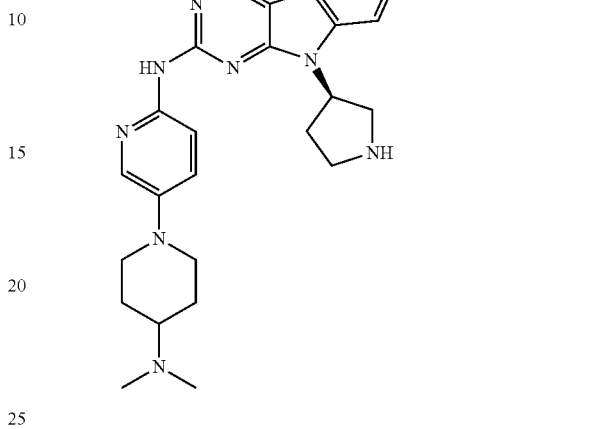 | 0.647 | 458.2 |
| 350 | 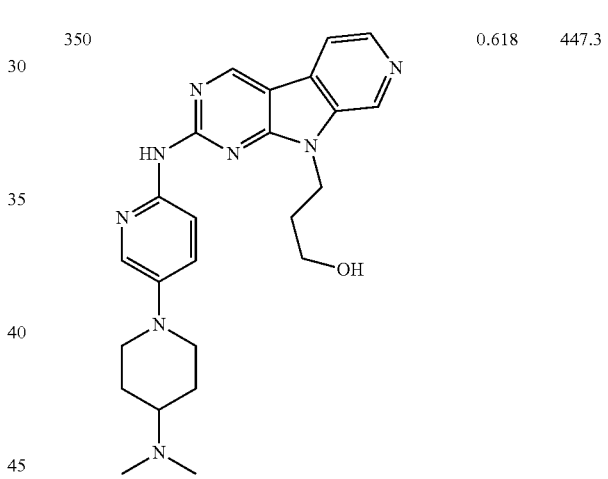 | 0.618 | 447.3 |
| 351 | 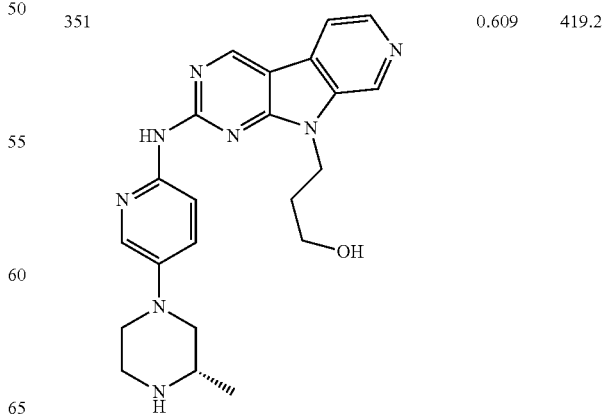 | 0.609 | 419.2 |

TABLE 7-continued

| Example # | Structure | LCMS retention time (min) | LCMS-ESI (M + 1) |
|---|---|---|---|
| 352 | 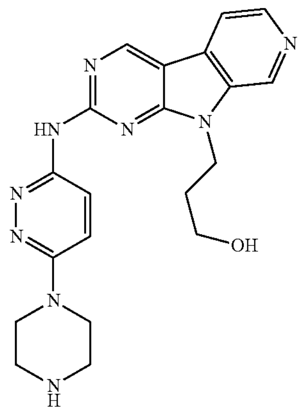 [SMILES: OCCCn1c2cnccc2c2cnc(Nc3ccc(N4CCNCC4)nn3)nc21] | 0.422 | 406.1 |
| 353 | 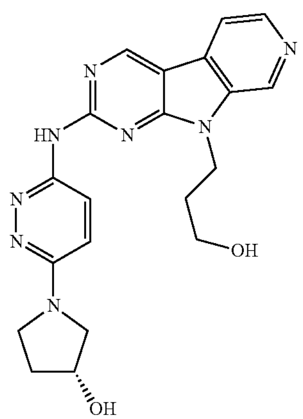 [SMILES: OCCCn1c2cnccc2c2cnc(Nc3ccc(N4CC[C@@H](O)C4)nn3)nc21] | 0.640 | 407.2 |
| 354 | 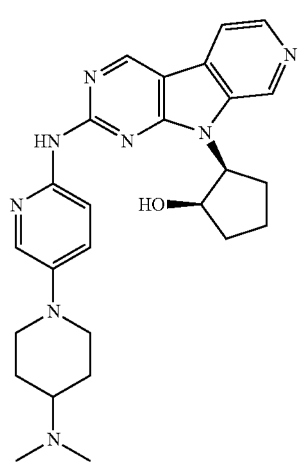 [SMILES: CN(C)C1CCN(c2ccc(Nc3ncc4c5ccncc5n([C@H]5CCC[C@H]5O)c4n3)nc2)CC1] | 0.693 | 473.2 |
| 355 | | 0.664 | 474.2 |
| 356 | | 0.565 | 405.2 |
| 357 | | 0.635 | 447.3 |

TABLE 7-continued
| Example # | Structure | LCMS retention time (min) | LCMS-ESI (M + 1) |
|---|---|---|---|
| 358 | 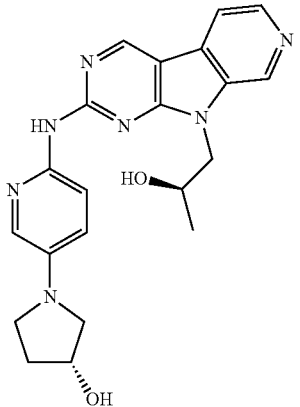 [SMILES: C[C@@H](O)Cn1c2cnccc2c2cnc(Nc3ccc(N4CC[C@@H](O)C4)cn3)nc21] | 0.735 | 406.1 |
| 359 | 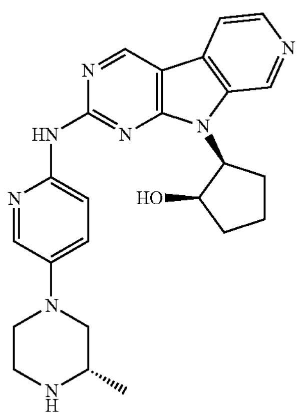 [SMILES: C[C@H]1CN(c2ccc(Nc3ncc4c5ccncc5n([C@H]5CCC[C@H]5O)c4n3)nc2)CCN1] | 0.687 | 445.3 |
| 360 | 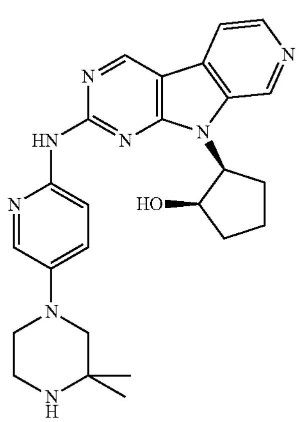 [SMILES: CC1(C)CN(c2ccc(Nc3ncc4c5ccncc5n([C@H]5CCC[C@H]5O)c4n3)nc2)CCN1] | 0.714 | 459.2 |
| 361 | | 0.669 | 431.2 |
| 362 | | 0.648 | 432.2 |
| 363 | | 0.66 | 446.2 |

TABLE 7-continued

| Example # | Structure | LCMS retention time (min) | LCMS-ESI (M + 1) |
|---|---|---|---|
| 364 | 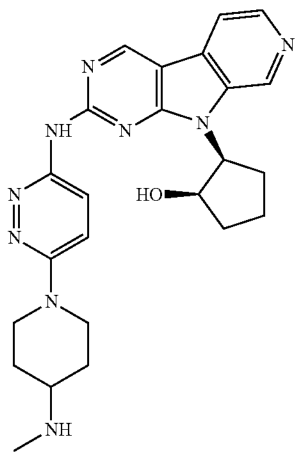 [SMILES: CNC1CCN(c2ccc(Nc3ncc4c5ccncc5n([C@H]5CCC[C@H]5O)c4n3)nn2)CC1] | 0.683 | 460.3 |
| 365 | 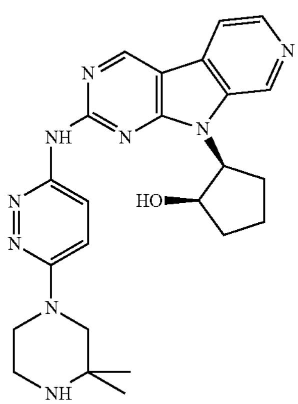 [SMILES: CC1(C)CN(c2ccc(Nc3ncc4c5ccncc5n([C@H]5CCC[C@H]5O)c4n3)nn2)CCN1] | 0.674 | 460.3 |
| 366 | 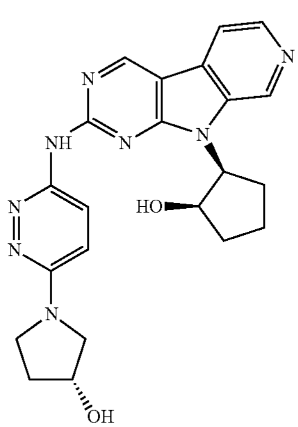 [SMILES: O[C@@H]1CCN(c2ccc(Nc3ncc4c5ccncc5n([C@H]5CCC[C@H]5O)c4n3)nn2)C1] | 0.705 | 433.1 |
| 367 | | 0.642 | 433.2 |
| 368 | | 0.757 | 406.1 |
| 369 | | 0.608 | 405.2 |

TABLE 7-continued
| Example # | Structure | LCMS retention time (min) | LCMS-ESI (M + 1) |
|---|---|---|---|
| 370 | 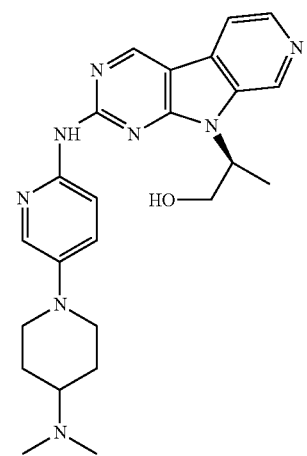 [SMILES: C[C@@H](CO)n1c2cnccc2c2cnc(Nc3ccc(N4CCC(N(C)C)CC4)cn3)nc21] | 0.655 | 447.2 |
| 371 | 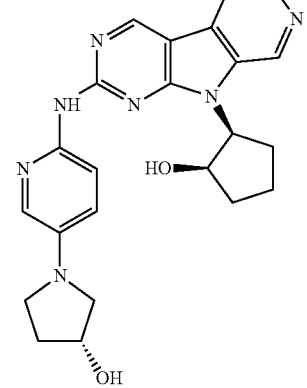 | 0.822 | 432.1 |
| 372 | 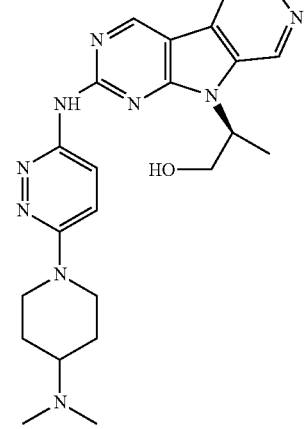 | 0.642 | 448.2 |
| 373 | 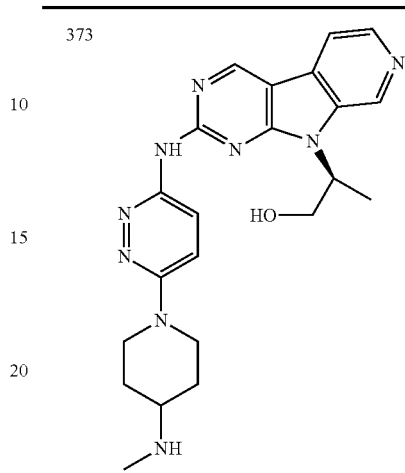 | 0.646 | 434.2 |
| 374 | 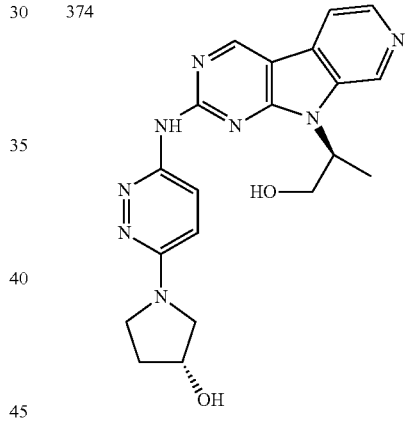 | 0.679 | 407.2 |
| 375 | 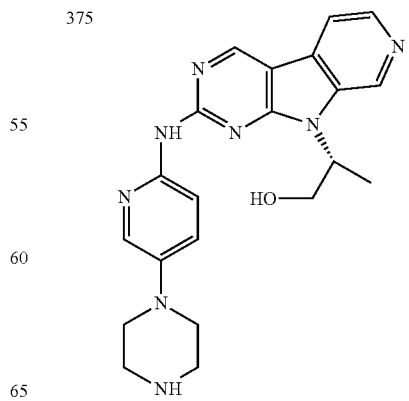 | 0.635 | 405.1 |

TABLE 7-continued
| Example # | Structure | LCMS retention time (min) | LCMS-ESI (M + 1) |
|---|---|---|---|
| 376 | 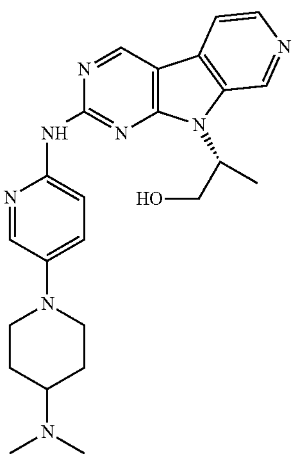 [SMILES: C[C@H](CO)n1c2cnccc2c2cnc(Nc3ccc(N4CCC(N(C)C)CC4)cn3)nc21] | 0.658 | 447.3 |
| 377 | 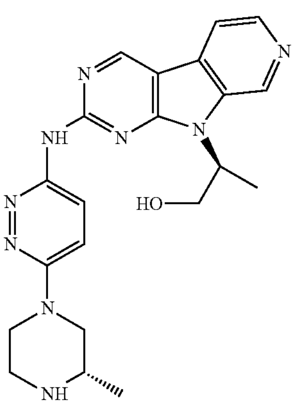 [SMILES: C[C@H]1CN(c2ccc(Nc3ncc4c5ccncc5n([C@@H](C)CO)c4n3)nn2)CCN1] | 0.628 | 420.2 |
| 378 | 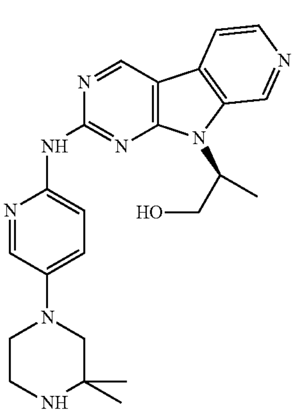 | 0.677 | 433.1 |
| 379 | 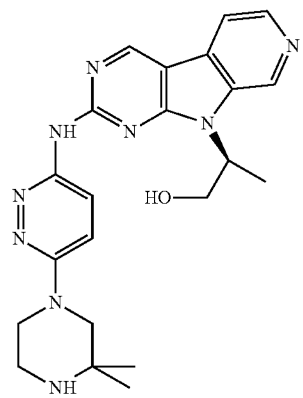 [SMILES: C[C@@H](CO)n1c2cnccc2c2cnc(Nc3ccc(N4CCNC(C)(C)C4)nn3)nc21] | 0.659 | 434.2 |
| 380 | 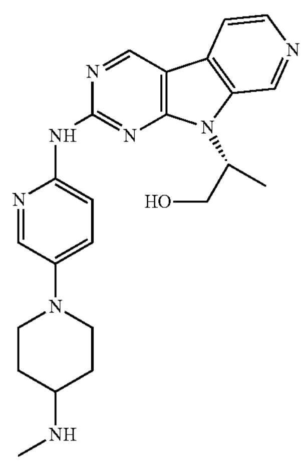 [SMILES: CNC1CCN(c2ccc(Nc3ncc4c5ccncc5n([C@H](C)CO)c4n3)nc2)CC1] | 0.664 | 433.1 |
| 381 | 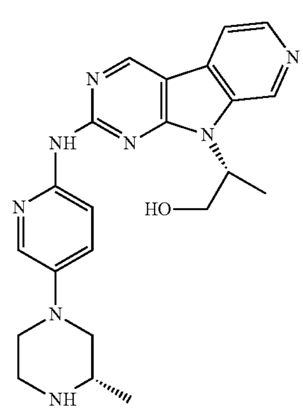 [SMILES: C[C@H](CO)n1c2cnccc2c2cnc(Nc3ccc(N4CCN[C@@H](C)C4)cn3)nc21] | 0.645 | 419.2 |
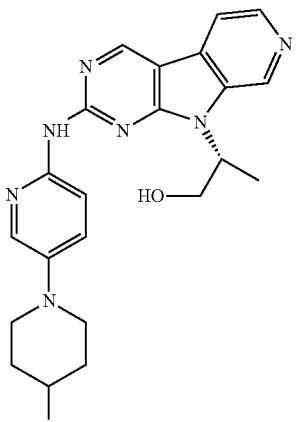

TABLE 7-continued
| Example # | Structure | LCMS retention time (min) | LCMS-ESI (M + 1) |
|---|---|---|---|
| 382 | 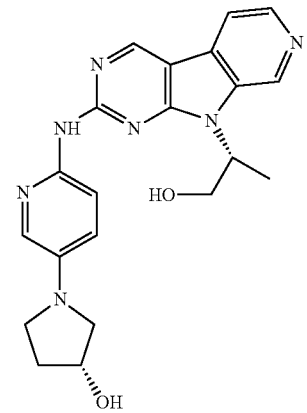 [SMILES: C[C@H](CO)n1c2cnccc2c2cnc(Nc3ccc(N4CC[C@@H](O)C4)cn3)nc21] | 0.788 | 406.1 |
| 383 | 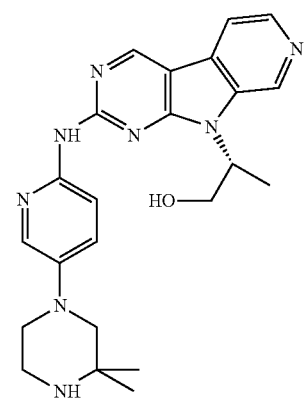 [SMILES: C[C@H](CO)n1c2cnccc2c2cnc(Nc3ccc(N4CCNC(C)(C)C4)cn3)nc21] | 0.702 | 433.1 |
| 384 | 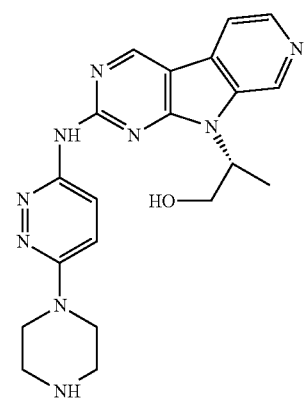 [SMILES: C[C@H](CO)n1c2cnccc2c2cnc(Nc3ccc(N4CCNCC4)nn3)nc21] | 0.648 | 406.1 |
TABLE 7-continued
| Example # | Structure | LCMS retention time (min) | LCMS-ESI (M + 1) |
|---|---|---|---|
| 385 | 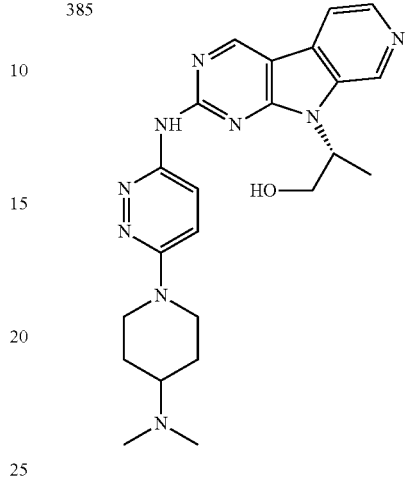 | 0.671 | 448.1 |
| 386 | 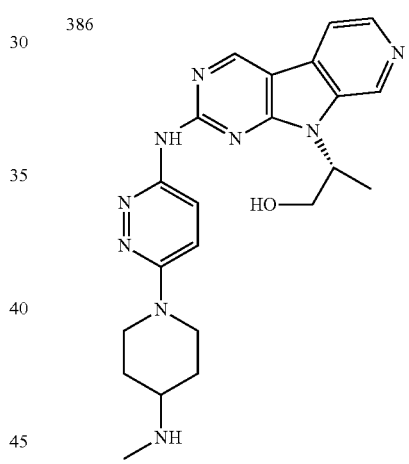 | 0.643 | 434.2 |
| 387 | 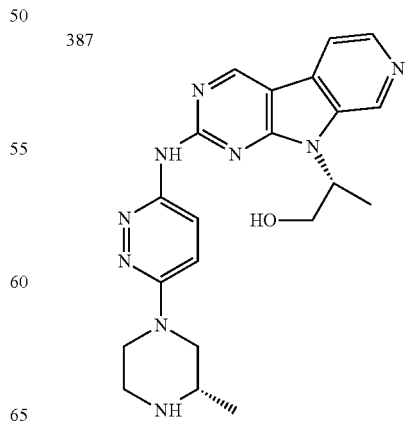 | 0.635 | 420.1 |

TABLE 7-continued
| Example # | Structure | LCMS retention time (min) | LCMS-ESI (M + 1) |
|---|---|---|---|
| 388 | 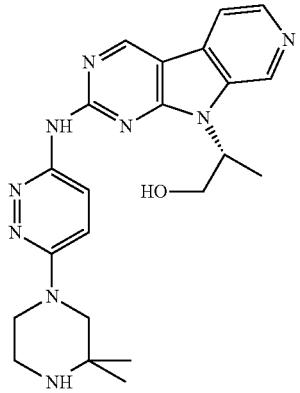 [SMILES: C[C@H](CO)n1c2cnccc2c2cnc(Nc3ccc(N4CCNC(C)(C)C4)nn3)nc21] | 0.646 | 434.2 |
| 389 | 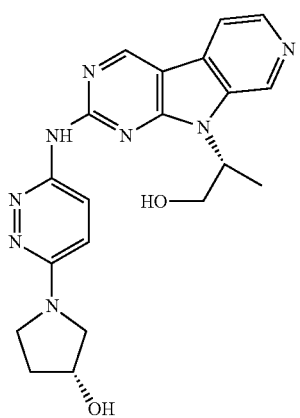 [SMILES: C[C@H](CO)n1c2cnccc2c2cnc(Nc3ccc(N4CC[C@@H](O)C4)nn3)nc21] | 0.674 | 407.2 |
| 390 | 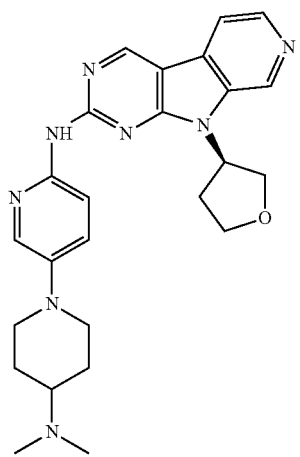 [SMILES: CN(C)C1CCN(c2ccc(Nc3ncc4c5ccncc5n([C@@H]5CCOC5)c4n3)nc2)CC1] | 0.701 | 470.2 |
| 391 | 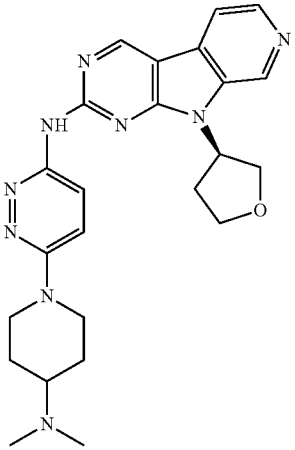 [SMILES: CN(C)C1CCN(c2ccc(Nc3ncc4c5ccncc5n([C@@H]5CCOC5)c4n3)nn2)CC1] | 0.675 | 460.1 |
| 392 | 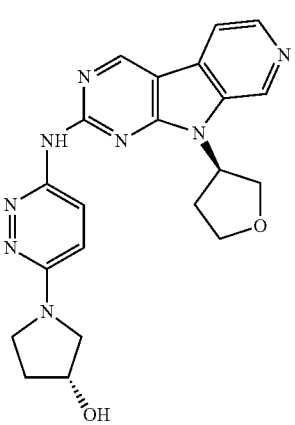 [SMILES: O[C@@H]1CCN(c2ccc(Nc3ncc4c5ccncc5n([C@@H]5CCOC5)c4n3)nn2)C1] | 0.696 | 419.2 |
| 393 | 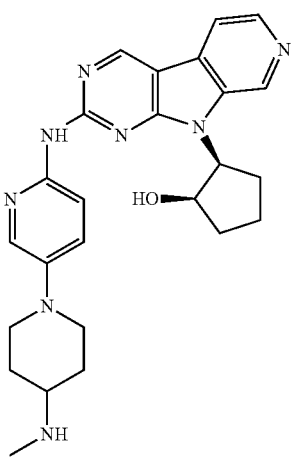 | 0.709 | 459.2 |

TABLE 7-continued

| Example # | Structure | LCMS retention time (min) | LCMS-ESI (M + 1) |
|---|---|---|---|
| 394 | 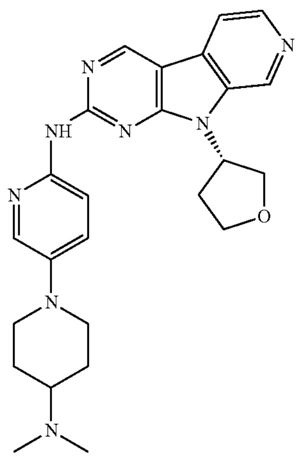 [SMILES: CN(C)C1CCN(c2ccc(Nc3ncc4c5ccncc5n([C@H]5CCOC5)c4n3)nc2)CC1] | 0.69 | 459.2 |
| 395 | 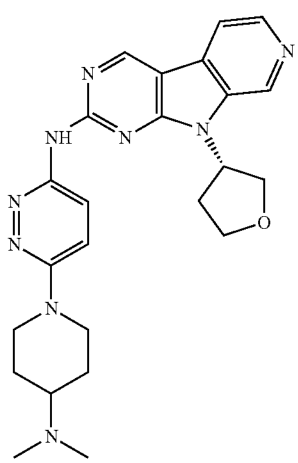 [SMILES: CN(C)C1CCN(c2ccc(Nc3ncc4c5ccncc5n([C@H]5CCOC5)c4n3)nn2)CC1] | 0.681 | 460.1 |
| 396 | 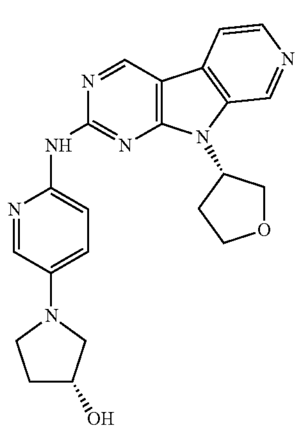 [SMILES: O[C@@H]1CCN(c2ccc(Nc3ncc4c5ccncc5n([C@H]5CCOC5)c4n3)nc2)C1] | 0.766 | 418.1 |
| 397 | | 0.694 | 419.2 |
| 398 | | 0.693 | 431.2 |
| 399 | | 0.722 | 473.2 |

TABLE 7-continued
| Example # | Structure | LCMS retention time (min) | LCMS-ESI (M + 1) |
|---|---|---|---|
| 400 | 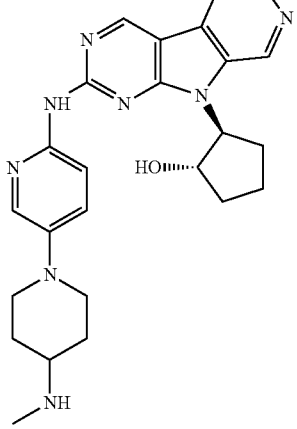 | 0.708 | 459.2 |
| 401 | 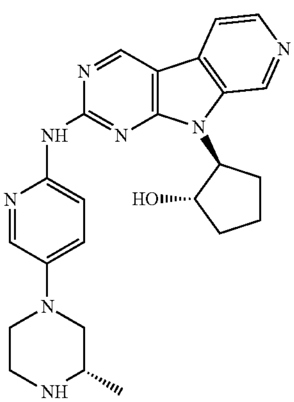 [SMILES: C[C@H]1CN(c2ccc(Nc3ncc4c5ccncc5n([C@H]5CCC[C@@H]5O)c4n3)nc2)CCN1] | 0.705 | 445.1 |
| 402 | 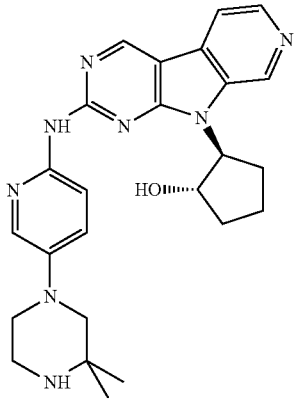 [SMILES: CC1(C)CN(c2ccc(Nc3ncc4c5ccncc5n([C@H]5CCC[C@@H]5O)c4n3)nc2)CCN1] | 0.737 | 459.2 |
TABLE 7-continued
| Example # | Structure | LCMS retention time (min) | LCMS-ESI (M + 1) |
|---|---|---|---|
| 403 | 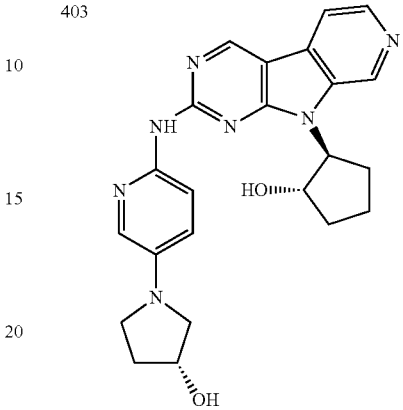 | 0.838 | 432.1 |
| 404 | 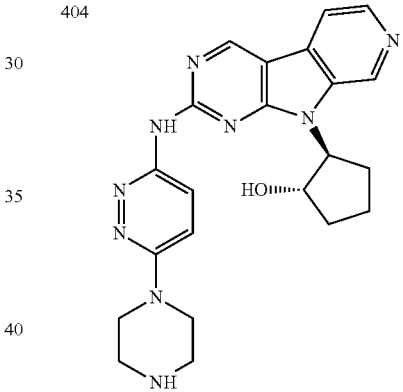 | 0.653 | 432.2 |
| 405 | 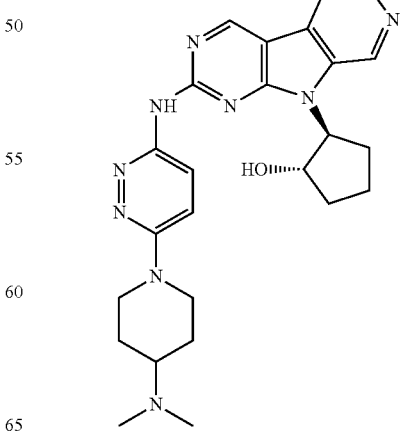 | 0.684 | 474.2 |

TABLE 7-continued
| Example # | Structure | LCMS retention time (min) | LCMS-ESI (M + 1) |
|---|---|---|---|
| 406 | 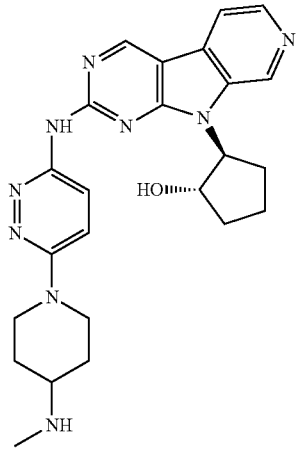 [SMILES: CNC1CCN(c2ccc(Nc3ncc4c5ccncc5n([C@H]5CCC[C@@H]5O)c4n3)nn2)CC1] | 0.672 | 460.1 |
| 407 | 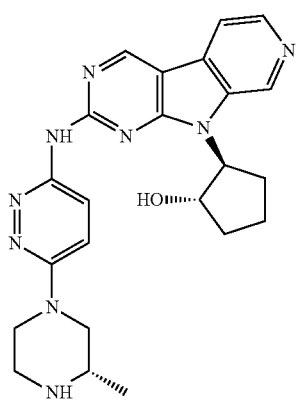 | 0.671 | 446.2 |
| 408 | 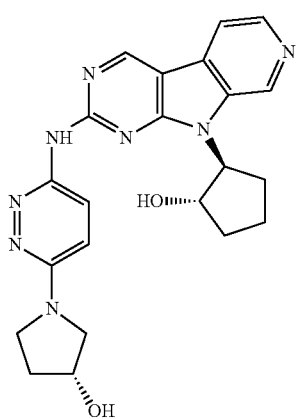 [SMILES: O[C@@H]1CCN(c2ccc(Nc3ncc4c5ccncc5n([C@H]5CCC[C@@H]5O)c4n3)nn2)C1] | 0.715 | 433.1 |
TABLE 7-continued
| Example # | Structure | LCMS retention time (min) | LCMS-ESI (M + 1) |
|---|---|---|---|
| 409 | 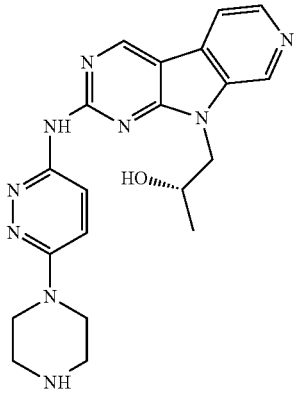 [SMILES: C[C@H](O)Cn1c2cnccc2c2cnc(Nc3ccc(N4CCNCC4)nn3)nc21] | 0.596 | 406.1 |
| 410 | 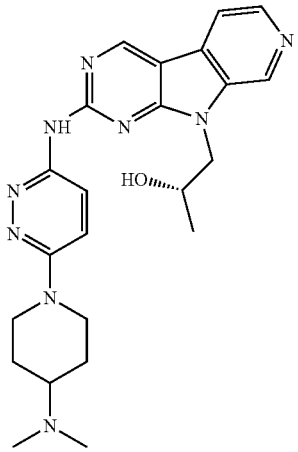 [SMILES: C[C@H](O)Cn1c2cnccc2c2cnc(Nc3ccc(N4CCC(N(C)C)CC4)nn3)nc21] | 0.62 | 448.1 |
| 411 | 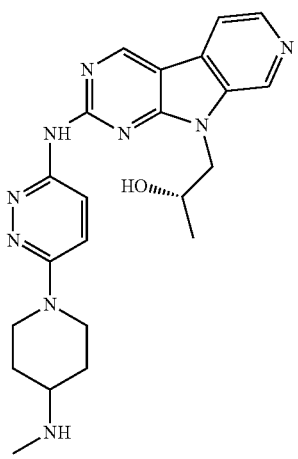 [SMILES: CNC1CCN(c2ccc(Nc3ncc4c5ccncc5n(C[C@H](C)O)c4n3)nn2)CC1] | 0.627 | 434.2 |

TABLE 7-continued

| Example # | Structure | LCMS retention time (min) | LCMS-ESI (M + 1) |
|---|---|---|---|
| 412 | 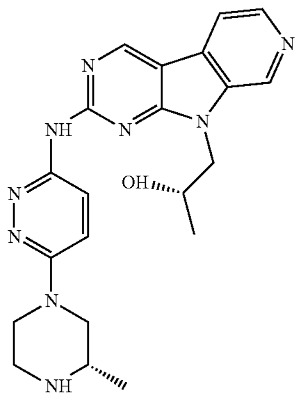 [SMILES: C[C@H](O)Cn1c2cnccc2c2cnc(Nc3ccc(N4CCN[C@@H](C)C4)nn3)nc21] | 0.622 | 420.2 |
| 413 | 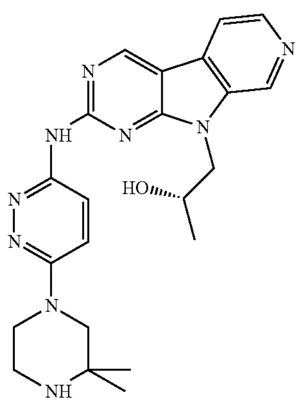 [SMILES: C[C@H](O)Cn1c2cnccc2c2cnc(Nc3ccc(N4CCNC(C)(C)C4)nn3)nc21] | 0.633 | 434.2 |
| 414 | 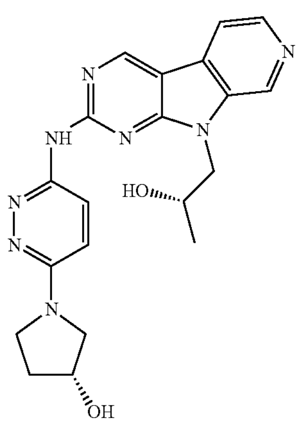 [SMILES: C[C@H](O)Cn1c2cnccc2c2cnc(Nc3ccc(N4CC[C@@H](O)C4)nn3)nc21] | 0.66 | 407.2 |
| 415 | 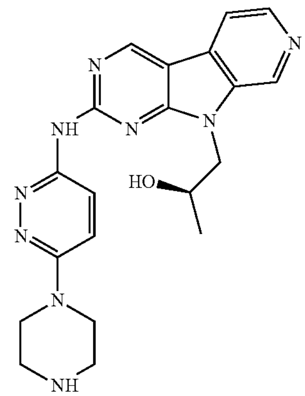 [SMILES: C[C@@H](O)Cn1c2cnccc2c2cnc(Nc3ccc(N4CCNCC4)nn3)nc21] | 0.606 | 406.1 |
| 416 | 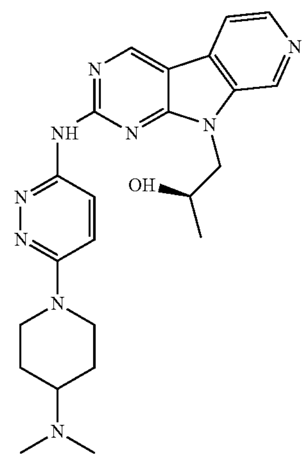 [SMILES: C[C@@H](O)Cn1c2cnccc2c2cnc(Nc3ccc(N4CCC(N(C)C)CC4)nn3)nc21] | 0.634 | 448.3 |
| 417 | 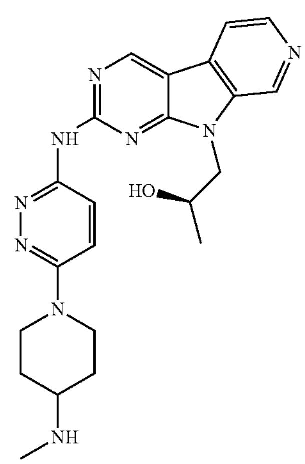 [SMILES: CNC1CCN(c2ccc(Nc3ncc4c5ccncc5n(C[C@@H](C)O)c4n3)nn2)CC1] | 0.669 | 434.2 |

TABLE 7-continued
| Example # | Structure | LCMS retention time (min) | LCMS-ESI (M + 1) |
|---|---|---|---|
| 418 | 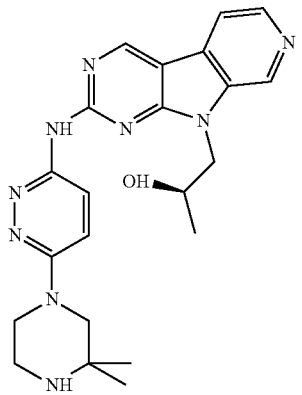 [SMILES: C[C@@H](O)Cn1c2cnccc2c2cnc(Nc3ccc(N4CCNC(C)(C)C4)nn3)nc21] | 0.679 | 434.2 |
| 419 | 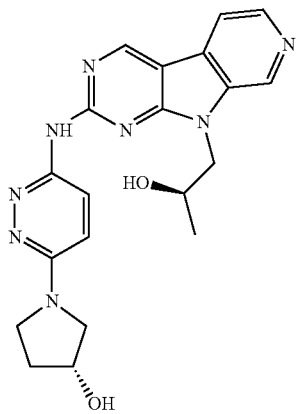 [SMILES: C[C@@H](O)Cn1c2cnccc2c2cnc(Nc3ccc(N4CC[C@@H](O)C4)nn3)nc21] | 0.652 | 407.2 |
| 420 | 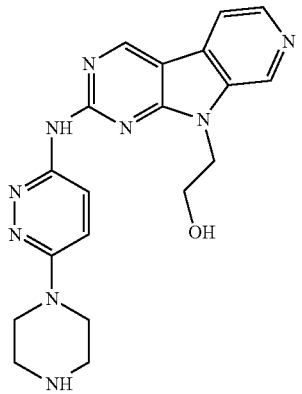 [SMILES: OCCn1c2cnccc2c2cnc(Nc3ccc(N4CCNCC4)nn3)nc21] | 0.587 | 391.1 |
TABLE 7-continued
| Example # | Structure | LCMS retention time (min) | LCMS-ESI (M + 1) |
|---|---|---|---|
| 421 | 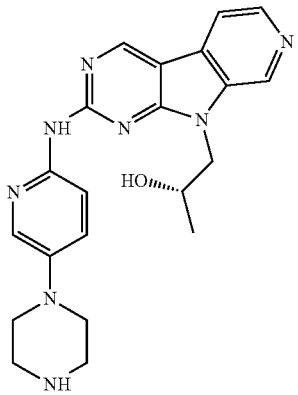 | 0.708 | 405.2 |
| 422 | 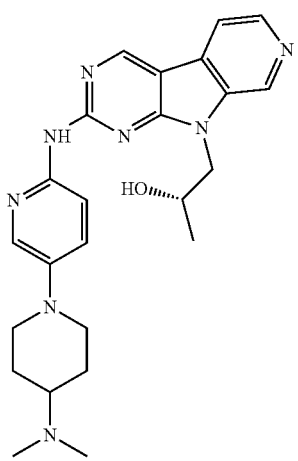 | 0.759 | 447.3 |
| 423 | 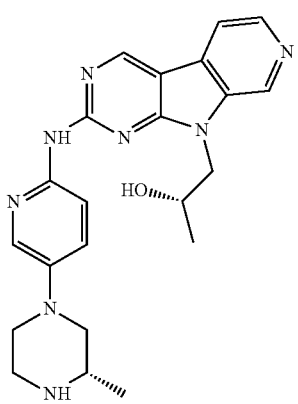 [SMILES: C[C@H](O)Cn1c2cnccc2c2cnc(Nc3ccc(N4CCN[C@@H](C)C4)cn3)nc21] | 0.603 | 419.2 |

TABLE 7-continued

| Example # | Structure | LCMS retention time (min) | LCMS-ESI (M + 1) |
|---|---|---|---|
| 424 | 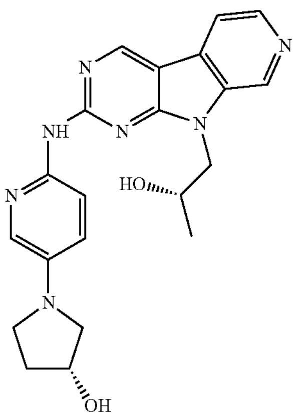 [SMILES: C[C@H](O)Cn1c2cnccc2c2cnc(Nc3ccc(N4CC[C@@H](O)C4)cn3)nc21] | 0.712 | 406.1 |
| 425 | 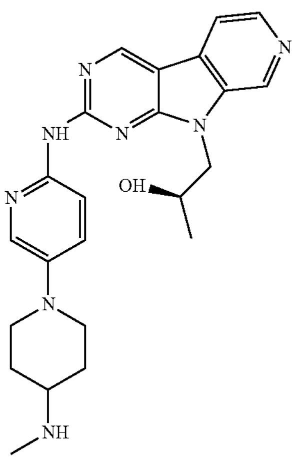 [SMILES: CNC1CCN(c2ccc(Nc3ncc4c5ccncc5n(C[C@@H](C)O)c4n3)nc2)CC1] | 0.685 | 433.2 |
| 426 | 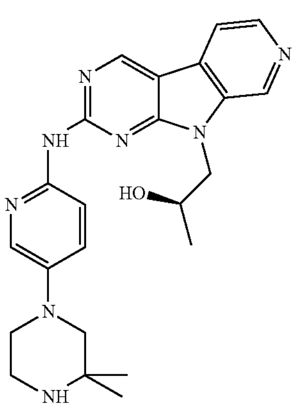 [SMILES: C[C@@H](O)Cn1c2cnccc2c2cnc(Nc3ccc(N4CCNC(C)(C)C4)cn3)nc21] | 0.672 | 433.2 |
| 427 | 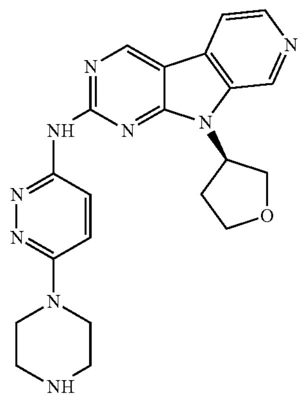 [SMILES: c1cc2c3cnc(Nc4ccc(N5CCNCC5)nn4)nc3n([C@@H]3CCOC3)c2cn1] | 0.595 | 418.1 |
| 428 | 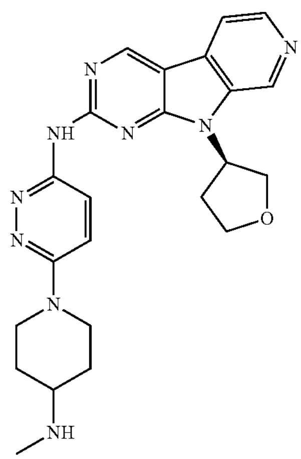 [SMILES: CNC1CCN(c2ccc(Nc3ncc4c5ccncc5n([C@@H]5CCOC5)c4n3)nn2)CC1] | 0.635 | 446.2 |
| 429 | 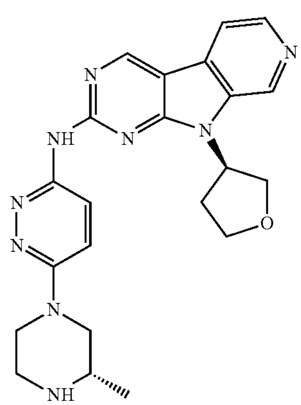 [SMILES: C[C@H]1CN(c2ccc(Nc3ncc4c5ccncc5n([C@@H]5CCOC5)c4n3)nn2)CCN1] | 0.618 | 432.2 |

TABLE 7-continued
| Example # | Structure | LCMS retention time (min) | LCMS-ESI (M + 1) |
|---|---|---|---|
| 430 | 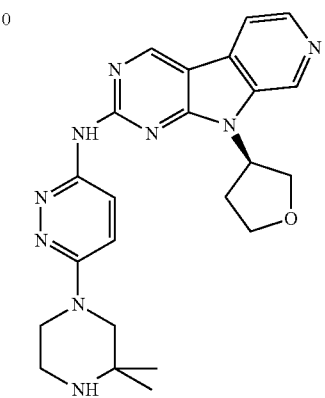 | 0.638 | 446.2 |
| 431 | 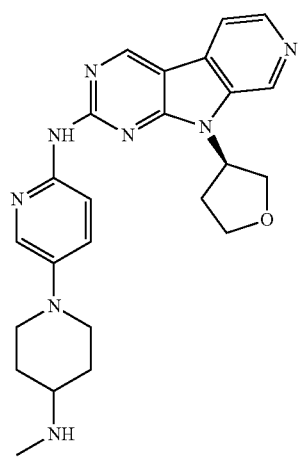 | 0.658 | 445.3 |
| 432 | 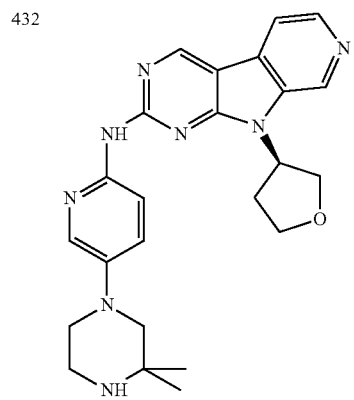 | 0.674 | 445.3 |
| 433 | 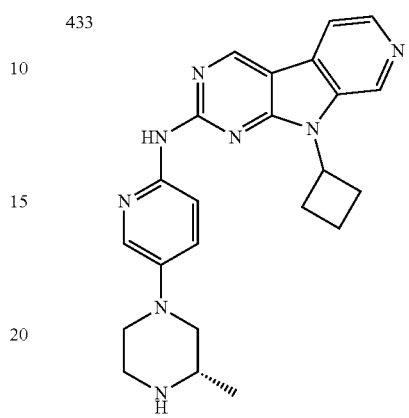 | 0.671 | 416.2 |
| 434 | 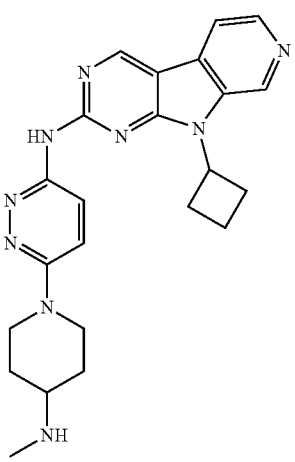 [SMILES: CNC1CCN(c2ccc(Nc3ncc4c5ccncc5n(C5CCC5)c4n3)nn2)CC1] | 0.680 | 430.1 |
| 435 | 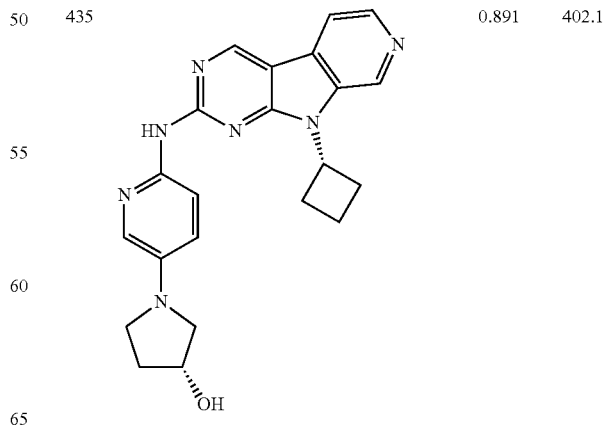 | 0.891 | 402.1 |

Example 436

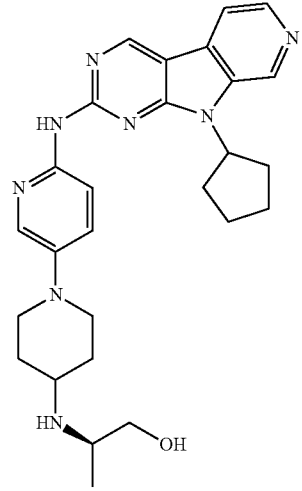

(2R)-2-((1-(6-((9-cyclopentyl-9H-pyrido[4',3':4,5]pyrrolo[2,3-d]pyrimidin-2-yl)amino)-3-pyridinyl)-4-piperidinyl)amino)-1-propanol

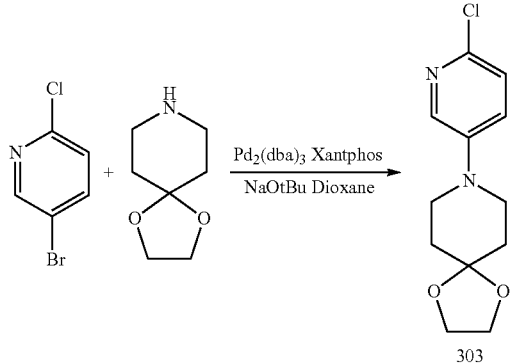

8-(6-chloro-3-pyridinyl)-1,4-dioxa-8-azaspiro[4.5]decane: A mixture of 5-bromo-2-chloropyridine (3.84 g, 20.0 mmol), 1,4-dioxa-8-azaspiro[4.5]decane (3.14 g, 21.9 mmol), Xantphos (1.73 g, 2.99 mmol), Pd₂(dba)₃ (1.37 g, 1.5 mmol), and sodium tert-butoxide (2.88 g, 29.9 mmol) in dioxane was purged with nitrogen gas for 10 minutes and then heated at 80° C. for 2 hours. After cooling to room temperature, the mixture was filtered through a celite pad and concentrated on a rotary evaporator. The crude product was purified via flash chromatography on silica gel eluting with a gradient of 0-40% ethyl acetate in hexane to give compound 303 (2.8 g, 55%). $^1$H NMR (500 MHz, CDCl₃) δ 8.07 (1H, d, J=3.1 Hz), 7.24 (1H, dd, J=3.1 Hz, J=8.8 Hz), 7.18 (1H, d, J=8.8 Hz), 4.02 (4H, s), 3.36 (4H, m), 1.87 (4H, m) ppm; LCMS-ESI (POS), M/Z, M+1: Found 255.1, Calculated 255.1.

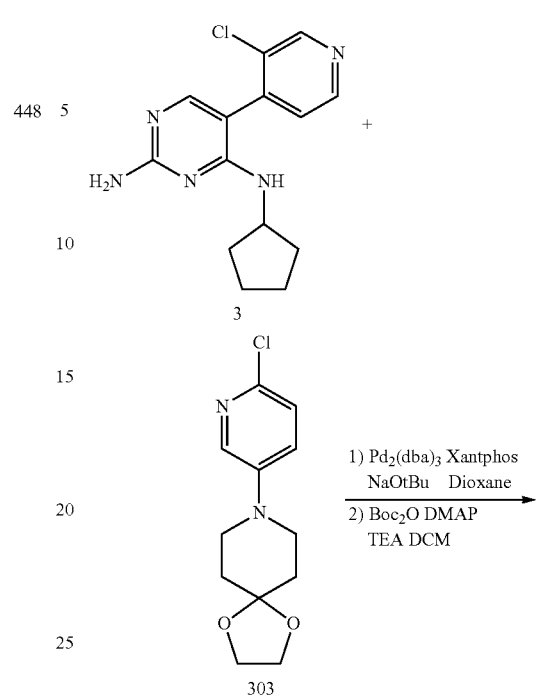

tert-Butyl (9-cyclopentyl-9H-pyrido[4',3':4,5]pyrrolo[2,3-d]pyrimidin-2-yl)(5-(1,4-dioxa-8-azaspiro[4.5]dec-8-yl)-2-pyridinyl)carbamate (450): A mixture of compound 3 (3.18 g, 11.0 mmol), compound 303 (2.80 g, 11.0 mmol), Xantphos (1.27 g, 2.19 mmol), Pd₂(dba)₃ (1.00 g, 1.1 mmol), and sodium tert-butoxide (1.58 g, 16.5 mmol) in dioxane was purged with nitrogen gas for 10 minutes and then heated at 125° C. for 2 hours. After cooling to room temperature, the mixture was diluted with 100 mL of DCM and partitioned over 200 mL of brine. The aqueous layer was extracted with two 100 mL portions of DCM and the combined DCM phases were dried over sodium sulfate. After concentration on a rotary evaporator, the crude product was treated with di-tert-butyl dicarbonate (2.4 g, 11.0 mmol), triethylamine (1.65 g, 0.17 mmol) and DMAP (0.25 g, 2.2 mmol) in DCM and stirred overnight at rt. The mixture was then washed with 3 portions of brine, dried over sodium sulfate and concentrated. The crude product was purified via flash chromatography on silica gel eluting with a gradient of 0-5% methanol in DCM in the presence of 0.5% NH₄OH to give compound 450 (2.8 g, 46%). LCMS-ESI (POS), M/Z, M+1: Found 572.2, Calculated 572.3.

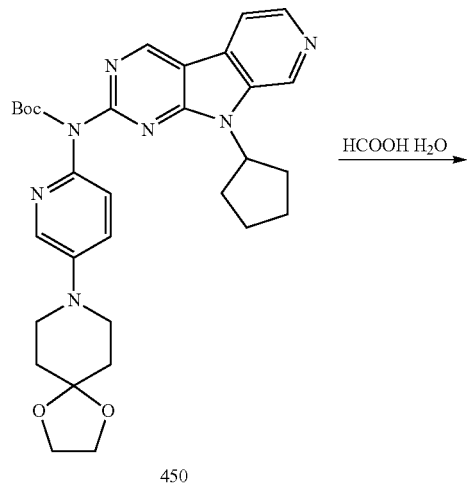

450

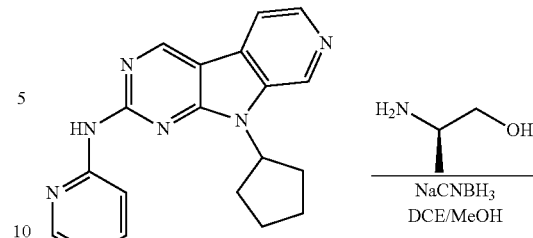

451

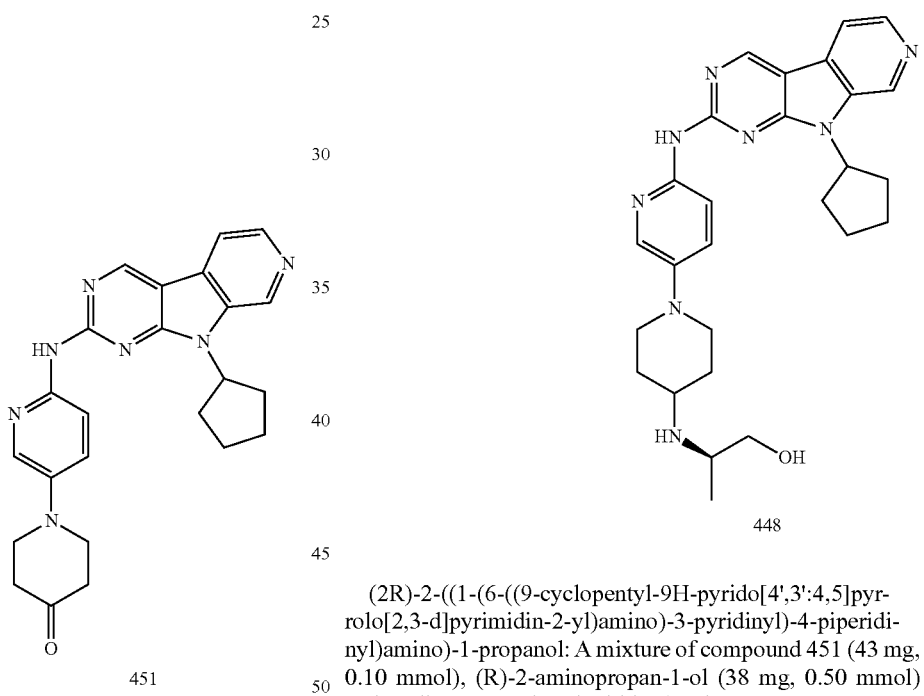

448

451

1-(6-((9-cyclopentyl-9H-pyrido[4',3':4,5]pyrrolo[2,3-d]pyrimidin-2-yl)amino)-3-pyridinyl)-4-piperidinone (451): A mixture of compound 450 (2.85 g, 5.0 mmol) and 50 mL of 50% aqueous formic acid was heated to 100° C. for 1 h. After cooling to room temperature, the reaction mixture was titrated to pH 12 with concentrated aqueous NaOH, while cooling through the addition of ice. The precipitated product was filtered, washed with water followed by a minimal volume of methanol and dried under vacuum to give compound 451 (2.1 g, 99%). ¹H NMR (400 MHz, CDCl₃) δ 9.05 (1H, s), 8.84 (1H, s), 8.44 (1H, d, J=5.9 Hz), 8.38 (1H, d, J=9 Hz), 8.09 (1H, d, J=2.7 Hz), 7.81 (1H, d, J=5.9 Hz), 7.38 (1H, dd, J=9.0 Hz, J=2.7 Hz), 5.31 (1H, m), 3.52 (4H, m), 3.42 (1H, s), 2.56 (4H, m), 2.37 (2H, m), 2.10 (4H, m), 1.82 (2H, m) ppm; LCMS-ESI (POS), M/Z, M+1: Found 428.2, Calculated 428.2.

(2R)-2-((1-(6-((9-cyclopentyl-9H-pyrido[4',3':4,5]pyrrolo[2,3-d]pyrimidin-2-yl)amino)-3-pyridinyl)-4-piperidinyl)amino)-1-propanol: A mixture of compound 451 (43 mg, 0.10 mmol), (R)-2-aminopropan-1-ol (38 mg, 0.50 mmol) and sodium cyanoborohydride (1M/THF: 0.26 mL, 0.26 mmol) in 3 mL of methanol/dichloroethane 2:1 was heated at 80° C. for 2 h. After concentration, the crude mixture was diluted with 2 mL of methanol/DMSO (1:1) and purified via reverse phase HPLC to give compound 448 (28 mg, 39%) ¹H NMR (400 MHz, CD₃OD) δ 9.71 (1H, s), 9.37 (1H, s) 8.74 (1H, d, J=6.5 Hz), 8.69 (1H, d, J=6.5 Hz), 8.20 (1H, dd, J=9.6 Hz, J=2.9 Hz), 8.02 (1H, d, J=2.9 Hz), 7.68 (1H, d, J=9.6 Hz), 5.48 (1H, m), 3.94 (2H, d, J=12.5), 3.87 (1H, dd, J=11.7 Hz, J=3.5 Hz), 3.64 (1H, dd, J=11.7 Hz, J=5.5 Hz), 3.55 (2H, m), 3.00 (2H, t, J=12.5 Hz), 2.53 (2H, m), 2.24 (7H, m), 1.88 (4H, m), 1.38 (3H, d, J=6.7 Hz) ppm; LCMS-ESI (POS), M/Z, M+1: Found 487.3, Calculated 487.3.

Examples 437-481 (table 8) were prepared using conditions as described for example 436 using the appropriate primary or secondary amine followed by deprotection when necessary.

TABLE 8

| Example # | Structure | LCMS retention time (min) | LCMS-ESI (M + 1) |
|---|---|---|---|
| 437 | 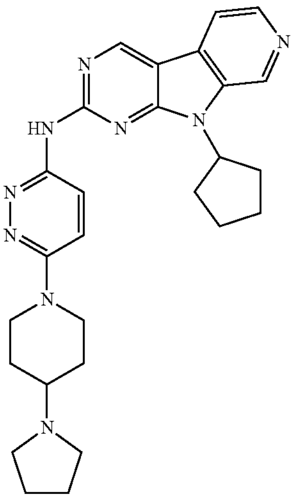 [SMILES: c1cc2c3cnc(Nc4ccc(N5CCC(N6CCCC6)CC5)nn4)nc3n(C3CCCC3)c2cn1] | 0.73 | 484.3 |
| 438 | 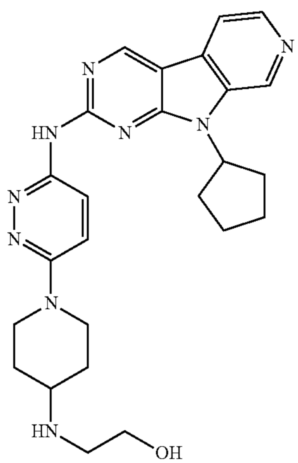 [SMILES: OCCNC1CCN(c2ccc(Nc3ncc4c5ccncc5n(C5CCCC5)c4n3)nn2)CC1] | 0.702 | 474.2 |
| 439 | 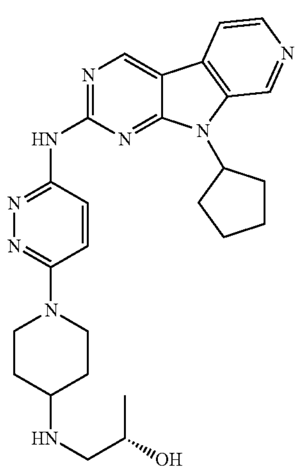 | 0.726 | 488.2 |

TABLE 8-continued

| Example # | Structure | LCMS retention time (min) | LCMS-ESI (M + 1) |
|---|---|---|---|
| 440 | 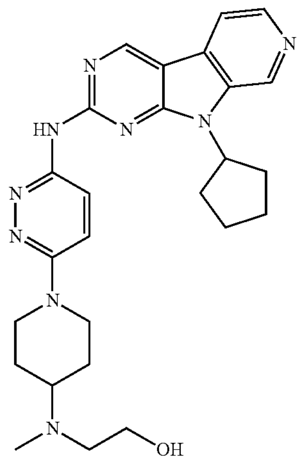 | 0.707 | 488.2 |
| 441 | 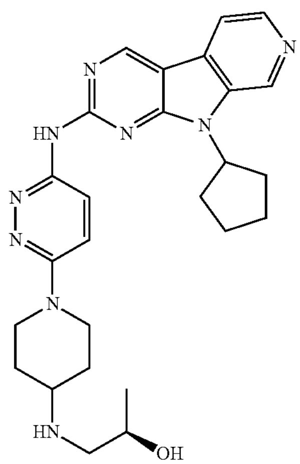 | 0.716 | 488.2 |
| 442 | 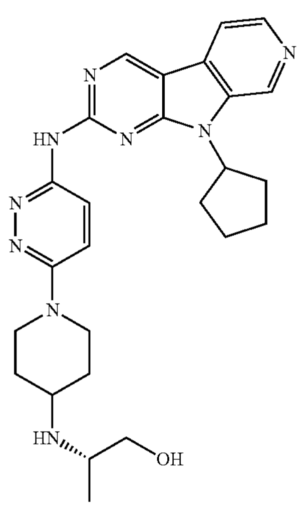 [SMILES: C[C@@H](CO)NC1CCN(c2ccc(Nc3ncc4c5ccncc5n(C5CCCC5)c4n3)nn2)CC1] | 0.723 | 488.2 |

TABLE 8-continued

| Example # | Structure | LCMS retention time (min) | LCMS-ESI (M + 1) |
|---|---|---|---|
| 443 | 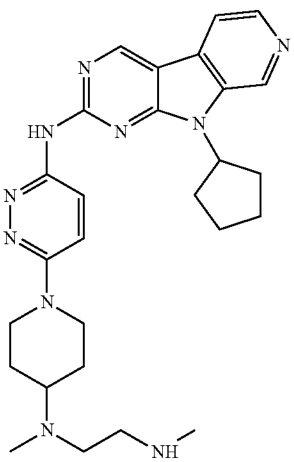 [SMILES: CNCCN(C)C1CCN(c2ccc(Nc3ncc4c5ccncc5n(C5CCCC5)c4n3)nn2)CC1] | 0.664 | 501.2 |
| 444 | 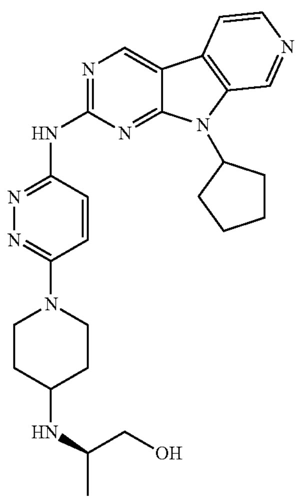 [SMILES: C[C@H](CO)NC1CCN(c2ccc(Nc3ncc4c5ccncc5n(C5CCCC5)c4n3)nn2)CC1] | 0.717 | 488.2 |
| 445 | 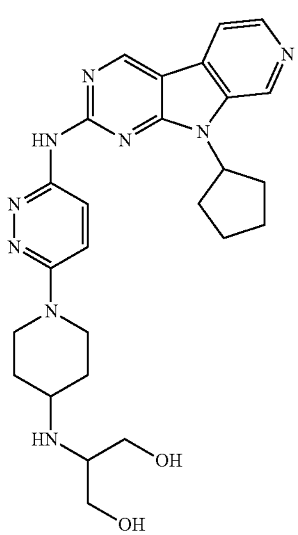 [SMILES: OCC(CO)NC1CCN(c2ccc(Nc3ncc4c5ccncc5n(C5CCCC5)c4n3)nn2)CC1] | 0.784 | 504.2 |
| 446 | | 0.789 | 504.2 |
| 447 | | 0.809 | 500.2 |
| 448 | | 0.78 | 486.2 |

TABLE 8-continued

| Example # | Structure | LCMS retention time (min) | LCMS-ESI (M + 1) |
|---|---|---|---|
| 449 | 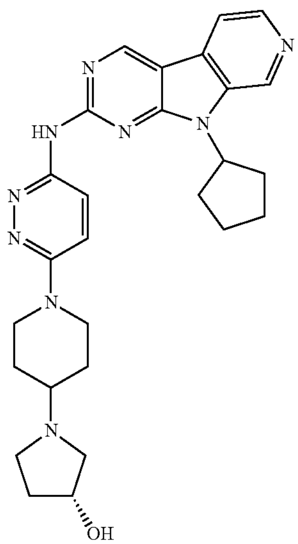 [SMILES: O[C@@H]1CCN(C2CCN(c3ccc(Nc4ncc5c6ccncc6n(C6CCCC6)c5n4)nn3)CC2)C1] | 0.786 | 500.2 |
| 450 | 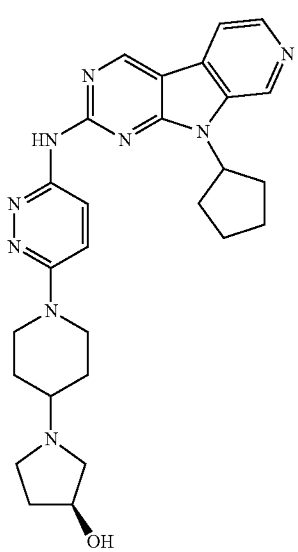 | 0.765 | 500.2 |
| 451 | 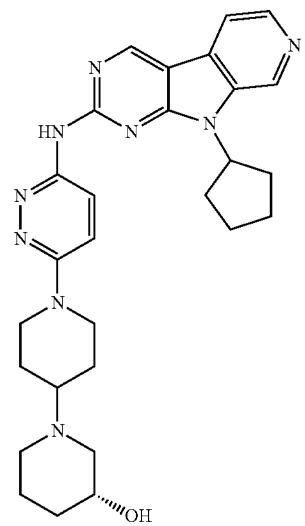 [SMILES: O[C@@H]1CCCN(C2CCN(c3ccc(Nc4ncc5c6ccncc6n(C6CCCC6)c5n4)nn3)CC2)C1] | 0.794 | 514.3 |
| 452 | 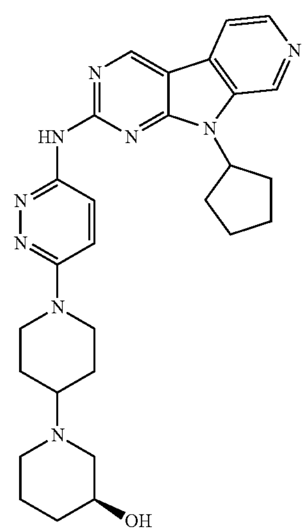 [SMILES: O[C@H]1CCCN(C2CCN(c3ccc(Nc4ncc5c6ccncc6n(C6CCCC6)c5n4)nn3)CC2)C1] | 0.809 | 514.3 |
| 453 | 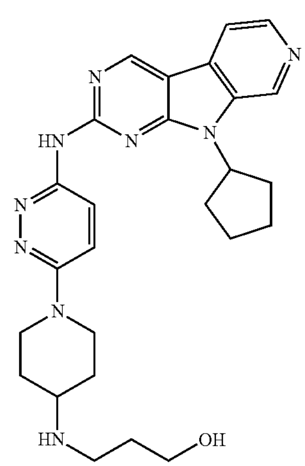 [SMILES: OCCCNC1CCN(c2ccc(Nc3ncc4c5ccncc5n(C5CCCC5)c4n3)nn2)CC1] | 0.794 | 488.2 |

TABLE 8-continued

| Example # | Structure | LCMS retention time (min) | LCMS-ESI (M + 1) |
|---|---|---|---|
| 454 | 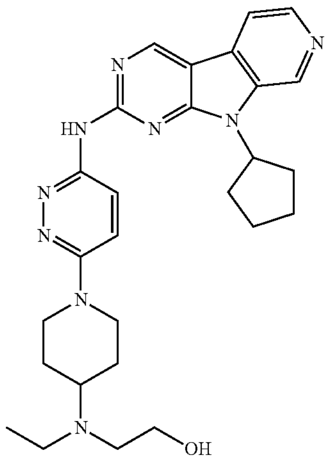 [SMILES: CCN(CCO)C1CCN(c2ccc(Nc3ncc4c5ccncc5n(C5CCCC5)c4n3)nn2)CC1] | 0.808 | 502.3 |
| 455 | 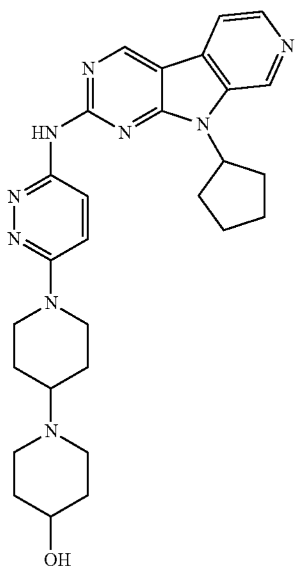 [SMILES: OC1CCN(C2CCN(c3ccc(Nc4ncc5c6ccncc6n(C6CCCC6)c5n4)nn3)CC2)CC1] | 0.791 | 514.3 |
| 456 | 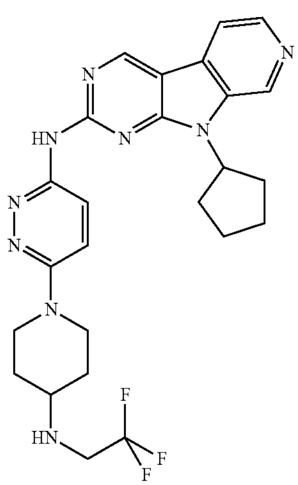 [SMILES: FC(F)(F)CNC1CCN(c2ccc(Nc3ncc4c5ccncc5n(C5CCCC5)c4n3)nn2)CC1] | 0.89 | 512.2 |
| 457 | | 0.782 | 487.3 |
| 458 | | 0.766 | 473.2 |
| 459 | | 0.825 | 487.3 |

TABLE 8-continued
| Example # | Structure | LCMS retention time (min) | LCMS-ESI (M + 1) |
|---|---|---|---|
| 460 | 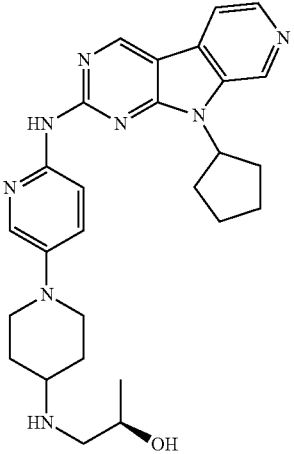 [SMILES: C[C@@H](O)CNC1CCN(c2ccc(Nc3ncc4c5ccncc5n(C5CCCC5)c4n3)nc2)CC1] | 0.772 | 487.3 |
| 461 | 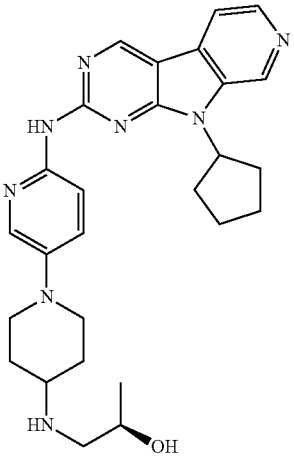 [SMILES: C[C@@H](O)CNC1CCN(c2ccc(Nc3ncc4c5ccncc5n(C5CCCC5)c4n3)nc2)CC1] | 0.732 | 499.2 |
| 462 | 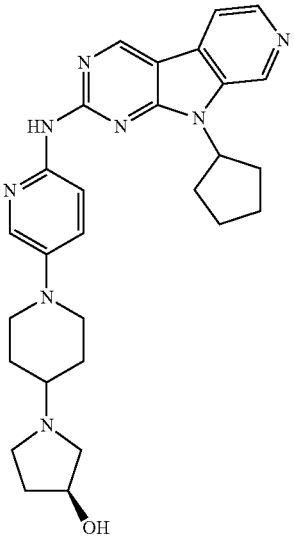 [SMILES: O[C@H]1CCN(C2CCN(c3ccc(Nc4ncc5c6ccncc6n(C6CCCC6)c5n4)nc3)CC2)C1] | 0.729 | 499.2 |
| 463 | 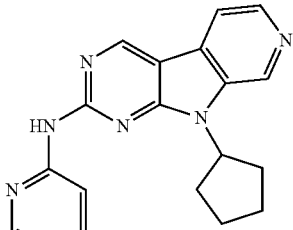 | 0.733 | 513.3 |
| 464 | 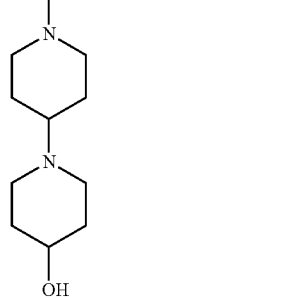 | 0.75 | 457.3 |
| 465 | 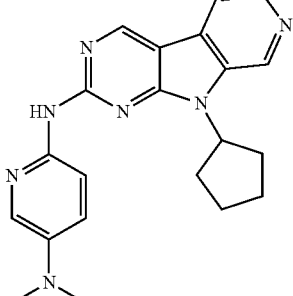 | 0.777 | 469.3 |

TABLE 8-continued

| Example # | Structure | LCMS retention time (min) | LCMS-ESI (M + 1) |
|---|---|---|---|
| 466 | 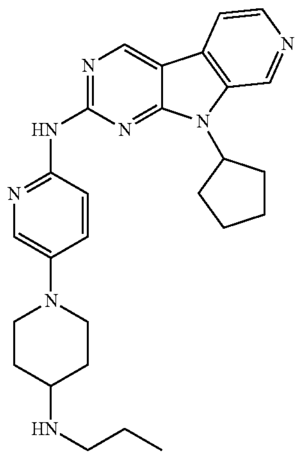 [SMILES: CCCNC1CCN(c2ccc(Nc3ncc4c5ccncc5n(C5CCCC5)c4n3)nc2)CC1] | 0.774 | 471.3 |
| 467 | 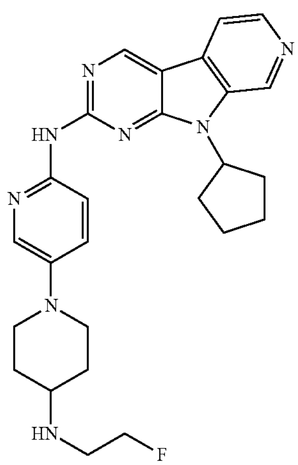 [SMILES: FCCNC1CCN(c2ccc(Nc3ncc4c5ccncc5n(C5CCCC5)c4n3)nc2)CC1] | 0.738 | 475.3 |
| 468 | 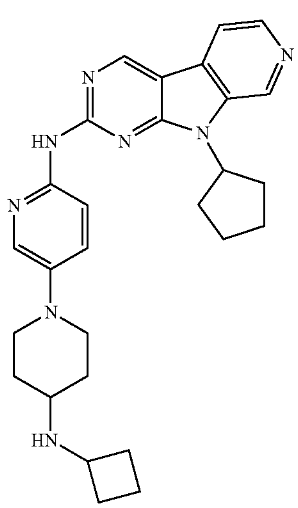 [SMILES: c1cc2c3cnc(Nc4ccc(N5CCC(NC6CCC6)CC5)cn4)nc3n(C3CCCC3)c2cn1] | 0.795 | 483.3 |
| 469 | | 0.779 | 471.3 |
| 470 | | 0.873 | 511.1 |
| 471 | | 0.798 | 501.2 |

TABLE 8-continued

| Example # | Structure | LCMS retention time (min) | LCMS-ESI (M + 1) |
|---|---|---|---|
| 472 | 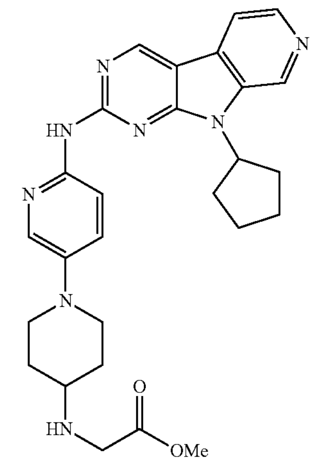 [SMILES: COC(=O)CNC1CCN(c2ccc(Nc3ncc4c5ccncc5n(C5CCCC5)c4n3)nc2)CC1] | 0.771 | 501.2 |
| 473 | 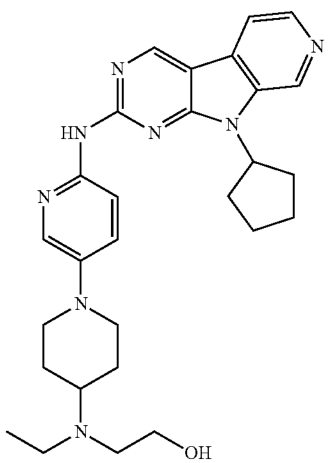 | 0.766 | 501.2 |
| 474 | 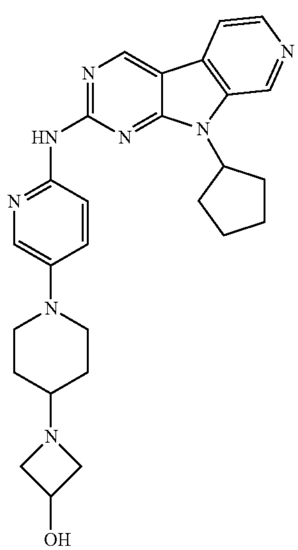 [SMILES: OC1CN(C2CCN(c3ccc(Nc4ncc5c6ccncc6n(C6CCCC6)c5n4)nc3)CC2)C1] | 0.762 | 485.2 |
| 475 | 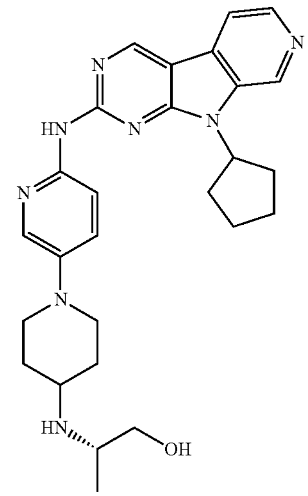 [SMILES: C[C@@H](CO)NC1CCN(c2ccc(Nc3ncc4c5ccncc5n(C5CCCC5)c4n3)nc2)CC1] | 0.764 | 487.1 |
| 476 | 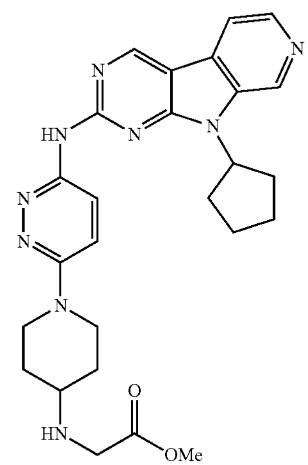 [SMILES: COC(=O)CNC1CCN(c2ccc(Nc3ncc4c5ccncc5n(C5CCCC5)c4n3)nn2)CC1] | 0.745 | 502.1 |
| 477 | 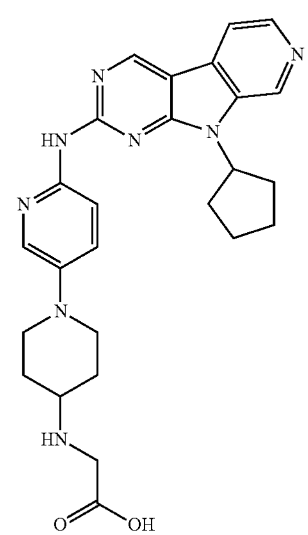 [SMILES: O=C(O)CNC1CCN(c2ccc(Nc3ncc4c5ccncc5n(C5CCCC5)c4n3)nc2)CC1] | 0.773 | 487.3 |

TABLE 8-continued

| Example # | Structure | LCMS retention time (min) | LCMS-ESI (M + 1) |
|---|---|---|---|
| 478 | 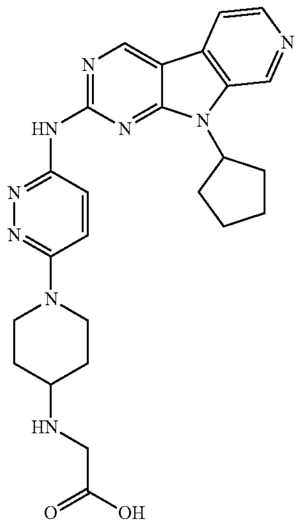 [SMILES: O=C(O)CNC1CCN(c2ccc(Nc3ncc4c5ccncc5n(C5CCCC5)c4n3)nn2)CC1] | 0.729 | 488.2 |
| 479 | 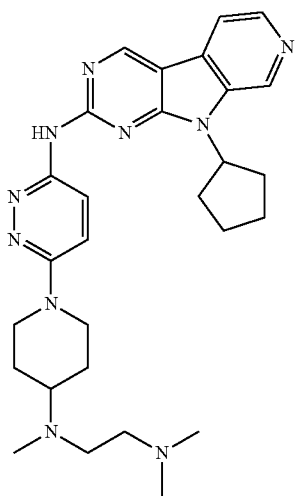 [SMILES: CN(C)CCN(C)C1CCN(c2ccc(Nc3ncc4c5ccncc5n(C5CCCC5)c4n3)nn2)CC1] | 0.731 | 515.3 |
| 480 | 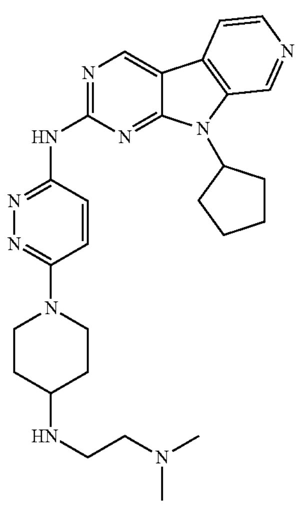 [SMILES: CN(C)CCNC1CCN(c2ccc(Nc3ncc4c5ccncc5n(C5CCCC5)c4n3)nn2)CC1] | 0.715 | 501.2 |
| 481 | | 0.698 | 504.2 |

BIOLOGICAL TESTING

The pharmacological properties of the compounds of this invention may be confirmed by in vitro assays such as those described below.

The Cdk4 and Cdk6 inhibitory activity of the compounds is measured with a kinase inhibition assay using recombinant Cdk4/CyclinD1 or Cdk6/CyclinD3 protein complexes. The protein substrate used in the assay is the retinoblastoma protein (Rb). The kinase reactions are carried out in a 96-well filter plate (MSDV N6B50, Millipore). Compounds are serially diluted in kinase buffer (20 mM Tris-HCl, pH 7.4, 50 mM NaCl, 1 mM DTT, 1 mg/ml BSA) and added to the reaction mixture containing 2.5 ng/ml Cdk4/CyclinD1 or Cdk6/CyclinD3, 25 μM ATP, 10 μCi/ml [$^{33}$P]-ATP, 0.1 μg/ml Rb in the kinase buffer. The mixture is incubated at room temperature for 1 hour and the proteins precipitated with an equal volume of 20% TCA. The plates are washed with 10% TCA according to the manufacturer's instruction and dried at room temperature. The amount of the phosphorylated Rb is determined with a TopCount (PerkinElmer). The IC$_{50}$ of a compound is determined by nonlinear regression curve fitting using software program Prism 5 (GraphPad Software).

The cellular activity of the compounds is measured with a cell-based DNA synthesis inhibition assay. Rb positive (e.g. Colo-205, MDA-MB-435) or Rb negative (e.g. MDA-MB-436, H2009) cancer cells are seeded in the 96-well Cytostar plates (GE Healthcare, Cat# RPNQ0163) at a density of 3000-5000 cells/well. Dilutions of compounds are added to the cells. After 24 hour incubation at 37 C, $^{14}$C-thymidine is added (0.1 μCi/well). After additional 48 hour incubation at 37 C, incorporation of $^{14}$C-thymidine into the DNA of the cells was measured with a TopCount (PerkinElmer). The IC$_{50}$ of a compound is determined by nonlinear regression curve fitting using software program Prism 5 (GraphPad Software).

The Cdk4 or Cdk6 inhibitory activity of the compounds may also be measured with kinase assays of a different format, e.g., a homogeneous time-resolved fluorescence energy transfer (HTRF) assay (Jia Y. et al, *Anal Biochem.* 2006; 356:273-281) or a fluorescence polarization (FP) assay (Sportsman J R, et al. *Comb Chem High Throughput Screen.* 2003; 6:195-200).

The compounds exemplified herein have been assayed and exhibit Cdk 4 IC$_{50}$s in a range from 0.13 nm to 430 nm, and exhibit Cdk 6 IC$_{50}$s, where determined from 0.36 nm to 500 nm. Illustrative activity values are provided in the following Table 9.

TABLE 9

| Example Number | Cdk 4 IC$_{50}$ (μM) | Cdk 6 IC$_{50}$ (μM) |
|---|---|---|
| 1 | 0.0032 | 0.0044 |
| 2 | 0.013 | 0.01 |
| 3 | 0.00045 | 0.0029 |
| 4 | 0.0039 | 0.0115 |
| 5 | 0.00091 | 0.0042 |
| 6 | 0.0015 | 0.0066 |
| 7 | 0.0014 | 0.0013 |
| 8 | 0.00013 | 0.0011 |
| 9 | 0.0038 | 0.0195 |
| 10 | 0.0022 | |
| 11 | 0.0031 | 0.01 |
| 12 | 0.0096 | |
| 13 | 0.001 | 0.0026 |
| 14 | 0.0022 | 0.008 |
| 15 | 0.0075 | 0.013 |
| 16 | 0.01 | 0.021 |
| 17 | 0.00032 | 0.00036 |
| 18 | 0.0016 | 0.0015 |
| 19 | 0.004 | 0.01 |
| 20 | 0.0081 | 0.057 |
| 21 | 0.001 | 0.00041 |
| 22 | 0.0013 | 0.0025 |
| 23 | 0.011 | 0.0131 |
| 24 | 0.00094 | 0.0051 |
| 25 | 0.03 | 0.038 |
| 26 | 0.0016 | 0.0035 |
| 27 | 0.0055 | 0.007 |
| 28 | 0.057 | 0.061 |
| 29 | 0.0039 | 0.0057 |
| 30 | 0.0046 | 0.0061 |
| 31 | 0.0025 | 0.0059 |
| 32 | 0.013 | 0.0304 |
| 33 | 0.0053 | 0.0089 |
| 34 | 0.011 | 0.021 |
| 35 | 0.0082 | 0.021 |
| 36 | 0.00083 | 0.0044 |
| 37 | 0.0043 | 0.0012 |
| 38 | 0.0021 | 0.0153 |
| 39 | 0.0021 | 0.0031 |
| 40 | 0.0049 | 0.0026 |
| 41 | 0.0027 | 0.0072 |
| 42 | 0.237 | 0.5 |
| 43 | 0.136 | 0.218 |
| 44 | 0.011 | 0.025 |
| 45 | 0.073 | 0.129 |
| 46 | 0.002 | 0.00075 |
| 47 | 0.002 | 0.0037 |
| 48 | 0.0016 | 0.0056 |
| 49 | 0.0025 | 0.0065 |
| 50 | 0.066 | 0.112 |
| 51 | 0.126 | 0.406 |
| 52 | 0.012 | 0.022 |
| 53 | 0.0047 | 0.011 |
| 54 | 0.02 | 0.047 |
| 55 | 0.0012 | 0.0044 |
| 56 | 0.00097 | |
| 57 | 0.002 | 0.017 |
| 58 | 0.0052 | |
| 59 | 0.015 | |
| 60 | 0.004 | |
| 61 | 0.0017 | |
| 62 | 0.002 | |
| 63 | 0.0034 | 0.02 |
| 64 | 0.0028 | 0.024 |
| 65 | 0.0096 | 0.024 |
| 66 | 0.0054 | 0.073 |
| 67 | 0.0013 | |
| 68 | 0.0041 | |
| 69 | 0.017 | 0.031 |
| 70 | 0.0036 | |
| 71 | 0.0041 | |
| 72 | 0.0023 | |
| 73 | 0.017 | |
| 74 | 0.056 | |
| 75 | 0.0014 | |
| 76 | 0.0059 | |
| 77 | 0.003 | 0.011 |
| 78 | 0.015 | |
| 79 | 0.012 | |
| 80 | 0.0035 | |
| 81 | 0.0092 | |
| 82 | 0.0026 | |
| 83 | 0.012 | |
| 84 | 0.022 | |
| 85 | 0.02 | |
| 86 | 0.0064 | |
| 87 | 0.043 | |
| 88 | 0.477 | |
| 89 | 0.0076 | |
| 90 | 0.0056 | |
| 91 | 0.0061 | 0.0112 |
| 92 | 0.0088 | 0.0151 |
| 93 | 0.0031 | 0.0159 |
| 94 | 0.0049 | 0.0092 |
| 95 | 0.0044 | |
| 96 | 0.0162 | 0.0124 |
| 97 | 0.43 | 0.396 |
| 98 | 0.0025 | 0.0266 |
| 99 | 0.0049 | |
| 100 | 0.0062 | |
| 101 | 0.004 | 0.0088 |
| 102 | 0.0031 | 0.0111 |
| 103 | 0.0056 | 0.0026 |
| 104 | 0.0033 | 0.014 |
| 105 | 0.0067 | 0.0071 |
| 106 | 0.004 | 0.0243 |
| 107 | 0.0084 | 0.048 |
| 108 | 0.012 | 0.0157 |
| 109 | 0.0019 | 0.011 |
| 110 | 0.0034 | |
| 111 | 0.0044 | 0.0197 |
| 112 | 0.0059 | |
| 113 | 0.0042 | |
| 114 | 0.0016 | 0.01 |
| 115 | 0.0023 | |
| 116 | 0.002 | |
| 117 | 0.0055 | 0.0068 |
| 118 | 0.0042 | |
| 119 | 0.0051 | |
| 120 | 0.019 | |
| 121 | 0.0043 | |
| 122 | 0.0087 | |
| 123 | 0.0481 | |
| 124 | 0.017 | |
| 125 | 0.012 | |
| 126 | 0.002 | |
| 127 | 0.0053 | |
| 128 | 0.029 | |
| 129 | 0.016 | |
| 130 | 0.02 | |
| 131 | 0.174 | |
| 132 | 0.302 | |
| 133 | 0.1 | |
| 134 | 0.19 | |
| 135 | 10 | |
| 136 | 0.0069 | |
| 137 | 0.011 | 0.027 |
| 138 | 0.0012 | |
| 139 | 0.016 | 0.0064 |
| 140 | 0.093 | 10 |
| 141 | 0.0022 | 0.0026 |
| 142 | 0.0018 | 0.0049 |
| 143 | 0.0038 | 0.0158 |
| 144 | 0.0034 | 0.0046 |
| 145 | 0.001 | 0.0058 |
| 146 | 0.05 | 0.033 |
| 147 | 0.041 | |
| 148 | 0.015 | |

TABLE 9-continued

| Example Number | Cdk 4 IC$_{50}$ (μM) | Cdk 6 IC$_{50}$ (μM) |
|---|---|---|
| 149 | 0.017 | |
| 150 | 0.011 | |
| 151 | 0.003 | |
| 152 | 0.002 | 0.0043 |
| 153 | 0.001 | 0.0028 |
| 154 | 0.02 | |
| 155 | 0.0041 | |
| 156 | 0.007 | 0.014 |
| 157 | 0.03 | 0.025 |
| 158 | 0.0054 | 0.0053 |
| 159 | 0.003 | |
| 160 | 0.0025 | 0.0048 |
| 161 | 0.0036 | 0.016 |
| 162 | 10 | 0.11 |
| 163 | 0.017 | 0.016 |
| 164 | 0.0036 | 0.0062 |
| 165 | 0.0085 | 0.017 |
| 166 | 0.0055 | |
| 167 | 0.011 | 0.021 |
| 168 | 10 | 10 |
| 169 | 0.14 | 0.15 |
| 170 | 0.0025 | |
| 171 | 0.019 | |
| 172 | 0.0056 | |
| 173 | 0.056 | |
| 174 | 0.033 | |
| 175 | 0.037 | |
| 176 | 0.93 | |
| 177 | 0.005 | |
| 178 | 0.005 | |
| 179 | 0.0034 | |
| 180 | 0.002 | |
| 181 | 0.015 | 0.026 |
| 182 | 0.113 | 0.016 |
| 183 | 0.142 | 0.104 |
| 184 | 0.0086 | 0.031 |
| 185 | 0.145 | 0.149 |
| 186A | 0.0019 | 0.002 |
| 186B | 0.002 | 0.0048 |
| 187 | 0.0029 | 0.0028 |
| 188 | 0.027 | 0.0134 |
| 189 | 0.02 | 0.022 |
| 190 | 0.0064 | 0.0076 |
| 191 | 0.0044 | 0.0049 |
| 192 | 0.0262 | |
| 193 | 0.068 | |
| 194 | 0.6 | |
| 195 | 0.013 | |
| 196 | 0.0024 | |
| 197 | 0.0042 | |
| 198 | 0.0046 | |
| 199 | 0.0045 | |
| 200 | 0.036 | 0.013 |
| 201 | 0.026 | |
| 202 | 0.141 | 0.52 |
| 203 | | |
| 204 | 0.0035 | 0.0011 |
| 205 | 0.0026 | |
| 206 | 0.014 | |
| 207 | 0.01 | |
| 208 | 0.0018 | |
| 209 | 0.011 | |
| 210 | 0.0066 | |
| 211 | 0.0098 | |
| 212 | 0.034 | 0.033 |
| 213 | 0.203 | 0.052 |
| 214 | 0.014 | 0.021 |
| 215 | 0.0044 | 0.0082 |
| 216 | 0.01 | 0.015 |
| 217 | 0.0036 | 0.0098 |
| 218 | 0.00139 | 0.0036 |
| 219 | 0.0053 | 0.011 |
| 220 | 0.001 | 0.0033 |
| 221 | 0.0014 | 0.008 |
| 222 | 0.006 | |
| 223 | 0.013 | |
| 224 | 0.52 | 0.86 |
| 225 | 0.004 | 0.003 |
| 226 | 0.0032 | 0.0027 |
| 227 | 0.003 | 0.0031 |
| 228 | 0.015 | 0.0039 |
| 229 | 0.0212 | 0.0205 |
| 230 | 0.016 | 0.016 |
| 231 | 0.0033 | |
| 232 | 0.0072 | |
| 233 | 0.0046 | 0.012 |
| 234 | 0.015 | 0.026 |
| 235 | 0.125 | 0.257 |
| 236 | 0.034 | 0.112 |
| 237 | 0.049 | 0.131 |
| 238 | 0.035 | 0.178 |
| 239 | 0.0068 | 0.017 |
| 240 | 0.0044 | 0.0046 |
| 241 | 0.177 | |
| 242 | 0.062 | |
| 243 | 0.007 | |
| 244 | 0.011 | |
| 245 | 0.0074 | |
| 246 | 0.07 | |
| 247 | 0.0034 | |
| 248 | 0.018 | |
| 249 | 0.0044 | |
| 250 | 0.016 | |
| 251 | 0.0032 | |
| 252 | 0.002 | 0.005 |
| 253 | 0.0039 | 0.027 |
| 254 | 0.022 | 0.04 |
| 255 | 0.0056 | 0.06 |
| 256 | 0.0013 | 0.007 |
| 257 | 0.007 | 0.0053 |
| 258 | 0.0062 | 0.0133 |
| 258a | 0.001 | 0.041 |
| 258b | 0.005 | 0.024 |
| 259 | 0.049 | 0.101 |
| 260 | 0.045 | 0.06 |
| 261 | 0.233 | 0.36 |
| 262 | 0.032 | 0.038 |
| 263 | 0.014 | |
| 264 | 0.0093 | 0.0166 |
| 265 | 0.0022 | 0.0022 |
| 266 | 0.0031 | 0.0065 |
| 267 | 0.073 | |
| 268 | 0.011 | |
| 269 | 0.035 | |
| 270 | 0.04 | 0.035 |
| 271 | 0.016 | 0.016 |
| 272 | 0.027 | 0.101 |
| 273 | 0.019 | |
| 274 | 1 | |
| 275 | 0.017 | |
| 276 | 0.096 | |
| 277 | 0.018 | |
| 278 | 0.0046 | |
| 279 | 0.59 | |
| 280 | 0.059 | |
| 281 | 0.011 | |
| 282 | 0.0028 | |
| 283 | 0.011 | |
| 284 | 0.005 | |
| 285 | 0.0026 | |
| 286 | | |
| 287 | 0.123 | |
| 288 | 0.014 | 0.04 |
| 289 | 0.0072 | 0.04 |
| 290 | 0.035 | 0.085 |
| 291 | 0.0039 | 0.0069 |
| 292 | 0.0049 | 0.0161 |
| 293 | 0.0046 | 0.016 |
| 294 | 0.0059 | 0.026 |
| 295 | 0.0068 | 0.0337 |
| 296 | 0.0055 | 0.014 |
| 297 | 0.0014 | 0.013 |
| 298 | 0.04 | 0.008 |
| 299 | 0.06 | 0.034 |
| 300 | 0.022 | 0.048 |
| 301 | 0.031 | 0.022 |

TABLE 9-continued

| Example Number | Cdk 4 IC$_{50}$ (μM) | Cdk 6 IC$_{50}$ (μM) |
|---|---|---|
| 302 | 0.047 | 0.023 |
| 303 | 0.031 | 0.03 |
| 304 | 0.046 | 0.027 |
| 305 | 0.149 | 0.111 |
| 306 | 0.013 | 0.039 |
| 307 | 0.011 | 0.0088 |
| 308 | 0.011 | 0.008 |
| 309 | 0.011 | 0.012 |
| 310 | 0.005 | 0.013 |
| 311 | 0.0086 | 0.024 |
| 312 | 0.37 | 0.79 |
| 313 | 0.34 | 0.4 |
| 314 | 0.38 | 1.5 |
| 315 | 1.38 | |
| 316 | 0.036 | 0.059 |
| 317 | 0.012 | 0.021 |
| 318 | 0.0029 | 0.027 |
| 319 | 0.022 | 0.049 |
| 320 | 0.0036 | 0.011 |
| 321 | 0.007 | 0.011 |
| 322 | 0.015 | 0.05 |
| 323 | 0.0096 | 0.023 |
| 324 | 0.011 | 0.02 |
| 325 | 0.011 | 0.042 |
| 326 | 0.62 | |
| 327 | 0.63 | |
| 328 | 0.051 | |
| 329 | 0.5 | |
| 330 | 0.248 | |
| 331 | 0.39 | |
| 332 | 0.016 | |
| 333 | 0.3 | |
| 334 | 0.8 | |
| 335 | 1.63 | |
| 336 | 0.002 | |
| 337 | 0.022 | |
| 338 | 0.302 | |
| 339 | 0.3 | |
| 340 | 0.37 | |
| 341 | 0.021 | 0.016 |
| 342 | 0.087 | 0.077 |
| 343 | 0.044 | 0.028 |
| 344 | 0.016 | 0.01 |
| 345 | 0.021 | 0.015 |
| 346 | 0.054 | 0.016 |
| 347 | 0.027 | 0.027 |
| 348 | 0.017 | 0.012 |
| 349 | 0.144 | 0.34 |
| 350 | 0.074 | 0.102 |
| 351 | 0.08 | 0.176 |
| 352 | 0.146 | 0.053 |
| 353 | 0.09 | 0.103 |
| 354 | 0.58 | 0.83 |
| 355 | 0.177 | 0.275 |
| 356 | 0.36 | 0.37 |
| 357 | 0.294 | 0.314 |
| 358 | 0.47 | 0.59 |
| 359 | 0.071 | |
| 360 | 0.066 | |
| 361 | 0.044 | 0.058 |
| 362 | 0.162 | |
| 363 | 0.211 | |
| 364 | 0.258 | |
| 365 | 0.159 | |
| 366 | 0.33 | |
| 367 | 0.35 | |
| 368 | 0.284 | |
| 369 | 0.045 | 0.029 |
| 370 | 0.161 | |
| 371 | 0.123 | |
| 372 | 0.129 | |
| 373 | 0.045 | |
| 374 | 0.086 | |
| 375 | 0.04 | |
| 376 | 0.05 | |
| 377 | 0.073 | |
| 378 | 0.085 | |
| 379 | 0.011 | |
| 380 | 0.261 | |
| 381 | 2 | |
| 382 | 0.152 | |
| 383 | 0.062 | |
| 384 | 0.143 | |
| 385 | 0.216 | |
| 386 | 0.053 | |
| 387 | 0.227 | |
| 388 | 0.218 | |
| 389 | 0.166 | |
| 390 | 0.032 | |
| 391 | 0.184 | |
| 392 | 0.219 | |
| 393 | 0.3 | |
| 394 | 1.19 | |
| 395 | 0.3 | |
| 396 | 0.238 | |
| 397 | 0.34 | |
| 398 | 0.33 | |
| 399 | 0.057 | |
| 400 | 0.301 | |
| 401 | 0.17 | |
| 402 | 0.175 | |
| 403 | 0.35 | |
| 404 | 0.82 | |
| 405 | 0.75 | |
| 406 | 0.36 | |
| 407 | 0.035 | |
| 408 | 0.044 | |
| 409 | 0.281 | |
| 410 | 0.24 | |
| 411 | 0.43 | |
| 412 | 0.014 | |
| 413 | 0.033 | |
| 414 | 0.0026 | |
| 415 | 0.259 | |
| 416 | 0.271 | |
| 417 | 0.151 | |
| 418 | 0.112 | |
| 419 | 0.162 | |
| 420 | 0.08 | |
| 421 | 0.077 | |
| 422 | 0.069 | |
| 423 | 0.075 | |
| 424 | 0.072 | |
| 425 | 0.073 | |
| 426 | 0.115 | |
| 427 | 0.024 | |
| 428 | 0.059 | |
| 429 | 0.092 | |
| 430 | 0.021 | |
| 431 | 0.012 | |
| 432 | 0.017 | |
| 433 | 0.02 | 0.08 |
| 434 | 0.013 | 0.019 |
| 435 | 0.042 | 0.092 |
| 436 | 0.013 | 0.0051 |
| 437 | 0.023 | 0.03 |
| 438 | 0.0042 | 0.012 |
| 439 | 0.0037 | 0.0057 |
| 440 | 0.0058 | 0.014 |
| 441 | 0.0017 | 0.0038 |
| 442 | 0.0015 | 0.013 |
| 443 | 0.0048 | 0.016 |
| 444 | 0.0019 | 0.011 |
| 445 | 0.0022 | 0.0063 |
| 446 | 0.0013 | 0.0048 |
| 447 | 0.0028 | 0.026 |
| 448 | 0.01 | 0.022 |
| 449 | 0.012 | 0.036 |
| 450 | 0.01 | 0.016 |
| 451 | 0.013 | 0.018 |
| 452 | 0.007 | 0.03 |
| 453 | 0.0046 | 0.013 |
| 454 | 0.0052 | 0.011 |
| 455 | 0.007 | 0.009 |
| 456 | 0.11 | 0.38 |
| 457 | 0.019 | 0.037 |

TABLE 9-continued

| Example Number | Cdk 4 IC$_{50}$ (μM) | Cdk 6 IC$_{50}$ (μM) |
|---|---|---|
| 458 | 0.0048 | 0.0051 |
| 459 | 0.012 | 0.014 |
| 460 | 0.0045 | 0.012 |
| 461 | 0.189 | 0.119 |
| 462 | 0.34 | 0.35 |
| 463 | 0.015 | 0.018 |
| 464 | 0.002 | 0.0031 |
| 465 | 0.0041 | 0.012 |
| 466 | 0.0047 | 0.014 |
| 467 | 0.0072 | 0.021 |
| 468 | 0.0042 | 0.019 |
| 469 | 0.0057 | 0.02 |
| 470 | 0.011 | 0.038 |
| 471 | 0.0041 | 0.018 |
| 472 | 0.024 | 0.034 |
| 473 | 0.0097 | 0.028 |
| 474 | 0.005 | 0.012 |
| 475 | 0.0026 | 0.008 |
| 476 | 0.0017 | 0.026 |
| 477 | 0.002 | 0.0051 |
| 478 | 0.002 | 0.0057 |
| 479 | 0.008 | 0.017 |
| 480 | 0.0049 | 0.01 |
| 481 | 0.008 | 0.012 |

FORMULATIONS

Also embraced within this invention is a class of pharmaceutical compositions comprising the active compounds of Formula I-II in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.01 and about 50 mg/kg, and more preferably about 0.01 and about 30 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes, which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

We claim:
1. A compound of Formula I

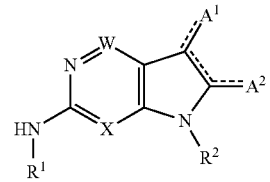

enantiomers, diastereomers, and salts thereof wherein
W is CH;
X is N;
$A^1$ and $A^2$ together with ring carbon atoms to which they are attached combine to form benzene, cyclopentadiene, pyridine, pyridone, pyrimidine, pyrazine, pyridazine, 2H-pyran, pyrrole, imidazole, pyrazole, triazole, furan, oxazole, isoxazole, oxadiazole, thiophene, thiazole, isothiazole or thiadiazole any of which may be optionally partially saturated, and any of which may be optionally independently substituted with one or more $R^x$ groups as allowed by valance;
$R^1$ is —Y-(alkylene)$_m$-$R^a$;
Y is cycylopentyl, cyclohexyl, piperazinyl, phenyl, pyridinyl, pyrmidinyl, cyclopentadienyl, pyrrolyl, imidazolyl, oxazolyl, or thiazolyl, any of which may be optionally substituted with one or more $R^x$ as allowed by valence;
$R^a$ is heterocyclo, heteroaryl, —NR$^3$R$^4$, —C(=O)NR$^3$R$^4$; —O—R$^5$, —S(O)$_n$-R$^5$, or —S(O)$_n$-NR$^3$R$^4$ any of which may be optionally independently substituted with one or more $R^x$ groups as allowed by valance, and wherein two groups bound to the same or adjacent atom may optionally combine to form a ring;
$R^2$ is alkyl, cycloalkyl, heterocyclo, aryl, —S(O)$_n$R$^5$, —C(=O)R$^5$, —C(=S)R$^5$, —C(=O)OR$^5$, —C(=S)OR$^5$, —C(=O)NR$^3$R$^4$, —C(=S)NR$^3$R$^4$, or —SO$_2$NR$^3$R$^4$, any of which may be optionally independently substituted with one or more R$^x$ groups as allowed by valance;

R$^3$ and R$^4$ at each occurance are independently
(i) hydrogen or
(ii) alkyl, cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance, and wherein two R$^x$ groups bound to the same or adjacent atom may optionally combine to form a ring;

or R$^3$ and R$^4$ together with the nitrogen atom to which they are attached may combine to form a heterocyclo ring optionally independently substituted with one or more R$^x$ groups as allowed by valance, and wherein two R$^x$ groups bound to the same or adjacent atom may optionally combine to form a ring;

R$^{3*}$ and R$^{4*}$ at each occurrence are independently
(i) hydrogen or
(ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance;

or R$^{3*}$ and R$^{4*}$ together with the nitrogen atom to which they are attached may combine to form a heterocyclo ring optionally independently substituted with one or more R$^x$ groups as allowed by valance;

R$^5$ and R$^{5*}$ at each occurrence is
(i) hydrogen or
(ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance;

R$^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-S(O)$_n$R$^5$, -(alkylene)$_m$-NR$^3$R$^4$, -(alkylene)$_m$-C(=O)R$^5$, -(alkylene)$_m$-C(=S)R$^5$, -(alkylene)$_m$-C(=O)OR$^5$, -(alkylene)$_m$-OC(=O)R$^5$, -(alkylene)$_m$-C(=S)OR$^5$, -(alkylene)$_m$-C(=O)NR$^3$R$^4$, -(alkylene)$_m$-C(=S)NR$^3$R$^4$, -(alkylene)$_m$-N(R$^3$)C(=O)NR$^3$R$^4$, -(alkylene)$_m$-N(R$^3$)C(=S)NR$^3$R$^4$, -(alkylene)$_m$-N(R$^3$)C(=O)R$^5$, -(alkylene)$_m$-N(R$^3$)C(=S)R$^5$, -(alkylene)$_m$-OC(=O)NR$^3$R$^4$, -(alkylene)$_m$-OC(=S)NR$^3$R$^4$, -(alkylene)$_m$-SO$_2$NR$^3$R$^4$, -(alkylene)$_m$-N(R$^3$)SO$_2$R$^5$, -(alkylene)$_m$-N(R$^3$)SO$_2$NR$^3$R$^4$, -(alkylene)$_m$-N(R$^3$)C(=O)OR$^5$, -(alkylene)$_m$-N(R$^3$)C(=S)OR$^5$, or -(alkylene)$_m$-N(R$^3$)SO$_2$R$^5$;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-CN, -(alkylene)$_m$-OR$^{5*}$, -(alkylene)$_m$-S(O)$_n$R$^{5*}$, -(alkylene)$_m$-NR$^{3*}$R$^{4*}$, -(alkylene), -C(=O)R$^{5*}$, -(alkylene)$_m$-C(=S)R$^{5*}$, -(alkylene)$_m$-C(=O)O R$^{5*}$, -(alkylene)$_m$-OC(=O)R$^{5*}$, -(alkylene)$_m$-C(=S)OR$^{5*}$, -(alkylene)$_m$-C(=O)NR$^{3*}$R$^{4*}$, -(alkylene)$_m$-C(=S)NR$^{3*}$R$^{4*}$, -(alkylene)$_m$-N(R$^{3*}$)C(=O)NR$^{3*}$R$^{4*}$, -(alkylene)$_m$-N(R$^{3*}$)C(=S)NR$^{3*}$R$^{4*}$, -(alkylene)$_m$-N(R$^{3*}$)C(=O)R$^{5*}$, -(alkylene)$_m$-N(R$^{3*}$)C(=S)R$^{5*}$, -(alkylene)$_m$-OC(=O)NR$^{3*}$R$^{4*}$, -(alkylene)$_m$-OC(=S)NR$^{3*}$R$^{4*}$, -(alkylene)$_m$-SO$_2$NR$^{3*}$R$^{4*}$, -(alkylene)$_m$-N(R$^{3*}$)SO$_2$R$^{5*}$, -(alky-lene)$_m$-N(R$^{3*}$)SO$_2$NR$^{3*}$R$^{4*}$, -(alkylene)$_m$-N(R$^{3*}$)C(=O)OR$^{5*}$, -(alkylene)$_m$-N(R$^{3*}$)C(=S)OR$^{5*}$, or -(alkylene)$_m$-N(R$^{3*}$)SO$_2$R$^{5*}$;

n is independently 0, 1 or 2; and m is independently 0 or 1.

2. A compound of claim 1 wherein A$^1$ and A$^2$ together with the ring atoms to which they are attached combine to form

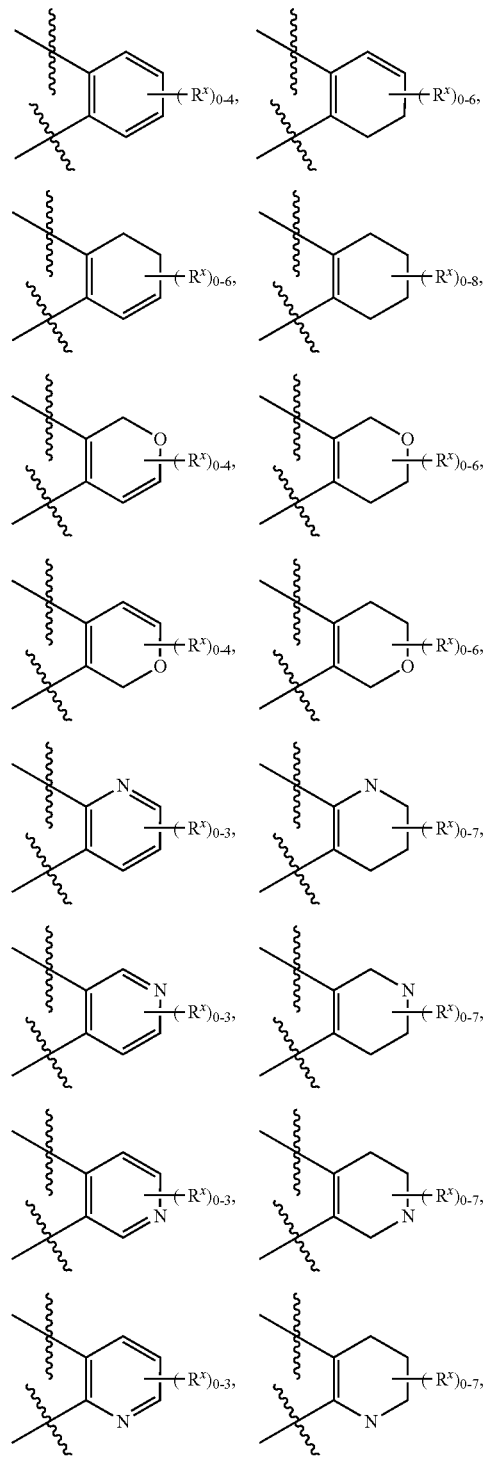

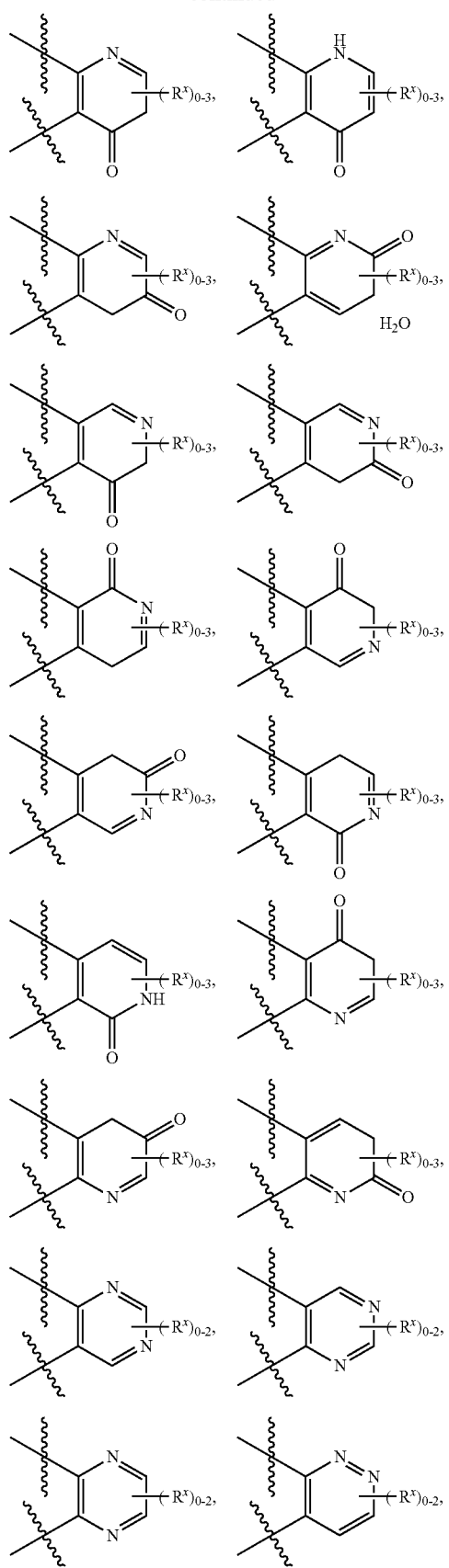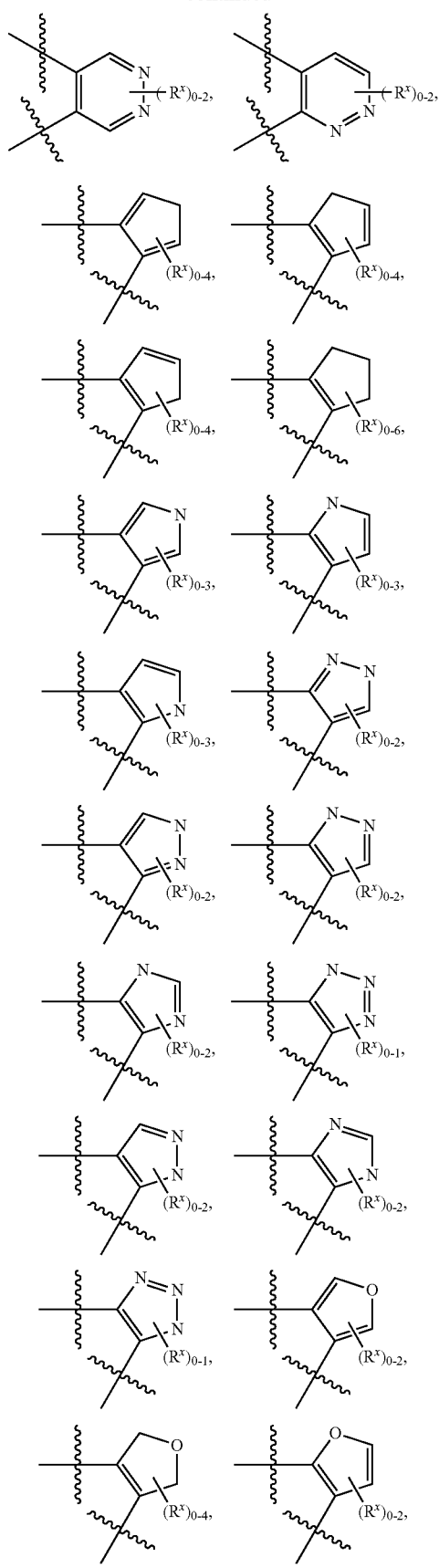

-continued
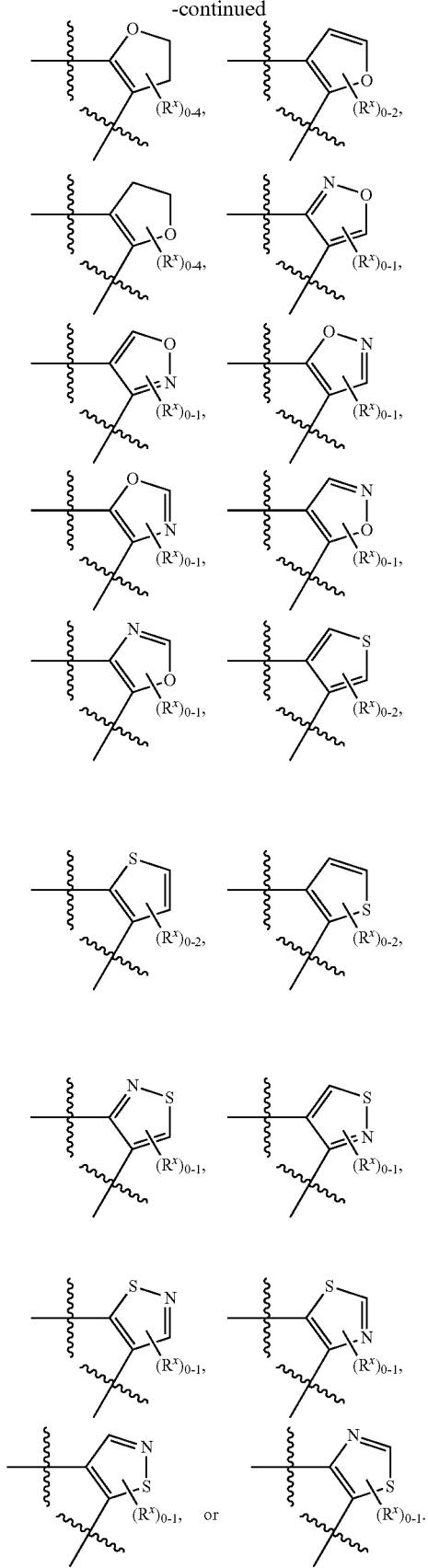
3. A compound of claim 1 wherein $R^1$ is selected from
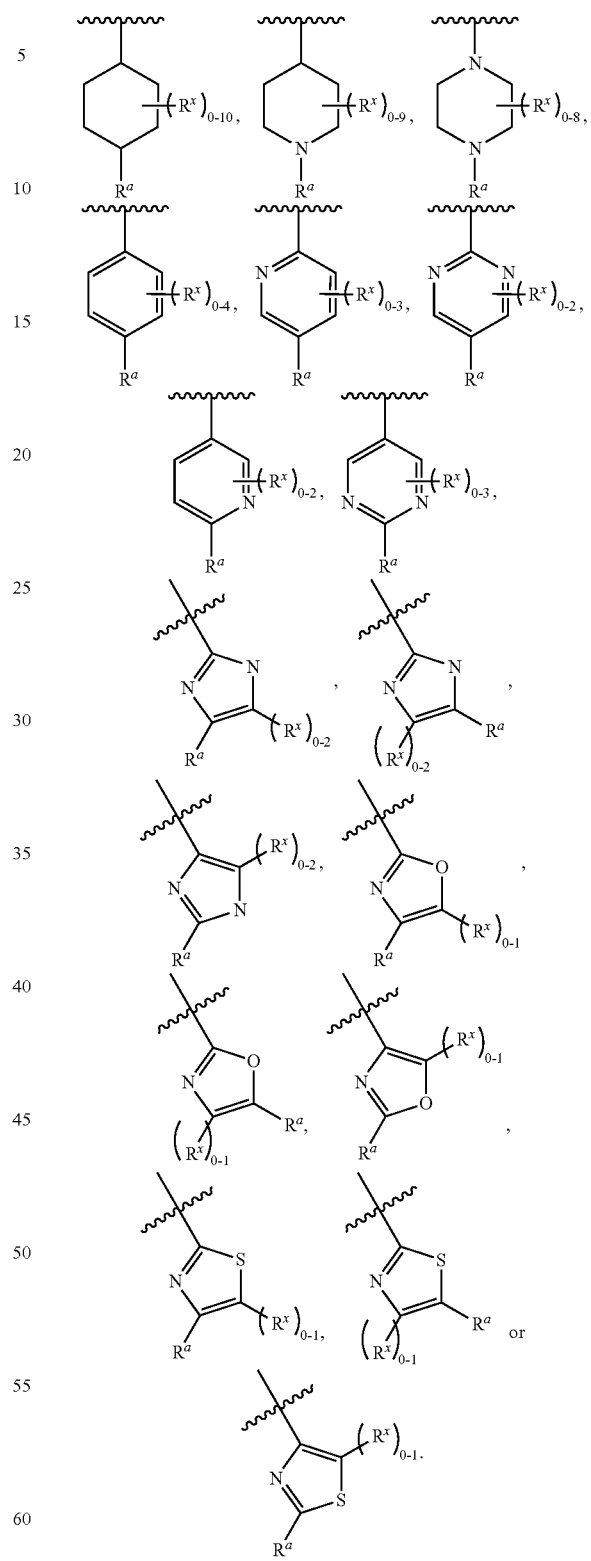
4. A compound of claim 3 where $R^a$ is selected from
(a) —$OR^5$ or —$S(O)_nR^5$ where $R^5$ is alkyl optionally independently substituted with one or more —$OR^{5*}$, or —$NR^{3*}R^{4*}$;

(b) —C(=O)NR³R⁴ or —NR³R⁴ where R³ and R⁴ are independently alkyl optionally independently substituted with one or more —OR⁵*, or —NR³*R⁴*;

or R³ and R⁴ together with the nitrogen atom to which they are attached combine to form

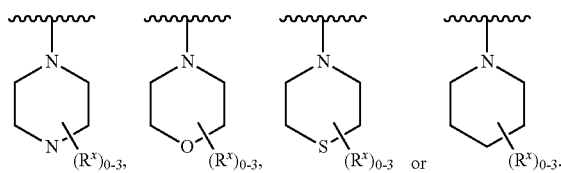

5. A compound of claim 4 wherein R² is

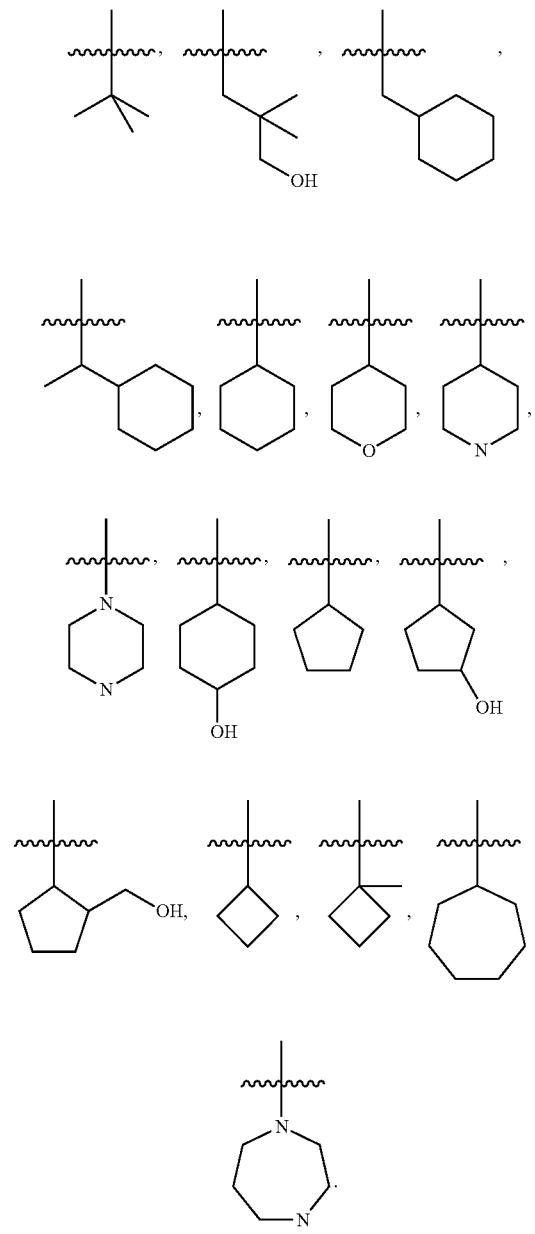

6. A compound of claim 1, wherein A¹ and A² together with the ring atoms to which they are attached combine to form

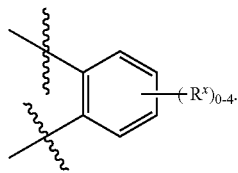

7. A compound of claim 6 wherein R¹ is selected from

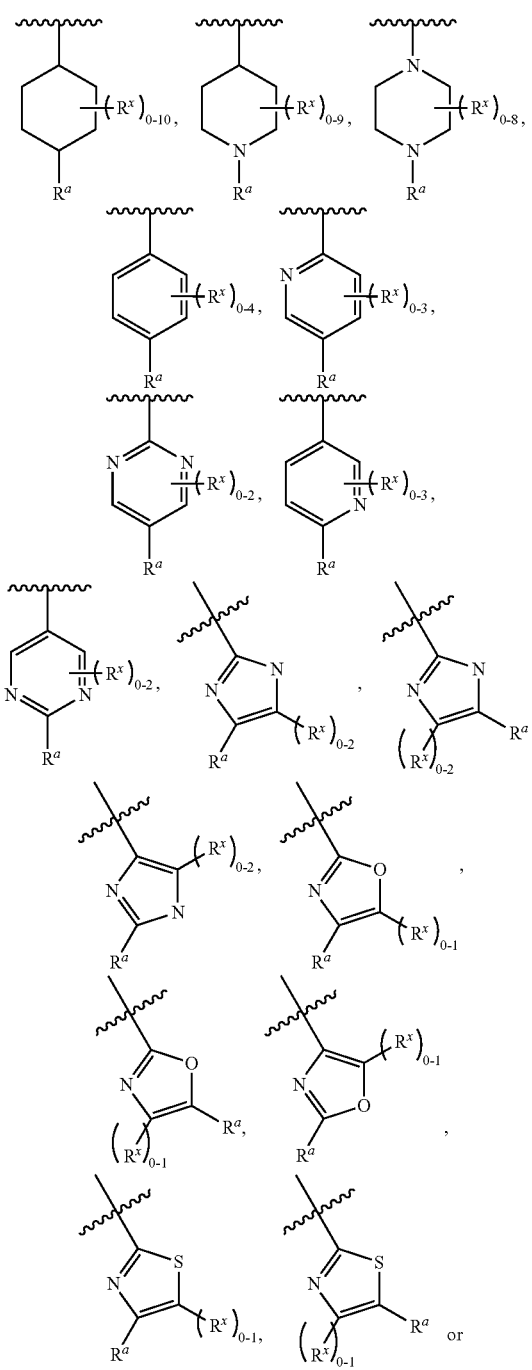

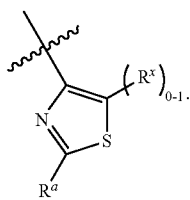

8. A compound of claim 7 where $R^a$ is selected from (a) —$OR^5$ or —$S(O)_nR^5$ where $R^5$ is alkyl optionally independently substituted with one or more —$OR^{5*}$, or —$NR^{3*}R^{4*}$;

(b) —$C(=O)NR^3R^4$ or —$NR^3R^4$ where $R^3$ and $R^4$ are independently alkyl optionally independently substituted with one or more —$OR^{5*}$, or —$NR^{3*}R^{4*}$;

or $R^3$ and $R^4$ together with the nitrogen atom to which they are attached combine to form

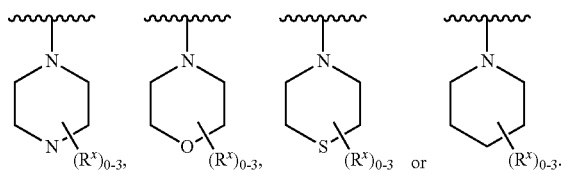

9. A compound of claim 8 wherein $R^2$ is

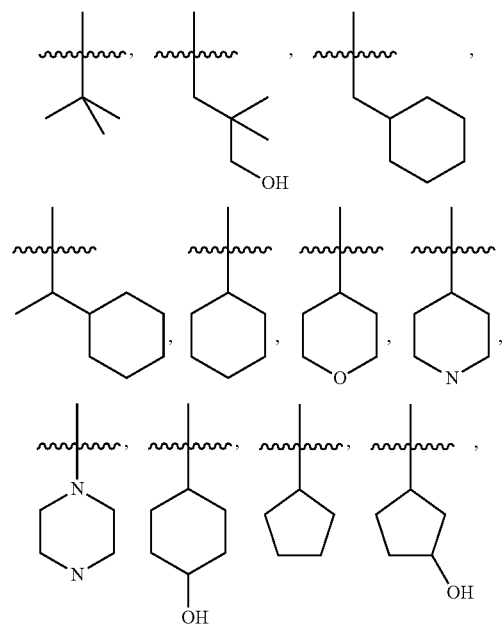

10. A compound of claim 7 wherein $R^1$ is selected from

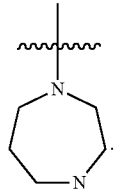

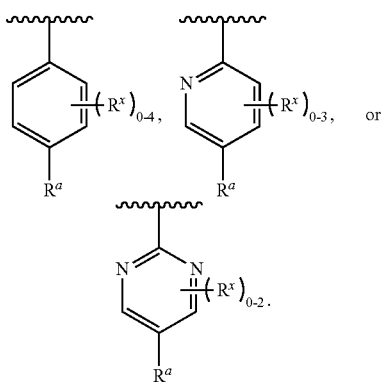

11. A compound of claim 10 where $R^8$ is selected from (a) —$OR^5$ or —$S(O)_nR^5$ where $R^5$ is alkyl optionally independently substituted with one or more —$OR^{5*}$, or —$NR^{3*}R^{4*}$;

(b) —$C(=O)NR^3R^4$ or —$NR^3R^4$ where $R^3$ and $R^4$ are independently alkyl optionally independently substituted with one or more —$OR^{5*}$, or —$NR^{3*}R^{4*}$;

or $R^3$ and $R^4$ together with the nitrogen atom to which they are attached combine to form

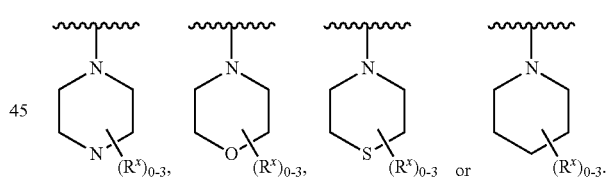

12. A compound of claim 11 wherein $R^2$ is

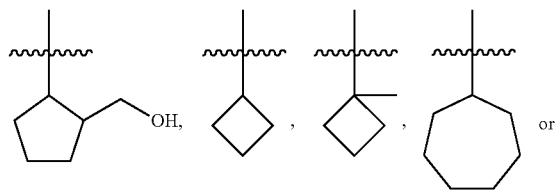

-continued

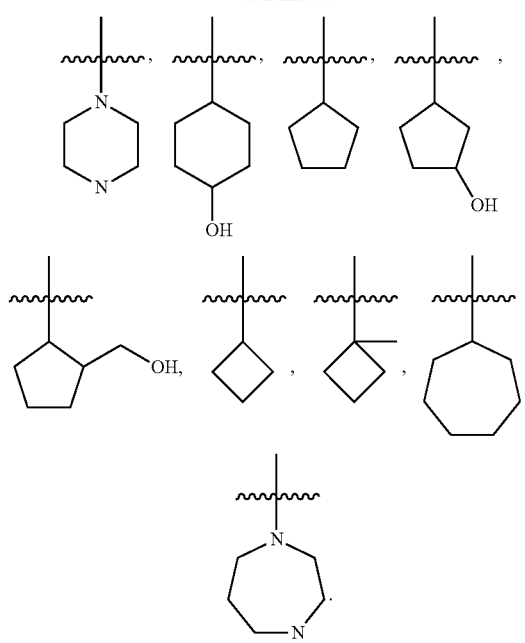

13. A compound of claim 1, wherein $A^1$ and $A^2$ together with the ring atoms to which they are attached combine to form

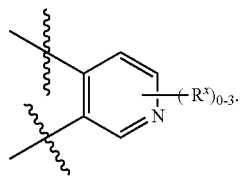

14. A compound of claim 13 wherein $R^1$ is selected from

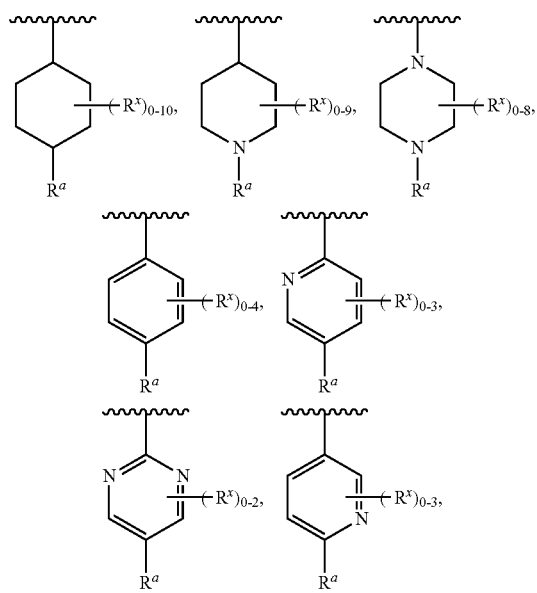

-continued

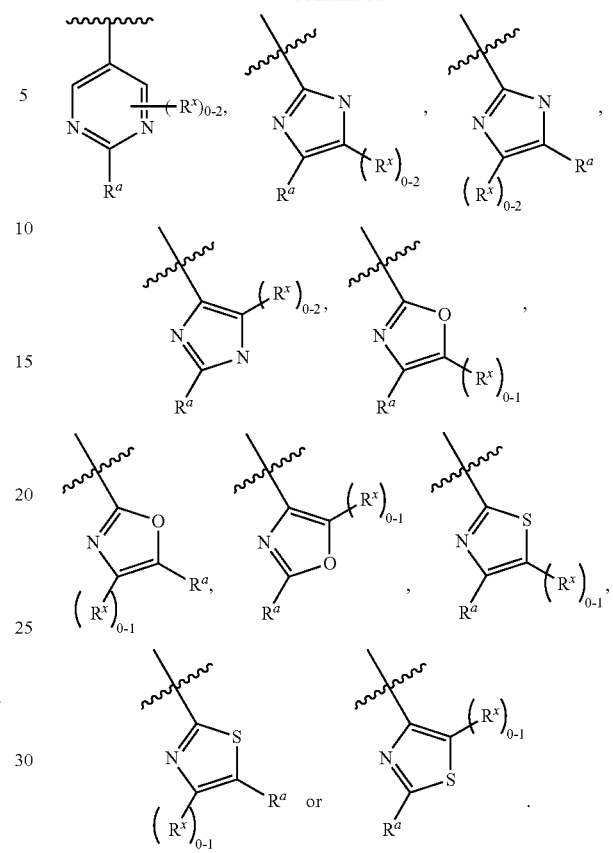

15. A compound of claim 14 where $R^a$ is selected from (a) —$OR^5$ or —$S(O)_nR^5$ where $R^5$ is alkyl optionally independently substituted with one or more —$OR^{5*}$, or —$NR^{3*}R^{4*}$;

(b) —$C(=O)NR^3R^4$ or —$NR^3R^4$ where $R^3$ and $R^4$ are independently alkyl optionally independently substituted with one or more —$OR^{5*}$, or —$NR^{3*}R^{4*}$;

or $R^3$ and $R^4$ together with the nitrogen atom to which they are attached combine to form

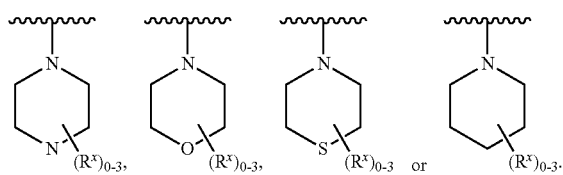

16. A compound of claim 15 wherein $R^2$ is

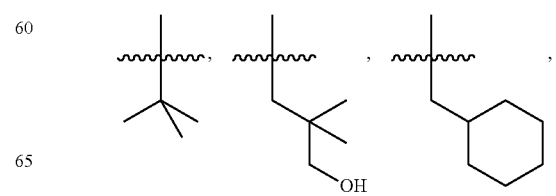

-continued

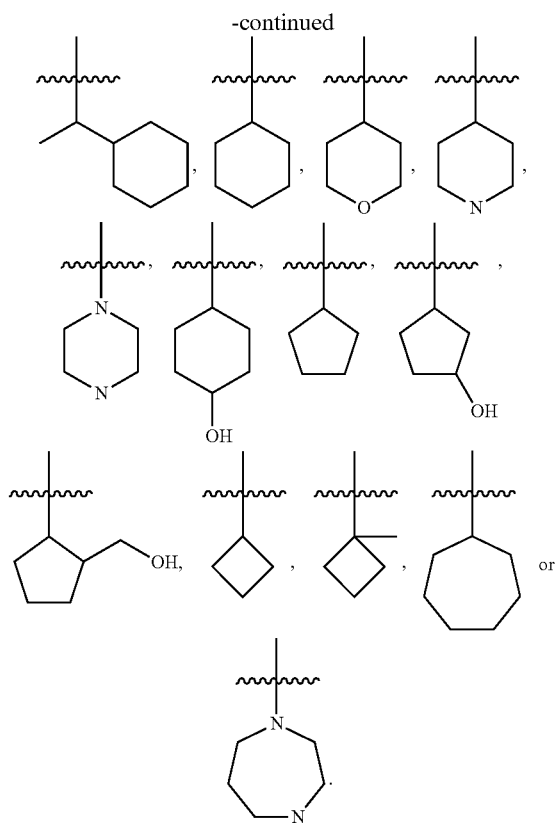

17. A compound of claim 14 wherein $R^1$ is selected from

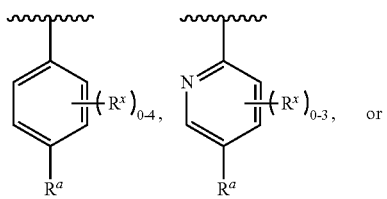

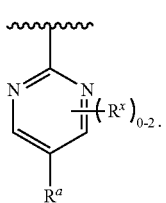

18. A compound of claim 17 where $R^a$ is selected from
(a) —$OR^5$ or —$S(O)_nR^5$ where $R^5$ is alkyl optionally independently substituted with one or more —$OR^{5*}$, or —$NR^3*R^{4*}$;
(b) —$C(=O)NR^3R^4$ or —$NR^3R^4$ where $R^3$ and $R^4$ are independently alkyl optionally independently substituted with one or more —$OR^{5*}$, or —$NR^3*R^{4*}$;
or $R^3$ and $R^4$ together with the nitrogen atom to which they are attached combine to form

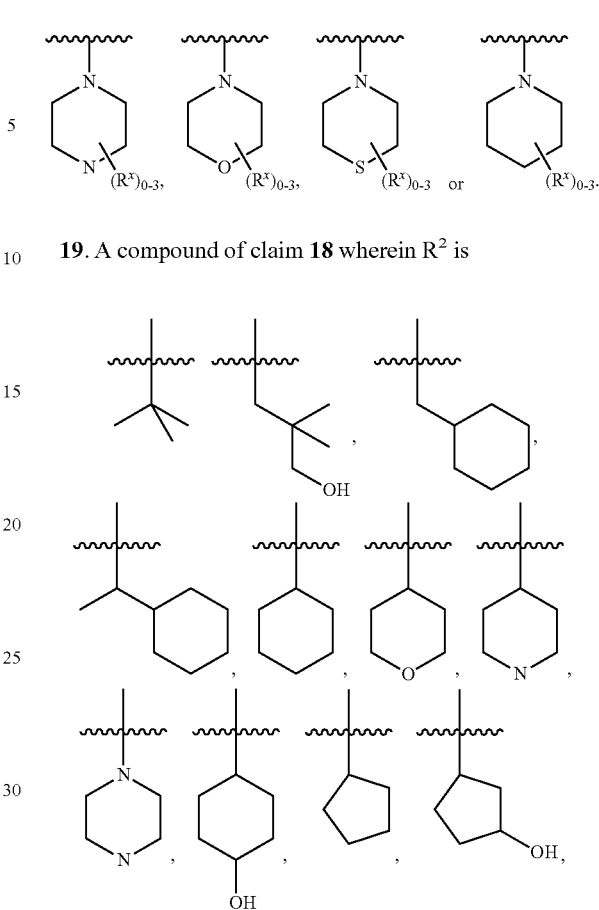

19. A compound of claim 18 wherein $R^2$ is

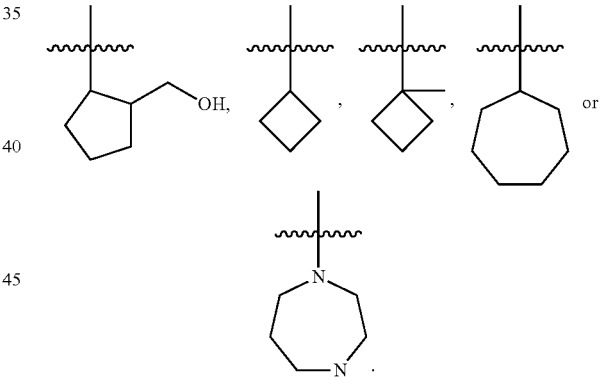

20. A compound of claim 1 having the following formula IC

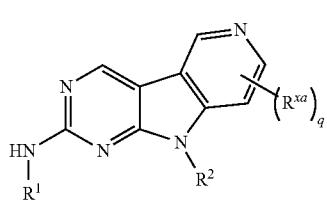

wherein $R^{xa}$ is at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-S(O)$_n$R$^5$, -(alkylene)$_m$-NR$^3$R$^4$, -(alkylene)$_m$-C(=O)R$^5$, -(alkylene)$_m$-C(=S)R$^5$, -(alkylene)$_m$-C(=O)OR$^5$, -(alkylene)$_m$-OC(=O)R$^5$, -(alkylene)$_m$-C(=S)OR$^5$, -(alkylene)$_m$-C(=O)NR$^3$R$^4$, -(alkylene)$_m$-C(=S)NR$^3$R$^4$, -(alkylene)$_m$-N(R$^3$)C(=O)NR$^3$R$^4$, -(alkylene)$_m$-N(R$^3$)C(=S)NR$^3$R$^4$, -(alkylene)$_m$-N(R$^3$)C(=O)R$^5$, -(alkylene)$_m$-N(R$^3$)C(=S)R$^5$, -(alkylene)$_m$-OC(=O)NR$^3$R$^4$, -(alkylene)$_m$-OC(=S)NR$^3$R$^4$, -(alkylene)$_m$-SO$_2$NR$^3$R$^4$, -(alkylene)$_m$-N(R$^3$)SO$_2$R$^5$, -(alkylene)$_m$-N(R$^3$)SO$_2$NR$^3$R$^4$, -(alkylene)$_m$-N(R$^3$)C(=O)OR$^5$, -(alkylene)$_m$-N(R$^3$)C(=S)OR$^5$, or -(alkylene)$_m$-N(R$^3$)SO$_2$R$^5$;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-OR$^{5*}$, -(alkylene)$_m$-S(O)R$^{5*}$, -(alkylene)$_m$-NR$^{3*}$R$^{4*}$, -(alkylene)$_m$-C(=O)R$^{5*}$, -(alkylene)$_m$-C(=S)R$^{5*}$, -(alkylene)$_m$-C(=O)O R$^{5*}$, -(alkylene)$_m$-OC(=O)R$^{5*}$, -(alkylene)$_m$-C(=S)OR$^{5*}$, -(alkylene)$_m$-C(=O)NR$^{3*}$R$^{4*}$, -(alkylene)$_m$-C(=S)NR$^{3*}$R$^{4*}$, -(alkylene)$_m$-N(R$^{3*}$)C(=O)NR$^{3*}$R$^{4*}$, -(alkylene)$_m$-N(R$^{3*}$)C(=S)NR$^{3*}$R$^{4*}$, -(alkylene)$_m$-N(R$^{3*}$)C(=O)R$^{5*}$, -(alkylene)$_m$-N(R$^{3*}$)C(=S)R$^{5*}$, -(alkylene)$_m$-OC(=O)NR$^{3*}$R$^{4*}$, -(alkylene)$_m$-OC(=S)NR$^{3*}$R$^{4*}$, -(alkylene)$_m$-SO$_2$NR$^{3*}$R$^{4*}$, -(alkylene)$_m$-N(R$^{3*}$)SO$_2$R$^{5*}$, -(alkylene)$_m$-N(R$^{3*}$)SO$_2$NR$^{3*}$R$^{4*}$, -(alkylene)$_m$-N(R$^{3*}$)C(=O)OR$^{5*}$, -(alkylene)$_m$-N(R$^{3*}$)C(=S)OR$^{5*}$, or -(alkylene)$_m$-N(R$^{3*}$)SO$_2$R$^{5*}$;

m is 0 or 1; and q is zero to two.

21. A compound of claim 20 wherein R$^1$ is selected from

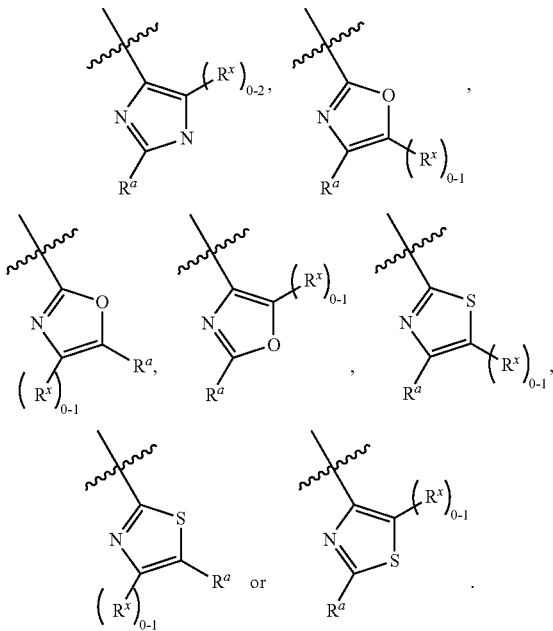

22. A compound of claim 21 where R$^a$ is selected from (a) —OR$^5$ or —S(O)$_n$R$^5$ where R$^5$ is alkyl optionally independently substituted with one or more —OR$^{5*}$, or —NR$^{3*}$R$^{4*}$;

(b) —C(=O)NR$^3$R$^4$ or —NR$^3$R$^4$ where R$^3$ and R$^4$ are independently alkyl optionally independently substituted with one or more —OR$^{5*}$, or —NR$^{3*}$R$^{4*}$;

or R$^3$ and R$^4$ together with the nitrogen atom to which they are attached combine to form 23. A compound of claim 22 wherein R$^2$ is

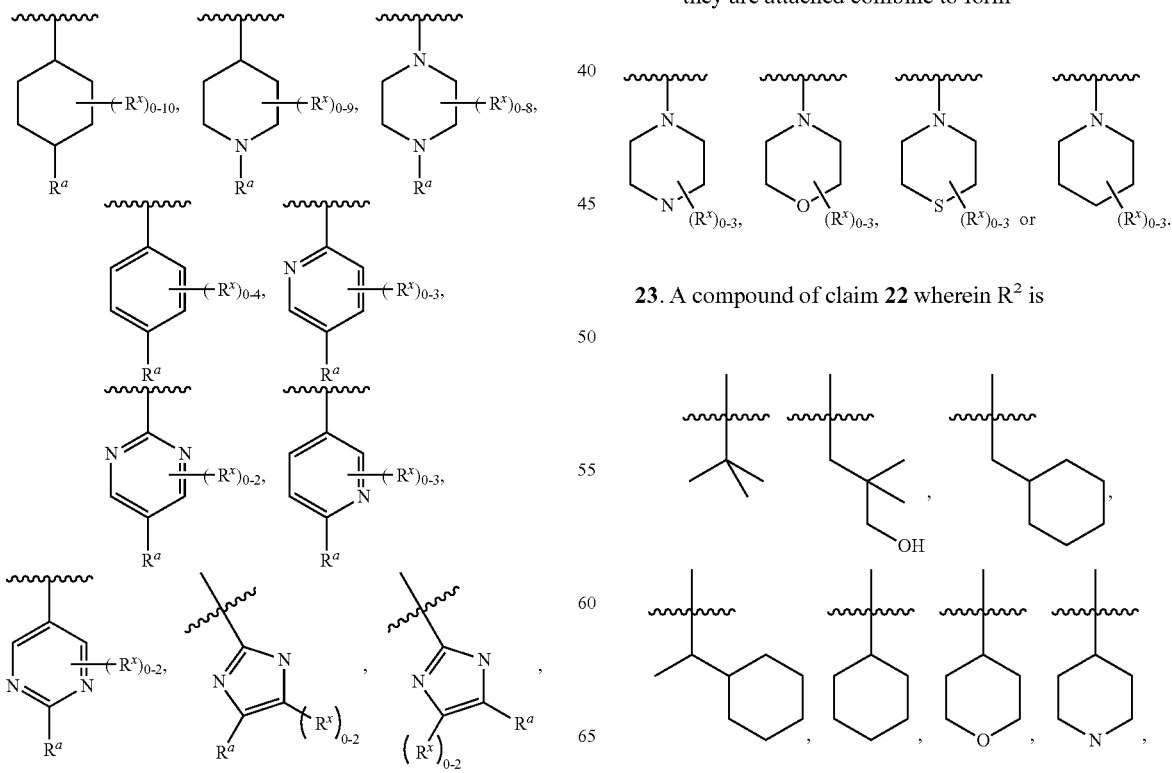

-continued

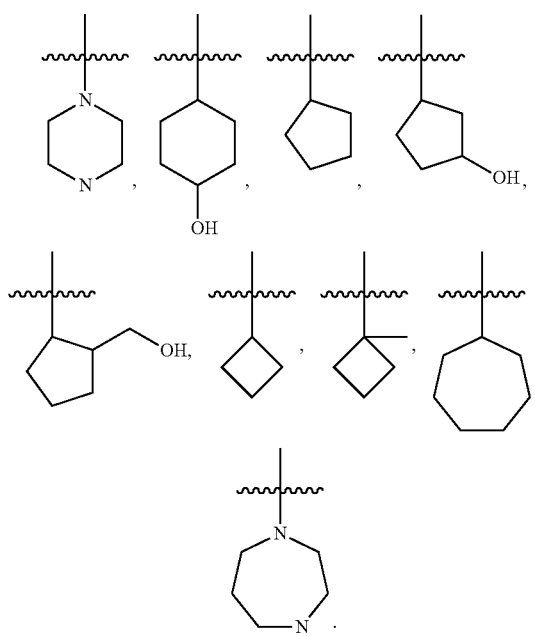

24. A compound of claim 21 wherein $R^1$ is selected from

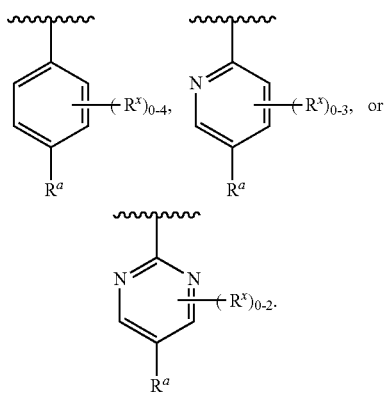

25. A compound of claim 24 where $R^a$ is selected from
(a) —$OR^5$ or —$S(O)_nR^5$ where $R^5$ is alkyl optionally independently substituted with one or more —$OR^{5*}$, or —$NR^3*R^{4*}$;
(b) —$C(=O)NR^3R^4$ or —$NR^3R^4$ where $R^3$ and $R^4$ are independently alkyl optionally independently substituted with one or more —$OR^{5*}$, or —$NR^3*R^{4*}$;
or $R^3$ and $R^4$ together with the nitrogen atom to which they are attached combine to form

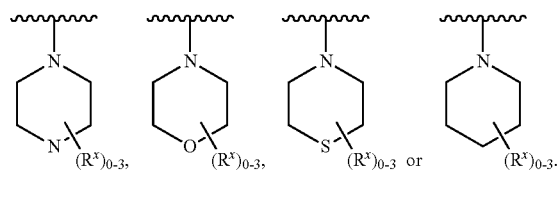

26. A compound of claim 25 wherein $R^2$ is

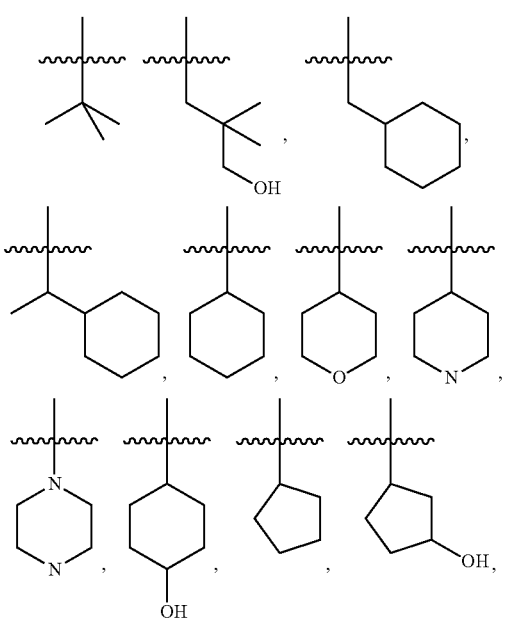

27. A compound of claim 1, wherein $A^1$ and $A^2$ together with the ring atoms to which they are attached combine to form

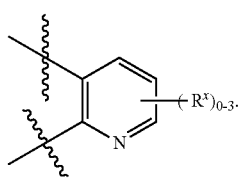

28. A compound of claim 27 wherein $R^1$ is selected from

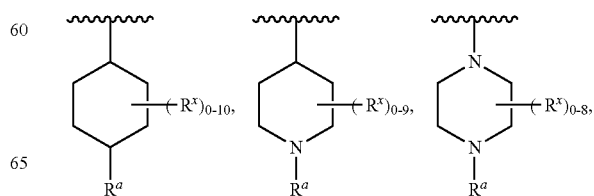

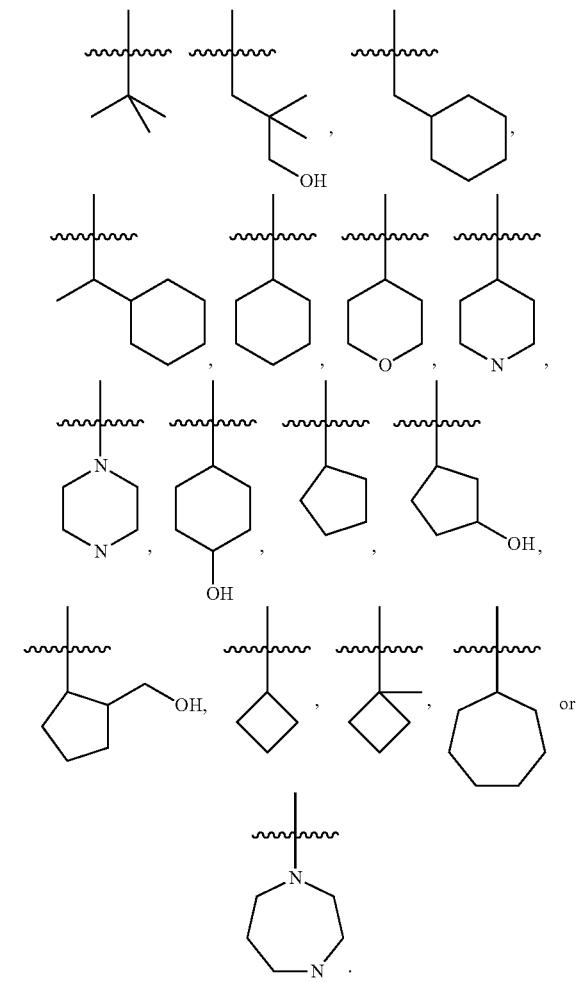

30. A compound of claim 29 wherein $R^2$ is

31. A compound of claim 28 wherein $R^1$ is selected from

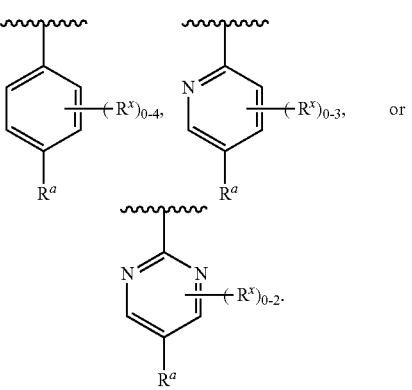

32. A compound of claim 31 where $R^a$ is selected from (a) —$OR^5$ or —$S(O)_nR^5$ where $R^5$ is alkyl optionally independently substituted with one or more —$OR^{5*}$, or —$NR^{3*}R^{4*}$;

(b) —$C(=O)NR^3R^4$ or —$NR^3R^4$ where $R^3$ and $R^4$ are independently alkyl optionally independently substituted with one or more —$OR^{5*}$, or —$NR^{3*}R^{4*}$;

-continued

29. A compound of claim 28 where $R^a$ is selected from (a) —$OR^5$ or —$S(O)_nR^5$ where $R^5$ is alkyl optionally independently substituted with one or more —$OR^{5*}$, or —$NR^{3*}R^{4*}$;

(b) —$C(=O)NR^3R^4$ or —$NR^3R^4$ where $R^3$ and $R^4$ are independently alkyl optionally independently substituted with one or more —$OR^{5*}$, or —$NR^{3*}R^{4*}$;

or $R^3$ and $R^4$ together with the nitrogen atom to which they are attached combine to form

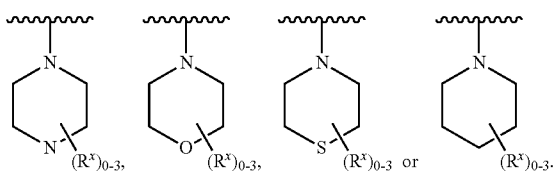

or R³ and R⁴ together with the nitrogen atom to which they are attached combine to form

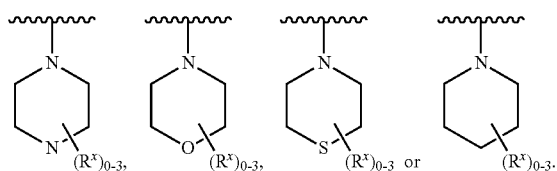

33. A compound of claim 32 wherein R² is

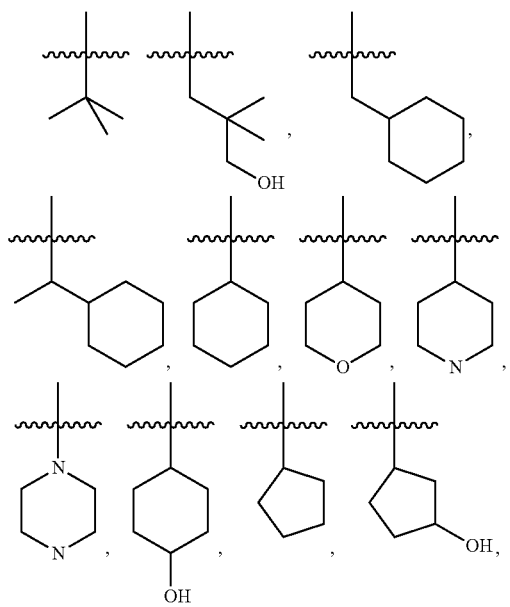

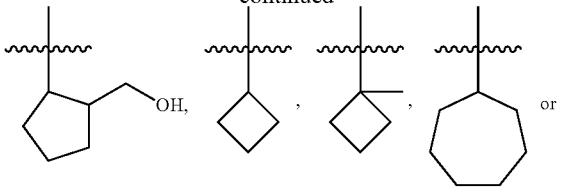

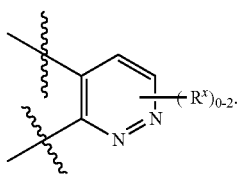

34. A compound of claim 1, wherein A¹ and A² together with the ring atoms to which they are attached combine to form $$\text{(structure with pyridazine ring, }(R^x)_{0-2})$$

35. A pharmaceutical composition comprising the compound of claim 1 together with a pharmaceutically acceptable vehicle adjuvant or diluent.

* * * * *